(12) United States Patent
Bruick et al.

(10) Patent No.: US 10,098,878 B2
(45) Date of Patent: Oct. 16, 2018

(54) HIF-2α INHIBITORS FOR TREATING IRON OVERLOAD DISORDERS

(71) Applicant: The Board of Regents of the University of Texas System, Austin, TX (US)

(72) Inventors: Richard Keith Bruick, Dallas, TX (US); Yaomin Chen, Plano, TX (US); Julio Cesar Francisco Ruiz, Garland, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/517,528

(22) PCT Filed: Sep. 25, 2015

(86) PCT No.: PCT/US2015/052279
§ 371 (c)(1),
(2) Date: Apr. 7, 2017

(87) PCT Pub. No.: WO2016/057242
PCT Pub. Date: Apr. 14, 2016

(65) Prior Publication Data
US 2017/0304300 A1 Oct. 26, 2017

Related U.S. Application Data

(60) Provisional application No. 62/062,419, filed on Oct. 10, 2014.

(51) Int. Cl.
| | |
|---|---|
| *A61K 31/075* | (2006.01) |
| *A61K 31/4965* | (2006.01) |
| *A61K 31/085* | (2006.01) |
| *A61K 31/10* | (2006.01) |
| *A61K 31/145* | (2006.01) |
| *A61K 31/277* | (2006.01) |
| *A61K 31/415* | (2006.01) |
| *A61K 31/416* | (2006.01) |
| *A61K 31/4245* | (2006.01) |
| *A61K 31/44* | (2006.01) |
| *A61P 7/00* | (2006.01) |
| *A61K 31/381* | (2006.01) |
| *A61K 31/09* | (2006.01) |
| *A61K 31/382* | (2006.01) |
| *A61K 31/4436* | (2006.01) |

(52) U.S. Cl.
CPC .......... *A61K 31/4965* (2013.01); *A61K 31/09* (2013.01); *A61K 31/10* (2013.01); *A61K 31/145* (2013.01); *A61K 31/277* (2013.01); *A61K 31/381* (2013.01); *A61K 31/382* (2013.01); *A61K 31/415* (2013.01); *A61K 31/416* (2013.01); *A61K 31/4245* (2013.01); *A61K 31/44* (2013.01); *A61K 31/4436* (2013.01)

(58) Field of Classification Search
CPC .. A61K 31/4965; A61K 31/085; A61K 31/09; A61K 31/10; A61K 31/145; A61K 31/277; A61K 31/415; A61K 31/416; A61K 31/4245; A61K 31/44
See application file for complete search history.

(56) References Cited

U.S. PATENT DOCUMENTS

| | | | |
|---|---|---|---|
| 2006/0051806 A1 | 3/2006 | Rothenberg et al. | |
| 2007/0124825 A1 | 5/2007 | Nicolas et al. | |
| 2009/0088475 A1 | 4/2009 | Allen et al. | |
| 2010/0093871 A1 | 4/2010 | Kagehara et al. | |
| 2012/0070369 A1 | 3/2012 | Iliopoulos et al. | |
| 2016/0251307 A1* | 9/2016 | Dixon ................ | C07C 255/56 514/344 |

FOREIGN PATENT DOCUMENTS

| | | |
|---|---|---|
| WO | WO 2014/078479 | 5/2014 |
| WO | WO 2014/132100 | 9/2014 |

OTHER PUBLICATIONS

Definition of prevent, Princeton University "About WordNet." WordNet. Princeton University. 2010. <http://wordnet.princeton. edu> accessed Sep. 18, 2012.*
Alexander et al. Genetics in Medicine 2009, 11 (5), 307-313.*
Gattermann Dtsch Arztebl Int 2009, 106(30), 499-504.*
Wallace Cancer Res. 2016, 76 (18), 5491-5500.*
Yu et al. Yonsei Medical J. 2017, 58(3), 489-496.*
Mastrogiannaki et al. Blood 2012, 119(2), 587-590.*
PCT International Search Report and Written Opinion issued in International Application No. PCT/US2015/052279, dated Dec. 15, 2015.
PCT International Preliminary Report on Patentability issued in International Application No. PCT/US2015/052279, dated Apr. 20, 2017.
Extended European Search Report issued in European Application No. 15849688.5, dated May 24, 2018.
Hider and Liu, "Emerging understanding of the advantage of small molecules such as hydroxypyridinones in the treatment of iron overload," *Current Medicinal Chemistry*, 10:1051-1064, 2003.

* cited by examiner

*Primary Examiner* — Irina Neagu
(74) *Attorney, Agent, or Firm* — Parker Highlander PLLC

(57) ABSTRACT

The present disclosure relates to HIF-2α inhibitors and methods of making and using them for treating iron overload disorders. Certain compounds were potent in HIF-2α scintillation proximity assay, luciferase assay, and VEGF ELISA assay, and reduced liver iron accumulation and serum iron parameters in both prophylactic and treatment mouse models.

18 Claims, 10 Drawing Sheets

Prophylactic Model

Treatment Model

HIF-2α INHIBITORS FOR TREATING IRON OVERLOAD DISORDERS

This application is a national phase application under 35 U.S.C. § 371 of International Application No. PCT/US2015/052279, filed Sep. 25, 2015, which claims benefit of priority to U.S. Provisional Application Ser. No. 62/062,419, filed Oct. 10, 2014, the entire contents of each of which are hereby incorporated by reference.

BACKGROUND

The iron export protein ferroportin is an essential regulator of systemic iron homeostasis. Following uptake by enterocytes, dietary iron can be effluxed into the plasma via the actions of ferroportin, a membrane bound iron transporter, to the basolateral side of intestinal epithelial cells. Ferroportin is also expressed on the cell surface of hepatocytes and macrophages where it plays a key role in releasing stored iron and iron recycled from phagocytosed erythrocytes, respectively (Andrews, et al. *Annu. Rev. Physiol.* 69 (2007), 69-85). Ferroportin stability is posttranslationally regulated by the hormone hepcidin, a circulating member of the defensin family of peptides that is secreted primarily by the liver (Andrews, et al. *Blood* 112 (2008), 219-230). When serum iron levels are sufficient to satisfy systemic demand, the gene encoding hepcidin (HAMP) is upregulated and hepcidin is secreted into the blood where it binds ferroportin (Nicolas, et al. *J. Clin. Invest.* 110 (2002), 1037-1044). This interaction induces structural changes within ferroportin that promotes its internalization and degradation, diminishing iron export to effectively reduce serum iron levels (Nemeth, et al. *Science* 306 (2004), 2090-2093). Transcription of the hepcidin gene is attenuated when systemic demand for iron is high, ultimately stabilizing ferroportin and increasing iron efflux into the serum (Nemeth, et al. Science 306 (2004), 2090-2093; Drakesmith, et al. *Blood* 106 (2005), 1092-1097; and Pietrangelo, *Blood Cells Mol. Dis.* 32 (2004), 131-138).

A number of proteins are employed by hepatocytes to integrate various cues indicating systemic iron demands and to signal appropriate responses in hepcidin expression. Mutations to these components can result in impaired hepcidin expression and constitutively elevated levels of ferroportin, leading to primary hemochromatosis. For example, unchecked iron absorption in the duodenum can eventually result in iron overload, characterized by the toxic accumulation of iron in tissues such as the liver (Barton, *Am. J. Med. Sci.* 346 (2013), 403-412; Crownover, et al. *Am. Family Physician* 87 (2013), 183-190). In addition, iron overload can also result from another disease or condition (secondary hemochromatosis). The disease and condition include but are not limited to certain types of anemia, such as thalassemias and sideroblastic anemia; atransferrinemia and aceruloplasminemia; and chronic liver diseases, such as chronic hepatitis C infection, alcoholic liver disease, or nonalcoholic steatohepatitis. Other factors can also lead to secondary hemochromatosis, including but are not limited to blood transfusions, oral iron pills or iron injections (with or without very high vitamin C intake), and long-term kidney dialysis.

The human hemochromatosis gene, or HFE, encodes a membrane protein employed by the liver to sense serum iron levels. When high transferrin-bound iron levels are recognized by transferrin receptor 2 (TfR2), it recruits HFE protein to engage a BMP/SMAD-dependent signaling pathway to induce HAMP transcription. Recent work suggests that common polymorphisms to the HFE gene (e.g., leading to HFE protein with C282Y/C282Y homozygous, C282Y/H63D heterozygous, or C282Y/S65C homozygous mutation) compromise HFE's ability to affect BMP/SMAD signaling (Wu, et al. *Blood* 124 (2014), 1335-1343). Consequently, hepcidin expression is impaired and individuals homozygous or heterozygous for these missense alleles can develop hemochromatosis accompanied by damage to the liver and other organs resulting from iron overload. This disease can by modeled in mice through targeted inactivation of the HFE gene (e.g., HFE$^{-/-}$ mice; reviewed in Fleming, et al. *Annu. Rev. Nutr.* 31 (2011), 117-137). Some hemochromatotic patients can be treated by phlebotomy. However, some patients with forms of secondary hemochromatosis may not be treated by phlebotomy due to low red cell mass. These patients are dependent on iron chelators to treat the iron overload. While iron chelators are somewhat effective, the treatment is associated with significant adverse side effects (Maggio, *Br. J. Haematol.* 138 (2007), 407-421).

Hypoxia Inducible Factors 1α and 2α (HIF-1α and HIF-2α) are heterodimeric transcription factors whose regulated alpha subunits can be induced under low oxygen or iron conditions to upregulate hundreds of potential downstream target genes (Keith, et al. *Nature Rev. Cancer* 12 (2012), 9-22). Genetic approaches with mice lacking HIF-2α expression in the duodenum have indicated that the HIF-2α isoform selectively regulates several genes critical for intestinal iron absorption. These targets include ferroportin, as well as the duodenal cytochrome B (DcytB) that reduces iron in the lumen so that it may be transported into enterocytes through the divalent metal transport protein 1 (DMT-1), also a HIF-2α target. Mice lacking intestinal HIF-2α expression, absorb less iron and are resistant to the consequences of mutations that would otherwise promote hemochromoatosis (Mastrogiannaki, et al. *J. Clin. Invest.* 119 (2009), 1159-1166; Mastrogiannaki, et al. *Blood* 119 (2012), 587-590; and Anderson, et al. *Proc. Natl. Acad. Sci. U.S.A.* 26 (2013), 4922-4930).

Therefore, there is a need to develop new therapies to treat patients suffering from iron overload disorders and related diseases. Small molecule inhibitors of HIF-2α may fulfill the need and offer other advantages over the existing therapies.

SUMMARY

Thus, in accordance with the disclosure, there is provided a method of preventing or treating an iron overload disorder comprising administering to a subject an effective amount of a small molecule HIF-2α inhibitor. The method small molecule HIF-2α inhibitor may have an IC$_{50}$ of less than 500 nM in HIF-2α scintillation proximity assay. The small molecule HIF-2α inhibitor may have an IC$_{50}$ of less than 100 nM in HIF-2α scintillation proximity assay. The small molecule may have the structures of Formulas I-V as defined herein below. The subject may be a human. The human may have an HFE gene mutation, such as an HFE protein with C282Y/C282Y homozygous mutation, or an HFE protein with C282Y/H63D heterozygous mutation, or an HFE protein with C282Y/S65C heterozygous mutation. The the iron overload disorder may be primary hemochromatosis. The iron overload disorder may be secondary hemochromatosis, such as resulting from β-thalassemia. In particular, the small molecule HIF-2α has any one of the formula of Compounds 1 through 210, as described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the disclosure, and vice versa. Furthermore, compositions and kits of the disclosure can be used to achieve methods of the disclosure.

The term "about" refers to ±10% of a stated number or value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF FIGURES

The disclosure may be better understood by reference to one or more of these drawings in combination with the detailed description of specific embodiments presented herein

DETAILED DESCRIPTION OF THE INVENTION

Figure 1:
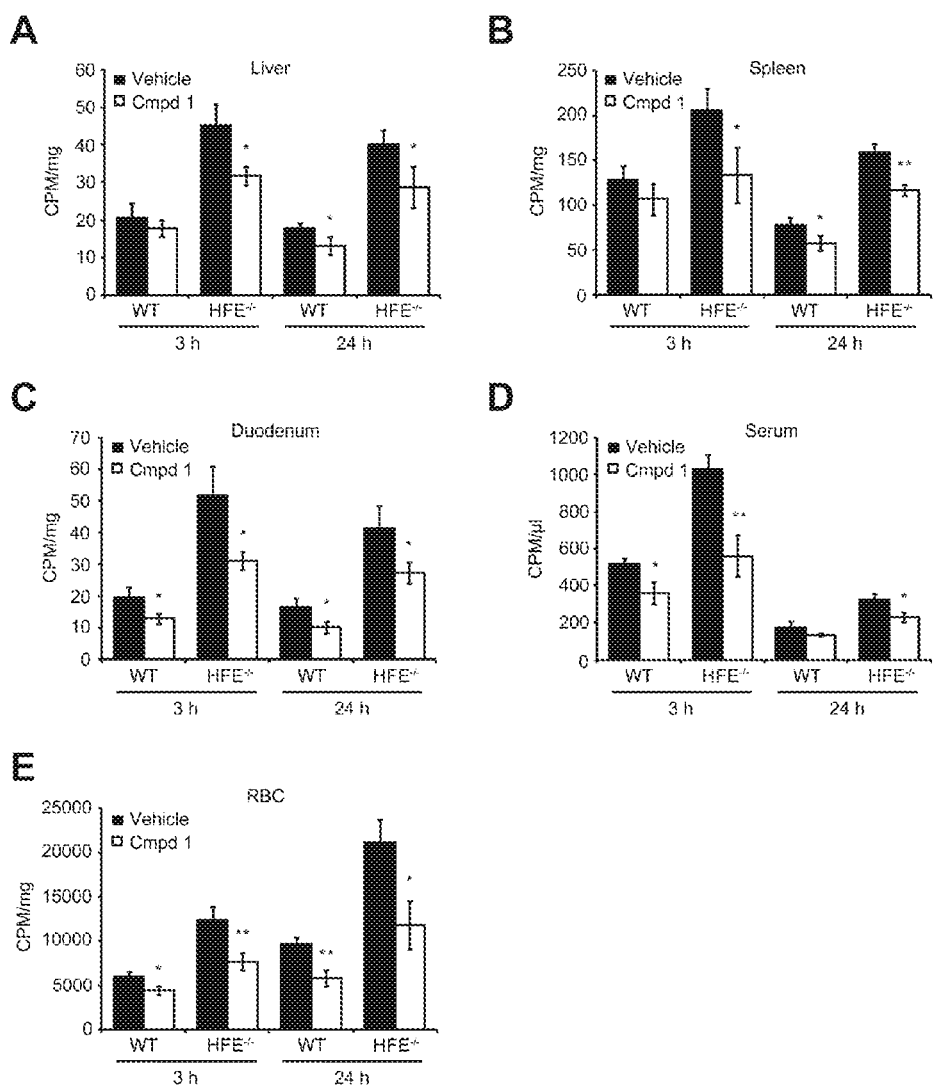
FIG. 1 shows that Compound 1 treatment in mice reduced iron absorption. Hemochromatosis gene deficient ($HRE^{-/-}$) and wild-type mice at 13 weeks of age were treated with either vehicle or 100 mg/kg Compound 1 by oral gavage twice a day (b.i.d.) for 3 days. Following an overnight fast, mice were gavaged with an olive-tipped needle containing 200 of PBS supplemented with 2.5 µCi $^{59}FeCl_3$ (PerkinElmer) and 0.5 M ascorbic acid. At 3 or 24 h, animals were exsanguinated and $^{59}Fe$ accumulation in tissues (liver, A; spleen, B; duodenum, C; serum, D; RBC, E) was measured in a Packard Cobra Gamma. Counter. $*p<0.05$, $**p<0.01$; n=3/group.

In one aspect, the present disclosure provides a method of preventing or treating an iron overload disorder comprising administering to a subject an effective amount of a small molecule HIF-2α inhibitor.

In some embodiments, the small molecule HIF-2α inhibitor has an $IC_{50}$ of less than 500 nM in HIF-2α scintillation proximity assay. In a further embodiment, the small molecule HIF-2α inhibitor has an $IC_{50}$ of less than 100 nM in HIF-2α scintillation proximity assay.

In another aspect, the present disclosure provides a method of preventing or treating an iron overload disorder comprising administering to a subject an effective amount of a compound is of Formula I or Formula II:

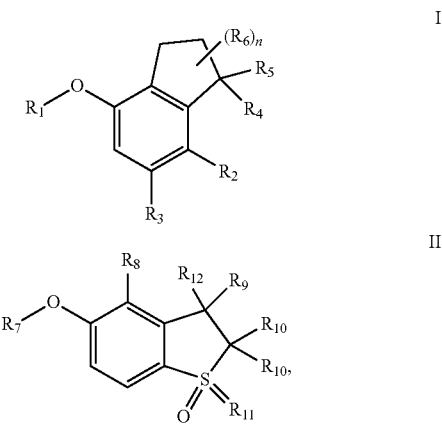

or a pharmaceutically acceptable salt thereof, wherein:

n is 1, 2, 3 or 4;

$R_1$ is aryl or heteroaryl;

$R_2$ is nitro, halo, cyano, alkyl, sulfinyl, sulfonamide, sulfonyl, or sulfoximinyl;

$R_3$ is hydrogen, halo, or alkyl;

$R_4$ is hydrogen, deuterium ($^2$H), hydroxy, alkylamino, alkoxy, or amino;

$R_5$ is hydrogen, alkyl, alkenyl, or alkynyl; or $R_4$ and $R_5$ in combination form oxo or oxime;

each of $R_6$ is independently selected from the group consisting of hydrogen, fluoro, chloro, hydroxy, NHBoc, alkenyl, and alkyl; or two $R_6$ and the carbon atom(s) they are attached to form a 3- to 8-membered cycloalkyl or heterocycloalkyl;

$R_7$ is alkyl, heteroalkyl, cycloalkyl, heterocycloalkyl, aryl, benzyl, or substituted benzyl, or heteroaryl;

$R_8$ is hydrogen, nitro, cyano, halo, alkyl, alkoxy, heteroalkyl, alkynyl, or alkenyl;

$R_9$ is hydrogen, deuterium ($^2$H), hydroxy, alkylamino, or amino; or $R_9$ and $R_{12}$ in combination form oxo or imino;

each of $R_{10}$ is independently selected from the group consisting of hydrogen, halo, alkyl, heteroalkyl, and cycloalkyl, or the two $R_{10}$s and the carbon they are attached to form C3-C8 cycloalkyl or C5-C8 heterocycloalkyl;

$R_{11}$ is O or $NR_{13}$, wherein $R_{13}$ is selected from the group consisting of hydrogen, alkyl, cycloalkyl, cyano, heterocycloalkyl, heteroaryl and heteroalkyl; and $R_{12}$ is hydrogen or alkyl.

In some embodiments, the subject is a human. In a further embodiment, the human has HFE gene mutation. The HFE gene mutation may lead to a HFE protein with homozygous C282Y/C282Y mutation, heterozygous C282Y/H63D mutation, or heterozygous C282Y/S65C mutation.

In some embodiments, the iron overload disorder is primary hemochromatosis. In some other embodiments, the iron overload disorder is secondary hemochromatosis. In a further embodiment, the secondary hemochromatosis results from β-thalassemia.

In some embodiments, the compound is of one of the formulae:

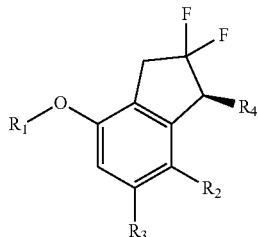

IIIa

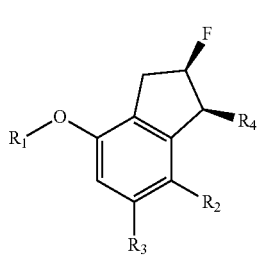

IIIb

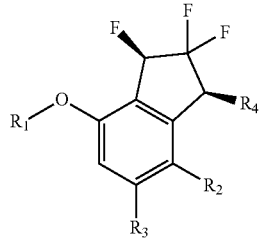

IIIc

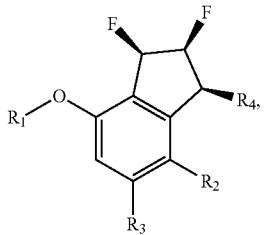

IIId wherein:

$R_1$ is aryl or heteroaryl;

$R_2$ is halo, cyano, alkyl, sulfonamide, sulfinyl, sulfonyl, or sulfoximinyl;

$R_3$ is hydrogen, halo, or alkyl; and $R_4$ is hydroxy, alkylamino, alkoxy, or amino.

In some embodiments, $R_1$ is phenyl or monocyclic heteroaryl. In some further embodiments, $R_1$ is phenyl or pyridyl, optionally substituted with one or more substituents selected from the group consisting of halo, alkyl, alkoxy, and cyano. In a further embodiment, $R_1$ is

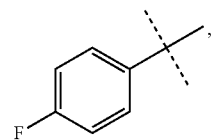

wherein the aryl ring is optionally substituted with one or more substituents selected from the group consisting of cyano, halo, alkyl, and alkoxy. In another further embodiment, $R_1$ is

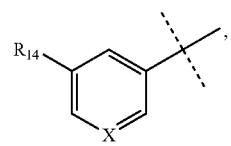

wherein X is N or $CR_{15}$, $R_{14}$ is cyano, halo, alkyl, or alkoxy, and $R_{15}$ is hydrogen, cyano, halo, alkyl, or alkoxy.

In some embodiments, $R_1$ is bicyclic heteroaryl.

In some embodiments, $R_1$ is selected from the group consisting of:

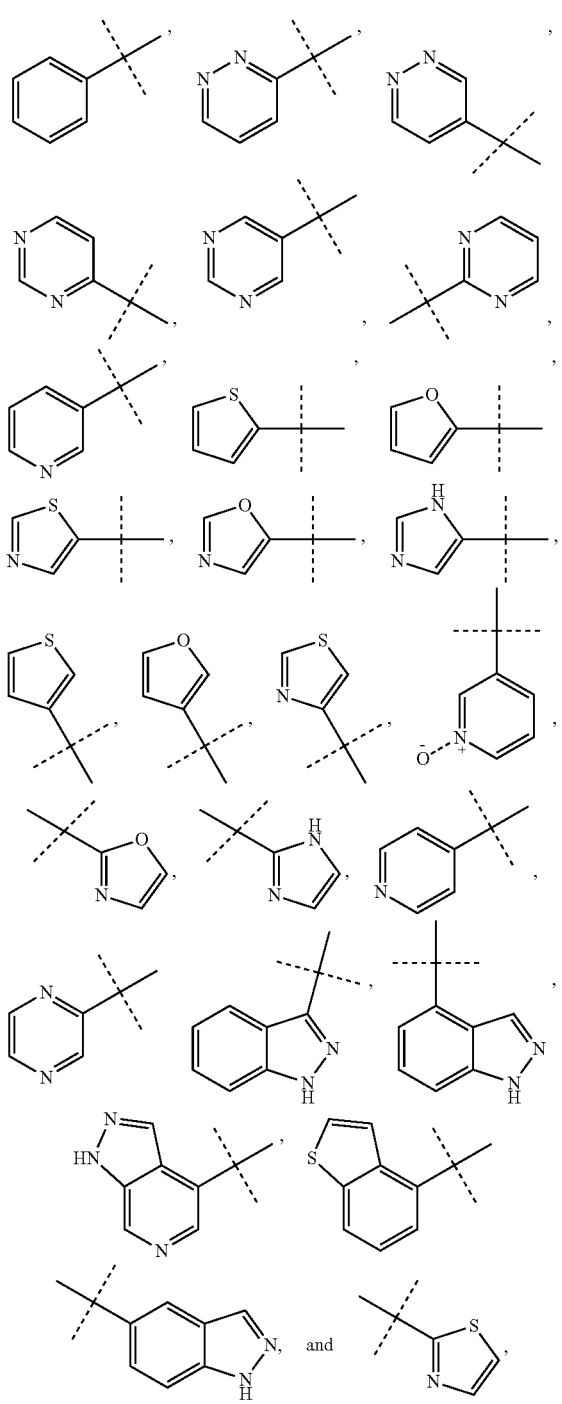

and the rings specified for $R_1$ may optionally be substituted with one or more substituents described for aryl and heteroaryl. In a further embodiment, the substituent(s) is selected from the group consisting of halo, C1-C4 alkyl, C1-C4 alkoxy, and cyano.

In some embodiments, $R_2$ is cyano, fluoroalkyl, sulfinyl, sulfonamide, sulfonyl, or sulfoximinyl. In a further embodiment, $R_2$ is fluoroalkyl, sulfonamide, sulfinyl, sulfonyl, or sulfoximinyl.

In some embodiments, $R_2$ is —S(=O)$_2R_a$, wherein $R_a$ is alkyl or cycloalkyl. In a further embodiment, $R_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$. In still a further embodiment, $R_a$ is methyl, optionally substituted with one or more fluorines. In some embodiments, $R_2$ is —S(=O)(=NR$_b$)R$_a$, wherein $R_a$ is alkyl or cycloalkyl and $R_b$ is hydrogen, cyano, or alkyl. In a further embodiment, $R_a$ is C1-C4 alkyl, optionally substituted with one or more fluorines. Suitable examples of fluorine-substituted C1-C4 alkyl include, but are not limited to, —CH$_2$F, —CHF$_2$, —CF$_3$, —CH$_2$CF$_3$, —CH$_2$CHF$_2$, —CH$_2$CH$_2$F, —CHFCH$_3$, and —CF$_2$CH$_3$.

In some embodiments, $R_2$ is —S(=O)$_2$—N(R$_a$)$_2$, wherein each of $R_a$ is independently hydrogen, alkyl, heteroalkyl, cycloalkyl, or heterocycloalkyl, and at least one $R_a$ is hydrogen. In a further embodiment, both $R_a$s are hydrogen. In another further embodiment, one $R_a$ is hydrogen and the other $R_a$ is C1-C4 alkyl.

In some embodiments, $R_2$ is selected from the group consisting of —CN, —CF$_3$, —S(=O)CH$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In some embodiments, $R_3$ is hydrogen, halo, or alkyl. In some other embodiments, $R_3$ is hydrogen. In some other embodiments, $R_3$ is alkyl. In a further embodiment, $R_3$ is C1-C4 alkyl.

In some embodiments, $R_4$ is hydroxy or amino. In a further embodiment, $R_4$ is hydroxy. In another further embodiment, $R_4$ is amino.

In some embodiments, $R_5$ is hydrogen.

In some embodiments, $R_6$ is fluoro. In a further embodiment, n is 1, 2 or 3.

In some embodiments, $R_1$ is phenyl, monocyclic heteroaryl, or bicyclic heteroaryl; $R_2$ is cyano, fluoroalkyl, sulfonamide, sulfinyl, sulfonyl or sulfoximinyl; $R_3$ is hydrogen; and $R_4$ is hydroxy or amino.

In some embodiments, $R_1$ is monocyclic aryl or monocyclic heteroaryl and $R_4$ is hydroxy or amino. In a further embodiment, $R_6$ is fluoro. In still a further embodiment, n is 1, 2 or 3.

In some embodiments, $R_1$ is phenyl or monocyclic heteroaryl, $R_4$ is hydroxy or amino, $R_6$ is fluoro, n is 1, 2 or 3 and $R_3$ is hydrogen.

In some embodiments, $R_1$ is bicyclic heteroaryl and $R_4$ is hydroxy or amino. In a further embodiment, $R_6$ is fluoro. In still a further embodiment, n is 1, 2 or 3.

In some embodiments, $R_1$ is bicyclic heteroaryl, $R_4$ is hydroxy or amino, $R_6$ is fluoro, n is 1, 2 or 3, and $R_3$ is hydrogen.

In some embodiments, $R_2$ is cyano, fluoroalkyl, sulfonamide, sulfinyl, sulfonyl, or sulfoximinyl, and $R_8$ is hydroxy or amino. In a further embodiment, $R_5$ is hydrogen. In another further embodiment, $R_6$ is fluoro. In still a further embodiment, n is 1, 2 or 3.

In some embodiments, $R_2$ is cyano, fluoroalkyl, sulfonamide, sulfonyl, sulfinyl, or sulfoximinyl; $R_4$ is hydroxy or amino; $R_6$ is fluoro; n is 1, 2 or 3; and $R_3$ is hydrogen. In a further embodiment, $R_5$ is hydrogen.

In some embodiments, $R_4$ is hydroxy or amino and $R_5$ is hydrogen. In a further embodiment, $R_6$ is fluoro. In still a further embodiment, n is 1, 2 or 3.

In some embodiments, $R_4$ is hydroxy or amino, $R_5$ is hydrogen, $R_6$ is fluoro, n is 1, 2 or 3, and $R_3$ is hydrogen. In a further embodiment, $R_2$ is selected from the group consisting of —CN, —CF$_3$, —S(=O)$_2$CH$_3$, —S(=O)$_2$CH$_2$F, —S(=O)$_2$CHF$_2$, —S(=O)$_2$CF$_3$, —S(=O)$_2$NH$_2$, —S(=O)$_2$NHCH$_3$, —S(=O)(=NH)CH$_3$, —S(=O)(=NH)CH$_2$F, —S(=O)(=NH)CHF$_2$, —S(=O)(=NH)CF$_3$, —S(=O)(=N—CN)CH$_3$, —S(=O)(=N—CN)CH$_2$F, —S(=O)(=N—CN)CHF$_2$, and —S(=O)(=N—CN)CF$_3$.

In some embodiments, the compound is of Formula IV:

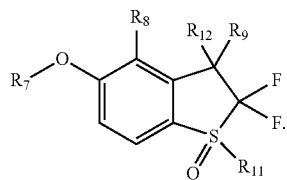

IV

In some embodiments, $R_7$ is alkyl, cycloalkyl, heterocycloalkyl, aryl or heteroaryl. In some embodiments, $R_7$ is cycloalkyl, heterocycloalkyl, aryl or heteroaryl. In some embodiments, $R_7$ is heterocycloalkyl, aryl or heteroaryl. In some embodiments, $R_7$ is cycloalkyl, aryl or heteroaryl. In some embodiments, $R_7$ is aryl or heteroaryl. In a further embodiment, $R_7$ is phenyl. In another further embodiment, $R_7$ is pyridyl. In still a further embodiment, the phenyl or pyridyl is substituted with at least one substituent selected from the group consisting of halo, alkoxy, cyano and alkyl.

In some embodiments, $R_7$ is selected from the group consisting of alkyl, cyclohexyl, tetrahydrofuranyl, cyclobutyl, and tetrahydropyranyl. Representative examples include but are not limited to the following:

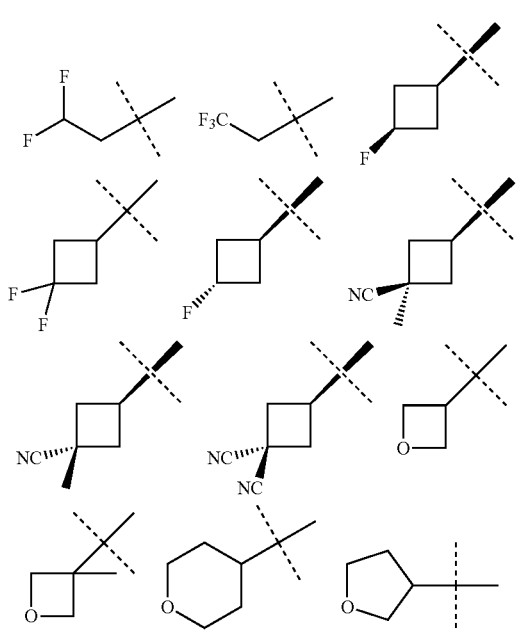

In some embodiments, $R_1$ is selected from the group consisting of:

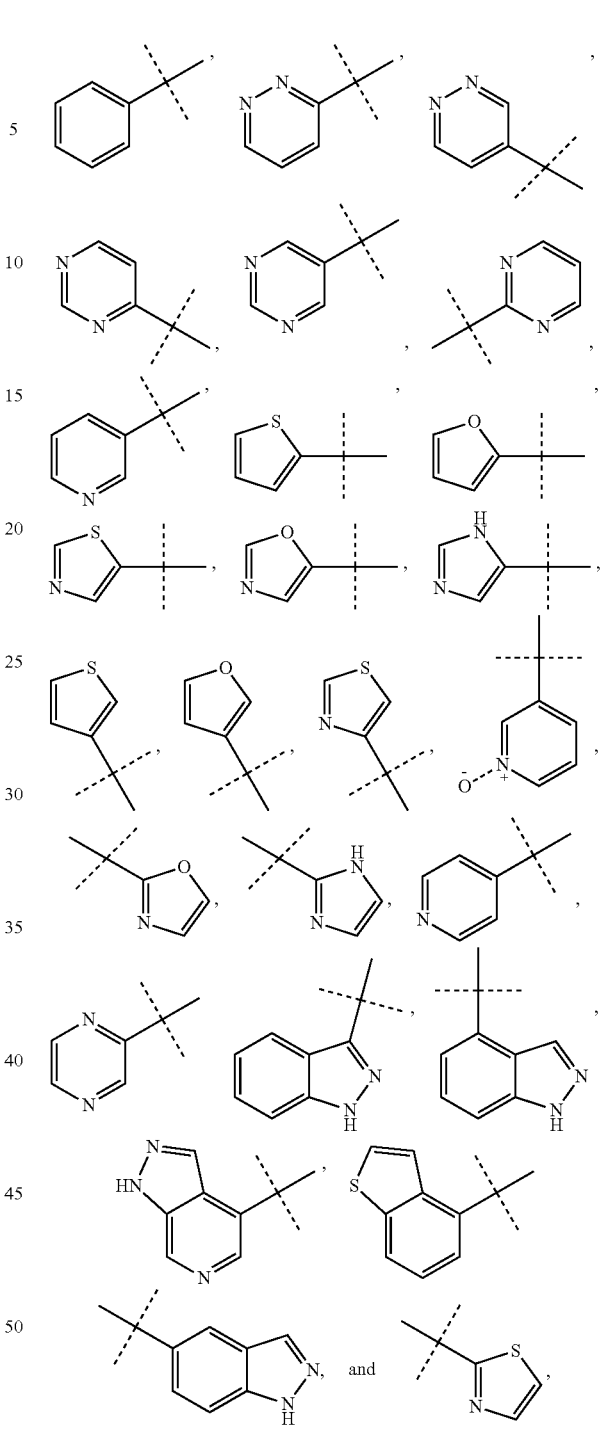

and the rings specified for $R_1$ may optionally be substituted with one or more substituents described for aryl and heteroaryl. In a further embodiment, the substituents) is selected from the group consisting of halo, C1-C4 alkyl, C1-C4 alkoxy, and cyano.

In some embodiments, $R_8$ is cyano, halo, or alkyl. In a further embodiment, $R_8$ is fluoroalkyl.

In some embodiments, $R_9$ is hydroxy or amino. In a further embodiment, $R_9$ is hydroxy.

In some embodiments, $R_H$ is O, NH, or N—CN.

In some embodiments, $R_7$ is aryl or heteroaryl, $R_{11}$ is O, $R_9$ is hydroxy or amino and $R_{12}$ is hydrogen. In a further embodiment, $R_8$ is cyano, halo, or alkyl. In a still further embodiment, $R_8$ is fluoroalkyl.

In some embodiments, the compound is of Formula V

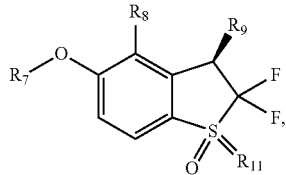

V wherein: $R_9$ is hydroxy or amino; and $R_{11}$ is O, NH, or N—CN. In some embodiments, the compound has the formula of Compounds 1-210. In some embodiments, the compound has the formula of Compounds 1-211.

For purposes of interpreting this disclosure, the following definitions will apply.

The term "HIF-2α" refers to a monomeric protein that contains several conserved structured domains: basic helix-loop-helix (bHLH), and two Per-ARNT-Sim (PAS) domains designated PAS-A and PAS-B, in addition to C-terminal regulatory regions. "HIF-2α" is also alternatively known by several other names in the scientific literature, including Endothelial PAS Domain Protein 1 (EPAS1), HIF2A, PASD2, HIF-2-Alpha, HIF2-Alpha, HLF, Hypoxia-Inducible Factor 2-Alpha, HIF-1 alpha-Like Factor, and MOP2. As a member of the bHLH/PAS family of transcription factors, "HIF-2α" forms an active heterodimeric transcription factor complex by binding to the ARNT (also known as HIF-1β) protein through non-covalent interactions.

The term "subject" includes, but is not limited to, humans of any age group, e.g., a pediatric subject (e.g., infant, child or adolescent) or adult subject (e.g., young adult, middle-aged adult or senior adult)) and/or other primates (e.g., cynomolgus monkeys or rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the terms "treatment", "treating", "palliating" and "ameliorating" are used interchangeably herein. These terms refer to an approach for obtaining beneficial or desired results including, but are not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions can be administered to a patient at risk of developing a particular disease, or to a patient reporting one or more of the physiological symptoms of a disease, even though a diagnosis of this disease may not have been made.

The term "small molecule" refers to an organic molecule which is not a polymer and which is 2000 Da or less. In an embodiment, the small molecule is 1000 Da or less.

The term "alkyl" refers to a straight or branched hydrocarbon chain radical comprising carbon and hydrogen atoms, containing no unsaturation, and having from one to ten carbon atoms (i.e., C1-C10 alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a C1-C4 alkyl group. Typical alkyl groups include, but are in no way limited to, methyl, ethyl, n-propyl, isopropyl, n-butyl, isobutyl, sec-butyl, tert-butyl, pentyl, isopentyl, neopentyl, hexyl, septyl, and the like. The alkyl is attached to the rest of the molecule by a single bond. Unless stated otherwise specifically in the specification, an alkyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "aromatic" or "aryl" refers to an aromatic radical with six to ten ring atoms (i.e., C6-C10 aromatic or C6-C10 aryl) which has at least one ring having a conjugated pi electron system which is carbocyclic (e.g., phenyl, fluorenyl, and naphthyl). Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, allynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)OR$^a$, —C(=O)R$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$N(R$^a$)$_2$ (where t is 1 or 2), —N(R$^a$)S(=O)$_t$R$^a$ (where t is 1 or 2), —S(=O)$_t$R$^a$ (where t is 1 or 2), —S(=O)$_t$N(R$^a$)$_2$ (where t is 1 or 2), or —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "heteroaryl" or, alternatively, "heteroaromatic" refers to a 5- to 18-membered aromatic radical (i.e., C5-C18 heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical, e.g., nitrogen or sulfur, is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —$SR^a$, —OC(=O)—$R^a$, —OC(=O)$OR^a$, —N($R^a$)$_2$, —C(=O)$OR^a$, —OC(=O)N($R^a$)$_2$, —C(=O)$R^a$, —C(=O)N($R^a$)$_2$, —N($R^a$)C(=O)$OR^a$, —N($R^a$)C(=O)N($R^a$)$_2$, —N($R^a$)C(=O)$R^a$, —N($R^a$)S(=O)$_t$$R^a$ (where t is 1 or 2), —N($R^a$)S(=O)$_t$N($R^a$)$_2$ (where t is 1 or 2), —S(=O)$_t$$R^a$ (where t is 1 or 2), —S(=O)$_t$N($R^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each $R^a$ is independently hydrogen, alkyl, heteroalkyl, cycloalkyl, heterocycloalkyl, aryl or heteroaryl. Examples of monocylic heteroaryls include, but are not limited to, imidazolyl, pyridinyl, pyrrolyl, pyrazinyl, pyrimidinyl, thiazolyl, furanyl and thienyl.

The term "acyl" refers to a —(C=O)R radical, wherein R is alkyl, cycloalkyl, aryl, heteroaryl, heteroalkyl, or heterocycloalkyl, which are as described herein. The R group is joined to the carbonyl through a carbon-carbon single bond. In some embodiments, it is a C1-C10 acyl radical which refers to the total number of chain or ring atoms of the alkyl, cycloalkyl, aryl, heteroalkyl, heteroaryl or heterocycloalkyl portion of the acyl group plus the carbonyl carbon of acyl, i.e. ring or chain atoms plus carbonyl. If the R radical is heteroaryl or heterocycloalkyl, the hetero ring or chain atoms contribute to the total number of chain or ring atoms. Unless stated otherwise specifically in the specification, the R of an acyl group is optionally substituted by one or more substituents which independently are: alkyl, heteroalkyl, alkenyl, alkynyl, cycloalkyl, heterocycloalkyl, aryl, heteroaryl, hydroxy, halo, cyano, trifluoromethyl, trifluoromethoxy, nitro, trimethylsilanyl, —$OR^a$, —$SR^a$, —OC(=O)—$R^a$, —OC(=O)$OR^a$, —N($R^a$)$_2$, —C(=O)$R^a$, —C(=O)$OR^a$, —OC(=O)N($R^a$)$_2$, —C(=O)N($R^a$)$_2$, —N($R^a$)C(=O)$OR^a$, —N($R^a$)C(=O)N($R^a$)$_2$, —N($R^a$)C(=O)$R^a$, —N($R^a$)S(=O)$_t$$R^a$ (where t is 1 or 2), —N($R^a$)S(=O)$_t$N($R^a$)$_2$ (where t is 1 or 2), —S(=O)$_t$$R^a$ (where t is 1 or 2), —S(=O)$_t$N($R^a$)$_2$ (where t is 1 or 2), or —P(=O)(O$R^a$)$_2$, wherein each of $R^a$ is independently hydrogen, alkyl, heteroalkyl, cycloalkyl, heterocycloalkyl, aryl or heteroaryl.

The term "halo", "halide", or alternatively, "halogen" means fluoro, chloro, bromo or iodo. The terms "haloalkyl" refers to alkyl structures that are substituted with one or more halo groups or combinations thereof. The terms "haloalkoxy" refers to alkoxy structures that are substituted with one or more halo groups or combinations thereof. The terms "fluoroalkyl" and "fluoroalkoxy" refer to haloalkyl and haloalkoxy groups, respectively, in which the halo is fluoro. Examples of fluoroalkyl include, but are not limited to, —CH$_2$F, —CHF$_2$, —CF$_3$, —CF$_2$CH$_3$, —CH$_2$CF$_3$, and —CF$_2$CF$_3$.

The term "cyano" refers to a —CN radical.

The term "alkoxy" refers to an —O-alkyl radical, wherein alkyl is as described herein and contains 1 to 10 carbons (i.e., C1-C10 alkoxy). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms. In some embodiments, it is a C1-C4 alkoxy group. Unless stated otherwise specifically in the specification, an alkoxy moiety may be substituted by one or more of the substituents described as suitable substituents for an alkyl radical.

The term "sp$^3$ hybridized carbon" refers to a carbon atom that is bonded to four other atoms. sp$^3$ hybridization results from the combination of the s orbital and all three p orbitals in the second energy level of carbon. It results in four equivalent orbitals and the geometric arrangement of those four orbitals is tetrahedral.

The term "sulfonyl" refers to a —S(=O)$_2$—R radical, wherein R is selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the R group may be substituted by one or more of the substituents described as suitable substituents for an alkyl, an aryl or a heteroaryl radical.

The term "sulfoximinyl" refers to a —S(=O)(=N$R^a$)—$R^b$ radical, wherein $R^a$ is selected from the group consisting of hydrogen, alkyl, cycloalkyl, alkenyl, aryl, cyano, carbamoyl, acyl, heteroaryl (bonded through a ring carbon) and heterocycloalkyl (bonded through a ring carbon) and $R^b$ is independently selected from the group consisting of alkyl, cycloalkyl, aryl, heteroalkyl, heteroaryl (bonded through a ring carbon) and heterocycloalkyl (bonded through a ring carbon). Unless stated otherwise specifically in the specification, the $R^a$ and $R^b$ group may be substituted by one or more of the substituents described as suitable substituents for an alkyl, an aryl or a heteroaryl radical.

The term "sulfonamide" refers to a —S(=O)$_2$—N(R$^a$)$_2$ radical, wherein each R$^a$ is independently hydrogen, alkyl, heteroalkyl, cycloalkyl or heterocycloalkyl, and at least one R$^a$ is hydrogen.

The term "cycloalkyl" refers to a monocyclic or polycyclic non-aromatic radical that contains carbon and hydrogen, and may be saturated, or partially unsaturated. Cycloalkyl groups include groups having from 3 to 10 ring atoms (i.e., C3-C10 cycloalkyl). Whenever it appears herein, a numerical range such as "3 to 10" refers to each integer in the given range; e.g., "3 to 10 carbon atoms" means that the cycloalkyl group may consist of 3 carbon ring atoms, 4 carbon ring atoms, 5 carbon ring atoms, etc., up to and including 10 carbon ring atoms. In some embodiments, it is a C3-C5 cycloalkyl radical. Illustrative examples of cycloalkyl groups include, but are not limited to the following moieties: cyclopropyl, cyclobutyl, cyclopentyl, cyclohexyl, cycloseptyl, cyclooctyl, cyclononyl, cyclodecyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "heterocyclyl" or "heterocycloalkyl" refers to a stable and not fully aromatic 3- to 18-membered ring (i.e., C3-C18 heterocycloalkyl) radical that comprises two to twelve ring carbon atoms and from one to six ring heteroatoms selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a C5-C10 heterocycloalkyl. In some embodiments, it is a C4-C10 heterocycloalkyl. In some embodiments, it is a C3-C10 heterocycloalkyl. Unless stated otherwise specifically in the specification, the heterocycloalkyl radical may be a monocyclic, bicyclic, tricyclic or tetracyclic ring system, which may include fused or bridged ring systems. The heteroatoms in the heterocycloalkyl radical may be optionally oxidized. One or more nitrogen atoms, if present, may optionally be quaternized. The heterocycloalkyl radical may be partially or fully saturated. The heterocycloalkyl may be attached to the rest of the molecule through any atom of the ring(s). Examples of such heterocycloalkyl radicals include, but are not limited to, 6,7-dihydro-5H-cyclopenta[b]pyridine, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The terms "heteroalkyl", "heteroalkenyl" and "heteroalkynyl" include optionally substituted alkyl, alkenyl and alkynyl radicals, which respectively have one or more skeletal chain atoms selected from an atom other than carbon, e.g., oxygen, nitrogen, sulfur, phosphorus or combinations thereof. A numerical range, which refers to the chain length in total, may be given. For example, C3-C4 heteroalkyl has a chain length of 3-4 atoms. For example, a —CH$_2$OCH$_2$CH$_3$ radical is referred to as a "C4 heteroalkyl", which includes the heteroatom in the atom chain length description. Connection to the rest of the molecule is through a carbon in the heteroalkyl chain. A heteroalkyl may be a substituted alkyl. The same definition applies to heteroalkenyl or heteroalkynyl. Unless otherwise stated in the specification, a heteroalkyl group may be substituted with one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$_a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N(R$^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each R$^a$ is independently hydrogen, alkyl, heteroalkyl, cycloalkyl, heterocycloalkyl, aryl or heteroaryl.

The term "amino" or "amine" refers to a NH$_2$ radical group.

The term "acyloxy" refers to a R(C=O)O— radical wherein R is alkyl, cycloalkyl, aryl, heteroalkyl, heteroaryl or heterocycloalkyl, which are as described herein. In some embodiments, it is a C2-C4 acyloxy radical, wherein the C2-C4 refers to the total number, i.e., 1-3 of the chain or ring atoms of the alkyl, cycloalkyl, aryl, heteroalkyl, heteroaryl or heterocycloalkyl portion of the acyloxy group plus the carbonyl carbon of acyl, i.e., the ring or chain atoms plus carbonyl. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N(R$^a$)$_2$, —N(R$^a$)$_2$, —C(=O)R$^a$, —C(=O)OR$^a$, —C(=O)N(R$^a$)$_2$, —N(R$^a$)C(=O)OR$^a$, —N(R$^a$)C(=O)N(R$^a$)$_2$, —N(R$^a$)C(=O)R$^a$, —N(R$^a$)S(=O)$_t$R$^a$ (where t is 1 or 2), —N(R$^a$)S(=O)$_t$N(R$^a$)$_2$ (where t is 1 or 2), —S(=O)$_t$R$^a$ (where t is 1 or 2), —S(=O)$_t$N $(R^a)_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each of $R^a$ is independently hydrogen, alkyl, heteroalkyl, cycloalkyl, heterocycloalkyl, aryl or heteroaryl.

The term "alkenyl" refers to a straight or branched hydrocarbon chain radical group comprising carbon and hydrogen atoms, containing at least one double bond, and having from two to ten carbon atoms (i.e., C2-C10 alkenyl). Whenever it appears herein, a numerical range such as "2 to 10" refers to each integer in the given range; e.g., "2 to 10 carbon atoms" means that the alkenyl group may contain 2 carbon atoms, 3 carbon atoms, etc., up to and including 10 carbon atoms. In certain embodiments, an alkenyl comprises two to eight carbon atoms (i.e., C2-C8 alkenyl). In other embodiments, an alkenyl comprises two to five carbon atoms (i.e., C2-C5 alkenyl). The alkenyl is attached to the rest of the molecule by a single bond, for example, ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N($R^a$)$_2$, —N($R^a$)$_2$, —C(=O)R$^a$, —C(=O)OR$^a$, —C(=O)N($R^a$)$_2$, —N($R^a$)C(=O)R$^a$, —N($R^a$)C(=O)OR$^a$, —N($R^a$)C(=O)N($R^a$)$_2$, —N($R^a$)S(=O)$_t$R$^a$ (where t is 1 or 2), —N($R^a$)S(=O)$_t$N($R^a$)$_2$ (where t is 1 or 2), —S(=O)$_t$R$^a$ (where t is 1 or 2), —S(=O)$_t$N($R^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each of $R^a$ is independently hydrogen, alkyl, heteroalkyl, cycloalkyl, heterocycloalkyl, aryl or heteroaryl.

The term "alkynyl" refers to a straight or branched hydrocarbon chain radical group comprising carbon and hydrogen atoms, containing at least one triple bond, and having from two to ten carbon atoms (i.e., C2-C10 alkynyl). In some embodiments, an alkynyl group may contain one or more double bonds. Whenever it appears herein, a numerical range such as "2 to 10" refers to each integer in the given range; e.g., "2 to 10 carbon atoms" means that the alkynyl group may contain 2 carbon atoms, 3 carbon atoms, etc., up to and including 10 carbon atoms. In certain embodiments, an alkynyl comprises two to eight carbon atoms (i.e., C2-C8 alkynyl). In other embodiments, an alkynyl has two to five carbon atoms (i.e., C2-C5 alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)—R$^a$, —OC(=O)OR$^a$, —OC(=O)N($R^a$)$_2$, —N($R^a$)$_2$, —C(=O)R$^a$, —C(=O)OR$^a$, —C(=O)N($R^a$)$_2$, —N($R^a$)C(=O)OR$^a$, —N($R^a$)C(=O)R$^a$, —N($R^a$)C(=O)N($R^a$)$_2$, —N($R^a$)S(=O)$_t$R$^a$ (where t is 1 or 2), —N($R^a$)S(=O)$_t$N($R^a$)$_2$ (where t is 1 or 2), —S(=O)$_t$R$^a$ (where t is 1 or 2), —S(=O)$_t$N($R^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each $R^a$ is independently hydrogen, alkyl, heteroalkyl, cycloalkyl, heterocycloalkyl, aryl or heteroaryl.

The term "alkylamino" refers to a chemical moiety with formula —N($R^a$)$_2$, wherein each $R^a$ is independently hydrogen, alkyl, heteroalkyl, cycloalkyl, or heterocycloalkyl, and at least one $R^a$ is not hydrogen. Two $R^a$s may optionally form a 3-8 membered ring.

The term "amide" or "amido" refers to a chemical moiety with formula —C(=O)N($R^a$)$_2$ or —NR$^a$C(=O)R$^a$, wherein each of $R^a$ is independently selected from the group consisting of hydrogen, alkyl, cycloalkyl, aryl, heteroaryl (bonded through a ring carbon) and heterocycloalkyl. Two $R^a$s, together with the atoms they are attached to, optionally form a 5-10 membered ring. In some embodiments, it is a C1-C4 amido or amide radical, which includes the amide carbonyl in the total number of carbons in the radical. Unless stated otherwise specifically in the specification, an amido group is optionally substituted independently by one or more of the substituents as described herein for alkyl, cycloalkyl, aryl, heteroaryl, or heterocycloalkyl. An amino acid or a peptide molecule may be attached to a compound having an amine or a carboxylic acid moiety, thereby forming a prodrug. The procedures and specific groups to make such amides are known to those of skilled in the art and can readily be found in reference sources such as Greene and Wuts, *Protective Groups in Organic Synthesis,* 3rd Ed., John Wiley & Sons, New York, N.Y., 1999.

"Carboxaldehyde" refers to a —(C=O)H radical.

"Carboxylic acid" refers to a —(C=O)OH radical.

"Ester" refers to a chemical radical of formula —C(=O)OR, where R is selected from the group consisting of alkyl, cycloalkyl, aryl, heteroaryl (bonded through a ring carbon) and heteroalkyl (bonded through a ring carbon). A hydroxy or carboxylic acid moiety on the compounds described herein may be esterified. The procedures and specific groups to make such esters are known to those skilled in the art and can readily be found in reference sources such as Greene and Wuts, *Protective Groups in Organic Synthesis,* 3rd Ed., John Wiley & Sons, New York, N.Y., 1999. Unless stated otherwise specifically in the specification, an ester group is optionally substituted by one or more substituents which independently are: alkyl, heteroalkyl, alkenyl, alkynyl, cycloalkyl, heterocycloalkyl, aryl, heteroaryl, hydroxy, halo, cyano, nitro, oxo, thioxo, trimethylsilanyl, —OR$^a$, —SR$^a$, —OC(=O)R$^a$, —OC(=O)OR$^a$, —OC(=O)N($R^a$)$_2$, —N($R^a$)$_2$, —C(=O)R$^a$, —C(=O)OR$^a$, —C(=O)N($R^a$)$_2$, —N($R^a$)C(=O)OR$^a$, —N($R^a$)C(=O)N($R^a$)$_2$, —N($R^a$)C(=O)R$^a$, —N($R^a$)S(=O)$_t$R$^a$ (where t is 1 or 2), —N($R^a$)S(=O)$_t$N($R^a$)$_2$ (where t is 1 or 2), —S(=O)$_t$OR$^a$ (where t is 1 or 2), —S(=O)$_t$N($R^a$)$_2$ (where t is 1 or 2), —OPO$_3$WY (where W and Y are independently hydrogen, methyl, ethyl, alkyl, lithium, sodium or potassium) or —OPO$_3$Z (where Z is calcium, magnesium or iron), wherein each of $R^a$ is independently hydrogen, alkyl, heteroalkyl, cycloalkyl, heterocycloalkyl, aryl, or heteroaryl.

"Imino" refers to a =N—R$^a$ radical, wherein $R^a$ is hydrogen, alkyl, heteroalkyl, cycloalkyl, cyano, aryl, heterocycloalkyl or heteroaryl.

"Isocyanato" refers to a —NCO radical.

"Isothiocyanato" refers to a —NCS radical.

"Mercaptyl" refers to an (alkyl)S— or (H)S— radical.

"Moiety" refers to a specific segment or functional group of a molecule. Chemical moieties are often recognized chemical entities embedded in or appended to a molecule.

"Hydroxy" refers to a —OH radical.

"Oxa" refers to a —O— radical.

"Oxo" refers to a =O radical.

"Nitro" refers to a —NO$_2$ radical.

"Oxime" refers to a —C(=N—OH)—R radical, where R is hydrogen or alkyl.

"Sulfinyl" refers to a —S(=O)R radical, where R is selected from the group consisting of alkyl, cycloalkyl, aryl, heteroalkyl, heteroaryl (bonded through a ring carbon) and heterocyclyl (bonded through a ring carbon). In some embodiments, R is fluoroalkyl.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroalkyl, heteroaryl (bonded through a ring carbon) and heteroalkyl (bonded through a ring carbon). The R group is optionally substituted by one or more of the substituents described for alkyl, heteroalkyl, cycloalkyl, heterocycloalkyl, aryl, and heteroaryl respectively.

"Thiocyanato" refers to a —CNS radical.

"Thioxo" refers to a =S radical.

"Substituted" means that the referenced group may be substituted with one or more additional group(s) individually and independently selected from acyl, alkyl, heteroalkyl, cycloalkyl, heterocycloalkyl, aryl, heteroaryl, hydroxy, alkoxy, mercapto, alkylthio, arylthio, cyano, halo, carbonyl, ester, thiocarbonyl, isocyanato, thiocyanato, isothiocyanato, nitro, perhaloalkyl, perfluoroalkyl, phosphate, silyl, sulfinyl, sulfonyl, sulfonamide, sulfoximinyl, alkylamino, and amino, and the protected derivatives thereof. The substituents themselves may be substituted, for example, a cycloalkyl substituent may have a halide substituted at one or more ring carbons, and the like. The protecting groups that may form the protective derivatives of the above substituents are known to those of skill in the art and may be found in references such as Greene and Wuts cited herein.

The term "optional" or "optionally" means that the subsequently described event or circumstance may or may not occur, and includes instances where the event or circumstance occurs and instances in which it does not. For example, "alkyl optionally substituted with" encompasses both "alkyl" and "alkyl" substituted with groups as defined herein. It will be understood by those skilled in the art, with respect to any group containing one or more substituents, that such groups are not intended to introduce any substitution or substitution patterns which would be deemed unacceptable by one of ordinary skill in the art.

The methods and formulations described herein include the use of N-oxides, crystalline forms (also known as polymorphs), or pharmaceutically acceptable salts of compounds having the structure of formulae described herein, as well as active metabolites of these compounds having the same type of activity. In addition, the compounds described herein can exist in unsolvated as well as solvated forms with pharmaceutically acceptable solvents such as water, ethanol, and the like. The solvated forms of the compounds presented herein are also considered to be disclosed herein.

The compounds described herein may exhibit their natural isotopic abundance, or one or more of the atoms may be artificially enriched in a particular isotope having the same atomic number, but an atomic mass or mass number different from the atomic mass or mass number predominantly found in nature. The present invention is meant to include all suitable isotopic variations of the compounds described herein. For example, hydrogen has three naturally occurring isotopes, denoted $^1$H (protium), $^2$H (deuterium), and $^3$H (tritium). Protium is the most abundant isotope in nature. In some embodiments, hydrogen is protium ($^1$H), deuterium ($^2$H), or tritium ($^3$H). Enriching for deuterium may afford certain therapeutic advantages, such as increased in vivo half-life and/or exposure, or may provide a compound useful for investigating in vivo routes of drug elimination and metabolism. Isotopically-enriched compounds may be prepared by conventional techniques well known to those skilled in the art or by processes analogous to those described in the Schemes and Examples herein using appropriate isotopically-enriched reagents and/or intermediates. See Pleiss and Voger, *Synthesis and Applications of Isotopically Labeled Compounds, Vol.* 7, Wiley, ISBN-10: 0471495018, published on Mar. 14, 2001.

Unless otherwise specified, chemical entities described herein may include, but are not limited to, when possible, their optical isomers, such as enantiomers and diastereomers, mixtures of enantiomers, including racemates, mixtures of diastereomers, and other mixtures thereof, to the extent they can be made by one of ordinary skill in the art by routine experimentation. In those situations, the single enantiomers or diastereomers, i.e., optically active forms, can be obtained by asymmetric synthesis or by resolution of the racemates or mixtures of diastereomers. Resolution of the racemates or mixtures of diastereomers, if needed, can be accomplished, for example, by conventional methods such as crystallization in the presence of a resolving agent, or chromatography, using, for example, a chiral high-pressure liquid chromatography (HPLC) column. In addition, chemical entities having carbon-carbon double bonds or carbon-nitrogen double bonds may exist in Z- or E-form (or cis- or trans-form). Furthermore, some chemical entities may exist in various tautomeric forms. Unless otherwise specified, chemical entities described herein are intended to include all Z-, E- and tautomeric forms as well.

The term "pharmaceutically acceptable" means that a chemical entity, such as a compound, a carrier, an additive or a salt, is acceptable for being administered to a subject.

The term "pharmaceutically acceptable salts" refers to salts prepared from pharmaceutically acceptable bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts derived from pharmaceutically acceptable organic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When chemical entities disclosed herein are basic, salts may be prepared using at least one pharmaceutically acceptable acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, trifluoroacetic acid, and p-toluenesulfonic acids. In some embodiments, such acid may be selected, for example, from citric, hydrobromic, hydrochloric, maleic, phosphoric, sulfuric, fumaric, and tartaric acids.

The term "pharmaceutically acceptable carrier" as used herein means a diluent, excipient, encapsulating material or formulation auxiliary, which may be non-toxic, and inert, which may not have undesirable effect on a subject, preferably a mammal, more preferably a human, or which may be suitable for delivering an active agent to the target site without affecting the activity of the agent.

The term "effective amount" or "therapeutically effective amount" refers to an amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compounds chosen, the dosing regimen to be followed, whether it is administered in combination with other agents, timing of administration, the tissue to which it is administered, and the physical delivery system in which it is carried.

Pharmaceutical Compositions and Dosage Forms

A compound or a pharmaceutically acceptable salt thereof may be formulated as a pharmaceutical composition prior to being administered to a subject. The pharmaceutical composition may comprise additional additives such as pharmaceutically acceptable excipients, carriers, and vehicles. Suitable pharmaceutically acceptable excipients, carriers, and vehicles include but are not limited to processing agents and drug delivery modifiers, for example, ethylene glycol, calcium phosphate, magnesium stearate, talc, monosaccharides, disaccharides, starch, gelatin, cellulose, methyl cellulose, hydroxypropyl cellulose, sodium carboxymethyl cellulose, dextrose, hydroxypropyl-β-cyclodextrin, polyvinylpyrrolidine, low melting waxes, ion exchange resins, and the like, as well as combinations of any two or more thereof.

A pharmaceutical composition comprising a compound or a pharmaceutically acceptable salt thereof may be administered enterally, orally, parenterally, sublingually, rectally, or topically in a unit dosage containing pharmaceutically acceptable excipients, carriers, or vehicles. Generally, the unit dosage is a dose sufficient for the compound or its pharmaceutically acceptable salt to achieve desired therapeutic effect. Suitable modes of administration include oral, subcutaneous, intra-arterial, intramuscular, intraperitoneal, intranasal, intraocular, subdural, vaginal, gastrointestinal, and the like. The compound or its salt can also be administered as prodrugs, wherein the prodrugs undergo transformation in the body of the treated subject to form a therapeutically active ingredient.

A pharmaceutical composition comprising a compound or a pharmaceutically acceptable salt described herein may be in any form suitable for the intended purpose of administration, including, for example, a solid or a liquid dosage form. The liquid dosage form may include solution, suspension, softgel, syrup, elixir, or emulsion. Liquid carriers are typically used in preparing solutions, suspensions, and emulsions. Liquid carriers contemplated for use in the practice of the present invention include, for example, water, saline, ethylene glycol, propylene glycol, pharmaceutically acceptable organic solvents, pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, sunflower oil, and the like. For parenteral administration, the carrier can also be an oily ester such as isopropyl myristate, and the like. Compositions of the present invention may also be in the form of nanoparticles, microparticles, microcapsules, liposomal encapsulates, and the like, as well as combinations of any two or more thereof. Solid dosage forms for oral administration may include capsule, tablet, pill, powder, and granule. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

In cases of a solid dosage form, examples of daily dosages of the compounds described herein which can be used are an effective amount within the dosage range of about 0.001 mg to about 2 mg per kilogram of body weight, about 0.001 mg to about 5 mg per kilogram of body weight, about 0.001 mg to about 10 mg per kilogram of body weight, about 0.001 mg to about 20 mg per kilogram of body weight, about 0.001 mg to about 50 mg per kilogram of body weight, about 0.001 mg to about 100 mg per kilogram of body weight, about 0.001 mg to about 200 mg per kilogram of body weight, or about 0.001 mg to about 300 mg per kilogram of body weight. When administered orally or by inhalation, examples of daily dosages are an effective amount within the dosage range of about 0.1 mg to about 10 mg, or about 0.1 mg to about 20 mg, or about 0.1 mg to about 30 mg, or about 0.1 mg to about 40 mg, or about 0.1 mg to about 50 mg, or about 0.1 mg to about 60 mg, or about 0.1 mg to about 70 mg, or about 0.1 mg to about 80 mg, or about 0.1 mg to about 90 mg, or about 0.1 mg to about 100 mg, or about 0.1 mg to about 200 mg, or about 0.1 mg to about 300 mg, or about 0.1 mg to about 400 mg, or about 0.1 mg to about 500 mg, or about 0.1 mg to about 600 mg, or about 0.1 mg to about 700 mg, or about 0.1 mg to about 800 mg, or about 0.1 mg to about 900 mg, or about 0.1 mg to about 1 g, or about 20 mg to 300 mg, or about 20 mg to 500 mg, or about 20 mg to 700 mg, or about 20 mg to 1000 mg, or about 50 mg to 1500 mg, or about 50 mg to 2000 mg. Preferred fixed daily doses include about 1 mg, about 2 mg, about 3 mg, about 4 mg, about 5 mg, about 6 mg, about 7 mg, about 8 mg, about 9 mg, about 10 mg, about 12 mg, about 15 mg, about 18 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, about 1200 mg, about 1500 mg, or about 2000 mg, independently of body weight. However, it is understood that pediatric patients may require smaller dosages, and depending on the severity of the disease and condition of the patient, dosages may vary. The compound will preferably be administered once daily, but may be administered two, three or four times daily, or every other day, or once or twice per week.

When formulated as a liquid, the concentration of the compounds described herein may be about 0.01 mg/ml to about 0.1 mg/ml or about 0.1 mg/ml to about 1 mg/ml, but can also be about 1 mg/ml to about 10 mg/ml or about 10 mg/ml to about 100 mg/ml. The liquid formulation could be a solution or a suspension. When formulated as a solid, for example as a tablet or as a powder for inhalation, the concentration, expressed as the weight of a compound divided by total weight, will typically be about 0.01% to about 0.1%, about 0.1% to about 1%, about 1% to about 10%, about 10% to about 20%, about 20% to about 40%, about 40% to about 60%, about 60% to about 80%, or about 80% to about 100%.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., "Methods in Cell Biology", Volume XIV, ISBN: 978-0-12-564114-2, Academic Press, New York, N.W., p. 33 (1976) and Medina, Zhu, and Kairemo, "Targeted liposomal drug delivery in cancer", *Current Pharm. Des.* 10: 2981-2989, 2004. For additional information regarding drug formulation and administration, see "Remington: The Science and Practice of Pharmacy," Lippincott Williams & Wilkins, Philadelphia, ISBN-10: 0781746736, 21$^{st}$ Edition (2005).

Method of Making

Compounds disclosed herein may be prepared by routes described below. Materials used herein are either commercially available or prepared by synthetic methods generally known in the art. These schemes are not limited to the compounds listed or by any particular substituents, which are employed for illustrative purposes. Although various steps are described and depicted in Schemes 1-17, the steps in some cases may be performed in a different order than the order shown. Various modifications to these synthetic reaction schemes may be made and will be suggested to one skilled in the art having referred to the disclosure contained in this Application. Numberings or R groups in each scheme do not necessarily correspond to that of claims or other schemes or tables.

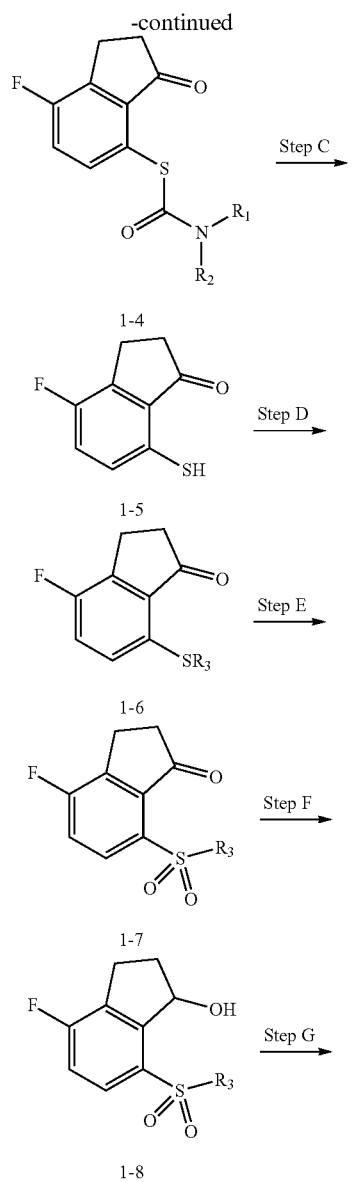

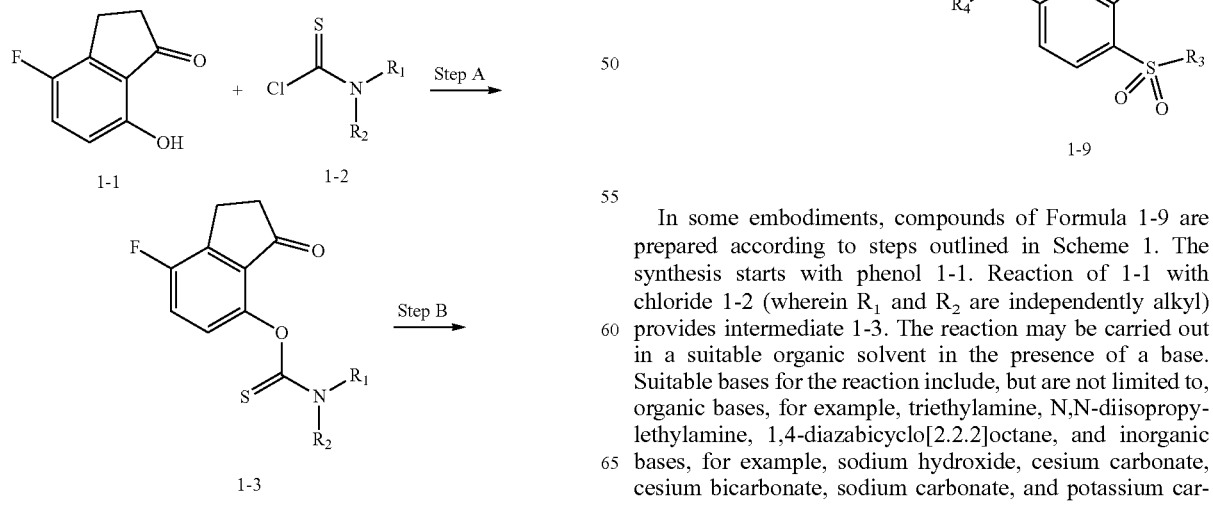

In some embodiments, compounds of Formula 1-9 are prepared according to steps outlined in Scheme 1. The synthesis starts with phenol 1-1. Reaction of 1-1 with chloride 1-2 (wherein $R_1$ and $R_2$ are independently alkyl) provides intermediate 1-3. The reaction may be carried out in a suitable organic solvent in the presence of a base. Suitable bases for the reaction include, but are not limited to, organic bases, for example, triethylamine, N,N-diisopropylethylamine, 1,4-diazabicyclo[2.2.2]octane, and inorganic bases, for example, sodium hydroxide, cesium carbonate, cesium bicarbonate, sodium carbonate, and potassium carbonate. Compound 1-3 is then subjected to a rearrangement reaction to give compound 1-4. Elevated temperature may be needed for the rearrangement to occur. The temperature may be in a range of 100° C. to 300° C. In some embodiments, the temperature is in a range of 180° C. to 240° C. Hydrolysis of compound 1-4 provides thiophenol 1-5, which is alkylated to provide compound 1-6. A variety of alkyl group may be introduced. In some embodiments, $R_3$ is a C1-C4 alkyl. In a further embodiment, $R_3$ is a C1-C4 fluoroalkyl. Oxidation of compound 1-6 may be accomplished by a variety of methods known in the art, including but are not limited to, $RuCl_3$ catalyzed oxidation in the presence of $NaIO_4$, oxidation with m-chloroperbenzoic acid (mCPBA) and oxidation with Oxone®. The ketone in 1-7 is then reduced to give alcohol 1-8, which then undergoes a nucleophilic aromatic substitution (SNAr) reaction with a suitable substrate $R_4OH$ (wherein $R_4$ is aryl or heteroaryl) to give compounds of Formula 1-9. Temperature for carrying out the SNAr reaction may depend on the reactivity of both $R_4OH$ and/or compound 1-8. The reaction may be carried out in a temperature range from room temperature to 200° C. In some embodiments, the temperature range is from room temperature to 60° C. In some other embodiments, the temperature range is from 60° C. to 100° C. In some other embodiments, the temperature range is from 100° C. to 200° C.

metric transfer hydrogenation is catalyzed by ruthenium. For examples of methods and catalysts for ruthenium catalyzed transfer hydrogenation, see U.S. Pat. Nos. 6,184,381 and 6,887,820. Exemplary catalysts for asymmetric transfer hydrogenation include, but are not limited to, the following (shown as the R, R configuration):

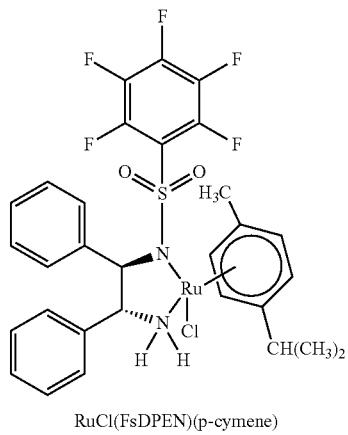

RuCl(FsDPEN)(p-cymene)

Scheme 2

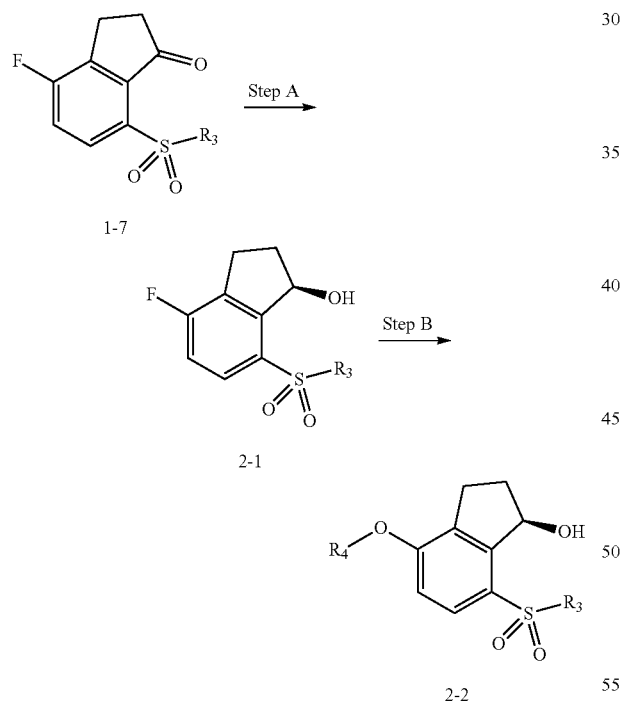

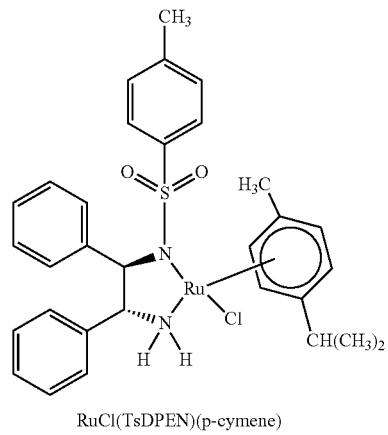

RuCl(TsDPEN)(p-cymene)

In some other embodiments, compounds of Formula 1-9 are prepared asymmetrically to give compounds of Formula 2-2 (Scheme 2). For example, direct asymmetric reduction of ketone 1-7 (Step A) may be accomplished chemically or enzymatically. For a recent review on enzymatic reduction of ketones, see Moore, et al. *Acc. Chem. Res.* 40: 1412-1419, 2007. Examples of chemical asymmetric reduction of ketone include, but are not limited to, Corey-Bakshi-Shibata (CBS) reduction, asymmetric hydrogenation, and asymmetric transfer hydrogenation. In some embodiments, the asym-

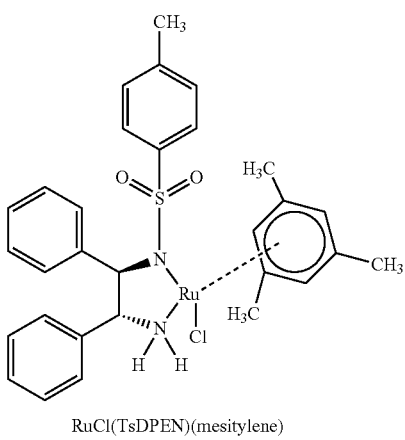

RuCl(TsDPEN)(mesitylene)

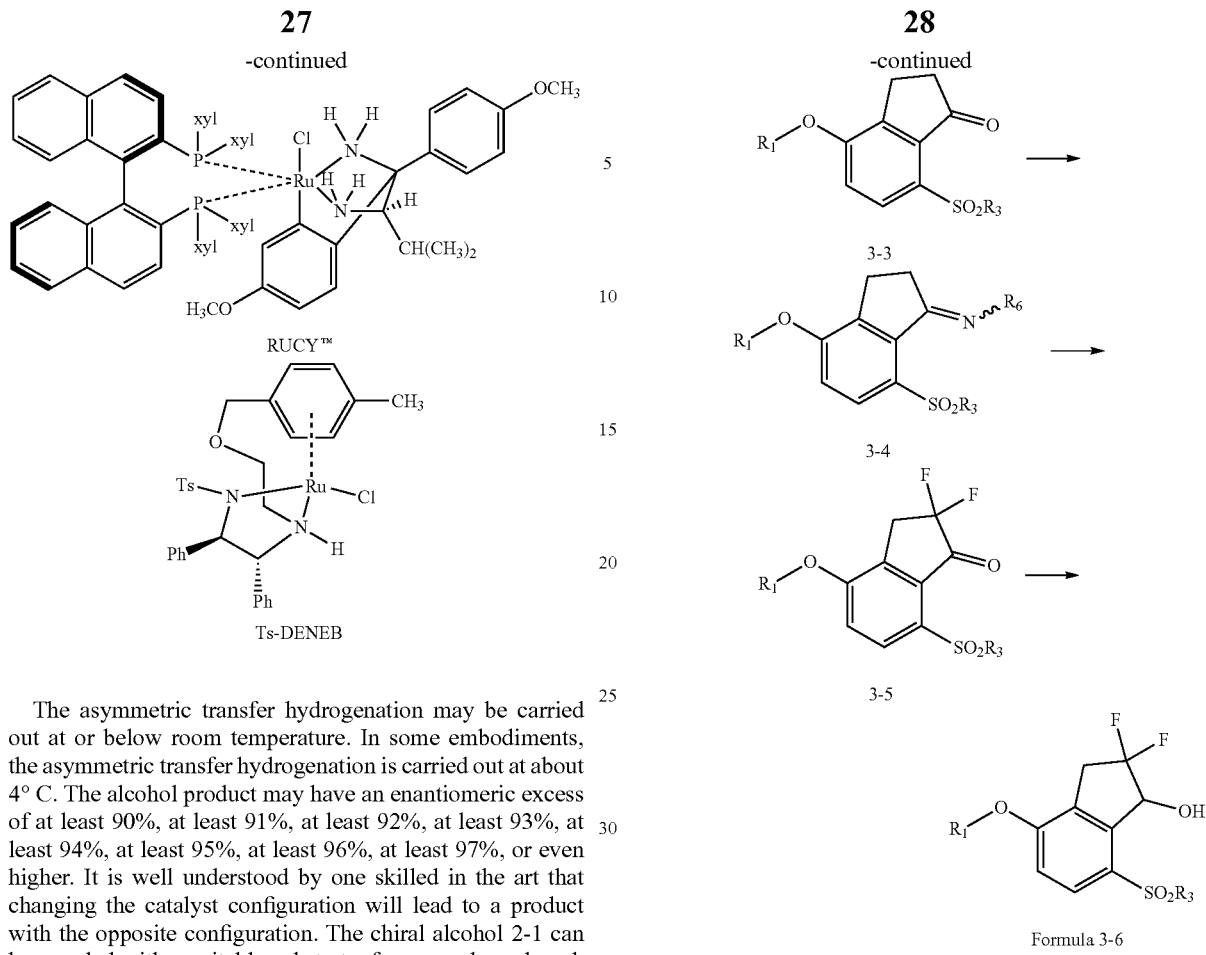

The asymmetric transfer hydrogenation may be carried out at or below room temperature. In some embodiments, the asymmetric transfer hydrogenation is carried out at about 4° C. The alcohol product may have an enantiomeric excess of at least 90%, at least 91%, at least 92%, at least 93%, at least 94%, at least 95%, at least 96%, at least 97%, or even higher. It is well understood by one skilled in the art that changing the catalyst configuration will lead to a product with the opposite configuration. The chiral alcohol 2-1 can be coupled with a suitable substrate, for example a phenol, to give compounds of Formula 2-2 without significant loss of enantiomeric excess. The loss of enantiomeric excess (ee) in the coupling step for 2-2 may be less than about 1%, less than about 2%, less than about 3%, less than about 4%, less than about 5%, less than about 6%, or less than about 8%.

In some embodiments, compounds of Formula 3-6 are prepared according to Scheme 3. The ketone in 1-7 is protected as a ketal to give compound 3-1, wherein each of $R_4$ and $R_5$ is independently an alkyl group. In addition, $R_4$ and $R_5$ may optionally be connected to form a cyclic ketal. Exemplary structures of ketal 3-1 include, but are not limited to, the following:

Ketal 3-1 and a suitable a suitable substrate $R_1OH$ (wherein $R_1$ is aryl or heteroaryl) may undergo a nucleophilic aromatic substitution reaction (SNAr) to give biaryl ether 3-2. Similarly to the SNAr reaction described in Step G of Scheme 1, the reaction temperature may depend on the reactivity of ketal 3-1 and/or $R_1OH$. Following deprotection of the ketal in 3-2, the resulting ketone 3-3 is condensed with an amine to form imine 3-4, wherein $R_6$ is alkyl. The imine functional group in 3-4 may exist as a mixture of E, Z isomers. Fluorination of 3-4 can be accomplished with a fluorinating reagent, for example, 1-(chloromethyl)-4-fluoro-1,4-diazoniabicyclo[2.2.2]octane ditetrafluoroborate, to give difluoroketone 3-5 after acid hydrolysis. Finally, reduction of the ketone in 3-5 with a hydride donor gives compounds of Formula 3-6.

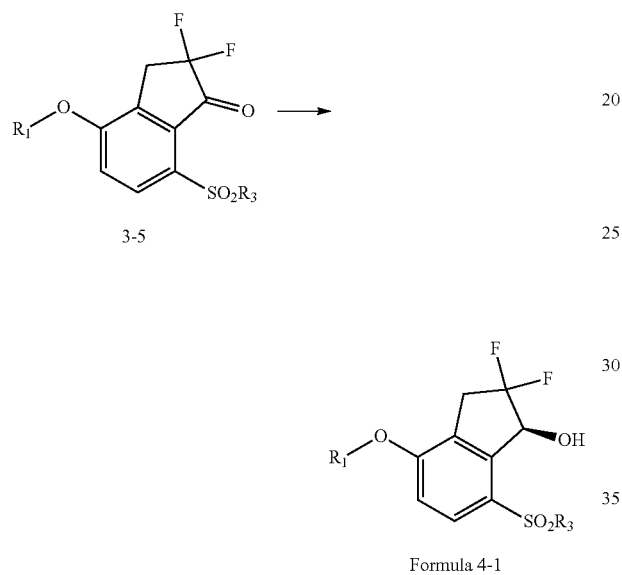

Similarly, compounds of Formula 4-1 can be prepared in asymmetric fashion by asymmetric reduction as outlined in Scheme 2. In some embodiments, the asymmetric reduction gives compounds of Formula 4-1 with an enantiomeric excess of at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or even higher. The enantiomeric excess of compounds of Formulae 2-2 and 4-1 may be determined by chiral HPLC or Mosher ester analysis. For determination of ee with Mosher ester, see Hoye, et al. *Natural Protocol*, 2: 2451, 2007.

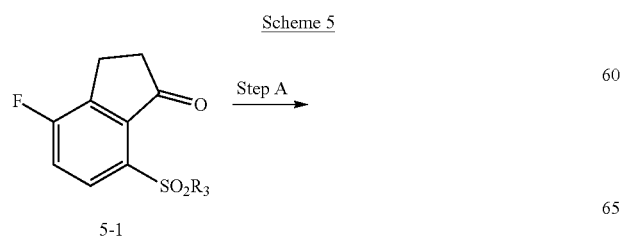

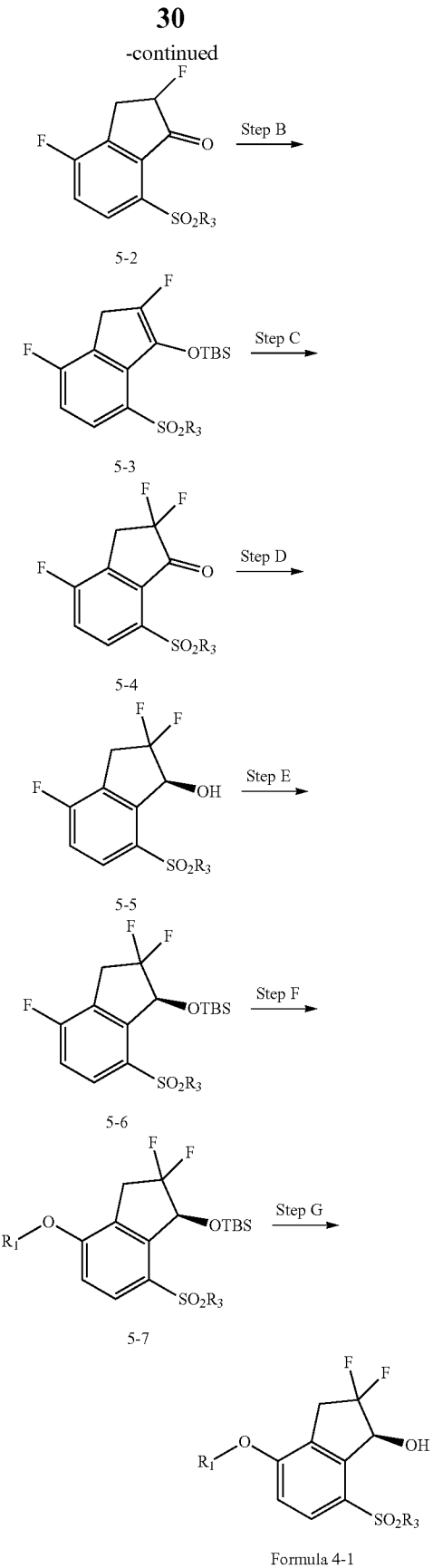

Alternatively, compounds of Formula 4-1 are prepared according to Scheme 5. The ketone in 5-1 is fluorinated to give monofluoroketone 5-2, which is then converted to a silylenol ether, e.g., TBS enol ether 5-3. Other silyl protecting groups, for example, triisopropylsilyl or diphenyl-t-butylsilyl, may also be used. The resulting enol ether is further fluorinated to give difluoroketone 5-4, which undergoes an asymmetric reduction, such as asymmetric transfer hydrogenation as described herein, to give chiral alcohol 5-5. Protection of the hydroxy moiety, followed by SNAr reaction and then deprotection provides compounds of Formula 4-1.

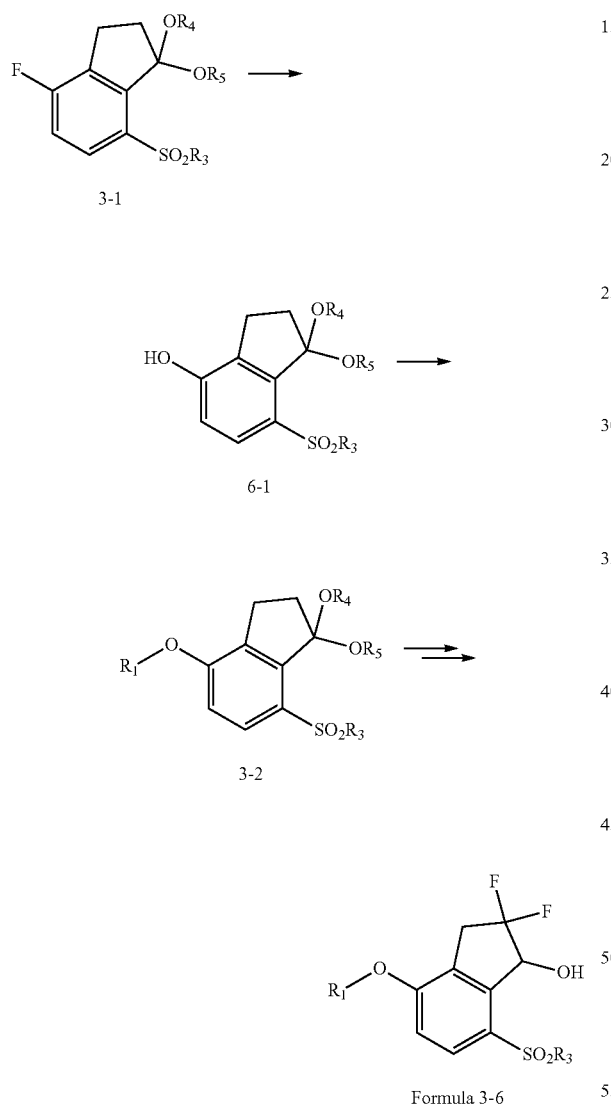

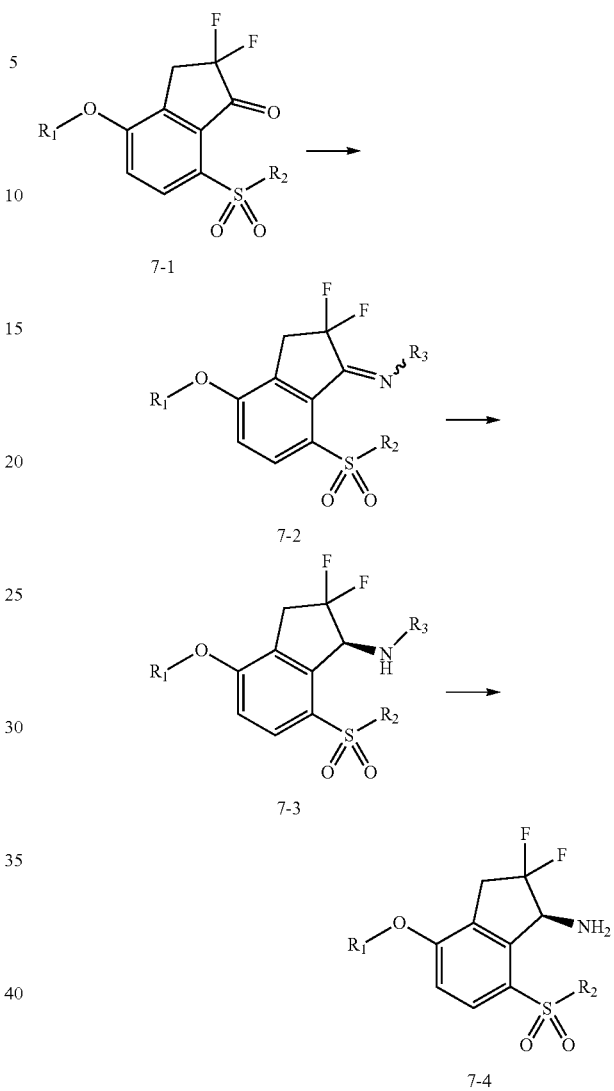

Alternatively, compounds of Formula 3-6 are prepared according to Scheme 6. Treatment of aryl fluoride 3-1 with a hydroxide source gives phenol 6-1. Suitable hydroxide sources include, but are not limited to, sodium hydroxide and potassium hydroxide. Suitable solvents for the reaction include, but are not limited to, DMSO, DMA, DMF or EtOH. The phenol 6-1 can react with an aryl or heteroaryl halide via a SNAr reaction to give biaryl ether 3-2, which can be converted to compounds of Formula 3-6 as described in Scheme 3.

Compounds of Formula 7-3 and 7-4 may be prepared according to Scheme 7. For example, condensation of $NH_2R_3$ with difluoroketone 7-1, wherein $R_1$ is aryl or heteroaryl and $R_2$ is aryl, heteroaryl, alkyl, heteroalkyl, heterocycle, or cycloalkyl, gives intermediate 7-2. In some embodiments, $R_3$ is a chiral auxiliary. Exemplary chiral auxiliaries include but are not limited to the following:

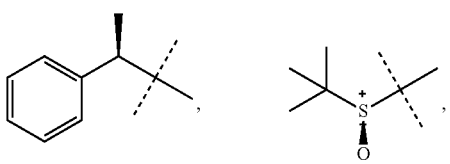

and their enantiomers thereof. Hydride reduction of intermediate 7-2 yields 7-3. At this stage, the chiral auxiliary may be cleaved under appropriate conditions, e.g., hydrogenation or acid treatment, to give chiral secondary amine 7-4. In some other embodiments, when compounds of Formula 7-3 are desirable, wherein $R_3$ is not hydrogen, asymmetric hydrogenation or asymmetric transfer hydrogenation is applied on intermediate 7-2 to give compounds of Formula 7-3. For a review on asymmetric hydrogenation and asymmetric transfer hydrogenation, see Iwao Ojima ed. *Catalytic Asymmetric Synthesis*, Wiley-VCH, Inc., 2000, ISBN 0-471-29805-0.

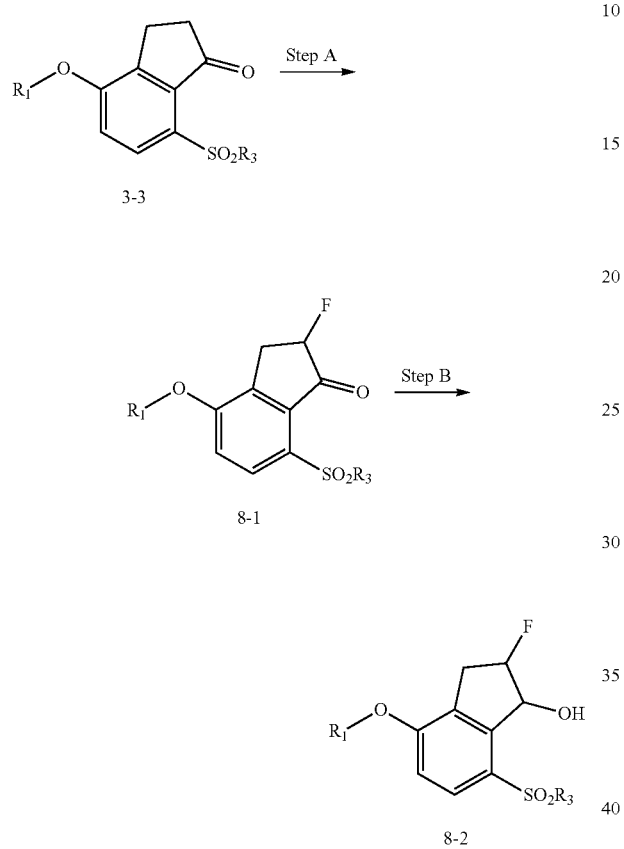

Scheme 8

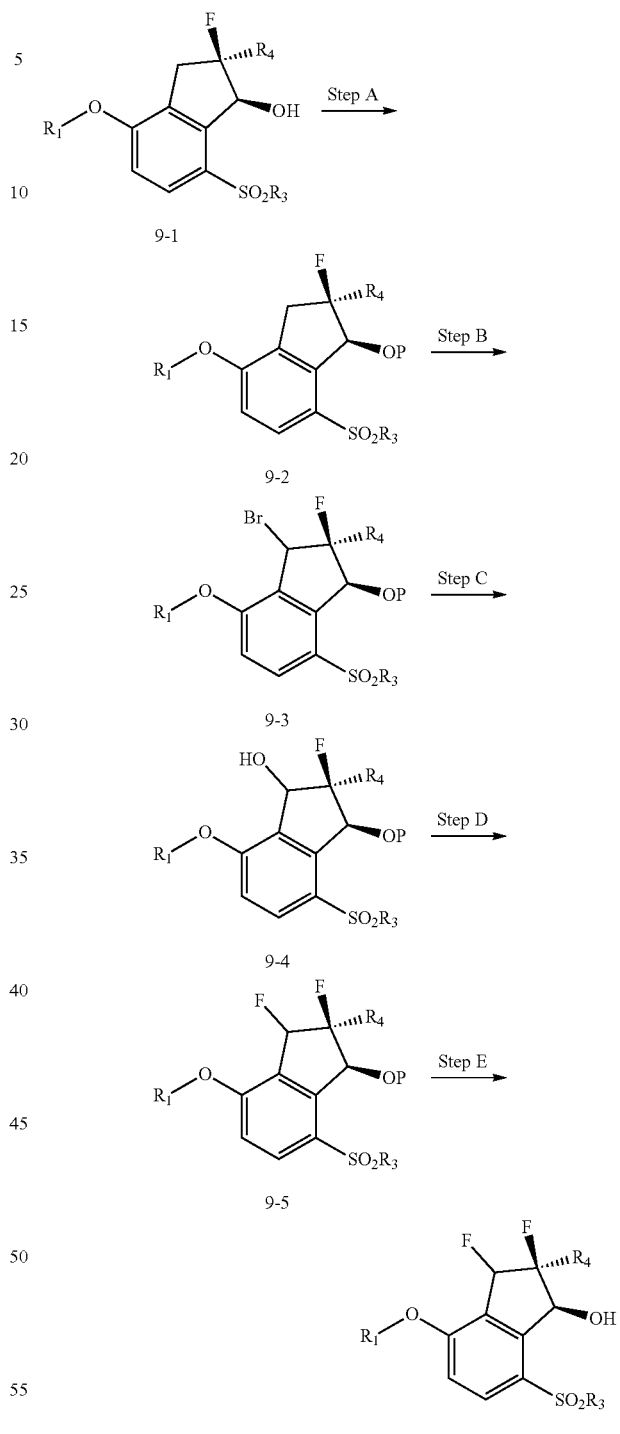

Scheme 9

In some embodiments, compounds of Formula 8-2 are prepared according to Scheme 8. For example, ketones of Formula 3-3 is monofluorinated to give monofluoroketones of Formula 8-1. The monofluorination can be acheived with a variety of fluorinating reagents, e.g., N-Fluoro-o-benzene-disulfonimide, acetyl hypofluorite, Accufluor®, Selectfluor®, Selectfluor® II, or N-Fluorobenzenesulfonimide, in the presence or absence of a base. The compounds of Formula 8-1 are reduced to give compounds of Formula 8-2. In some cases, the reduction is highly diasteroselective to give compounds of Formula 8-2 with greater than 80%, greater than 82%, greater than 84%, greater than 86%, greater than 88%, greater than 90%, greater than 92%, greater than 94%, greater than 96%, or even greater than 96% diasteroselectivity. In some cases, the reduction is highly enantioselective to give compounds of Formula 8-2 with greater than 80%, greater than 82%, greater than 84%, greater than 86%, greater than 88%, greater than 90%, greater than 92%, greater than 94%, greater than 96%, or even greater than 96% enantioselectivity. Reduction conditions to achieve high enantioselectivity include, but are not limited to, asymmetric transfer hydrogenation and enzymatic reduction as described herein.

In some embodiments, compounds of Formula 9-6 are prepared according to Scheme 9, wherein $R_4$ is hydrogen, alkyl or fluoro. The hydroxy group in compounds of Formula 9-1 may be protected with, e.g., acyl or methoxymethyl ether (MOM), to give compounds of Formula 9-2. Benzylic bromination in Step B may be carried out with a bromide source, e.g., N-bromosuccinimide, in the presence of a radical initiator, e.g., 2,2'-azobis(2-methylpropionitrile)

(AIBN) or benzyol peroxide. The bromide in compounds of Formula 9-3 can be replaced with a hydroxy group in a solvent comprising water in the presence of a silver salt, e.g., Ag$_2$CO$_3$ or AgClO$_4$ or AgBF$_4$. Finally, fluorination of the hydroxy group in Formula 9-4 followed by deprotection gives compounds of Formula 9-6. In some cases, direct benzylic oxidation may be used for converting compounds of Formula 9-2 to compounds of Formula 9-4, thus bypassing an intermediate bromination step.

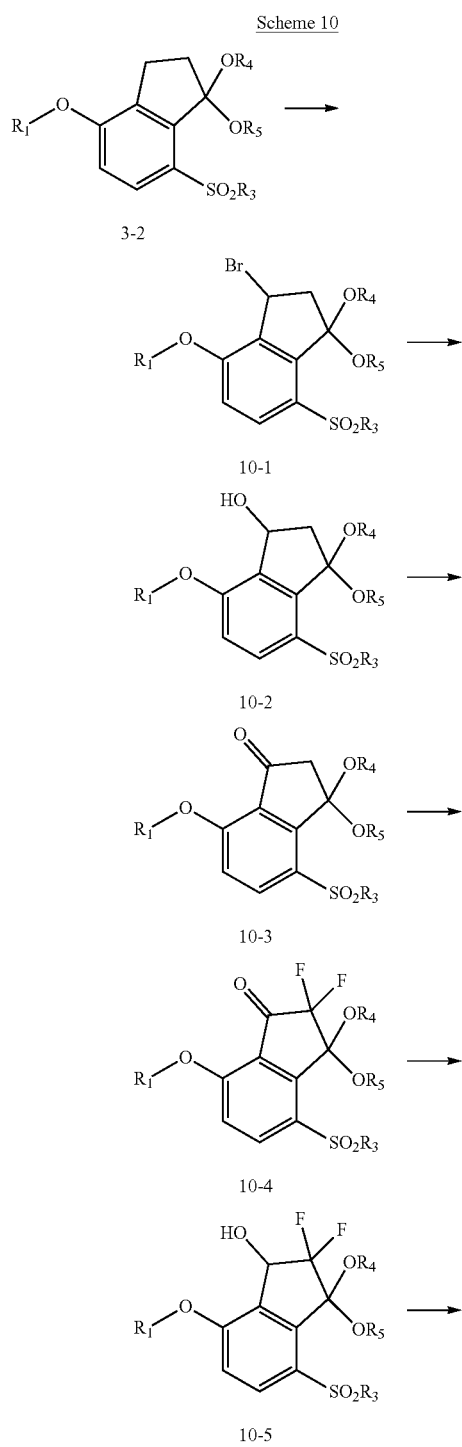

Scheme 10

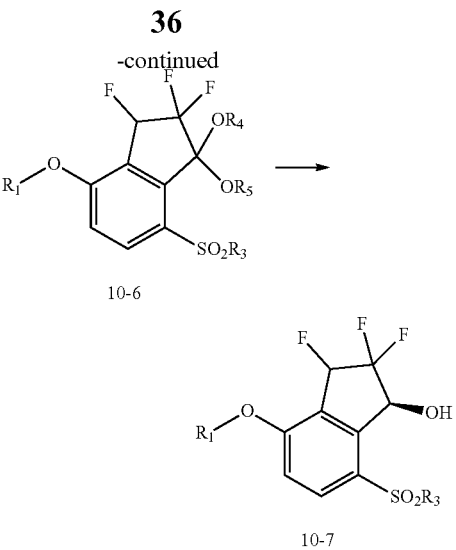

In some embodiments, compounds of Formula 10-7 are prepared according to Scheme 10. For example, compounds of Formula 10-3 may be prepared from compounds of Formula 3-2 by following a similar sequence as outlined in Scheme 9. Further functional group manupilations lead to compounds of Formula 10-7.

Scheme 11

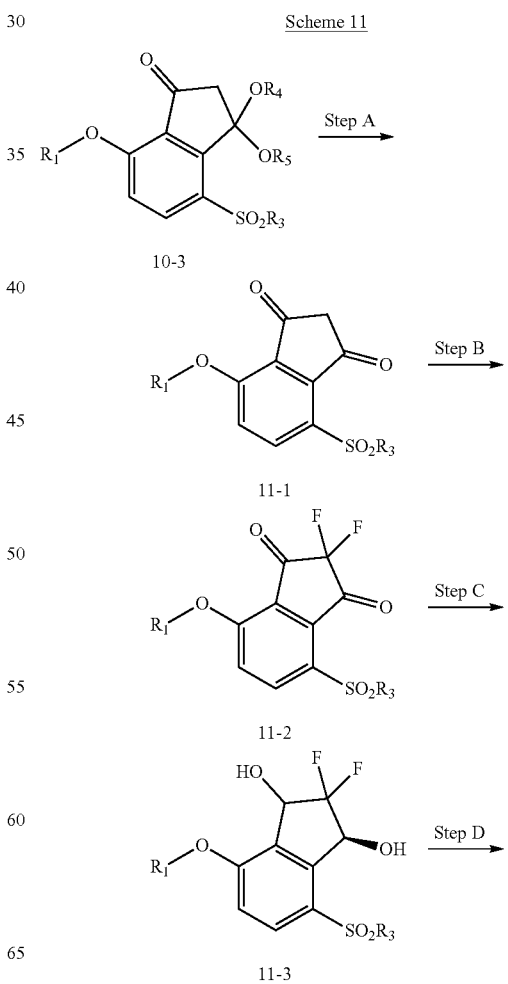

37

-continued

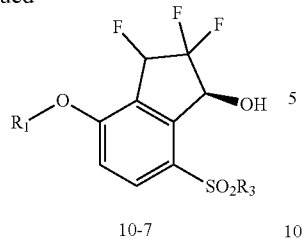

10-7

Alternatively, compounds of Formula 10-3 are deprotected to give diketone 11-1, which is fluorinated to give difluoro diketone 11-2. Asymmetric reduction of 11-2 provides diol 11-2. In some embodiments, one of the hydroxy groups is selectively fluorinated to give compounds of Formula 10-7.

Scheme 12

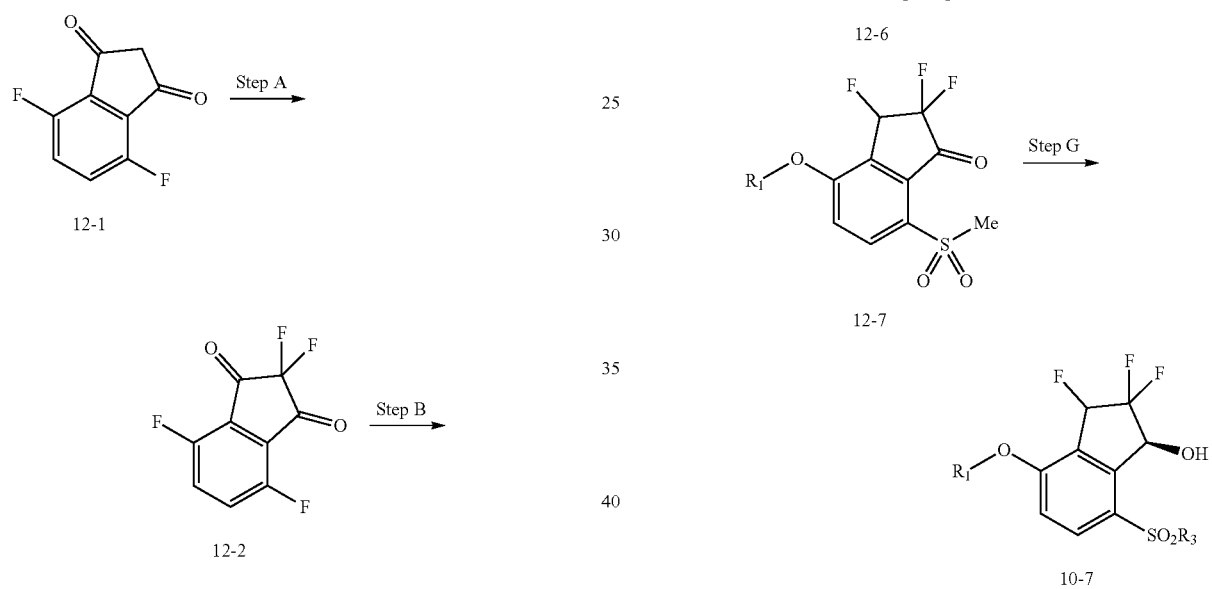

12-1

12-2

12-3

12-4

38

-continued

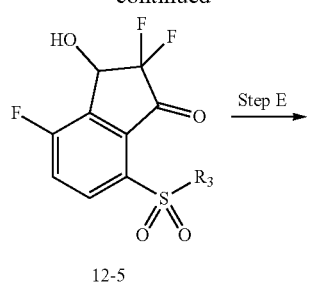

12-5

12-6

12-7

10-7

Alternatively, compounds of Formula 10-7 are prepared according to Scheme 12. For example, difluoroketone 12-2 is reduced to give hydroxyketone 12-3. The reduction may be enantioselective under transfer hydrogenation conditions with a Ru-catalysis as described herein. One of the aryl fluorine may be selective displaced with an alkyl thoil to give compounds of Formula 12-4. Oxidation, fluorination, followed by nucleophilic aromatic substitution give compounds of Formula 10-7.

Scheme 13

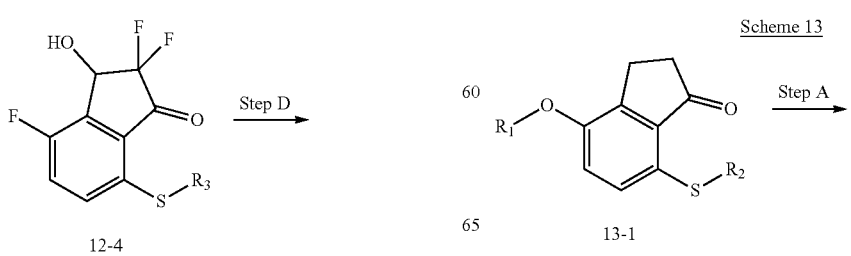

13-1

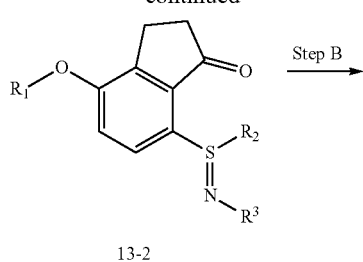

13-2

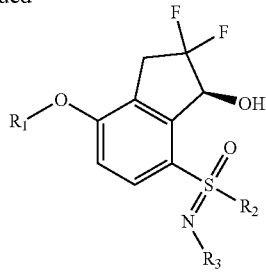

13-4

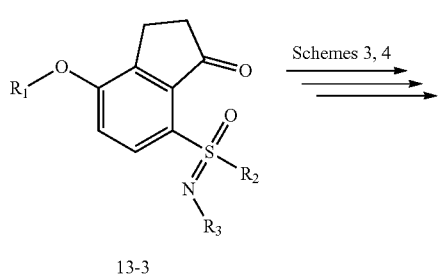

13-3

In some embodiments, compounds of Formula 13-4 are prepared according to Scheme 13. Aryl sulfides 13-1 are treated with $H_2N-R_3$ and an oxidant, e.g., diacetoxyiodobenzene or dipivaloyloxyiodobenzene, in a suitable solvent, such as acetoniltrile, to obtain aryl sulfinimides 13-2. In some embodiments, for compounds of Formula 13-1 with fluoroalkyl $R_2$ substituents, the presence of rhodium(II) acetate or $Rh_2(esp)_2$ catalyst, along with magnesium oxide, is helpful. Oxidation of the aryl sulfinimides 13-2 to substituted sulfoximines 13-3 may be accomplished with catalytic ruthenium(III) chloride and sodium periodate in a suitable solvent, such as a mixture of water, acetonitrile, and carbon tetrachloride. Substituted sulfoximines 13-3 are then manipulated similarly as described in Schemes 3 and 4 to afford sulfoximines of Formula 13-4 as a diastereomeric mixture. The diastereomers may be separated by column chromatography.

Scheme 14

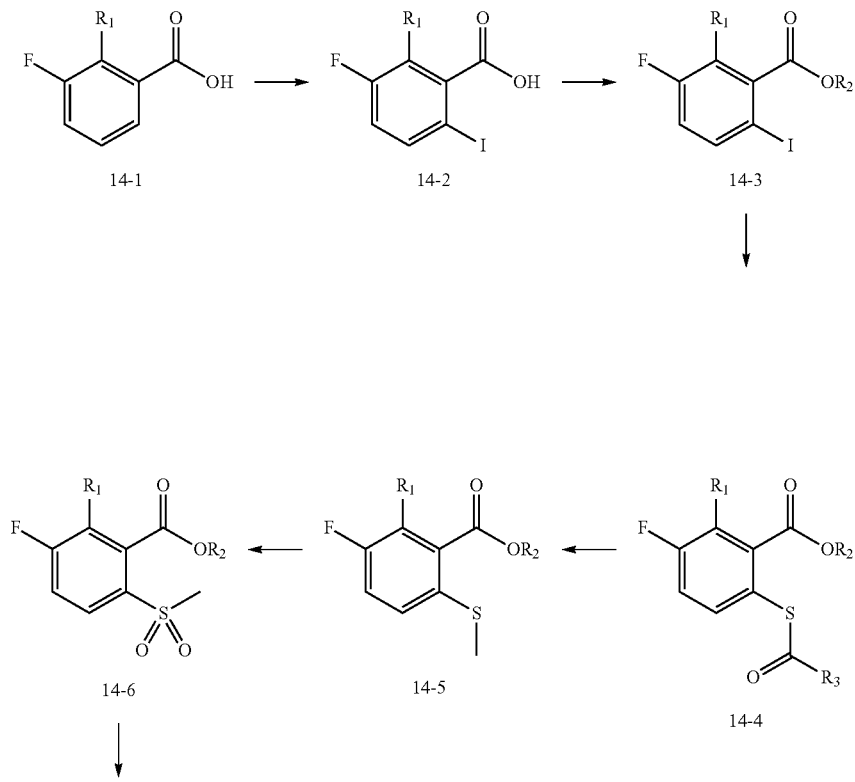

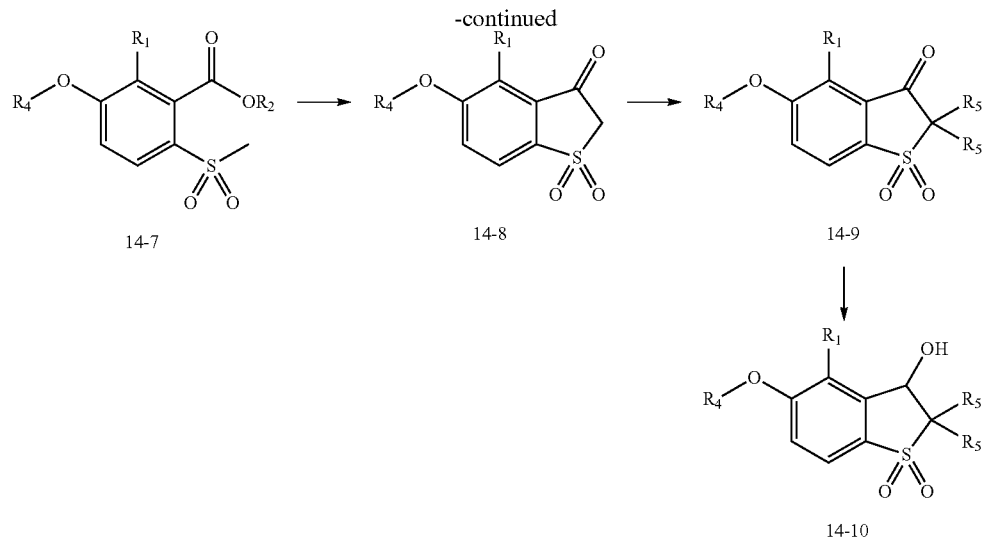

In some embodiments, compounds of Formula 14-10 are prepared according to steps outlined in Scheme 14, wherein $R_1$ is halo, cyano, alkyl, alkenyl or alkynyl, $R_4$ is alkyl, cycloalkyl, heterocycloalkyl, aryl, or heteroaryl, and $R_5$ is fluoro or alkyl, or two R5s and the carbon they are attached to form C3-C8 cycloalkyl or C5-C8 heterocycloalkyl. The synthesis starts with compounds of Formula 14-1. Orthoiodination of 14-1 provides compounds of Formula 14-2. The reaction may be carried out in a suitable organic solvent in the presence of iodine and a palladium catalyst at an elevated temperature if needed. After esterification of 14-2, the resulting ester 14-3 may undergo a transition-metal catalyzed coupling reaction with a thioate, e.g., potassium ethanethioate or sodium ethanethioate, to give compounds of Formula 14-4. Suitable transition-metal catalysts include but are not limited to $Pd(PPh_3)_4$, $Pd_2(dba)_3$ chloroform complex or $Pd(OAc)_2$ in the presence or absence of a suitable ligand. Hydrolysis of compounds of Formula 14-4 followed by alkylation of the resulting thiophenol intermediate with an alkyl halide, e.g., methyl iodide, gives compounds of Formula 14-5. The hydrolysis and alkylation may be carried out in a one-pot procedure without purification. In some embodiments, this is carried out by treating compounds of Formula 14-4 with a carbonate base in a suitable solvent at or near room temperature for a period ranging from 0.1 to 24 hours followed by addition of an alkyl halide. Carbonate bases include but are not limited to sodium carbonate, potassium carbonate, cesium carbonate, potassium bicarbonate and cesium bicarbonate. Oxidation of compounds of Formula 14-5 to give compounds of Formula 14-6 may be accomplished by a variety of methods known in the art, including but are not limited to, $RuCl_3$ catalyzed oxidation in the presence of $NaIO_4$, oxidation with m-chloroperbenzoic acid (mCPBA) and oxidation with Oxone®. Compounds of Formula 14-6 are then subjected to Nucleophilic Aromatic substitution (SNAr) reaction with $R_4OH$ (wherein $R_4$ is alkyl, aryl or heteroaryl) to give compounds of Formula 14-7. Temperature for carrying out the SNAr reaction may depend on the reactivity of both $R_4OH$ and/or compounds of Formula 14-6. The reaction may be carried out in a temperature ranging from −10° C. to 200° C. In some embodiments, the temperature range is from 30° C. to 120° C. In some other embodiments, the temperature range is from 0° C. to room temperature. Cyclization of compounds of Formula 14-7 may be effected with a base, e.g., sodium hydride, in a suitable solvent to yield compounds of Formula 14-8. After the cyclization, a variety of $R_5$ groups may be introduced. In some embodiments, compounds of Formula 14-8 are difluorinated to give compounds of Formula 14-9 by treating with a fluorinating agent, e.g., 1-(chloromethyl)-4-fluoro-1,4-diazo niabicyclo[2.2.2]octane ditetrafluoroborate (Selectfluor®), in the presence of suitable base, e.g., sodium carbonate. Reduction of compounds of Formula 14-9 yields compounds of Formula 14-10.

Scheme 15

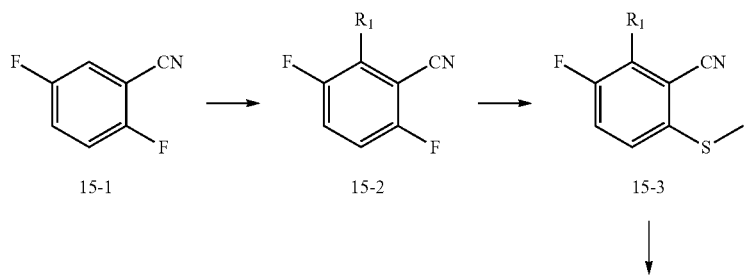

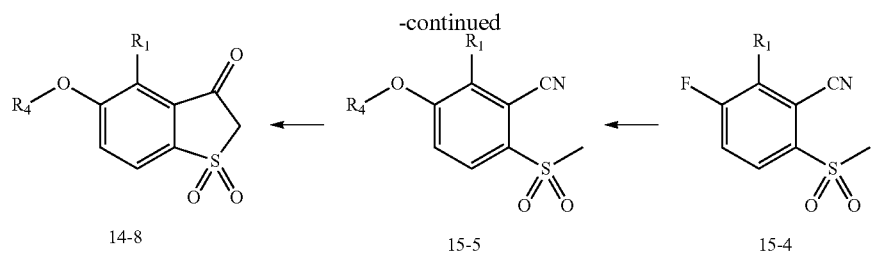

Alternatively, compounds of Formula 14-8 are prepared according to Scheme 15. For example, lithiation of compound 15-1 followed by trapping the resulting lithio intermediate with a suitable electrophile gives compounds of Formula 15-2. In some embodiments, the electrophile is N,N-dimethylformamide and the $R_1$ is —CHO. In a further embodiment, —CHO is converted to —CHF$_2$ by treating with a fluorinating reagent, e.g., diethylaminosulfur trifluoride. One of the fluorines in compounds of Formula 15-2 may be selected displaced with a thiomethoxide, e.g., sodium thiomethoxide, to give compounds of Formula 15-3. The reaction temperature may be in a range of −50 to 40° C. In some embodiments, the temperature is at or about 0° C. Oxidation of compounds of Formula 15-3, followed by SNAr reaction with $R_4OH$ and base-mediated cyclization, provides compounds of Formula 14-8.

The amount of oxidant used for the oxidation may be about 1.5 equivalent, about 1.4 equivalent, about 1.3 equivalent, about 1.2 equivalent, about 1.1 equivalent or about 1.0 equivalent. SNAr reaction of compounds of Formula 16-1 with $R_4OH$ (wherein $R_4$ is alkyl, cycloalkyl, heterocycloalkyl, aryl or heteroaryl) in the presence of a base gives compounds of Formula 16-2. At this stage, sulfoximine moiety may be introduced to give compounds of Formula 16-3 through transition-metal catalyzed insertion reaction of a suitable nitrogen donor. Suitable transition-metal catalysts include but are not limited to copper and rhodium catalysts, e.g., bis(rhodium(α,α,α',α'-tetramethyl-1,3-benezenedipropionic acid)) and dirhodium tetraacetate. Suitable nitrogen donors include but are not limited to PhI=NNs, cyanamide, and fluoroalkylamides, e.g., trifluoromethyl acetamide. Cyclization of compounds of Formula 16-3 to give com-

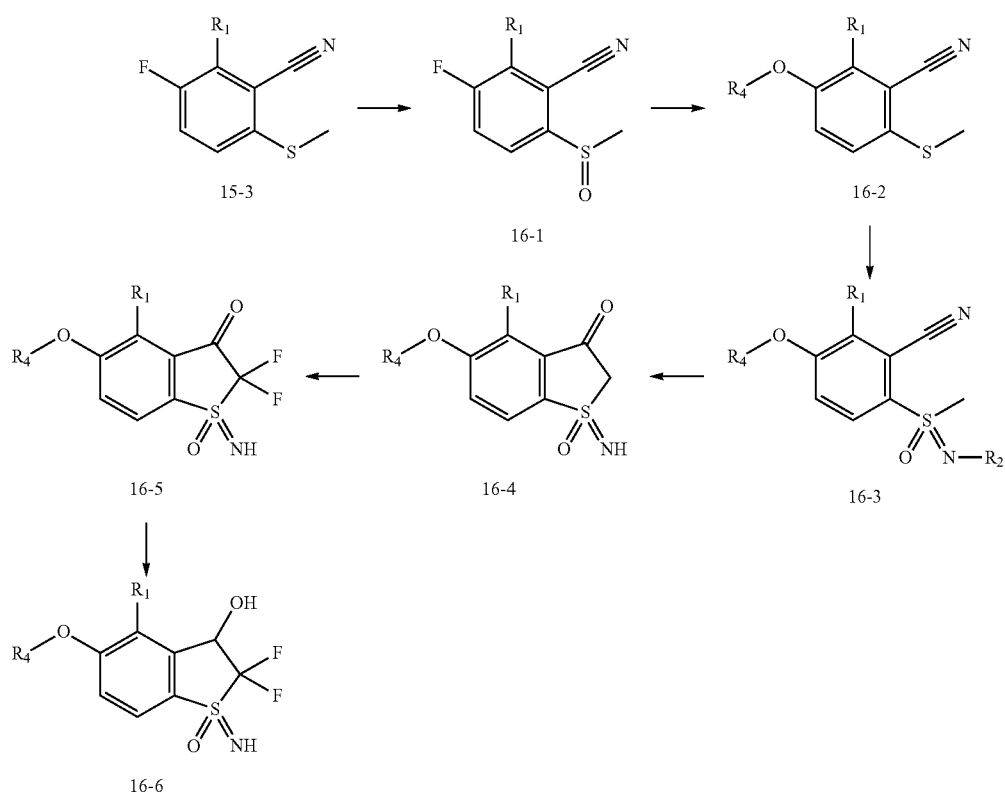

In some embodiments, compounds of Formula 16-6 are prepared according to Scheme 3. Oxidation of compounds of Formula 15-3 gives compounds of Formula 16-1. The oxidation may be accomplished with Oxone® or mCPBA.

pounds of Formula 16-4 may be achieved with a base, e.g., sodium hydride, at about room temperature. Finally, reduction of compounds of Formula 16-5 provides compounds of Formula 16-6. Compounds of Formula 16-6 may exist as a mixture of diastereomers and/or enantiomers. Diastereomers may be separated by conventional column chromatography while enantiomers may be separated by chiral column chromatography.

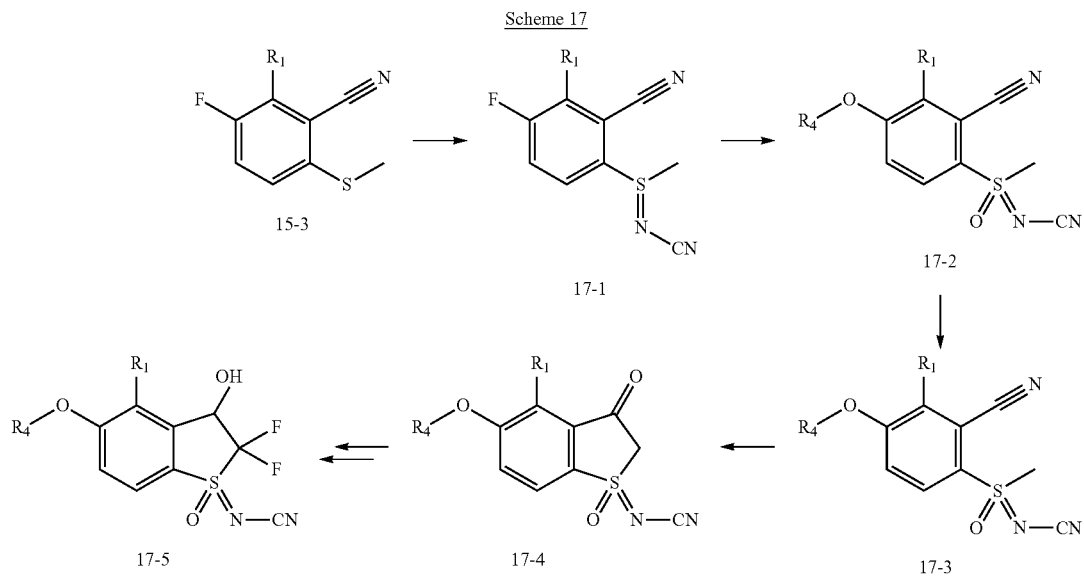

Scheme 17

In some embodiments, compounds of Formula 17-5 are prepared according to Scheme 17. Reaction of compounds of Formula 15-3 with cyanamide in the presence of an oxidant, e.g., (diacetoxyiodo)benzene, affords compounds of Formula 17-1. Further oxidation of compounds of Formula 17-1 provides compounds of Formula 17-2, which undergoes SNAr reaction, cyclization, and reduction to give compounds of Formula 17-5.

EXPERIMENTS

The examples below are intended to be purely exemplary and should not be considered to be limiting in any way. Efforts have been made to ensure accuracy with respect to numbers used (for example, amounts, temperature, etc.) but some experimental errors and deviations should be taken into account.

The following abbreviations and terms have the indicated meanings throughout:

DAST=Diethylaminosulfur trifluoride
DCM=Dichloromethane
MTBE=Methyl t-butyl ether
HATU=O-(7-azabenzotriazol-1-yl)-N,N,N',N'-tetramethyluronium hexafluorophosphate
NBS=N-Bromosuccinimide
NMP=N-Methyl-2-pyrrolidone
e.e. or ee=Enantiomeric excess
PPTS=Pyridinium p-toluenesulfonate
DMAP=4-Dimethylaminopyridine
DMF=N,N-Dimethylformamide $^1$H and $^{19}$F NMR analysis of intermediates and exemplified compounds were performed on an Agilent Technologies 400/54 magnet system (operating at 399.85 MHz or 376.24 MHz). Vnmrj VERSION 3.2 software Pulse sequences were selected from the default experiment set. Reference frequency was set using TMS as an internal standard. Typical deuterated solvents were utilized as indicated in the individual examples.

LCMS analysis of intermediates and exemplified compounds was performed on an Agilent Technologies 1200 Series HPLC system coupled to an Agilent Technologies 6150 Quadrapole LC/MS detector. Analytes were detected by UV absorbance at 220 and 254 nm. Analyte ions were detected by mass spectrometry in both negative and positive modes (110-800 amu scan range, API-ES ionization). A long HPLC method was run on a Phenomenex® Kinetex 2.6 µM C18 100 Å, 30×3.00 mm column. The column temperature was set at 40° C. UV absorptions were detected at 220 and 254 nm. Samples were prepared as a solution in about 1:1 (v/v) acetonitrile:water mixture. Flow rate was about 0.80 mL/minute. Elution solvents were acetonitrile and water each containing 0.1% formic acid. In a typical run, a linear gradient starting with 5% acetonitrile and 95% water and ending with 95% acetonitrile and 5% water over 12 minutes was carried out. At the end of each run, the column was washed with 95% acetonitrile and 5% water for 2 minutes.

Enantiomeric excess was determined by Mosher ester analysis or with chiral HPLC. The chiral HPLC analysis was performed on an Agilent Technologies 1200 Series HPLC system. Analytes were detected by UV absorbance at 220 and 254 nm. A detailed description of the analytical method is provided below:

Column Lux® 5 u Cellulose-4 5.0 µM 1000 Å, 150×4.60 mm
Flow rate: 1.5 mL/min
Mobile phase A: 0.1% Formic acid in water
Mobile phase B: 0.1% Formic acid in Acetonitrile
Strong needle wash: 90% Acetonitrile, 10% Water
Weak needle wash: 10% Water, 90% Acetonitrile
Injection volume: 2 µL
Column temperature: 40° C.
Autosampler temperature: Room temperature
Run time: 5.0 min
Gradient: 60% mobile phase A and 40% mobile phase B Routine chromatographic purification was performed using Biotage Isolera One automated systems running Biotage Isolera One 2.0.6 software (Biotage LLC, Charlotte, N.C.). Flow rates were the default values specified for the particular column in use. Reverse phase chromatography was performed using elution gradients of water and acetonitrile on KP-C18-HS Flash+ columns (Biotage LLC) of various sizes. Typical loading was between 1:50 and 1:1000 crude sample: RP SiO$_2$ by weight. Normal phase chromatography was performed using elution gradients of various solvents (e.g. hexane, ethyl acetate, methylene chloride, methanol, acetone, chloroform, MTBE, etc.). The columns were SNAP Cartridges containing KP-SIL or SNAP Ultra (25 µm spherical particles) of various sizes (Biotage LLC). Typical loading was between 1:10 to 1:150 crude sample: SiO$_2$ by weight.

Compound names were generated with ChemBioDraw ultra 13.0.0.3015 or OpenEye Scientific Software's mol2nam application.

Example 1

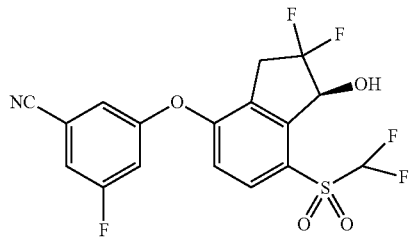 [SMILES: N#Cc1cc(F)cc(Oc2ccc(S(=O)(=O)C(F)F)c3c2CC(F)(F)[C@H]3O)c1]

3-[(1S)-7-(difluoromethylsulfonyl)-2,2-difluoro-1-hydroxy-indan-4-yl]oxy-5-fluoro-benzonitrile (Compound 1)

Step A: Preparation of 3-((7-((difluoromethyl)sulfonyl)-2,3-dihydrospiro[indene-1,2'-[1,3]dioxolan]-4-yl)oxy)-5-fluorobenzonitrile: A mixture of 3-fluoro-5-hydroxy-benzonitrile (1.33 g, 9.7 mmol), 7'-(difluoromethylsulfonyl)-4'-fluoro-spiro[1,3-dioxolane-2,1'-indane] (1.0 g, 3.24 mmol), and cesium bicarbonate (1.26 g, 6.5 mmol) in 1-methyl-2-pyrrolidone (1.8 mL) was heated under N$_2$ at 110° C. (microwave) for 1 hour and 5 minutes. The reaction was repeated ten times. The reaction mixtures were combined, diluted with EtOAc, and washed twice with 1 N NaOH. The combined aqueous layer was extracted with EtOAc. The EtOAc extracts were combined and washed with brine, dried over Na$_2$SO$_4$, filtered, and concentrated to about 100 mL to give a suspension. The suspension was filtered to give 3-((7-((difluoromethyl)sulfonyl)-2,3-dihydrospiro[indene-1,2'-[1,3]dioxolan]-4-yl)oxy)-5-fluorobenzonitrile as an off-white solid (6.25 g). The filtrate was diluted with EtOAc, washed with brine (3×), dried over Na$_2$SO$_4$, filtered, and concentrated. The residue was purified by flash column chromatography on silica gel with EtOAc/hexane (0% to 40%) to give additional 3-((7-((difluoromethyl)sulfonyl)-2,2-difluoro-2,3-dihydrospiro[indene-1,2'-[1,3]dioxolan]-4-yl)oxy)-5-fluorobenzonitrile (3.3 g, 69% combined yield) as a white solid. LCMS ESI (+) m/z 426 (M+H).

Step B: Preparation of 3-((7-((difluoromethyl)sulfonyl)-1-oxo-2,3-dihydro-1H-inden-4-yl)oxy)-5-fluorobenzonitrile: A mixture of 3-((7-((difluoromethyl)sulfonyl)-2,3-dihydrospiro[indene-1,2'-[1,3]dioxolan]-4-yl)oxy)-5-fluorobenzonitrile (10.9 g, 25.6 mmol) and PPTS (667 mg, 2.66 mmol) in acetone (100 mL)/water (15 mL) was heated at 82° C. for 5 hours and then 75° C. overnight. The reaction mixture was cooled to room temperature, concentrated under reduced pressure, diluted with EtOAc, washed with saturated aqueous NaHCO$_3$, dried over MgSO$_4$, filtered, and concentrated. The residue was filtered and washed with water. The solid obtained was briefly dried under vacuum at 50° C. and then triturated with EtOAc/hexane to give 3-((7-((difluoromethyl)sulfonyl)-1-oxo-2,3-dihydro-1H-inden-4-yl)oxy)-5-fluorobenzonitrile (8 g). Flash column chromatography of the mother liquor on silica gel with EtOAc/hexane (0% to 80%) provided additional 3-((7-((difluoromethyl)sulfonyl)-1-oxo-2,3-dihydro-1H-inden-4-yl)oxy)-5-fluorobenzonitrile (1.3 g, combined 9.3 g, quant. yield). LCMS ESI (+) m/z 382 (M+H).

Step C: Preparation of (E, Z)-3-((1-(butylimino)-7-((difluoromethyl)sulfonyl)-2,3-dihydro-1H-inden-4-yl)oxy)-5-fluorobenzonitrile: A mixture of 3-((7-((difluoromethyl)sulfonyl)-1-oxo-2,3-dihydro-1H-inden-4-yl)oxy)-5-fluorobenzonitrile (1.42 g, 3.72 mmol), butylamine (6.0 mL) and 5 drops of trifluoroacetic acid (0.1 mL) in benzene (40 mL) was refluxed overnight with removal of water using a Dean-Stark trap. The reaction mixture was concentrated under reduced pressure, diluted with methyl tert-butyl ether, washed with saturated aqueous NaHCO$_3$ and brine, dried over Na$_2$SO$_4$, filtered, and concentrated. The residue was used in the next step without further purification.

Step D: Preparation of 3-((7-((difluoromethyl)sulfonyl)-2,2-difluoro-1-oxo-2,3-dihydro-1H-inden-4-yl)oxy)-5-fluorobenzonitrile: A mixture of (E, Z)-3-((1-(butylimino)-7-((difluoromethyl)sulfonyl)-2,3-dihydro-1H-inden-4-yl)oxy)-5-fluorobenzonitrile (1.29 g, 3 mmol, crude from step C), Selectfluor® (2.62 g, 7.4 mmol) and sodium sulfate (4 g, 28.2 mmol) under N$_2$ was heated at 82° C. for 4 hours. After cooling to room temperature, concentrated HCl (37%, 3 mL) was added. The mixture was stirred at room temperature for 15 minutes and then concentrated under reduced pressure. The residue was diluted with methyl t-butyl ether, washed with half saturated aqueous NaHCO$_3$ and then brine, dried over Na$_2$SO$_4$, filtered, and triturated with EtOAc/hexane to give 3-((7-((difluoromethyl)sulfonyl)-2,2-difluoro-1-oxo-2,3-dihydro-1H-inden-4-yl)oxy)-5-fluorobenzonitrile as an off-white solid (0.5 g). The mother liquor was purified by flash column chromatography with EtOAc/hexane (5% to 40%) to give additional 3-((7-((difluoromethyl)sulfonyl)-2,2-difluoro-1-oxo-2,3-dihydro-1H-inden-4-yl)oxy)-5-fluorobenzonitrile (0.13 g, 51% combined yield). LCMS ESI (+) m/z 418 (M+H) and 435 (M+NH$_4$).

Step E: Preparation of (S)-3-((7-((difluoromethyl)sulfonyl)-2,2-difluoro-1-hydroxy-2,3-dihydro-1H-inden-4-yl)oxy)-5-fluorobenzonitrile (Compound 1): An ice cold solution of RuCl(p-cymene)[(R,R)-Ts-DPEN] (0.6 mg) in dichloromethane (0.2 mL) was added by syringe under nitrogen to an ice cold solution of 3-[7-(difluoromethylsulfonyl)-2,2-difluoro-1-oxo-indan-4-yl]oxy-5-fluoro-benzonitrile (28 mg, 0.07 mmol), triethylamine (18.7 µL, 0.13 mmol) and formic acid (7.6 µL, 0.2 mmol) in dichloromethane (0.5 mL) and then placed in a refrigerator at 4° C. overnight. The reaction mixture was directly purified on preparative TLC with EtOAc/hexane (40%) to give Compound 1 (23.4 mg, 0.06 mmol, 83% yield). The ee was determined to be greater than 95% by $^{19}$F NMR analysis of the corresponding Mosher ester. LCMS ESI (+) m/z 420 (M+H); $^1$H NMR (400 MHz, CDCl$_3$): δ 7.94 (d, 1H), 7.33-6.98 (m, 4H), 6.44 (t, 1H), 5.51 (d, 1H), 3.61-3.45 (m, 2H).

Example 2

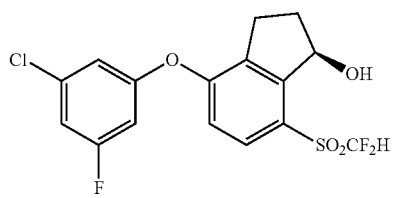

(R)-4-(3-chloro-5-fluorophenoxy)-7-((difluoromethyl)sulfonyl)-2,3-dihydro-1H-inden-1-ol (Compound 2)

Step A: Preparation of O-(7-fluoro-3-oxo-indan-4-yl)-N,N-dimethylcarbamothioate: A mixture of 4-fluoro-7-hydroxy-indan-1-one (17.0 g, 102 mmol), DMF (340 mL), N,N-dimethylcarbamothioyl chloride (37.9 g, 307 mmol), and 1,4-diazabicyclo[2.2.2]octane (34.4 g, 307 mmol) was stirred at ambient temperature for 2 hours. The reaction was poured into cold water and extracted with EtOAc. The combined organic layers were washed with water and brine, dried and concentrated. The resulting solid was recrystallized from 1:1 hexane:EtOAc (240 mL) to give O-(7-fluoro-3-oxo-indan-4-yl)-N,N-dimethylcarbamothioate as a white solid (12.0 g). The mother liquid was concentrated and purified by flash chromatography on silica gel (0-1% EtOAc in dichloromethane) to give a solid, which was triturated with 4:1 hexane:EtOAc to give additional O-(7-fluoro-3-oxo-indan-4-yl)-N,N-dimethylcarbamothioate (6.9 g, combined yield 18.9 g, 73%). LCMS ESI (+) m/z 254 (M+H).

Step B: Preparation of S-(7-fluoro-3-oxo-indan-4-yl)-N,N-dimethylcarbamothioate: A mixture of O-(7-fluoro-3-oxo-indan-4-yl)-N,N-dimethylcarbamothioate (18.9 g, 74.6 mmol) and diphenyl ether (200 mL) was heated at 220° C. under nitrogen for 30 minutes. After cooling, the reaction mixture was diluted with hexane. The mixture was passed through a short silica gel pad eluting with hexane to remove diphenyl ether. Further elution with EtOAc afforded the crude product, which was purified by flash chromatography on silica gel (15-40% EtOAc/hexane) to afford S-(7-fluoro-3-oxo-indan-4-yl)-N,N-dimethylcarbamothioate (18.0 g, 95%) as a solid. LCMS ESI (+) m/z 254 (M+H).

Step C: Preparation of 4-fluoro-7-sulfanyl-indan-1-one: A stirred mixture of S-(7-fluoro-3-oxo-indan-4-yl)-N,N-dimethylcarbamothioate (25.0 g, 98.7 mmol), 95% ethanol (490 mL) and 3N NaOH (173 mL, 691 mmol) was heated under nitrogen at reflux for 30 minutes. After cooling, the reaction mixture was cooled to 0° C. using an ice bath. 3N HCl was added dropwise to adjust the pH to 4-5. Most ethanol was evaporated under reduced pressure. The precipitated solid was collected by filtration, washed with water and dried to give 4-fluoro-7-sulfanyl-indan-1-one (17.0 g, 95%), which was used in the next step without further purification.

Step D: Preparation of 7-(difluoromethylsulfanyl)-4-fluoro-indan-1-one: To a stirred solution of 4-fluoro-7-sulfanyl-indan-1-one (crude from Step C, 17.0 g, 93.3 mmol) in acetonitrile (490 mL) was added a solution of KOH (104.7 g, 1866 mmol) in water (490 mL). The reaction mixture was purged with nitrogen and then cooled to −78° C. Bromodifluoromethyl diethylphosphonate (33.2 mL, 187 mmol) was added all in once. The resulting mixture was allowed to warm to ambient temperature and vigorously stirred for 2 hours. The reaction mixture was partitioned between EtOAc and water. The aqueous layer was extracted with EtOAc. The combined organics were washed with water and brine, dried over $Na_2SO_4$, filtered, and concentrated to dryness. The residue was purified by passing through a short silica gel pad eluting with 10% EtOAc in hexane to give 7-(difluoromethylsulfanyl)-4-fluoro-indan-1-one (18.3 g, 84%), which was used in the next step without further purification. LCMS ESI (+) m/z 233 (M+H).

Step E: Preparation of 7-((difluoromethyl)sulfonyl)-4-fluoro-2,3-dihydro-1H-inden-1-one: Sodium periodate (41.9 g, 196 mmol) was added all at once to 7-(difluoromethylsulfanyl)-4-fluoro-indan-1-one (18.2 g, 78.4 mmol) and ruthenium(III) chloride (0.41 g, 2.0 mmol) in acetonitrile (392 mL)/carbon tetrachloride (392 mL)/water (392 mL). The reaction mixture was stirred at ambient temperature for 5 hours. Solids were removed by filtration through Celite and rinsed with $CH_2Cl_2$. The organic layer was separated. The aqueous layer was extracted with $CH_2Cl_2$. The combined organics were washed with brine, dried over $Na_2SO_4$, filtered and concentrated in vacuo. The crude product was passed through a short silica gel pad eluting with 30% EtOAc/hexane to give 7-(difluoromethylsulfonyl)-4-fluoro-indan-1-one (18.8 g, 91%) as a white solid. LCMS ESI (+) m/z 265 (M+H).

Step F: Preparation of (1R)-7-(difluoromethylsulfonyl)-4-fluoro-indan-1-ol: A pear-shaped flask was charged with 7-(difluoromethylsulfonyl)-4-fluoro-indan-1-one (992 mg, 3.75 mmol), formic acid (0.178 mL, 4.69 mmol), triethylamine (0.576 mL, 4.13 mmol), and dichloromethane (25 mL). The reaction mixture was backfilled with nitrogen. RuCl(p-cymene)[(R,R)-Ts-DPEN] (48 mg, 0.08 mmol) was added in one portion, and the reaction mixture was stirred at ambient temperature overnight. The reaction was concentrated under reduced pressure. The residue was purified by flash chromatography on silica gel (5-20% EtOAc in hexanes) to give (1R)-7-(difluoromethylsulfonyl)-4-fluoro-indan-1-ol (990 mg, 99%) as a solid. The ee was determined to be 98% by $^{19}F$ NMR analysis of the corresponding Mosher ester. LCMS ESI (+) m/z 267 (M+H); ESI (−) m/z 311 (M−H+46).

Step G: Preparation of (R)-4-(3-chloro-5-fluorophenoxy)-7-((difluoromethyl)sulfonyl)-2,3-dihydro-1H-inden-1-ol (Compound 2): A solution of 3-chloro-5-fluoro-phenol (24 mg, 0.17 mmol) and (1R)-7-(difluoromethylsulfonyl)-4-fluoro-indan-1-ol (40 mg, 0.15 mmol) in NMP (1 mL) at ambient temperature was treated with $NaHCO_3$ (37 mg, 0.45 mmol). The reaction mixture was stirred at 90° C. under nitrogen for 4 hours. After cooling, the reaction mixture was partitioned between EtOAc and water. The aqueous layer was extracted with EtOAc. The combined organic layers were washed with water and brine, dried and concentrated. The residue was purified by C18 reverse phase flash chromatography (Biotage Isolera One unit, C18 Flash 12+M column, 10-60% $CH_3CN$/water) to give Compound 2 (25 mg, 42%). The ee was determined to be 98% by $^{19}F$ NMR analysis of the corresponding Mosher ester. LCMS ESI (+) m/z 393 (M+H); ESI (−) m/z 437, 439 (M−H+46); $^1H$ NMR (400 MHz, $CDCl_3$): δ 7.81 (d, 1H), 7.00-6.89 (m, 3H), 6.73-6.71 (m, 1H), 6.35 (t, 1H), 5.66-5.65 (m, 1H), 3.19-3.13 (m, 2H), 2.96-2.90 (m, 1H), 2.50-2.40 (m, 1H), 2.30-2.24 (m, 1H).

Alternative synthesis of 4-fluoro-7-sulfanyl-indan-1-one:
Step A: A solution of (7-fluoro-3-oxo-indan-4-yl) trifluoromethanesulfonate (237.0 mg, 0.79 mmol) and Xantphos (50.6 mg, 0.09 mmol) in 1,4-Dioxane (3 mL) was sparged with nitrogen for 3 mins. The reaction mixture was then treated sequentially with S-Potassium Thioacetate (136.1 mg, 1.19 mmol) and Tris(dibenzylideneacetone)dipalladium (0) (36.4 mg, 0.04 mmol) under continuous nitrogen stream. The vessel was sealed and heated to 100° C. for 4 hours. The reaction mixture was filtered to remove insolubles with $CH_2Cl_2$ used as a rinse. The filtrate was concentrated and purification was achieved by chromatography on silica using 10%-30% EtOAc/hexane to give S-(7-fluoro-3-oxo-indan-4-yl) ethanethioate (99 mg, 0.44 mmol, 46% yield). LCMS ESI (+) m/z 225 (M+H).

Step B: To a round bottom flask containing S-(7-fluoro-3-oxo-indan-4-yl) ethanethioate (99.0 mg, 0.4400 mmol) dissolved in 4.4 mL of degassed THF (sparged with nitrogen for 5 min) was added ammonium hydroxide (620 μL, 4.45 mmol). The resulting reaction mixture stirred for 40 minutes under nitrogen atmosphere. TLC indicates consumption of starting material and LCMS identifies the desired product. The reaction mixture was concentrated to remove excess THF and then poured into 1 mL of 1 M NaOH and 15 mL of water and rinsed with 2×20 mL of $CH_2Cl_2$. The remaining aqueous phase was acidified with 10 mL of 1 M HCl and extracted with 3×20 mL of $CH_2Cl_2$. The combined organic extracts were dried with $MgSO_4$, filtered, and concentrated to dryness. The product was used without further purification to give 4-fluoro-7-sulfanyl-indan-1-one (44 mg, 0.24 mmol, 55% yield).

Example 3

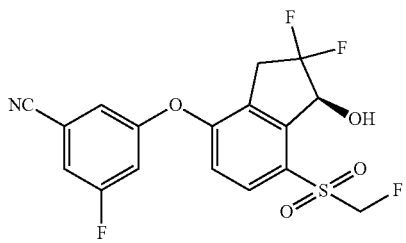 [SMILES: N#Cc1cc(F)cc(Oc2ccc(S(=O)(=O)CF)c3c2CC(F)(F)[C@H]3O)c1]

(S)-3-((2,2-difluoro-7-((fluoromethyl)sulfonyl)-1-hydroxy-2,3-dihydro-1H-inden-4-yl)oxy)-5-fluorobenzonitrile (Compound 3)

Step A: 4'-Fluoro-7'-(fluoromethylsulfonyl)spiro[1,3-dioxolane-2,1'-indane]: Trimethylsilyl trifluoromethanesulfonate (0.1 mL, 0.570 mmol) was added to a solution of 4-fluoro-7-(fluoromethylsulfonyl)indan-1-one (700 mg, 2.8 mmol) and trimethyl(2-trimethylsilyloxyethoxy)silane (1.4 mL, 5.7 mmol) in dichloromethane (50 mL) cooled to −78° C. The reaction mixture was allowed to warm to ambient temperature. After 5.5 hours, the reaction mixture was quenched with triethylamine (1.58 mL, 11.4 mmol) and evaporated. The residue was partitioned between EtOAc and dilute NaCl. The EtOAc was washed with water, brine, dried over $MgSO_4$, filtered, and evaporated to afford 4'-fluoro-7'-(fluoromethylsulfonyl)spiro[1,3-dioxolane-2,1'-indane] (630 mg, 2.2 mmol, 76% yield).

Step B: 3-Fluoro-5-[7'-(fluoromethylsulfonyl)spiro[1,3-dioxolane-2,1'-indane]-4'-yl]oxy-benzonitrile: A solution of sodium hydrogen carbonate (108.5 mg, 1.29 mmol), 3-fluoro-5-hydroxy-benzonitrile (85.0 mg, 0.62 mmol), and 4'-fluoro-7'-(fluoromethylsulfonyl)spiro[1,3-dioxolane-2,1'-indane] (150 mg, 0.52 mmol) in DMF (3 mL) in a vial were heated at 110° C. overnight. The reaction mixture was partitioned between EtOAc and dilute NaOH. The EtOAc was washed with water, brine, dried over $MgSO_4$, filtered, and evaporated. The residue was chromatographed on a Biotage 25 g SNAP column with a 10% to 60% EtOAc:hexane gradient to give 3-fluoro-5-[7'-(fluoromethylsulfonyl)spiro[1,3-dioxolane-2,1'-indane]-4'-yl]oxy-benzonitrile (101 mg, 0.25 mmol, 48% yield) as a colorless glass.

Step C: 3-Fluoro-5-[7-(fluoromethylsulfonyl)-1-oxo-indan-4-yl]oxy-benzonitrile: 3-Fluoro-5-[7'-(fluoromethylsulfonyl)spiro[1,3-dioxolane-2,1'-indane]-4'-yl]oxy-benzonitrile (101 mg, 0.25 mmol) was added to a solution of 4-methylbenzenesulfonate pyridin-1-ium (62.3 mg, 0.25 mmol) in acetone (6 mL) and water (0.75 mL) in a vial. The vial was sealed and the mixture was heated at 85° C. After 2.5 hours, the reaction mixture was evaporated and the residue was partitioned between EtOAc and water. The EtOAc was washed with brine, dried over $MgSO_4$, filtered, and evaporated to yield 3-fluoro-5-[7-(fluoromethylsulfonyl)-1-oxo-indan-4-yl]oxy-benzonitrile (84.5 mg, 0.23 mmol, 94% yield). m/z (ES-API-pos) [M+H]=364.

Step D: 3-[(E, Z)-1-Butylimino-7-(fluoromethylsulfonyl)indan-4-yl]oxy-5-fluoro-benzonitrile: Trifluoroacetic acid (0.0036 mL, 0.05 mmol) was added to a solution of 3-fluoro-5-[7-(fluoromethylsulfonyl)-1-oxo-indan-4-yl]oxy-benzonitrile (84.5 mg, 0.23 mmol) and butan-1-amine (2.3 mL, 23.3 mmol) in benzene (10 mL). The mixture was heated at reflux for 5 hours with a Dean-Stark trap attached. The reaction mixture was evaporated and the residue was partitioned between EtOAc and saturated aqueous $NaHCO_3$. The EtOAc was washed with brine, dried over $MgSO_4$, filtered, and evaporated to yield 3-[(E, Z)-1-butylimino-7-(fluoromethylsulfonyl)indan-4-yl]oxy-5-fluoro-benzonitrile (99 mg, 0.24 mmol, 100% yield).

Step E: 3-[2,2-Difluoro-7-(fluoromethylsulfonyl)-1-oxo-indan-4-yl]oxy-5-fluoro-benzonitrile: 1-(Chloromethyl)-4-fluoro-1,4-diazoniabicyclo[2.2.2]octane ditetrafluoroborate (209 mg, 0.59 mmol) was added to a solution of 3-[(E, Z)-1-butylimino-7-(fluoromethylsulfonyl)indan-4-yl]oxy-5-fluoro-benzonitrile (99 mg, 0.240 mmol) and sodium sulfate (33.6 mg, 0.24 mmol) in acetonitrile (6 mL) in a vial. The vial was sealed and heated at 100° C. for 6 hours. The reaction mixture was treated with 1 mL 6 M HCl and stirred for 5 minutes. The reaction mixture was partitioned between EtOAc and water. The EtOAc was washed with brine, dried over $MgSO_4$, filtered, and evaporated. The residue was chromatographed on a Biotage 10 g SNAP column with a 10% to 60% EtOAc:hexane gradient to give 3-[2,2-difluoro-7-(fluoromethylsulfonyl)-1-oxo-indan-4-yl]oxy-5-fluoro-benzonitrile (37.2 mg, 0.09 mmol, 39% yield) as a white solid.

Step F: (S)-3-((2,2-difluoro-7-((fluoromethyl)sulfonyl)-1-hydroxy-2,3-dihydro-1H-inden-4-yl)oxy)-5-fluorobenzonitrile (Compound 3): RuCl(p-cymene)[(R,R)-Ts-DPEN] (1.19 mg, 0.002 mmol) was added to a nitrogen-sparged solution of 3-[2,2-difluoro-7-(fluoromethylsulfonyl)-1-oxo-indan-4-yl]oxy-5-fluoro-benzonitrile (37.2 mg, 0.09 mmol), formic acid (0.0044 mL, 0.12 mmol), and triethylamine (0.014 mL, 0.10 mmol) in dichloromethane (6 mL). This was stirred at ambient temperature for 3.5 hours. The reaction mixture was evaporated and the residue was chromatographed on a Biotage 10 g SNAP column with a 10% to 40% EtOAc:hexane gradient to give Compound 3 (30.8 mg, 0.08 mmol, 82% yield). $^1$H NMR (400 MHz, $CDCl_3$): δ 7.93 (d, 1H), 7.30-7.26 (m, 1H), 7.20-7.19 (m, 1H), 7.10-7.07 (m, 1H), 7.00 (d, 1H), 5.59-5.13 (m, 3H), 3.58-3.38 (m, 1H). m/z (ES-API-neg) [M−H+46]=446. $^{19}$F NMR (CDCl₃) showed an e.e. of 89% based on the Mosher ester analysis of the trifluoromethyl resonance.

Example 4

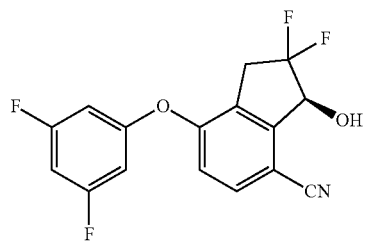 [SMILES: N#Cc1ccc(Oc2cc(F)cc(F)c2)c2c1[C@H](O)C(F)(F)C2]

(S)-7-(3,5-Difluorophenoxy)-2,2-difluoro-3-hydroxy-2,3-dihydro-1H-indene-4-carbonitrile (Compound 4)

Step A: (E, Z)-3-Butylimino-7-(3,5-difluorophenoxy)indane-4-carbonitrile: A solution of 7-(3,5-difluorophenoxy)-3-oxo-indane-4-carbonitrile (82.7 mg, 0.29 mmol), butan-1-amine (2.87 mL, 29 mmol), and trifluoroacetic acid (0.0044 mL, 0.058 mmol) in benzene (20 mL) was heated at reflux for 9 hours with a Dean-Stark trap attached. The reaction mixture was evaporated and the residue was partitioned between EtOAc and dilute NaHCO₃. The EtOAc was washed with brine, dried over MgSO₄, filtered, and evaporated to afford (E, Z)-3-butylimino-7-(3,5-difluorophenoxy)indane-4-carbonitrile (92 mg, 0.27 mmol, 93% yield).

Step B: 7-(3,5-Difluorophenoxy)-2,2-difluoro-3-oxo-indane-4-carbonitrile: 1-(Chloromethyl)-4-fluoro-1,4-diazoniabicyclo[2.2.2]octane ditetrafluoroborate (239 mg, 0.68 mmol) was added to a solution of (E, Z)-3-butylimino-7-(3,5-difluorophenoxy)indane-4-carbonitrile (92 mg, 0.27 mmol) and sodium sulfate (38.4 mg, 0.270 mmol) in acetonitrile (6 mL) in a vial. The vial was sealed and heated at 100° C. for 6 hours. After cooling, the reaction mixture was treated with ~1 mL 6 M HCl and stirred for 15 minutes. The reaction mixture was partitioned between EtOAc and water. The EtOAc was washed with brine, dried over MgSO₄, filtered, and evaporated. The residue was chromatographed on a Biotage 10 g SNAP column with a 10% to 60% EtOAc:hexane gradient to give 7-(3,5-difluorophenoxy)-2,2-difluoro-3-oxo-indane-4-carbonitrile (29.8 mg, 0.09 mmol, 34% yield) as a white solid. m/z (ES-API-pos) [M+H+18]=339.

Step C: (S)-7-(3,5-Difluorophenoxy)-2,2-difluoro-3-hydroxy-2,3-dihydro-1H-indene-4-carbonitrile (Compound 4): RuCl(p-cymene)[(R,R)-Ts-DPEN] (1.2 mg, 0.002 mmol) was added to a nitrogen-sparged solution of 7-(3,5-difluorophenoxy)-2,2-difluoro-3-oxo-indane-4-carbonitrile (29.8 mg, 0.09 mmol), formic acid (0.004 mL, 0.12 mmol), and triethylamine (0.014 mL, 0.100 mmol) in dichloromethane (6 mL). The mixture was stirred at ambient temperature for 3.5 hours. The reaction mixture was evaporated and the residue was chromatographed on a Biotage 10 g SNAP column with a 10% to 60% EtOAc:hexane gradient to give Compound 4 (24.5 mg, 0.08 mmol, 82% yield) as a waxy white crystalline solid. ¹H NMR (400 MHz, CDCl₃): δ 7.62 (d, 1H), 6.94 (d, 1H), 6.72-6.67 (m, 1H), 6.61-6.54 (m, 2H), 5.36-5.30 (m, 1H), 3.54-3.30 (m, 2H), 3.13-3.10 (m, 1H). m/z (ES-API-neg) [M−H+46]=368. ¹⁹F NMR (CDCl₃) showed an e.e. of 50% based on the Mosher ester analysis of the trifluoromethyl resonance.

Example 5

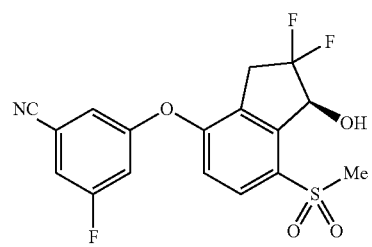

(S)-3-((2,2-Difluoro-1-hydroxy-7-(methylsulfonyl)-2,3-dihydro-1H-inden-4-yl)oxy)-5-fluorobenzonitrile (Compound 5)

Step A: Preparation of 4'-(3-bromo-5-fluoro-phenoxy)-7'-methylsulfonyl-spiro[1,3-dioxolane-2,1'-indane]: Cesium hydrogen carbonate (142 mg, 0.73 mmol) was added all at once to 4'-fluoro-7'-methylsulfonyl-spiro[1,3-dioxolane-2, 1'-indane] (100 mg, 0.37 mmol) and 3-bromo-5-fluoro-phenol (105 mg, 0.55 mmol) in 1-methyl-2-pyrrolidone (1.5 mL) at room temperature in a microwave reaction vial equipped with a stir bar. The flask was flushed with nitrogen then sealed with a crimp cap. The reaction was heated to 150° C. for 7 hours, cooled to ambient temperature then purified directly on reverse phase silica gel (25+M, 14 CV, 20-100% MeCN/water) affording 4'-(3-bromo-5-fluoro-phenoxy)-7'-methylsulfonyl-spiro[1,3-dioxolane-2,1'-indane] (118 mg, 0.26 mmol, 72% yield).

Step B: Preparation of 3-fluoro-5-(7'-methylsulfonylspiro [1,3-dioxolane-2,1'-indane]-4'-yl)oxy-benzonitrile: Dichloro[1;1'-bis(diphenylphosphino)ferrocene]palladium (II) dichloromethane adduct (784 mg, 0.97 mmol) was quickly added to a degassed mixture of 4'-(3-bromo-5-fluoro-phenoxy)-7'-methylsulfonyl-spiro[1,3-dioxolane-2, 1'-indane] (4.3 g, 9.7 mmol), zinc cyanide (1.14 g, 9.7 mmol) and zinc powder (761 mg, 11.6 mmol) in DMF (60 mL) under nitrogen. The reaction mixture was then warmed to 110° C. for 2 hours. After cooling, the mixture was filtered through a pad of celite. The filtrate was diluted with water (100 mL), extracted with MTBE (5×100 mL), washed with brine (100 mL), dried over MgSO₄, filtered and concentrated in vacuo. The crude product was purified on silica gel (100 g SNAP, 14 CV, 15-100% EtOAc/hexanes) then purified again on silica gel (25 g Ultra SNAP, 14 CV, 0-20% dichloromethane/EtOAc) affording 3-fluoro-5-(7'-methylsulfonylspiro[1,3-dioxolane-2,1'-indane]-4'-yl)oxy-benzonitrile (3.77 g, 9.7 mmol, 100% yield).

Step C: Preparation of 3-fluoro-5-(7-methylsulfonyl-1-oxo-indan-4-yl)oxy-benzonitrile: Pyridinium para-toluenesulfonate (354 mg, 1.4 mmol) was added all at once to a solution of 3-fluoro-5-(7'-methylsulfonylspiro[1,3-dioxolane-2,1'-indane]-4'-yl)oxy-benzonitrile (550 mg, 1.4 mmol) in acetone (6 mL)/water (2 mL) at room temperature and then warmed to reflux until completion. The mixture was concentrated in vacuo then purified on silica gel (10 g SNAP, 14 CV, 20-100% EtOAc/hexane) affording 3-fluoro-5-(7-methylsulfonyl-1-oxo-indan-4-yl)oxy-benzonitrile (450 mg, 1.3 mmol, 92% yield).

Step D: Preparation of 3-[(E, Z)-1-butylimino-7-methylsulfonyl-indan-4-yl]oxy-5-fluoro-benzonitrile: Butan-1-amine (5.15 mL, 52 mmol) was added to 3-fluoro-5-(7-methylsulfonyl-1-oxo-indan-4-yl)oxy-benzonitrile (450 mg, 1.3 mmol) and trifluoroacetic acid (19.96 µL, 0.26 mmol) in benzene (10 mL) at room temperature then warmed to reflux with the azeotropic removal of water by a Dean-Stark apparatus. Progress of the reaction was monitored by ¹HNMR. When complete, the reaction was cooled to room temperature then concentrated in vacuo. The residue was diluted with water (10 mL), extracted with MTBE (3×10 mL), washed with brine and dried over $Na_2SO_4$, filtered and concentrated. Crude 3-[(E, Z)-1-butylimino-7-methylsulfonyl-indan-4-yl]oxy-5-fluoro-benzonitrile was used immediately without purification in the next step.

Step E: Preparation of 3-(2,2-difluoro-7-methylsulfonyl-1-oxo-indan-4-yl)oxy-5-fluoro-benzonitrile: Selectfluor® (1.15 g, 3.25 mmol) was added to crude 3-[(E, Z)-1-butylimino-7-methylsulfonyl-indan-4-yl]oxy-5-fluoro-benzonitrile (520 mg, 1.3 mmol) and sodium sulfate (369 mg, 2.6 mmol) in acetonitrile (10 mL) then warmed to reflux for 6 hours. The reaction was cooled to room temperature, concentrated HCl (1.0 mL, 12 mmol) was added and stirred for 15 minutes. The mixture was diluted with water (10 mL), extracted with EtOAc (3×10 mL), washed with brine (10 mL), dried over $MgSO_4$, filtered and concentrated in vacuo. The residue was purified on silica gel (25 g SNAP, 14 CV, 20-100% EtOAc/hexane) afforded 3-(2,2-difluoro-7-methylsulfonyl-1-oxo-indan-4-yl)oxy-5-fluoro-benzonitrile (437 mg, 1.2 mmol, 88% yield).

Step F: Preparation of (S)-3-((2,2-difluoro-1-hydroxy-7-(methylsulfonyl)-2,3-dihydro-1H-inden-4-yl)oxy)-5-fluorobenzonitrile (Compound 5): An ice cold solution of RuCl (p-cymene)[(R,R)-Ts-DPEN] (40.7 mg, 0.06 mmol) in $CH_2Cl_2$ (30 mL) was added by syringe under nitrogen to an ice cold solution of 3-(2,2-difluoro-7-methylsulfonyl-1-oxo-indan-4-yl)oxy-5-fluoro-benzonitrile (2.44 g, 6.4 mmol), triethylamine (1.78 mL, 12.8 mmol) and formic acid (724 µL, 19.2 mmol) in $CH_2Cl_2$ (30 mL). The reaction was placed in a refrigerator at 4° C. for 16 hours. The mixture was concentrated to 10 mL then purified directly on silica gel (25 g SNAP ULTRA, 14 CV, 10-50% EtOAc/hexane) affording Compound 5 (2.15 g, 5.6 mmol, 87% yield). Enantiomeric excess (98%) was determined by chiral HPLC. Retention time for (S)-enantiomer: 1.93 minutes; retention time for (R)-enantiomer: 2.32 minutes. LCMS ESI (−) 428 (M+HCO$_2^−$). ¹HNMR (400 MHz, CDCl$_3$): δ 7.93 (d, 1H), 7.27-7.24 (m, 1H), 7.15-7.14 (m, 1H), 7.07-7.03 (m, 1H), 7.00 (d, 1H), 5.63-5.58 (m, 1H), 3.56-3.35 (m, 3H), 3.24 (s, 3H).

Alternative protocol for the synthesis of 3-fluoro-5-(7'-methylsulfonylspiro[1,3-dioxolane-2,1'-indane]-4'-yl)oxy-benzonitrile: Cesium hydrogen carbonate (320.48 mg, 1.65 mmol) was added all at once to 4'-fluoro-7'-methylsulfonyl-spiro[1,3-dioxolane-2,1'-indane] (300 mg, 1.1 mmol) and 3-fluoro-5-hydroxy-benzonitrile (227 mg, 1.65 mmol) in 1-methyl-2-pyrrolidone (4.4 mL) at room temperature in a microwave reaction vial equipped with a stir bar, flushed with nitrogen then sealed with a crimp cap. The reaction mixture was heated to 160° C. for 2 hours in a microwave reactor. Additional CsHCO$_3$ (100 mg) was added and the mixture was heated at 160° C. for 30 minutes in a microwave reactor. The mixture was purified directly on reverse phase column (25+M, 14 CV, 20-100% MeCN/water) affording 3-fluoro-5-(7'-methylsulfonylspiro[1,3-dioxolane-2,1'-indane]-4'-yl)oxy-benzonitrile (104 mg, 0.26 mmol, 24% yield).

Alternative preparation of 3-fluoro-5-((7-(methylsulfonyl)-2,3-dihydrospiro[indene-1,2'-[1,3]dioxolan]-4-yl)oxy) benzonitrile

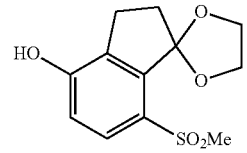

7-(Methylsulfonyl)-2,3-dihydrospiro[indene-1,2'-[1,3]dioxolan]-4-ol

Step A: Preparation of 7-(methylsulfonyl)-2,3-dihydrospiro[indene-1,2'-[1,3]dioxolan]-4-ol: Sodium hydroxide (3 M, 62.4 mL, 187.3 mmol) was added by syringe to a solution of 4'-fluoro-7'-methylsulfonyl-spiro[1,3-dioxolane-2,1'-indane] (25.5 g, 93.6 mmol) in DMSO (280 mL) under nitrogen then the mixture was warmed to 75° C. until complete as judged by LC-MS (5 hours). The reaction mixture was cooled to room temperature then poured into ice cold 0.7 M KHSO$_4$ (255 mL), adjusted to pH 5-6 with saturated NaHCO$_3$, then extracted with EtOAc (5×300 mL). The combined organic layers were washed with water (100 mL), brine (100 mL), dried over Na$_2$SO$_4$, filtered and concentrated in vacuo affording 7-(methylsulfonyl)-2,3-dihydrospiro[indene-1,2'-[1,3]dioxolan]-4-ol (24.6 g, 97% yield). LCMS ESI (+) m/z 271 (M+H).

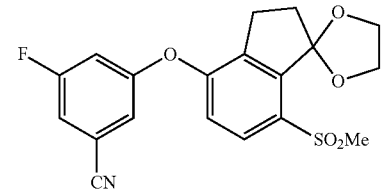 [SMILES: CS(=O)(=O)c1ccc(Oc2cc(F)cc(C#N)c2)c2c1C1(CC2)OCCO1]

3-Fluoro-5-((7-(methylsulfonyl)-2,3-dihydrospiro[indene-1,2'-[1,3]dioxolan]-4-yl)oxy)benzonitrile Step B: Preparation of 3-fluoro-5-((7-(methylsulfonyl)-2,3-dihydrospiro[indene-1,2'-[1,3]dioxolan]-4-yl)oxy)benzonitrile: Cesium carbonate (6.33 g, 19.4 mmol) was added all at once to a solution of 3,5-difluorobenzonitrile (5.4 g, 38.85 mmol) and 7'-methylsulfonylspiro[1,3-dioxolane-2,1'-indane]-4'-ol (3.50 g, 13 mmol) in 1-methyl-2-pyrrolidone (45 mL) at room temperature. The reaction mixture was warmed to 110° C. under nitrogen until complete as judged by LC-MS (3 hours). The reaction mixture was diluted with 3 N NaOH (10 mL) and water (20 mL), extracted with EtOAc (5×30 mL). The combined organic layers were washed with brine (30 mL), dried over MgSO$_4$, filtered and concentrated in vacuo. The residue was purified on silica gel (100 g SNAP Ultra, 14 CV, 10-80% EtOAc/hexanes) affording 3-fluoro-5-(7'-methylsulfonylspiro[1,3-dioxo lane-2,1'-indane]-4'-yl)oxy-benzonitrile (3.70 g, 9.5 mmol, 73% yield). LCMS ESI (+) m/z 390 (M+H).

Alternative protocol for the synthesis of 3-fluoro-5-(7-methylsulfonyl-1-oxo-indan-4-yl)oxy-benzonitrile:

Step A: Preparation of 2-hydroxy-5-(methylthio)benzaldehyde: To a suspension of 4-methylsulfanylphenol (50 g, 357 mmol), paraformaldehyde (72.3 g, 2407 mmol), and anhydrous magnesium chloride (50.9 g, 535 mmol) in acetonitrile (500 mL) was added triethyl amine (186 mL, 1337 mmol) at ambient temperature. After the addition, the reaction mixture was stirred at 60° C. for 5 hours. After cooling to 0° C., 1 N HCl was added slowly until two phase separated (ca. 1.5 L). MTBE (700 mL) was added. The organic layer was separated, washed with brine, dried (sodium sulfate), filtered and concentrated under reduced pressure. The residue obtained was purified by flash chromatography on silica gel eluting with 1:1 hexane/dichloromethane to give 2-hydroxy-5-methylsulfanyl-benzaldehyde (50.5 g, 300 mmol, 84% yield) as semisolid.

Step B: Preparation of 3-(2-hydroxy-5-(methylthio)phenyl)propanoic acid: Triethylamine (2.5 mL, 17.8 mmol) was added slowly to formic acid (1.55 mL, 41.0 mmol) at 0° C. Then 2,2-dimethyl-1,3-dioxane-4,6-dione (1.84 g, 12.9 mmol) was added, followed by a solution of 2-hydroxy-5-methylsulfanyl-benzaldehyde (2.0 g, 11.9 mmol) in N,N-dimethylacetamide (4 mL). The reaction mixture was stirred at ambient temperature for 1 hour and then it was stirred at 100° C. for 6 hours. After cooling to ambient temperature, water (100 mL) was added and the pH was adjusted with 3N NaOH to pH-9. Ethyl acetate (50 mL) was added. The aqueous layer was separated, then acidified with saturated potassium hydrogen sulfate to pH-3. This aqueous layer was extracted with MTBE (50 mL). The organic layer was separated, washed with brine, dried (sodium sulfate), filtered and concentrated under reduced pressure. The residue obtained was purified by flash chromatography on silica gel with 1:1 hexane/ethyl acetate to give 3-(2-hydroxy-5-methylsulfanyl-phenyl)propanoic acid (1.67 g, 7.9 mmol, 66% yield) as solid.

Step C: Preparation of 3-[2-(3-cyano-5-fluoro-phenoxy)-5-methylsulfanyl-phenyl]propanoic acid: A suspension of 3-(2-hydroxy-5-methylsulfanyl-phenyl)propanoic acid (2.14 g, 10 mmol), 3,5-difluorobenzonitrile (3.51 g, 25 mmol), and cesium carbonate (9.85 g, 30 mmol) in sulfolane (36 mL) and s-butanol (4 mL) was stirred at 105° C. for 4 hours. After cooled to ambient temperature, water (100 mL) and MTBE (100 mL) were added. The liquid layer was separated, acidified with saturated potassium hydrogen sulfate to pH-3-4 and extracted with MTBE. The organic layer was washed with brine, dried (sodium sulfate), filtered and concentrated under reduced pressure. Water (50 mL) was added and the mixture was stirred at ambient temperature for 30 minutes. The resulting solid was collected by filtration and dried under vacuum. The filtered solid was suspended in 3:1 hexane/MTBE (~20 mL) and stirred at ambient temperature for 30 minutes. The solid was collected by filtration, washed with hexane and dried to give 3-[2-(3-cyano-5-fluoro-phenoxy)-5-methylsulfanyl-phenyl]propanoic acid (2.9 g, 8.8 mmol, 87% yield) as solid.

Step D: Preparation of 3-fluoro-5-(7-methylsulfanyl-1-oxo-indan-4-yl)oxy-benzonitrile: To a solution of 3-[2-(3-cyano-5-fluoro-phenoxy)-5-methylsulfanyl-phenyl]propanoic acid (8.44 g, 25.5 mmol) in dichloromethane (50 mL) was added a drop of DMF, then followed by addition of oxalyl chloride (2.62 mL, 30.6 mmol). The reaction mixture was stirred at ambient temperature for 1 hour. Volatile solvents were removed under reduced pressure. Dichloromethane (20 mL) was added. The resulting mixture was added slowly to a suspension of trichloroalumane (6.79 g, 50.0 mmol) in dichloromethane (50 mL). The mixture was stirred at ambient temperature for 1 hour. The reaction mixture was cooled to 0° C. Aqueous 1 N HCl (20 mL) was added slowly, followed by water (50 mL) and dichloromethane (100 mL). The organic layer was separated, washed with saturated sodium bicarbonate, dried (sodium sulfate), filtered and concentrated under reduced pressure to give 3-fluoro-5-(7-methylsulfanyl-1-oxo-indan-4-yl)oxy-benzonitrile (7.98 g, 25.5 mmol, 100% yield) as solid.

Step E: Preparation of 3-fluoro-5-(7-methylsulfanyl-1-oxo-indan-4-yl)oxy-benzonitrile: A suspension of 3-fluoro-5-(7-methylsulfanyl-1-oxo-indan-4-yl)oxy-benzonitrile (7.98 g, 25.5 mmol), Oxone® (53.6 g, 87 mmol) in acetonitrile (40 mL) and water (20 mL) was stirred at ambient temperature for 18 hours. Solid was removed by filtration and washed with dichloromethane (40 mL). The organics was removed under reduced pressure. Acetone (20 mL) and water (40 mL) were added. The resulting suspension was stirred at ambient temperature for 30 minutes. The solid was collected by filtration and dried to give 3-fluoro-5-(7-methylsulfonyl-1-oxo-indan-4-yl)oxy-benzonitrile (7.3 g, 21 mmol, 83% yield) as solid.

Example 6

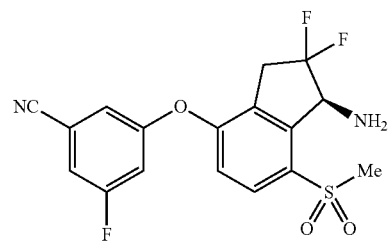 [SMILES: CS(=O)(=O)c1ccc(Oc2cc(F)cc(C#N)c2)c2c1[C@H](N)C(F)(F)C2]

3-[(1S)-1-Amino-2,2-difluoro-7-methylsulfonyl-indan-4-yl]oxy-5-fluoro-benzonitrile (Compound 6)

Step A: Preparation of (R)—N-(4-(3-cyano-5-fluorophenoxy)-2,2-difluoro-7-(methylsulfonyl)-2,3-dihydro-1H-inden-1-ylidene)-2-methylpropane-2-sulfinamide: Titanium tetraethoxide (49.5 µL, 0.24 mmol) was added dropwise to 3-(2,2-difluoro-7-methylsulfonyl-1-oxo-indan-4-yl)oxy-5-fluoro-benzonitrile (30 mg, 0.08 mmol) and (S)-(−)-2-methyl-2-propanesulfinamide (11 mg, 0.09 mmol) in tetrahydrofuran (0.8 mL) at room temperature under nitrogen then warmed to 45° C. for 8 hours. The reaction was quenched with water (0.1 mL) at room temperature, the solids were removed by filtration, washed with EtOAc (20 mL) and concentrated in vacuo. The crude product was purified on silica gel (10 g SNAP, 14 CV, 15-100% EtOAc/hexane) affording (R)—N-(4-(3-cyano-5-fluorophenoxy)-2,2-difluoro-7-(methylsulfonyl)-2,3-dihydro-1H-inden-1-ylidene)-2-methylpropane-2-sulfinamide (24 mg, 0.05 mmol, 63% yield).

Step B: Preparation of (R)—N—((S)-4-(3-cyano-5-fluorophenoxy)-2,2-difluoro-7-(methylsulfonyl)-2,3-dihydro-1H-inden-1-yl)-2-methylpropane-2-sulfinamide: Sodium borohydride (5.6 mg, 0.15 mmol) was added all at once to an ice cold solution of (R)—N-[4-(3-cyano-5-fluoro-phenoxy)-2,2-difluoro-7-methylsulfonyl-indan-1-ylidene]-2-methylpropane-2-sulfinamide (24 mg, 0.05 mmol) in tetrahydrofuran (0.5 mL) then stirred until complete as judged by LC-MS. Quenched with water (1 mL), extracted with EtOAc (3×5 mL), washed with brine (5 mL), dried over MgSO$_4$, filtered and concentrated in vacuo. The residue was purified on silica gel (10 g SNAP Ultra, 14 CV, 18-100% EtOAc/ hexane) affording (R)—N—((S)-4-(3-cyano-5-fluorophenoxy)-2,2-difluoro-7-(methylsulfonyl)-2,3-dihydro-1H-inden-1-yl)-2-methylpropane-2-sulfinamide (7 mg, 0.01 mmol, 29% yield).

Step C: Preparation of 3-[(1S)-1-amino-2,2-difluoro-7-methylsulfonyl-indan-4-yl]oxy-5-fluoro-benzonitrile (Compound 6): Hydrogen chloride (4.0 M solution in dioxane, 0.2 mL, 0.8 mmol) was added dropwise to a solution of (R)—N-(4-(3-cyano-5-fluorophenoxy)-2,2-difluoro-7-(methylsulfonyl)-2,3-dihydro-1H-inden-1-ylidene)-2-methylpropane-2-sulfinamide (7 mg, 0.01 mmol) in methanol (0.2 mL) at room temperature then stirred for 30 minutes. The reaction was carefully quenched by dropwise addition of saturated NaHCO$_3$ (2 mL), extracted with EtOAc (3×5 mL), washed with brine (5 mL), dried over Na$_2$SO$_4$, filtered and concentrated in vacuo. The crude product was purified on silica gel (10 g SNAP, 14 CV, 15-100% EtOAc/hexane) affording Compound 6 (2.3 mg, 0.006 mmol, 42% yield). LCMS ESI (+) 383 (M+H). $^1$HNMR (400 MHz, CDCl$_3$): δ 7.93-7.91 (m, 1H), 7.25-7.22 (m, 1H), 7.14-7.13 (m, 1H), 7.06-7.02 (m, 1H), 6.96 (d, 1H), 4.97-4.93 (m, 1H), 3.55-3.37 (m, 2H), 3.32 (s, 3H).

Example 7

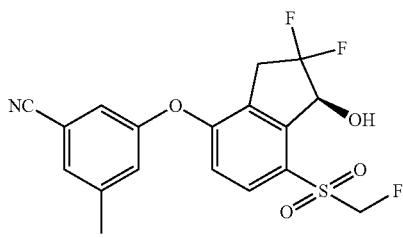 [SMILES: Cc1cc(C#N)cc(Oc2ccc(S(=O)(=O)CF)c3c2CC(F)(F)[C@H]3O)c1]

(S)-3-((2,2-Difluoro-7-((fluoromethyl)sulfonyl)-1-hydroxy-2,3-dihydro-1H-inden-4-yl)oxy)-5-methylbenzonitrile (Compound 7): m/z (ES-API-neg) [M−H+46]=442; $^1$H NMR (400 MHz, CDCl$_3$) δ 7.87 (d, 1H), 7.38 (br s, 1H), 7.16 (br d, 1H), 6.88 (d, 1H), 5.58-5.12 (m, 3H), 3.59-3.44 (m, 3H). Enantiomeric excess was 95% as determined by Mosher ester analysis.

Example 8

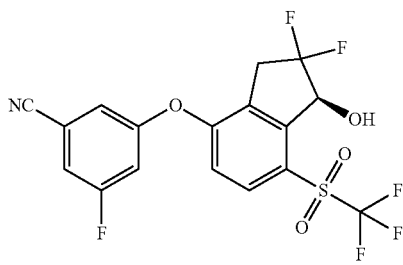 [SMILES: N#Cc1cc(F)cc(Oc2ccc(S(=O)(=O)C(F)(F)F)c3c2CC(F)(F)[C@H]3O)c1]

(S)-3-((2,2-Difluoro-1-hydroxy-7-((trifluoromethyl)sulfonyl)-2,3-dihydro-1H-inden-4-yl)oxy)-5-fluorobenzonitrile (Compound 8)

Step A: 3-Fluoro-5-((1-oxo-7-((trifluoromethyl)sulfonyl)-2,3-dihydro-1H-inden-4-yl)oxy)benzonitrile: Dess Martin periodinane (192 mg, 0.45 mmol) was added to a solution of 3-fluoro-5-[(1R)-1-hydroxy-7-(trifluoromethylsulfonyl)indan-4-yl]oxy-benzonitrile (121 mg, 0.3 mmol) in dichloromethane (4 mL). The mixture was stirred at ambient temperature. After 1 hour, the reaction mixture was partitioned between EtOAc and water. The EtOAc was washed with brine, dried over MgSO$_4$, filtered, and evaporated. The residue was chromatographed on a Biotage 10 g SNAP column with a 20% to 80% EtOAc:hexane gradient to afford 3-fluoro-5-((1-oxo-7-((trifluoromethyl)sulfonyl)-2,3-dihydro-1H-inden-4-yl)oxy)benzonitrile (102 mg, 0.26 mmol, 85% yield) as a colorless glass. m/z (ES-API-pos) [M+H]=400

Step B: (E, Z)-3-((1-(Butylimino)-7-((trifluoromethyl)sulfonyl)-2,3-dihydro-1H-inden-4-yl)oxy)-5-fluorobenzonitrile: Trifluoroacetic acid (0.0039 mL, 0.05 mmol) was added to a solution of 3-fluoro-5-((1-oxo-7-((trifluoromethyl)sulfonyl)-2,3-dihydro-1H-inden-4-yl)oxy)benzonitrile (102 mg, 0.26 mmol) and butan-1-amine (1.26 mL, 12.8 mmol) in benzene (15 mL). The mixture was heated at reflux with a Hickman still attached. After 6 hours, the reaction mixture was evaporated and the residue was partitioned between EtOAc and saturated aqueous NaHCO$_3$. The EtOAc was washed with brine, dried over MgSO$_4$, filtered, and evaporated to yield (E, Z)-3-((1-(butylimino)-7-((trifluoromethyl)sulfonyl)-2,3-dihydro-1H-inden-4-yl)oxy)-5-fluorobenzonitrile (100 mg, 0.2 mmol, 86% yield) as a green film.

Step C: 3-((2,2-Difluoro-1-oxo-7-((trifluoromethyl)sulfonyl)-2,3-dihydro-1H-inden-4-yl)oxy)-5-fluorobenzonitrile: 1-(Chloromethyl)-4-fluoro-1,4-diazoniabicyclo[2.2.2]octane ditetrafluoroborate (195 mg, 0.55 mmol) was added to a mixture of crude (E, Z)-3-((1-(butylimino)-7-((trifluoromethyl)sulfonyl)-2,3-dihydro-1H-inden-4-yl)oxy)-5-fluorobenzonitrile (100 mg, 0.22 mmol) and sodium sulfate (31 mg, 0.22 mmol) in acetonitrile (8 mL). The reaction mixture was heated at 80° C. for 5 hours then stirred at ambient temperature overnight. The reaction mixture was treated with 6 M HCl (1 mL) and water (1 mL) and stirred for 15 minutes. The reaction mixture was partitioned between EtOAc and water. The EtOAc was washed with brine, dried over MgSO$_4$, filtered, and evaporated. The residue was chromatographed on a Biotage 10 g SNAP column with a 10% to 60% EtOAc:hexane gradient to afford 3-((2,2-difluoro-1-oxo-7-((trifluoromethyl)sulfonyl)-2,3-dihydro-1H-inden-4-yl)oxy)-5-fluorobenzonitrile (55 mg, 0.13 mmol, 58% yield) as a colorless oil.

Step D: (S)-3-((2,2-difluoro-1-hydroxy-7-((trifluoromethyl)sulfonyl)-2,3-dihydro-1H-inden-4-yl)oxy)-5-fluorobenzonitrile (Compound 8): RuCl(p-cymene)[(R,R)-Ts-DPEN] (1.6 mg, 0.0025 mmol) was added to a nitrogen-sparged ice-cold solution of 3-((2,2-difluoro-1-oxo-7-((trifluoromethyl)sulfonyl)-2,3-dihydro-1H-inden-4-yl)oxy)-5-fluorobenzonitrile (55 mg, 0.13 mmol), formic acid (0.006 mL, 0.16 mmol), and triethylamine (0.02 mL, 0.14 mmol) in dichloromethane (5 mL). The vial was sealed and stored at 4° C. overnight. The reaction mixture was evaporated. The residue was chromatographed on a Biotage 10 g SNAP column with a 10% to 60% EtOAc:hexane gradient to afford Compound 8 (45 mg, 0.1 mmol, 81% yield) as a colorless glass that solidified to a white solid. $^1$H NMR (400 MHz, CDCl$_3$): δ 7.95 (d, 1H), 7.35-7.31 (m, 1H), 7.26-7.23 (m, 1H), 7.15-7.11 (m, 1H), 6.99 (d, 1H), 5.46-5.39 (m, 1H), 3.63-3.41 (m, 2H), 3.36 (d, 1H). m/z (ES-API-neg) [M−H]=436. 93% e.e. based on the Mosher ester analysis of the trifluoromethyl resonance.

Example 9

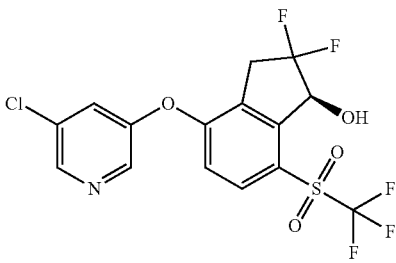 [SMILES: O=S(=O)(c1ccc(Oc2cncc(Cl)c2)c2c1[C@H](O)C(F)(F)C2)C(F)(F)F]

(S)-4-((5-Chloropyridin-3-yl)oxy)-2,2-difluoro-7-((trifluoromethyl)sulfonyl)-2,3-dihydro-1H-inden-1-ol (Compound 9): $^1$H NMR (400 MHz, CDCl$_3$): δ 8.55 (d, 1H), 8.40 (d, 1H), 7.91 (d, 1H), 7.52 (t, 1H), 6.94 (d, 1H), 5.46-5.40 (m, 1H), 3.85 (d, 1H), 3.66-3.47 (m, 2H). m/z (ES-API-pos) [M+H]=430. 95% e.e. based on the Mosher ester analysis of the trifluoromethyl resonance.

Example 10

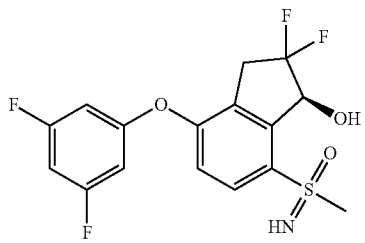 [SMILES: CS(=N)(=O)c1ccc(Oc2cc(F)cc(F)c2)c2c1[C@H](O)C(F)(F)C2]

((S)-7-(3,5-Difluorophenoxy)-2,2-difluoro-3-hydroxy-2,3-dihydro-1H-inden-4-yl)(imino)(methyl)-λ$^6$-sulfanone (Compound 10)

Step A: (7-(3,5-Difluorophenoxy)-3-oxo-2,3-dihydro-1H-inden-4-yl)(imino)(methyl)-λ$^6$-sulfanone: Dess-Martin periodinane (192 mg, 0.452 mmol) was added to a solution of (7-(3,5-Difluorophenoxy)-3-hydroxy-2,3-dihydro-1H-inden-4-yl)(imino)(methyl)-λ$^6$-sulfanone (69 mg, 0.2 mmol) in dichloromethane (10 mL). The mixture was stirred at ambient temperature. After 15 minutes, the reaction mixture was evaporated and the residue was partitioned between EtOAc and a mixture of 1 M sodium thiosulfate and saturated aqueous NaHCO$_3$. The EtOAc was washed with saturated aqueous NaHCO$_3$, brine, dried over MgSO$_4$, filtered, and evaporated. The residue was chromatographed on a Biotage 10 g SNAP column with a 80% to 100% EtOAc:hexane gradient to afford the desired ketone product. An adduct of the desired product and the periodinane (49 mg) was also obtained. The adduct was taken up in methanol (3 mL) and treated with 1 M HCl (10 drops). After 10 minutes, the reaction mixture was evaporated and the residue was partitioned between EtOAc and dilute NaHCO$_3$. The EtOAc was washed with brine, dried over MgSO$_4$, filtered, and evaporated. The residue was chromatographed on a Biotage 10 g SNAP column with a 80% to 100% EtOAc:hexane gradient. Desired fractions were evaporated and combined with the previously obtained product to afford (7-(3,5-difluorophenoxy)-3-oxo-2,3-dihydro-1H-inden-4-yl)(imino)(methyl)-λ$^6$-sulfanone (36 mg, 0.11 mmol, 53% yield) as a white solid. m/z (ES-API-pos) [M+H]=338.

Step B: (3-(Butylimino)-7-(3,5-difluorophenoxy)-2,3-dihydro-1H-inden-4-yl)(imino)(methyl)-λ$^6$-sulfanone: Trifluoroacetic acid (0.0013 mL, 0.02 mmol) was added to a solution of (7-(3,5-difluorophenoxy)-3-oxo-2,3-dihydro-1H-inden-4-yl)(imino)(methyl)-λ$^6$-sulfanone (27.9 mg, 0.08 mmol) and butan-1-amine (0.41 mL, 4.1 mmol) in benzene (10 mL). The mixture was refluxed with a Hickman still attached. After 6 hours, the reaction mixture was evaporated and the residue was partitioned between EtOAc and saturated aqueous NaHCO$_3$. The EtOAc was washed with brine, dried over MgSO$_4$, filtered, and evaporated to afford (3-(butylimino)-7-(3,5-difluorophenoxy)-2,3-dihydro-1H-inden-4-yl)(imino)(methyl)-λ$^6$-sulfanone (32 mg, 0.08 mmol, 100% yield) as a yellow film.

Step C: (7-(3,5-Difluorophenoxy)-2,2-difluoro-3-oxo-2,3-dihydro-1H-inden-4-yl)(imino)(methyl)-λ$^6$-sulfanone: 1-(Chloromethyl)-4-fluoro-1,4-diazoniabicyclo[2.2.2]octane ditetrafluoroborate (72 mg, 0.2 mmol) was added to a mixture of crude (3-(butylimino)-7-(3,5-difluorophenoxy)-2,3-dihydro-1H-inden-4-yl)(imino)(methyl)-λ$^6$-sulfanone (32 mg, 0.08 mmol) and sodium sulfate (11.6 mg, 0.08 mmol) in acetonitrile (3 mL). The reaction mixture was heated at 80° C. for 6 hours, then stirred at ambient temperature overnight. The mixture was treated with 6 M HCl (0.5 mL) and water (1 mL), and stirred for 15 minutes. The reaction mixture was partitioned between EtOAc and water. The EtOAc was washed with brine, dried over MgSO$_4$, filtered, and evaporated. The residue was chromatographed on a Biotage 10 g SNAP column with a 40% to 100% EtOAc:hexane gradient to afford (7-(3,5-difluorophenoxy)-2,2-difluoro-3-oxo-2,3-dihydro-1H-inden-4-yl)(imino)(methyl)-λ$^6$-sulfanone (13.7 mg, 0.04 mmol, 45% yield) as a pale yellow glass. m/z (ES-API-pos) [M+H]=374.

Step D: ((S)-7-(3,5-Difluorophenoxy)-2,2-difluoro-3-hydroxy-2,3-dihydro-1H-inden-4-yl)(imino)(methyl)-λ$^6$-sulfanone (Compound 10): RuCl(p-cymene)[(R,R)-Ts-DPEN] (0.47 mg, 0.0007 mmol) was added to a nitrogen-sparged ice-cold solution of (7-(3,5-difluorophenoxy)-2,2-difluoro-3-oxo-2,3-dihydro-1H-inden-4-yl)(imino)(methyl)-λ$^6$-sulfanone (13.7 mg, 0.037 mmol), formic acid (0.0035 mL, 0.09 mmol), and triethylamine (0.01 mL, 0.07 mmol) in dichloromethane (5 mL). The mixture was stored at 4° C. overnight. The reaction mixture was evaporated and the residue was chromatographed on a Biotage 10 g SNAP column with a 40% to 100% EtOAc:hexane gradient to afford Compound 10 (10 mg, 0.028 mmol, 76% yield) as a colorless film. $^1$H NMR (400 MHz, CDCl$_3$): δ 7.96-7.89 (m, 1H), 7.03-6.98 (m, 1H), 6.73-6.66 (m, 1H), 6.63-6.55 (m, 2H), 5.62-5.56 (m, 1H), 5.47-5.41 (m, 1H), 3.57-3.30 (m, 2H), 3.28 (s, 3H) 3.24-2.88 (m, 1H). m/z (ES-API-pos) [M+H]=376.

Example 11

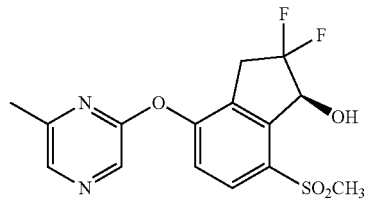 [SMILES: Cc1cncc(Oc2ccc(S(C)(=O)=O)c3c2CC(F)(F)[C@H]3O)n1]

(S)-2,2-Difluoro-4-((6-methylpyrazin-2-yl)oxy)-7-(methylsulfonyl)-2,3-dihydro-1H-inden-1-ol (Compound 11): LCMS ESI (−) m/z (M+HCOOH—H) 401; ¹H NMR (400 MHz, CDCl₃) δ 8.31 (s, 1H), 8.28 (s, 1H), 7.94 (d, 1H), 7.33 (d, 1H), 5.61-5.58 (m, 1H), 3.57 (d, 1H), 3.51-3.28 (m, 2H), 3.24 (s, 3H), 2.44 (s, 3H).

Example 12

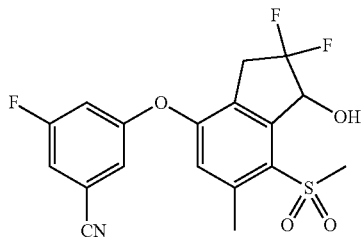 [SMILES: Cc1cc(Oc2cc(F)cc(C#N)c2)c2c(c1S(C)(=O)=O)C(O)C(F)(F)C2]

3-((2,2-Difluoro-1-hydroxy-6-methyl-7-(methylsulfonyl)-2,3-dihydro-1H-inden-4-yl)oxy)-5-fluorobenzonitrile (Compound 12): ¹HNMR (400 MHz, CDCl₃): δ 7.22-7.25 (m, 1H), 7.08 and 7.12 (m 1H), 6.98-7.04 (m 1H), 6.80 (s, 1H), 5.58 and 5.78 (m 1H), 3.69 (d, 1H), 3.20 and 3.23 (s, 3H), 3.08-3.47 (m, 2H), 2.68 (s, 3H).

Example 13

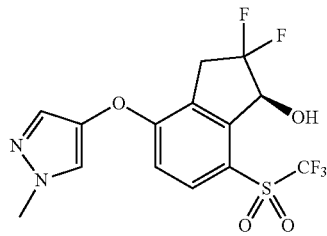 [SMILES: Cn1cc(Oc2ccc(S(=O)(=O)C(F)(F)F)c3c2CC(F)(F)[C@H]3O)cn1]

(S)-2,2-Difluoro-4-((1-methyl-1H-pyrazol-4-yl)oxy)-7-((trifluoromethyl)sulfonyl)-2,3-dihydro-1H-inden-1-ol (Compound 13): LC-MS ESI (+) m/z 399 (M+H); ¹HNMR (400 MHz, CDCl₃): δ 7.87 (d, 1H), 7.40 (s, 1H), 7.36 (s, 1H), 7.08 (d, 1H), 5.42-5.38 (m, 1H), 3.94 (s, 3H), 3.59-3.52 (m, 2H), 3.21 (d, 1H).

Example 14

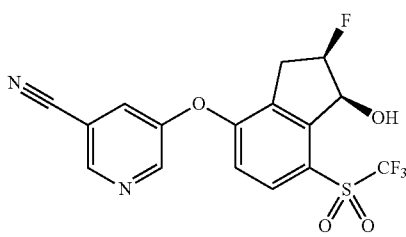 [SMILES: N#Cc1cncc(Oc2ccc(S(=O)(=O)C(F)(F)F)c3c2C[C@@H](F)[C@H]3O)c1]

5-(((1S,2R)-2-Fluoro-1-hydroxy-7-((trifluoromethyl)sulfonyl)-2,3-dihydro-1H-inden-4-yl)oxy)nicotinonitrile (Compound 14)

Step A: Preparation of 5-[7'-(trifluoromethylsulfonyl)spiro[1,3-dioxolane-2,1'-indane]-4'-yl]oxypyridine-3-carbonitrile: Cesium carbonate (1.93 g, 5.94 mmol) was added all at once to 4'-fluoro-7'-(trifluoromethylsulfonyl)spiro[1,3-dioxolane-2,1'-indane] (775 mg, 2.38 mmol) and 3-cyano-5-hydroxypyridine (371 mg, 3.1 mmol) in 1-methyl-2-pyrrolidone (15 mL) then warmed to 100° C. for 90 minutes. The reaction mixture was diluted with water, extracted with methyl t-butyl ether, washed with brine, dried over Na₂SO₄, filtered and concentrated in vacuo. Crude 5-[7'-(trifluoromethylsulfonyl)spiro[1,3-dioxolane-2,1'-indane]-4'-yl]oxypyridine-3-carbonitrile was used without further purification. LC-MS ESI (+) m/z 427 (M+H).

Step B: Preparation of 5-[1-oxo-7-(trifluoromethylsulfonyl)indan-4-yl]oxypyridine-3-carbonitrile: Concentrated HCl (3.24 mL, 9.38 mmol) was added to 5-[7'-(trifluoromethylsulfonyl)spiro[1,3-dioxolane-2,1'-indane]-4'-yl]oxypyridine-3-carbonitrile (1.0 g, 2.35 mmol) in acetone (15 mL) at room temperature and stirred for 4 hours. The reaction mixture was quenched with saturated NaHCO₃, extracted with ethyl acetate, washed with brine, dried over MgSO₄, filtered and concentrated in vacuo. The residue was purified on silica gel (25 g SNAP Ultra, 14 CV, 20-100% ethyl acetate/hexane) affording 5-[1-oxo-7-(trifluoromethylsulfonyl)indan-4-yl]oxypyridine-3-carbonitrile (737 mg, 1.93 mmol, 82% yield). LC-MS ESI (+) m/z 383 (M+H).

Step C: Preparation of 5-[2-fluoro-1-oxo-7-(trifluoromethylsulfonyl)indan-4-yl]oxypyridine-3-carbonitrile: 1-Chloromethyl-4-fluoro-1,4-diazoniabicyclo[2.2.2]octane bis(tetrafluoroborate) (499 mg, 1.4 mmol) was added all at once to 5-[1-oxo-7-(trifluoromethylsulfonyl)indan-4-yl]oxypyridine-3-carbonitrile (269 mg, 0.7 mmol) in 2-propanol (10 mL) at room temperature then warmed to reflux until the reaction was complete as judged by LC-MS. The reaction mixture was diluted with water, extracted with ethyl acetate, washed with brine, dried over Na₂SO₄, filtered and dried in vacuo. The residue was purified on silica gel (10 g SNAP Ultra, 14 CV, 20-100% ethyl acetate/hexane) affording 5-[2-fluoro-1-oxo-7-(trifluoromethylsulfonyl)indan-4-yl]oxypyridine-3-carbonitrile (260 mg, 0.65 mmol, 92% yield). LC-MS ESI (−) m/z 399 (M−H).

Step D: Preparation of 5-[(1S,2R)-2-fluoro-1-hydroxy-7-(trifluoromethylsulfonyl)indan-4-yl]oxypyridine-3-carbonitrile (Compound 14): Chloro{[(1R,2R)-(−)-2-amino-1,2-diphenylethyl] (4-toluenesulfonyl)amido}(p-cymene)ruthenium(II) (2.1 mg, 0.007 mmol) was added all at once to an ice cold mixture of 5-[2-fluoro-1-oxo-7-(trifluoromethylsulfonyl)indan-4-yl]oxypyridine-3-carbonitrile (130 mg, 0.32 mmol), triethylamine (91 μL, 0.65 mmol) and formic acid (37 μL, 0.97 mmol) in dichloromethane (5 mL) then sealed with a teflon cap and placed in a 4° C. refridgerator overnight. The reaction mixture was purified directly on silica gel (10 g SNAP Ultra, 14 CV, 20-100% ethyl acetate/hexane) affording Compound 14 (112 mg, 0.28 mmol, 86% yield). LC-MS ESI (−) m/z 401 (M−H); ¹HNMR (400 MHz, CDCl₃): δ 8.82 (d, 1H), 8.70 (d, 1H), 7.95 (d, 1H), 7.71-7.69 (m, 1H), 6.94 (d, 1H), 5.64-5.59 (m, 1H), 5.46-5.31 (m, 1H), 3.36-3.27 (m, 2H), 3.19 (d, 1H).

Example 15

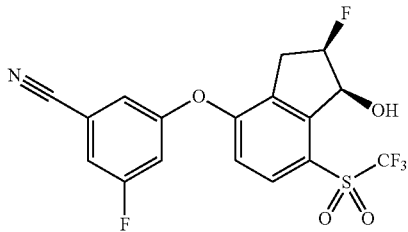 [SMILES: N#Cc1cc(F)cc(Oc2ccc(S(=O)(=O)C(F)(F)F)c3c2C[C@@H](F)[C@H]3O)c1]

3-Fluoro-5-(((1S,2R)-2-fluoro-1-hydroxy-7-((trifluoromethyl)sulfonyl)-2,3-dihydro-1H-inden-4-yl)oxy)benzonitrile (Compound 15): LC-MS ESI (−) m/z 464 (M+HCO$_2^-$); $^1$HNMR (400 MHz, CDCl$_3$): δ 7.94 (d, 1H), 7.31-7.29 (m, 1H), 7.21 (s, 1H), 7.11-7.08 (m, 1H), 6.98 (d, 1H), 5.62-5.58 (m, 1H), 5.40-5.27 (m, 1H), 3.40-3.26 (m, 2H), 3.20 (d, 1H).

Example 16

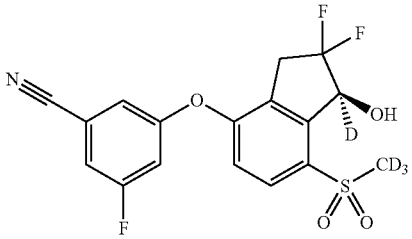 [SMILES: [2H]C([2H])([2H])S(=O)(=O)c1ccc(Oc2cc(F)cc(C#N)c2)c2c1[C@]([2H])(O)C(F)(F)C2]

3-[(1S)-1-Deuterio-2,2-difluoro-1-hydroxy-7-(trideuteriomethylsulfonyl)indan-4-yl]oxy-5-fluorobenzonitrile (Compound 16)

Step A: Preparation of 2-hydroxy-5-(trideuteriomethylsulfanyl)benzaldehyde: To a suspension of 4-(trideuteriomethylsulfanyl)phenol (13.9 g, 77.4 mmol) and paraformaldehyde (13.9 g, 464 mmol) in acetonitrile (55 mL) at 0° C. was added magnesium chloride (11.8 g, 124 mmol) followed by triethylamine (27 mL, 193 mmol). The reaction mixture was then warmed to 68° C. in an oil bath until complete as judged by LC-MS (2.5 hours). The yellow reaction mixture was cooled to 0° C. then quenched by the dropwise addition of 1 N HCl (60 mL), and extracted with methyl t-butyl ether (3×60 mL). Solids was removed by filtration. The organic layer was washed with brine, dried over MgSO$_4$, filtered and concentrated in vacuo. The residue was separated and washed with methyl t-butyl ether and then dried in vacuo affording 2-hydroxy-5-(trideuteriomethylsulfanyl)benzaldehyde. Remaining crude material in the mother liquor was purified on silica gel (100 g SNAP Ultra, 14 CV, 5-100% ethyl acetate/hexane) affording 2-hydroxy-5-(trideuteriomethylsulfanyl)benzaldehyde as a yellow solid.

Step B: Preparation of 2-oxo-6-(trideuteriomethylsulfanyl)chromene-3 carboxylic acid: To a solution of 2-hydroxy-5-(trideuteriomethylsulfanyl)benzaldehyde (4.65 g, 27 mmol) and 2,2-dimethyl-1,3-dioxane-4,6-dione (3.91 g, 27 mmol) in 95% ethanol (70 mL) was added potassium phosphate tribasic (0.58 g, 2.7 mmol) in water (210 mL) at ambient temperature. The mixture was stirred at ambient temperature for 1 hour (slightly exothermic). The reaction mixture was acidified with 1 N HCl to pH ~3-4. The solid was collected by filtration, washed with water and then 5:1 hexane/methyl t-butyl ether and dried to give 2-oxo-6-(trideuteriomethylsulfanyl)chromene-3-carboxylic acid (5.95 g, 25 mmol, 92% yield) as yellow solid.

Step C: Preparation of 3-[2-hydroxy-5-(trideuteriomethylsulfanyl)phenyl]propanoic acid: Triethylamine (8.3 mL, 60 mmol) was added slowly to formic acid (5.6 mL, 149 mmol) in N,N-dimethylformamide (12 mL) at 0° C. The mixture was warmed to 100° C. (internal) then 2-oxo-6-(trideuteriomethylsulfanyl)chromene-3-carboxylic acid (5.95 g, 24.9 mmol) was added in 5 portions (~1.2 g per 5 minutes). After the addition (ca. 30 minutes), the reaction mixture was stirred at 100° C. (internal) for 1 hour. After cooling to ambient temperature, 6N NaOH (49.74 mL, 149.2 mmol) was added. The reaction mixture was stirred at ambient temperature for 30 minutes. Methyl t-butyl ether (40 mL) was added. The aqueous layer was separated, acidified with concentrated HCl to pH ~3-4 and extracted with methyl t-butyl ether (3×50 mL). The combined organic layer was washed with brine, dried (sodium sulfate), filtered and concentrated under reduced pressure to give 3-[2-hydroxy-5-(trideuteriomethylsulfanyl)phenyl]propanoic acid (4.8 g, 22.4 mmol, 90% yield), which was used directly in the next step without purification.

Step D: Preparation of 3-[2-(3-cyano-5-fluoro-phenoxy)-5 (trideuteriomethylsulfanyl)phenyl]propanoic acid: A suspension of 3-[2-hydroxy-5-(trideuteriomethylsulfanyl)phenyl]propanoic acid (4.82 g, 22.4 mmol), 3,5-difluorobenzonitrile (6.23 g, 44.8 mmol), and cesium carbonate (16.1 g, 49.3 mmol) in dimethyl sulfoxide (22 mL) was stirred at 72.6° C. (internal) for 7 h. After cooling to ambient temperature, water (50 mL) and MTBE (50 mL) were added. The organic layer was separated, the aqueous layer was acidified with 1 N HCl to pH~3-4 with stirring and extracted with ethyl acetate (3×50 mL). The organic layers were combined and washed with brine (30 mL), dried over Na$_2$SO$_4$, filtered and concentrated in vacuo affording 3-[2-(3-cyano-5-fluoro-phenoxy)-5-(trideuteriomethylsulfanyl)phenyl]propanoic acid, which was used in the next step without further purification. LC-MS ESI (−) m/z 333 (M−H).

Step E: Preparation of 3-fluoro-5-[1-oxo-7-(trideuteriomethylsulfanyl)indan-4-yl]oxy-benzonitrile: DMF (10 μL) was added to 3-[2-(3-cyano-5-fluoro-phenoxy)-5-(trideuteriomethylsulfanyl)phenyl]propanoic acid (7.48 g, 22.4 mmol) in dichloromethane (40 mL) at room temperature followed by oxalyl chloride (2.1 mL, 24.6 mmol). The reaction mixture was stirred for 2.5 hours then added dropwise to trichloroalumane (5.97 g, 44.7 mmol) in dichloromethane (40 mL) and stirred for 1 hour. The reaction mixture was then cooled to 0° C., quenched dropwise with 1 N HCl (20 mL), and extracted with dichloromethane (3×50 mL). The organic layer was washed with saturated NaHCO$_3$ (50 mL), brine (30 mL), dried over MgSO$_4$, filtered through a pad of silica gel, washed with 1:1 dichloromethane/methyl t-butyl ether and concentrated in vacuo. The residue was suspended in 2:1 acetonitrile/water (35 mL) and stirred for 30 minutes, filtered, washed with 2:1 MeCN/water (10 mL) and then dried in vacuo affording 3-fluoro-5-[1-oxo-7-(trideuteriomethylsulfanyl)indan-4-yl]oxy-benzonitrile (5.0 g, 15.8 mmol, 71% yield over two steps). LC-MS ESI (+) m/z 317 (M+H).

Step F: Preparation of 3-fluoro-5-[1-oxo-7-(trideuteriomethylsulfonyl)indan-4-yl]oxy-benzonitrile: Oxone® (21.4 g, 34.8 mmol) was added all at once to a suspension of 3-fluoro-5-[1-oxo-7 (trideuteriomethylsulfanyl)indan-4-yl]oxy-benzonitrile (5.0 g, 15.8 mmol) in a mixture of acetonitrile (50 mL) and water (25 mL) at room temperature. The reaction mixture was stirred overnight. Solids were removed by filtration then the acetonitrile was removed in vacuo. The residue was suspended in water (25 mL) and stirred for 30 minutes. The resulting solid was rinsed with water (100 mL), washed with methyl t-butyl ether (50 mL), and then dried in vacuo affording 3-fluoro-5-[1-oxo-7-(trideuteriomethylsulfonyl)indan-4-yl]oxy-benzonitrile (4.8 g, 13.8 mmol, 87% yield) as a yellow solid. LC-MS ESI (+) m/z 349 (M+H).

Step G: Preparation of 3-[2,2-difluoro-1-oxo-7-(trideuteriomethylsulfonyl)indan-4-yl]oxy-5-fluoro-benzonitrile:

3-Methoxypropan-1-amine (913 μL, 9.0 mmol) was added to 3-fluoro-5-[1-oxo-7-(trideuteriomethylsulfonyl)indan-4-yl]oxy-benzonitrile (2.6 g, 7.5 mmol) and 2,2-dimethylpropanoic acid (76 mg, 0.75 mmol) in a mixture of cyclohexane (40 mL) and toluene (40 mL) at room temperature and then warmed to reflux with the azeotropic removal of water via a Dean-Stark trap for 3 hours. The reaction mixture was cooled to room temperature, filtered through a frit, and then concentrated in vacuo to give crude 3-fluoro-5-[(1E/Z)-1-(3-methoxypropylimino)-7-(trideuteriomethylsulfonyl)indan-4-yl]oxy-benzonitrile. A solution of 3-fluoro-5-[(1E/Z)-1-(3-methoxypropylimino)-7-(trideuteriomethylsulfonyl)indan-4-yl]oxy-benzonitrile (3.13 g, 7.5 mmol) in acetonitrile (10 mL) was added dropwise by syringe to Selectfluor® (6.6 g, 18.7 mmol) and sodium sulfate (2.12 g, 14.9 mmol) in acetonitrile (40 mL) at 60° C. then stirred until complete as judged by LC-MS (1 hour). The reaction mixture was cooled to room temperature, and diluted with 50 mL of water. Concentrated HCl (2.5 mL, 30 mmol) was added and the reaction mixture stirred for 1 hour. Acetonitrile was removed in vacuo then solids were filtered, washed with water, methyl t-butyl ether and then dried in vacuo affording 3-[2,2-difluoro-1-oxo-7-(trideuteriomethylsulfonyl)indan-4-yl]oxy-5-fluoro-benzonitrile (2.2 g, 5.7 mmol, 77% yield). LC-MS ESI (+) m/z 402 (M+NH$_4^+$).

Step H: Preparation of 3-[(1S)-1-deuterio-2,2-difluoro-1-hydroxy-7-(trideuteriomethylsulfonyl)indan-4-yl]oxy-5-fluoro-benzonitrile (Compound 16): RuCl(p-cymene)[(R,R)-Ts-DPEN] (58 mg, 0.09 mmol) was added all at once to an ice cold solution of 3-[2,2-difluoro-1-oxo-7-(trideuteriomethylsulfonyl)indan-4-yl]oxy-5-fluoro-benzonitrile (3.53 g, 9.17 mmol), triethylamine (2.56 mL, 18.4 mmol) and deuterio deuterioformate (1.09 mL, 27.6 mmol). The reaction flask was sealed with a rubber septum with a limp balloon and placed in a 4° C. refridgerator overnight. The reaction mixture was concentrated in vacuo until 10 mL of solvent remained then purified directly on silica gel (25 g SNAP Ultra, 14 CV, 10-60% EtOAc/hexane) affording Compound 16, which was further purified by dissolving in refluxing 95% ethanol (10 mL) then slowly cooled to room temperature with stirring to give a white crystalline solid (2.44 g, 6.3 mmol, 69% yield). LC-MS ESI (−) m/z 432 (M+HCO$_2^-$); $^1$HNMR (400 MHz, CDCl$_3$): δ 7.92 (d, 1H), 7.26-7.24 (m, 1H), 7.15 (s, 1H), 7.06-7.03 (m, 1H), 7.01 (d, 1H), 3.56-3.35 (m, 3H).

Example 17

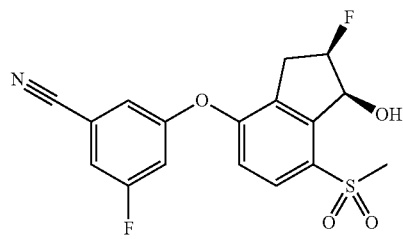 [SMILES: CS(=O)(=O)c1ccc(Oc2cc(F)cc(C#N)c2)c2c1[C@H](O)[C@H](F)C2]

3-Fluoro-5-(((1S,2R)-2-fluoro-1-hydroxy-7-(methylsulfonyl)-2,3-dihydro-1H-inden-4-yl)oxy)benzonitrile (Compound 17)

Step A: Preparation of 3-fluoro-5-((2-fluoro-7-(methylsulfonyl)-1-oxo-2,3-dihydro-1H-inden-4-yl)oxy)benzonitrile: Selectfluor® (18.1 g, 51 mmol) was added all at once to 3-fluoro-5-(7-methylsulfonyl-1-oxo-indan-4-yl)oxy-benzonitrile (11 g, 31.9 mmol) in methanol (300 mL) at room temperature and then warmed to reflux for 24 hours. The reaction mixture was cooled to room temperature, and filtered. The solids was washed with ethyl acetate then the filtrate was concentrated in vacuo. The residue was dissolved in ethyl acetate, washed with 1 N HCl and brine, dried over Na$_2$SO$_4$, filtered and concentrated in vacuo affording 3-fluoro-5-(2-fluoro-7-methylsulfonyl-1-oxo-indan-4-yl)oxy-benzonitrile as a light yellow foam which was used without further purification. LC-MS ESI (+) m/z 364 (M+H).

Step B: Preparation of 3-fluoro-5-(((1S,2R)-2-fluoro-1-hydroxy-7-(methylsulfonyl)-2,3-dihydro-1H-inden-4-yl)oxy)benzonitrile (Compound 17): RuCl(p-cymene)[(R,R)-Ts-DPEN] (203 mg, 0.32 mmol) was added all at once to an ice cold solution of 3-fluoro-5-(2-fluoro-7-methylsulfonyl-1-oxo-indan-4-yl)oxy-benzonitrile (11.6 g, 31.8 mmol), triethylamine (8.9 mL, 63.7 mmol) and formic acid (3.6 mL, 95.5 mmol) in dichloromethane (200 mL). The reaction flask was sealed with a septum equipped with a limp balloon and placed in a 4° C. refridgerator overnight. The reaction mixture was poured into saturated NaHCO$_3$, extracted with dichloromethane, washed with brine, dried over Na$_2$SO$_4$, filtered and concentrated in vacuo until 25 mL of solvent remained. Approximately 50% of the material precipitated on top of the column (100 g SNAP Ultra, 14 CV, 15-80% ethyl acetate/hexanes). The solid was removed and the material absorbed on the column was purified. The precipitated material was dissolved in 250-300 mL of warm dichloromethane then purified on a plug of silica gel eluting with 50% then 60% ethyl acetate/hexane affording Compound 17 (9.65 g, 26.4 mmol, 83% yield over two steps) as an off-white solid. Enantiomeric excess was determined by chiral HPLC (>99% ee). LC-MS ESI (+) m/z 383 (M+NH$_4^+$); $^1$HNMR (400 MHz, CDCl$_3$): δ 7.92 (d, 1H), 7.21-7.20 (m, 1H), 7.12-7.11 (m, 1H), 7.03-6.98 (m, 2H), 5.71-5.65 (m, 1H), 5.46-5.33 (m, 1H), 3.66 (dd, 1H), 3.31 (s, 3H), 3.27-3.05 (m, 2H).

Example 18

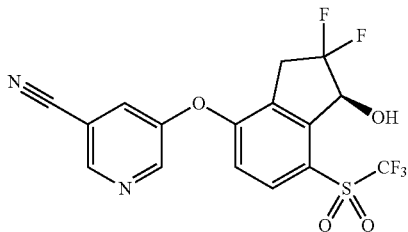 [SMILES: N#Cc1cncc(Oc2ccc(S(=O)(=O)C(F)(F)F)c3c2CC(F)(F)[C@H]3O)c1]

(S)-5-((2,2-Difluoro-1-hydroxy-7-((trifluoromethyl)sulfonyl)-2,3-dihydro-1H-inden-4-yl)oxy)nicotinonitrile (Compound 18): LC-MS ESI (–) m/z 419 (M–H). $^1$HNMR (400 MHz, CDCl$_3$): δ 8.84 (d, 1H), 8.73 (d, 1H), 7.96 (d, 1H), 7.75-7.74 (m, 1H), 6.95 (d, 1H), 5.45 (dd, 1H), 3.64-3.48 (m, 2H), 3.31 (d, 1H).

Example 19

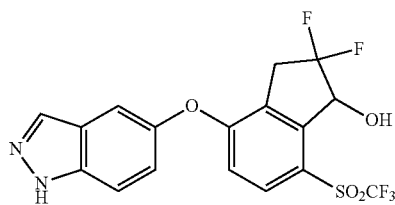

4-((1H-Indazol-5-yl)oxy)-2,2-difluoro-7-((trifluoromethyl)sulfonyl)-2,3-dihydro-1H-inden-1-ol (Compound 19)

Step A: 4-Fluoro-7-((trifluoromethyl)sulfonyl)-2,3-dihydrospiro[indene-1,2'-[1,3]dioxolane]: Trimethylsily trifluoromethanesulfonate (10.6 g, 47.8 mmol) was added dropwise to a solution of 4-fluoro-7-(trifluoromethylsulfonyl)indan-1-one (27 g, 95.7 mmol) and trimethyl(2-trimethylsilyloxyethoxy)silane (23.7 g, 115 mmol) in dichloromethane (500 mL) at −78° C. The reaction mixture was allowed to warm to room temperature. After 2 hours, the reaction was then quenched with triethylamine and evaporated. The residue was taken up in EtOAc (500 mL) and the organic layer was washed with 2×200 mL water then 1×500 mL saturated brine solution. The organic layer was separated, dried (NaSO$_4$), and concentrated to dryness. The crude was purified by flash column chromatography eluting with 20% EtOAc in hexane to give 4-fluoro-7-((trifluoromethyl)sulfonyl)-2,3-dihydrospiro[indene-1,2'-[1,3]dioxolane] (2.1 g, 6.4 mmol, 55% yield) as a white solid.

Step B: 5-((7-((Trifluoromethyl)sulfonyl)-2,3-dihydrospiro[indene-1,2'-[1,3]dioxolan]-4-yl)oxy)-1H-indazole: Sodium hydrogen carbonate (64.4 mg, 0.77 mmol) was added to a vial containing 4-fluoro-7-((trifluoromethyl)sulfonyl)-2,3-dihydrospiro[indene-1,2'-[1,3]dioxolane] (100 mg, 0.31 mmol) and 1H-indazol-5-ol (61.7 mg, 0.46 mmol) in DMF (2.5 mL). The sealed vial was heated at 80° C. for a total of 10.5 hours. The reaction mixture was diluted with water and the resulting solid was collected by vacuum filtration. The solid was chromatographed on a Biotage 10 g SNAP column with a 10% to 80% EtOAc:hexane gradient to afford 5-((7-((trifluoromethyl)sulfonyl)-2,3-dihydrospiro[indene-1,2'-[1,3]dioxolan]-4-yl)oxy)-1H-indazole (59 mg, 0.133 mmol, 43% yield. m/z (ES-API-pos) [M+1]=441.

Step C: 4-((1H-indazol-5-yl)oxy)-7-((trifluoromethyl)sulfonyl)-2,3-dihydro-1H-inden-1-one: Hydrochloric acid (6 M, 0.066 mL, 0.4 mmol) was added to a solution of 5-((7-((trifluoromethyl)sulfonyl)-2,3-dihydrospiro[indene-1,2'-[1,3]dioxolan]-4-yl)oxy)-1H-indazole (59 mg, 0.13 mmol) in acetone (3.0 mL) and water (0.50 mL). The mixture was stirred at 50° C. After 3.5 hours, the reaction mixture was evaporated and the residue was partitioned between EtOAc and dilute aqueous NaHCO$_3$. The EtOAc was washed with brine, dried over MgSO$_4$, filtered, and evaporated to afford 4-((1H-indazol-5-yl)oxy)-7-((trifluoromethyl)sulfonyl)-2,3-dihydro-1H-inden-1-one (48 mg, 0.12 mmol, 91% yield as a pale yellow film. m/z (ES-API-pos) [M+H]=397.

Step D: (E/Z)-4-((1H-Indazol-5-yl)oxy)-N-(3-methoxypropyl)-7-((trifluoromethyl)sulfonyl)-2,3-dihydro-1H-inden-1-imine 2,2-dimethylpropanoic acid (2.5 mg, 0.024 mmol) was added to a mixture of 4-((1H-indazol-5-yl)oxy)-7-((trifluoromethyl)sulfonyl)-2,3-dihydro-1H-inden-1-one (48 mg, 0.12 mmol) and 3-methoxypropan-1-amine (0.03 mL, 0.3 mmol) in toluene (4 mL) and cyclohexane (4 mL). The reaction mixture was refluxed with a Hickman still attached. After 5 hours, the cooled reaction mixture was evaporated and the residue was used as is in the next step.

Step E: 4-((1H-Indazol-5-yl)oxy)-2,2-difluoro-7-((trifluoromethyl)sulfonyl)-2,3-dihydro-1H-inden-1-one: 1-(Chloromethyl)-4-fluoro-1,4-diazoniabicyclo[2.2.2]octane ditetrafluoroborate (Selectfluor®, 106 mg, 0.3 mmol) was added to a flask containing (/ZE)-4-((1H-indazol-5-yl)oxy)-N-(3-methoxypropyl)-7-((trifluoromethyl)sulfonyl)-2,3-dihydro-1H-inden-1-imine (56 mg, 0.12 mmol) and sodium sulfate (43 mg, 0.30 mmol) in acetonitrile (5 mL). This was heated at 60° C. After 30 minutes, 1M hydrochloric acid (0.36 mL, 0.36 mmol) was added. The reaction mixture was stirred for 20 minutes, and then partitioned between EtOAc and water. The EtOAc layer was washed with brine, dried over MgSO$_4$, filtered, and evaporated. The residue was chromatographed on a Biotage 10 g SNAP column with a 10% to 60% EtOAc:hexane gradient to afford 4-((1H-indazol-5-yl)oxy)-2,2-difluoro-7-((trifluoromethyl)sulfonyl)-2,3-dihydro-1H-inden-1-one (31 mg, 0.073 mmol, 61% yield). m/z (ES-API-pos) [M+H]=433.

Step F: 4-((1H-Indazol-5-yl)oxy)-2,2-difluoro-7-((trifluoromethyl)sulfonyl)-2,3-dihydro-1H-inden-1-ol (Compound 19): Sodium borohydride (1.6 mg, 0.043 mmol) was added to a solution of 4-((1H-indazol-5-yl)oxy)-2,2-difluoro-7-((trifluoromethyl)sulfonyl)-2,3-dihydro-1H-inden-1-one (18 mg, 0.043 mmol) in methanol (3 mL). After 10 minutes, the reaction mixture was evaporated and the residue was partitioned between EtOAc and water. The EtOAc layer was washed with brine, dried over MgSO$_4$, filtered, and evaporated to afford Compound 19 (18 mg, 0.042 mmol, 98% yield) as a colorless film. $^1$H NMR (400 MHz, CDCl$_3$): δ 10.35 (br s, 1H), 8.14 (s, 1H), 7.82 (d, 1H), 7.61 (d, 1H), 7.51 (d, 1H), 7.21-7.17 (m, 1H), 6.82 (d, 1H), 5.44 (d, 1H), 3.70-3.57 (m, 2H), 3.40 (br s, 1H). m/z (ES-API-pos) [M+H]=435.

Example 20

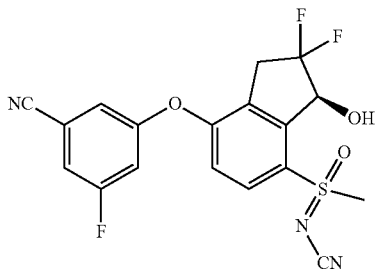 [SMILES: CS(=O)(=NC#N)c1ccc(Oc2cc(F)cc(C#N)c2)c2c1[C@H](O)C(F)(F)C2]

Isomer 1 of N—((S)-7-(3-Cyano-5-fluorophenoxy)-2,2-difluoro-3-hydroxy-2,3-dihydro-1H-inden-4-yl)(methyl)(oxo)-λ⁶-sulfanylidene)cyanamide (Compound 20)

Step A: N-((7-(3-cyano-5-fluorophenoxy)-3-hydroxy-2,3-dihydro-1H-inden-4-yl)(methyl)(oxo)-λ⁶-sulfanylidene)cyanamide: Sodium hydrogen carbonate (79.3 mg, 0.94 mmol) was added to a solution of 3-fluoro-5-hydroxybenzonitrile (86.27 mg, 0.63 mmol) and N-((7-fluoro-3-hydroxy-2,3-dihydro-1H-inden-4-yl)(methyl)(oxo)-λ⁶-sulfanylidene)cyanamide (80 mg, 0.31 mmol) (Example 189, Step C) in DMF (3 mL). The vial was sealed and heated at 100° C. over a weekend. The reaction mixture was partitioned between EtOAc and dilute aqueous NaOH. The EtOAc was washed with water, two portions of brine, dried over MgSO₄, filtered, and evaporated. The residue was chromatographed on a Biotage 25M reverse phase column with a 20% to 90% ACN:water gradient to afford N-((7-(3-cyano-5-fluorophenoxy)-3-hydroxy-2,3-dihydro-1H-inden-4-yl)(methyl)(oxo)-λ⁶-sulfanylidene)cyanamide (80 mg, 0.21 mmol, 69% yield). m/z (ES-API-pos) [M+H]=372.

Step B: N-((7-(3-cyano-5-fluorophenoxy)-3-oxo-2,3-dihydro-1H-inden-4-yl)(methyl)(oxo)-λ⁶-sulfanylidene)cyanamide: Dess-Martin periodinane (192 mg, 0.45 mmol) was added to a solution of N-((7-(3-cyano-5-fluorophenoxy)-3-hydroxy-2,3-dihydro-1H-inden-4-yl)(methyl)(oxo)-λ⁶-sulfanylidene)cyanamide (200 mg, 0.54 mmol) in dichloromethane (50 mL). After 10 minutes, the reaction mixture was evaporated and the residue was partitioned between EtOAc and aqueous sodium thiosulfate and saturated aqueous NaHCO₃. The EtOAc layer was washed with water, brine, dried over MgSO₄, filtered, and evaporated to afford N-((7-(3-cyano-5-fluorophenoxy)-3-oxo-2,3-dihydro-1H-inden-4-yl)(methyl)(oxo)-λ⁶-sulfanylidene)cyanamide (174 mg, 0.47 mmol, 88% yield) as a colorless film. m/z (ES-API-pos) [M+H]=370.

Step C: (E/Z)—N-((7-(3-cyano-5-fluorophenoxy)-3-((3-methoxypropyl)imino)-2,3-dihydro-1H-inden-4-yl)(methyl)(oxo)-λ⁶-sulfanylidene)cyanamide: Pivalic acid (9.4 mg, 0.09 mmol) was added to a mixture of N-((7-(3-cyano-5-fluorophenoxy)-3-oxo-2,3-dihydro-1H-inden-4-yl)(methyl)(oxo)-λ⁶-sulfanylidene)cyanamide (170 mg, 0.46 mmol) and 3-methoxypropylamine (0.12 mL, 1.2 mmol) in cyclohexane (7 mL) and toluene (7 mL). The mixture was heated at reflux with a Hickman still attached. After 1 hour, the reaction mixture was evaporated and the residue was used as is in the next step.

Step D: N-((7-(3-cyano-5-fluorophenoxy)-2,2-difluoro-3-oxo-2,3-dihydro-1H-inden-4-yl)(methyl)(oxo)-λ⁶-sulfanylidene)cyanamide: 1-Chloromethyl-4-fluoro-1,4-diazoniabicyclo[2.2.2]octane bis(tetrafluoroborate) (406 mg, 1.15 mmol) was added to a mixture of (E/Z)—N-((7-(3-cyano-5-fluorophenoxy)-3-((3-methoxypropyl)imino)-2,3-dihydro-1H-inden-4-yl)(methyl)(oxo)-λ⁶-sulfanylidene)cyanamide (202 mg, 0.46 mmol) and sodium sulfate (162 mg, 1.15 mmol) in acetonitrile (5 mL). The mixture was heated at 70° C. After 3.5 hours, the reaction mixture was evaporated and the residue was partitioned between EtOAc and water. The EtOAc was washed with brine, dried over MgSO₄, filtered, and evaporated. The residue was taken up in EtOAc, absorbed on silica gel, and chromatographed on a Biotage 25 g SNAP column with a 50% to 100% EtOAc:hexane gradient to afford N-((7-(3-cyano-5-fluorophenoxy)-2,2-difluoro-3-oxo-2,3-dihydro-1H-inden-4-yl)(methyl)(oxo)-λ⁶-sulfanylidene)cyanamide (48 mg, 0.118 mmol, 26% yield. m/z (ES-API-pos) [M+H]=406.

Step E: N—(((S)-7-(3-cyano-5-fluorophenoxy)-2,2-difluoro-3-hydroxy-2,3-dihydro-1H-inden-4-yl)(methyl)(oxo)-λ⁶-sulfanylidene)cyanamide (Compound 20): RuCl(p-cymene)[(R,R)-Ts-DPEN] (1.5 mg, 0.020 mmol) was added to a nitrogen-sparged, ice-cold solution of N-((7-(3-cyano-5-fluorophenoxy)-2,2-difluoro-3-oxo-2,3-dihydro-1H-inden-4-yl)(methyl)(oxo)-λ⁶-sulfanylidene)cyanamide (49 mg, 0.120 mmol), triethylamine (0.022 mL, 0.16 mmol), and formic acid (0.01 mL, 0.24 mmol) in dichloromethane (5 mL). The flask was placed in a 4° C. refrigerator over a weekend. The reaction mixture was evaporated and the residue was chromatographed on a Biotage 10 g SNAP Ultra column with a 20% to 80% EtOAc:hexane gradient to afford a solid, which was triturated twice with chloroform to afford Compound 20 (8.6 mg, 0.021 mmol, 18% yield) as a single diastereomer in 93% d.e. by chiral chromatography. ¹H NMR (400 MHz, CD₃OD): δ 8.01 (d, 1H), 7.54-7.49 (m, 1H), 7.46-7.44 (m, 1H), 7.40-7.36 (m, 1H), 7.20-7.14 (m, 1H), 5.56 (d, 1H), 3.78-3.61 (m, 1H), 3.62 (s, 3H), 3.55-3.47 (m, 1H). m/z (ES-API-pos) [M+H]=408.

Example 21

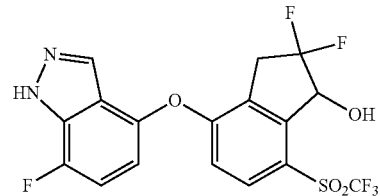

2,2-Difluoro-4-((7-fluoro-1H-indazol-4-yl)oxy)-7-((trifluoromethyl)sulfonyl)-2,3-dihydro-1H-inden-1-ol (Compound 21)

Step A: 2,2-difluoro-4-((7-fluoro-1H-indazol-4-yl)oxy)-7-((trifluoromethyl)sulfonyl)-2,3-dihydro-1H-inden-1-one: 1-(Chloromethyl)-4-fluoro-1,4-diazoniabicyclo[2.2.2]octane ditetrafluoroborate (129 mg, 0.36 mmol) was added to a flask containing (E/Z)-4-((1H-indazol-4-yl)oxy)-N-(3-methoxypropyl)-7-((trifluoromethyl)sulfonyl)-2,3-dihydro-1H-inden-1-imine (68 mg, 0.15 mmol) (Example 243, Step C) and sodium sulfate (52 mg, 0.36 mmol) in acetonitrile (5 mL). The reaction mixture was heated at 70° C. for 6 hour, then stirred at room temperature overnight. Hydrochloric acid (1 M, 0.44 mL, 0.440 mmol) was added. The resulting mixture was stirred for 20 minutes, and partitioned between EtOAc and water. The EtOAc layer was washed with brine, dried over MgSO₄, filtered, and evaporated. The residue was chromatographed on a Biotage 10 g SNAP column with a 10% to 60% EtOAc:hexane gradient to afford 2,2-difluoro-4-((7-fluoro-1H-indazol-4-yl)oxy)-7-((trifluoromethyl)sulfonyl)-2,3-dihydro-1H-inden-1-one (9 mg, 0.02 mmol, 14% yield); m/z (ES-API-neg) [M–H]=449; 441H-indazol-4-yl)oxy)-2,2-difluoro-7-((trifluoromethyl)sulfonyl)-2,3-dihydro-1H-inden-1-one (12 mg, 0.03 mmol, 19% yield), m/z (ES-API-neg) [M–H]=431; and 2,2-difluoro-4-((5-fluoro-1H-indazol-4-yl)oxy)-7-((trifluoromethyl)sulfonyl)-2,3-dihydro-1H-inden-1-one (10 mg, 0.023 mmol, 16% yield); m/z (ES-API-neg) [M–H]=449.

Step B: 2,2-Difluoro-4-((7-fluoro-1H-indazol-4-yl)oxy)-7-((trifluoromethyl)sulfonyl)-2,3-dihydro-1H-inden-1-ol (Compound 21): Sodium borohydride (0.76 mg, 0.020 mmol) was added to a solution of 2,2-difluoro-4-((7-fluoro-1H-indazol-4-yl)oxy)-7-((trifluoromethyl)sulfonyl)-2,3-dihydro-1H-inden-1-one (9 mg, 0.02 mmol) in methanol (3 mL). After 1 hour, the reaction mixture was evaporated and the residue was partitioned between EtOAc and water. The EtOAc was washed with brine, dried over MgSO₄, filtered, and evaporated. The residue was chromatographed on a Biotage 10 g SNAP Ultra column with a 0% to 50% EtOAc:dichloromethane gradient to afford Compound 21 (3.4 mg, 0.0075 mmol, 38% yield) as a colorless film. ¹H NMR (400 MHz, CDCl₃): δ 10.55 (br s, 1H), 7.94 (d, 1H), 7.83 (d, 1H), 7.16-7.10 (m, 1H), 6.86 (d, 1H), 6.83-6.78 (m, 1H), 5.46 (d, 1H), 3.72-3.59 (m, 2H), 3.34 (br s, 1H); m/z (ES-API-pos) [M+1]=453.

Example 22

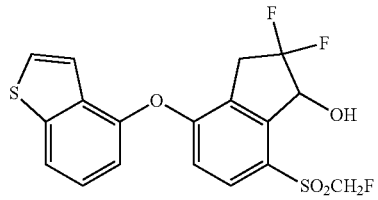

4-(Benzo[b]thiophen-4-yloxy)-2,2-difluoro-7-((fluoromethyl)sulfonyl)-2,3-dihydro-1H-inden-1-ol (Compound 22)

Step A: 4-(Benzo[b]thiophen-4-yloxy)-7-((fluoromethyl)sulfonyl)-2,3-dihydrospiro[indene-1,2'-[1,3]dioxolane]: Sodium hydrogen carbonate (51 mg, 0.6 mmol) was added to a vial containing 4'-fluoro-7'-(fluoromethylsulfonyl)spiro[1,3-dioxolane-2,1'-indane] (70 mg, 0.24 mmol) (Example 63, Step A) and benzothiophen-4-ol (65 mg, 0.43 mmol) in DMF (1.5 mL). The vial was sealed and heated at 110° C. for 9.5 hours, then stirred at room temperature. The reaction mixture was partitioned between EtOAc and water. The EtOAc was washed with 2 portions of brine, dried over MgSO₄, filtered, and evaporated. The residue was chromatographed on a Biotage 10 g SNAP column with a 10% to 80% EtOAc:hexane gradient to afford 4-(benzo[b]thiophen-4-yloxy)-7-((fluoromethyl)sulfonyl)-2,3-dihydrospiro[indene-1,2'-[1,3]dioxolane] (62 mg, 0.15 mmol, 61% yield).

Step B: 4-(Benzo[b]thiophen-4-yloxy)-7-((fluoromethyl)sulfonyl)-2,3-dihydro-1H-inden-1-one: Pyridin-1-ium-4-methylbenzenesulfonate (43 mg, 0.17 mmol) was added to a solution of 4-(benzo[b]thiophen-4-yloxy)-7-((fluoromethyl)sulfonyl)-2,3-dihydrospiro[indene-1,2'-[1,3]dioxolane] (62 mg, 0.15 mmol) in acetone (4 mL) and water (0.50 mL) in a vial. The vial was sealed and heated at 80° C. for 5 hours. The reaction mixture was evaporated and the residue was partitioned between EtOAc and water. The EtOAc was washed with brine, dried over MgSO₄, filtered, and evaporated. The residue was chromatographed on a Biotage 12+M reverse phase column with a 20% to 80% ACN:water gradient to afford 4-(benzo[b]thiophen-4-yloxy)-7-((fluoromethyl)sulfonyl)-2,3-dihydro-1H-inden-1-one (27 mg, 0.072 mmol, 49% yield). m/z (ES-API-pos) [M+H]=377.

Step C: (E/Z)-4-(Benzo[b]thiophen-4-yloxy)-7-((fluoromethyl)sulfonyl)-N-(3-methoxypropyl)-2,3-dihydro-1H-inden-1-imine: 2,2-Dimethylpropanoic acid (2.21 mg, 0.02 mmol) was added to a flask containing a suspension of 4-(benzo[b]thiophen-4-yloxy)-7-((fluoromethyl)sulfonyl)-2,3-dihydro-1H-inden-1-one (27 mg, 0.072 mmol) and 3-methoxypropan-1-amine (0.01 mL, 0.11 mmol) in a mixture of toluene (3 mL) and cyclohexane (3 mL). This was refluxed with a Hickman still attached. After 5 hours, the reaction mixture was evaporated and the crude product was used as is in the next step.

Step D: 4-(Benzo[b]thiophen-4-yloxy)-2,2-difluoro-7-((fluoromethyl)sulfonyl)-2,3-dihydro-1H-inden-1-one: 1-(Chloromethyl)-4-fluoro-1,4-diazoniabicyclo[2.2.2]octane ditetrafluoroborate (63 mg, 0.18 mmol) was added to a vial containing crude (E/Z)-4-(benzo[b]thiophen-4-yloxy)-7-((fluoromethyl)sulfonyl)-N-(3-methoxypropyl)-2,3-dihydro-1H-inden-1-imine (32 mg, 0.07 mmol) and sodium sulfate (25 mg, 0.18 mmol) in acetonitrile (3 mL). The vial was sealed and heated at 80° C. overnight. The reaction mixture was treated with water (1 mL) and HCl (6 M, 0.5 mL), stirred for 15 minutes, and the reaction mixture was partitioned between EtOAc and water. The EtOAc layer was washed with brine, dried over MgSO₄, filtered, and evaporated. The residue was chromatographed on a Biotage 10 g SNAP Ultra column with a 20% to 80% EtOAc:hexane gradient to afford 4-(benzo[b]thiophen-4-yloxy)-2,2-difluoro-7-((fluoromethyl)sulfonyl)-2,3-dihydro-1H-inden-1-one (4 mg, 0.01 mmol, 14% yield). m/z (ES-API-pos) [M+H+H₂O]=430.

Step E: 4-(Benzo[b]thiophen-4-yloxy)-2,2-difluoro-7-((fluoromethyl)sulfonyl)-2,3-dihydro-1H-inden-1-ol (Compound 22): Sodium borohydride (0.5 mg, 0.012 mmol) was added to a solution of 4-(benzo[b]thiophen-4-yloxy)-2,2-difluoro-7-((fluoromethyl)sulfonyl)-2,3-dihydro-1H-inden-1-one (4 mg, 0.012 mmol) in methanol (2 mL). After 20 minutes, the reaction mixture was evaporated and the residue was partitioned between EtOAc and water. The EtOAc layer was washed with brine, dried over MgSO₄, filtered, and evaporated to afford Compound 22 (3.6 mg, 0.009 mmol, 87% yield). ¹H NMR (400 MHz, CDCl₃): δ 7.83-7.76 (m, 2H), 7.47 (d, 1H), 7.40 (t, 1H), 7.21-7.19 (m, 1H), 7.05 (d, 1H), 6.76 (d, 1H), 5.61-5.11 (m, 3H), 3.71-3.57 (m, 2H), 3.30 (br s, 1H). m/z (ES-API-pos) [M+formic acid]=459.

Example 23

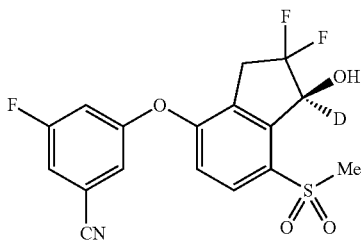 [SMILES: [2H][C@]1(O)c2c(S(C)(=O)=O)ccc(Oc3cc(F)cc(C#N)c3)c2CC1(F)F]

(S)-3-((2,2-Difluoro-1-hydroxy-7-(methylsulfonyl)-2,3-dihydro-1H-inden-4-yl-1-d)oxy)-5-fluorobenzonitrile (Compound 23): The ee was determined to be >99% by $^{19}$F NMR analysis of the corresponding Mosher ester. Retention time on chiral HPLC column 2.05 min. LCMS ESI (+) (M+H) m/z 385; $^1$H NMR (400 MHz, CDCl$_3$): δ 7.93 (d, 1H), 7.27-7.23 (m, 1H), 7.16-7.13 (m, 1H), 7.07-6.98 (m, 2H), 3.56-3.34 (m, 3H), 3.24 (s, 3H).

Example 24

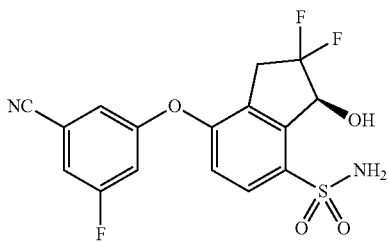 [SMILES: N#Cc1cc(F)cc(Oc2ccc(S(N)(=O)=O)c3c2CC(F)(F)[C@H]3O)c1]

(S)-7-(3-Cyano-5-fluorophenoxy)-2,2-difluoro-3-hydroxy-2,3-dihydro-1H-indene-4-sulfonamide (Compound 24)

Step A: 7-fluoro-3-oxo-indane-4-sulfonamide: To a stirred solution of 7-fluoro-3-oxo-indane-4-sulfonyl chloride (3.33 g, 13.4 mmol) and triethylamine (3.73 mL, 26.8 mmol) in dichloromethane (67 mL) was added dropwise a solution of ammonia in dioxane (0.5 M, 40.2 mL, 20.1 mmol) at 0° C. The reaction mixture was stirred at 0° C. for 1 hour. The solvent was removed under reduced pressure. The residue was purified by flash chromatography on silica gel (20-60% EtOAc/hexane) to give 7-fluoro-3-oxo-indane-4-sulfonamide (2.12 g, 69%). LCMS ESI (+) m/z 230 (M+H).

Step B: 7'-fluorospiro[1,3-dioxolane-2,3'-indane]-4'-sulfonamide: A mixture of 7-fluoro-3-oxo-indane-4-sulfonamide (2.22 g, 9.68 mmol), ethylene glycol (20 mL, 2.15 mmol), p-toluenesulfonic acid monohydrate (0.28 g, 1.5 mmol) and toluene (96 mL) was refluxed with azotropic removal of water for 4 hours. After cooling, the reaction mixture was washed with saturated aqueous NaHCO$_3$ and brine, dried over Na$_2$SO$_4$, filtered and concentrated. The residue was purified by flash chromatography on silica gel (10-50% EtOAc/hexane) to give 7'-fluorospiro[1,3-dioxolane-2,3'-indane]-4'-sulfonamide (0.51 g, 19%). LCMS ESI (+) m/z 274 (M+H).

Step C: 7'-(3-bromo-5-fluoro-phenoxy)spiro[1,3-dioxolane-2,3'-indane]-4'-sulfonamide: To a stirred solution of 7'-fluorospiro[1,3-dioxolane-2,3'-indane]-4'-sulfonamide (490 mg, 1.79 mmol) and 3-bromo-5-fluoro-phenol (685 mg, 3.59 mmol) in NMP (6 mL) was added sodium bicarbonate (452 mg, 5.38 mmol). The reaction mixture was heated at 160° C. under nitrogen for 10 hours. After cooling, the reaction mixture was partitioned between EtOAc and water. The aqueous layer was extracted with EtOAc. The combined organic layers were washed with water and brine, dried and concentrated. The residue was purified by C18 reverse phase flash chromatography (20-95% MeCN/water) to give 7'-(3-bromo-5-fluoro-phenoxy)spiro[1,3-dioxolane-2,3'-indane]-4'-sulfonamide (85 mg, 11%). LCMS ESI (+) m/z 444, 446 (M+H).

Step D: 7'-(3-cyano-5-fluoro-phenoxy)spiro[1,3-dioxolane-2,3'-indane]-4'-sulfonamide: Dichloro[1;1'-bis(diphenylphosphino)ferrocene]palladium (II) dichloromethane adduct (10.4 mg, 0.01 mmol) was added to a degassed mixture of 7'-(3-bromo-5-fluoro-phenoxy)spiro[1,3-dioxolane-2,3'-indane]-4'-sulfonamide (57 mg, 0.13 mmol), zinc cyanide (18.1 mg, 0.15 mmol) and zinc powder (8.4 mg, 0.13 mmol) in DMF (0.6 mL) under nitrogen. The reaction vial was quickly sealed under a blanket of nitrogen then warmed to 110° C. for 1 hour. After cooling, the reaction mixture was partitioned between EtOAc and water. The aqueous layer was extracted with EtOAc. The combined organic layers were washed with water and brine, dried and concentrated. The residue was purified by flash chromatography on silica gel (30-70% EtOAc/hexane) to give 7'-(3-cyano-5-fluoro-phenoxy)spiro[1,3-dioxolane-2,3'-indane]-4'-sulfonamide (40 mg, 80%). LCMS ESI (+) m/z 391 (M+H).

Step E: 7-(3-cyano-5-fluoro-phenoxy)-3-oxo-indane-4-sulfonamide: To a stirred solution of 7'-(3-cyano-5-fluoro-phenoxy)spiro[1,3-dioxolane-2,3'-indane]-4'-sulfonamide (40 mg, 0.10 mmol) in acetone (1 mL) was added 1 N HCl (0.31 mL, 0.31 mmol). The reaction mixture was stirred at ambient temperature for 1 hour. The reaction was then partitioned between EtOAc and water. The aqueous layer was extracted with EtOAc. The combined organic layers were washed with water and brine, dried and concentrated. The crude was used in the next step without further purification. LCMS ESI (+) m/z 347 (M+H).

Step F: 7-(3-cyano-5-fluoro-phenoxy)-2,2-difluoro-3-oxo-indane-4-sulfonamide: To a stirred suspension of 7-(3-cyano-5-fluoro-phenoxy)-3-oxo-indane-4-sulfonamide (35 mg, 0.10 mmol) in toluene (0.5 mL) and cyclohexane (0.5 mL) was added trifluoroacetic acid (2 µL) and 3-methoxy-propan-1-amine (21 µL, 0.020 mmol). The reaction mixture was heated to 92° C. with removal of water by a Dean-Stark apparatus. After 4 hours, the reaction was cooled to ambient temperature. The reaction was concentrated in vacuo, diluted with EtOAc, washed with saturated sodium bicarbonate solution and brine, dried over Na$_2$SO$_4$, and concentrated. The crude was dissolved in acetonitrile (1 mL). Sodium sulfate (74 mg, 0.52 mmol) and Selectfluor® (93 mg, 0.26 mmol) were sequential added. The reaction mixture was heated at reflux for 2 hours. After cooling to ambient temperature, 1N HCl (0.31 mL, 0.31 mmol) was added. The mixture was stirred for 10 minutes, diluted with water and extracted with EtOAc. The combined organic layers were washed with brine, dried, filtered and concentrated in vacuo. The residue was purified by flash chromatography on silica gel (10-60% EtOAc/hexane) to give 7-(3-cyano-5-fluoro-phenoxy)-2,2-difluoro-3-oxo-indane-4-sulfonamide (23 mg, 58%). LCMS ESI (+) m/z 383 (M+H).

Step G: (S)-7-(3-cyano-5-fluorophenoxy)-2,2-difluoro-3-hydroxy-2,3-dihydro-1H-indene-4-sulfonamide (Compound 24): To a stirred solution of 7-(3-cyano-5-fluoro-phenoxy)-2,2-difluoro-3-oxo-indane-4-sulfonamide (23 mg, 0.060 mmol), triethylamine (17 μL, 0.12 mmol) and formic acid (6.8 μL, 0.18 mmol) in dichloromethane (0.6 mL) was added RuCl(p-cymene)[(R,R)-Ts-DPEN] (0.77 mg) under nitrogen. The reaction vial was then placed in a 4° C. refrigerator overnight. The solvents were evaporated. The residue was purified by C18 reverse phase flash chromatography (20-95% MeCN/water) affording Compound 24 (15 mg, 65%). LCMS ESI (−) m/z 383 (M−H); $^1$H NMR (400 MHz, CDCl$_3$): δ 7.93 (d, 1H), 7.26-7.20 (m, 1H), 7.12 (br s, 1H), 7.04-6.96 (m, 2H), 5.74-5.66 (m, 1H), 5.28 (br s, 2H), 3.50-3.32 (m, 2H).

Alternative synthesis of 7-(3-cyano-5-fluoro-phenoxy)-3-oxo-indane-4-sulfonamide Step A: 3-fluoro-5-(7-methylsulfinyl-1-oxo-indan-4-yl)oxy-benzonitrile: To a suspension of 3-fluoro-5-(7-methylsulfanyl-1-oxo-indan-4-yl)oxy-benzonitrile (16.0 g, 51.1 mmol) in formic acid (68 mL) was added dropwise 30% hydrogen peroxide solution in water (3.6 mL, 56.2 mmol). The reaction mixture was stirred at ambient temperature for 1 hour. Water (300 mL) was added, and the reaction mixture was stirred for 15 minutes. The precipitated solid was collected by filtration, washed with water, and dried in vacuo to give 3-fluoro-5-(7-methylsulfinyl-1-oxo-indan-4-yl)oxy-benzonitrile (16.1 g, 96%). LCMS ESI (+) m/z 330 (M+H).

Step B: 3-fluoro-5-(1-oxo-7-sulfanyl-indan-4-yl)oxy-benzonitrile: Trifluoroacetic anhydride (57.8 mL, 416 mmol) was added dropwise to a solution of 3-fluoro-5-(7-methylsulfinyl-1-oxo-indan-4-yl)oxy-benzonitrile (16.1 g, 48.9 mmol) in dichloromethane (400 mL) at ambient temperature under nitrogen. The reaction mixture was stirred for 5 hours. The reaction mixture was then concentrated under reduced pressure. The residue was dissolved in MeOH (50 mL) and Et$_3$N (50 mL), and stirred at ambient temperature for 30 minutes. The solvents were evaporated in vacuo. The residue was partitioned between methyl t-butyl ether and 1 N NaOH. The aqueous layer was separated and pH was adjusted to 3-4 by dropwise addition of 3 N HCl. The mixture was extracted with EtOAc. The combined organic layers were washed with water and brine, dried and concentrated to give 3-fluoro-5-(1-oxo-7-sulfanyl-indan-4-yl)oxy-benzonitrile (8.6 g, 59%), which was used in the next step without further purification. LCMS ESI (−) m/z 298 (M−H).

Step C: 7-(3-cyano-5-fluoro-phenoxy)-3-oxo-indane-4-sulfonyl chloride: A solution of 3-fluoro-5-(1-oxo-7-sulfanyl-indan-4-yl)oxy-benzonitrile (0.91 g, 3.0 mmol) in acetonitrile (4 mL) was added dropwise to a suspension of N-chlorosuccinimide (1.62 g, 12.2 mmol) in acetonitrile (4 mL) and 2 M HCl (2 mL) while maintaining the internal temperature below 15° C. using an ice bath. The reaction mixture was stirred at ambient temperature for 2 hours, and then partitioned between EtOAc and water. The aqueous layer was extracted with EtOAc. The combined organic layers were washed with saturated aqueous NaHCO$_3$ and brine, dried, and concentrated in vacuo to give crude 7-(3-cyano-5-fluoro-phenoxy)-3-oxo-indane-4-sulfonyl chloride, which was used in the next step without further purification. LCMS ESI (+) m/z 366 (M+H).

Step D: 7-(3-cyano-5-fluoro-phenoxy)-3-oxo-indane-4-sulfonamide: To a stirred solution of 7-(3-cyano-5-fluoro-phenoxy)-3-oxo-indane-4-sulfonyl chloride (655 mg, 1.79 mmol) in THF (6 mL) was added dropwise a solution of ammonia in dioxane (0.5 M, 17.9 mL, 8.9 mmol) at 0° C. The reaction mixture was stirred at 0° C. for 30 minutes. The solvents were removed under reduced pressure. The residue was dissolved in EtOAc, washed with saturated aqueous NaHCO$_3$ and brine, dried and concentrated. The residue was purified by flash chromatography on silica gel (20-60% EtOAc/hexane) to give 7-(3-cyano-5-fluoro-phenoxy)-3-oxo-indane-4-sulfonamide (507 mg, 82%). LCMS ESI (+) m/z 347 (M+H).

Example 25

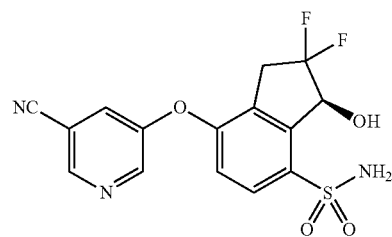 [SMILES: N#Cc1cncc(Oc2ccc(S(N)(=O)=O)c3c2CC(F)(F)[C@H]3O)c1]

(S)-7-((5-Cyanopyridin-3-yl)oxy)-2,2-difluoro-3-hydroxy-2,3-dihydro-1H-indene-4-sulfonamide (Compound 25): Prepared similarly as Compound 24. LCMS ESI (+) m/z 368 (M+H); $^1$H NMR (400 MHz, CDCl$_3$): δ 8.67 (s, 1H), 8.58 (s, 1H), 7.85 (d, 1H), 7.58 (s, 1H), 6.89 (d, 1H), 5.54 (d, 2H), 3.50-3.24 (m, 2H).

Example 26

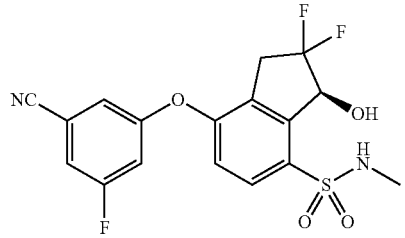 [SMILES: CNS(=O)(=O)c1ccc(Oc2cc(F)cc(C#N)c2)c2c1[C@H](O)C(F)(F)C2]

(S)-7-(3-Cyano-5-fluorophenoxy)-2,2-difluoro-3-hydroxy-N-methyl-2,3-dihydro-1H-indene-4-sulfonamide (Compound 26): Prepared similarly as Compound 24. LCMS ESI (+) m/z 399 (M+H); $^1$H NMR (400 MHz, CDCl$_3$): δ 7.85 (d, 1H), 7.25-7.18 (m, 1H), 7.13 (brs, 1H), 7.08-6.92 (m, 2H), 5.68-5.56 (m, 1H), 5.05 (br s, 1H), 3.58-3.30 (m, 2H), 2.65 (s, 3H).

Example 27

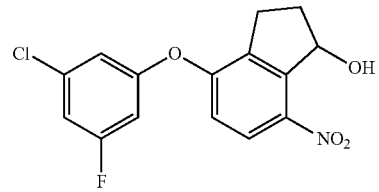 [SMILES: O=[N+]([O-])c1ccc(Oc2cc(F)cc(Cl)c2)c2c1C(O)CC2]

4-(3-Chloro-5-fluorophenoxy)-7-nitro-2,3-dihydro-1H-inden-1-ol (Compound 27): LCMS ESI (−) m/z 322 (M−H); $^1$H NMR (400 MHz, CDCl$_3$): δ 8.06 (d, 1H), 6.97-6.93 (m, 1H), 6.85-6.83 (m, 1H), 6.69-6.66 (m, 1H), 3.37 (d, 1H), 3.20-3.12 (m, 1H), 2.93-2.85 (m, 1H), 2.52-2.43 (m, 1H), 2.32-2.25 (m, 1H).

Example 28

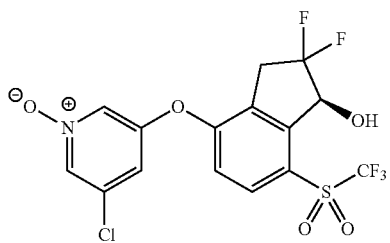 [SMILES: O=S(=O)(c1ccc(Oc2cc(Cl)c[n+]([O-])c2)c2c1[C@H](O)C(F)(F)C2)C(F)(F)F]

(S)-3-Chloro-5-((2,2-difluoro-1-hydroxy-7-((trifluoromethyl)sulfonyl)-2,3-dihydro-1H-inden-4-yl)oxy)pyridine 1-oxide (Compound 28): A solution of (S)-4-((5-chloropyridin-3-yl)oxy)-2,2-difluoro-7-((trifluoromethyl)sulfonyl)-2,3-dihydro-1H-inden-1-ol (14 mg, 0.032 mmol) in dichloromethane (1.0 mL) was treated with 3-chloroperbenzoic acid (77%, 9.8 mg, 0.040 mmol) and stirred at 45° C. for 8 hours. A further portion of 3-chloroperbenzoic acid (77%, 4.9 mg, 0.020 mmol) was added and the reaction mixture left to stir for 2 days at room temperature. The reaction mixture was poured into 20 mL of a 1:1 mixture of saturated aqueous NaHCO$_3$ and saturated aqueous Na$_2$S$_2$O$_3$ and extracted with 3×10 mL 30% isopropyl alcohol/CHCl$_3$. The combined organics were rinsed with 10 mL of brine, dried with MgSO$_4$, filtered, and concentrated to dryness. Purification was achieved by chromatography on silica using 50-100% EtOAc/hexane to yield Compound 28 as a white solid (8.5 mg, 60%). LCMS ESI (+) (M+H) m/z 446, 448; $^1$H NMR (400 MHz, CDCl$_3$): δ 8.17 (s, 1H), 8.03 (s, 1H), 7.99 (d, 1H), 7.11 (d, 1H), 7.08 (s, 1H), 5.44 (dd, 1H), 3.64-3.42 (m, 3H).

Example 29

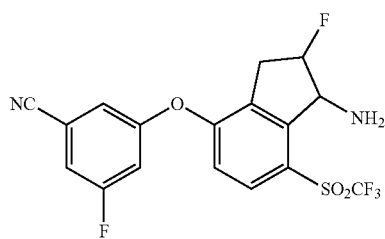

Diastereomer 1 of 3-((1-amino-2-fluoro-7-((trifluoromethyl)sulfonyl)-2,3-dihydro-1H-inden-4-yl)oxy)-5-fluorobenzonitrile (Compound 29)

Step A: Diastereomer 1 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide: To a stirred mixture of 3-fluoro-5-[2-fluoro-1-oxo-7-(trifluoromethylsulfonyl)indan-4-yl]oxy-benzonitrile (150 mg, 0.36 mmol) and (S)-(−)-2-methyl-2-propanesulfinamide (52 mg, 0.43 mmol) in tetrahydrofuran (3.6 mL), titanium ethoxide (226 μL, 1.08 mmol) was added dropwise at ambient temperature under nitrogen. The reaction mixture was warmed to 60° C. and stirred overnight. After cooling to ambient temperature, water was added. Solids were removed by filtration and washed with EtOAc. The organic phase of the filtrate was separated, washed with brine, dried and concentrated in vacuo. The residue was purified by flash chromatography on silica gel (10-20% EtOAc/hexane) to give the desired product, which was further purified by C18 reverse phase flash chromatography (Biotage Isolera One unit, C18 Flash, 25+M column, 10-95% CH$_3$CN/water) to afford diastereomer 1 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide (74 mg, 40%). LCMS ESI (+) m/z 521 (M+H).

Step B: (S)—N-(4-(3-cyano-5-fluorophenoxy)-2-fluoro-7-((trifluoromethyl)sulfonyl)-2,3-dihydro-1H-inden-1-yl)-2-methylpropane-2-sulfinamide: To a stirred solution of the diastereomer 1 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide (59 mg, 0.11 mmol) in tetrahydrofuran (1 mL) was added sodium borohydride (17 mg, 0.45 mmol) at −78° C. under nitrogen. The reaction mixture was stirred at −78° C. for 10 minutes and then quenched by the addition of water. The reaction mixture was partitioned between EtOAc and water. The aqueous layer was extracted with EtOAc. The combined organic layers were washed with brine, dried and concentrated. The residue was purified by flash chromatography on silica gel (5-50% EtOAc/hexane) to give (S)—N-(4-(3-cyano-5-fluorophenoxy)-2-fluoro-7-((trifluoromethyl)sulfonyl)-2,3-dihydro-1H-inden-1-yl)-2-methylpropane-2-sulfinamide (46 mg, 78%) as a mixture of two diastereomers. LCMS ESI (+) m/z 521 (M+H).

Step C: Diastereomer 1 of 3-((1-amino-2-fluoro-7-((trifluoromethyl)sulfonyl)-2,3-dihydro-1H-inden-4-yl)oxy)-5-fluorobenzonitrile (Compound 29): To a stirred solution of (S)—N-(4-(3-cyano-5-fluorophenoxy)-2-fluoro-7-((trifluoromethyl)sulfonyl)-2,3-dihydro-1H-inden-1-yl)-2-methylpropane-2-sulfinamide from Example 265 Step B (46 mg, 0.09 mmol) in methanol (0.6 mL), 4 N HCl in dioxane (0.44 mL, 1.8 mmol) was added at ambient temperature. The reaction mixture was stirred for 30 minutes, and then evaporated under reduced pressure. The residue was dissolved in EtOAc, washed with saturated aqueous NaHCO$_3$ solution and brine, dried and concentrated. The residue was purified by flash chromatography on silica gel (10-30% EtOAc/hexanes) to give Compound 29 (33 mg, 90%) as the major product. LCMS ESI (+) m/z 419 (M+H); $^1$H NMR (400 MHz, CDCl$_3$): δ 7.90 (d, 1H), 7.30-7.28 (m, 1H), 7.19 (br s, 1H), 7.10-7.06 (m, 1H), 6.92 (d, 1H), 5.44-5.26 (m, 1H), 4.93 (t, 1H), 3.40-3.24 (m, 2H), 1.95 (br s, 2H).

Example 30

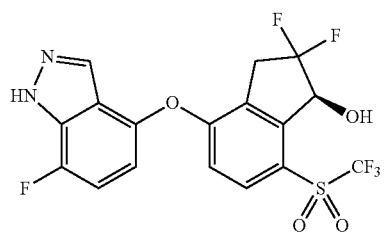 [SMILES: O=S(=O)(c1ccc(Oc2ccc(F)c3[nH]ncc23)c2c1[C@H](O)C(F)(F)C2)C(F)(F)F]

(S)-2,2-difluoro-4-((7-fluoro-1H-indazol-4-yl)oxy)-7-((trifluoromethyl)sulfonyl)-2,3-dihydro-1H-inden-1-ol (Compound 30): LCMS ESI (+) (M+H) m/z 453; $^1$H NMR (400 MHz, CDCl$_3$): δ 7.96 (s, 1H), 7.83 (d, 1H), 7.36 (t, 1H), 6.81 (d, 1H), 6.68 (d, 1H), 5.47 (d, 1H), 3.74-3.65 (m, 2H), 3.28 (br s, 1H).

Example 31

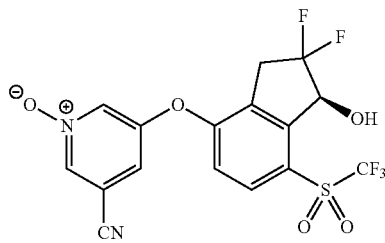 [SMILES: N#Cc1cc(Oc2ccc(S(=O)(=O)C(F)(F)F)c3c2CC(F)(F)[C@H]3O)c[n+]([O-])c1]

(S)-3-cyano-5-((2,2-difluoro-1-hydroxy-7-((trifluoromethyl)sulfonyl)-2,3-dihydro-1H-inden-4-yl)oxy)pyridine 1-oxide (Compound 31): LCMS ESI (−) (M−H) m/z 435; $^1$H NMR (400 MHz, CDCl$_3$): δ 8.32 (s, 1H), 8.23 (s, 1H), 8.03 (d, 1H), 7.23 (s, 1H), 7.13 (d, 1H), 5.46 (dd, 1H), 3.64-3.42 (m, 2H), 3.25 (d, 1H).

Example 32

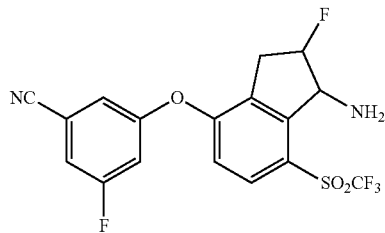

Diasteromer 2 of 3-((1-amino-2-fluoro-7-((trifluoromethyl)sulfonyl)-2,3-dihydro-1H-inden-4-yl)oxy)-5-fluorobenzonitrile (Compound 32)

Step A: Diastereomer 2 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide: To a stirred mixture of 3-fluoro-5-[2-fluoro-1-oxo-7-(trifluoromethylsulfonyl)indan-4-yl]oxy-benzonitrile (150 mg, 0.36 mmol) and (R)-(−)-2-Methyl-2-propanesulfinamide (65 mg, 0.54 mmol) in toluene (3.6 mL), titanium ethoxide (301 μL, 1.44 mmol) was added dropwise at ambient temperature under nitrogen. The reaction mixture was warmed to 60° C. and stirred overnight. After cooling to ambient temperature, water was added. Solids were removed by filtration and washed with EtOAc. The organic phase of the filtrate was separated, washed with brine, dried and concentrated in vacuo. The residue was purified by flash chromatography on silica gel (10-20% EtOAc/hexane) to afford diastereomer 2 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide (102 mg, 54%) as the less polar diastereomer. LCMS ESI (+) m/z 521 (M+H).

Step B: Diasteromer 2 of 3-((1-amino-2-fluoro-7-((trifluoromethyl)sulfonyl)-2,3-dihydro-1H-inden-4-yl)oxy)-5-fluorobenzonitrile (Compound 32): To a stirred solution of diastereomer 2 of N-(4-(3-cyano-5-fluorophenoxy)-2-fluoro-7-((trifluoromethyl)sulfonyl)-2,3-dihydro-1H-inden-1-ylidene)-2-methylpropane-2-sulfinamide (102 mg, 0.2 mmol) in tetrahydrofuran (2 mL), sodium borohydride (30 mg, 0.78 mmol) was added at ambient temperature under nitrogen. The reaction mixture was stirred for 10 minutes and then quenched by the addition of water. The reaction mixture was partitioned between EtOAc and water. The aqueous layer was extracted with EtOAc. The combined organic layers were washed with brine, dried and concentrated. The residue was dissolved in MeOH (1.3 mL) and 4 N HCl in dioxane (0.98 mL, 3.9 mmol) was added dropwise to the reaction mixture at ambient temperature. The reaction was stirred for 30 minutes, and then evaporated under reduced pressure. The residue was taken up in EtOAc, washed with saturated aqueous NaHCO$_3$ solution and brine, dried and concentrated. The residue was purified by flash chromatography on silica gel (10-50% EtOAc/hexane) to give Compound 32 (15 mg, 18%). LCMS ESI (+) m/z 419 (M+H); $^1$H NMR (400 MHz, CDCl$_3$): δ 7.90 (d, 1H), 7.30-7.28 (m, 1H), 7.22 (br s, 1H), 7.12-7.08 (m, 1H), 6.95 (d, 1H), 5.25-5.12 (m, 1H), 4.95 (d, 1H), 3.52-3.46 (m, 1H), 3.29-3.18 (m, 1H), 1.73 (br s, 2H).

Example 33

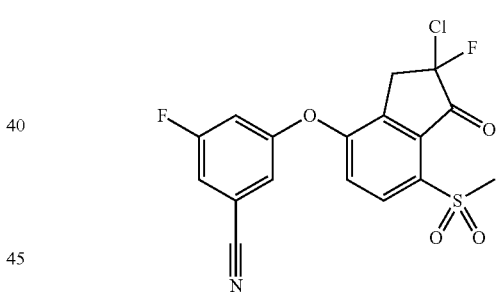

3-((2-chloro-2-fluoro-7-(methylsulfonyl)-1-oxo-2,3-dihydro-1H-inden-4-yl)oxy)-5-fluorobenzonitrile (Compound 33): Trimethylsilyl trifluoromethanesulfonate (60 μL, 0.33 mmol) was added to an ice cold solution of 3-fluoro-5-(2-fluoro-7-methylsulfonyl-1-oxo-indan-4-yl)oxy-benzonitrile (from Step A, Compound 231) (100 mg, 0.28 mmol) and triethylamine (46 μL, 0.33 mmol) in dichloromethane (1.0 mL) under nitrogen then stirred for 1.5 h. N-Chlorosuccinimide (44 mg, 0.33 mmol) was added all at once as a solid and the reaction mixture was stirred until complete as judged by LC-MS (1 hour). The reaction mixture was quenched with water, extracted with ethyl acetate, washed with brine and dried over sodium sulfate. The residue was purified on silica gel (10 g SNAP Ultra, 14 CV, 20-100% ethyl acetate/hexane) affording Compound 33 (54 mg, 0.14 mmol, 42% yield). LC-MS ESI (+) m/z 398/400 (M+NH$_4$$^+$); $^1$HNMR (400 MHz, CDCl$_3$): δ 8.23-8.21 (m, 1H), 7.35-7.32 (m, 1H), 7.26-7.24 (m, 1H), 7.23-7.21 (m, 1H), 7.14-7.10 (m, 1H), 3.97-3.78 (m, 2H), 3.43 (s, 3H).

Example 34

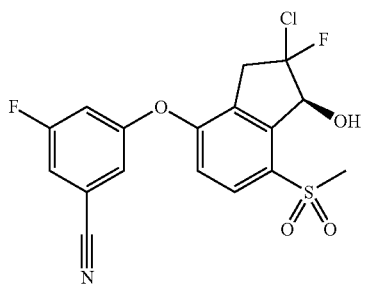 [SMILES: CS(=O)(=O)c1ccc(Oc2cc(F)cc(C#N)c2)c2c1[C@H](O)C(F)(Cl)C2]

3-(((1S)-2-chloro-2-fluoro-1-hydroxy-7-(methylsulfonyl)-2,3-dihydro-1H-inden-4-yl)oxy)-5-fluorobenzonitrile (Compound 34): Isolated as a minor byproduct in the synthesis of Compound 5. ESI (+) m/z 417/419 (M+NH$_4^+$); $^1$HNMR (400 MHz, CDCl$_3$): δ 7.95-7.91 (m, 1H), 7.26-7.23 (m, 1H), 7.14-7.13 (m, 1H), 7.06-7.00 (m, 2H), 5.80-5.78 (m, 0.5H), 5.65-5.61 (m, 0.5H), 3.81-3.55 (m, 3.5H), 3.25 (s, 1.5H), 3.24 (s, 1.5H).

Example 35

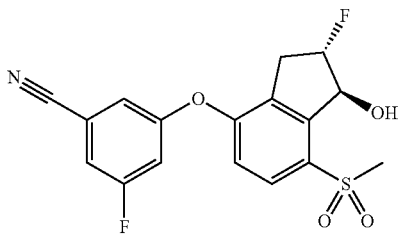 [SMILES: CS(=O)(=O)c1ccc(Oc2cc(F)cc(C#N)c2)c2c1[C@H](O)[C@@H](F)C2]

3-fluoro-5-(((1S,2S)-2-fluoro-1-hydroxy-7-(methylsulfonyl)-2,3-dihydro-1H-inden-4-yl)oxy)benzonitrile (Compound 35): LC-MS ESI (+) m/z 383 (M+NH$_4^+$); $^1$HNMR (400 MHz, CDCl$_3$): δ 7.87 (d, 1H), 7.23-7.21 (m, 1H), 7.13-7.12 (m, 1H), 7.05-7.00 (m, 2H), 5.62-5.56 (m, 1H), 5.44-5.29 (m, 1H), 3.66 (dd, 1H), 3.49-3.35 (m, 1H), 3.20 (s, 3H), 3.17-3.06 (m, 1H).

Example 36

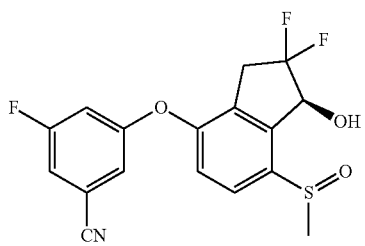 [SMILES: CS(=O)c1ccc(Oc2cc(F)cc(C#N)c2)c2c1[C@H](O)C(F)(F)C2]

3-[(1S)-2,2-Difluoro-1-hydroxy-7-methylsulfinyl-indan-4-yl]oxy-5-fluoro-benzonitrile (Compound 36)

Step A: 3-Fluoro-5-(7-methylsulfinyl-1-oxo-indan-4-yl)oxy-benzonitrile: 3-Chloroperbenzoic acid (734 mg, 3.19 mmol) was added to an ice-cold solution of 3-fluoro-5-(7-methylsulfanyl-1-oxo-indan-4-yl)oxy-benzonitrile (1000 mg, 3.19 mmol) (Example 163) in dichloromethane (30 mL). After 5 minutes, the reaction mixture was diluted with DCM and was washed with 2 portions of saturated aqueous NaHCO$_3$/Na$_2$S$_2$O$_3$ mixture, brine, dried over MgSO$_4$, filtered, and evaporated to afford 3-fluoro-5-(7-methylsulfinyl-1-oxo-indan-4-yl)oxy-benzonitrile (1030 mg, 3.13 mmol, 98% yield) as a pale yellow solid. (ES-API-pos) [M+H]=330.

Step B: (E, Z)-3-Fluoro-5-[1-(3-methoxypropylimino)-7-methylsulfinyl-indan-4-yl]oxy-benzonitrile: Pivalic acid (64 mg, 0.63 mmol) was added to a suspension of 3-fluoro-5-(7-methylsulfinyl-1-oxo-indan-4-yl)oxy-benzonitrile (1030 mg, 3.13 mmol) and 3-methoxypropylamine (1.6 mL, 15.6 mmol) in toluene (30 mL) and cyclohexane (20 mL). The mixture was heated at reflux with a Dean-Stark trap attached. After 5 hours, the reaction mixture was evaporated and the residue was used as is.

Step C: 3-(2,2-Difluoro-7-methylsulfinyl-1-oxo-indan-4-yl)oxy-5-fluoro-benzonitrile: 1-Chloromethyl-4-fluoro-1,4-diazoniabicyclo[2.2.2]octane bis(tetrafluoroborate) (2769 mg, 7.82 mmol) was added to a solution of crude (E, Z)-3-fluoro-5-[1-(3-methoxypropylimino)-7-methylsulfinyl-indan-4-yl]oxy-benzonitrile (1252 mg, 3.13 mmol) in acetonitrile (50 mL). The reaction mixture was stirred at 70° C. After 1 h, the cooled reaction mixture was treated with 1M HCl (9.38 mL, 9.38 mmol), stirred for 15 minutes, and evaporated. The residue was partitioned between EtOAc and water. The EtOAc layer was washed with brine, dried over MgSO$_4$, filtered, and evaporated. The residue was chromatographed on a Biotage 50 g SNAP column with a 30% to 100% EtOAc:hexane gradient to afford 3-(2,2-difluoro-7-methylsulfinyl-1-oxo-indan-4-yl)oxy-5-fluoro-benzonitrile (430 mg, 1.18 mmol, 38% yield). (ES-API-pos) [M+H]=366.

Step D: 3-[(1S)-2,2-Difluoro-1-hydroxy-7-methylsulfinyl-indan-4-yl]oxy-5-fluoro-benzonitrile (Compound 36): RuCl(p-cymene)[(R,R)-Ts-DPEN] (5.2 mg, 0.01 mmol) was added to a nitrogen-sparged, ice cold solution of 3-(2,2-difluoro-7-methylsulfinyl-1-oxo-indan-4-yl)oxy-5-fluoro-benzonitrile (108 mg, 0.27 mmol), formic acid (0.04 mL, 1.09 mmol), and triethylamine (0.1 mL, 0.68 mmol) in dichloromethane (5 mL). The flask was sealed and kept in a 4° C. refrigerator overnight. The reaction mixture was evaporated and the residue was chromatographed on a Biotage 10 g ultra SNAP column with a 60% to 100% EtOAc:hexane gradient to afford Compound 36 (85 mg, 0.23 mmol, 85% yield). $^1$H NMR (400 MHz, CDCl$_3$): δ 7.84-7.80 (m, 1H), 7.19-7.16 (m, 1H), 7.10 (d, 1H), 7.08-7.06 (m, 1H), 7.00-6.96 (m, 1H), 5.40 (d, 1H), 4.48-4.36 (m, 1H), 3.49-3.27 (m, 2H), 2.93 (s, 3H). (ES-API-pos) [M+1]=368.

Example 37

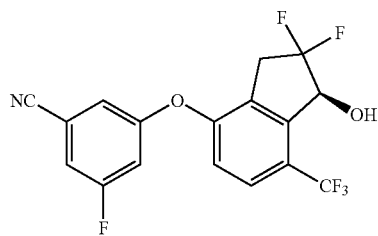 [SMILES: N#Cc1cc(F)cc(Oc2ccc(C(F)(F)F)c3c2CC(F)(F)[C@H]3O)c1]

3-[(1S)-2,2-Difluoro-1-hydroxy-7-(trifluoromethyl) indan-4-yl]oxy-5-fluoro-benzonitrile (Compound 37)

Step A: 7-Iodo-4-methoxy-indan-1-one: 1-Chloromethyl-4-fluoro-1,4-diazoniabicyclo[2.2.2]octane bis(tetrafluoroborate) (1970 mg, 5.6 mmol) was added to an ice-cold solution of iodine (1721 mg, 6.8 mmol) in acetonitrile (100 mL). The resulting solution was stirred at 0° C. for a few minutes, then 4-methoxyindanone (1000 mg, 6.17 mmol) was added. The resulting mixture was stirred at ambient temperature. After 3 hours, the reaction mixture was evaporated and the residue was partitioned between EtOAc and dilute aqueous sodium thiosulfate. The EtOAc was washed with saturated aqueous sodium thiosulfate, brine, dried over $MgSO_4$, filtered, and evaporated to afford 7-iodo-4-methoxy-indan-1-one (1310 mg, 4.6 mmol, 74% yield). (ES-API-pos) [M+H]=289.

Step B: 4-Hydroxy-7-iodo-indan-1-one: Trimethylammonium chloride (1260 mg, 13.2 mmol) was added to an ice-cold suspension of aluminium chloride (3638 mg, 27.3 mmol) in DCM (10 mL). This yellow suspension was stirred in ice. After 3 hours of warming slowly to room temperature, the resulting liquid was added to a solution of 7-iodo-4-methoxy-indan-1-one (1310 mg, 4.55 mmol) in DCM (40 mL). The reaction mixture turned a dark brown color. The flask was heated at 50° C. overnight. The mixture was pipetted into 40 mL 1M HCl with stirring. The tan suspension was extracted with two portions of EtOAc. The EtOAc was washed with brine, dried over $MgSO_4$, filtered, and evaporated to yield 4-hydroxy-7-iodo-indan-1-one (1260 mg, 4.6 mmol, quantitative yield). (ES-API-neg) [M−H]=273.

Step C: 7-Iodoindane-1,4-diol: Sodium borohydride (345 mg, 9.1 mmol) was added to an ice-cold solution of 4-hydroxy-7-iodo-indan-1-one (1250 mg, 4.6 mmol) in methanol (100 mL). Additional sodium borohydride was added until LC/MS showed complete reduction. The reaction mixture was evaporated and the residue was partitioned between EtOAc and dilute HCl. The EtOAc was washed with brine, dried over $MgSO_4$, filtered, and evaporated to afford 7-iodoindane-1,4-diol (1230 mg, 4.5 mmol, 98% yield). (ES-API-neg) [M−H]=275, 311.

Step D: 3-Fluoro-5-(1-hydroxy-7-iodo-indan-4-yl)oxy-benzonitrile: Potassium carbonate (300 mg, 2.2 mmol) was added to a vial containing a solution of 7-iodoindane-1,4-diol (200 mg, 0.72 mmol) and 3,5-difluorobenzonitrile (151 mg, 1.1 mmol) in DMF (5 mL). The sealed vial was heated overnight at 110° C. The cooled reaction mixture was treated with dilute aqueous NaCl and extracted with 2 portions of EtOAc. The EtOAc was washed with 2 portions of brine, dried over $MgSO_4$, filtered, and evaporated. The residue was chromatographed on a Biotage 25 g SNAP column with a 10% to 60% EtOAc:hexane to afford 3-fluoro-5-(1-hydroxy-7-iodo-indan-4-yl)oxy-benzonitrile (180 mg, 0.46 mmol, 63% yield). (ES-API-pos) [M+H]=378.

Step E: 3-Fluoro-5-(7-iodo-1-oxo-indan-4-yl)oxy-benzonitrile: Dess-Martin periodinane (192 mg, 0.45 mmol) was added to a solution of 3-fluoro-5-(1-hydroxy-7-iodo-indan-4-yl)oxy-benzonitrile (180 mg, 0.46 mmol) in dichloromethane (20 mL). After 15 minutes, the reaction mixture was evaporated and the residue was partitioned between EtOAc and aqueous sodium thiosulfate and saturated aqueous $NaHCO_3$. The EtOAc was washed with water, brine, dried over $MgSO_4$, filtered, and evaporated to afford 3-fluoro-5-(7-iodo-1-oxo-indan-4-yl)oxy-benzonitrile (170 mg, 0.43 mmol, 95% yield) as a colorless film. (ES-API-pos) [M+H]=394.

Step F: (E, Z)-3-Fluoro-5-[7-iodo-1-(3-methoxypropylimino)indan-4-yl]oxy-benzonitrile: Pivalic acid (8.83 mg, 0.090 mmol) was added to a suspension of 3-fluoro-5-(7-iodo-1-oxo-indan-4-yl)oxy-benzonitrile (170 mg, 0.430 mmol) and 3-methoxypropylamine (0.22 mL, 2.16 mmol) in toluene (10 mL) and cyclohexane (5 mL). The mixture was heated at reflux overnight with a Dean-Stark trap attached. The reaction mixture was evaporated and the residue was used as is in the next step.

Step G: 3-(2,2-Difluoro-7-iodo-1-oxo-indan-4-yl)oxy-5-fluoro-benzonitrile: A solution of 1-chloromethyl-4-fluoro-1,4-diazoniabicyclo[2.2.2]octane bis(tetrafluoroborate) (381 mg, 1.1 mmol) in acetonitrile (5 mL) was treated with sodium sulfate (122 mg, 0.86 mmol) and heated to 70° C. To this was added dropwise, a solution of crude (E, Z)-3-fluoro-5-[7-iodo-1-(3-methoxypropylimino)indan-4-yl]oxy-benzonitrile (200 mg, 0.43 mmol) in acetonitrile (5 mL). After 1 hour, the cooled reaction mixture was treated with 1M HCl (1.29 mL, 1.29 mmol) and stirred for 10 minutes at ambient temperature. The reaction mixture was concentrated and the residue was partitioned between EtOAc and water. The EtOAc was washed with brine, dried over $MgSO_4$, filtered, and evaporated. The residue was chromatographed on a Biotage 25 g ultra SNAP column with a 5% to 50% EtOAc:DCM to afford 3-(2,2-difluoro-7-iodo-1-oxo-indan-4-yl)oxy-5-fluoro-benzonitrile (73 mg, 0.17 mmol, 39% yield). (ES-API-pos) [M+H]=430.

Step H: 3-[2,2-Difluoro-1-oxo-7-(trifluoromethyl)indan-4-yl]oxy-5-fluoro-benzonitrile: Methyl 2,2-difluoro-2-fluorosulfonyl-acetate (0.089 mL, 0.7 mmol) was added to a vial (equipped with a nitrogen-filled balloon) containing 3-(2,2-difluoro-7-iodo-1-oxo-indan-4-yl)oxy-5-fluoro-benzonitrile (60 mg, 0.14 mmol) and copper(I) iodide (53 mg, 0.28 mmol) in DMF (3 mL). The sealed vial was heated at 100° C. for 4 hours. The reaction mixture was partitioned between EtOAc and dilute aqueous NaCl. The EtOAc was washed with 2 portions of brine, dried over $MgSO_4$, filtered, and evaporated. The residue was chromatographed on a Biotage 10 g ultraSNAP column with a 5% to 50% EtOAc:hexane to afford 3-[2,2-difluoro-1-oxo-7-(trifluoromethyl)indan-4-yl]oxy-5-fluoro-benzonitrile (29 mg, 0.078 mmol, 56% yield). (ES-API-pos) [M+H]=372.

Step I: 3-[(1S)-2,2-Difluoro-1-hydroxy-7-(trifluoromethyl)indan-4-yl]oxy-5-fluoro-benzonitrile (Compound 37): RuCl(p-cymene)[(R,R)-Ts-DPEN] (1.5 mg, 0.0082 mmol) was added to a nitrogen-sparged, ice-cold solution of 3-[2,2-difluoro-1-oxo-7-(trifluoromethyl)indan-4-yl]oxy-5-fluoro-benzonitrile (29 mg, 0.078 mmol), formic acid (0.0117 mL, 0.31 mmol), and triethylamine (0.027 mL, 0.195 mmol) in dichloromethane (2 mL). The flask was sealed and kept in a 4° C. refrigerator overnight. The reaction mixture was evaporated and the residue was chromatographed on a Biotage 10 g ultraSNAP column with a 5% to 60% EtOAc:hexane gradient to afford Compound 37 (25 mg, 0.066 mmol, 85% yield) in 98% e.e. by chiral HPLC analysis. $^1$H NMR (400 MHz, $CDCl_3$): δ 7.63 (d, 1H), 7.21-7.18 (m, 1H), 7.11-7.09 (m, 1H), 7.03-6.97 (m, 2H), 5.29 (d, 1H), 3.51-3.28 (m, 2H), 2.76 (br s, 1H). m/z (ES-API-neg) [M+formate-H]=418.

Examples 38 and 39

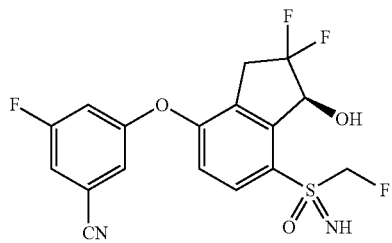

Compound 38

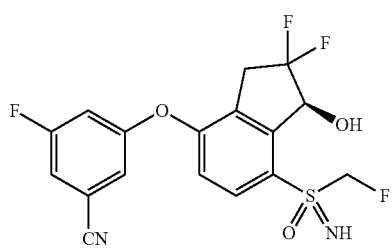

Compound 39

Isomer 1 of 3-(((1S)-2,2-difluoro-7-(S-(fluoromethyl)sulfonimidoyl)-1-hydroxy-2,3-dihydro-1H-inden-4-yl)oxy)-5-fluorobenzonitrile (Compound 38) and isomer 2 of 3-(((1S)-2,2-difluoro-7-(S-(fluoromethyl)sulfonimidoyl)-1-hydroxy-2,3-dihydro-1H-inden-4-yl)oxy)-5-fluorobenzonitrile (Compound 39)

Step A: Preparation of (N-((7-(3-cyano-5-fluorophenoxy)-3-oxo-2,3-dihydro-1H-inden-4-yl)(fluoromethyl)-$\lambda^4$-sulfanylidene)cyanamide: A solution of 3-fluoro-5-((7-((fluoromethyl)thio)-1-oxo-2,3-dihydro-1H-inden-4-yl)oxy)benzonitrile (620 mg, 1.87 mmol), bis(tert-butylcarbonyloxy)iodobenzene (1140 mg, 2.8 mmol), magnesium oxide (302 mg, 7.48 mmol), and cyanamide (157 mg, 3.74 mmol) in dichloromethane (25 mL) was treated with bis[rhodium(α,α,α',α'-tetramethyl-1,3-benzenedipropionic acid)] (14.3 mg, 0.019 mmol). The vessel was sealed and left to stir at 25° C. for 3 h. The reaction mixture was filtered through celite, concentrated, and used without further purification. LCMS ESI (+) (M+H) m/z 372.

Step B: Preparation of N-((7-(3-cyano-5-fluorophenoxy)-3-oxo-2,3-dihydro-1H-inden-4-yl)(fluoromethyl)(oxo)-$\lambda^6$-sulfanylidene)cyanamide: A solution of (N-((7-(3-cyano-5-fluorophenoxy)-3-oxo-2,3-dihydro-1H-inden-4-yl)(fluoromethyl)-$\lambda^4$-sulfanylidene)cyanamide (691 mg, 1.87 mmol) and ruthenium(III) chloride (9.7 mg, 0.047 mmol) in a mixture of water (18.6 mL), carbon tetrachloride (18.6 mL), and acetonitrile (18.6 mL) was treated with sodium periodate (1.19 g, 5.58 mmol) and stirred at 25° C. for 2 days. The reaction mixture was cooled to room temperature and quenched by the addition of 20 mL of saturated $Na_2S_2O_3$ solution. The mixture was stirred for 10 minutes and then poured into 40 mL of water and extracted with 3×30 mL EtOAc. The combined organics were rinsed with 10 mL of brine, dried with MgSO4, filtered, and concentrated to dryness. Purification was achieved by chromatography on silica using 10-55% EtOAc/hexane to afford N-((7-(3-cyano-5-fluorophenoxy)-3-oxo-2,3-dihydro-1H-inden-4-yl)(fluoromethyl)(oxo)-$\lambda^6$-sulfanylidene)cyanamide (630 mg, 87%). LCMS ESI (+) (M+H) m/z 388.

Step C: Preparation of N-((7-(3-cyano-5-fluorophenoxy)-3-oxo-2,3-dihydro-1H-inden-4-yl)(fluoromethyl)(oxo)-$\lambda^6$-sulfanylidene)-2,2,2-trifluoroacetamide: A solution of N-((7-(3-cyano-5-fluorophenoxy)-3-oxo-2,3-dihydro-1H-inden-4-yl)(fluoromethyl)(oxo)-$\lambda^6$-sulfanylidene)cyanamide (94 mg, 0.24 mmol) in dichloromethane (4.9 mL) at 25° C. was treated with trifluoroacetic anhydride (0.10 mL, 0.73 mmol) and stirred overnight. Volatiles were removed by concentration under reduced pressure and the resulting solid was used without further purification after drying for 1 hour under high vacuum. LCMS ESI (−) (M−H) m/z 457.

Step D: Preparation of (E, Z)-3-fluoro-5-((7-(S-(fluoromethyl)sulfonimidoyl)-1-((3-methoxypropyl)imino)-2,3-dihydro-1H-inden-4-yl)oxy)benzonitrile: A solution of N-((7-(3-cyano-5-fluorophenoxy)-3-oxo-2,3-dihydro-1H-inden-4-yl)(fluoromethyl)(oxo)-$\lambda^6$-sulfanylidene)-2,2,2-trifluoroacetamide (110 mg, 0.24 mmol) and 2,2-dimethylpropanoic acid (4.9 mg, 0.048 mmol) in a mixture of toluene (2.4 mL) and cyclohexane (2.4 mL) was treated with 3-methoxypropan-1-amine (74 µL, 0.72 mmol). The reaction vessel was equipped with a Hickman still and a reflux condenser and heated at 104° C. for 2.5 h. LCMS analysis was achieved by taking an aliquot of the reaction mixture and adding it to a solution of MeOH containing excess NaBH4. LCMS indicated formation of the amine via imine reduction. Once complete, volatiles were removed by concentration under reduced pressure. The residue was used without further purification. LCMS ESI (+) (M+H) m/z 436.

Step E: Preparation of 3-((2,2-difluoro-7-(S-(fluoromethyl)sulfonimidoyl)-1-oxo-2,3-dihydro-1H-inden-4-yl)oxy)-5-fluorobenzonitrile: A solution of (E, Z)-3-fluoro-5-((7-(S-(fluoromethyl)sulfonimidoyl)-1-((3-methoxypropyl)imino)-2,3-dihydro-1H-inden-4-yl)oxy)benzonitrile (104 mg, 0.24 mmol) and sodium sulfate (85 mg, 0.60 mmol) in acetonitrile (2.4 mL) was treated with 1-(chloromethyl)-4-fluoro-1,4-diazoniabicyclo[2.2.2]octane ditetrafluoroborate (213 mg, 0.60 mmol) and stirred at 70° C. for 2 h. The reaction mixture was treated with 1 mL of 10% aqueous HCl solution and stirred for 20 minutes. The reaction mixture was poured into 30 mL of water and extracted with 3×20 mL EtOAc. The combined organics were rinsed with 10 mL of brine, dried with MgSO4, filtered, and concentrated to dryness. Purification was achieved by chromatography on silica using 20-65% EtOAc/hexane to give 3-((2,2-difluoro-7-(S-(fluoromethyl)sulfonimidoyl)-1-oxo-2,3-dihydro-1H-inden-4-yl)oxy)-5-fluorobenzonitrile as a beige solid (21 mg, 21%). LCMS ESI (+) (M+H) m/z 399.

Step F: Preparation of 3-(((1S)-2,2-difluoro-7-(S-(fluoromethyl)sulfonimidoyl)-1-hydroxy-2,3-dihydro-1H-inden-4-yl)oxy)-5-fluorobenzonitrile: A solution of 3-((2,2-difluoro-7-(S-(fluoromethyl)sulfonimidoyl)-1-oxo-2,3-dihydro-1H-inden-4-yl)oxy)-5-fluorobenzonitrile (20.5 mg, 0.052 mmol) in dichloromethane (2.1 mL) was cooled to 0° C. and sparged with nitrogen for 5 minutes. During this time formic acid (5.8 µL, 0.15 mmol) and triethylamine (14.3 µL, 0.10 mmol) were sequentially added. Once sparging was complete, RuCl(p-cymene)[(R,R)-Ts-DPEN] (1.0 mg, 3 mol %) was added to the reaction mixture under a continuous stream of nitrogen. The reaction vessel was sealed and stored at 4° C. overnight. The reaction mixture was poured into 10 mL of saturated aqueous NaHCO3 and extracted with 3×15 mL $CH_2Cl_2$. The combined organics were rinsed with 10 mL of brine, dried with MgSO4, filtered, and concentrated to dryness. Purification was achieved by chromatography on silica using 10-55% EtOAc/hexane to afford two isomers.

Data for isomer 1 (Compound 38): 3.7 mg (18% yield); HPLC Retention time (long method)=4.28 min; LCMS ESI (+) (M+H) m/z 401; $^1$H NMR (400 MHz, CDCl$_3$): δ 7.95 (d, 1H), 7.28-7.25 (m, 1H), 7.17-7.15 (m, 1H), 7.06 (dt, 1H), 7.00 (d, 1H), 5.62-5.56 (m, 1H), 5.37 (dd, 1H), 5.24 (dd, 1H), 4.26 (d, 1H), 3.57-3.34 (m, 2H), 3.20 (br d, 1H).

Data for isomer 2 (Compound 39): 8.4 mg (41% yield); HPLC Retention time (long method)=4.39 min; LCMS ESI (+) (M+H) m/z 401; $^1$H NMR (400 MHz, CDCl$_3$): δ 7.96 (d, 1H), 7.28-7.25 (m, 1H), 7.18-7.16 (m, 1H), 7.06 (dt, 1H), 7.01 (d, 1H), 5.42 (dd, 1H), 5.27 (dd, 1H), 5.15 (dd, 1H), 5.04-5.02 (m, 1H), 3.62-3.38 (m, 2H), 3.33 (br s, 1H).

Example 40 and 41

Compound 40

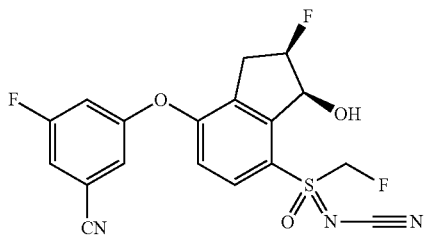

Compound 41

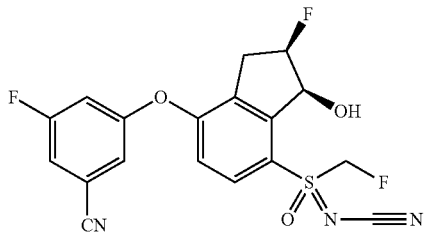

Isomer 1 of N-(((2R,3S)-7-(3-cyano-5-fluorophenoxy)-2-fluoro-3-hydroxy-2,3-dihydro-1H-inden-4-yl)(fluoromethyl)(oxo)-λ$^6$-sulfanylidene)cyanamide (Compound 40) and isomer 2 of N-(((2R,3S)-7-(3-cyano-5-fluorophenoxy)-2-fluoro-3-hydroxy-2,3-dihydro-1H-inden-4-yl)(fluoromethyl)(oxo)-λ$^6$-sulfanylidene)cyanamide (Compound 41)

Step A: Preparation of N-((7-(3-cyano-5-fluorophenoxy)-2-fluoro-3-oxo-2,3-dihydro-1H-inden-4-yl)(fluoromethyl)(oxo)-λ$^6$-sulfanylidene)cyanamide: A solution of N-((7-(3-cyano-5-fluorophenoxy)-3-oxo-2,3-dihydro-1H-inden-4-yl)(fluoromethyl)(oxo)-λ$^6$-sulfanylidene)cyanamide (103 mg, 0.27 mmol) in acetonitrile (3.0 mL) was treated with Accufluor® (171 mg, 0.27 mmol) and heated to 84° C. for 3 hours. An additional portion of Accufluor® (171 mg, 0.27 mmol) was added and the reaction mixture was heated for an additional 3 hours. The reaction mixture was poured into 40 mL of water and extracted with 3×15 mL EtOAc. The combined organics were rinsed with 10 mL of brine, dried with MgSO$_4$, filtered, and concentrated to dryness. The residue was purified by chromatography on silica using 20-55% EtOAc/hexane to afford N-((7-(3-cyano-5-fluorophenoxy)-2-fluoro-3-oxo-2,3-dihydro-1H-inden-4-yl)(fluoromethyl)(oxo)-λ$^6$-sulfanylidene)cyanamide (51 mg, 47%). LCMS ESI (+) (M+H) m/z 406.

Step B: Preparation of N-(((2R,3S)-7-(3-cyano-5-fluorophenoxy)-2-fluoro-3-hydroxy-2,3-dihydro-1H-inden-4-yl)(fluoromethyl)(oxo)-λ$^6$-sulfanylidene)cyanamide: A solution of N-((7-(3-cyano-5-fluorophenoxy)-2-fluoro-3-oxo-2,3-dihydro-1H-inden-4-yl)(fluoromethyl)(oxo)-λ$^6$-sulfanylidene)cyanamide (50.6 mg, 0.125 mmol) in dichloromethane (4.0 mL) was cooled to 0° C. and sparged with nitrogen for 5 minutes. During this time formic acid (14.1 µL, 0.375 mmol) and triethylamine (34.6 µL, 0.250 mmol) were sequentially added. Once the sparging was complete, RuCl(p-cymene)[(R,R)-Ts-DPEN] (2.4 mg, 3 mol %) was added under a continuous stream of nitrogen. The reaction vessel was sealed and kept at 4° C. overnight. The reaction mixture was poured into 10 mL of saturated aqueous NaHCO$_3$ and extracted with 3×15 mL CH$_2$Cl$_2$. The combined organics were rinsed with 10 mL of brine, dried with MgSO$_4$, filtered, and concentrated to dryness. Purification by chromatography on silica using 15-55% EtOAc/hexane (25 g Biotage Ultra) afforded two isomers.

Data for isomer 1 (Compound 40): 5.8 mg (11% yield); HPLC retention time (long method)=4.46 min; LCMS ESI (+) (M+H) m/z 408; $^1$H NMR (400 MHz, CDCl$_3$): δ 8.00 (d, 1H), 7.30 (ddd, 1H), 7.21-7.19 (m, 1H), 7.09 (dt, 1H), 6.99 (d, 1H), 5.92 (dd, 1H), 5.76-5.69 (m, 1H), 5.65 (dd, 1H), 5.55-5.37 (m, 1H), 3.43-3.18 (m, 2H), 3.22 (dd, 1H).

Data for isomer 2 (Compound 41): 7.8 mg (15% yield); HPLC retention time (long method)=4.58 min; LCMS ESI (+) (M+H) m/z 408; $^1$H NMR (400 MHz, CDCl$_3$): δ 8.04 (d, 1H), 7.31 (ddd, 1H), 7.24-7.22 (m, 1H), 7.11 (dt, 1H), 7.00 (d, 1H), 6.27 (dd, 1H), 5.75-5.69 (m, 1H), 5.55 (dd, 1H), 5.56-5.39 (m, 1H), 3.45-3.22 (m, 2H), 3.12 (t, 1H).

Example 42

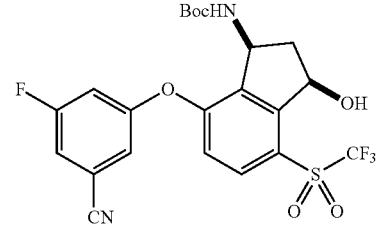 [SMILES: CC(C)(C)OC(=O)N[C@H]1C[C@@H](O)c2c(S(=O)(=O)C(F)(F)F)ccc(Oc3cc(F)cc(C#N)c3)c21]

tert-butyl(cis-7-(3-cyano-5-fluorophenoxy)-3-hydroxy-4-((trifluoromethyl)sulfonyl)-2,3-dihydro-1H-inden-1-yl)carbamate (Compound 42)

Step A: Preparation of 3-bromo-4-(3-bromo-5-fluorophenoxy)-7-((trifluoromethyl)sulfonyl)-2,3-dihydrospiro[indene-1,2'-[1,3]dioxolane]: The diaryl ether starting material, 4-(3-bromo-5-fluorophenoxy)-7-((trifluoromethyl)sulfonyl)-2,3-dihydrospiro[indene-1,2'-[1,3]dioxolane], was prepared similarly according to Example 212, Steps A-B, substituting 3-bromo-5-fluorophenol for 4-fluorophenol. A solution of 4'-(3-bromo-5-fluoro-phenoxy)-7'-(trifluoromethylsulfonyl)spiro[1,3-dioxolane-2,1'-indane] (930 mg, 1.87 mmol) and N-bromosuccinimide (399 mg, 2.24 mmol) in carbon tetrachloride (12.5 mL) was sparged with nitrogen for 5 minutes and treated with benzoyl peroxide (91 mg, 0.37 mmol). The reaction vessel was fitted with a reflux condenser. The condenser was flushed with nitrogen for 5 minutes. The vessel was then sealed, placed under nitrogen atmosphere and stirred at 88° C. for 1 day. An additional portion of benzoyl peroxide (91 mg, 0.37 mmol) was added and the reaction was heated for an additional day. The reaction mixture was poured into 10 mL of 1 M NaOH and extracted with 3×20 mL $CH_2Cl_2$. The combined organics were rinsed with 10 mL of brine, dried with $MgSO_4$, filtered, and concentrated to dryness. Purification was achieved by chromatography on silica using 20-70% $CH_2Cl_2$/hexane to afford 3-bromo-4-(3-bromo-5-fluorophenoxy)-7-((trifluoromethyl)sulfonyl)-2,3-dihydrospiro[indene-1,2'-[1,3]dioxolane] (448 mg, 42%). LCMS ESI (+) (M+H) m/z: 575, 577, 579.

Step B: Preparation of 3-azido-4-(3-bromo-5-fluorophenoxy)-7-((trifluoromethyl)sulfonyl)-2,3-dihydrospiro[indene-1,2'-[1,3]dioxolane]: A solution of 3-bromo-4-(3-bromo-5-fluorophenoxy)-7-((trifluoromethyl)sulfonyl)-2,3-dihydrospiro[indene-1,2'-[1,3]dioxolane] (448 mg, 0.78 mmol) in DMF (4.0 mL) at 25° C. was treated with sodium azide (50.6 mg, 0.78 mmol) and stirred at 25° C. for 1 hour. The reaction mixture was poured into 40 mL of water and extracted with 3×15 mL $Et_2O$. The combined organics were rinsed with 10 mL of brine, dried with $MgSO_4$, filtered, and concentrated to dryness. The residue was used without further purification. LCMS ESI (+) (M–$N_2$+H) m/z: 510, 512.

Step C: Preparation of 4-(3-bromo-5-fluorophenoxy)-7-((trifluoromethyl)sulfonyl)-2,3-dihydrospiro[indene-1,2'-[1,3]dioxolan]-3-amine: A solution of 3-azido-4-(3-bromo-5-fluorophenoxy)-7-((trifluoromethyl)sulfonyl)-2,3-dihydrospiro[indene-1,2'-[1,3]dioxolane] (675 mg, 1.25 mmol) in a mixture of tetrahydrofuran (6.0 mL) and water (0.4 mL) at 25° C. was treated with trimethylphosphine solution (~1.0 M in THF, 1.5 mL, 1.5 mmol) and stirred for 30 minutes. Gas evolution was observed during this time. The reaction mixture was heated to 60° C. for 2 h. Volatiles were removed by concentration under reduced pressure. The resulting residue was dried under high vacuum overnight. Purification was achieved by chromatography on silica using 1-9% MeOH/$CH_2Cl_2$+1% $NH_4OH$ to afford 4-(3-bromo-5-fluorophenoxy)-7-((trifluoromethyl)sulfonyl)-2,3-dihydrospiro[indene-1,2'-[1,3]dioxolan]-3-amine (630 mg, 98%). LCMS ESI (+) (M+H) m/z: 512, 514.

Step D: Preparation of tert-butyl (4-(3-bromo-5-fluorophenoxy)-7-((trifluoromethyl)sulfonyl)-2,3-dihydrospiro[indene-1,2'-[1,3]dioxolan]-3-yl)carbamate: A solution of 4-(3-bromo-5-fluorophenoxy)-7-((trifluoromethyl)sulfonyl)-2,3-dihydrospiro[indene-1,2'-[1,3]dioxolan]-3-amine (65 mg, 0.13 mmol) in dichloromethane (2.0 mL) at 25° C. was treated with di-tert-butyl pyrocarbonate (30.5 mg, 0.14 mmol) and stirred overnight. Volatiles were removed by concentration under reduced pressure. The product residue was used without further purification. LCMS ESI (–) (M–H) m/z: 610, 612.

Step E: Preparation of tert-butyl (7-(3-bromo-5-fluorophenoxy)-3-oxo-4-((trifluoromethyl)sulfonyl)-2,3-dihydro-1H-inden-1-yl)carbamate: In a pressure tube, a sample of tert-butyl (4-(3-bromo-5-fluorophenoxy)-7-((trifluoromethyl)sulfonyl)-2,3-dihydrospiro[indene-1,2'-[1,3]dioxolan]-3-yl)carbamate (77 mg, 0.13 mmol) was dissolved in a mixture of acetic acid (1.0 mL), tetrahydrofuran (0.5 mL), and water (0.5 mL). The reaction mixture was sealed and heated to 80° C. for 14 hours. LCMS analysis indicates a relatively clean reaction with formation of the desired product, unreacted starting material, and the corresponding Boc deprotected materials predominating. Volatiles were removed by concentration under reduced pressure. The leftover residue was poured into 20 mL of saturated $NaHCO_3$ and extracted with 3×15 mL EtOAc. The combined organics were rinsed with 10 mL of brine, dried with $MgSO_4$, filtered, and concentrated to dryness. The residue was dissolved in 3 mL of $CH_2Cl_2$ and treated with di-tert-butyl pyrocarbonate (13.8 mg, 0.063 mmol). The mixture was left to stir overnight. Volatiles were removed by concentration under reduced pressure. Purification was achieved by chromatography on silica using 5-35% EtOAc/hexane to afford tert-butyl (7-(3-bromo-5-fluorophenoxy)-3-oxo-4-((trifluoromethyl)sulfonyl)-2,3-dihydro-1H-inden-1-yl)carbamate (50 mg, 70%). LCMS ESI (–) (M–H) m/z: 566, 568.

Step F: Preparation of tert-butyl (cis-7-(3-bromo-5-fluorophenoxy)-3-hydroxy-4-((trifluoromethyl)sulfonyl)-2,3-dihydro-1H-inden-1-yl)carbamate: A solution of tert-butyl (7-(3-bromo-5-fluorophenoxy)-3-oxo-4-((trifluoromethyl)sulfonyl)-2,3-dihydro-1H-inden-1-yl)carbamate (50 mg, 0.088 mmol) in methanol (2.0 mL) at 25° C. was treated with sodium borohydride (3.3 mg, 0.088 mmol) and stirred at 25° C. for 1 hour. The reaction mixture was quenched by the addition of 0.5 mL of aqueous saturated $NH_4Cl$ and stirred for 5 minutes. Volatiles were removed by concentration under reduced pressure. The reaction mixture was poured into 10 mL of water and extracted with 3×10 mL EtOAc. The combined organics were rinsed with 10 mL of brine, dried with $MgSO_4$, filtered, and concentrated to dryness. Purification was achieved by chromatography on silica using 10-35% EtOAc/hexane to afford tert-butyl (cis-7-(3-bromo-5-fluorophenoxy)-3-hydroxy-4-((trifluoromethyl)sulfonyl)-2,3-dihydro-1H-inden-1-yl)carbamate (25 mg, 50%) as a clear solid film. LCMS ESI (–) (M–H) m/z: 568, 570.

Step G: Preparation of tert-butyl (cis-7-(3-cyano-5-fluorophenoxy)-3-hydroxy-4-((trifluoromethyl)sulfonyl)-2,3-dihydro-1H-inden-1-yl)carbamate (Compound 42): A solution of tert-butyl (cis-7-(3-bromo-5-fluorophenoxy)-3-hydroxy-4-((trifluoromethyl)sulfonyl)-2,3-dihydro-1H-inden-1-yl)carbamate (20.5 mg, 0.036 mmol) and zinc cyanide (4.6 mg, 0.04 mmol) in DMF (0.36 mL) was sparged with nitrogen for 3 minutes. The reaction mixture was then treated sequentially with dichloro[1;1'-bis(diphenylphosphino)ferrocene]palladium(II) dichloromethane adduct (2.9 mg, 10 mol %) and zinc powder (2.8 mg, 0.043 mmol) under continuous nitrogen stream. The vessel was sealed and heated to 110° C. for 4 hours. The reaction mixture was poured into 30 mL of water and extracted with 3×10 mL $Et_2O$. The combined organics were rinsed with 10 mL of brine, dried with $MgSO_4$, filtered, and concentrated to dryness. Purification was achieved by chromatography on silica using 5-30% EtOAc/hexane to afford Compound 42 as a white solid (13.4 mg, 72%). LCMS ESI (–) (M+Cl⁻) m/z: 551, 553; $^1$H NMR (400 MHz, $CDCl_3$): δ 7.97 (d, 1H), 7.27-7.23 (m, 1H), 7.17-7.13 (m, 1H), 7.07 (dt, 1H), 7.02 (d, 1H), 5.54 (dd, 1H), 5.49-5.41 (m, 1H), 5.12 (br d, 1H), 3.33 (br s, 1H), 2.73-2.64 (m, 1H), 2.22 (d, 1H), 1.35 (s, 9H).

Example 43

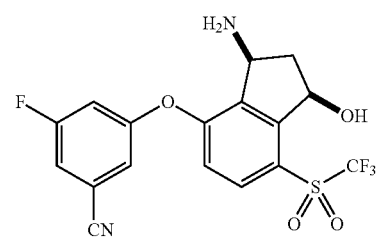 [SMILES: N#Cc1cc(F)cc(Oc2ccc(S(=O)(=O)C(F)(F)F)c3c2[C@@H](N)C[C@H]3O)c1]

3-((cis-3-amino-1-hydroxy-7-((trifluoromethyl)sulfonyl)-2,3-dihydro-1H-inden-4-yl)oxy)-5-fluorobenzonitrile (Compound 43): A solution of tert-butyl (cis-7-(3-cyano-5-fluorophenoxy)-3-hydroxy-4-((trifluoromethyl)sulfonyl)-2,3-dihydro-1H-inden-1-yl)carbamate (10.5 mg, 0.020 mmol) in dichloromethane (0.5 mL) at 25° C. was treated with trifluoroacetic acid (0.5 mL) and stirred at 25° C. for 1 hour. Volatiles were removed by concentration under reduced pressure. The reaction mixture was poured into 10 mL of saturated aqueous NaHCO$_3$ and extracted with 3×10 mL 30% isopropyl alcohol in CHCl$_3$. The combined organics were rinsed with 10 mL of brine, dried with MgSO$_4$, filtered, and concentrated to dryness to afford Compound 43 (6.5 mg, 77%). LCMS ESI (+) (M+H) m/z 417; $^1$H NMR (400 MHz, CDCl$_3$): δ 7.93 (d, 1H), 7.31 (ddd, 1H), 7.26-7.24 (m, 1H), 7.16 (dt, 1H), 6.94 (d, 1H), 5.53 (d, 1H), 4.59 (d, 1H), 2.69-2.61 (m, 1H), 2.35-1.95 (m, 4H).

Examples 44 and 45

Compound 44

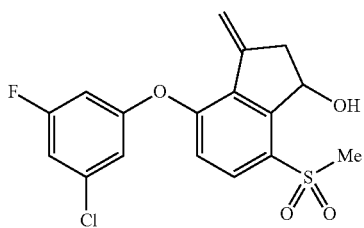

Compound 45

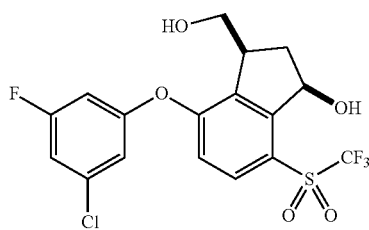

4-(3-chloro-5-fluorophenoxy)-3-methylene-7-(methylsulfonyl)-2,3-dihydro-1H-inden-1-ol (Compound 44) and (1R,3S)-4-(3-chloro-5-fluorophenoxy)-3-(hydroxymethyl)-7-((trifluoromethyl)sulfonyl)-2,3-dihydro-1H-inden-1-ol (Compound 45)

Step A: Preparation of 3,7-dibromo-4-fluoro-2,3-dihydrospiro[indene-1,2'-[1,3]dioxolane]: A solution of 7'-bromo-4'-fluoro-spiro[1,3-dioxolane-2,1'-indane] (2.55 g, 9.34 mmol) and AIBN (23 mg, 0.14 mmol) in carbon tetrachloride (65 mL) was treated with N-bromosuccinimide (1.99 g, 11.2 mmol). The resulting mixture was sparged with nitrogen for 5 minutes. The reaction vessel was sealed and heated to 80° C. for 3 hours. The reaction mixture was poured into 50 mL of water and extracted with 3×30 mL CH$_2$Cl$_2$. The combined organics were rinsed with 10 mL of brine, dried with MgSO$_4$, filtered, and concentrated to dryness. The product was used without further purification. $^1$H NMR (400 MHz, CDCl$_3$): δ 7.52 (dd, 1H), 6.98 (dt, 1H), 5.41 (dd, 1H), 4.47-4.33 (m, 2H), 4.19-4.08 (m, 2H), 2.91-2.88 (m, 1H), 2.76 (dd, 1H).

Step B: Preparation of 7-bromo-4-fluoro-2,3-dihydrospiro[indene-1,2'-[1,3]dioxolane]-3-carbonitrile: A solution of 3,7-dibromo-4-fluoro-2,3-dihydrospiro[indene-1,2'-[1,3]dioxolane] (3.27 g, 9.3 mmol) in DMF (9.3 mL) was treated with sodium cyanide (501 mg, 10.2 mmol) and stirred at 60° C. overnight. The reaction mixture was poured into 150 mL of water and extracted with 3×50 mL Et$_2$O. The combined organics were rinsed with 10 mL of brine, dried with MgSO$_4$, filtered, and concentrated to dryness. Purification was achieved by chromatography on silica using 10-40% EtOAc/hexane to afford 7-bromo-4-fluoro-2,3-dihydrospiro[indene-1,2'-[1,3]dioxolane]-3-carbonitrile (750 mg, 27%). LCMS ESI (+) (M+H) m/z: 298, 300.

Step C: Preparation of 4-bromo-7-fluoro-3-oxo-2,3-dihydro-1H-indene-1-carboxylic acid: A solution of 7-bromo-4-fluoro-2,3-dihydrospiro[indene-1,2'-[1,3]dioxolane]-3-carbonitrile (166 mg, 0.56 mmol) in 1,4-Dioxane (2.5 mL) was treated with concentrated aqueous HCl solution (1.9 mL) and stirred at 105° C. for 1 hour. Volatiles were removed by concentration under reduced pressure. The remaining reaction mixture was poured into 20 mL of water and extracted with 3×15 mL EtOAc. The combined organics were rinsed with 10 mL of brine, dried with MgSO$_4$, filtered, and concentrated to dryness. The product was used without further purification. LCMS ESI (+) (M+H) m/z: 273, 275.

Step D: Preparation of cis-7-bromo-4-fluoro-3-(hydroxymethyl)-2,3-dihydro-1H-inden-1-ol: A solution of 4-bromo-7-fluoro-3-oxo-2,3-dihydro-1H-indene-1-carboxylic acid (581 mg, 2.1 mmol) in tetrahydrofuran (10.6 mL) was treated with borane dimethyl sulfide complex (504 μL, 5.3 mmol). The resulting mixture was stirred at 70° C. for 1 hour. The reaction mixture was cooled and an additional portion of borane dimethyl sulfide complex (504 μL, 5.3 mmol) was added. The reaction mixture was heated to 80° C. for 2 hours. After cooling to room temperature, the reaction mixture was quenched by the careful dropwise addition of water. Once effervescence had ceased, the reaction mixture was poured into 20 mL of saturated aqueous NaHCO$_3$ and extracted with 4×10 mL 30% isopropyl alcohol in CHCl$_3$. The combined organics were rinsed with 10 mL of brine, dried with MgSO$_4$, filtered, and concentrated to dryness. Purification was achieved by chromatography on silica using 15-80% EtOAc/hexane to afford cis-7-bromo-4-fluoro-3-(hydroxymethyl)-2,3-dihydro-1H-inden-1-ol (210 mg, 38%). $^1$H NMR (400 MHz, CDCl$_3$): δ 7.36 (dd, 1H), 6.87 (dt, 1H), 5.13-5.06 (m, 1H), 4.00 (dd, 1H), 3.91-3.83 (m, 1H), 3.81 (dd, 1H), 3.66-3.60 (m, 1H), 2.68-2.58 (m, 1H), 2.60 (ddd, 1H), 2.00 (d, 1H).

Step E: Preparation of cis-4-fluoro-3-(hydroxymethyl)-7-(methylthio)-2,3-dihydro-1H-inden-1-ol: A solution of cis-7-bromo-4-fluoro-3-(hydroxymethyl)-2,3-dihydro-1H-inden-1-ol (195 mg, 0.75 mmol) and palladium diacetate (5.0 mg, 0.022 mmol) and (R)-Josiphos (12.3 mg, 0.022 mmol) in 1,2-dimethoxyethane (2.0 mL) was sparged with nitrogen for 3 minutes. The reaction mixture was then treated with sodium thiomethoxide (78.5 mg, 1.12 mmol) under continuous nitrogen stream. The vessel was sealed and heated to 110° C. over 2 days. The reaction mixture was poured into 20 mL of water and extracted with 3×10 mL 30% isopropyl alcohol in CHCl$_3$. The combined organics were rinsed with 10 mL of brine, dried with MgSO$_4$, filtered, and concentrated to dryness. Purification was achieved by chromatography on silica using 20-60% EtOAc/hexane to afford cis-4-fluoro-3-(hydroxymethyl)-7-(methylthio)-2,3-dihydro-1H-inden-1-ol (31 mg, 18%). LCMS ESI (+) (M+Na) m/z 251.

Step F: Preparation of cis-4-fluoro-3-(hydroxymethyl)-7-(methylsulfonyl)-2,3-dihydro-1H-inden-1-ol: A solution of cis-4-fluoro-3-(hydroxymethyl)-7-(methylthio)-2,3-dihydro-1H-inden-1-ol (31 mg, 0.13 mmol) in dichloromethane (2.7 mL) at 25° C. was treated with 3-chloroperbenzoic acid (82 mg, 0.33 mmol) and stirred at 25° C. overnight. The reaction mixture was poured into 10 mL of 1M aqueous NaOH solution and extracted with 3×10 mL 30% isopropyl alcohol in CHCl₃. The combined organics were rinsed with 10 mL of brine, dried with MgSO₄, filtered, and concentrated to dryness. Purification was achieved by chromatography on silica using 40-100% EtOAc/hexane to afford cis-4-fluoro-3-(hydroxymethyl)-7-(methylsulfonyl)-2,3-dihydro-1H-inden-1-ol (23 mg, 66%). LCMS ESI (+) (M+H) m/z: 261.

Step G: Preparation of 4-(3-chloro-5-fluorophenoxy)-3-methylene-7-(methylsulfonyl)-2,3-dihydro-1H-inden-1-ol (Compound 44) and cis-4-(3-chloro-5-fluorophenoxy)-3-(hydroxymethyl)-7-((trifluoromethyl)sulfonyl)-2,3-dihydro-1H-inden-1-ol (Compound 45): A solution of cis-4-fluoro-3-(hydroxymethyl)-7-(methylsulfonyl)-2,3-dihydro-1H-inden-1-ol (23 mg, 0.089 mmol) and 3-chloro-5-fluorophenol (13 mg, 0.089 mmol) in 1-methyl-2-pyrrolidone (0.9 mL) was treated with cesium bicarbonate (21 mg, 0.11 mmol) and stirred at 145° C. for 4 hours. The reaction mixture was poured into 30 mL of water and extracted with 3×10 mL Et₂O. The combined organics were rinsed with 10 mL of brine, dried with MgSO₄, filtered, and concentrated to dryness. Purification was achieved by chromatography on silica using 30-100% EtOAc/hexane to afford Compound 44 as a white solid (1.3 mg, 4%) and Compound 45 as a thin film (3.2 mg, 9%).

Data for 4-(3-chloro-5-fluorophenoxy)-3-methylene-7-(methylsulfonyl)-2,3-dihydro-1H-inden-1-ol (Compound 44): LCMS ESI (+) (M+H) m/z: 369, 371; ¹H NMR (400 MHz, CDCl₃): δ 7.79 (d, 1H), 6.98 (ddd, 1H), 6.91 (d, 1H), 6.91-6.89 (m, 1H), 6.74 (dt, 1H), 5.97 (t, 1H), 5.68 (dt, 1H), 5.41 (t, 1H), 3.75 (d, 1H), 3.26-3.17 (m, 1H), 3.20 (s, 3H), 2.91-2.84 (m, 1H).

Data for cis-4-(3-chloro-5-fluorophenoxy)-3-(hydroxymethyl)-7-((trifluoromethyl)sulfonyl)-2,3-dihydro-1H-inden-1-ol (Compound 45): LCMS ESI (+) (M+H) m/z: 387, 389; ¹H NMR (400 MHz, CDCl₃): δ 7.85 (d, 1H), 6.95 (ddd, 1H), 6.92 (d, 1H), 6.88-6.85 (m, 1H), 6.70 (dt, 1H), 5.65 (d, 1H), 4.24-4.06 (br m, 1H), 4.08 (dd, 1H), 3.88 (dd, 1H), 3.64-3.59 (m, 1H), 3.26 (s, 3H), 2.69 (ddd, 1H), 2.66-2.48 (br m, 1H), 2.12 (d, 1H).

Examples 46 and 47

Isomer 1 of N—(((R)-7-(3-cyano-5-fluorophenoxy)-3-hydroxy-2,3-dihydro-1H-inden-4-yl)(fluoromethyl)(oxo)-λ⁶-sulfanylidene)cyanamide (Compound 46) and isomer 2 of N—(((R)-7-(3-cyano-5-fluorophenoxy)-3-hydroxy-2,3-dihydro-1H-inden-4-yl)(fluoromethyl)(oxo)-λ⁶-sulfanylidene)cyanamide (Compound 47): A solution of N-((7-(3-cyano-5-fluorophenoxy)-3-oxo-2,3-dihydro-1H-inden-4-yl)(fluoromethyl)(oxo)-λ⁶-sulfanylidene)cyanamide (85 mg, 0.22 mmol) in dichloromethane (2.2 mL) was cooled to 0° C. and sparged with nitrogen for 5 minutes. During this time formic acid (25 μL, 0.66 mmol) and triethylamine (31 μL, 0.44 mmol) were sequentially added. Once sparging was complete, RuCl(p-cymene)[(R,R)-Ts-DPEN] (4.2 mg, 3 mol %) was added under a continuous stream of nitrogen. The reaction vessel was sealed and stored at 4° C. overnight. The reaction mixture was poured into 10 mL of saturated aqueous NaHCO₃ and extracted with 3×15 mL CH₂Cl₂. The combined organics were rinsed with 10 mL of brine, dried with MgSO₄, filtered, and concentrated to dryness. Purification was achieved by chromatography on silica using 10-45% EtOAc/CH₂Cl₂ to afford two isomers.

Data for isomer 1 (Compound 46): 17.9 mg (21%); HPLC Retention time (long method)=4.75 min; LCMS ESI (+) (M+H) m/z 390; ¹H NMR (400 MHz, CDCl₃): δ 7.93 (d, 1H), 7.27 (ddd, 1H), 7.20-7.18 (m, 1H), 7.08 (dt, 1H), 7.00 (d, 1H), 5.98 (dd, 1H), 5.80-5.75 (m, 1H), 5.49 (dd, 1H), 3.17 (dt, 1H), 2.94 (ddd, 1H), 2.86 (d, 1H), 2.62-2.51 (m, 1H), 2.29-2.20 (m, 1H).

Data for isomer 2 (Compound 47): 14 mg (16%); HPLC Retention time (long method)=4.69 min; LCMS ESI (+) (M+H) m/z 390; ¹H NMR (400 MHz, CDCl₃): δ 7.91 (d, 1H), 7.27 (ddd, 1H), 7.19-7.16 (m, 1H), 7.06 (dt, 1H), 6.98 (d, 1H), 5.85-5.79 (m, 1H), 5.72 (dd, 1H), 5.61 (dd, 1H), 3.15 (ddd, 1H), 2.97 (d, 1H), 2.89 (ddd, 1H), 2.62-2.52 (m, 1H), 2.27-2.18 (m, 1H).

Example 48

Compound 46

Compound 47

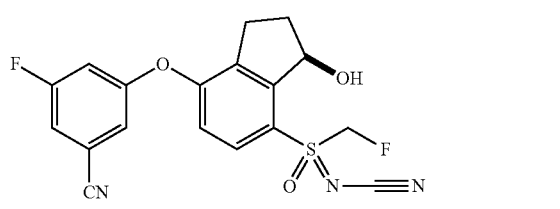

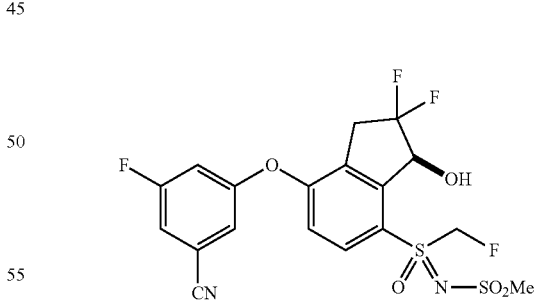

N—(((S)-7-(3-cyano-5-fluorophenoxy)-2,2-difluoro-3-hydroxy-2,3-dihydro-1H-inden-4-yl)(fluoromethyl)(oxo)-λ⁶-sulfanylidene)methanesulfonamide (Compound 48): LCMS ESI (+) (M+H) m/z 479; ¹H NMR (400 MHz, CDCl₃): δ 8.04 (d, 1H), 7.30 (ddd, 1H), 7.22-7.19 (m, 1H), 7.10 (dt, 1H), 7.01 (d, 1H), 5.97 (dd, 1H), 5.70 (dd, 1H), 5.60 (dd, 1H), 3.68 (d, 1H), 3.61-3.39 (m, 2H), 3.23 (s, 3H).

Examples 49 and 50

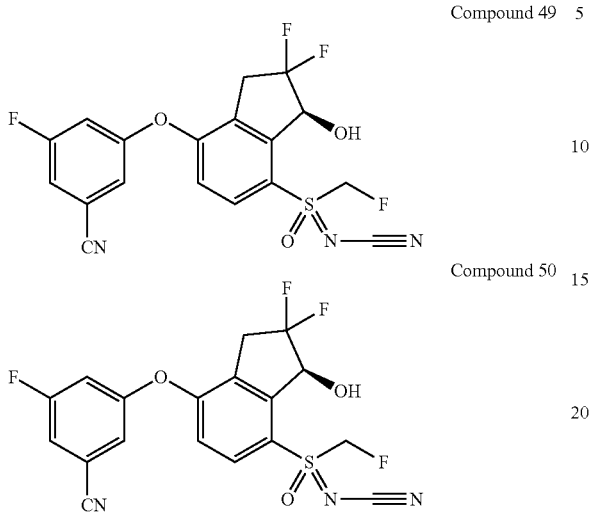

Isomer 1 of N—(((S)-7-(3-cyano-5-fluorophenoxy)-2,2-difluoro-3-hydroxy-2,3-dihydro-1H-inden-4-yl)(fluoromethyl)(oxo)-λ⁶-sulfanylidene)cyanamide (Compound 49) and isomer 2 of N—(((S)-7-(3-cyano-5-fluorophenoxy)-2,2-difluoro-3-hydroxy-2,3-dihydro-1H-inden-4-yl)(fluoromethyl)(oxo)-λ⁶-sulfanylidene)cyanamide (Compound 50)

Data for isomer 1 (Compound 49): 1.1 mg (2% yield); HPLC retention time (long method)=4.91 min; LCMS ESI (+) (M+H) m/z 426; ¹H NMR (400 MHz, CDCl₃): δ 8.01 (d, 1H), 7.34 (ddd, 1H), 7.25-7.22 (m, 1H), 7.12 (dt, 1H), 7.01 (d, 1H), 5.75 (dd, 1H), 5.71-5.65 (m, 1H), 5.61 (dd, 1H), 3.64-3.45 (m, 2H), 3.14 (dd, 1H).

Data for isomer 2 (Compound 50): 1.0 mg (2% yield); HPLC retention time (long method)=4.89 min; LCMS ESI (+) (M+H) m/z 426; ¹H NMR (400 MHz, CDCl₃): δ 8.03 (d, 1H), 7.34 (ddd, 1H), 7.26-7.24 (m, 1H), 7.14 (dt, 1H), 7.02 (d, 1H), 6.02 (dd, 1H), 5.65-5.59 (m, 1H), 5.54 (dd, 1H), 3.66-3.48 (m, 2H), 3.30 (dd, 1H).

Example 51

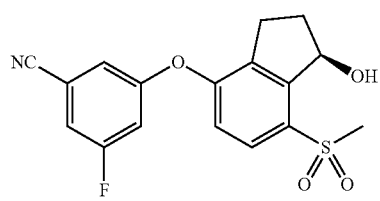 [SMILES: CS(=O)(=O)c1ccc(Oc2cc(F)cc(C#N)c2)c2c1[C@H](O)CC2]

3-fluoro-5-[(1R)-1-hydroxy-7-methylsulfonyl-indan-4-yl]oxy-benzonitrile (Compound 51): LCMS ESI (−) m/z 392 (M+HCO₂⁻); ¹H NMR (400 MHz, CDCl₃): δ 7.83 (d, 1H), 7.19-7.16 (m, 1H), 7.09-7.07 (m, 1H), 7.01-6.96 (m, 2H), 5.71-5.67 (m, 1H), 3.64 (d, 1H), 3.21 (s, 3H), 3.12-3.02 (m, 1H), 2.84-2.75 (m, 1H), 2.52-2.42 (m, 1H), 2.27-2.18 (m, 1H).

Example 52

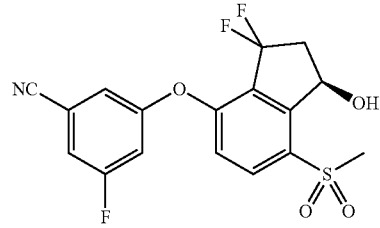 [SMILES: CS(=O)(=O)c1ccc(Oc2cc(F)cc(C#N)c2)c2c1[C@H](O)CC2(F)F]

3-[(1R)-3,3-difluoro-1-hydroxy-7-methylsulfonyl-indan-4-yl]oxy-5-fluoro-benzonitrile (Compound 52)

Step A: [(1R)-4-(3-cyano-5-fluoro-phenoxy)-7-methylsulfonyl-indan-1-yl] acetate: To a stirred solution of 3-fluoro-5-[(1R)-1-hydroxy-7-methylsulfonyl-indan-4-yl]oxy-benzonitrile (1.05 g, 3.0 mmol) in DCM (29 mL) was added 4-(dimethylamino)pyridine (0.369 g, 3.0 mmol) and triethylamine (0.84 mL, 6.1 mmol). Acetyl chloride (0.43 mL, 6.1 mmol) was added dropwise at 0° C. under nitrogen. The reaction mixture was stirred at ambient temperature for 2 hours. The reaction mixture was diluted with DCM, washed with saturated aqueous NaHCO₃ and brine, dried and concentrated. The residue was purified by flash chromatography on silica gel (20-50% EtOAc/hexane) to give [(1R)-4-(3-cyano-5-fluoro-phenoxy)-7-methylsulfonyl-indan-1-yl] acetate (0.72 g, 61%). LCMS ESI (−) m/z 434 (M+HCO₂⁻).

Step B: [(1R,3R)-3-bromo-4-(3-cyano-5-fluoro-phenoxy)-7-methylsulfonyl-indan-1-yl] acetate: To a stirred solution of [(1R)-4-(3-cyano-5-fluoro-phenoxy)-7-methylsulfonyl-indan-1-yl] acetate (720 mg, 1.85 mmol) in carbon tetrachloride (18 mL) was added N-bromosuccinimide (362 mg, 2.0 mmol) and 2,2'-azobisisobutyronitrile (3 mg, 0.02 mmol). The reaction mixture was heated at 80° C. for 2 hours. After cooling, the reaction mixture was diluted with DCM, washed with saturated aqueous NaHCO₃ and brine, dried and concentrated. The residue was purified by column chromatography on silica gel (10-40% EtOAc/hexanes) to give [(1R,3R)-3-bromo-4-(3-cyano-5-fluoro-phenoxy)-7-methylsulfonyl-indan-1-yl] acetate (514 mg, 59%) and a 1:2 mixture of (1R,3R)-3-bromo-4-(3-cyano-5-fluoro-phenoxy)-7-methylsulfonyl-indan-1-yl] acetate and [(1R,3S)-3-bromo-4-(3-cyano-5-fluoro-phenoxy)-7-methylsulfonyl-indan-1-yl] acetate (360 mg, 41%). LCMS ESI (−) m/z: 512, 514 (M+HCO₂).

Step C: [(1R,3S)-4-(3-cyano-5-fluoro-phenoxy)-3-hydroxy-7-methylsulfonyl-indan-1-yl] acetate: To a stirred solution of [(1R,3R)-3-bromo-4-(3-cyano-5-fluoro-phenoxy)-7-methylsulfonyl-indan-1-yl] acetate (423 mg, 0.9 mmol) in 1,2-dimethoxyethane (5 mL) and water (2 mL) was added silver carbonate (374 mg, 1.35 mmol). The reaction mixture was stirred at ambient temperature overnight. The mixture was diluted with EtOAc and filtered through Celite. The filtrate was washed with water and brine, dried and concentrated. The crude was used in the next step without further purification. LCMS ESI (−) m/z 450 (M+HCO₂⁻).

Step D: [(1R)-4-(3-cyano-5-fluoro-phenoxy)-7-methylsulfonyl-3-oxo-indan-1-yl] acetate: To a stirred solution of [(1R,3S)-4-(3-cyano-5-fluoro-phenoxy)-3-hydroxy-7-methylsulfonyl-indan-1-yl] acetate (366 mg, 0.9 mmol) in DCM (9 mL) was added Dess-Martin periodinane (574 mg, 1.35 mmol). The reaction mixture was stirred at ambient temperature for 1 hour. The reaction mixture was partitioned between EtOAc and saturated aqueous NaHCO$_3$. The aqueous layer was extracted with EtOAc. The combined organic layers were washed with water and brine, dried and concentrated. The crude was purified by flash chromatography on silica gel (10-50% EtOAc/hexane) to give [(1R)-4-(3-cyano-5-fluoro-phenoxy)-7-methylsulfonyl-3-oxo-indan-1-yl] acetate (320 mg, 88%). LCMS ESI (−) m/z 402 (M−H).

Step E: [(1R)-4-(3-cyano-5-fluoro-phenoxy)-3,3-difluoro-7-methylsulfonyl-indan-1-yl] acetate: To a plastic tube containing [(1R)-4-(3-cyano-5-fluoro-phenoxy)-7-methylsulfonyl-3-oxo-indan-1-yl] acetate (109 mg, 0.27 mmol) and DCM (1.2 mL) was added 4-(tert-butyl)-2,6-dimethylphenyl sulfur trifluoride (115 mg, 0.46 mmol) under nitrogen. Hydrogen fluoride pyridine (70%, 0.02 mL, 0.27 mmol) was added, and the mixture was stirred at ambient temperature for 4 hours. The solvent was removed under reduced pressure. The residue was taken up in EtOAc, washed with saturated aqueous NaHCO$_3$ and brine, dried and concentrated. The residue was purified by flash chromatography on silica gel (10-50% EtOAc/hexane) to give [(1R)-4-(3-cyano-5-fluoro-phenoxy)-3,3-difluoro-7-methylsulfonyl-indan-1-yl] acetate (97 mg, 84%). LCMS ESI (+) m/z 426 (M+H).

Step F: [(1R)-3,3-difluoro-1-hydroxy-7-methylsulfonyl-indan-4-yl]oxy-5-fluoro-benzonitrile (Compound 52): To a stirred solution of [(1R)-4-(3-cyano-5-fluoro-phenoxy)-3,3-difluoro-7-methylsulfonyl-indan-1-yl] acetate (97 mg, 0.23 mmol) in tetrahydrofuran (1.5 mL) was added 0.5 N LiOH solution (0.68 mL, 0.34 mmol) at 0° C. under nitrogen. The reaction mixture was stirred at 0° C. for 1 hour. The reaction was then partitioned between EtOAc and water. The aqueous layer was extracted with EtOAc. The combined organic layers were washed with water and brine, dried and concentrated. The residue was purified by flash chromatography on silica gel (30-70% EtOAc/hexane) to give Compound 52 (75 mg, 86%). LCMS ESI (−) m/z 428 (M+HCO$_2^-$); $^1$H NMR (400 MHz, CDCl$_3$): δ 8.08 (d, 1H), 7.29-7.23 (m, 1H), 7.19 (brs, 1H), 7.15-7.08 (m, 1H), 7.02 (d, 1H), 5.78-5.70 (m, 1H), 3.89 (d, 1H), 3.23 (s, 3H), 3.17-3.02 (m, 1H), 2.80-2.64 (m, 1H).

Example 53

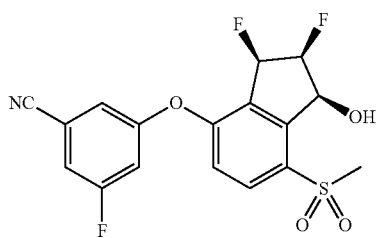 [SMILES: CS(=O)(=O)c1ccc(Oc2cc(F)cc(C#N)c2)c2c1[C@H](O)[C@H](F)[C@@H]2F]

3-[(1S,2S,3R)-2,3-difluoro-1-hydroxy-7-methylsulfonyl-indan-4-yl]oxy-5-fluoro-benzonitrile (Compound 53)

Step A: [(1S,2R)-4-(3-cyano-5-fluoro-phenoxy)-2-fluoro-7-methylsulfonyl-indan-1-yl] acetate: To a stirred solution of 3-fluoro-5-[(1S,2R)-2-fluoro-1-hydroxy-7-methylsulfonyl-indan-4-yl]oxy-benzonitrile (2.00 g, 5.47 mmol) in DCM (27 mL) was added 4-(dimethylamino)pyridine (0.2 g, 1.64 mmol) and triethylamine (1.53 mL, 10.9 mmol). Acetic anhydride (1.00 mL, 10.9 mmol) was added dropwise at 0° C. under nitrogen. The reaction mixture was stirred at ambient temperature overnight. The reaction mixture was diluted with DCM, washed with saturated aqueous NaHCO$_3$ and brine, dried and concentrated. The residue was purified by flash chromatography on silica gel (20-40% EtOAc/hexane) to give [(1S,2R)-4-(3-cyano-5-fluoro-phenoxy)-2-fluoro-7-methylsulfonyl-indan-1-yl] acetate (1.95 g, 87%). LCMS ESI (+) m/z 408 (M+H).

Step B: [(1S,2S,3S)-3-bromo-4-(3-cyano-5-fluoro-phenoxy)-2-fluoro-7-methylsulfonyl-indan-1-yl] acetate and [(1S,2S,3R)-3-bromo-4-(3-cyano-5-fluoro-phenoxy)-2-fluoro-7-methylsulfonyl-indan-1-yl] acetate: To a stirred solution of [(1S,2R)-4-(3-cyano-5-fluoro-phenoxy)-2-fluoro-7-methylsulfonyl-indan-1-yl] acetate (1.95 g, 4.79 mmol) in 1,2-dichloroethane (24 mL) was added N-bromosuccinimide (0.94 g, 5.27 mmol) and 2,2'-azobisisobutyronitrile (8 mg, 0.05 mmol). The reaction mixture was heated at 80° C. for 3 hours. After cooling, the reaction mixture was diluted with DCM, washed with saturated aqueous NaHCO$_3$ and brine, dried and concentrated. The residue was purified by column chromatography on silica gel (20-30% EtOAc/hexane) to give [(1S,2S,3S)-3-bromo-4-(3-cyano-5-fluoro-phenoxy)-2-fluoro-7-methylsulfonyl-indan-1-yl] acetate (1.52 g, 65%). LCMS ESI (+) m/z 486, 488 (M+H). Further elution with 30-50% EtOAc/hexane gave the more polar product [(1S,2S,3R)-3-bromo-4-(3-cyano-5-fluoro-phenoxy)-2-fluoro-7-methylsulfonyl-indan-1-yl] acetate (0.583 g, 25%). LCMS ESI (+) m/z 486, 488 (M+H).

Step C: [(1S,2R,3S)-4-(3-cyano-5-fluoro-phenoxy)-2-fluoro-3-hydroxy-7-methylsulfonyl-indan-1-yl] acetate: To a combined mixture of [(1S,2S,3S)-3-bromo-4-(3-cyano-5-fluoro-phenoxy)-2-fluoro-7-methylsulfonyl-indan-1-yl] acetate and [(1S,2S,3R)-3-bromo-4-(3-cyano-5-fluoro-phenoxy)-2-fluoro-7-methylsulfonyl-indan-1-yl] acetate prepared in Step B (2.05 g, 4.22 mmol) were added 1,2-dimethoxyethane (28 mL) and water (0.050 mL) followed by silver perchlorate hydrate (1.42 g, 6.32 mmol). The reaction mixture was heated at 70° C. for 2 hours. After cooling, the reaction mixture was diluted with EtOAc and filtered through Celite. The filtrate was washed with water and brine, dried and concentrated. The residue was purified by flash chromatography on silica gel (20-50%) to give [(1S,2R,3S)-4-(3-cyano-5-fluoro-phenoxy)-2-fluoro-3-hydroxy-7-methylsulfonyl-indan-1-yl] acetate (0.416 g, 23%) as the less polar product. LCMS ESI (+) m/z 441 (M+NH$_4^+$). Further elution with 60% EtOAc/hexane gave [(1S,2R,3R)-4-(3-cyano-5-fluoro-phenoxy)-2-fluoro-3-hydroxy-7-methylsulfonyl-indan-1-yl] acetate (0.58 g, 32%). LCMS ESI (+) m/z 441 (m+NH$_4^+$).

Step D: [(1S,2S,3R)-4-(3-cyano-5-fluoro-phenoxy)-2,3-difluoro-7-methylsulfonyl-indan-1-yl] acetate: To a stirred solution of [(1S,2R,3S)-4-(3-cyano-5-fluoro-phenoxy)-2-fluoro-3-hydroxy-7-methylsulfonyl-indan-1-yl] acetate (416 mg, 0.98 mmol) in DCM (10 mL) was added (diethylamino)sulfur trifluoride (DAST) (0.26 mL, 2.0 mmol) at −78° C. under nitrogen. The reaction mixture was allowed to warm to 0° C. and stirred for 15 minutes. The reaction was quenched by saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (20-40% EtOAc/hexane) to give [(1S,2S,3R)-4-(3-cyano-5-fluorophenoxy)-2,3-difluoro-7-methylsulfonyl-indan-1-yl] acetate (310 mg, 74%). LCMS ESI (+) m/z 426 (M+H).

Step E: 3-[(1S,2S,3R)-2,3-difluoro-1-hydroxy-7-methylsulfonyl-indan-4-yl]oxy-5-fluoro-benzonitrile (Compound 53): Prepared similarly as described in Example 52 Step F substituting [(1R)-4-(3-cyano-5-fluoro-phenoxy)-3,3-difluoro-7-methylsulfonyl-indan-1-yl] acetate with [(1S,2S,3R)-4-(3-cyano-5-fluoro-phenoxy)-2,3-difluoro-7-methylsulfonyl-indan-1-yl] acetate. LCMS ESI (+) m/z 384 (M+H); $^1$H NMR (400 MHz, CDCl$_3$): δ 8.13 (d, 1H), 7.31-7.25 (m, 1H), 7.23-7.19 (m, 1H), 7.14-7.09 (m, 1H), 7.04 (d, 1H), 6.09-5.91 (m, 1H), 5.87-5.80 (m, 1H), 5.25-5.05 (m, 1H), 3.32 (s, 3H), 2.95 (d, 1H).

Example 54

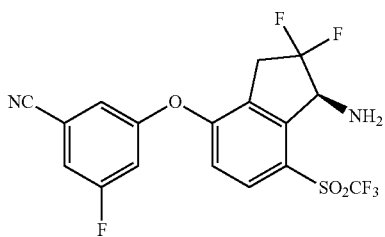

3-[(1S)-1-amino-2,2-difluoro-7-(trifluoromethylsulfonyl)indan-4-yl]oxy-5-fluoro-benzonitrile (Compound 54): LCMS ESI (+) m/z 437 (M+H); $^1$H NMR (400 MHz, CDCl$_3$): δ 7.92 (d, 1H), 7.34-7.30 (m, 1H), 7.24-7.22 (m, 1H), 7.14-7.10 (m, 1H), 6.94 (d, 1H), 4.85 (d, 1H), 3.65-3.41 (m, 2H).

Example 55

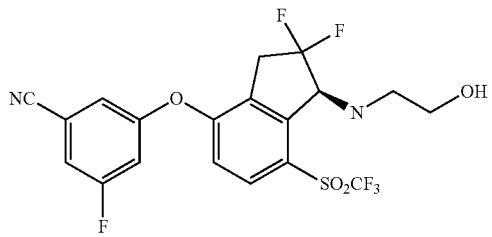

3-[(1S)-2,2-difluoro-1-(2-hydroxyethylamino)-7-(trifluoromethylsulfonyl)indan-4-yl]oxy-5-fluoro-benzonitrile (Compound 55)

Step A: 3-[(1S)-1-[2-[tert-butyl(dimethyl)silyl]oxyethylamino]-2,2-difluoro-7-(trifluoromethylsulfonyl)indan-4-yl]oxy-5-fluoro-benzonitrile: To a stirred solution of 3-[(1S)-1-amino-2,2-difluoro-7-(trifluoromethylsulfonyl)indan-4-yl]oxy-5-fluoro-benzonitrile (18 mg, 0.04 mmol) and 2-[tert-butyl(dimethyl)silyl]oxyacetaldehyde (36 mg, 0.21 mmol) in 1,2-dichloroethane (0.4 mL) was added NaB(OAc)$_3$H (306 mg, 1.44 mmol). The reaction mixture was stirred at ambient temperature for 2 hours. The reaction was partitioned between EtOAc and water. The aqueous layer was extracted with EtOAc. The combined organic layers were washed with brine, dried and concentrated. The residue was purified by flash chromatography on silica gel (5-20% EtOAc/hexane) to give 3-[(1S)-1-[2-[tert-butyl(dimethyl)silyl]oxyethylamino]-2,2-difluoro-7-(trifluoromethylsulfonyl)indan-4-yl]oxy-5-fluoro-benzonitrile (7 mg, 29%). LCMS ESI (+) m/z 595 (M+H).

Step B: 3-[(1S)-2,2-difluoro-1-(2-hydroxyethylamino)-7-(trifluoromethylsulfonyl)indan-4-yl]oxy-5-fluoro-benzonitrile (Compound 55): A mixture of 3-[(1S)-1-[2-[tert-butyl(dimethyl)silyl]oxyethylamino]-2,2-difluoro-7-(trifluoromethylsulfonyl)indan-4-yl]oxy-5-fluoro-benzonitrile (7 mg, 0.01 mmol) in DCM (0.2 mL) was treated with 5 N HCl in isopropanol (0.07 mL, 0.35 mmol) for 1 hour. The solvent was evaporated. The residue was taken up in EtOAc, washed with saturated aqueous NaHCO$_3$ and brine, dried and concentrated. The residue was purified by flash chromatography (20-50% EtOAc/hexane) to give Compound 55 (5 mg, 88%). LCMS ESI (+) m/z 481 (M+H); $^1$H NMR (400 MHz, CDCl$_3$): δ 7.95 (d, 1H), 7.35-7.31 (m, 1H), 7.24-7.22 (m, 1H), 7.14-7.10 (m, 1H), 6.95 (d, 1H), 4.59 (d, 1H), 3.77-3.52 (m, 2H), 3.42 (t, 2H), 3.06 (t, 2H).

Example 56

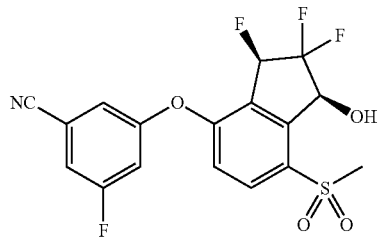 [SMILES: CS(=O)(=O)c1ccc(Oc2cc(F)cc(C#N)c2)c2c1[C@H](O)C(F)(F)[C@@H]2F]

3-fluoro-5-[(1S,3R)-2,2,3-trifluoro-1-hydroxy-7-methylsulfonyl-indan-4-yl]oxy-benzonitrile (Compound 56)

Step A: [(1S,3S)-4-(3-cyano-5-fluoro-phenoxy)-2,2-difluoro-3-hydroxy-7-methylsulfonyl-indan-1-yl] acetate and [(1S,3R)-4-(3-cyano-5-fluoro-phenoxy)-2,2-difluoro-3-hydroxy-7-methylsulfonyl-indan-1-yl] acetate: To a stirred solution of [(1S)-4-(3-cyano-5-fluoro-phenoxy)-2,2-difluoro-7-methylsulfonyl-indan-1-yl] acetate (1.0 g, 2.35 mmol) in DCE (24 mL) were added N-bromosuccinimide (0.46 g, 2.59 mmol) and 2,2'-azobisisobutyronitrile (4 mg, 0.02 mmol). The reaction mixture was heated at 80° C. overnight. After cooling, the reaction mixture was diluted with DCM, washed with saturated aqueous NaHCO$_3$ and brine, dried and concentrated. The crude product was dissolved in 1,2-dimethoxyethane (11 mL) and water (0.11 mL). Silver perchlorate hydrate (0.35 g, 1.55 mmol) was added. The reaction mixture was heated at 70° C. overnight. After cooling, the reaction mixture was diluted with EtOAc and filtered through Celite. The filtrate was washed with water and brine, dried and concentrated. The residue was purified by flash chromatography on silica gel (20-60% EtOAc/hexane) to give [(1S,3S)-4-(3-cyano-5-fluoro-phenoxy)-2,2-difluoro-3-hydroxy-7-methylsulfonyl-indan-1-yl] acetate (39 mg, 9% yield) as the less polar product. LCMS ESI (+) m/z 459 (M+NH$_4^+$). Further elution gave [(1S,3R)-4-(3-cyano-5-fluoro-phenoxy)-2,2-difluoro-3-hydroxy-7-methylsulfonyl-indan-1-yl] acetate (80 mg, 18%). LCMS ESI (+) m/z 459 (M+NH$_4^+$).

Step B: [(1S,3R)-4-(3-cyano-5-fluoro-phenoxy)-2,2,3-trifluoro-7-methylsulfonyl-indan-1-yl] acetate: Prepared similarly as described in Example 53 Step D substituting [(1S,2R,3S)-4-(3-cyano-5-fluoro-phenoxy)-2-fluoro-3-hydroxy-7-methylsulfonyl-indan-1-yl] acetate with [(1S,3S)-4-(3-cyano-5-fluoro-phenoxy)-2,2-difluoro-3-hydroxy-7-methylsulfonyl-indan-1-yl] acetate. LCMS ESI (+) m/z 444 (M+H).

Step C: 3-fluoro-5-[(1S,3R)-2,2,3-trifluoro-1-hydroxy-7-methylsulfonyl-indan-4-yl]oxy-benzonitrile: Prepared similarly as described in Example 53 Step F substituting [(1R)-4-(3-cyano-5-fluoro-phenoxy)-3,3-difluoro-7-methylsulfonyl-indan-1-yl] acetate with [(1S,3R)-4-(3-cyano-5-fluoro-phenoxy)-2,2,3-trifluoro-7-methylsulfonyl-indan-1-yl] acetate. LCMS ESI (+) m/z 419 (M+NH$_4^+$); $^1$H NMR (400 MHz, CDCl$_3$): δ 8.14-8.11 (m, 1H), 7.33-7.29 (m, 1H), 7.25-7.23 (m, 1H), 7.16-7.12 (m, 1H), 7.05 (d, 1H), 5.91-5.75 (m, 1H), 5.71-5.65 (m, 1H), 3.39 (d, 1H), 3.25 (s, 3H).

Alternative synthesis 1 of 3-fluoro-5-[(1S,3R)-2,2,3-trifluoro-1-hydroxy-7-methylsulfonyl-indan-4-yl]oxy-benzonitrile (Compound 56)

Step A: 3-fluoro-5-(2'-fluoro-7'-methylsulfonyl-3'-oxo-spiro[1,3-dioxolane-2,1'-indane]-4'-yl)oxy-benzonitrile: To a stirred solution of 3-fluoro-5-(7'-methylsulfonyl-3'-oxo-spiro[1,3-dioxolane-2,1'-indane]-4'-yl)oxy-benzonitrile (1.0 g, 2.48 mmol) and triethylamine (2.07 mL, 14.9 mmol) in DCM (24.8 mL) was added dropwise [tert-butyl(dimethyl)silyl] trifluoromethanesulfonate (0.85 mL, 3.7 mmol) at 0° C. under nitrogen. The reaction was allowed to warm to ambient temperature and stir overnight. The reaction was diluted with EtOAc, washed with saturated aqueous NaHCO$_3$ solution and brine, dried and concentrated. The crude was dissolved in acetonitrile (25 mL). Selectfluor® (1.14 g, 3.2 mmol) was added to the reaction mixture. The reaction was stirred at ambient temperature for 1 hour. The solvent was evaporated under reduced pressure. The residue was taken up in DCM, washed with water and brine, dried over Na$_2$SO$_4$, filtered, and concentrated to dryness. The residue was purified by flash chromatography on silica gel (20-50% EtOAc/hexane) to give 3-fluoro-5-(2'-fluoro-7'-methylsulfonyl-3'-oxo-spiro[1,3-dioxolane-2,1'-indane]-4'-yl)oxy-benzonitrile (0.81 g, 78%). LCMS ESI (+) m/z 422 (M+H).

Step B: 3-(2',2'-difluoro-7'-methylsulfonyl-3'-oxo-spiro[1,3-dioxolane-2,1'-indane]-4'-yl)oxy-5-fluoro-benzonitrile: To a stirred solution of 3-fluoro-5-(2'-fluoro-7'-methylsulfonyl-3'-oxo-spiro[1,3-dioxolane-2,1'-indane]-4'-yl)oxy-benzonitrile (455 mg, 1.08 mmol) and triethylamine (0.90 mL, 6.5 mmol) in DCM (11 mL) was added dropwise [tert-butyl(dimethyl)silyl] trifluoromethanesulfonate (0.37 mL, 1.6 mmol) at 0° C. under nitrogen. The reaction was allowed to warm to ambient temperature and stir overnight. The reaction was diluted with EtOAc, washed with saturated aqueous NaHCO$_3$ solution and brine, dried and concentrated. The crude was dissolved in acetonitrile (11 mL). Selectfluor® (612 mg, 1.73 mmol) was added and the reaction mixture was stirred at ambient temperature for 2 hours. The solvent was evaporated under reduced pressure. The residue was taken up in DCM, washed with water and brine, dried over Na$_2$SO$_4$, filtered, and concentrated. The residue was purified by flash chromatography on silica gel (20-50% EtOAc/hexane) to give 3-(2',2'-difluoro-7'-methylsulfonyl-3'-oxo-spiro[1,3-dioxolane-2,1'-indane]-4'-yl)oxy-5-fluoro-benzonitrile (337 mg, 71%). LCMS ESI (+) m/z 440 (M+H).

Step C: 3-[(3'S)-2',2'-difluoro-3'-hydroxy-7'-methylsulfonyl-spiro[1,3-dioxolane-2,1'-indane]-4'-yl]oxy-5-fluoro-benzonitrile: Formic acid (0.087 mL, 2.3 mmol) was added slowly to a solution of triethylamine (0.21 mL, 1.5 mmol) in DCM (8 mL) at 0° C. 3-(2',2'-difluoro-7'-methylsulfonyl-3'-oxo-spiro[1,3-dioxolane-2,1'-indane]-4'-yl)oxy-5-fluoro-benzonitrile (337 mg, 0.77 mmol) was then added followed by the addition of RuCl(p-cymene)[(R,R)-Ts-DPEN] (5.5 mg, 0.01 mmol) under nitrogen. The flask was then placed in a 4° C. refrigerator overnight. The reaction mixture was diluted with DCM, washed with saturated aqueous NaHCO$_3$ and brine, dried and concentrated. The residue was purified by flash chromatography on silica gel (20-60% EtOAc/hexanes) to give 3-[(3'S)-2',2'-difluoro-3'-hydroxy-7'-methylsulfonyl-spiro[1,3-dioxolane-2,1'-indane]-4'-yl]oxy-5-fluoro-benzonitrile (335 mg, 99%). LCMS ESI (+) m/z 424 (M+H).

Step D: 3-fluoro-5-[(3'R)-2',2',3'-trifluoro-7'-methylsulfonyl-spiro[1,3-dioxolane-2,1'-indane]-4'-yl]oxy-benzonitrile: To a stirred solution of 3-[(3'S)-2',2'-difluoro-3'-hydroxy-7'-methylsulfonyl-spiro[1,3-dioxolane-2,1'-indane]-4'-yl]oxy-5-fluoro-benzonitrile (285 mg, 0.650 mmol) in DCM (6 mL) was added (diethylamino)sulfur trifluoride (DAST) (0.17 mL, 1.3 mmol) at −78° C. under nitrogen. The reaction mixture was allowed to warm to 0° C. and stirred for 30 minutes. The reaction was quenched by the addition of saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (20-60% EtOAc/hexane) to give 3-fluoro-5-[(3'R)-2',2',3'-trifluoro-7'-methylsulfonyl-spiro[1,3-dioxolane-2,1'-indane]-4'-yl]oxy-benzonitrile (248 mg, 87%). LCMS ESI (+) m/z 444 (M+H).

Step E: 3-fluoro-5-[(3R)-2,2,3-trifluoro-7-methylsulfonyl-1-oxo-indan-4-yl]oxy-benzonitrile: To a stirred solution of 3-fluoro-5-[(3'R)-2',2',3'-trifluoro-7'-methylsulfonyl-spiro[1,3-dioxolane-2,1'-indane]-4'-yl]oxy-benzonitrile (286 mg, 0.65 mmol) in DCM (6 mL) was added 70% perchloric acid (2 mL). The reaction mixture was stirred at ambient temperature for 3 days. The reaction was diluted with EtOAc, washed with water, saturated aqueous NaHCO$_3$ and brine, dried and concentrated. The residue was purified by flash chromatography on silica gel (30-60% EtOAc/hexanes) to give 3-fluoro-5-[(3R)-2,2,3-trifluoro-7-methylsulfonyl-1-oxo-indan-4-yl]oxy-benzonitrile (145 mg, 56%). LCMS ESI (+) m/z 400 (M+H).

Step F: 3-fluoro-5-[(1S,3R)-2,2,3-trifluoro-1-hydroxy-7-methylsulfonyl-indan-4-yl]oxy-benzonitrile (Compound 56): To a stirred solution of 3-fluoro-5-[(3R)-2,2,3-trifluoro-7-methylsulfonyl-1-oxo-indan-4-yl]oxy-benzonitrile (144 mg, 0.36 mmol) in DCM (3.6 mL) was added formic acid (0.041 mL, 1.1 mmol) followed by triethylamine (0.1 mL, 0.72 mmol). The reaction mixture was purged with nitrogen. RuCl(p-cymene)[(R,R)-Ts-DPEN] (1.1 mg) was added under nitrogen. The reaction vial was then placed in a 4° C. refrigerator overnight. The solvents were evaporated. The residue was purified by flash chromatography on silica gel (20-60% EtOAc/hexane) to give Compound 56 (92 mg, 64%).

Alternative synthesis 2 of 3-fluoro-5-[(1S,3R)-2,2,3-trifluoro-1-hydroxy-7-methylsulfonyl-indan-4-yl]oxy-benzonitrile (Compound 56)

Step A: 3-fluoro-5-(7-methylsulfonyl-1,3-dioxo-indan-4-yl)oxy-benzonitrile: To a stirred solution of 3-fluoro-5-(7'-methylsulfonyl-3'-oxo-spiro[1,3-dioxolane-2,1'-indane]-4'-yl)oxy-benzonitrile (500 mg, 1.24 mmol) in tetrahydrofuran (6 mL) was added 4N HCl (3.1 mL, 12 mmol). The reaction was heated at reflux for 2 hours. After cooling, the reaction mixture was partitioned between EtOAc and water. The aqueous layer was extracted with EtOAc. The combined organic layers were washed with water and brine, dried and concentrated. The crude was used in the next step without further purification. LCMS ESI (+) m/z 360 (M+H).

Step B: 3-(2,2-difluoro-7-methylsulfonyl-1,3-dioxo-indan-4-yl)oxy-5-fluoro-benzonitrile: To a stirred solution of 3-fluoro-5-(7-methylsulfonyl-1,3-dioxo-indan-4-yl)oxy-benzonitrile (crude product from Step A, 445 mg, 1.24 mmol) in acetonitrile (12 mL) at 25° C. was added anhydrous sodium carbonate (289 mg, 2.72 mmol) under nitrogen. Selectfluor® (965 mg, 2.72 mmol) was added and the reaction mixture was stirred at 25° C. for 2 hours. The reaction mixture was partitioned between EtOAc and water. The aqueous layer was extracted with EtOAc. The combined organic layers were washed with water and brine, dried and concentrated. The residue was purified by flash chromatography on silica gel (20-60% EtOAc/hexane) to give 3-(2,2-difluoro-7-methylsulfonyl-1,3-dioxo-indan-4-yl)oxy-5-fluoro-benzonitrile (230 mg, 47%). LCMS ESI (+) m/z 396 (M+H).

Step C: 3-[(1S,3S)-2,2-difluoro-1,3-dihydroxy-7-methylsulfonyl-indan-4-yl]oxy-5-fluoro-benzonitrile: Formic acid (0.049 mL, 1.3 mmol) was added slowly to a solution of triethylamine (0.12 mL, 0.86 mmol) in DCM (4 mL) at 0° C. 3-(2,2-Difluoro-7-methylsulfonyl-1,3-dioxo-indan-4-yl)oxy-5-fluoro-benzonitrile (170 mg, 0.43 mmol) was then added followed by the addition of RuCl(p-cymene)[(R,R)-Ts-DPEN] (5.5 mg, 0.01 mmol) under nitrogen. The flask was then placed in a 4° C. refrigerator overnight. The reaction mixture was diluted with DCM, washed with saturated aqueous NaHCO$_3$ and brine, dried and concentrated. The residue was purified by flash chromatography on silica gel (20-60% EtOAc/hexane) to give 3-[(1S,3S)-2,2-difluoro-1,3-dihydroxy-7-methylsulfonyl-indan-4-yl]oxy-5-fluoro-benzonitrile (70 mg, 41%) and 3-[(1S,3R)-2,2-difluoro-1,3-dihydroxy-7-methylsulfonyl-indan-4-yl]oxy-5-fluoro-benzonitrile (65 mg, 38%). LCMS ESI (+) m/z 400 (M+H).

Step D: 3-fluoro-5-[(1S,3R)-2,2,3-trifluoro-1-hydroxy-7-methylsulfonyl-indan-4-yl]oxy-benzonitrile (Compound 56): To a stirred solution of 3-[(1S,3S)-2,2-difluoro-1,3-dihydroxy-7-methylsulfonyl-indan-4-yl]oxy-5-fluoro-benzonitrile (70 mg, 0.18 mmol) in DCM (2 mL) was added (diethylamino)sulfur trifluoride (DAST) (0.058 mL, 0.44 mmol) at −78° C. under nitrogen. The reaction mixture was allowed to warm to −20° C. and stirred for 1 hour. The reaction was quenched by the addition of saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (20-60% EtOAc/hexane) to give Compound 56 (31 mg, 44%).

Example 57

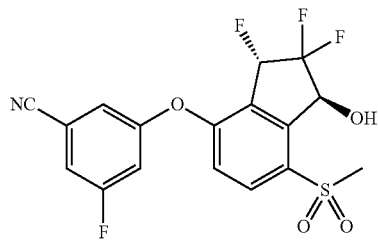 [SMILES: CS(=O)(=O)c1ccc(Oc2cc(F)cc(C#N)c2)c2c1[C@H](O)C(F)(F)[C@H]2F]

3-fluoro-5-[(1S,3S)-2,2,3-trifluoro-1-hydroxy-7-methylsulfonyl-indan-4-yl]oxy-benzonitrile (Compound 57): LCMS ESI (+) m/z 419 (M+NH$_4^+$); $^1$H NMR (400 MHz, CDCl$_3$): δ 8.10-8.07 (m, 1H), 7.32-7.28 (m, 1H), 7.23-7.20 (m, 1H), 7.15-7.10 (m, 1H), 7.02 (d, 1H), 6.07-5.90 (m, 1H), 5.87-5.80 (m, 1H), 3.95 (d, 1H), 3.26 (s, 3H).

Example 58

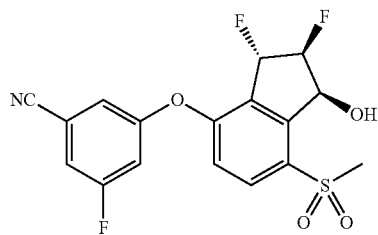 [SMILES: CS(=O)(=O)c1ccc(Oc2cc(F)cc(C#N)c2)c2c1[C@H](O)[C@H](F)[C@H]2F]

3-[(1S,2S,3S)-2,3-difluoro-1-hydroxy-7-methylsulfonyl-indan-4-yl]oxy-5-fluoro-benzonitrile (Compound 58): LCMS ESI (+) m/z 384 (M+H); $^1$H NMR (400 MHz, CDCl$_3$): δ 8.09-8.06 (m, 1H), 7.27-7.24 (m, 1H), 7.19-7.17 (m, 1H), 7.10-7.07 (m, 1H), 7.04 (d, 1H), 6.30-6.12 (m, 1H), 5.96-5.89 (m, 1H), 5.46-5.27 (m, 1H), 3.53-3.51 (m, 1H), 3.27 (s, 3H).

Example 59

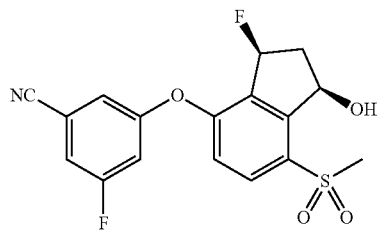 [SMILES: CS(=O)(=O)c1ccc(Oc2cc(F)cc(C#N)c2)c2c1[C@H](O)C[C@@H]2F]

3-fluoro-5-[(1R,3S)-3-fluoro-1-hydroxy-7-methylsulfonyl-indan-4-yl]oxy-benzonitrile (Compound 59): LCMS ESI (+) m/z 383 (M+NH$_4^+$); $^1$H NMR (400 MHz, CDCl$_3$): δ 8.04-8.01 (m, 1H), 7.25-7.22 (m, 1H), 7.18-7.16 (m, 1H), 7.11-7.06 (m, 1H), 7.00 (d, 1H), 6.09-5.79 (m, 1H), 5.69-5.61 (m, 1H), 3.54 (d, 1H), 3.23 (s, 3H), 2.94-2.80 (m, 1H), 2.52-2.41 (m, 1H).

Example 60

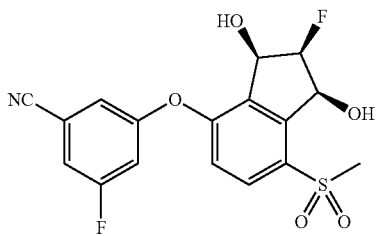 [SMILES: CS(=O)(=O)c1ccc(Oc2cc(F)cc(C#N)c2)c2c1[C@H](O)[C@H](F)[C@@H]2O]

3-fluoro-5-[(1S,2R,3R)-2-fluoro-1,3-dihydroxy-7-methylsulfonyl-indan-4-yl]oxy-benzonitrile (Compound 60): LCMS ESI (+) m/z 399 (M+NH$_4^+$); $^1$H NMR (400 MHz, CDCl$_3$): δ 8.05 (d, 1H), 7.26-7.22 (m, 1H), 7.19-7.17 (m, 1H), 7.12-7.07 (m, 1H), 7.05 (d, 1H), 5.76-5.70 (m, 1H), 5.30-5.24 (m, 1H), 5.18-5.01 (m, 1H), 3.29 (s, 3H).

Example 61

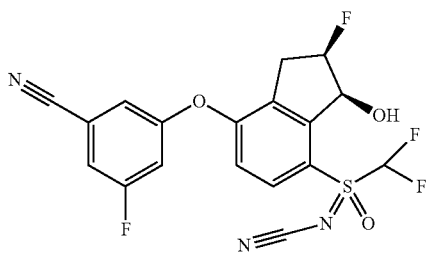 [SMILES: N#CN=S(=O)(c1ccc(Oc2cc(F)cc(C#N)c2)c2c1[C@H](O)[C@H](F)C2)C(F)F]

Isomer 1 of N-(((2R,3S)-7-(3-cyano-5-fluorophenoxy)-2-fluoro-3-hydroxy-2,3-dihydro-1H-inden-4-yl)(difluoromethyl)(oxo)-λ$^6$-sulfanylidene)cyanamide (Compound 61)

Step A: Preparation of 3-fluoro-5-((7-mercapto-1-oxo-2,3-dihydro-1H-inden-4-yl)oxy)benzonitrile: A mixture of 3-fluoro-5-((7-(methylsulfonyl)-1-oxo-2,3-dihydro-1H-inden-4-yl)oxy)benzonitrile and 3-fluoro-5-((7-(methylsulfinyl)-1-oxo-2,3-dihydro-1H-inden-4-yl)oxy)benzonitrile (ca. 1:2 ratio) was dissolved in methylene chloride (100 mL) under nitrogen. Trifluoroacetic anhydride (21.1 mL, 152 mmol) was added dropwise at ambient temperature. After about two hours, the reaction mixture was concentrated in vacuo. The residue was dissolved in MeOH (25 mL). Triethylamine (25 mL, 179 mmol) was added slowly under nitrogen. The reaction mixture was stirred at ambient temperature for 30 minutes then concentrated in vacuo. The residue was partitioned between 1 N NaOH and MTBE and the aqueous layer was separated. The aqueous was cooled to 0° C. and the pH was adjusted to 3-4 using 10% KHSO$_4$. The aqueous layer was extracted twice with ethyl acetate. The combined organic layers were washed with saturated NaCl, dried over Na$_2$SO$_4$ and concentrated in vacuo. The crude product was used in the subsequent alkylation without delay. LCMS ESI (+) m/z 300 (M+H).

Step B: Preparation of 3-((7-((difluoromethyl)thio)-1-oxo-2,3-dihydro-1H-inden-4-yl)oxy)-5-fluorobenzonitrile: 3-Fluoro-5-(1-oxo-7-sulfanyl-indan-4-yl)oxy-benzonitrile (4.54 g, 15.2 mmol) was dissolved in acetonitrile (54 mL) and treated with a solution of KOH (17.0 g, 303 mmol) in water (54 mL). The mixture was purged with argon, cooled to −20° C. then treated with bromodifluoromethyldiethylphosphonate (5.4 mL, 30.4 mmol). The resulting mixture was allowed to warm to ambient temperature and stirred for 2 hours. The mixture was concentrated gently to remove MeCN, then MTBE and water were added (ca. 50-70 mL each). The layers were separated. The aqueous layer was cooled in an ice bath and adjusted to pH 3-4 with 10% KHSO$_4$. The aqueous was treated with MTBE/ethyl acetate (1:1, ca. 200 mL) and separated. The aqueous was extracted with ethyl acetate then the combined organics were washed with water, saturated NaHCO$_3$, water, saturated NaCl, saturated NaHCO$_3$, saturated NaCl, dried over Na$_2$SO$_4$, and then concentrated in vacuo. The residue was chromatographed on SiO$_2$ (Biotage SNAP 10 g) and eluted with a gradient of ethyl acetate/hexane to give the desired product as a pinkish solid (ca. 650 mg). The mixed fractions were re-chromatographed on SiO$_2$ (Biotage SNAP 50 g) with chloroform to give the desired product (0.87 g, combined yield of 29%). LCMS ESI (+) m/z 350 (M+H).

Step C: Preparation of N-((7-(3-cyano-5-fluorophenoxy)-3-oxo-2,3-dihydro-1H-inden-4-yl)(difluoromethyl)-λ$^4$-sulfanylidene)cyanamide: A solution of 3-((7-((difluoromethyl)thio)-1-oxo-2,3-dihydro-1H-inden-4-yl)oxy)-5-fluorobenzonitrile (573 mg, 1.64 mmol), bis(tert-butylcarbonyloxy)iodobenzene (1330 mg, 3.28 mmol), magnesium oxide (264 mg, 6.56 mmol), and cyanamide (138 mg, 3.28 mmol) in dichloromethane (22 mL) was treated with bis[rhodium(α α α' α'-tetramethyl-1,3-benzenepropionic acid)] (100 mg, 0.13 mmol). The reaction was stirred at ambient temperature for 90 minutes. The reaction was filtered through celite, washed with dichloromethane and concentrated in vacuo. The residue was used without further purification. LCMS ESI (+) m/z 390 (M+H).

Step D: Preparation of N-((7-(3-cyano-5-fluorophenoxy)-3-oxo-2,3-dihydro-1H-inden-4-yl)(difluoromethyl)(oxo)-λ$^6$-sulfanylidene)cyanamide: [[7-(3-cyano-5-fluoro-phenoxy)-3-oxo-indan-4-yl]-(difluoromethyl)-λ$^4$-sulfanylidene]cyanamide (638 mg, 1.64 mmol) was dissolved in a mixture of carbon tetrachloride (4 mL), acetonitrile (4 mL) and water (8 mL). This solution was treated with ruthenium (III) trichloride (6.8 mg, 0.03 mmol) followed by sodium periodate (1.05 g, 4.92 mmol). The mixture was stirred at ambient temperature for 14 hours. Additional ruthenium (III) trichloride (6.8 mg, 0.03 mmol) and sodium periodate (1.05 g, 4.92 mmol) were added and stirring was continued for an additional 24 hours. The heterogeneous mixture was diluted with methylene chloride and one-half saturated sodium thiosulfate solution and stirred for 1 hour then filtered through a pad of celite. The aqueous layer was washed with methylene chloride. The combined organic layers were washed with dilute sodium thiosulfate, water, then dried over Na$_2$SO$_4$ and concentrated in vacuo. The crude material was chromatographed on SiO$_2$ (Biotage SNAP 25g) with a gradient of ethyl acetate/hexane to afford the desired product (304 mg). LCMS ESI (+) m/z 406 (M+H).

Step E: Preparation of N—(((R)-7-(3-cyano-5-fluorophenoxy)-2-fluoro-3-oxo-2,3-dihydro-1H-inden-4-yl)(difluoromethyl)(oxo)-λ$^6$-sulfanylidene)cyanamide: A solution of cyano-[[7-(3-cyano-5-fluoro-phenoxy)-3-oxo-indan-4-yl]-(difluoromethyl)-oxo-λ$^6$-sulfanylidene]ammonium (136 mg, 0.33 mmol) in acetonitrile (3.8 mL) was treated with [1-fluoro-4-hydroxy-1,4-diazoniabicyclo[2,2,2]octane bis (tetrafluoroborate) on aluminum oxide (Accufluor® 50 wt %) and stirred at reflux for 9 hours then allowed to cool with the bath and stirred overnight. The solvent was removed with a stream of nitrogen gas. The crude material was chromatographed on SiO₂ (Biotage SNAP 10 g) with a gradient of ethyl acetate/hexane to afford the desired product (78 mg). LCMS ESI (+) m/z 424 (M+H).

Step F: Preparation of N-(((2R,3S)-7-(3-cyano-5-fluorophenoxy)-2-fluoro-3-hydroxy-2,3-dihydro-1H-inden-4-yl)(difluoromethyl)(oxo)-λ⁶-sulfanylidene)cyanamide (Compound 61): N—(((R)-7-(3-cyano-5-fluorophenoxy)-2-fluoro-3-oxo-2,3-dihydro-1H-inden-4-yl)(difluoromethyl)(oxo)-λ⁶-sulfanylidene)cyanamide (78 mg, 0.18 mmol) (containing some N-((7-(3-cyano-5-fluorophenoxy)-3-oxo-2,3-dihydro-1H-inden-4-yl)(difluoromethyl)(oxo)-λ⁶-sulfanylidene)cyanamide from the previous reaction) was dissolved in isopropanol (0.9 mL) and treated with triethylamine (0.05 mL, 0.37 mmol), formic acid (0.02 mL, 0.55 mmol) and RuCl(p-cymene)[(R,R)-Ts-DPEN] (1.2 mg, 0.002 mmol). The reaction mixture was stirred at ambient temperature for 14 hours. The reaction mixture was concentrated in a stream of nitrogen then chromatographed on SiO₂ (Biotage SNAP 10 g) with a gradient of ethyl acetate/hexane. A second purification on SiO₂ (Biotage SNAP 25g Ultra) with a gradient of ethyl acetate/hexane afforded Compound 61 (2.7 mg). LCMS ESI (+) m/z 426 (M+H); ¹H NMR (400 MHz, CDCl₃): δ 8.04 (d, 1H), 7.34-7.30 (m, 1H), 7.25-7.22 (m, 1H), 7.23 (t, J=54 Hz, 1H), 7.14-7.10 (m, 1H), 7.00 (d, 1H), 5.71-5.63 (m, 1H), 5.56-5.52 (m, 0.5H), 5.43-5.39 (m, 0.5H), 3.59 (t, 1H), 3.46-3.18 (m, 2H).

Example 62

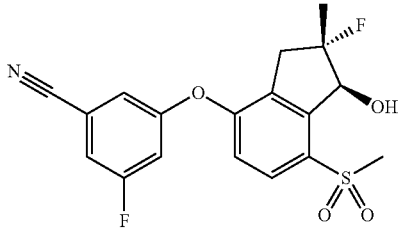 [SMILES: C[C@]1(F)Cc2c(Oc3cc(F)cc(C#N)c3)ccc(S(C)(=O)=O)c2[C@@H]1O]

3-fluoro-5-(((1S,2S)-2-fluoro-1-hydroxy-2-methyl-7-(methylsulfonyl)-2,3-dihydro-1H-inden-4-yl)oxy)benzonitrile (Compound 62)

Step A: Preparation of 3-fluoro-5-((2-fluoro-2-methyl-7-(methylsulfonyl)-1-oxo-2,3-dihydro-1H-inden-4-yl)oxy)benzonitrile: 3-fluoro-5-(2-fluoro-7-methylsulfonyl-1-oxo-indan-4-yl)oxy-benzonitrile (192 mg, 0.53 mmol) was dissolved in DMF (1.5 mL) and treated with cesium carbonate (343 mg, 1.06 mmol). Iodomethane (0.16 mL, 2.6 mmol) was added. The mixture was stirred at ambient temperature for 60 hours. The reaction mixture was sparged with nitrogen gas for several minutes then diluted with methylene chloride/ethyl acetate (1:1). The suspension was filtered through paper and then the filtrate was diluted with water and mixed gently. After the slow separation, the organic layer was washed twice with water, saturated NaCl, dried over Na₂SO₄ and concentrated in vacuo (315 mg). The crude material was chromatographed on SiO₂ (Biotage SNAP Ultra 10 g) with a gradient of ethyl acetate/hexane to give the desired product as colorless oil (61 mg). LCMS ESI (+) m/z 378 (M+H)

Step B: Preparation of 3-fluoro-5-(((1S,2S)-2-fluoro-1-hydroxy-2-methyl-7-(methylsulfonyl)-2,3-dihydro-1H-inden-4-yl)oxy)benzonitrile (Compound 62): 3-Fluoro-5-(2-fluoro-2-methyl-7-methylsulfonyl-1-oxo-indan-4-yl)oxy-benzonitrile (61 mg, 0.16 mmol) was suspended in methylene chloride (1.2 mL), cooled to 0° C. and treated with triethylamine (0.05 mL, 0.32 mmol), formic acid (0.02 mL, 0.48 mmol) and RuCl(p-cymene)[(R,R)-Ts-DPEN] (1.03 mg, 0.002 mmol). The reaction mixture was stirred at 0° C. for 20 hours. The solvent was removed by exposure to a stream of nitrogen gas. The residue was purified by preparative TLC with 2% MeOH/methylene chloride to give Compound 62 (8.6 mg). LCMS ESI (+) m/z 397 (M+NH₄); ¹H NMR (400 MHz, CDCl₃): δ 7.85 (d, 1H), 7.22-7.19 (m, 1H), 7.12-7.09 (m, 1H), 7.03-6.98 (m, 2H), 5.29-5.23 (m, 1H), 3.57-3.53 (m, 1H), 3.26-3.04 (m, 2H), 3.19 (s, 3H), 1.70 (d, J=22 Hz, 3H)

Example 63

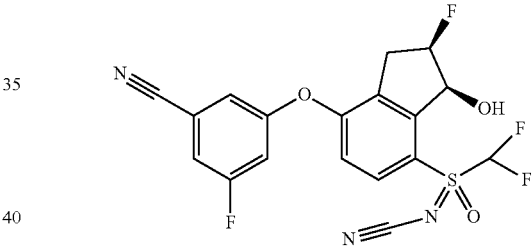

Isomer 2 of N-(((2R,3S)-7-(3-cyano-5-fluorophenoxy)-2-fluoro-3-hydroxy-2,3-dihydro-1H-inden-4-yl)(difluoromethyl)(oxo)-λ⁶-sulfanylidene)cyanamide (Compound 63): LCMS ESI (+) m/z 426 (M+H); ¹H NMR (400 MHz, CDCl₃): δ 8.03 (d, 1H), 7.34-7.30 (m, 1H), 7.23-7.21 (m, 1H), 7.13-7.09 (m, 1H), 7.01 (t, J=53 Hz, 1H), 6.99 (d, 1H), 5.73-5.66 (m, 1H), 5.56-5.52 (m, 0.5H), 5.43-5.39 (m, 0.5H), 3.45-3.34 (m, 1H), 3.35-3.19 (m, 2H)

Example 64

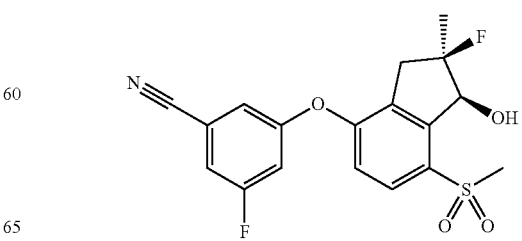

3-fluoro-5-(((1S,2R)-2-fluoro-1-hydroxy-2-methyl-7-(methylsulfonyl)-2,3-dihydro-1H-inden-4-yl)oxy)benzonitrile (Compound 64): Prepared similarly as described in Example 62. LCMS ESI (+) m/z 397 (M+NH$_4$); $^1$H NMR (400 MHz, CDCl$_3$): δ 7.90 (d, 1H), 7.21-7.19 (m, 1H), 7.10-7.08 (m, 1H), 6.99 (dt, 1H), 6.98 (d, 1H), 5.40-5.35 (m, 1H), 3.79-3.77 (m, 1H), 3.36-3.27 (m, 1H), 3.32 (s, 3H), 2.95-2.84 (m, 1H), 1.70 (d, 3H)

Example 65

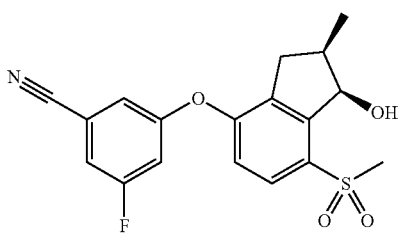 [SMILES: C[C@@H]1Cc2c(Oc3cc(F)cc(C#N)c3)ccc(S(C)(=O)=O)c2[C@@H]1O]

3-fluoro-5-(((1R,2R)-1-hydroxy-2-methyl-7-(methylsulfonyl)-2,3-dihydro-1H-inden-4-yl)oxy)benzonitrile (Compound 65)

Step A: Preparation of 3-fluoro-5-((2-methyl-7-(methylsulfonyl)-1-oxo-2,3-dihydro-1H-inden-4-yl)oxy)benzonitrile: A solution of diisopropylamine (0.28 mL, 2.0 mmol) in THF (2 mL) was cooled to 0° C. and treated with n-BuLi (2.26 M in hexanes, 0.83 mL, 1.9 mmol) then stirred for 15 minutes. The solvents were removed from the mixture under high vacuum while maintaining the flask at 0° C. The resulting white solid was dissolved in fresh THF (1.8 mL). This solution was added dropwise to a flask containing a solution of 3-fluoro-5-(7-methylsulfonyl-1-oxo-indan-4-yl)oxy-benzonitrile (500 mg, 1.45 mmol) dissolved in a mixture of THF (2 mL) and 1,3-dimethyl-3,4,5,6-tetrahydro-2(1H)-pyrimidinone (1 mL) which was cooled to −40° C. The dark solution was stirred for 30 minutes at −40° C. then iodomethane (0.13 mL, 2.0 mmol) was added. The mixture was allowed to warm to ambient temperature with the bath and stirred for 10 hours. The dark reaction mixture was cooled to 0° C. and poured into cold 10% KHSO$_4$ and stirred for several minutes. Ethyl acetate was added. The pH of the aqueous was adjusted to about 8 with solid NaHCO$_3$ and the layers were separated. The aqueous layer was washed with ethyl acetate and the combined organics were washed with saturated NaHCO$_3$, saturated NaCl, dried over Na$_2$SO$_4$ and concentrated in vacuo. The crude material was chromatographed on SiO$_2$ (Biotage SNAP 25g) with a gradient of ethyl acetate/hexane. The desired material was isolated as a white solid (55 mg). LCMS ESI (+) m/z 360 (M+H).

Step B: Preparation of 3-fluoro-5-(((1R,2R)-1-hydroxy-2-methyl-7-(methylsulfonyl)-2,3-dihydro-1H-inden-4-yl)oxy)benzonitrile (Compound 65): 3-Fluoro-5-(2-methyl-7-methylsulfonyl-1-oxo-indan-4-yl)oxy-benzonitrile (26 mg, 0.07 mmol) was suspended in isopropanol (0.2 mL) and treated with triethylamine (0.02 mL, 0.14 mmol), formic acid (0.01 mL, 0.22 mmol) and RuCl(p-cymene)[(R,R)-Ts-DPEN] (0.46 mg, 0.001 mmol). The reaction mixture was stirred at ambient temperature for 14 hours. Additional methylene chloride (about 100 µL) was added. The reaction mixture was treated with fresh triethylamine (0.02 mL, 0.14 mmol), formic acid (0.01 mL, 0.22 mmol), and RuCl(p-cymene)[(R,R)-Ts-DPEN] (0.46 mg, 0.001 mmol) and stirring was continued at ambient temperature for 4 hours. The reaction mixture was concentrated in a stream of nitrogen gas and then chromatographed on SiO$_2$ (Biotage SNAP 10 g) with a gradient of ethyl acetate/hexane to give Compound 65 (19 mg). LCMS ESI (+) m/z 379 (M+NH$_4$); $^1$H NMR (400 MHz, CDCl$_3$): δ 7.84 (d, 1H), 7.19-7.15 (m, 1H), 7.07-7.06 (m, 1H), 6.98 (d, 1H), 6.97 (dt, 1H), 5.46-5.43 (m, 1H), 3.12 (s, 3H), 3.08 (d, 1H), 2.97-2.91 (m, 1H), 2.68-2.53 (m, 2H), 1.25 (d, 3H).

Example 66

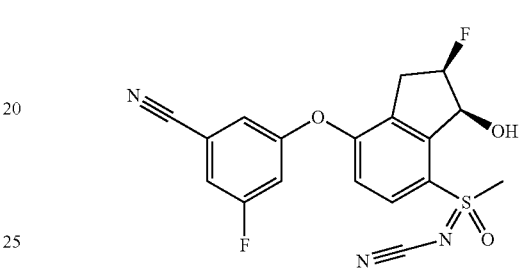

N-(((2R,3S)-7-(3-cyano-5-fluorophenoxy)-2-fluoro-3-hydroxy-2,3-dihydro-1H-inden-4-yl)(methyl)(oxo)-λ$^6$-sulfanylidene)cyanamide (Compound 66)

Step A: Preparation of [[7-(3-cyano-5-fluoro-phenoxy)-2-fluoro-3-oxo-indan-4-yl]-methyl-oxo-λ$^6$-sulfanylidene]cyanamide: [[7-(3-cyano-5-fluoro-phenoxy)-3-oxo-indan-4-yl]-methyl-oxo-λ$^6$-sulfanylidene]cyanamide (250 mg, 0.69 mmol) was dissolved in MeOH (3 mL) and treated with Selectfluor® (365 mg, 1.03 mmol). The mixture was heated to reflux for 24 hours. Additional fresh MeOH (3 mL) was added followed by Selectfluor® (365 mg, 1.03 mmol) and the mixture was heated for an additional 30 hours. The mixture was diluted with ethyl acetate and water and then separated. The organic layer was washed with water, saturated NaHCO$_3$, saturated NaCl, dried over Na$_2$SO$_4$ and concentrated in vacuo to give a brown solid (297 mg). The crude material was chromatographed on SiO$_2$ (Biotage SNAP 10 g) with a gradient of 10% ethyl acetate in methylene chloride to give the desired product as a mixture of isomers (17 mg). LCMS ESI (−) m/z 432 (M+HCOO$^-$).

Step B: Preparation of N-(((2R,3S)-7-(3-cyano-5-fluorophenoxy)-2-fluoro-3-hydroxy-2,3-dihydro-1H-inden-4-yl)(methyl)(oxo)-λ$^6$-sulfanylidene)cyanamide (Compound 66): [[7-(3-cyano-5-fluoro-phenoxy)-2-fluoro-3-oxo-indan-4-yl]-methyl-oxo-λ$^6$-sulfanylidene]cyanamide (17 mg, 0.04 mmol) was dissolved in methylene chloride (0.14 mL), cooled to 0° C., and treated with triethylamine (12 µL, 0.09 mmol) and formic acid (5 µL, 0.13 mmol). A separate solution containing RuCl(p-cymene)[(R,R)-Ts-DPEN] (0.28 mg, 0.0004 mmol) dissolved in dichloromethane (0.14 mL) was chilled to 0° C. and then added to the first solution. The reaction mixture was transferred to a refrigerator (4° C.) and allowed to stand for 120 hours. The reaction mixture was concentrated in a stream of nitrogen gas and then chromatographed on SiO$_2$ with a stepped-gradient of hexane/ethyl acetate (3:1, 3:2, 1:1, 2:3) to give Compound 66 (8.8 mg) as a mixture of isomers at sulfur. LCMS ESI (+) m/z 390 (M+H); $^1$H NMR (400 MHz, CDCl$_3$): δ 8.00 (d, J=8.7 Hz, 0.5H), 7.95 (d, J=8.7 Hz, 0.5H), 7.29-7.25 (m, 1H), 7.19-7.16 (m, 1H), 7.10-7.05 (m, 1H), 7.01 (d, 1H), 5.78-5.69 (m, 1H), 5.54-5.50 (m, 0.5H), 5.40-5.37 (m, 0.5H), 3.50 (d, J=42 Hz, 3H), 3.39-3.11 (m, 3H).

Example 67

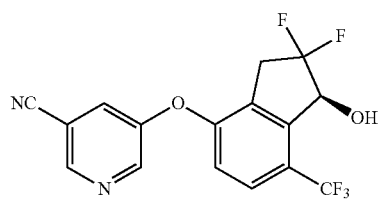

5-[(1S)-2,2-difluoro-1-hydroxy-7-(trifluoromethyl)indan-4-yl]oxypyridine-3-carbonitrile (Compound 67): The product was determined to have 98% e.e. by chiral HPLC analysis. $^1$H NMR (400 MHz, CDCl$_3$): δ 8.72 (s, 1H), 8.64 (s, 1H), 7.64 (d, 1H), 7.59-7.57 (m, 1H), 6.97 (d, 1H), 5.33-5.28 (m, 1H), 3.55-3.32 (m, 2H), 2.86-2.82 (m, 1H). m/z (ES-API-pos) [M+H]=357.

Example 68

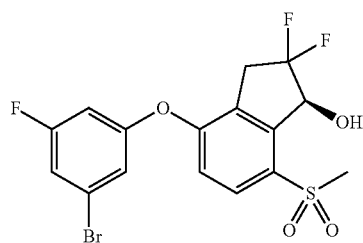 [SMILES: CS(=O)(=O)c1ccc(Oc2cc(F)cc(Br)c2)c2c1[C@H](O)C(F)(F)C2]

(S)-4-(3-bromo-5-fluorophenoxy)-2,2-difluoro-7-(methylsulfonyl)-2,3-dihydro-1H-inden-1-ol (Compound 68): LC-MS ESI (+) m/z 437, 439 (M+H$^+$); $^1$HNMR (400 MHz, CDCl$_3$): δ 7.88 (d, 1H), 7.17-7.13 (m, 1H), 7.04-7.02 (m, 1H), 6.98 (d, 1H), 6.77-6.74 (m, 1H), 5.61-5.56 (m, 1H), 3.57-3.36 (m 3H), 3.22 (s, 3H).

Examples 69 and 70

Compound 69

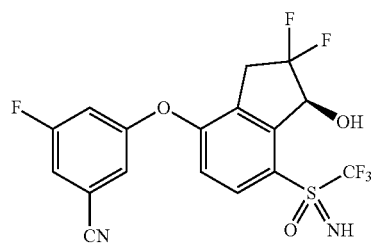

Compound 70

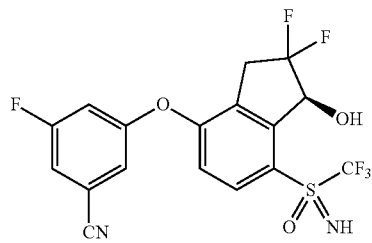

Isomer 1 of 3-(((1S)-2,2-difluoro-1-hydroxy-7-(S-(trifluoromethyl)sulfonimidoyl)-2,3-dihydro-1H-inden-4-yl)oxy)-5-fluorobenzonitrile (Compound 69) and isomer 2 of 3-(((1S)-2,2-difluoro-1-hydroxy-7-(S-(trifluoromethyl)sulfonimidoyl)-2,3-dihydro-1H-inden-4-yl)oxy)-5-fluorobenzonitrile (Compound 70)

Data for isomer 1 (Compound 69): 12 mg (38% yield); chiral HPLC Retention time=2.25 min; LCMS ESI (+) (M+H) m/z 437; $^1$H NMR (400 MHz, CDCl$_3$): δ 8.01 (d, 1H), 7.32 (ddd, 1H), 7.24-7.22 (m, 1H), 7.12 (dt, 1H), 6.99 (d, 1H), 5.35 (dd, 1H), 4.73-4.71 (m, 1H), 3.97 (br s, 1H), 3.63-3.46 (m, 2H).

Data for isomer 2 (Compound 70): 17 mg (52%); chiral HPLC Retention time=2.08 min; LCMS ESI (+) (M+H) m/z 437; $^1$H NMR (400 MHz, CDCl$_3$): δ 8.07 (d, 1H), 7.30 (ddd, 1H), 7.23-7.21 (m, 1H), 7.11 (dt, 1H), 6.98 (d, 1H), 5.59 (ddd, 1H), 3.97 (d, 1H), 3.81 (br s, 1H), 3.61-3.39 (m, 2H).

Examples 71 and 72

Compound 71

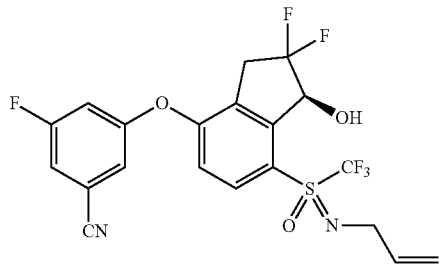

Compound 72

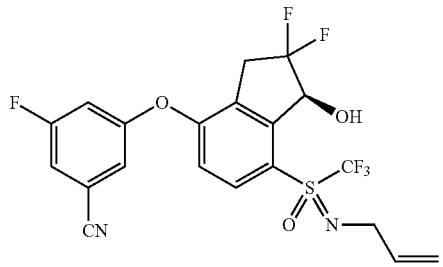

Isomer 1 of 3-(((1S)-7-(N-allyl-S-(trifluoromethyl)sulfonimidoyl)-2,2-difluoro-1-hydroxy-2,3-dihydro-1H-inden-4-yl)oxy)-5-fluorobenzonitrile (Compound 71) and isomer 2 of 3-(((1S)-7-(N-allyl-S-(trifluoromethyl)sulfonimidoyl)-2,2-difluoro-1-hydroxy-2,3-dihydro-1H-inden-4-yl)oxy)-5-fluorobenzonitrile (Compound 72)

Step A: Preparation of 3-((7-(N-allyl-S-(trifluoromethyl)sulfonimidoyl)-2,2-difluoro-1-oxo-2,3-dihydro-1H-inden-4-yl)oxy)-5-fluorobenzonitrile: A solution of 3-fluoro-5-((1-oxo-7-(S-(trifluoromethyl)sulfonimidoyl)-2,3-dihydro-1H-inden-4-yl)oxy)benzonitrile (25.7 mg, 0.064 mmol) and Selectfluor® (50.3 mg, 0.14 mmol) in DMF (3.0 mL) at 25° C. was treated with cesium carbonate (46.3 mg, 0.14 mmol) and stirred at 25° C. After 1 hour, allyl iodide (7.1 µL, 0.077 mmol) and cesium carbonate (23.1 mg, 0.071 mmol) were added to the reaction mixture. The resulting mixture stirred for 1 hour and was then poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 5%->35% EtOAc/hexane to afford 3-((7-(N-allyl-S-(trifluoromethyl)sulfonimidoyl)-2,2-difluoro-1-oxo-2,3-dihydro-1H-inden-4-yl)oxy)-5-fluorobenzonitrile (4.5 mg, 16%). LCMS ESI (+) (M+H) m/z 475.

Step B: Preparation of 3-(((1S)-7-(N-allyl-S-(trifluoromethyl)sulfonimidoyl)-2,2-difluoro-1-hydroxy-2,3-dihydro-1H-inden-4-yl)oxy)-5-fluorobenzonitrile: A solution of 3-((7-(N-allyl-S-(trifluoromethyl)sulfonimidoyl)-2,2-difluoro-1-oxo-2,3-dihydro-1H-inden-4-yl)oxy)-5-fluorobenzonitrile (4.5 mg, 0.01 mmol) in dichloromethane (1.0 mL) was cooled to 0° C. and sparged with nitrogen for 5 minutes. During this time formic acid (1.1 µL, 0.029 mmol) and triethylamine (2.6 µL, 0.019 mmol) were sequentially added. Once the sparging was complete, RuCl(p-cymene)[(R,R)-Ts-DPEN] (0.2 mg, 3 mol %) was added under a continuous stream of nitrogen. The reaction vessel was stored at 4° C. overnight. The reaction mixture was poured into 10 mL of saturated aqueous NaHCO$_3$ and extracted with 3×10 mL CH$_2$Cl$_2$. The combined organics were rinsed with 10 mL of brine, dried with MgSO$_4$, filtered, and concentrated to dryness. Purification was achieved by chromatography on silica using 5-25% EtOAc/hexane to afford two isomers.

Data for isomer 1 (Compound 71): Retention time (Chiral HPLC)=3.50 min; LCMS ESI (+) (M+H) m/z 477; $^1$H NMR (400 MHz, CDCl$_3$): δ 7.99 (d, 1H), 7.30 (ddd, 1H), 7.23-7.20 (m, 1H), 7.10 (dt, 1H), 6.98 (d, 1H), 6.04-5.93 (m, 1H), 5.35-5.28 (m, 2H), 5.21 (dq, 1H), 4.87 (br s, 1H), 4.16-4.09 (m, 1H), 4.04-3.96 (m, 1H), 3.61-3.44 (m, 2H).

Data for isomer 2 (Compound 72): Retention time (chiral HPLC)=3.05 min; LCMS ESI (+) (M+H) m/z 477; $^1$H NMR (400 MHz, CDCl$_3$): δ 8.04 (d, 1H), 7.29 (ddd, 1H), 7.21-7.19 (m, 1H), 7.09 (dt, 1H), 6.97 (d, 1H), 5.98 (ddt, 1H), 5.58 (dd, 1H), 5.34 (dq, 1H), 5.19 (dq, 1H), 4.13-4.05 (m, 1H), 4.03-3.95 (m, 1H), 3.59-3.33 (m, 3H).

Example 73

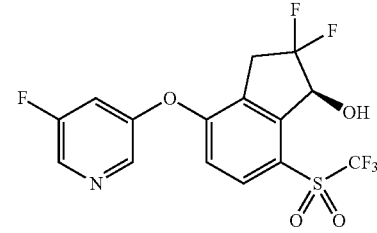 [SMILES: O=S(=O)(c1ccc(Oc2cncc(F)c2)c2c1[C@H](O)C(F)(F)C2)C(F)(F)F]

(S)-2,2-difluoro-4-((5-fluoropyridin-3-yl)oxy)-7-((trifluoromethyl)sulfonyl)-2,3-dihydro-1H-inden-1-ol (Compound 73): LCMS ESI (+) (M+H) m/z 414; $^1$H NMR (400 MHz, CDCl$_3$): δ 8.49 (d, 1H), 8.37 (d, 1H), 7.93 (d, 1H), 7.26 (dt, 1H), 6.95 (d, 1H), 5.44 (dd, 1H), 3.67-3.48 (m, 2H), 3.42 (d, 1H).

Example 74

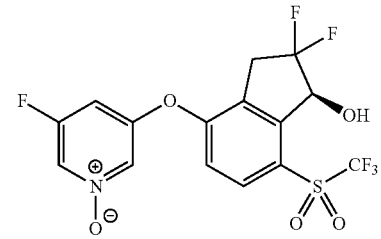 [SMILES: O=S(=O)(c1ccc(Oc2cc(F)c[n+]([O-])c2)c2c1[C@H](O)C(F)(F)C2)C(F)(F)F]

(S)-3-((2,2-difluoro-1-hydroxy-7-((trifluoromethyl)sulfonyl)-2,3-dihydro-1H-inden-4-yl)oxonio)-5-fluoropyridine 1-oxide (Compound 74): A solution of (S)-2,2-difluoro-4-((5-fluoropyridin-3-yl)oxy)-7-((trifluoromethyl)sulfonyl)-2,3-dihydro-1H-inden-1-ol (324 mg, 0.78 mmol) and urea hydrogen peroxide (155 mg, 1.65 mmol) in acetonitrile (7.9 mL) was cooled to 0° C. and treated with trifluoroacetic anhydride (217 µL, 1.57 mmol). After 15 minutes, the ice bath was removed and the reaction left to stir for 1 hour. The reaction was quenched by the addition of 3 mL of saturated aqueous Na$_2$S$_2$O$_3$. The resulting biphasic mixture stirred for 15 minutes and was then poured into 20 mL of water and extracted with 4×15 mL 30% isopropyl alcohol in CHCl$_3$. The combined organics were rinsed with 10 mL of brine, dried with MgSO$_4$, filtered, and concentrated to dryness. Purification was achieved by chromatography on silica using 70-100% EtOAc/hexane to afford Compound 74 as a white solid (310 mg, 92%). LCMS ESI (+) (M+H) m/z 430; $^1$H NMR (400 MHz, CDCl$_3$): δ 8.11-8.08 (m, 1H), 8.01-7.97 (m, 2H), 7.14 (d, 1H), 6.90 (dt, 1H), 5.43 (dd, 1H), 3.95 (d, 1H), 3.62-3.41 (m, 2H).

Example 75

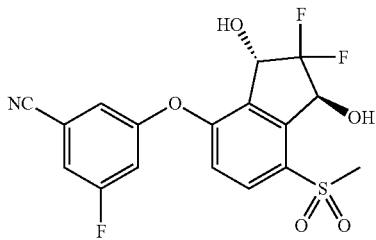 [SMILES: CS(=O)(=O)c1ccc(Oc2cc(F)cc(C#N)c2)c2c1[C@H](O)C(F)(F)[C@H]2O]

3-[(1S,3S)-2,2-difluoro-1,3-dihydroxy-7-methylsulfonyl-indan-4-yl]oxy-5-fluoro-benzonitrile (Compound 75): LCMS ESI (+) m/z 400 (M+H); $^1$H NMR (400 MHz, CDCl$_3$): δ 8.00 (d, 1H), 7.27-7.25 (m, 1H), 7.20-7.18 (m, 1H), 7.12-7.07 (m, 1H), 7.03 (d, 1H), 5.81-5.74 (m, 1H), 5.43-5.36 (m, 1H), 3.81 (d, 1H), 3.25 (s, 3H), 2.71 (m, 1H).

Example 76

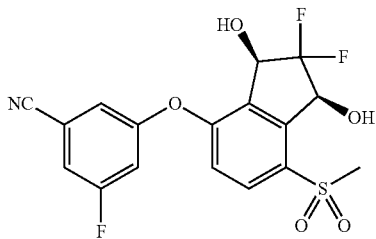 [SMILES: CS(=O)(=O)c1ccc(Oc2cc(F)cc(C#N)c2)c2c1[C@H](O)C(F)(F)[C@@H]2O]

3-[(1S,3R)-2,2-difluoro-1,3-dihydroxy-7-methylsulfonyl-indan-4-yl]oxy-5-fluoro-benzonitrile (Compound 76): LCMS ESI (+) m/z 400 (M+H); $^1$H NMR (400 MHz, CDCl$_3$): δ 8.05 (d, 1H), 7.29-7.20 (m, 2H), 7.15-7.10 (m, 1H), 7.05 (d, 1H), 5.63-5.57 (m, 1H), 5.22-5.15 (m, 1H), 3.53-3.48 (m, 1H), 3.24 (s, 3H), 2.73 (d, 1H).

Example 77

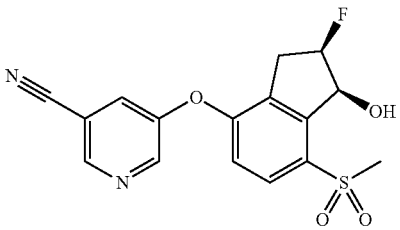 [SMILES: CS(=O)(=O)c1ccc(Oc2cncc(C#N)c2)c2c1[C@H](O)[C@H](F)C2]

5-(((1S,2R)-2-fluoro-1-hydroxy-7-(methylsulfonyl)-2,3-dihydro-1H-inden-4-yl)oxy)nicotinonitrile (Compound 77)

Step A: Preparation of 4-fluoro-7-(methylthio)-2,3-dihydro-1H-inden-1-one: S-(7-Fluoro-3-oxo-indan-4-yl) N,N-dimethylcarbamothioate (10 g, 37 mmol) was suspended in 95% ethanol (140 mL) and treated with 4 M aqueous sodium hydroxide (79 mL, 320 mmol) then the mixture was heated to reflux for 30 minutes. The reaction was cooled to 0° C. and treated dropwise with iodomethane (3.2 mL, 51.5 mmol) and the mixture was stirred for 1 hour at 0° C. The mixture was concentrated in vacuo, and then the residue was partitioned between ethyl acetate and water. After separation, the aqueous was washed with ethyl acetate and the organic layers were combined. The ethyl acetate was washed three times with water, saturated NaHCO$_3$, saturated NaCl, dried over Na$_2$SO$_4$ and concentrated in vacuo to a dark solid (7.1 g). The crude material was chromatographed on SiO$_2$ eluting with a gradient of ethyl acetate/hexane to give a dark solid (5.9 g). LCMS ESI (+) m/z 197 (M+H).

Step B: Preparation of 4-fluoro-7-(methylsulfonyl)-2,3-dihydro-1H-inden-1-one: 4-Fluoro-7-methylsulfanyl-indan-1-one (5.9 g, 30 mmol) was dissolved in MeOH (200 mL) and the reaction was treated dropwise with a solution of Oxone® (40.8 g, 66.3 mmol) which had been dissolved in water (200 mL). The mixture was stirred at ambient temperature for 20 hours. The reaction mixture was filtered, the solids were washed with ethyl acetate and the filtrate was concentrated in vacuo. The aqueous filtrate was extracted three times with ethyl acetate then the combined organics were washed with saturated NaCl, dried over Na$_2$SO$_4$ and concentrated in vacuo to a tan solid (9.43 g). LCMS ESI (+) m/z 229 (M+H).

Step C: Preparation of 4-fluoro-7-(methylsulfonyl)-2,3-dihydrospiro[indene-1,2'-[1,3]dioxolane]: 4-Fluoro-7-methylsulfonyl-indan-1-one (6.58 g, 28.8 mmol) and trimethyl (2-trimethylsilyloxyethoxy)silane (9.9 mL, 40.4 mmol) were dissolved in dichloromethane (105 mL), cooled to −78° C. then the reaction was treated dropwise with trimethylsilyl trifluoromethanesulfonate (1.67 mL, 9.23 mmol). After the addition, the reaction mixture was allowed to warm to ambient temperature without the bath and stirred for 4.5 hours. The reaction was quenched by addition of triethylamine (16.1 mL, 115 mmol) at ambient temperature and the reaction mixture was concentrated in vacuo. The dark residue was dissolved in ethyl acetate and washed with half-saturated NaCl. The aqueous was washed with ethyl acetate and the combined organics were washed with water, saturated NaCl, dried over Na$_2$SO$_4$ and concentrated in vacuo to give a dark residue. The sticky semi-solid was suspended in 3:1 hexane/ethyl acetate (250 mL) and stirred for one hour. The dark solids were collected by filtration, washed with 3:1 hexane/ethyl acetate and air-dried to a greenish solid (4.66 g). The filtrate was concentrated and triturated with acetone (ca. 25 mL) and stirred for 20 minutes. The mixture was diluted with approximately an equal portion of hexanes then filtered. The solid was washed with 9:1 hexane/ethyl acetate and air-dried to give additional product as a lighter green solid (1.1 g). LCMS ESI (+) m/z 273 (M+H).

Step D: Preparation of 5-((7-(methylsulfonyl)-2,3-dihydrospiro[indene-1,2'-[1,3]dioxolan]-4-yl)oxy)nicotinonitrile: 4'-Fluoro-7'-methylsulfonyl-spiro[1,3-dioxolane-2,1'-indane] (2.0 g, 7.4 mmol) was combined with 3-cyano-5-hydroxypyridine (1.06 g, 8.8 mmol) in NMP (14 mL) and the solution was treated with potassium phosphate tribasic (4.68 g, 22 mmol) in a single portion. The reaction was heated to 120° C. for 14 hours. The mixture was cooled to ambient temperature then diluted with ethyl acetate (50-70 mL) and the undissolved solids were removed by filtration through a frit and washed with additional ethyl acetate. The filtrate was diluted with an equal volume of water. This caused some dark solids to form in the mixture. Addition of 25% isopropanol/methylene chloride redissolved the solids and the layers were separated. The organic layer was washed five times with water, saturated NaCl, dried over Na$_2$SO$_4$ then concentrated to a dark solid (1.15 g). The crude material was chromatographed on SiO₂ (Biotage SNAP 50 g) and eluted with a gradient of ethyl acetate/hexane. The desired product was concentrated to a light pink solid (0.50 g). LCMS ESI (+) m/z 373 (M+H)

Step E: Preparation of 5-((7-(methylsulfonyl)-1-oxo-2,3-dihydro-1H-inden-4-yl)oxy)nicotinonitrile: 5-(7'-Methylsulfonylspiro[1,3-dioxolane-2,1'-indane]-4'-yl)oxypyridine-3-carbonitrile (0.5 g, 1.3 mmol) was slurried in acetone (6 mL) and treated with 10% aqueous HCl (2.3 mL, 6.7 mmol). The solution was stirred at ambient temperature for 1 hour. The reaction mixture was adjusted to pH 8 with saturated NaHCO₃ then concentrated in vacuo to remove acetone. The resulting solids were collected by filtration and air-dried (0.44 g). LCMS ESI (+) m/z 329.1 (M+H).

Step F: Preparation of 5-((2-fluoro-7-(methylsulfonyl)-1-oxo-2,3-dihydro-1H-inden-4-yl)oxy)nicotinonitrile: 5-(7-Methylsulfonyl-1-oxo-indan-4-yl)oxypyridine-3-carbonitrile (0.44 g, 1.3 mmol) was dissolved in MeOH (4 mL) and treated with Selectfluor® (760 mg, 2.2 mmol). The mixture was heated to reflux for 40 hours. Acetonitrile (2 mL) was added and heating continued for 7 additional hours. The mixture was stirred overnight at ambient temperature then diluted with water, ethyl acetate and methylene chloride. The suspension was filtered and the solids were washed with ethyl acetate. The filtrate was concentrated in vacuo then the residual water was treated with acetone (2 mL) and 10% HCl (2 mL) and warmed to 50° C. for 30 minutes. The mixture was adjusted to pH 8 with solid NaHCO₃ then concentrated in vacuo. The resulting aqueous was washed twice with ethyl acetate and the combined organics were washed with saturated NaHCO₃, saturated NaCl, dried over Na₂SO₄ and concentrated in vacuo to a light yellow oil (447 mg). The crude material was chromatographed on SiO₂ (Biotage SNAP 25g) and eluted with a gradient of MeOH/methylene chloride. The desired material was concentrated to a yellow film (274 mg). LCMS ESI (−) m/z 345.0 (M−H).

Step G: Preparation of 5-(((1S,2R)-2-fluoro-1-hydroxy-7-(methylsulfonyl)-2,3-dihydro-1H-inden-4-yl)oxy)nicotinonitrile (Compound 77): 5-(2-Fluoro-7-methylsulfonyl-1-oxo-indan-4-yl)oxypyridine-3-carbonitrile (274 mg, 0.79 mmol) was suspended in methylene chloride (3 mL), cooled to 0° C., then treated with triethylamine (0.22 mL, 1.6 mmol), formic acid (0.09 mL, 2.4 mmol) and RuCl(p-cymene)[(R,R)-Ts-DPEN] (5 mg, 0.01 mmol). The reaction mixture was allowed to stand at 0° C. for 15 hours. The mixture was concentrated and chromatographed on SiO₂ (Biotage SNAP 10 g) and eluted with a gradient of ethyl acetate/hexane to give Compound 77 as a white solid (120 mg). LCMS ESI (+) m/z 349 (M+H); ¹H NMR (400 MHz, CDCl₃): δ 8.75-8.72 (m, 1H), 8.66-8.64 (m, 1H), 7.92 (d, 1H), 7.61-7.59 (m, 1H), 6.95 (d, 1H), 5.73-5.65 (m, 1H), 5.51-5.47 (m, 0.5H), 5.38-5.34 (m, 0.5H), 3.71-3.68 (m, 1H), 3.36-3.38 (m, 2H), 3.31 (s, 3H).

Examples 78 and 79

Compound 78

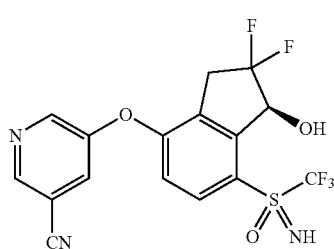

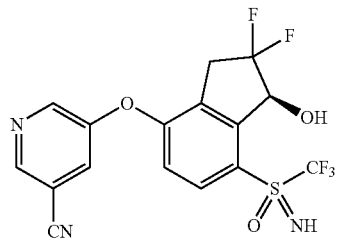

Compound 79

5-(((1S)-2,2-difluoro-1-hydroxy-7-(S-(trifluoromethyl)sulfonimidoyl)-2,3-dihydro-1H-inden-4-yl)oxy)nicotinonitrile (Compound 78) and 5-(((1S)-2,2-difluoro-1-hydroxy-7-(S-(trifluoromethyl)sulfonimidoyl)-2,3-dihydro-1H-inden-4-yl)oxy)nicotinonitrile (Compound 79)

Data for 5-(((1S)-2,2-difluoro-1-hydroxy-7-(S-(trifluoromethyl)sulfonimidoyl)-2,3-dihydro-1H-inden-4-yl)oxy)nicotinonitrile (Compound 78): Retention time HPLC (long method)=4.46 min; LCMS ESI (+) (M+H) m/z 420; ¹H NMR (400 MHz, CDCl₃): δ 8.83 (d, 1H), 8.72 (d, 1H), 8.02 (d, 1H), 7.73 (dd, 1H), 6.95 (d, 1H), 5.35 (dd, 1H), 4.73-4.70 (m s, 1H), 3.99 (br s, 1H), 3.67-3.49 (m, 2H).

Data for 5-(((1S)-2,2-difluoro-1-hydroxy-7-(S-(trifluoromethyl)sulfonimidoyl)-2,3-dihydro-1H-inden-4-yl)oxy)nicotinonitrile (Compound 79): Retention time HPLC (long method)=4.17 min; LCMS ESI (+) (M+H) m/z 420; ¹H NMR (400 MHz, CDCl₃): δ 8.82 (d, 1H), 8.71 (d, 1H), 8.08 (d, 1H), 7.72 (dd, 1H), 6.93 (d, 1H), 5.63-5.57 (m, 1H), 3.97 (d, 1H), 3.82 (br s, 1H), 3.65-3.43 (m, 2H).

Examples 80, 81, and 82

Compound 80

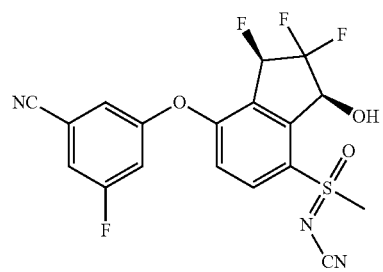

Compound 81

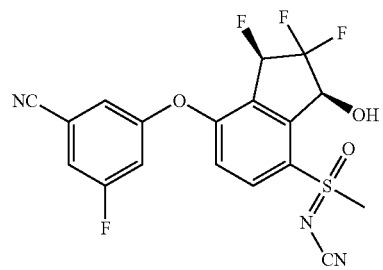

Compound 82

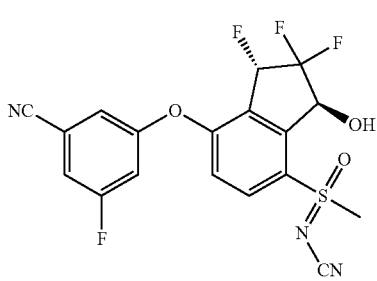

Isomer 1 of [[(1R,3S)-7-(3-cyano-5-fluoro-phenoxy)-1,2,2-trifluoro-3-hydroxy-indan-4-yl]-methyl-oxo-$\lambda^6$-sulfanyhdene]cyanamide (Compound 80), isomer 2 of [[(1R,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 81), and isomer 1 of [[(1S,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 82)

Step A: Preparation of 2,2,3,4-tetrafluoro-7-methylsulfanyl-indan-1-one: Diethylaminosulfur trifluoride (0.089 mL, 0.67 mmol) was added to an ice-cold solution of 2,2,4-trifluoro-3-hydroxy-7-methylsulfanyl-indan-1-one (139 mg, 0.56 mmol) in dichloromethane (10 mL). The reaction mixture was allowed to warm to ambient temperature. Additional diethylaminosulfur trifluoride was added after 1 hour to allow the reaction to go to completion. The mixture was treated carefully with aqueous NaHCO$_3$ and partitioned between EtOAc and water. The EtOAc was washed with brine, dried over MgSO$_4$, filtered, and evaporated to afford 2,2,3,4-tetrafluoro-7-methylsulfanyl-indan-1-one (120 mg, 0.48 mmol, 86% yield) as an orange oil. m/z (ES-API-pos) [M+H]=250.

Step B: Preparation of [methyl-[(1R)-1,2,2,7-tetrafluoro-3-oxo-indan-4-yl]-$\lambda^4$-sulfanylidene]cyanamide: (Diacetoxyiodo)benzene (170 mg, 0.53 mmol) was added to an ice-cold solution of 2,2,3,4-tetrafluoro-7-methylsulfanyl-indan-1-one (120 mg, 0.48 mmol) and cyanamide (24 mg, 0.58 mmol) in dichloromethane (10 mL). The reaction mixture was treated with bis[rhodium(α, α, α', α'-tetramethyl-1,3-benzenedipropionic acid)] (3.6 mg, 0.0048 mmol) and allowed to warm to ambient temperature. After 1 hour, the reaction mixture was evaporated and the residue was partitioned between EtOAc and dilute aqueous sodium thiosulfate. The EtOAc was washed with brine, dried over MgSO$_4$, filtered, and evaporated to afford [methyl-[1,2,2,7-tetrafluoro-3-oxo-indan-4-yl]-$\lambda^4$-sulfanylidene]cyanamide (100 mg, 0.35 mmol, 72% yield) as a brown foam. m/z (ES-API-pos) [M+H+18]=309.

Step C: Preparation of [methyl-oxo-[1,2,2,7-tetrafluoro-3-oxo-indan-4-yl]-$\lambda^6$-sulfanylidene]cyanamide: Ruthenium (III) chloride (1.4 mg, 0.007 mmol) was added to an ice-cold mixture of [methyl-[1,2,2,7-tetrafluoro-3-oxo-indan-4-yl]-$\lambda^4$-sulfanylidene]cyanamide (100 mg, 0.34 mmol) and sodium periodate (221 mg, 1.0 mmol) in a mixture of carbon tetrachloride (4 mL), acetonitrile (4 mL), and water (8 mL). The mixture was stirred vigorously in an ice bath. After 45 minutes, the reaction mixture was diluted with dichloromethane and was washed with dilute aqueous sodium thiosulfate solution. The dichloromethane was washed with brine, dried over MgSO$_4$, filtered, and evaporated to afford [methyl-oxo-[1,2,2,7-tetrafluoro-3-oxo-indan-4-yl]-$\lambda^6$-sulfanylidene]cyanamide (70 mg, 0.23 mmol, 66% yield). m/z (ES-API-pos) [M+H+18]=325.

Step D: Preparation of [[7-(3-cyano-5-fluoro-phenoxy)-1,2,2-trifluoro-3-oxo-indan-4-yl]-methyl-oxo-$\lambda^\{6\}$-sulfanylidene]cyanamide: Cesium bicarbonate (88.6 mg, 0.46 mmol) was added to a solution of 3-fluoro-5-hydroxy-benzonitrile (40.7 mg, 0.3 mmol) and [methyl-oxo-[1,2,2,7-tetrafluoro-3-oxo-indan-4-yl]-$\lambda^6$-sulfanylidene]cyanamide (70 mg, 0.23 mmol) in N,N-dimethylformamide (3 mL). The mixture was stirred at ambient temperature. After 25 minutes, the reaction mixture was partitioned between EtOAc and dilute aqueous NaCl. The EtOAc was washed with 2 portions of brine, dried over MgSO$_4$, filtered, and evaporated.

The residue was chromatographed on a Biotage 10 g ultra SNAP column with a 20% to 80% EtOAc:hexane gradient to afford [[7-(3-cyano-5-fluoro-phenoxy)-1,2,2-trifluoro-3-oxo-indan-4-yl]-methyl-oxo-$\lambda^6$-sulfanylidene]cyanamide (35.5 mg, 0.084 mmol, 37% yield) as a diastereomeric mixture. m/z (ES-API-pos) [M+H+18]=442.

Step E: Preparation of isomer 1 of [[(1R,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 80), isomer 2 of [[(1R,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 81), and isomer 1 of [[(1S,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 82): RuCl(p-cymene)[(R,R)-Ts-DPEN] (1.6 mg, 0.0025 mmol) was added to a nitrogen-sparged, ice-cold solution of [[7-(3-cyano-5-fluoro-phenoxy)-1,2,2-trifluoro-3-oxo-indan-4-yl]-methyl-oxo-$\lambda^6$-sulfanylidene]cyanamide (35.5 mg, 0.084 mmol), formic acid (0.013 mL, 0.34 mmol), and triethylamine (0.029 mL, 0.21 mmol) in dichloromethane (5 mL). The flask was sealed and kept at 4° C. overnight. The reaction mixture was evaporated and the residue was purified by chromatography on Biotage ultra SNAP columns with EtOAc:hexane gradients to afford 3 isomers.

Data for isomer 1 [[(1R,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 80; 1.9 mg; 0.0045 mmol; 5% yield): $^1$H NMR (400 MHz, CD$_3$OD): δ 8.21 (dd, 1H), 7.59-7.56 (m, 1H), 7.54-7.53 (m, 1H), 7.46 (dt, 1H), 7.25 (d, 1H), 6.00 (dd, 1H), 5.60-5.56 (m, 1H), 3.64 (s, 3H); m/z (ES-API-pos) [M+H]=426.

Data for isomer 2 [[(1R,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 81; 3.4 mg; 0.008 mmol; 10% yield): $^1$H NMR (400 MHz, CDCl$_3$): δ 8.23-8.20 (m, 1H), 7.38-7.34 (m, 1H), 7.30-7.28 (m, 1H), 7.21-7.17 (m, 1H), 7.09 (d, 1H), 5.90 (dd, 1H), 5.71-5.66 (m, 1H), 3.90-3.88 (m, 1H), 3.64 (s, 3H); m/z (ES-API-pos) [M+H]=426.

Data for isomer 1 of [[(1S,3S)-7-(3-cyano-5-fluoro-phenoxy)-1,2,2-trifluoro-3-hydroxy-indan-4-yl]-methyl-oxo-$\lambda^6$-sulfanylidene]cyanamide (Compound 82; 3.4 mg; 0.008 mmol; 10% yield): $^1$H NMR (400 MHz, CDCl$_3$): δ 8.13 (dd, 1H), 7.37-7.33 (m, 1H), 7.28-7.27 (m, 1H), 7.19-7.15 (m, 1H), 7.05 (d, 1H), 6.08-5.84 (m, 2H), 4.08 (d, 1H), 3.54 (s, 3H); m/z (ES-API-pos) [M+H]=426.

Examples 83, 84, 85, and 86

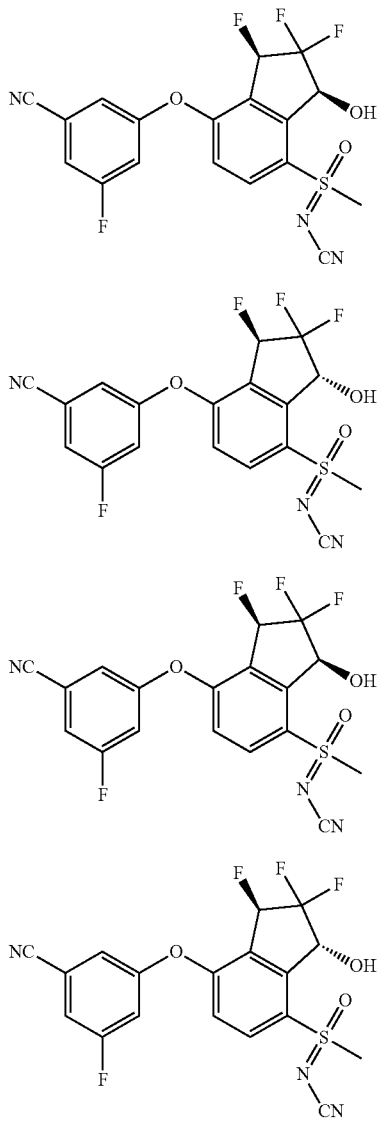

Compound 83

Compound 84

Compound 85

Compound 86

Isomer 1 of [[(1R,3S)-7-[(5-Cyano-3-pyridyl)oxy]-1,2,2-trifluoro-3-hydroxy-indan-4-yl]-methyl-oxo-$\lambda^6$-sulfanylidene]cyanamide (Compound 83); isomer 1 of [[(1R,3R)-7-(3-cyano-5-fluoro-phenoxy)-1,2,2-trifluoro-3-hydroxy-indan-4-yl]-methyl-oxo-$\lambda^6$-sulfanylidene]cyanamide (Compound 84); isomer 2 of [[(1R,3S)-7-[(5-cyano-3-pyridyl)oxy]-1,2,2-trifluoro-3-hydroxy-indan-4-yl]-methyl-oxo-$\lambda^6$-sulfanylidene]cyanamide (Compound 85); and isomer 2 of [[(1R,3R)-7-(3-cyano-5-fluoro-phenoxy)-1,2,2-trifluoro-3-hydroxy-indan-4-yl]-methyl-oxo-$\lambda^6$-sulfanylidene]cyanamide (Compound 86)

Step A: Preparation of (3S)-2,2,4-trifluoro-3-hydroxy-7-methylsulfanyl-indan-1-one: A solution of (3S)-2,2,4,7-tetrafluoro-3-hydroxy-indan-1-one (966 mg, 4.39 mmol) in acetonitrile (40 mL) at 0° C. was sparged with nitrogen for 5 minutes and treated with sodium thiomethoxide (354 mg, 5.05 mmol). The ice bath was removed and the reaction mixture was stirred at ambient temperature. After 2 hours, the reaction mixture was evaporated and the residue was partitioned between EtOAc and water. The aqueous layer was extracted with 2 additional portions of EtOAc. The combined EtOAc extracts were washed with brine, dried over MgSO$_4$, filtered, and evaporated. The residue was chromatographed on a Biotage 100 g SNAP column with a 10% to 60% EtOAc:hexane to afford (3S)-2,2,4-trifluoro-3-hydroxy-7-methylsulfanyl-indan-1-one (870 mg, 3.51 mmol, 80% yield) as a yellow solid. m/z (ES-API-pos) [M+H]=249.

Step B: Preparation of (3R)-2,2,3,4-tetrafluoro-7-methylsulfanyl-indan-1-one: Diethylaminosulfur trifluoride (0.08 mL, 0.6 mmol) was added to an ice-cold solution of (3S)-2,2,4-trifluoro-3-hydroxy-7-methylsulfanyl-indan-1-one (100 mg, 0.4 mmol) in dichloromethane (10 mL). The reaction mixture was stirred overnight at ambient temperature. A small amount of additional diethylaminosulfur trifluoride was added and stirring continued. After 1 hour, the mixture was treated carefully with aqueous NaHCO$_3$, stirred for 10 minutes, and concentrated. The aqueous slurry was partitioned between EtOAc and dilute aqueous NaHCO$_3$. The aqueous layer was extracted with another portion of EtOAc. The combined EtOAc was washed with brine, dried over MgSO$_4$, filtered, and evaporated to afford (3R)-2,2,3,4-tetrafluoro-7-methylsulfanyl-indan-1-one (99 mg, 0.4 mmol, 98% yield) as a yellow semi-crystalline solid. m/z (ES-API-pos) [M+H]=250.

Step C: Preparation of [methyl-[(1R)-1,2,2,7-tetrafluoro-3-oxo-indan-4-yl]-$\lambda^4$-sulfanylidene]cyanamide diastereomers: Bis[rhodium($\alpha$, $\alpha$, $\alpha'$, $\alpha'$-tetramethyl-1,3-benzenedipropionic acid)] (3.05 mg, 0.004 mmol) was added to an ice-cold solution of (3R)-2,2,3,4-tetrafluoro-7-methylsulfanyl-indan-1-one (100 mg, 0.4 mmol), cyanamide (33.6 mg, 0.8 mmol), and (diacetoxyiodo)benzene (155 mg, 0.48 mmol) in dichloromethane (10 mL). The reaction mixture was allowed to warm to ambient temperature. After 1 hour, the reaction mixture was evaporated and the residue was chromatographed on a Biotage 25 g ultra SNAP column with a 50% to 100% EtOAc:hexane to afford two isomers of [methyl-[(1R)-1,2,2,7-tetrafluoro-3-oxo-indan-4-yl]-$\lambda^4$-sulfanylidene]cyanamide (isomer A: 59.5 mg, 0.21 mmol, 51% yield, m/z (ES-API-pos) [M+H+18]=309; isomer B: 39.2 mg, 0.135 mmol, 34% yield, m/z (ES-API-pos) [M+H+18]=309).

Step D: Preparation of [methyl-oxo-[(1R)-1,2,2,7-tetrafluoro-3-oxo-indan-4-yl]-$\lambda^6$-sulfanylidene]cyanamide: (Parallel reactions with separated isomers from Step C) Ruthenium(III) chloride (0.85 mg, 0.004 mmol) was added to an ice-cold mixture of isomer A of [methyl-[(1R)-1,2,2,7-tetrafluoro-3-oxo-indan-4-yl]-$\lambda^4$-sulfanylidene]cyanamide (59.5 mg, 0.21 mmol) and sodium periodate (131 mg, 0.62 mmol) in carbon tetrachloride (3 mL), acetonitrile (3 mL), and water (6 mL). The mixture was stirred vigorously in ice. The ice bath was removed and the mixture was allowed to warm to ambient temperature. After 1.5 hours, the reaction mixture was diluted with EtOAc and was washed with dilute sodium thiosulfate solution. The aqueous layer was extracted with another portion of EtOAc. The EtOAc was washed with brine, dried over MgSO$_4$, filtered, and evaporated to afford isomer A of [methyl-oxo-[(1R)-1,2,2,7-tetrafluoro-3-oxo-indan-4-yl]-$\lambda^6$-sulfanylidene]cyanamide (55.2 mg, 0.18 mmol, 88% yield). m/z (ES-API-pos) [M+H+18]=325. Isomer B of [methyl-oxo-[(1R)-1,2,2,7-tetrafluoro-3-oxo-indan-4-yl]-$\lambda^6$-sulfanylidene]cyanamide was prepared in a similar fashion. m/z (ES-API-pos) [M+H+18]=325.

Step E: Preparation of [[(1R)-7-[(5-cyano-3-pyridyl)oxy]-1,2,2-trifluoro-3-oxo-indan-4-yl]-methyl-oxo-$\lambda^6$-sulfanylidene]cyanamide: (Parallel reactions with each isomer from Step D) Isomer A of [methyl-oxo-[(1R)-1,2,2,7-tetrafluoro-3-oxo-indan-4-yl]-λ⁶-sulfanylidene]cyanamide (47.7 mg, 0.16 mmol) was added to a solution of cesium bicarbonate (45 mg, 0.23 mmol) in tetrahydrofuran (5 mL) at ambient temperature. The mixture was stirred for 10 minutes, then added to a solution of 3-cyano-5-hydroxypyridine (24.3 mg, 0.2 mmol) in tetrahydrofuran (5 mL). The reaction mixture was stirred overnight at ambient temperature. The reaction mixture was evaporated, and the residue was partitioned between EtOAc and dilute aqueous NaCl. The aqueous layer was extracted with another portion of EtOAc. The combined EtOAc was washed with brine, dried over MgSO$_4$, filtered, and evaporated. The residue was chromatographed on a Biotage 10 g ultra SNAP column with a 50% to 100% EtOAc:hexane to afford isomer A of [[(1R)-7-[(5-cyano-3-pyridyl)oxy]-1,2,2-trifluoro-3-oxo-indan-4-yl]-methyl-oxo-λ⁶-sulfanylidene]cyanamide (52 mg, 0.13 mmol, 82% yield) as a white solid. m/z (ES-API-pos) [M+H+18]=425. Isomer B of [[(1R)-7-[(5-cyano-3-pyridyl)oxy]-1,2,2-trifluoro-3-oxo-indan-4-yl]-methyl-oxo-λ⁶-sulfanylidene]cyanamide was prepared in a similar fashion. m/z (ES-API-pos) [M+H+18]=425.

Step F: Preparation of [[(1R,3S)-7-[(5-cyano-3-pyridyl)oxy]-1,2,2-trifluoro-3-hydroxy-indan-4-yl]-methyl-oxo-λ⁶-sulfanylidene]cyanamide (Compound 83); [[(1R,3R)-7-(3-cyano-5-fluoro-phenoxy)-1,2,2-trifluoro-3-hydroxy-indan-4-yl]-methyl-oxo-λ⁶-sulfanylidene]cyanamide (Compound 84); [[(1R,3S)-7-[(5-cyano-3-pyridyl)oxy]-1,2,2-trifluoro-3-hydroxy-indan-4-yl]-methyl-oxo-λ⁶-sulfanylidene]cyanamide (Compound 85); and [[(1R,3R)-7-(3-cyano-5-fluoro-phenoxy)-1,2,2-trifluoro-3-hydroxy-indan-4-yl]-methyl-oxo-λ⁶-sulfanylidene]cyanamide (Compound 86) (Parallel reactions with each isomer from Step E) RuCl(p-cymene)[(R,R)-Ts-DPEN] (2.44 mg, 0.0038 mmol) was added to an ice-cold nitrogen-sparged solution of isomer A of [[(1R)-7-[(5-cyano-3-pyridyl)oxy]-1,2,2-trifluoro-3-oxo-indan-4-yl]-methyl-oxo-λ⁶-sulfanylidene]cyanamide (52 mg, 0.13 mmol), formic acid (0.019 mL, 0.51 mmol), and triethylamine (0.045 mL, 0.32 mmol) in dichloromethane (10 mL). The flask was sealed and stored at 4° C. overnight. The reaction mixture was evaporated and the residue was chromatographed on a Biotage 25 g SNAP ultra column with a 50% to 100% EtOAc:hexane gradient to afford 2 isomeric products.

Data for isomer 1 of [[(1R,3S)-7-[(5-cyano-3-pyridyl)oxy]-1,2,2-trifluoro-3-hydroxy-indan-4-yl]-methyl-oxo-λ⁶-sulfanylidene]cyanamide (Compound 83): (25.5 mg, 0.062 mmol, 49% yield); ¹H NMR (400 MHz, CD$_3$COCD$_3$): δ 8.95 (d, 1H), 8.94 (d, 1H), 8.34-8.32 (m, 1H), 8.23-8.20 (m, 1H), 7.45 (d, 1H), 6.43-6.40 (m, 1H), 6.15 (dd, 1H), 5.72-5.66 (m, 1H), 3.69 (s, 3H); m/z (ES-API-pos) [M+H]=409. Data for isomer 1 of [[(1R,3R)-7-(3-cyano-5-fluoro-phenoxy)-1,2,2-trifluoro-3-hydroxy-indan-4-yl]-methyl-oxo-λ⁶-sulfanylidene]cyanamide (Compound 84): (8.1 mg, 0.02 mmol, 16% yield); ¹H NMR (400 MHz, CD$_3$COCD$_3$): δ 8.96-8.95 (m, 1H), 8.94-8.92 (m, 1H), 8.34-8.32 (m, 1H), 8.24-8.20 (m, 1H), 7.44-7.41 (m, 1H), 6.51-6.31 (m, 2H), 5.90-5.83 (m, 1H), 3.81 (s, 3H); m/z (ES-API-pos) [M+H]=409.

Compounds 85 and 86 were synthesized in a similar fashion.

Data for isomer 2 of [[(1R,3S)-7-[(5-cyano-3-pyridyl)oxy]-1,2,2-trifluoro-3-hydroxy-indan-4-yl]-methyl-oxo-λ⁶-sulfanylidene]cyanamide (Compound 85): (12.1 mg, 0.03 mmol, 40% yield); ¹H NMR (400 MHz, CD$_3$COCD$_3$): δ 8.97-8.96 (m, 1H), 8.96-8.94 (m, 1H), 8.35 (dd, 1H), 8.25 (dd, 1H), 7.45 (d, 1H), 6.50 (brs, 1H), 6.16 (dd, 1H), 5.68-5.30 (m, 1H), 3.80 (s, 3H); m/z (ES-API-pos) [M+H]=409.

Data for isomer 2 of [[(1R,3R)-7-(3-cyano-5-fluoro-phenoxy)-1,2,2-trifluoro-3-hydroxy-indan-4-yl]-methyl-oxo-λ⁶-sulfanylidene]cyanamide (Compound 86): (4.9 mg, 0.012 mmol, 16% yield);); ¹H NMR (400 MHz, CD$_3$COCD$_3$): δ 8.95-8.94 (m, 1H), 8.94-8.92 (m, 1H), 8.33 (dd, 1H), 8.19 (dd, 1H), 7.41 (d, 1H), 6.50-6.28 (m, 2H), 5.90-5.85 (m, 1H), 3.70 (s, 3H); m/z (ES-API-pos) [M+H]=409.

Example 87

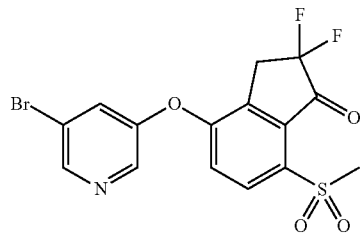 [SMILES: CS(=O)(=O)c1ccc(Oc2cncc(Br)c2)c2c1C(=O)C(F)(F)C2]

4-((5-Bromopyridin-3-yl)oxy)-2,2-difluoro-7-(methylsulfonyl)-2,3-dihydro-1H-inden-1-one (Compound 87): LCMS ESI (+) m/z 418, 420 (M+H); ¹H NMR (400 MHz, CD$_3$COCD$_3$): δ 8.65-8.63 (m, 1H), 8.60-8.59 (m, 1H), 8.15-8.12 (m, 1H), 8.02-8.00 (m, 1H), 7.60-7.57 (m, 1H), 3.86-3.79 (m, 2H), 3.39 (s, 3H).

Example 88

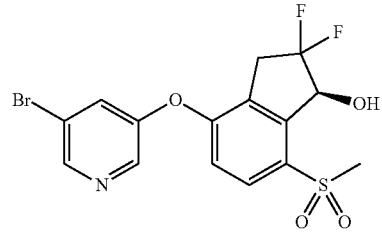 [SMILES: CS(=O)(=O)c1ccc(Oc2cncc(Br)c2)c2c1[C@H](O)C(F)(F)C2]

(S)-4-((5-Bromopyridin-3-yl)oxy)-2,2-difluoro-7-(methylsulfonyl)-2,3-dihydro-1H-inden-1-ol (Compound 88): LCMS ESI (+) m/z 420, 422 (M+H); ¹H NMR (400 MHz, CDCl$_3$): δ 8.61-8.59 (m, 1H), 8.41-8.39 (m, 1H), 7.91-7.87 (d, 1H), 7.61-7.58 (m, 1H), 6.95-6.9' (d, 1H), 5.63-5.57 (m, 1H), 3.61-3.40 (m, 3H), 3.23 (s, 3H).

Example 89

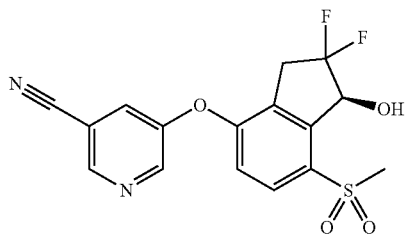 [SMILES: CS(=O)(=O)c1ccc(Oc2cncc(C#N)c2)c2c1[C@H](O)C(F)(F)C2]

(S)-5-((2,2-Difluoro-1-hydroxy-7-(methylsulfonyl)-2,3-dihydro-1H-inden-4-yl)oxy)nicotinonitrile (Compound 89): (1S)-4-[(5-bromo-3-pyridyl)oxy]-2,2-difluoro-7-methylsulfonyl-indan-1-ol (0.028 g, 0.066 mmol) was combined with zinc powder (7.3 mg, 0.11 mmol) and zinc cyanide (11 mg, 0.093 mmol) in dry DMF (0.25 mL) then the suspension was sparged with argon for several minutes. The solution was treated with dichloro[1,1'-bis(diphenylphosphino)ferrocene] palladium (II) dichloromethane adduct (2.7 mg, 0.003 mmol) and the mixture was sparged again for several minutes then heated to 100° C. for 3 hours in the microwave reactor, then allowed to stand overnight at ambient temperature. The reaction was filtered through celite and the filtered solids were washed with DMF then with ethyl acetate. The filtrate was concentrated in a stream of nitrogen gas to an orange residue. The crude material was chromatographed on SiO₂ (Biotage SNAP 10 g) and eluted with a gradient of ethyl acetate/hexane to give Compound 89 as a white solid (17 mg). LCMS ESI (+) m/z 367 (M+H); $^1$H NMR (400 MHz, CDCl₃): δ 8.76-8.75 (m, 1H), 8.67-8.66 (m, 1H), 7.95 (d, 1H), 7.70-7.68 (m, 1H), 6.98 (d, 1H), 5.60 (d, 1H), 3.57-3.35 (m, 3H), 3.22 (s, 3H).

Example 90

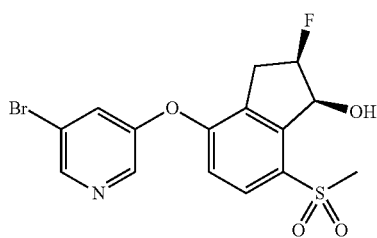 [SMILES: CS(=O)(=O)c1ccc(Oc2cncc(Br)c2)c2c1[C@H](O)[C@H](F)C2]

(1S,2R)-4-((5-Bromopyridin-3-yl)oxy)-2-fluoro-7-(methylsulfonyl)-2,3-dihydro-1H-inden-1-ol (Compound 90): LCMS ESI (+) m/z 402, 404 (M+H); $^1$H NMR (400 MHz, CDCl₃): δ 8.57-8.56 (m, 1H), 8.39-8.38 (m, 1H), 7.88 (d, 1H), 7.56-7.54 (m, 1H), 6.91 (d, 1H), 5.72-5.65 (m, 1H), 5.51-5.47 (m, 0.5H), 5.38-5.34 (m, 0.5H), 3.71-3.69 (m, 1H), 3.38-3.09 (m, 3H), 3.29 (s, 3H)

Example 91

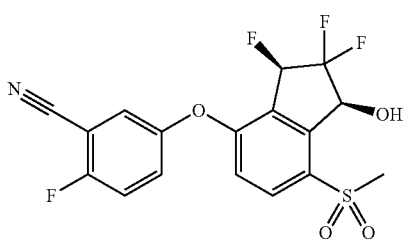 [SMILES: CS(=O)(=O)c1ccc(Oc2ccc(F)c(C#N)c2)c2c1[C@H](O)C(F)(F)[C@@H]2F]

2-Fluoro-5-(((1S,3R)-2,2,3-trifluoro-1-hydroxy-7-(methylsulfonyl)-2,3-dihydro-1H-inden-4-yl)oxy)benzonitrile (Compound 91)

Step A: Preparation of 4,7-difluoro-1H-indene-1,3(2H)-dione: A solution of 3,6 difluorophthalic anhydride (4.25 g, 23.1 mmol), tert-butyl 3-oxobutanoate (4.29 mL, 25.9 mmol) and acetic anhydride (21.0 mL, 221.6 mmol) at 25° C. was treated with triethylamine (11.7 mL, 84.3 mmol) and stirred at ambient temperature for 18 hours. The reaction mixture was cooled to 0° C. and treated with 10% hydrochloric acid (65 mL, 211 mmol) by dropwise addition. Once the addition was complete, the ice bath was removed and the mixture stirred at ambient for 10 minutes. The mixture was then heated to 75° C. for 10 minutes. During this time gas evolution was observed. The suspension slowly broke up to form a clear red mixture. The reaction mixture was poured into 100 mL of water and extracted with 3×50 mL CH₂Cl₂. The combined organics were dried with MgSO₄, filtered, and concentrated to dryness. The product was used without further purification.

Step B: Preparation of 2,2,4,7-tetrafluoro-1H-indene-1,3(2H)-dione: A solution of the unpurified 4,7-difluoro-1H-indene-1,3(2H)-dione (4.2 g, 23.1 mmol) in acetonitrile (100 mL) cooled in a 25° C. water bath was treated with sodium carbonate (5.38 g, 50.7 mmol). Selectfluor® (17.97 g, 50.7 mmol) was added and the reaction mixture was stirred at ambient temperature for 1 hour. Volatiles were removed under reduced pressure and the residue was poured into 100 mL of 0.1% HCl and extracted with 3×50 mL EtOAc. The combined organics were rinsed with 40 mL of brine, dried with MgSO₄, filtered, and concentrated to dryness. The residue was purified by flash chromatography on silica gel 1:1 hexane/ethyl acetate to give 2,2,4,7-tetrafluoro-1H-indene-1,3(2H)-dione (3.5 g, 70%) as a solid. $^1$H NMR (400 MHz, CDCl₃): δ 7.70 (t, 2H).

Step C: Preparation of (S)-2,2,4,7-tetrafluoro-3-hydroxy-2,3-dihydro-1H-inden-1-one: To a solution of 2,2,4,7-tetrafluoro-1H-indene-1,3(2H)-dione (3.48 g, 16.0 mmol) in dichloromethane (150 mL) at 0° C. was added formic acid (600 μL, 16.0 mmol) and triethylamine (1.55 mL, 11.2 mmol). The resulting mixture was sparged with nitrogen for 5 minutes and then RuCl(p-cymene)[(S,S)-Ts-DPEN] (203.6 mg, 0.32 mmol) was added. The reaction vessel was sealed and put into a 4° C. refrigerator to stand for 18 hours. The reaction mixture was poured into 40 mL 1 N HCl. The CH₂Cl₂ layer was separated and the aqueous layer extracted with ethyl acetate (2×50 mL). The combined organics were dried with Na₂SO₄, filtered and concentrated under reduced pressure. The residue was purified by flash chromatography on silica gel using 25% EtOAc/hexane to give (S)-2,2,4,7-tetrafluoro-3-hydroxy-2,3-dihydro-1H-inden-1-one (2.9 g, 83%) as an oil. $^1$H NMR (400 MHz, CDCl₃): δ 7.51 (ddd, 1H), 7.29-7.23 (m, 1H), 5.44 (dd, 1H), 2.79 (dd, 1H).

Step D: Preparation of (S)-2,2,4-trifluoro-3-hydroxy-7-(methylthio)-2,3-dihydro-1H-inden-1-one: A solution of (S)-2,2,4,7-tetrafluoro-3-hydroxy-2,3-dihydro-1H-inden-1-one (966 mg, 4.39 mmol) in acetonitrile (40 mL) at 0° C. was sparged with nitrogen for 5 minutes and treated with sodium thiomethoxice (353.7 mg, 5.05 mmol). The ice bath was removed and the reaction mixture was allowed to stir at ambient temperature for 2 hours. The reaction mixture was evaporated and the residue partitioned between 40 mL of EtOAc and 40 mL of water. The aqueous layer was further extracted with 2×40 mL of EtOAc. The combined organic extracts were washed with brine, dried over MgSO₄, filtered, and evaporated. The residue was chromatographed on silica using 10-60% EtOAc/hexane to afford (S)-2,2,4-trifluoro-3-hydroxy-7-(methylthio)-2,3-dihydro-1H-inden-1-one (870 mg, 80%) as a yellow solid. LCMS ESI (+) m/z 249 (M+H).

Step E: Preparation of (S)-2,2,4-trifluoro-3-hydroxy-7-(methylsulfonyl)-2,3-dihydro-1H-inden-1-one: (S)-2,2,4-trifluoro-3-hydroxy-7-(methylthio)-2,3-dihydro-1H-inden- 1-one (400 mg, 1.6 mmol) was dissolved in MeOH (10 mL) and the reaction was treated dropwise with a solution of Oxone® (2.18 g, 3.55 mmol) dissolved in water (10 mL). The mixture was stirred at ambient temperature for 14 hours. The reaction mixture was filtered, the solids were washed with ethyl acetate and the filtrate was concentrated in vacuo. The aqueous filtrate was extracted 3×30 mL of EtOAc and then the combined organics were washed with saturated NaCl, dried over Na₂SO₄ and concentrated in vacuo to a yellow solid that was used without further purification (467 mg). LCMS ESI (+) m/z 281.1 (M+H).

Step F: Preparation of (R)-2,2,3,4-tetrafluoro-7-(methylsulfonyl)-2,3-dihydro-1H-inden-1-one: (S)-2,2,4-trifluoro-3-hydroxy-7-(methylsulfonyl)-2,3-dihydro-1H-inden-1-one (450 mg, 1.6 mmol) was dissolved in dichloromethane (16 mL), cooled to 0° C. and treated dropwise with diethylaminosulfur trifluoride (0.32 mL, 2.4 mmol) and the mixture was stirred at 0° C. for 2 hours, then the whole homogeneous reaction mixture was placed into the refrigerator overnight. The reaction was treated with additional diethylaminosulfur trifluoride (0.32 mL, 2.4 mmol) and stirring continued for 6 hours at 0° C. The cold reaction was treated with saturated NaHCO₃ (10 mL) and stirred vigorously for 20 minutes. The mixture was diluted with additional methylene chloride and the layers were separated. The aqueous was re-extracted with methylene chloride and the combined organic layers were dried over Na₂SO₄ and concentrated in vacuo to a yellow solid. The crude material was chromatographed on SiO₂ (Biotage SNAP Ultra) and eluted with a gradient of ethyl acetate/hexanes. The desired material was concentrated to a pale yellow solid (258 mg). LCMS ESI (+) m/z 283 (M+H).

Step G: Preparation of (R)-2-fluoro-5-((2,2,3-trifluoro-7-(methylsulfonyl)-1-oxo-2,3-dihydro-1H-inden-4-yl)oxy)benzonitrile: (3R)-2,2,3,4-Tetrafluoro-7-methylsulfonyl-indan-1-one (0.066 g, 0.24 mmol) and 2-fluoro-5-hydroxybenzenecarbonitrile (35 mg, 0.26 mmol) were dissolved in DMF (1 mL) and treated with cesium bicarbonate (59 mg, 0.31 mmol). The mixture was stirred at ambient temperature for 3 hours. The reaction was concentrated in a stream of nitrogen to remove most of the DMF then redissolved in dichloromethane. The crude material was chromatographed on SiO₂ (Biotage SNAP) and eluted with a gradient of ethyl acetate/hexane. The product was concentrated to colorless oil (97 mg). LCMS ESI (+) m/z 400.1 (M+H).

Step H: Preparation of 2-fluoro-5-(((1S,3R)-2,2,3-trifluoro-1-hydroxy-7-(methylsulfonyl)-2,3-dihydro-1H-inden-4-yl)oxy)benzonitrile (Compound 91): 2-Fluoro-5-[(3R)-2,2,3-trifluoro-7-methylsulfonyl-1-oxo-indan-4-yl]oxy-benzonitrile (0.097 g, 0.24 mmol) was suspended in methylene chloride (1.6 mL), cooled to 0° C. and treated with triethylamine (0.068 mL, 0.49 mmol), formic acid (0.027 mL, 0.73 mmol) and RuCl(p-cymene)[(R,R)-Ts-DPEN] (1.5 mg, 0.002 mmol). The reaction mixture was stirred at 0° C. in the refrigerator for 14 hours. The mixture was concentrated in a stream of nitrogen gas then chromatographed on SiO₂ (Biotage SNAP) and eluted with a gradient of ethyl acetate/hexane to provide Compound 91 as off-white solid (26 mg). LCMS ESI (+) m/z 402 (M+H); ¹H NMR (400 MHz, CDCl₃): δ 8.10-8.06 (m, 1H), 7.44-7.32 (m, 3H), 6.91 (d, 1H), 5.95-5.91 (m, 0.5H), 5.81-5.78 (m, 0.5H), 5.70-5.64 (m, 1H), 4.00-3.97 (m, 1H), 3.24 (s, 3H).

Example 92

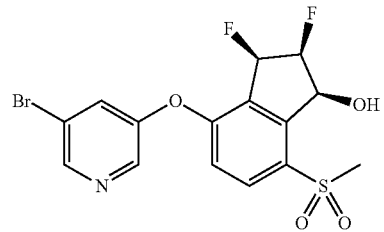 [SMILES: CS(=O)(=O)c1ccc(Oc2cncc(Br)c2)c2c1[C@H](O)[C@H](F)[C@@H]2F]

(1S,2S,3R)-4-((5-Bromopyridin-3-yl)oxy)-2,3-difluoro-7-(methylsulfonyl)-2,3-dihydro-1H-inden-1-ol (Compound 92)

Step A: Preparation of (1S,2R)-4-((5-bromopyridin-3-yl)oxy)-2-fluoro-7-(methylsulfonyl)-2,3-dihydro-1H-inden-1-ol: Prepared in a similar manner to that described in Example 313, Steps D-G substituting 5-bromopyridin-3-ol for 3-cyano-5-hydroxypyridine in Step D. LCMS ESI (+) m/z 402, 404 (M+H).

Step B: Preparation of (1S,2R)-4-((5-bromopyridin-3-yl)oxy)-2-fluoro-7-(methylsulfonyl)-2,3-dihydro-1H-inden-1-yl acetate: (1S,2R)-4-[(5-Bromo-3-pyridyl)oxy]-2-fluoro-7-methylsulfonyl-indan-1-ol (0.88 g, 2.2 mmol) was dissolved in dichloromethane (21 mL), treated with 4-dimethylaminopyridine (80 mg, 0.66 mmol) and triethylamine (0.61 mL, 4.4 mmol) then cooled to 0° C. The mixture was treated dropwise with acetic anhydride (0.41 mL, 4.4 mmol) then allowed to warm to ambient temperature and stirred for 2 hours. The mixture was diluted with additional methylene chloride and washed with water, 1N KHSO₄, water, one-half saturated NaHCO₃, dried over Na₂SO₄ and concentrated in vacuo to white solid (0.97 g). LCMS ESI (+) m/z 444, 446 (M+H).

Step C: Preparation of (1S,2S)-3-bromo-4-((5-bromopyridin-3-yl)oxy)-2-fluoro-7-(methylsulfonyl)-2,3-dihydro-1H-inden-1-yl acetate: [(1S,2R)-4-[(5-Bromo-3-pyridyl)oxy]-2-fluoro-7-methylsulfonyl-indan-1-yl] acetate (0.97 g, 2.2 mmol) was dissolved in 1,2-dichloroethane (13 mL) and treated with freshly-recrystallized N-bromosuccinimide (427 mg, 2.4 mmol) and azobisisobutyronitrile (36 mg, 0.22 mmol). The reaction mixture was placed under an argon atmosphere and heated to 80° C. for 30 minutes. Two additional portions of fresh azobisisobutyronitrile (36 mg, 0.22 mmol) were added at 30 minute intervals. After 100 minutes, the reaction was cooled and concentrated in vacuo. The residue was dissolved with methylene chloride, washed with saturated NaHCO₃, saturated NaCl, dried over Na₂SO₄ and concentrated in vacuo to orange residue. This crude mixture isomers (1.1 g), was used without further purification. LCMS ESI (+) m/z 522, 524, 526 (M+H).

Step D: Preparation of (1S,2R,3S)-4-((5-bromopyridin-3-yl)oxy)-2-fluoro-3-hydroxy-7-(methylsulfonyl)-2,3-dihydro-1H-inden-1-yl acetate: [(1S,2S)-3-Bromo-4-[(5-bromo-3-pyridyl)oxy]-2-fluoro-7-methylsulfonyl-indan-1-yl] acetate (1.1 g, 2.1 mmol) was dissolved in 1,2-dimethoxyethane (15 mL) and water (0.07 mL) and the solution was treated with silver perchlorate hydrate (710 mg, 3.2 mmol). The mixture was heated to 70° C. for 1.5 hours. The reaction was cooled, diluted with hexane then with ethyl acetate and filtered through celite. The filtrate was concentrated in vacuo to an insoluble residue. The oily solid was dissolved in ethyl acetate/methylene chloride and concentrated onto powdered Na₂SO₄. The dry load was placed atop a column pre-equilibrated with 20% ethyl acetate/hexane and chromatographed on SiO₂ (Biotage SNAP Ultra 100 g) eluting with a gradient of MeOH/methylene chloride. The mixed fractions from the first column were concentrated to a yellow oil and re-chromatographed on SiO₂ (Biotage SNAP Ultra 25g) and eluted with a gradient of ethyl acetate/hexane to give a colorless oil (33 mg). LCMS ESI (+) m/z 460, 462 (M+H).

Step E: Preparation of (1S,2S,3R)-4-((5-bromopyridin-3-yl)oxy)-2,3-difluoro-7-(methylsulfonyl)-2,3-dihydro-1H-inden-1-yl acetate: [(1S,2R,3S)-4-[(5-Bromo-3-pyridyl)oxy]-2-fluoro-3-hydroxy-7-methylsulfonyl-indan-1-yl] acetate (0.053 g, 0.12 mmol) was dissolved in dichloromethane (1.2 mL), cooled to 0° C. and treated dropwise with diethylaminosulfur trifluoride (0.023 mL, 0.17 mmol) then stirred at 0° C. for 1 hour. The mixture was removed from the ice bath and allowed to warm to ambient temperature for 30 minutes, then the reaction was recooled to 0° C., treated with saturated NaHCO₃ (5 mL) and stirred vigorously for 20 minutes. The mixture was diluted with additional dichloromethane and separated. The aqueous was washed twice with dichloromethane and the combined organic layers were dried over Na₂SO₄ and concentrated in vacuo. The crude product was chromatographed on SiO₂ (Biotage SNAP Ultra 10 g) and eluted with a gradient of ethyl acetate/hexane to give a colorless film (47 mg). LCMS ESI (+) m/z 462, 464 (M+H).

Step F: Preparation of (1S,2S,3R)-4-((5-bromopyridin-3-yl)oxy)-2,3-difluoro-7-(methylsulfonyl)-2,3-dihydro-1H-inden-1-ol (Compound 92): [(1S,2S,3R)-4-[(5-bromo-3-pyridyl)oxy]-2,3-difluoro-7-methylsulfonyl-indan-1-yl] acetate (0.046 g, 0.10 mmol) was dissolved in THF/MeOH (1:1, 1.25 mL), cooled to 0° C., and treated with a solution containing lithium hydroxide hydrate (7.9 mg, 0.20 mmol) in water (0.65 mL). The reaction was stirred at 0° C. for 90 minutes. The reaction was quenched at 0° C. with 10% citric acid to pH 4 then saturated NaHCO₃ was added to pH 8. The aqueous was extracted three times with ethyl acetate and the combined organics were washed with saturated NaHCO₃, saturated NaCl, dried over Na₂SO₄ and concentrated in vacuo. The crude material was chromatographed on SiO₂ (Biotage SNAP 10 g) and eluted with a gradient of ethyl acetate/hexane. The fractions were assayed by LCMS and those containing pure product were combined and concentrated in vacuo to give Compound 92 as white film (28 mg). LCMS ESI (+) m/z 420, 422 (M+H); ¹H NMR (400 MHz, CDCl₃): δ 8.63-8.61 (m, 1H), 8.45-8.43 (m, 1H), 8.11-8.07 (m, 1H), 7.66-7.64 (m, 1H), 6.96 (d, 1H), 6.13-6.11 (m, 0.5H), 5.99-5.97 (m, 0.5H), 5.86-5.82 (m, 1H), 5.24-5.04 (m, 1H), 3.30 (s, 3H), 3.03-3.00 (m, 1H).

Example 93

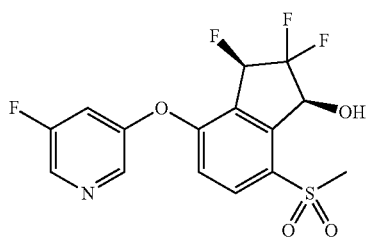 [SMILES: CS(=O)(=O)c1ccc(Oc2cncc(F)c2)c2c1[C@H](O)C(F)(F)[C@@H]2F]

(1S,3R)-2,2,3-trifluoro-4-((5-fluoropyridin-3-yl)oxy)-7-(methylsulfonyl)-2,3-dihydro-1H-inden-1-ol (Compound 93): LCMS ESI (+) m/z 378 (M+H); ¹H NMR (400 MHz, CDCl₃): δ 8.49-8.47 (m, 1H), 8.39-8.37 (m, 1H), 8.11-8.07 (m, 1H), 7.29-7.25 (m, 1H), 7.00 (d, 1H), 5.96-5.93 (m, 0.5H), 5.83-5.79 (m, 0.5H), 5.71-5.65 (m, 1H), 3.65-3.63 (m, 1H), 3.24 (s, 3H).

Example 94

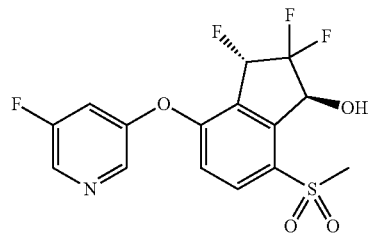 [SMILES: CS(=O)(=O)c1ccc(Oc2cncc(F)c2)c2c1[C@H](O)C(F)(F)[C@H]2F]

(1S,3S)-2,2,3-trifluoro-4-((5-fluoropyridin-3-yl)oxy)-7-(methylsulfonyl)-2,3-dihydro-1H-inden-1-ol (Compound 94): LCMS ESI (+) m/z 378 (M+H); ¹H NMR (400 MHz, CDCl₃): δ 8.49-8.46 (m, 1H), 8.39-8.36 (m, 1H), 8.08-8.04 (m, 1H), 8.28-8.24 (m, 1H), 6.98 (d, 1H), 6.12-6.08 (m, 0.5H), 5.99-5.95 (m, 0.5H), 5.88-5.81 (m, 1H), 4.10-4.06 (m, 1H), 3.26 (s, 3H).

Example 95

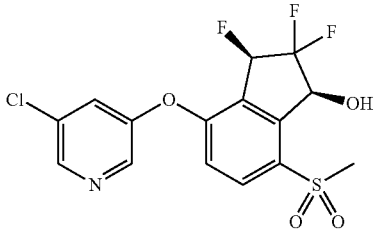 [SMILES: CS(=O)(=O)c1ccc(Oc2cncc(Cl)c2)c2c1[C@H](O)C(F)(F)[C@@H]2F]

(1S,3R)-4-((5-chloropyridin-3-yl)oxy)-2,2,3-trifluoro-7-(methylsulfonyl)-2,3-dihydro-1H-inden-1-ol (Compound 95): LCMS ESI (+) m/z 394, 396 (M+H); ¹H NMR (400 MHz, CDCl₃): δ 8.56-8.55 (m, 1H), 8.44-8.43 (m, 1H), 8.11-8.08 (m, 1H), 7.54-7.52 (m, 1H), 6.99 (d, 1H), 5.96-5.92 (m, 0.5H), 5.83-5.79 (m, 0.5H), 5.71-5.65 (m, 1H), 3.66-3.64 (m, 1H), 3.25 (s, 3H).

Example 96

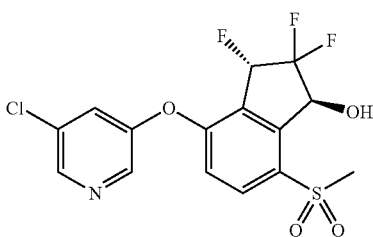 [SMILES: CS(=O)(=O)c1ccc(Oc2cncc(Cl)c2)c2c1[C@H](O)C(F)(F)[C@H]2F]

(1S,3S)-4-((5-chloropyridin-3-yl)oxy)-2,2,3-trifluoro-7-(methylsulfonyl)-2,3-dihydro-1H-inden-1-ol (Compound 96): LCMS ESI (+) m/z 394, 396 (M+H); $^1$H NMR (400 MHz, CDCl$_3$): δ 8.56-8.54 (m, 1H), 8.43-8.41 (m, 1H), 8.08-8.04 (m, 1H), 7.52-7.50 (m, 1H), 6.96 (d, 1H), 6.12-6.08 (m, 0.5H), 5.98-5.94 (m, 0.5H), 5.88-5.81 (m, 1H), 4.02-3.99 (m, 1H), 3.26 (s, 3H).

Example 97

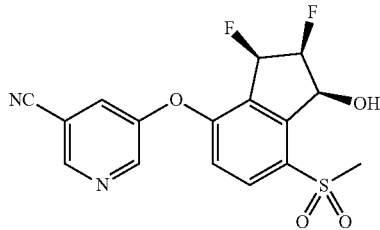 [SMILES: CS(=O)(=O)c1ccc(Oc2cncc(C#N)c2)c2c1[C@H](O)[C@H](F)[C@@H]2F]

5-(((1S,2S,3R)-2,3-difluoro-1-hydroxy-7-(methylsulfonyl)-2,3-dihydro-1H-inden-4-yl)oxy)nicotinonitrile (Compound 97): (1S,2S,3R)-4-[(5-Bromo-3-pyridyl)oxy]-2,3-difluoro-7-methylsulfonyl-indan-1-ol (0.015 g, 0.035 mmol) was combined with zinc powder (4.0 mg, 0.06 mmol) and zinc cyanide (5.9 mg, 0.05 mmol) in dry DMF (0.25 mL) then the suspension was sparged with argon for several minutes. The solution was treated with dichloro[1,1'-bis(diphenylphosphino)ferrocene]palladium (II) dichloromethane adduct (1.4 mg, 0.0018 mmol) and the mixture was sparged again for several minutes then heated to 150° C. for 2 hours in the microwave reactor. The solvent was removed in a stream of nitrogen gas. The residue was chromatographed on SiO$_2$ (Biotage SNAP 10) and eluted with a gradient of ethyl acetate/hexane. The desired material was concentrated to afford Compound 97 as white solid (8.5 mg). LCMS ESI (+) m/z 367 (M+H); $^1$H NMR (400 MHz, CD$_3$COCD$_3$): δ 8.88-8.86 (m, 1H), 8.82-8.80 (m, 1H), 8.13-8.08 (m, 2H), 7.33 (d, 1H), 6.21-6.18 (m, 0.5H), 6.07-6.04 (m, 0.5H), 5.83-5.79 (m, 1H), 5.36-5.29 (m, 0.5H), 5.25-5.16 (m, 0.5H), 5.07-5.04 (m, 1H), 3.33 (s, 3H).

Example 98

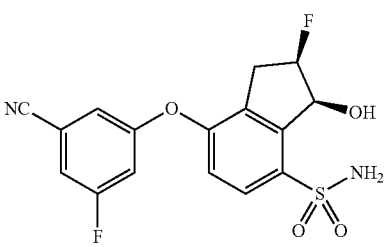 [SMILES: N#Cc1cc(F)cc(Oc2ccc(S(N)(=O)=O)c3c2C[C@@H](F)[C@H]3O)c1]

(2R,3S)-7-(3-cyano-5-fluoro-phenoxy)-2-fluoro-3-hydroxy-indane-4-sulfonamide (Compound 98): LCMS ESI (-) m/z 365 (M-H); $^1$H NMR (400 MHz, CD$_3$OD): δ 7.87 (d, 1H), 7.42-7.35 (m, 1H), 7.26-7.13 (m, 2H), 7.08 (d, 1H), 5.63-5.51 (m, 1H), 5.40-5.18 (m, 1H), 3.20-3.15 (m, 2H).

Example 99

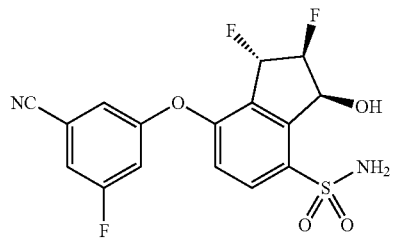 [SMILES: N#Cc1cc(F)cc(Oc2ccc(S(N)(=O)=O)c3c2[C@H](F)[C@@H](F)[C@H]3O)c1]

(1S,2S,3S)-7-(3-cyano-5-fluoro-phenoxy)-1,2-difluoro-3-hydroxy-indane-4-sulfonamide (Compound 99)

Step A: [(1S,2R)-7-(acetylsulfamoyl)-4-(3-cyano-5-fluoro-phenoxy)-2-fluoro-indan-1-yl] acetate: To a stirred solution of (2R,3S)-7-(3-cyano-5-fluoro-phenoxy)-2-fluoro-3-hydroxy-indane-4-sulfonamide (0.115 g, 0.32 mmol) in DCM (3 mL) was added 4-(dimethylamino)pyridine (0.012 g, 0.097 mmol) and triethylamine (0.090 mL, 0.64 mmol). Acetic anhydride (0.061 mL, 0.64 mmol) was added dropwise at 0° C. under nitrogen. The reaction mixture was allowed to warm to ambient temperature and stirred overnight. The reaction mixture was diluted with DCM, washed with saturated aqueous NaHCO$_3$ and brine, dried and concentrated. The residue was purified by column chromatography on silica gel (20-50% EtOAc/hexane) to give [(1S,2R)-7-(acetylsulfamoyl)-4-(3-cyano-5-fluoro-phenoxy)-2-fluoro-indan-1-yl] acetate (0.111 g, 77%). LCMS ESI (-) m/z 449 (M-H).

Step B: [(1S,2S)-7-(acetylsulfamoyl)-3-bromo-4-(3-cyano-5-fluoro-phenoxy)-2-fluoro-indan-1-yl] acetate: To a stirred solution of [(1S,2R)-7-(acetylsulfamoyl)-4-(3-cyano-5-fluoro-phenoxy)-2-fluoro-indan-1-yl] acetate (111 mg, 0.25 mmol) in DCE (2.7 mL) was added N-bromosuccinimide (66 mg, 0.37 mmol) and 2,2'-azobisisobutyronitrile (0.8 mg, 0.005 mmol). The reaction mixture was heated at 80° C. for 3 hours. After cooling, the reaction mixture was diluted with DCM, washed with saturated aqueous NaHCO$_3$ and brine, dried and concentrated. The residue was purified by column chromatography on silica gel (30-75% EtOAc/hexane) to give [(1S,2S)-7-(acetylsulfamoyl)-3-bromo-4-(3-cyano-5-fluoro-phenoxy)-2-fluoro-indan-1-yl] acetate (144 mg). LCMS ESI (-) m/z 527/529 (M-H).

Step C: [(1S,2R,3R)-7-(acetylsulfamoyl)-4-(3-cyano-5-fluoro-phenoxy)-2-fluoro-3-hydroxy-indan-1-yl] acetate and [(1S,2R,3S)-7-(acetylsulfamoyl)-4-(3-cyano-5-fluoro-phenoxy)-2-fluoro-3-hydroxy-indan-1-yl] acetate: To a stirred solution of [(1S,2S)-7-(acetylsulfamoyl)-3-bromo-4-(3-cyano-5-fluoro-phenoxy)-2-fluoro-indan-1-yl] acetate (0.144 g, 0.272 mmol) in 1,2-dimethoxyethane (0.90 mL) and water (0.090 mL) was added silver perchlorate hydrate (0.092 g, 0.41 mmol). The reaction mixture was heated at 70° C. for 30 minutes. After cooling, the reaction mixture was diluted with EtOAc and filtered through Celite. The filtrate was washed with water and brine, dried and concentrated. The residue was purified by column chromatography on silica gel (30-60% EtOAc/hexane) to give [(1S,2R,3S)-7-(acetylsulfamoyl)-4-(3-cyano-5-fluoro-phenoxy)-2-fluoro-3-hydroxy-indan-1-yl] acetate, which were further purified by C18 reverse phase flash chromatography (Biotage Isolera One unit, C18 Flash) with 20-60% CH₃CN/water affording [(1S,2R,3S)-7-(acetylsulfamoyl)-4-(3-cyano-5-fluoro-phenoxy)-2-fluoro-3-hydroxy-indan-1-yl] acetate (0.032 g, 25%). LCMS ESI (−) m/z 465 (M−H). Further elution of the silica gel column with 60-80% EtOAc/hexane gave [(1S,2R,3R)-7-(acetylsulfamoyl)-4-(3-cyano-5-fluoro-phenoxy)-2-fluoro-3-hydroxy-indan-1-yl] acetate (0.023 g, 18%). LCMS ESI (−) m/z 465 (M−H).

Step D: [(1S,2S,3S)-7-(acetylsulfamoyl)-4-(3-cyano-5-fluoro-phenoxy)-2,3-difluoro-indan-1-yl] acetate: To a stirred solution of [(1S,2R,3R)-7-(acetylsulfamoyl)-4-(3-cyano-5-fluoro-phenoxy)-2-fluoro-3-hydroxy-indan-1-yl] acetate (23 mg, 0.050 mmol) in DCM (0.5 mL) was added (diethylamino)sulfur trifluoride (DAST) (0.013 mL, 0.099 mmol) at −78° C. under nitrogen. The reaction mixture was allowed to warm to 0° C. and stirred for 15 minutes. The reaction was quenched by saturated aqueous NaHCO₃ solution. The mixture was partitioned between EtOAc and water. The aqueous layer was extracted with EtOAc. The combined organic layers were washed with brine, dried and concentrated. The residue was purified by flash chromatography on silica gel (20-50% EtOAc/hexanes) to give [(1S,2S,3S)-7-(acetylsulfamoyl)-4-(3-cyano-5-fluoro-phenoxy)-2,3-difluoro-indan-1-yl] acetate (20 mg, 87%). LCMS ESI (−) m/z 467 (M−H).

Step E: N-[(1S,2S,3S)-7-(3-cyano-5-fluoro-phenoxy)-1,2-difluoro-3-hydroxy-indan-4-yl]sulfonylacetamide: To a stirred solution of (1S,2S,3S)-7-(acetylsulfamoyl)-4-(3-cyano-5-fluoro-phenoxy)-2,3-difluoro-indan-1-yl] acetate (20 mg, 0.043 mmol) in tetrahydrofuran (0.3 mL) was added 0.5 N LiOH solution (0.26 mL, 0.13 mmol) at 0° C. under nitrogen. The reaction mixture was allowed to warm to ambient temperature and stirred for 3 hours. The reaction was partitioned between EtOAc and water. The aqueous layer was extracted with EtOAc. The combined organic layers were washed with water and brine, dried and concentrated. The crude was used in the next step without further purification. LCMS ESI (+) m/z 425 (M+H).

Step F: (1S,2S,3S)-7-(3-cyano-5-fluoro-phenoxy)-1,2-difluoro-3-hydroxy-indane-4-sulfonamide (Compound 99): To a stirred solution of N-[(1S,2S,3S)-7-(3-cyano-5-fluoro-phenoxy)-1,2-difluoro-3-hydroxy-indan-4-yl]sulfonylacetamide (18 mg, 0.042 mmol) in tetrahydrofuran (0.3 mL) was added 3 N HCl (0.084 mL, 9.2 mmol). The reaction mixture was heated at reflux for 12 hours. After cooling, the reaction was partitioned between EtOAc and water. The aqueous layer was extracted with EtOAc. The combined organic layers were washed with water and brine, dried and concentrated. The residue was purified by flash chromatography on silica gel (20-50% EtOAc/hexane) to give Compound 99 (8 mg, 49%). LCMS ESI (−) m/z 383 (M−H); ¹H NMR (400 MHz, CD₃OD): δ 8.04 (d, 1H), 7.45-7.41 (m, 1H), 7.31-7.29 (m, 1H), 7.26-7.21 (m, 1H), 7.18 (d, 1H), 6.30-6.11 (m, 1H), 5.80 (t, 1H), 5.37-5.17 (m, 1H).

Example 100

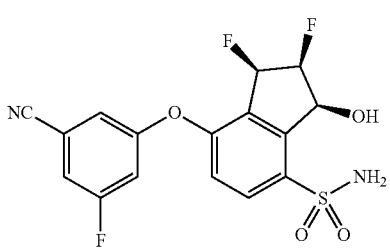 [SMILES: N#Cc1cc(F)cc(Oc2ccc(S(N)(=O)=O)c3c2[C@@H](F)[C@@H](F)[C@H]3O)c1]

(1R,2S,3S)-7-(3-cyano-5-fluoro-phenoxy)-1,2-difluoro-3-hydroxy-indane-4-sulfonamide (Compound 100): LCMS ESI (−) m/z 383 (M−H).

Example 101

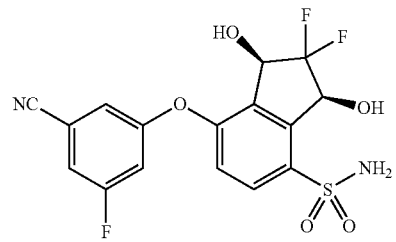 [SMILES: N#Cc1cc(F)cc(Oc2ccc(S(N)(=O)=O)c3c2[C@@H](O)C(F)(F)[C@H]3O)c1]

(1R,3S)-7-(3-cyano-5-fluoro-phenoxy)-2,2-difluoro-1,3-dihydroxy-indane-4-sulfonamide (Compound 101)

Step A: 7'-(3-cyano-5-fluoro-phenoxy)spiro[1,3-dioxolane-2,3'-indane]-4'-sulfonamide: To a stirred solution of 7-(3-cyano-5-fluoro-phenoxy)-3-oxo-indane-4-sulfonamide (2.80 g, 8.1 mmol) in DCM (54 mL) was added trimethyl(2-trimethylsilyloxyethoxy)silane (2.78 mL, 11.3 mmol). The reaction mixture was cooled to −78° C. Trimethylsilyl trifluoromethanesulfonate (0.58 mL, 3.2 mmol) was added dropwise under nitrogen. The reaction mixture was allowed to warm to ambient temperature. After stirring for 2 hours, additional trimethyl(2-trimethylsilyloxyethoxy)silane (1.40 mL, 5.60 mmol) was added, and the reaction was stirred at ambient temperature for additional 1 hour. Triethylamine (3.38 mL, 24.3 mmol) was added dropwise. After stirring for 10 minutes, the reaction was concentrated under reduced pressure. The residue was purified by flash chromatography on silica gel (20-50% EtOAc/hexane) to give 7'-(3-cyano-5-fluoro-phenoxy)spiro[1,3-dioxolane-2,3'-indane]-4'-sulfonamide (1.41 g, 45%). LCMS ESI (−) m/z 389 (M−H).

Step B: 1'-bromo-7'-(3-cyano-5-fluoro-phenoxy)spiro[1,3-dioxolane-2,3'-indane]-4'-sulfonamide: To a stirred solution of 7'-(3-cyano-5-fluoro-phenoxy)spiro[1,3-dioxolane-2,3'-indane]-4'-sulfonamide (1.41 g, 3.61 mmol) in DCE (24 mL) was added N-bromosuccinimide (0.707 g, 3.97 mmol) and 2,2'-azobisisobutyronitrile (0.006 g, 0.04 mmol). The reaction mixture was heated at 80° C. for 30 minutes. After cooling, the reaction mixture was diluted with DCM, washed with saturated aqueous NaHCO₃ and brine, dried and concentrated. The residue was purified by column chromatography on silica gel (20-50% EtOAc/hexane) to give 1'-bromo-7'-(3-cyano-5-fluoro-phenoxy)spiro[1,3-dioxolane-2,3'-indane]-4'-sulfonamide (1.19 g, 70%). LCMS ESI (+) m/z 467, 469 (M−H).

Step C: 7'-(3-cyano-5-fluoro-phenoxy)-1'-hydroxy-spiro[1,3-dioxolane-2,3'-indane]-4'-sulfonamide: To a stirred solution of 1'-bromo-7'-(3-cyano-5-fluoro-phenoxy)spiro[1,3-dioxolane-2,3'-indane]-4'-sulfonamide (1.19 g, 2.54 mmol) in 1,2-dimethoxyethane (21 mL) and water (7 mL) was added disilver carbonate (1.05 g, 3.8 mmol). The reaction mixture was stirred at ambient temperature overnight. The mixture was diluted with EtOAc and filtered through Celite. The filtrate was washed with water and brine, dried and concentrated. The crude was used in the next step without further purification. LCMS ESI (−) m/z 405 (M−H).

Step D: 7'-(3-cyano-5-fluoro-phenoxy)-1'-oxo-spiro[1,3-dioxolane-2,3'-indane]-4'-sulfonamide: To a stirred solution of 7'-(3-cyano-5-fluoro-phenoxy)-1'-hydroxy-spiro[1,3-dioxolane-2,3'-indane]-4'-sulfonamide (1.03 g, 2.53 mmol) in DCM (25 mL) was added Dess-Martin periodinane (1.61 g, 3.80 mmol). The reaction mixture was stirred at ambient temperature for 1 hour. The reaction mixture was partitioned between EtOAc and saturated aqueous NaHCO₃. The aqueous layer was extracted with EtOAc. The combined organic layers were washed with water and brine, dried and concentrated. The crude was purified by flash chromatography on silica gel (20-60% EtOAc/hexane) to give 7'-(3-cyano-5-fluoro-phenoxy)-1'-oxo-spiro[1,3-dioxolane-2,3'-indane]-4'-sulfonamide (0.460 g, 45%). LCMS ESI (−) m/z 403 (M−H).

Step E: 7-(3-cyano-5-fluoro-phenoxy)-1,3-dioxo-indane-4-sulfonamide: To a stirred solution of 7'-(3-cyano-5-fluoro-phenoxy)-1'-oxo-spiro[1,3-dioxo lane-2,3'-indane]-4'-sulfonamide (250 mg, 0.620 mmol) in tetrahydrofuran (3 mL) was added 4 N HCl (1.55 mL, 6.18 mmol). The reaction was heated at 60° C. for 1 hour. After cooling, the reaction mixture was partitioned between EtOAc and water. The aqueous layer was extracted with EtOAc. The combined organic layers were washed with water and brine, dried and concentrated. The crude was used in the next step without further purification. LCMS ESI (−) m/z 359 (M−H).

Step F: 7-(3-cyano-5-fluoro-phenoxy)-2,2-difluoro-1,3-dioxo-indane-4-sulfonamide: To a stirred solution of 7-(3-cyano-5-fluoro-phenoxy)-1,3-dioxo-indane-4-sulfonamide (223 mg, 0.620 mmol) in acetonitrile (6 mL) was added sodium carbonate (144 mg, 1.36 mmol) at ambient temperature under nitrogen. Selectfluor® (482 mg, 1.36 mmol) was added and the reaction mixture was stirred at 25° C. for 30 minutes. The reaction mixture was partitioned between EtOAc and water. The aqueous layer was extracted with EtOAc. The combined organic layers were washed with water and brine, dried and concentrated. The residue was purified by flash chromatography on silica gel (20-50% EtOAc/hexanes) to give 7-(3-cyano-5-fluoro-phenoxy)-2,2-difluoro-1,3-dioxo-indane-4-sulfonamide (161 mg, 66%). LCMS ESI (−) m/z 395 (M−H).

Step G: (1R,3S)-7-(3-cyano-5-fluoro-phenoxy)-2,2-difluoro-1,3-dihydroxy-indane-4-sulfonamide (Compound 101): Formic acid (0.092 mL, 2.4 mmol) was added slowly to a solution of triethylamine (0.227 mL, 1.63 mmol) in DCM (4 mL) at 0° C. 7-(3-cyano-5-fluoro-phenoxy)-2,2-difluoro-1,3-dioxo-indane-4-sulfonamide (161 mg, 0.410 mmol) was then added followed by the addition of RuCl(p-cymene)[(R,R)-Ts-DPEN] (7.8 mg, 0.012 mmol) under nitrogen. The flask was placed in a 4° C. refrigerator overnight. The reaction mixture was diluted with DCM, washed with saturated aqueous NaHCO₃ and brine, dried, and concentrated. The residue was purified by flash chromatography on silica gel (20-60% EtOAc/hexane) to give (1S,3S)-7-(3-cyano-5-fluoro-phenoxy)-2,2-difluoro-1,3-dihydroxy-indane-4-sulfonamide (43 mg, 26%). LCMS ESI (−) m/z 399 (M−H). Further elution afforded Compound 101 (26 mg, 16%). LCMS ESI (−) m/z 399 (M−H). ¹H NMR (400 MHz, CD₃OD): δ 8.00 (d, 1H), 7.44-7.41 (m, 1H), 7.35-7.32 (m, 1H), 7.29-7.24 (m, 1H), 7.14 (d, 1H), 5.46 (d, 1H), 5.06 (d, 1H).

Example 102

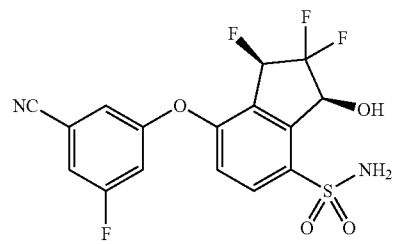 [SMILES: N#Cc1cc(F)cc(Oc2ccc(S(N)(=O)=O)c3c2[C@@H](F)C(F)(F)[C@H]3O)c1]

(1R,3S)-7-(3-cyano-5-fluoro-phenoxy)-1,2,2-trifluoro-3-hydroxy-indane-4-sulfonamide (Compound 102): To a stirred solution of (1S,3S)-7-(3-cyano-5-fluoro-phenoxy)-2,2-difluoro-1,3-dihydroxy-indane-4-sulfonamide (43 mg, 0.11 mmol) in DCM (1 mL) was added (diethylamino)sulfur trifluoride (DAST) (0.028 mL, 0.21 mmol) at −78° C. under nitrogen. The reaction mixture was allowed to warm to 0° C. and stirred for 1 hour. The reaction was quenched by the addition of saturated aqueous NaHCO₃. The mixture was partitioned between EtOAc and water. The aqueous layer was extracted with EtOAc. The combined organic layers were washed with brine, dried and concentrated. The residue was dissolved in DCM (1 mL). 5 N HCl in isopropanol (0.3 mL) was added. The reaction mixture was stirred for 15 minutes and then concentrated under reduced pressure. The residue was purified by flash chromatography on silica gel (20-50% EtOAc/hexane) to give Compound 102 (16 mg, 37%). LCMS ESI (−) m/z 401 (M−H); ¹H NMR (400 MHz, CD₃OD): δ 8.03-8.00 (m, 1H), 7.24-7.20 (m, 1H), 7.17-7.15 (m, 1H), 7.08-7.04 (m, 1H), 6.96 (d, 1H), 5.82-5.65 (m, 1H), 5.54-5.48 (m, 1H).

Example 103

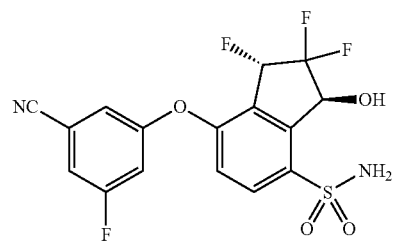 [SMILES: N#Cc1cc(F)cc(Oc2ccc(S(N)(=O)=O)c3c2[C@H](F)C(F)(F)[C@H]3O)c1]

(1S,3S)-7-(3-cyano-5-fluoro-phenoxy)-1,2,2-trifluoro-3-hydroxy-indane-4-sulfonamide (Compound 103): LCMS ESI (−) m/z 401 (M−H); ¹H NMR (400 MHz, CD₃OD): δ 8.09-8.05 (m, 1H), 7.50-7.46 (m, 1H), 7.39-7.38 (m, 1H), 7.33-7.29 (m, 1H), 7.14 (d, 1H), 6.19-6.02 (m, 1H), 5.72-5.65 (m, 1H).

Example 104

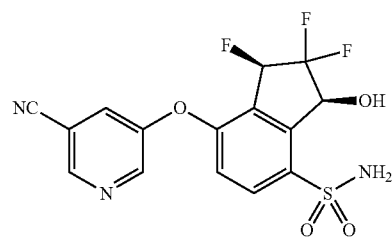 [SMILES: N#Cc1cncc(Oc2ccc(S(N)(=O)=O)c3c2[C@@H](F)C(F)(F)[C@H]3O)c1]

(1R,3S)-7-[(5-cyano-3-pyridyl)oxy]-1,2,2-trifluoro-3-hydroxy-indane-4-sulfonamide (Compound 104)

Step A: (3S)-7-benzylsulfanyl-2,2,4-trifluoro-3-hydroxy-indan-1-one: To a stirred mixture of (3S)-2,2,4,7-tetrafluoro-3-hydroxy-indan-1-one (250 mg, 1.14 mmol) and cesium carbonate (555 mg, 1.7 mmol) in DMF (8 mL) was added dropwise benzyl mercaptan (0.15 mL, 1.3 mmol) at 0° C. under nitrogen. The reaction mixture was stirred at 0° C. for 30 minutes. The reaction was partitioned between EtOAc and water. The aqueous layer was extracted with EtOAc. The combined organic layers were washed with water and brine, dried and concentrated. The residue was purified by flash chromatography on silica gel (20-40% EtOAc/hexane) to give (3S)-7-benzylsulfanyl-2,2,4-trifluoro-3-hydroxy-indan-1-one (350 mg, 95%). LCMS ESI (+) m/z 342 (M+NH$_4^+$).

Step B: (3R)-7-benzylsulfanyl-2,2,3,4-tetrafluoro-indan-1-one: To a stirred solution of (3S)-7-benzylsulfanyl-2,2,4-trifluoro-3-hydroxy-indan-1-one (350 mg, 1.08 mmol) in DCM (10 mL) was added dropwise (diethylamino)sulfur trifluoride (DAST) (0.228 mL, 1.73 mmol) at 0° C. under nitrogen. The reaction mixture was stirred at 0° C. for 5 hours. The reaction was quenched by the addition of saturated aqueous NaHCO$_3$. The mixture was partitioned between EtOAc and water. The aqueous layer was extracted with EtOAc. The combined organic layers were washed with brine, dried and concentrated. The residue was purified by flash chromatography on silica gel (5-20% EtOAc/hexane) to give (3R)-7-benzylsulfanyl-2,2,3,4-tetrafluoro-indan-1-one (210 mg, 60%). LCMS ESI (−) m/z 325 (M−H).

Step C: (1R)-1,2,2,7-tetrafluoro-3-oxo-indane-4-sulfonamide: To a stirred suspension of (3R)-7-benzylsulfanyl-2,2,3,4-tetrafluoro-indan-1-one (290 mg, 0.89 mmol) in acetic acid (9 mL) and water (1 mL) was added N-chlorosuccinimide (356 mg, 2.67 mmol) at 0° C. The reaction mixture was allowed to warm to ambient temperature and stirred for 2 hours. The reaction was partitioned between EtOAc and water. The aqueous layer was extracted with EtOAc. The combined organic layers were washed with water and brine, dried and concentrated. The crude was used in the next step without further purification. The crude was dissolved in DCM (3 mL) and added dropwise to a stirred solution of 0.5 N ammonia in dioxane (8.9 mL, 4.4 mmol) 0° C. under nitrogen. The reaction mixture was stirred for 15 minutes and then concentrated under reduced pressure. The residue was partitioned between EtOAc and water. The organic layer was washed successively with saturated aqueous NaHCO$_3$, water and brine, dried and concentrated. The residue was purified by flash chromatography on silica gel (20-50% EtOAc/hexanes) to give (1R)-1,2,2,7-tetrafluoro-3-oxo-indane-4-sulfonamide (142 mg, 56%). LCMS ESI (+) m/z 284 (M+H).

Step D: (1R)-7-[(5-cyano-3-pyridyl)oxy]-1,2,2-trifluoro-3-oxo-indane-4-sulfonamide: A mixture of (1R)-1,2,2,7-tetrafluoro-3-oxo-indane-4-sulfonamide (66 mg, 0.23 mmol), 3-cyano-5-hydroxypyridine (42 mg, 0.35 mmol) and cesium bicarbonate (59 mg, 0.3 mmol) in NMP (2.3 mL) was heated at 60° C. for 1 hour. After cooling, the reaction mixture was partitioned between EtOAc and water. The aqueous layer was extracted with EtOAc. The combined organic layers were washed with water and brine, dried and concentrated. The residue was purified by flash chromatography on silica gel (30-80% EtOAc/hexane) to give (1R)-7-[(5-cyano-3-pyridyl)oxy]-1,2,2-trifluoro-3-oxo-indane-4-sulfonamide (19 mg, 21%). LCMS ESI (−) m/z 382 (M−H).

Step E: (1R,3S)-7-[(5-cyano-3-pyridyl)oxy]-1,2,2-trifluoro-3-hydroxy-indane-4-sulfonamide (Compound 104): To a stirred solution of (1R)-7-[(5-cyano-3-pyridyl)oxy]-1,2,2-trifluoro-3-oxo-indane-4-sulfonamide (19 mg, 0.05 mmol) in DCM (0.5 mL) were added formic acid (0.0056 mL, 0.15 mmol) and triethylamine (0.014 mL, 0.10 mmol) followed by RuCl(p-cymene)[(R,R)-Ts-DPEN] (0.6 mg, 0.001 mmol) under nitrogen. The flask was then placed in a 4° C. refrigerator overnight. The reaction mixture was concentrated in vacuo. The residue was purified by flash chromatography on silica gel (20-60% EtOAc/hexane) to give Compound 104 (7 mg, 37%). LCMS ESI (−) m/z 384 (M−H); $^1$H NMR (400 MHz, CD$_3$OD): δ 8.81 (d, 1H), 8.73 (d, 1H), 8.11-8.07 (m, 1H), 8.06-8.04 (m, 1H), 7.18 (d, 1H), 6.04-5.86 (m, 1H), 5.57-5.51 (m, 1H).

Example 105

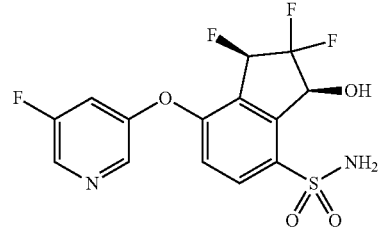 [SMILES: NS(=O)(=O)c1ccc(Oc2cncc(F)c2)c2c1[C@H](O)C(F)(F)[C@@H]2F]

(1R,3S)-1,2,2-trifluoro-7-[(5-fluoro-3-pyridyl)oxy]-3-hydroxy-indane-4-sulfonamide (Compound 105)

Step A: (1R)-1,2,2-trifluoro-7-[(5-fluoro-3-pyridyl)oxy]-3-oxo-indane-4-sulfonamide: A mixture of (1R)-1,2,2,7-tetrafluoro-3-oxo-indane-4-sulfonamide (70 mg, 0.25 mmol), 3-fluoro-5-hydroxypyridine (42 mg, 0.37 mmol) and cesium bicarbonate (62 mg, 0.32 mmol) in NMP (1.2 mL) was heated at 60° C. for 8 hours. After cooling, the reaction mixture was partitioned between EtOAc and water. The aqueous layer was extracted with EtOAc. The combined organic layers were washed with water and brine, dried and concentrated. The residue was purified by flash chromatography on silica gel (30-70% EtOAc/hexane) to give (1R)-1,2,2-trifluoro-7-[(5-fluoro-3-pyridyl)oxy]-3-oxo-indane-4-sulfonamide (28 mg, 30%). LCMS ESI (−) m/z 375 (M−H).

Step B: (1R,3S)-1,2,2-trifluoro-7-[(5-fluoro-3-pyridyl)oxy]-3-hydroxy-indane-4-sulfonamide (Compound 105): To a stirred solution of (1R)-1,2,2-trifluoro-7-[(5-fluoro-3-pyridyl)oxy]-3-oxo-indane-4-sulfonamide (28 mg, 0.070 mmol) in DCM (0.7 mL) were added formic acid (0.0084 mL, 0.22 mmol) and triethylamine (0.021 mL, 0.15 mmol) followed by RuCl(p-cymene)[(R,R)-Ts-DPEN] (1 mg, 0.002 mmol) under nitrogen. The flask was then placed in a 4° C. refrigerator overnight. The reaction mixture was concentrated in vacuo. The residue was purified by flash chromatography on silica gel (20-60% EtOAc/hexane) to give Compound 105 (12 mg, 43%). LCMS ESI (−) m/z 377 (M−H); $^1$H NMR (400 MHz, CD$_3$OD): δ 8.43 (d, 1H), 8.35 (d, 1H), 8.10-8.06 (m, 1H), 7.59-7.54 (m, 1H), 7.15 (d, 1H), 6.03-5.85 (m, 1H), 5.56-5.50 (m, 1H).

Examples 106 and 107

Compound 106

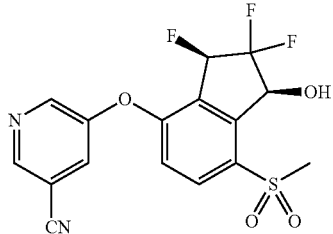

Compound 107

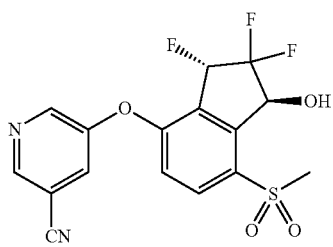

Data for 5-(((1S,3R)-2,2,3-trifluoro-1-hydroxy-7-(methylsulfonyl)-2,3-dihydro-1H-inden-4-yl)oxy)nicotinonitrile (Compound 106): LCMS ESI (+) (M+H) m/z 385; $^1$H NMR (400 MHz, CDCl$_3$): δ 8.82 (d, 1H), 8.74 (d, 1H), 8.14 (dd, 1H), 7.74 (dd, 1H), 7.02 (d, 1H), 5.87 (dd, 1H), 5.73-5.66 (m, 1H), 3.58 (d, 1H), 3.26 (s, 3H).

Data for 5-(((1S,3S)-2,2,3-trifluoro-1-hydroxy-7-(methylsulfonyl)-2,3-dihydro-1H-inden-4-yl)oxy)nicotinonitrile (Compound 107): LCMS ESI (+) (M+H) m/z 385; $^1$H NMR (400 MHz, (CD$_3$)$_2$CO): δ 8.89 (dd, 1H), 8.86 (d, 1H), 8.21 (dd, 1H), 8.11 (dd, 1H), 7.36 (d, 1H), 6.36 (ddd, 1H), 6.10 (d, 1H), 5.87-5.80 (m, 1H), 3.31 (s, 3H).

Examples 108 and 109

Compound 108

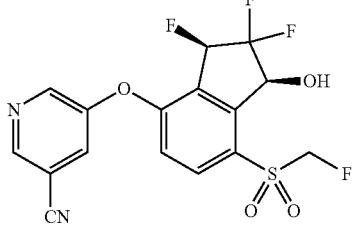

Compound 109

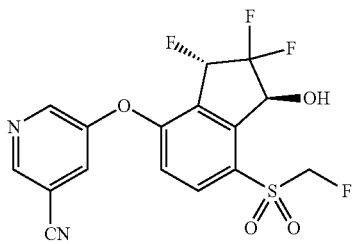

5-(((1S,3R)-2,2,3-trifluoro-7-((fluoromethyl)sulfonyl)-1-hydroxy-2,3-dihydro-1H-inden-4-yl)oxy)nicotinonitrile (Compound 108) and 5-(((1S,3S)-2,2,3-trifluoro-7-((fluoromethyl)sulfonyl)-1-hydroxy-2,3-dihydro-1H-inden-4-yl)oxy)nicotinonitrile (Compound 109)

Data for Compound 108: LCMS ESI (+) (M+H) m/z 403; $^1$H NMR (400 MHz, CDCl$_3$): δ 8.84 (d, 1H), 8.75 (d, 1H), 8.15 (dd, 1H), 7.77 (dd, 1H), 7.02 (d, 1H), 5.83 (dd, 1H), 5.68-5.62 (m, 1H), 5.43 (dd, 1H), 5.31 (dd, 1H), 3.43 (dd, 1H).

Data for Compound 109: LCMS ESI (+) (M+H) m/z 403; $^1$H NMR (400 MHz, (CD$_3$)$_2$CO): δ 8.93 (dd, 1H), 8.90 (dd, 1H), 8.26 (dd, 1H), 8.13 (dd, 1H), 7.38 (d, 1H), 6.39 (ddd, 1H), 5.73 (dd, 1H), 5.80 (ddd, 1H), 5.61 (dd, 1H).

Example 110

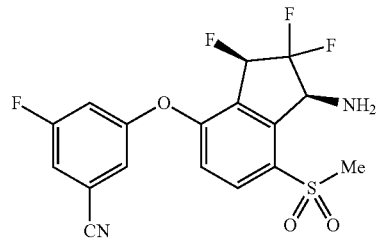 [SMILES: CS(=O)(=O)c1ccc(Oc2cc(F)cc(C#N)c2)c2c1[C@H](N)C(F)(F)[C@@H]2F]

(1S,3R)-2,2,3-trifluoro-4-(3-fluoro-5-(iminomethyl)phenoxy)-7-(methylsulfonyl)-2,3-dihydro-1H-inden-1-amine (Compound 110): LCMS ESI (+) (M+H) m/z 401; $^1$H NMR (400 MHz, CDCl$_3$): δ 8.14 (dd, 1H), 7.30 (ddd, 1H), 7.24-7.22 (m, 1H), 7.14 (dt, 1H), 6.98 (d, 1H), 5.77 (dd, 1H), 5.10-5.01 (m, 1H), 3.45 (s, 3H), 1.82 (br d, 2H).

Example 111

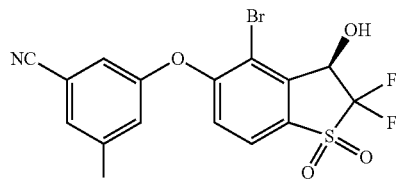

(R)-3-((4-bromo-2,2-difluoro-3-hydroxy-1,1-dioxido-2,3-dihydrobenzo[b]thiophen-5-yl)oxy)-5-fluorobenzonitrile (Compound 111)

Step A: Preparation of methyl 2-bromo-3-(3-cyano-5-fluorophenoxy)-6-(methylsulfonyl)benzoate: Methyl 2-bromo-3-fluoro-6-methylsulfonyl-benzoate (200 mg, 0.64 mmol) was combined with 3-fluoro-5-hydroxy-benzonitrile (132 mg, 0.96 mmol) and N,N-dimethylformamide (2.5 mL). The solution was treated in a single portion with sodium bicarbonate (108 mg, 1.3 mmol) and the reaction mixture was heated to 90° C. for 16 hours. The reaction mixture was cooled, diluted with Et$_2$O and water and then separated. The aqueous layer was washed with Et$_2$O, then the combined organics were washed with water, three times with 10% K$_2$CO$_3$, saturated NaCl, dried over Na$_2$SO$_4$ and concentrated in vacuo to an orange oil to provide methyl 2-bromo-3-(3-cyano-5-fluorophenoxy)-6-(methylsulfonyl) benzoate (276 mg, quant.). $^1$H NMR (400 MHz, CDCl$_3$): δ 8.03 (d, 1H), 7.25-7.22 (m, 1H), 7.14 (d, 1H), 7.10-7.09 (m, 1H), 7.03-7.00 (m, 1H), 4.04 (s, 3H), 3.20 (s, 3H).

Step B: Preparation of 3-((4-bromo-1,1-dioxido-3-oxo-2, 3-dihydrobenzo[b]thiophen-5-yl)oxy)-5-fluorobenzonitrile: Sodium hydride (60% in mineral oil, 77 mg, 1.9 mmol) was washed three times with hexane, then resuspended in tetrahydrofuran (3.5 mL). The suspension was cooled to 0° C. and treated dropwise with a solution of methyl 2-bromo-3-(3-cyano-5-fluoro-phenoxy)-6-methylsulfonyl-benzoate (276 mg, 0.64 mmol) dissolved in tetrahydrofuran (3.7 mL). After the addition, the reaction was warmed to ambient temperature and stirred for 5 hours. The reaction was quenched with saturated NH$_4$Cl and concentrated in vacuo. Ethyl acetate and some water were added, the solids were resolubilized, then the pH of the aqueous was adjusted to 3-4 with 10% KHSO$_4$. After separation, the aqueous was washed twice with ethyl acetate. The combined organics were washed twice with water, saturated NaCl, dried over Na$_2$SO$_4$ and concentrated in vacuo. 3-((4-Bromo-1,1-dioxido-3-oxo-2,3-dihydrobenzo[b]thiophen-5-yl)oxy)-5-fluorobenzonitrile was obtained as a pale yellow solid (214 mg, 84%). $^1$H NMR (400 MHz, CDCl$_3$): δ 8.00-7.98 (m, 1H), 7.52-7.50 (m, 1H), 7.25-7.22 (m, 1H), 7.06-7.04 (m, 1H), 6.99-6.95 (m, 1H), 4.22 (m, 2H).

Step C: Preparation of 3-((4-bromo-2,2-difluoro-1,1-dioxido-3-oxo-2,3-dihydrobenzo[b]thiophen-5-yl)oxy)-5-fluorobenzonitrile: A solution of 3-((4-bromo-1,1-dioxido-3-oxo-2,3-dihydrobenzo[b]thiophen-5-yl)oxy)-5-fluorobenzonitrile (84 mg, 0.21 mmol) slurried in acetonitrile (1.2 mL) was treated with Selectfluor® (225 mg, 0.64 mmol) and sodium carbonate (67 mg, 0.64 mmol) and the resulting suspension was stirred at ambient temperature for 2 hours. The mixture was diluted with water and ethyl acetate and then separated. The aqueous was washed with ethyl acetate. The combined organic layers were washed with saturated NaHCO$_3$, saturated NaCl, dried over Na$_2$SO$_4$ and concentrated in vacuo to a light yellow film. The material was chromatographed on SiO$_2$ eluting with a gradient of ethyl acetate/hexanes. 3-((4-Bromo-2,2-difluoro-1,1-dioxido-3-oxo-2,3-dihydrobenzo[b]thiophen-5-yl)oxy)-5-fluorobenzonitrile was obtained as an off-white solid (68 mg, 42%). $^1$H NMR (400 MHz, CDCl$_3$): δ 8.05 (d, 1H), 7.56 (d, 1H), 7.32-7.28 (m, 1H), 7.14-7.11 (m, 1H), 7.06-7.02 (m, 1H).

Step D: Preparation of (R)-3-((4-bromo-2,2-difluoro-3-hydroxy-1,1-dioxido-2,3-dihydrobenzo[b]thiophen-5-yl) oxy)-5-fluorobenzonitrile: 3-((4-Bromo-2,2-difluoro-1,1-dioxido-3-oxo-2,3-dihydrobenzo[b]thiophen-5-yl)oxy)-5-fluorobenzonitrile (34 mg, 0.08 mmol) was dissolved in dichloromethane (freshly degassed by sparging with nitrogen, 0.6 mL) and the solution was treated with triethylamine (22 µL, 0.16 mmol) and formic acid (8.9 µL, 0.24 mmol). After cooling to 0° C., the solution was treated with a pre-cooled (0° C.) solution of N-[(1R,2R)-1,2-diphenyl-2-(2-(4-methylbenzyloxy)ethylamino)-ethyl]-4-methylbenzene sulfonamide(chloro)ruthenium(II) ((R,R)-Ts-DENEB™, 0.51 mg, 0.8 µmol) dissolved in dichloromethane (0.6 mL). The resulting suspension was placed in the refrigerator and allowed to stand at 4° C. for 32 hours. The reaction was concentrated with a stream of nitrogen gas, then chromatographed on SiO$_2$ eluting with a gradient of ethyl acetate/chloroform. (R)-3-((4-Bromo-2,2-difluoro-3-hydroxy-1,1-dioxido-2,3-dihydrobenzo[b]thiophen-5-yl)oxy)-5-fluorobenzonitrile was isolated as a white solid (28 mg, 82%, >89% ee by Mosher ester analysis). $^1$H NMR (400 MHz, CDCl$_3$): δ 7.86 (d, 1H), 7.27 (d, 1H), 7.27-7.24 (m, 1H), 7.13-7.11 (m, 1H), 7.04-7.00 (m, 1H), 5.41-5.37 (m, 1H), 3.06 (d, 1H).

Example 112

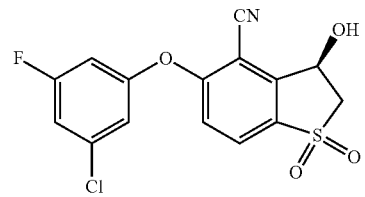 [SMILES: N#Cc1c(Oc2cc(F)cc(Cl)c2)ccc2c1[C@@H](O)CS2(=O)=O]

(3R)-5-(3-chloro-5-fluoro-phenoxy)-3-hydroxy-1,1-dioxo-2,3-dihydrobenzothiophene-4-carbonitrile
(Compound 112)

Step A: Preparation of 2-bromo-3-fluoro-6-iodobenzoic acid: To a flask containing 2-bromo-3-fluorobenzoic acid (2.5 g, 11.4 mmol), palladium (II) acetate (128 mg, 5 mol %), iodine (2.9 g, 11.4 mmol), and diacetoxy iodobenzene (3.68 g, 11.4 mmol) were added, followed by N,N-dimethylformamide (55 mL). The resulting suspension was stirred for 24 hours at 100° C. After cooling, the reaction mixture was concentrated under reduced pressure to near dryness. The remaining residue was poured into 0.1 M HCl, then extracted four times with diethyl ether (100 mL portions). The combined organics were washed with 1 M Na$_2$S$_2$O$_3$ solution until the purple color of the iodine was dissipated, then washed with saturated NaCl, dried over MgSO$_4$, filtered, and concentrated to provide 2-bromo-3-fluoro-6-iodobenzoic acid as a beige solid (1.2 g, 30% yield). The crude solid was used without further purification.

Step B: Preparation of methyl 2-bromo-3-fluoro-6-iodobenzoate: 2-Bromo-3-fluoro-6-iodo-benzoic acid (0.81 g, 2.3 mmol) was dissolved in N,N-dimethylformamide (5 mL), then treated with potassium carbonate (970 mg, 7.0 mmol) and iodomethane (0.44 mL, 7.0 mmol). The mixture was stirred at ambient temperature for 60 hours. The suspension was dissolved in diethyl ether and water and separated. The organic layer was washed five times with water, then with saturated NaCl, dried over Na$_2$SO$_4$ and concentrated in vacuo to a white solid (0.76 g, 90% yield). LCMS ESI (+) m/z 359/361 (M+H).

Step C: Preparation of methyl 6-(acetylthio)-2-bromo-3-fluorobenzoate: Methyl 2-bromo-3-fluoro-6-iodobenzoate (1.26 g, 3.5 mmol) and 4,5-bis(diphenylphosphino)-9,9-dimethylxanthene (Xantphos, 243 mg, 0.42 mmol) were suspended in 2:1 toluene/acetone (17 mL). The mixture was sparged with argon, then treated with tris(dibenzylideneacetone)dipalladium(0) (Pd$_2$dba$_3$, 192 mg, 0.21 mmol) and potassium ethanethioate (500 mg, 4.4 mmol). The reaction mixture was sealed in a tube, stirred vigorously, and heated to 70° C. for 2 hours. The reaction was cooled, diluted with methylene chloride, treated with celite, then filtered through a pad of celite. The filtrate was concentrated in vacuo to orange oil. The crude mixture was chromatographed on SiO$_2$ eluting with a gradient of hexanes/ethyl acetate. Methyl 6-(acetylthio)-2-bromo-3-fluorobenzoate was obtained as a yellow oil (0.71 g, quant.). $^1$H NMR (400 MHz, CDCl$_3$): δ 7.44-7.41 (m, 1H), 7.25-7.21 (m, 1H), 3.95 (s, 3H), 2.41 (s, 3H).

Step D: Preparation of methyl 2-bromo-3-fluoro-6-(methylthio)benzoate: Methyl 6-(acetylthio)-2-bromo-3-fluorobenzoate (1.21 g, 3.9 mmol) was dissolved in methanol (12 mL) and degassed with bubbling argon for 5 minutes. The solution was treated with cesium carbonate (1.66 g, 5.1 mmol), then the solution was stirred at ambient temperature for 55 minutes. The reaction mixture was treated with iodomethane (1.22 mL, 20 mmol) and stirred overnight under argon. The reaction mixture was concentrated in vacuo and redissolved in diethyl ether and water. The layers were separated and the aqueous was washed with diethyl ether. The combined organic layers were washed with saturated NaHCO$_3$, saturated NaCl, dried over Na$_2$SO$_4$, and concentrated in vacuo. Methyl 2-bromo-3-fluoro-6-(methylthio)benzoate was obtained as a yellow oil (0.97 g, 88%). $^1$H NMR (400 MHz, CDCl$_3$): δ 7.38-7.35 (m, 1H), 7.16-7.11 (m, 1H), 3.98 (s, 3H), 2.45 (s, 3H).

Step E: Preparation of methyl 2-bromo-3-fluoro-6-(methylsulfonyl)benzoate: A solution of methyl 2-bromo-3-fluoro-6-(methylthio)benzoate (3.57 g, 12.8 mmol) in methanol (63 mL) was added dropwise to a solution of Oxone® (23.6 g, 38.4 mmol) in water (63 mL). The reaction mixture was stirred at ambient temperature for 20 hours, and then heated at 60° C. for 6 hours. The reaction mixture was concentrated in vacuo. The residue was diluted with water and ethyl acetate and then separated. The aqueous layer was washed with a second portion of ethyl acetate and then the combined organics were washed with saturated NaHCO$_3$, saturated NaCl, dried over Na$_2$SO$_4$ and concentrated in vacuo to a yellowish solid (3.7 g). The crude material was chromatographed on SiO$_2$ eluting with ethyl acetate/hexanes. Methyl 2-bromo-3-fluoro-6-(methylsulfonyl)benzoate was isolated as a white solid (3.07 g, 77%). $^1$H NMR (400 MHz, CDCl$_3$): δ 8.04-8.01 (m, 1H), 7.37-7.33 (m, 1H), 4.02 (s, 3H), 3.17 (s, 3H).

Step F: Preparation of methyl 2-bromo-3-(3-chloro-5-fluoro-phenoxy)-6-methylsulfonyl-benzoate: Methyl 2-bromo-3-fluoro-6-methylsulfonyl-benzoate (400 mg, 1.29 mmol) was combined with 3-chloro-5-fluoro-phenol (245 mg, 1.67 mmol) and N,N-dimethylformamide (3.0 mL). The solution was treated in a single portion with sodium bicarbonate (216 mg, 2.57 mmol) and the reaction mixture was heated to 90° C. for 24 hours. The reaction mixture was cooled to room temperature, then purified directly on reverse phase silica gel (40+M, 14 CV, 20-100% acetonitrile/water) affording methyl 2-bromo-3-(3-chloro-5-fluoro-phenoxy)-6-methylsulfonyl-benzoate (510 mg, 1.17 mmol, 91% yield). LCMS ESI (+) m/z 435/437/439.

Step G: Preparation of 4-bromo-5-(3-chloro-5-fluoro-phenoxy)-1,1-dioxo-benzothiophen-3-one: Sodium hydride (60% in mineral oil, 140 mg, 3.5 mmol) was washed three times with hexane, then resuspended in tetrahydrofuran (3.0 mL). The suspension was cooled to 0° C. and treated dropwise with a solution of methyl 2-bromo-3-(3-chloro-5-fluoro-phenoxy)-6-methylsulfonyl-benzoate (510 mg, 1.17 mmol) dissolved in tetrahydrofuran (7.0 mL). After the addition, the reaction mixture was warmed to ambient temperature and stirred for 1 hour. The reaction was quenched with saturated NH$_4$Cl and concentrated in vacuo. Ethyl acetate and some water were added, the solids were resolubilized, then the pH of the aqueous was adjusted to 3-4 with 10% KHSO$_4$. After separation, the aqueous was washed twice with ethyl acetate. The combined organics were washed twice with water, saturated NaCl, dried over Na$_2$SO$_4$ and concentrated in vacuo to give 4-bromo-5-(3-chloro-5-fluoro-phenoxy)-1,1-dioxo-benzothiophen-3-one (333 mg, 0.82 mmol, 70% yield). LCMS ESI (−) m/z 403/405/407.

Step H: Preparation of (3R)-4-bromo-5-(3-chloro-5-fluoro-phenoxy)-1,1-dioxo-2,3-dihydrobenzothiophen-3-ol: An ice cold solution of N-[(1R,2R)-1,2-Diphenyl-2-(2-(4-methylbenzyloxy)ethylamino)-ethyl]-4-methylbenzene sulfonamide(chloro)ruthenium(II) ((R,R)-Ts-DENEB™, 0.8 mg, 0.001 mmol) in dichloromethane (0.3 mL) was added by syringe to an ice cold solution of 4-bromo-5-(3-chloro-5-fluoro-phenoxy)-1,1-dioxo-benzothiophen-3-one (25 mg, 0.06 mmol), triethylamine (17 µL, 0.12 mmol) and formic acid (7 µL, 0.18 mmol) in dichloromethane (0.3 mL) under nitrogen. The reaction vial was then placed in a 4° C. refrigerator overnight. The reaction mixture was warmed to room temperature, then purified directly on silica gel (10 g SNAP, 14 CV, 5-50% ethyl acetate/hexane) affording (3R)-4-bromo-5-(3-chloro-5-fluoro-phenoxy)-1,1-dioxo-2,3-dihydrobenzothiophen-3-ol (21 mg, 0.05 mmol, 84% yield). The ee was determined to be 80% by $^{19}$F NMR analysis of the corresponding Mosher ester. LCMS ESI (−) m/z 451/453/455 (M−H).

Step I: Preparation of (3R)-5-(3-chloro-5-fluoro-phenoxy)-3-hydroxy-1,1-dioxo-2,3-dihydrobenzothiophene-4-carbonitrile (Compound 112): Copper (I) cyanide (31 mg, 0.34 mmol) was added to (3R)-4-bromo-5-(3-chloro-5-fluoro-phenoxy)-1,1-dioxo-2,3-dihydrobenzothiophen-3-ol (100 mg, 0.25 mmol) in a microwave vial equipped with a stir bar. 1-Methyl-2-pyrrolidone (1.0 mL) was added followed by flushing with nitrogen and sealing the vial with a teflon lined crimp cap. The reaction mixture was warmed to 160° C. for 75 minutes under microwave irradiation. The reaction mixture was cooled to room temperature, then purified directly on reverse phase silica gel (25+M, 14 CV, 20-100% acetonitrile/water) affording Compound 112 (69 mg, 0.20 mmol, 80% yield). Dichloromethane (0.2 mL) was added to the obtained oil and after standing for 10 minutes, a white solid formed. After drying, the ee was determined to be 80% by $^{19}$F NMR analysis of the corresponding Mosher ester. LCMS ESI (−) m/z 352/354 (M−H); $^1$H NMR (CDCl$_3$, 400 MHz) δ 7.89 (d, 1H), 7.13 (d, 1H), 7.09-7.06 (m, 1H), 6.96-6.94 (m, 1H), 6.80 (dt, 1H), 5.78-5.74 (m, 1H), 3.91 (dd, 1H), 3.65 (dd, 1H), 3.41 (d, 1H).

Example 113

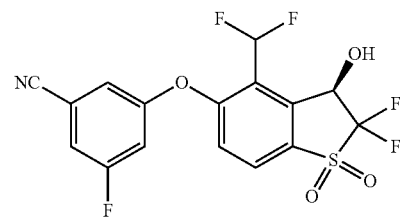 [SMILES: N#Cc1cc(F)cc(Oc2ccc3c(c2C(F)F)[C@@H](O)C(F)(F)S3(=O)=O)c1]

(R)-3-((4-(difluoromethyl)-2,2-difluoro-3-hydroxy-1,1-dioxido-2,3-dihydrobenzo[b]thiophen-5-yl)oxy)-5-fluorobenzonitrile (Compound 113)

Step A: Preparation of 2-bromo-3-(difluoromethyl)-1,4-difluorobenzene: A solution of 2-bromo-3,6-difluorobenzaldehyde (40.0 g, 181 mmol) dissolved in dichloromethane (800 mL) was cooled to 0° C., then treated with (diethylamino)sulfur trifluoride (70.0 g, 454 mmol). After the addition, the reaction mixture was warmed to ambient temperature and stirred at this temperature for 4 hours. Saturated aqueous sodium bicarbonate solution was added slowly until the pH was 8-9. The organic layer was separated, dried over sodium sulfate, filtered and concentrated under reduced pressure to give 2-bromo-3-(difluoromethyl)-1,4-difluorobenzene (44.0 g, quant.) as solid which was used immediately in the next step without purification. $^1$H NMR (400 MHz, CDCl$_3$): δ 7.28-7.22 (m, 1H), 7.17-7.10 (m, 1H), 7.04 (t, 1H).

Step B: Preparation of 2-(difluoromethyl)-3,6-difluorobenzonitrile: A suspension of 2-bromo-3-(difluoromethyl)-1,4-difluorobenzene (44.0 g, 181 mmol) and copper (I) cyanide (21.1 g, 235 mmol) in 1-methyl-2-pyrrolidinone (400 mL) was heated to 180° C. for 2 hours. After cooling to ambient temperature, the reaction mixture was poured into water and extracted with diethyl ether. The organic layer was washed with brine, dried over sodium sulfate, filtered and then concentrated under reduced pressure. The crude product was purified by flash chromatography on silica gel eluting with hexane/ethyl acetate. 2-(Difluoromethyl)-3,6-difluorobenzonitrile was isolated as a solid (23 g, 67%). $^1$H NMR (400 MHz, CDCl$_3$): δ 7.48-7.35 (m, 2H), 6.98 (t, 1H).

Step C: Preparation of 2-(difluoromethyl)-3-fluoro-6-(methylthio)benzonitrile: A solution of 2-(difluoromethyl)-3,6-difluorobenzonitrile (31.3 g, 65.5 mmol) in acetonitrile (500 mL) was cooled to −30° C., then treated with sodium methanethiolate (12.8 g, 174 mmol). After addition of the solid, the reaction mixture was stirred for 7 hours while maintaining the temperature between −30° C. and −40° C. A mixture of water (200 mL) and methyl t-butyl ether (500 mL) were added and the reaction mixture was warmed to ambient temperature. The organic layer was separated, washed with brine, dried over sodium sulfate, filtered and concentrated under reduced pressure to give 2-(difluoromethyl)-3-fluoro-6-methylsulfanyl-benzonitrile as yellow solid (36.3 g, 150 mmol, 91%). $^1$H NMR (400 MHz, CDCl$_3$): δ 7.47-7.44 (m, 1H), 7.36-7.32 (m, 1H), 6.99 (t, 1H), 2.58 (s, 3H).

Step D: Preparation of 2-(difluoromethyl)-3-fluoro-6-(methylsulfonyl)benzonitrile: A slurry of 2-(difluoromethyl)-3-fluoro-6-methylsulfanyl-benzonitrile (36.3 g, 167 mmol) in acetonitrile (350 mL) and water (175 mL) was treated with Oxone® (257 g, 418 mmol), then the mixture was heated at 56° C. for 4 hours. After cooling to ambient temperature, the remaining solids were removed by filtration and washed with dichloromethane (300 mL). The filtrate was concentrated in vacuo to remove volatile solvents. The resulting aqueous solution was extracted with dichloromethane (400 mL). The organic layer was dried over sodium sulfate, filtered and concentrated under reduced pressure. The resulting solid was suspended in 4:1 hexanes/methyl t-butyl ether (200 mL) and stirred for 10 minutes at ambient temperature. The undissolved solid was collected by filtration and air-dried to give 2-(difluoromethyl)-3-fluoro-6-(methylsulfonyl)benzonitrile (29.9 g, 71%). $^1$H NMR (400 MHz, CDCl$_3$): δ 8.41-8.37 (m, 1H), 7.66-7.61 (m, 1H), 7.11 (t, 1H), 3.34 (s, 3H).

Step E: Preparation of 3-(3-cyano-5-fluorophenoxy)-2-(difluoromethyl)-6-(methylsulfonyl)benzonitrile: A suspension of 2-(difluoromethyl)-3-fluoro-6-(methylsulfonyl)benzonitrile (9.52 g, 38.2 mmol), 3-fluoro-5-hydroxybenzonitrile (5.23 g, 38.2 mmol), and cesium carbonate (7.77 g, 40.1 mmol) in N,N-dimethylformamide (76 mL) was heated to 45° C. for 3 hours. Additional cesium carbonate (0.46 g, 1.4 mmol) was added and the reaction mixture was heated at 45° C. for three hours, then stirred at ambient temperature for 54 hours. The reaction mixture was vigorously stirred while water (800 mL) was added. The resulting suspension was stirred for 30 minutes, then the solids were collected by filtration, washed with water (1.2 L), and dried under high vacuum. 3-(3-Cyano-5-fluorophenoxy)-2-(difluoromethyl)-6-(methylsulfonyl)benzonitrile was recovered as a white solid (13.3 g, 96%). LCMS ESI (+) m/z 384 (M+NH$_4$). $^1$H NMR (400 MHz, DMSO-d$_6$): δ 8.22 (d, 1H), 7.86-7.82 (m, 1H), 7.72-7.62 (m, 3H), 7.49 (t, 1H), 3.44 (s, 3H).

Step F: Preparation of 3-((4-(difluoromethyl)-1,1-dioxido-3-oxo-2,3-dihydrobenzo[b]thiophen-5-yl)oxy)-5-fluorobenzonitrile: A solution of 3-(3-cyano-5-fluorophenoxy)-2-(difluoromethyl)-6-(methylsulfonyl)benzonitrile (13.3 g, 36 mmol) was dissolved in tetrahydrofuran (380 mL) and treated with sodium hydride (60% in mineral oil, 2.26 g, 56 mmol) in two equal portions at five minute intervals. The resulting suspension was stirred at ambient temperature for 60 minutes. The reaction mixture was quenched by addition of a mixture of 4:1 methanol/10% aqueous HCl (200 mL) and the resulting suspension was stirred for 1 hour. The mixture was concentrated to remove volatile solvents, then the remaining slurry was diluted with additional water (800 mL) and stirred for an additional 30 minutes. The solids were recovered by filtration and washed with additional water and the resulting beige solid was dried under high vacuum in the presence of solid NaOH. 3-((4-(Difluoromethyl)-1,1-dioxido-3-oxo-2,3-dihydrobenzo[b]thiophen-5-yl)oxy)-5-fluorobenzonitrile was obtained as a beige solid (13.3 g, quant.) and was used without further purification. LCMS ESI (−) m/z 366 (M−H). $^1$H NMR (400 MHz, DMSO-d$_6$): δ 8.35 (d, 1H), 7.79 (d, 1H), 7.76 (t, 1H), 7.76-7.72 (m, 1H), 7.56-7.50 (m, 2H), 4.72 (s, 2H).

Step G: Preparation of 3-((4-(difluoromethyl)-2,2-difluoro-1,1-dioxido-3-oxo-2,3-dihydrobenzo[b]thiophen-5-yl)oxy)-5-fluorobenzonitrile: A solution of 3-((4-(difluoromethyl)-1,1-dioxido-3-oxo-2,3-dihydrobenzo[b]thiophen-5-yl)oxy)-5-fluorobenzonitrile (1.40 g, 3.82 mmol) dissolved in acetonitrile (38 mL) was treated at ambient temperature with sodium carbonate (890 mg, 8.4 mmol) followed by Selectfluor® (2.98 g, 8.4 mmol). The reaction mixture was stirred at ambient temperature for 90 minutes. The reaction mixture was concentrated in vacuo to remove volatile solvents, then the residue was diluted with water (100 mL) and extracted three times with ethyl acetate (50 mL portions). The combined organic layers were washed with saturated NaCl, dried over MgSO$_4$, filtered and concentrated in vacuo. 3-((4-(Difluoromethyl)-2,2-difluoro-1,1-dioxido-3-oxo-2,3-dihydrobenzo[b]thiophen-5-yl)oxy)-5-fluorobenzonitrile was obtained as a solid (1.48 g, quant.). $^1$H NMR (400 MHz, DMSO-d$_6$, sample exists as hydrate): δ 8.81 (s, 2H), 8.29 (d, 1H), 7.80-7.76 (m, 1H), 7.74 (t, 1H), 7.57-7.50 (m, 3H).

Step H: Preparation of 3-((4-(difluoromethyl)-2,2-difluoro-3-hydroxy-1,1-dioxido-2,3-dihydrobenzo[b]thiophen-5-yl)oxy)-5-fluorobenzonitrile: A solution of 3-((4-(difluoromethyl)-2,2-difluoro-1,1-dioxido-3-oxo-2,3-dihydrobenzo[b]thiophen-5-yl)oxy)-5-fluorobenzonitrile (1.48 g, 3.67 mmol) in methanol (37 mL) was cooled to 0° C., then treated with sodium borohydride (139 mg, 3.7 mmol) and stirred for 1 hour. The reaction was quenched by addition of water (0.5 mL) and saturated NH$_4$Cl (0.25 mL). The reaction mixture was concentrated in vacuo to remove volatile solvents, then diluted with 0.5 M NaOH (10 mL). The aqueous was extracted three times with ethyl acetate and the combined organic layers were washed with saturated NaCl, dried over MgSO$_4$, filtered and concentrated in vacuo. The crude product was chromatographed on SiO$_2$ eluting with a gradient of ethyl acetate/hexanes. 3-((4-(Difluoromethyl)-2,2-difluoro-3-hydroxy-1,1-dioxido-2,3-dihydrobenzo[b]thiophen-5-yl)oxy)-5-fluorobenzonitrile was isolated as a white solid (1.24 g, 83%).

Step I: Preparation of (R)-3-((4-(difluoromethyl)-2,2-difluoro-3-hydroxy-1,1-dioxido-2,3-dihydrobenzo[b]thiophen-5-yl)oxy)-5-fluorobenzonitrile (Compound 113): 3-((4-(Difluoromethyl)-2,2-difluoro-3-hydroxy-1,1-dioxido-2,3-dihydrobenzo[b]thiophen-5-yl)oxy)-5-fluorobenzonitrile was resolved using preparative SFC chromatography under the following conditions: ChiralPak AS(-H) (2×15 cm) column, 20% ethanol with carbon dioxide at 100 bar, 60 mL/min flow rate, injection volume was 0.5 mL of a 20 mg/mL solution in ethanol, peak detection at 220 nm. Compound 113 was recovered as the first peak (1.5 minutes) from the column. LCMS ESI (−) m/z 404 (M−H). $^1$H NMR (400 MHz, CDCl$_3$): δ 7.98 (d, 1H), 7.33-7.30 (m, 1H), 7.23 (t, 1H), 7.22-7.18 (m, 2H), 7.10-7.06 (m, 1H), 5.69-5.65 (m, 1H), 3.23 (d, 1H).

Example 114

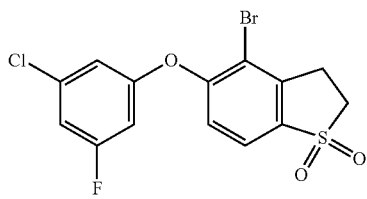 [SMILES: O=S1(=O)CCc2c1ccc(Oc1cc(F)cc(Cl)c1)c2Br]

4-Bromo-5-(3-chloro-5-fluorophenoxy)-2,3-dihydrobenzo[b]thiophene 1,1-dioxide (Compound 114)

Step A: Preparation of 2-bromo-3-fluoro-6-iodobenzoic acid: 2-Bromo-3-fluoro-benzoic acid (7.5 g, 34.3 mmol) was combined with palladium (II) acetate (384 mg, 1.7 mmol), iodine (8.7 g, 34.3 mmol), diacetoxy iodobenzene (11.0 g, 34.3 mmol) and N,N-dimethylformamide (165 mL). The resulting suspension was heated to 120° C. for 28 hours, then stirred at ambient temperature for 40 hours. The reaction mixture was concentrated to remove most of the N,N-dimethylformamide, then the residue was poured into 0.1 M HCl (resultant pH<3) and solid Na$_2$S$_2$O$_3$ was added to dissipate some of the iodine color. The aqueous layer was washed three times with Et$_2$O (100 mL each), then the combined organic layers were washed with 1M Na$_2$S$_2$O$_3$ to remove the remaining purple color. The organic layer was washed with saturated NaCl, dried over Na$_2$SO$_4$ and concentrated in vacuo. The crude product solidified after standing under vacuum (8 g, 67%).

Step B: Preparation of 2-bromo-3-fluoro-6-iodobenzamide: 2-Bromo-3-fluoro-6-iodobenzoic acid (2.33 g, 6.76 mmol) was dissolved in tetrahydrofuran (20 mL) and cooled to 0° C. The solution was treated with N,N-dimethylformamide (10 drops) followed by dropwise addition of thionyl chloride (1.0 mL, 10.1 mmol), then stirred for 10 minutes. The reaction mixture was warmed to ambient temperature, stirred for two hours, cooled to 0° C. and treated with concentrated ammonium hydroxide (5 mL). The resulting mixture was allowed to warm to ambient temperature with the bath and stirred overnight. The mixture was concentrated in vacuo, then redissolved in saturated NaHCO$_3$ and ethyl acetate. The layers were separated and the organic phase was washed with saturated NaHCO$_3$, saturated NaCl, dried over Na$_2$SO$_4$ and concentrated in vacuo to give a white solid (2.20 g, 94%).

Step C: Preparation of 2-bromo-3-fluoro-6-iodobenzonitrile: 2-Bromo-3-fluoro-6-iodobenzamide (10 g, 29 mmol) was suspended in phosphorus oxychloride (41 mL), treated with triethylamine (12.2 mL, 87.2 mmol) then the mixture was heated to 75° C. for 3 hours. The reaction mixture was cooled to ambient temperature with the bath and stirred overnight. The mixture was concentrated in vacuo to remove excess POCl$_3$, then the semi-dry residue was treated with a combination of ice and water. The mixture was stirred until the ice melted and the beige solid was collected by filtration, washed with water and air-dried (8.04 g, quant.).

Step D: Preparation of 2-bromo-3-fluoro-6-iodobenzaldehyde: A sample of 2-bromo-3-fluoro-6-iodobenzonitrile (100 mg, 0.307 mmol) was dissolved in CH$_2$Cl$_2$ (2 mL) and cooled to 0° C. The resulting solution was treated with diisobutylaluminum hydride (~1.0 M in heptanes, 370 μL, 0.37 mmol). The reaction was allowed to warm to room temperature after the addition for one hour, then 10% aqueous HCl (1 mL) was added to the reaction mixture and it was vigorously stirred for 1 hour. A solution of 20% sodium potassium tartrate (1 mL) was added and the reaction was stirred vigorously for an additional hour. The resulting solution was made basic by the addition of 10% NaOH solution. The reaction mixture was extracted with 3×20 mL CH$_2$Cl$_2$. The combined organics were rinsed with 20 mL of brine, dried with MgSO$_4$, filtered, and concentrated to dryness. The product was used without further purification.

Step E: Preparation of 2-bromo-1-fluoro-4-iodo-3-vinylbenzene: A sample of bromo(methyl)triphenylphosphorane (130 mg, 0.37 mmol) in anhydrous tetrahydrofuran (3.7 mL) was cooled to −40° C. and treated with 2.5 M n-butyl lithium in hexanes (140 μL, 0.34 mmol) by dropwise addition. The resulting solution was allowed to warm to −10° C. and stirred for 30 minutes at that temperature. The reaction mixture was cooled to −30° C. and treated with a solution of 2-bromo-3-fluoro-6-iodobenzaldehyde (75 mg, 0.23 mmol) in anhydrous tetrahydrofuran (3.7 mL) by dropwise addition. The reaction mixture was allowed to warm to room temperature and stirred overnight. The reaction mixture was poured into 30 mL of saturated aqueous NH$_4$Cl and extracted with 3×20 mL Et$_2$O. The combined organics were rinsed with 20 mL of brine, dried with MgSO$_4$, filtered, and concentrated to dryness. The crude residue was purified on silica using 0-40% CH$_2$Cl$_2$/hexanes to afford 2-bromo-1-fluoro-4-iodo-3-vinylbenzene (54 mg, 72% yield).

Step F: Preparation of S-(3-bromo-4-fluoro-2-vinylphenyl) ethanethioate: A reaction vial was charged with 2-bromo-1-fluoro-4-iodo-3-vinylbenzene (54 mg, 0.17 mmol) and (9,9-dimethyl-9H-xanthene-4,5-diyl)bis(diphenylphosphine) (11.5 mg, 0.02 mmol). The mixture was suspended in 1 mL of a 2:1 mixture of toluene/acetone and then sparged by bubbling nitrogen through the mixture for 3 minutes. Under continuous stream of nitrogen, tris(dibenzylideneacetone)dipalladium(0) (9.0 mg, 0.009 mmol) and potassium ethanethioate (23.6 mg, 0.21 mmol) were added. The vessel was sealed and heated to 70° C. After 2 hours of heating, the reaction mixture was filtered. The filtered residue was rinsed with excess CH$_2$Cl$_2$ and the combined filtrates were concentrated. The crude residue was purified directly on silica using 10-50% CH$_2$Cl$_2$/hexanes as eluent.

S-(3-Bromo-4-fluoro-2-vinylphenyl) ethanethioate was isolated as a yellow solid (45.4 mg, 98%). LCMS ESI (−) (M−H) m/z 273/275.

Step G: Preparation of 3-bromo-4-fluoro-2-vinylbenzenethiol: To a round bottom flask containing S-(3-bromo-4-fluoro-2-vinyl-phenyl) ethanethioate (45 mg, 0.17 mmol) dissolved in 2 mL of degassed tetrahydrofuran (sparged with nitrogen for 5 minutes) was added ammonium hydroxide (ACS reagent, 0.06 mL, 1.65 mmol). The resulting reaction mixture was stirred for 40 minutes under nitrogen atmosphere. The reaction mixture was poured into 20 mL of a 1:1 mixture of brine and 1 M HCl and extracted with 3×15 mL of EtOAc. The combined organics were dried with $MgSO_4$, filtered, and concentrated to dryness. The product was used without further purification. LCMS ESI (−) (M−H) m/z 231/233.

Step H: Preparation of 4-bromo-5-fluoro-2,3-dihydrobenzo[b]thiophene 1-oxide: A solution of 3-bromo-4-fluoro-2-vinyl-benzenethiol (28 mg, 0.12 mmol) and azobisisobutyronitrile (4 mg, 0.02 mmol) in benzene (2 mL) was sparged with nitrogen for 5 minutes. The vessel was sealed and heated to 80° C. for 4 hours. The reaction mixture was concentrated to dryness and the product residue was dissolved in 2 mL of MeOH and 1 mL of water. Oxone® (18.7 mg, 0.06 mmol) was added and the resulting mixture was stirred for 2 hours at room temperature. The reaction mixture was concentrated to dryness and the residue purified directly on reverse phase by injection as a solution in N,N-dimethylformamide (Biotage Isolera One unit, C18 Flash 12+M column, 0-100% $CH_3CN$/water, 8.5 mg, 30%). LCMS ESI (+) (M+H) m/z 249/251.

Step I: Preparation of 4-bromo-5-fluoro-2,3-dihydrobenzo[b]thiophene 1,1-dioxide: A solution of 4-bromo-5-fluoro-2,3-dihydrobenzothiophene[b] 1-oxide (8.5 mg, 0.03 mmol) in dichloromethane (1 mL) was treated with 3-chloroperbenzoic acid (9.2 mg, 0.04 mmol) and stirred at 25° C. overnight. The reaction mixture was poured into 10 mL of 1 M NaOH and extracted with 3×20 mL EtOAc. The combined organics were rinsed with 20 mL of brine, dried with $MgSO_4$, filtered, and concentrated to dryness. The product was used without further purification. LCMS ESI (+) (M+H) m/z 265/267.

Step J: Preparation of 4-bromo-5-(3-chloro-5-fluorophenoxy)-2,3-dihydrobenzo[b]thiophene 1,1-dioxide (Compound 114): A solution of 4-bromo-5-fluoro-2,3-dihydrobenzothiophene[b] 1,1-dioxide (9.0 mg, 0.03 mmol) and 3-chloro-5-fluoro-phenol (6.0 mg, 0.04 mmol) in N,N-dimethylformamide (0.7 mL) was treated with potassium carbonate (5.6 mg, 0.04 mmol) and stirred at 90° C. for 4 hours. The reaction mixture was poured into 30 mL of water and extracted with 3×20 mL $Et_2O$. The combined organics were rinsed with 20 mL of brine, dried with $MgSO_4$, filtered, and concentrated to dryness. The residue was purified directly on reverse phase by injection as a solution in N,N-dimethylformamide (Biotage Isolera One unit, C18 Flash 12+M column, 20-90% $CH_3CN$/water) to afford Compound 114 as a white solid (7.4 mg, 56%). LCMS ESI (+) (M+H) m/z 391, 393, 395; $^1$H NMR (400 MHz, $CDCl_3$): δ 7.70 (d, 1H), 7.10 (d, 1H), 6.93 (ddd, 1H), 6.78-6.76 (m, 1H), 6.63 (dt, 1H), 3.62-3.58 (m, 2H), 3.42-3.37 (m, 2H).

Example 115

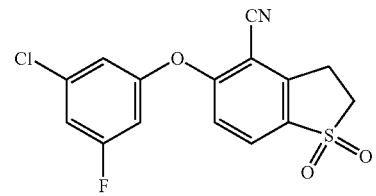 [SMILES: N#Cc1c(Oc2cc(F)cc(Cl)c2)ccc2c1CCS2(=O)=O]

5-(3-Chloro-5-fluorophenoxy)-2,3-dihydrobenzo[b]thiophene-4-carbonitrile 1,1-dioxide (Compound 115): A solution of zinc cyanide (2.3 mg, 0.02 mmol) and 4-bromo-5-(3-chloro-5-fluoro-phenoxy)-2,3-dihydrobenzo[b]thiophene 1,1-dioxide (6.5 mg, 0.02 mmol) in N,N-dimethylformamide (0.2 mL) was treated with 1,1'-bis(diphenylphosphino)ferrocene-palladium(II)dichloride dichloromethane complex (4.1 mg, 30 mol %) and heated at 170° C. by microwave irradiation for 45 minutes. The reaction mixture was purified directly by reverse phase chromatography by injection of the dimethylformamide reaction solution (Biotage Isolera One unit, C18 Flash 12+M column, 20-80% $CH_3CN$/water) to afford Compound 115 as a beige solid (2.8 mg, 50%). LCMS ESI (−) (M−H) m/z 336/338; $^1$H NMR (400 MHz, $CDCl_3$): δ 7.87 (d, 1H), 7.06 (dt, 1H), 7.03 (d, 1H), 6.94-6.92 (m, 1H), 6.78 (dt, 1H), 3.66-3.61 (m, 2H), 3.60-3.55 (m, 2H).

Example 116

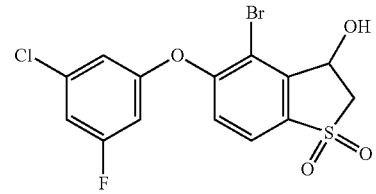 [SMILES: O=S1(=O)CC(O)c2c1ccc(Oc1cc(F)cc(Cl)c1)c2Br]

4-Bromo-5-(3-chloro-5-fluorophenoxy)-3-hydroxy-2,3-dihydrobenzo[b]thiophene 1,1-dioxide (Compound 116): The ketone starting material, 4-bromo-5-(3-chloro-5-fluorophenoxy)benzo[b]thiophen-3(2H)-one 1,1-dioxide, was prepared similarly according to Example 1, Steps A-G, substituting 3-chloro-5-fluorophenol for 3-fluoro-5-hydroxybenzonitrile. A solution of 4-bromo-5-(3-chloro-5-fluorophenoxy)-1,1-dioxo-benzo[b]thiophen-3-one (31 mg, 0.08 mmol) in methanol (1.5 mL) and dichloromethane (0.75 mL) at 0° C. was treated with sodium borohydride (1.5 mg, 0.04 mmol) and stirred at 0° C. for 45 minutes. The reaction mixture was quenched by the addition of 1 mL of water. Volatiles were removed by concentration under reduced pressure. The reaction mixture was poured into 10 mL of water and extracted with 3×15 mL EtOAc. The combined organics were rinsed with 10 mL of brine, dried with $MgSO_4$, filtered, and concentrated to dryness. Purification was achieved by chromatography on silica using 20-70% EtOAc/hexane to give Compound 116 as a clear thin film (22 mg, 71%). LCMS ESI (+) (M+$NH_4$) m/z 424, 426, 428; $^1$H NMR (400 MHz, $CDCl_3$): δ 7.72 (d, 1H), 7.19 (d, 1H), 6.98-6.94 (ddd, 1H), 6.82-6.80 (m, 1H), 6.67 (dt, 1H), 5.60 (td, 1H), 3.80 (dd, 1H), 3.68 (dd, 1H), 2.89 (d, 1H).

Example 117

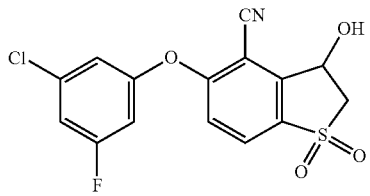 [SMILES: N#Cc1c(Oc2cc(F)cc(Cl)c2)ccc2c1C(O)CS2(=O)=O]

5-(3-chloro-5-fluorophenoxy)-3-hydroxy-2,3-dihydrobenzo[b]thiophene-4-carbonitrile 1,1-dioxide (Compound 117): A solution of 4-bromo-5-(3-chloro-5-fluoro-phenoxy)-1,1-dioxo-2,3-dihydrobenzothiophen-3-ol (17.3 mg, 0.04 mmol) in 1-methyl-2-pyrrolidone (0.25 mL) was treated with copper (I) cyanide (4.6 mg, 0.05 mmol) and heated at 160° C. by microwave irradiation for 30 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 20-60% EtOAc/hexane to afford Compound 117 as a white solid (9.7 mg, 65%). LCMS ESI (−) (M−H) m/z 352/354; $^1$H NMR (400 MHz, CDCl$_3$): δ 7.89 (d, 1H), 7.13 (d, 1H), 7.07 (ddd, 1H), 6.97-6.94 (m, 1H), 6.80 (dt, 1H), 5.79-5.72 (m, 1H), 3.91 (dd, 1H), 3.64 (dd, 1H), 3.57 (br d, 1H).

Example 118

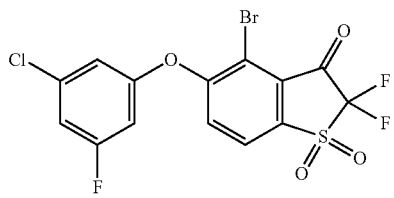 [SMILES: O=C1c2c(ccc(Oc3cc(F)cc(Cl)c3)c2Br)S(=O)(=O)C1(F)F]

4-Bromo-5-(3-chloro-5-fluorobenzo[b]thiophen-3(2H)-one 1,1-dioxide (Compound 118): Preparation of 4-bromo-5-(3-chloro-5-fluorophenoxy)-3-hydroxy-2,3-dihydrobenzo[b]thiophene 1,1-dioxide: 4-Bromo-5-(3-chloro-5-fluorophenoxy)-2,2-difluorobenzo[b]thiophen-3(2H)-one 1,1-dioxide (Compound 118) was prepared similarly according to Example 111, Steps A-H, substituting 3-chloro-5-fluorophenol for 3-fluoro-5-hydroxy-benzonitrile. Purification was achieved by chromatography on silica using 10-30% EtOAc/hexane to afford Compound 118 as a white solid (26.6 mg, 31%). $^1$H NMR (400 MHz, CDCl$_3$): δ 7.89 (d, 1H), 7.50 (d, 1H), 7.06 (ddd, 1H), 6.89-6.86 (m, 1H), 6.73 (dt, 1H).

Example 119

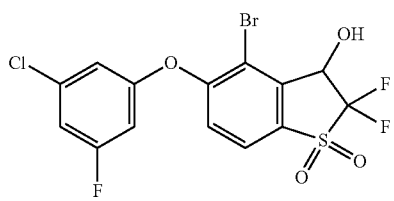 [SMILES: O=S1(=O)c2ccc(Oc3cc(F)cc(Cl)c3)c(Br)c2C(O)C1(F)F]

4-Bromo-5-(3-chloro-5-fluorophenoxy)-2,2-difluoro-3-hydroxy-2,3-dihydrobenzo[b]thiophene 1,1-dioxide (Compound 119): A solution of 4-bromo-5-(3-chloro-5-fluorophenoxy)-2,2-difluoro-1,1-dioxo-benzo[b]thiophen-3-one (18 mg, 0.04 mmol) in methanol (2.0 mL) at 0° C. was treated with sodium borohydride (1.5 mg, 0.04 mmol) and stirred at 0° C. for 30 minutes. The reaction mixture was quenched by the addition of 0.5 mL of water. Volatiles were removed by concentration under reduced pressure. The mixture was poured into 10 mL of water and extracted with 3×20 mL EtOAc. The combined organics were rinsed with 10 mL of brine, dried with MgSO$_4$, filtered, and concentrated to dryness. Purification was achieved by chromatography on silica using 10-30% EtOAc/hexane to afford Compound 119 as a white solid (13 mg, 72%). LCMS ESI (+) (M−OH) m/z 425, 427, 429; $^1$H NMR (400 MHz, CDCl$_3$): δ 7.80 (d, 1H), 7.22 (d, 1H), 7.01 (dt, 1H), 6.87-6.85 (m, 1H), 6.71 (dt, 1H), 5.38 (d, 1H), 2.98 (br s, 1H).

Example 120

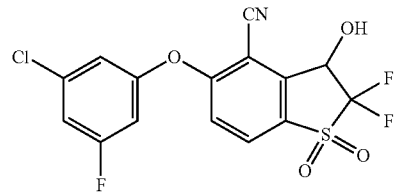 [SMILES: O=S1(=O)c2ccc(Oc3cc(F)cc(Cl)c3)c(Cl)c2C(O)C1(F)F]

5-(3-chloro-5-fluorophenoxy)-2,2-difluoro-3-hydroxy-2,3-dihydrobenzo[b]thiophene-4-carbonitrile 1,1-dioxide (Compound 120): A solution of 4-bromo-5-(3-chloro-5-fluoro-phenoxy)-2,2-difluoro-1,1-dioxo-3H-benzothiophen-3-ol (18.9 mg, 0.04 mmol) in 1-methyl-2-pyrrolidone (0.25 mL) was treated with copper (I) cyanide (4.6 mg, 0.05 mmol) and heated at 160° C. by microwave irradiation for 30 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 10-30% EtOAc/hexane to afford Compound 120 as a white solid (2.9 mg, 17%). LCMS ESI (−) (M−H) m/z 388, 390; $^1$H NMR (400 MHz, CDCl$_3$): δ 7.97 (d, 1H), 7.19 (d, 1H), 7.12 (ddd, 1H), 6.99-6.97 (m, 1H), 6.83 (dt, 1H), 5.58-5.51 (m, 1H), 3.51 (br d, 1H).

Example 121

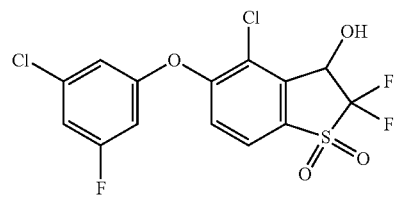

4-Chloro-5-(3-chloro-5-fluorophenoxy)-2,2-difluoro-3-hydroxy-2,3-dihydrobenzo[b]thiophene 1,1-dioxide (Compound 121): A solution of 4-bromo-5-(3-chloro-5-fluorophenoxy)-2,2-difluoro-1,1-dioxo-3H-benzo[b]thiophen-3-ol (5.8 mg, 0.013 mmol) in 1-methyl-2-pyrrolidone (0.5 mL)

was treated with copper(I) chloride (12.9 mg, 0.13 mmol) and stirred at 170° C. by microwave irradiation for 30 minutes. The reaction mixture was poured into 30 mL of water and extracted with 3×10 mL Et₂O. The combined organics were rinsed with 10 mL of brine, dried with MgSO₄, filtered, and concentrated to dryness. Purification was achieved by chromatography on silica using 0-10% EtOAc/CH₂Cl₂ to afford Compound 121 as a white solid (2.6 mg, 50%). LCMS ESI (−) (M−H) m/z 397, 399; ¹H NMR (400 MHz, CDCl₃): δ 7.76 (d, 1H), 7.26 (d, 1H), 7.01 (ddd, 1H), 6.87-6.85 (m, 1H), 6.71 (dt, 1H), 5.44 (dd, 1H), 2.94 (d, 1H).

Example 122

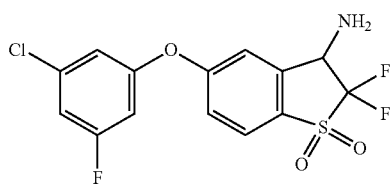

3-Amino-5-(3-chloro-5-fluorophenoxy)-2,2-difluoro-2,3-dihydrobenzo[b]thiophene 1,1-dioxide (Compound 122): A solution of 4-bromo-5-(3-chloro-5-fluoro-phenoxy)-2,2-difluoro-1,1-dioxo-benzo[b]thiophen-3-one (18.8 mg, 0.043 mmol) in toluene (0.45 mL) at 25° C. was treated with lithium bis(trimethylsilyl)amide (1.0 M in tetrahydrofuran, 50 µL, 0.05 mmol) by dropwise addition over a 10 minutes period. The reaction was left to stir for 25 minutes at room temperature and was then treated with borane dimethylsulfide complex (10 µL, 0.09 mmol). The reaction mixture stirred for 30 minutes. The reaction mixture was then cooled to 0° C. and carefully treated with 2 N NaOH (1 mL) and stirred for 90 minutes. The reaction mixture was poured into 5 mL of 2 N NaOH and extracted with 3×10 mL EtOAc. The combined organics were rinsed with 10 mL of brine, dried with MgSO₄, filtered, and concentrated to dryness. Purification was achieved by chromatography on silica using 5-20% EtOAc/hexane to afford Compound 122 as a thin film (2.2 mg, 14%). LCMS ESI (+) (M+H) m/z 364, 366; ¹H NMR (400 MHz, CDCl₃): δ 7.81 (d, 1H), 7.36 (dd, 1H), 7.20 (ddd, 1H), 6.99 (ddd, 1H), 6.89-6.86 (m, 1H), 6.71 (dt, 1H), 4.73-4.61 (m, 1H), 1.79 (br d, 2H).

Example 123

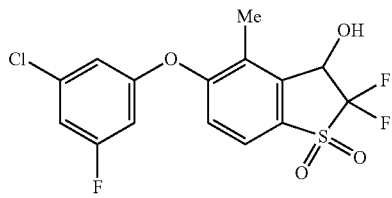

5-(3-Chloro-5-fluorophenoxy)-2,2-difluoro-3-hydroxy-4-methyl-2,3-dihydrobenzo[b]thiophene 1,1-dioxide (Compound 123): A solution of 4-bromo-5-(3-chloro-5-fluoro-phenoxy)-2,2-difluoro-1,1-dioxo-3H-benzothiophen-3-ol (10.6 mg, 0.024 mmol) and potassium trifluoro(methyl)boranuide (4.4 mg, 0.036 mmol) in 1,4-dioxane (0.5 mL) and water (50 µL) was sparged with nitrogen for 3 minutes. The reaction mixture was then treated sequentially with cesium carbonate (39 mg, 0.12 mmol) and dichloro[1;1'-bis(diphenylphosphino)ferrocene]palladium(II) dichloromethane (1.9 mg, 10 mol %) adduct under continuous nitrogen stream. The vessel was sealed and heated to 100° C. overnight. The reaction mixture was poured into 20 mL of water and extracted with 3×10 mL EtOAc. The combined organics were rinsed with 10 mL of brine, dried with MgSO₄, filtered, and concentrated to dryness. Purification was achieved by chromatography on silica using 10-15% EtOAc/hexane to afford Compound 123 as a white solid (2.5 mg, 28%). LCMS ESI (−) (M−H) m/z 377, 379; ¹H NMR (400 MHz, CDCl₃): δ 7.70 (d, 1H), 7.16 (d, 1H), 6.95 (ddd, 1H), 6.80-6.78 (m, 1H), 6.64 (dt, 1H), 5.30 (dd, 1H), 2.72 (dd, 1H), 2.43 (s, 3H).

Example 124

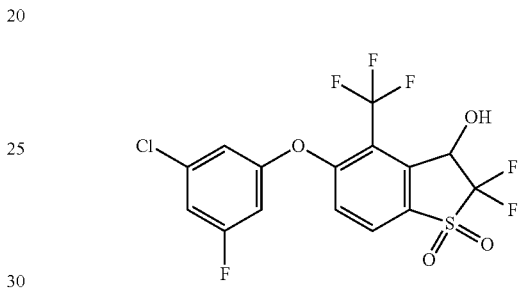

5-(3-Chloro-5-fluorophenoxy)-2,2-difluoro-3-hydroxy-4-(trifluoromethyl)-2,3-dihydrobenzo[b]thiophene 1,1-dioxide (Compound 124)

Step A: Preparation of 5-(3-chloro-5-fluorophenoxy)-2,2-difluoro-3-hydroxy-4-iodo-2,3-dihydrobenzo[b]thiophene 1,1-dioxide: A solution of 4-bromo-5-(3-chloro-5-fluoro-phenoxy)-2,2-difluoro-1,1-dioxo-3H-benzothiophen-3-ol (32.4 mg, 0.07 mmol) in 1-methyl-2-pyrrolidone (1.5 mL) was treated with copper (I) iodide (208 mg, 1.1 mmol) and heated at 180° C. by microwave irradiation for 1 hour. The reaction mixture was poured into 30 mL of water and extracted with 3×10 mL Et₂O. The combined organics were rinsed with 10 mL of brine, dried with MgSO₄, filtered, and concentrated to dryness. Purification was achieved by chromatography on silica using 5-20% EtOAc/hexanes to afford 5-(3-chloro-5-fluorophenoxy)-2,2-difluoro-3-hydroxy-4-iodo-2,3-dihydrobenzo[b]thiophene 1,1-dioxide as a beige solid (20 mg, 56%). LCMS ESI (−) (M−H) m/z 489, 491.

Step B: Preparation of 5-(3-chloro-5-fluorophenoxy)-2,2-difluoro-3-hydroxy-4-(trifluoromethyl)-2,3-dihydrobenzo[b]thiophene 1,1-dioxide: A solution of 5-(3-chloro-5-fluoro-phenoxy)-2,2-difluoro-4-iodo-1,1-dioxo-3H-benzothiophen-3-ol (20 mg, 0.04 mmol) in N,N-dimethylformamide (0.8 mL) was sparged with nitrogen for 3 minutes, treated with (1,10-phenanthroline)(trifluoromethyl)copper(I) (19 mg, 0.06 mmol) under a stream of nitrogen, sealed, and stirred overnight at 50° C. After 18 hours, the reaction mixture was diluted with Et₂O and filtered through a pad of celite. The celite pad was washed with Et₂O. The combined filtrate was washed sequentially with 1M aqueous HCl, saturated aqueous NaHCO₃ solution and brine, and dried over Na₂SO₄. After filtration and evaporation of the solvent, the crude mixture was purified by flash silica gel column chromatography using 10-20%

EtOAc/hexane to afford Compound 124 as a thin film (4.9 mg, 28%). LCMS ESI (−) (M−H) m/z 431, 433; ¹H NMR (400 MHz, CDCl₃): δ 8.00 (d, 1H), 7.29 (d, 1H), 7.04 (ddd, 1H), 6.91-6.89 (m, 1H), 6.74 (dt, 1H), 5.58 (d, 1H), 3.16 (br s, 1H).

Example 125

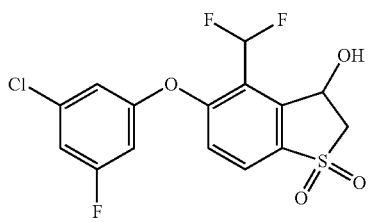 [SMILES: O=S1(=O)CC(O)c2c1ccc(Oc1cc(F)cc(Cl)c1)c2C(F)F]

5-(3-Chloro-5-fluorophenoxy)-4-(difluoromethyl)-3-hydroxy-2,3-dihydrobenzo[b]thiophene 1,1-dioxide (Compound 125): The ketone starting material, 5-(3-chloro-5-fluoro-phenoxy)-4-(difluoromethyl)-1,1-dioxo-benzothiophen-3-one, was prepared similarly according to Example 113, Steps A-F, substituting 3-chloro-5-fluorophenol for 3-fluoro-5-hydroxy-benzonitrile. A solution of 5-(3-chloro-5-fluoro-phenoxy)-4-(difluoromethyl)-1,1-dioxo-benzothiophen-3-one (14.7 mg, 0.04 mmol) in methanol (2.5 mL) at 0° C. was treated with sodium borohydride (1.5 mg, 0.04 mmol) and stirred at 0° C. for 1 hour. The reaction mixture was quenched by the addition of 0.5 mL of water and 0.25 mL of saturated aqueous NH₄Cl. Volatiles were removed by concentration under reduced pressure. The reaction mixture was poured into 10 mL of water and extracted with 3×15 mL EtOAc. The combined organics were rinsed with 10 mL of brine, dried with MgSO₄, filtered, and concentrated to dryness. Purification was achieved by chromatography on silica using 15-50% EtOAc/hexane to afford Compound 125 as a white solid (8.9 mg, 57%). LCMS ESI (−) (M−H) m/z 377, 379; ¹H NMR (400 MHz, CDCl₃): δ 7.85 (d, 1H), 7.22 (t, 1H), 7.14 (dt, 1H), 7.01 (ddd, 1H), 6.87-6.85 (m, 1H), 6.71 (dt, 1H), 5.90-5.85 (m, 1H), 3.77 (ddd, 1H), 3.67 (dd, 1H), 2.87 (t, 1H).

Example 126

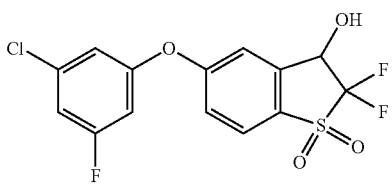 [SMILES: O=S1(=O)c2ccc(Oc3cc(F)cc(Cl)c3)cc2C(O)C1(F)F]

5-(3-Chloro-5-fluorophenoxy)-2,2-difluoro-3-hydroxy-2,3-dihydrobenzo[b]thiophene 1,1-dioxide (Compound 126): A solution of 4-bromo-5-(3-chloro-5-fluoro-phenoxy)-2,2-difluoro-1,1-dioxo-3H-benzothiophen-3-ol (12 mg, 0.03 mmol) in toluene (0.4 mL) at 25° C. was treated with borane methylsulfanylmethane (0.15 mL, 1.58 mmol) and stirred at 25° C. overnight. Lithium borohydride solution (~1.0 M in tetrahydrofuran, 270 µL, 0.27 mmol) was added. The resulting mixture was heated to 60° C. for 1 day. Volatiles were removed by concentration under reduced pressure. The remaining residue was solubilized with 30 mL 3 of 10% aqueous HCl and extracted with 3×15 mL EtOAc. The combined organics were rinsed with 10 mL of brine, dried with MgSO₄, filtered, and concentrated to dryness. Repeated purifications (3×) by chromatography on silica using 10-15% EtOAc/hexane afforded Compound 126 as a thin film (1.6 mg, 15%). LCMS ESI (−) (M−H) m/z 363, 365; ¹H NMR (400 MHz, CDCl₃): δ 7.84 (d, 1H), 7.27-7.23 (m, 2H), 7.01 (dt, 1H), 6.90-6.88 (m, 1H), 6.72 (dt, 1H), 5.35 (q, 1H), 2.79 (dd, 1H).

Example 127

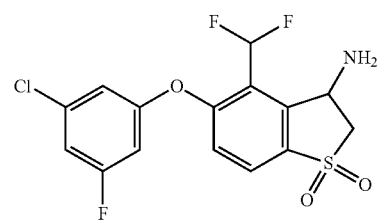 [SMILES: NC1CS(=O)(=O)c2ccc(Oc3cc(F)cc(Cl)c3)c(C(F)F)c21]

3-Amino-5-(3-chloro-5-fluorophenoxy)-4-(difluoromethyl)-2,3-dihydrobenzo[b]thiophene 1,1-dioxide (Compound 127)

Step A: Preparation of 3-amino-5-(3-chloro-5-fluorophenoxy)-4-(difluoromethyl)benzo[b]thiophene 1,1-dioxide: 3-(3-Chloro-5-fluoro-phenoxy)-2-(difluoromethyl)-6-methylsulfonyl-benzonitrile was prepared similarly according to Example 113, Steps A-E, substituting 3-chloro-5-fluorophenol for 3-fluoro-5-hydroxy-benzonitrile. A solution of 3-(3-chloro-5-fluoro-phenoxy)-2-(difluoromethyl)-6-methylsulfonyl-benzonitrile (16.5 mg, 0.044 mmol) in tetrahydrofuran (1 mL) at 25° C. was treated with sodium hydride (2.1 mg, 0.053 mmol). The resulting suspension was stirred for 30 minutes. The reaction mixture was poured into 10 mL of saturated aqueous NH₄Cl and extracted with 3×15 mL EtOAc. The combined organics were rinsed with 10 mL of brine, dried with MgSO₄, filtered, and concentrated to dryness. Purification was achieved by chromatography on silica using 10-35% EtOAc/hexane to afford 3-amino-5-(3-chloro-5-fluorophenoxy)-4-(difluoromethyl)benzo[b]thiophene 1,1-dioxide as a yellow solid (12.7 mg, 77%).

Step B: Preparation of 3-amino-5-(3-chloro-5-fluorophenoxy)-4-(difluoromethyl)-2,3-dihydrobenzo[b]thiophene 1,1-dioxide: A solution of 5-(3-chloro-5-fluoro-phenoxy)-4-(difluoromethyl)-1,1-dioxo-benzothiophen-3-amine (10 mg, 0.027 mmol) in methanol (4.0 mL) at 25° C. was treated with sodium borohydride (20.1 mg, 0.53 mmol). Additional portions of sodium borohydride were added until the reaction was complete. The reaction mixture was quenched with 2 mL of water and concentrated to dryness. The residue was poured into 20 mL of water and extracted with 3×15 mL 30% isopropyl alcohol/CHCl₃. The combined organics were rinsed with 10 mL of brine, dried with MgSO₄, filtered, and concentrated to dryness. Purification was achieved by chromatography on silica using 20-60% EtOAc/hexane to afford Compound 127 as a white solid (3.9 mg, 39%). LCMS ESI (+) (M+H) m/z 378, 380; ¹H NMR (400 MHz, CDCl₃): δ 7.80 (d, 1H), 7.22 (t, 1H), 7.06 (dt, 1H), 7.00 (dt, 1H), 6.87-6.84 (m, 1H), 6.70 (dt, 1H), 5.16-5.03 (br s, 1H), 3.75 (dd, 1H), 3.49 (dd, 1H), 2.20-1.97 (br s, 2H).

Example 128

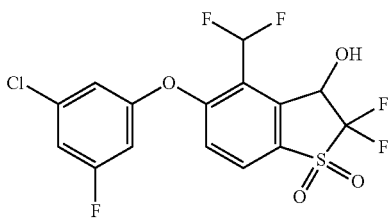 [SMILES: O=S1(=O)c2ccc(Oc3cc(F)cc(Cl)c3)c(C(F)F)c2C(O)C1(F)F]

5-(3-Chloro-5-fluorophenoxy)-4-(difluoromethyl)-2,2-difluoro-3-hydroxy-2,3-dihydrobenzo[b]thiophene 1,1-dioxide (Compound 128): 5-(3-Chloro-5-fluoro-phenoxy)-4-(difluoromethyl)-2,2-difluoro-1,1-dioxo-benzothiophen-3-one was prepared similarly according to Example 113, Steps A-G, substituting 3-chloro-5-fluorophenol for 3-fluoro-5-hydroxy-benzonitrile. A solution of 5-(3-chloro-5-fluorophenoxy)-4-(difluoromethyl)-2,2-difluoro-1,1-dioxo-benzothiophen-3-one (27 mg, 0.066 mmol) in methanol (1.3 mL) at 0° C. was treated with sodium borohydride (2.7 mg, 0.073 mmol) and stirred at 0° C. for 1 hour. The reaction mixture was quenched by the addition of 0.5 mL of water and 0.25 mL of saturated NH$_4$Cl. Volatiles were removed by concentration under reduced pressure. The reaction mixture was poured into 20 mL of water and extracted with 3×15 mL EtOAc. The combined organics were rinsed with 10 mL of brine, dried with MgSO$_4$, filtered, and concentrated to dryness. Purification was achieved by chromatography on silica using 10-30% EtOAc/hexanes to afford Compound 128 as a thin film (8.6 mg, 31%). LCMS ESI (−) (M−H) m/z 413, 415; $^1$H NMR (400 MHz, CDCl$_3$): δ 7.93 (d, 1H), 7.25 (t, 1H), 7.21-7.17 (m, 1H), 7.06 (ddd, 1H), 6.92-6.89 (m, 1H), 6.75 (dt, 1H), 5.67 (dd, 1H), 3.10 (dd, 1H).

Examples 129 and 130

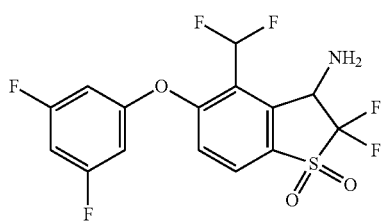

Compound 129

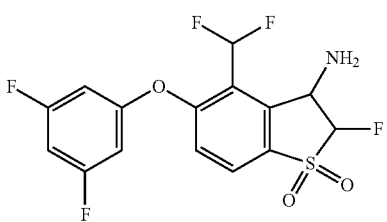

Compound 130

3-Amino-4-(difluoromethyl)-5-(3,5-difluorophenoxy)-2,2-difluoro-2,3-dihydrobenzo[b]thiophene 1,1-dioxide (Compound 129) and 3-amino-4-(difluoromethyl)-5-(3,5-difluorophenoxy)-2-fluoro-2,3-dihydrobenzo[b]thiophene 1,1-dioxide (Compound 130)

Step A: Preparation of 3-amino-4-(difluoromethyl)-5-(3,5-difluorophenoxy)-2,2-difluoro-2,3-dihydrobenzo[b]thiophene 1,1-dioxide (Compound 129) and 3-amino-4-(difluoromethyl)-5-(3,5-difluorophenoxy)-2-fluoro-2,3-dihydrobenzo[b]thiophene 1,1-dioxide (Compound 130): 4-(Difluoromethyl)-5-(3,5-difluorophenoxy)-1,1-dioxo-benzothiophen-3-amine was prepared similarly according to Example 127, Step A. A solution of 4-(difluoromethyl)-5-(3,5-difluorophenoxy)-1,1-dioxo-benzothiophen-3-amine (24.4 mg, 0.07 mmol) in acetonitrile (1.3 mL) at 25° C. was treated with sodium carbonate (15.8 mg, 0.15 mmol). The resulting suspension was stirred for 5 minutes and then Selectfluor® (53 mg, 0.15 mmol) was added. The reaction mixture was stirred at 25° C. for 1.5 hours. Volatiles were removed by concentration under reduced pressure. The residue was dissolved in 2 mL of MeOH and treated with sodium borohydride (5.1 mg, 0.14 mmol). The reaction mixture was allowed to stir for 1 hour at 25° C. Volatiles were removed by concentration under reduced pressure and the residue was poured into 20 mL of water and extracted with 3×15 mL 30% isopropyl alcohol/CHCl$_3$. The combined organics were rinsed with 10 mL of brine, dried with MgSO$_4$, filtered, and concentrated to dryness. Purification was achieved by chromatography on silica using 60-100% CH$_2$Cl$_2$/hexane to afford 3-amino-4-(difluoromethyl)-5-(3,5-difluorophenoxy)-2,2-difluoro-2,3-dihydrobenzo[b]thiophene 1,1-dioxide (Compound 129) as a thin film (6.0 mg, 22%) and 3-amino-4-(difluoromethyl)-5-(3,5-difluorophenoxy)-2-fluoro-2,3-dihydrobenzo[b]thiophene 1,1-dioxide (Compound 130) as a white solid (5.6 mg, 21%).

Data for 3-amino-4-(difluoromethyl)-5-(3,5-difluorophenoxy)-2,2-difluoro-2,3-dihydrobenzo[b]thiophene 1,1-dioxide (Compound 129): HPLC retention time=3.07 minutes; LCMS ESI (+) (M+H) m/z 398; $^1$H NMR (400 MHz, CDCl$_3$): δ 7.90 (d, 1H), 7.28 (dd, 1H), 7.18-7.14 (m, 1H), 6.76 (tt, 1H), 6.67-6.60 (m, 2H), 4.98 (dt, 1H), 2.01 (br d, 2H).

Data for 3-amino-4-(difluoromethyl)-5-(3,5-difluorophenoxy)-2-fluoro-2,3-dihydrobenzo[b]thiophene 1,1-dioxide (Compound 130): HPLC retention time=2.64 minutes; LCMS ESI (+) (M+H) m/z 380; $^1$H NMR (400 MHz, CDCl$_3$): δ 7.87 (d, 1H), 7.44 (dd, 1H), 7.15 (d, 1H), 6.73 (tt, 1H), 6.64-6.57 (m, 2H), 5.58 (dd, 1H), 5.17-5.07 (m, 1H), 2.02-1.93 (m, 2H).

Example 131

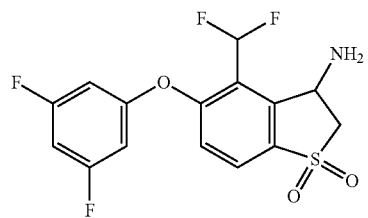 [SMILES: NC1CS(=O)(=O)c2ccc(Oc3cc(F)cc(F)c3)c(C(F)F)c21]

3-Amino-4-(difluoromethyl)-5-(3,5-difluorophenoxy)-2-fluoro-2,3-dihydrobenzo[b]thiophene 1,1-dioxide (Compound 131): Prepared similarly according to Example 127, Steps A-B, substituting 3,5-difluorophenol for 3-chloro-5-fluorophenol. The residue was purified by C18 reverse phase flash chromatography (Biotage Isolera One unit, C18 Flash 12+M column, 10-80% CH$_3$CN/water) to afford Compound 131 as a white solid (3.4 mg, 19%). LCMS ESI (+) (M+H) m/z 362; $^1$H NMR (400 MHz, CDCl$_3$): δ 7.81 (d, 1H), 7.22

(t, 1H), 7.10-7.06 (m, 1H), 6.72 (tt, 1H), 6.63-6.56 (m, 2H), 5.14-5.07 (m, 1H), 3.75 (dd, 1H), 3.49 (dd, 1H), 2.12-2.04 (m, 2H).

Examples 132 and 133

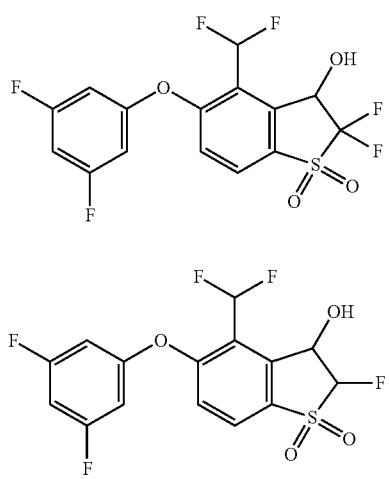

Compound 132

Compound 133

4-(Difluoromethyl)-5-(3,5-difluorophenoxy)-2,2-difluoro-3-hydroxy-2,3-dihydrobenzo[b]thiophene 1,1-dioxide (Compound 132) and 4-(difluoromethyl)-5-(3,5-difluorophenoxy)-2-fluoro-3-hydroxy-2,3-dihydrobenzo[b]thiophene 1,1-dioxide (Compound 133): 4-(Difluoromethyl)-5-(3,5-difluorophenoxy)-1,1-dioxo-benzothiophen-3-one was prepared similarly according to Example 113, Steps A-F, substituting 3,5-difluorophenol for 3-fluoro-5-hydroxy-benzonitrile. A solution of 4-(difluoromethyl)-5-(3,5-difluorophenoxy)-1,1-dioxo-benzothiophen-3-one (19 mg, 0.053 mmol) in acetonitrile (2.1 mL) at 25° C. was treated with sodium carbonate (12.3 mg, 0.12 mmol). The resulting suspension was stirred for 5 minutes. Selectfluor® (41 mg, 0.12 mmol) was added and the reaction mixture was stirred at 25° C. for 1.5 hours. Volatiles were removed by concentration under reduced pressure. The residue was dissolved in 2 mL of MeOH and treated with sodium borohydride (2.0 mg, 0.053 mmol). The reaction mixture was allowed to stir for 3 hours at room temperature. Volatiles were removed by concentration under reduced pressure and the residue was poured into 20 mL of water and extracted with 3×20 mL EtOAc. The combined organics were rinsed with 10 mL of brine, dried with MgSO$_4$, filtered, and concentrated to dryness. Purification was achieved by chromatography on silica using 0-10% EtOAc/CH$_2$Cl$_2$ to afford 4-(difluoromethyl)-5-(3,5-difluorophenoxy)-2,2-difluoro-3-hydroxy-2,3-dihydrobenzo[b]thiophene 1,1-dioxide (Compound 132) as a thin film (1.7 mg, 8%) and 4-(difluoromethyl)-5-(3,5-difluorophenoxy)-2-fluoro-3-hydroxy-2,3-dihydrobenzo[b]thiophene 1,1-dioxide (Compound 133) as a white solid (3.6 mg, 18%).

Data for 4-(difluoromethyl)-5-(3,5-difluorophenoxy)-2,2-difluoro-3-hydroxy-2,3-dihydrobenzo[b]thiophene 1,1-dioxide (Compound 132): HPLC retention time=2.96 minutes; LCMS ESI (−) (M−H) m/z 397; $^1$H NMR (400 MHz, CDCl$_3$): δ 7.93 (d, 1H), 7.25 (t, 1H), 7.23-7.19 (m, 2H), 6.78 (tt, 1H), 6.68-6.61 (m, 2H), 5.67 (dd, 1H), 3.09 (dd, 1H).

Data for 4-(difluoromethyl)-5-(3,5-difluorophenoxy)-2-fluoro-3-hydroxy-2,3-dihydrobenzo[b]thiophene 1,1-dioxide (Compound 133): HPLC retention time=2.73 minutes; LCMS ESI (−) (M−H) m/z 379; $^1$H NMR (400 MHz, CDCl$_3$): δ 7.89 (d, 1H), 7.29 (t, 1H), 7.19 (d, 1H), 6.74 (tt, 1H), 6.65-6.58 (m, 2H), 5.87-5.80 (m, 1H), 5.66 (dd, 1H), 2.98 (ddd, 1H).

Example 134

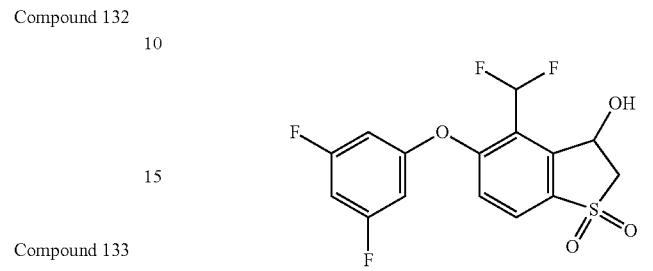

4-(Difluoromethyl)-5-(3,5-difluorophenoxy)-3-hydroxy-2,3-dihydrobenzo[b]thiophene 1,1-dioxide (Compound 134): 4-(Difluoromethyl)-5-(3,5-difluorophenoxy)benzo[b]thiophen-3(2H)-one 1,1-dioxide was prepared similarly according to Example 125, Steps A-F, substituting 3,5-difluorophenol for 3-fluoro-5-hydroxy-benzonitrile. Reduction proceeded similarly as described in Example 125. Purification was achieved by chromatography on silica using 20-50% EtOAc/hexanes to afford Compound 134 as a beige solid (5.6 mg, 58%). LCMS ESI (+) (M+H) m/z 363; $^1$H NMR (400 MHz, CDCl$_3$): δ 7.85 (d, 1H), 7.25 (t, 1H), 7.16 (dt, 1H), 6.73 (tt, 1H), 6.63-6.56 (m, 1H), 5.90-5.86 (m, 1H), 5.90-5.85 (m, 1H), 3.78 (ddd, 1H), 3.67 (dd, 1H), 2.89 (t, 1H).

Example 135

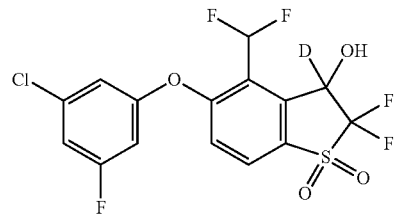 [SMILES: [2H]C1(O)c2c(ccc(Oc3cc(F)cc(Cl)c3)c2C(F)F)S(=O)(=O)C1(F)F]

5-(3-Chloro-5-fluorophenoxy)-4-(difluoromethyl)-2,2-difluoro-3-hydroxy-2,3-dihydrobenzo[b]thiophene 1,1-dioxide-3-d (Compound 135): 5-(3-chloro-5-fluoro-phenoxy)-4-(difluoromethyl)-2,2-difluoro-1,1-dioxo-benzothiophen-3-one was prepared similarly according to Example 113, Steps A-G, substituting 3-chloro-5-fluorophenol for 3-fluoro-5-hydroxy-benzonitrile. A solution of 5-(3-chloro-5-fluoro-phenoxy)-4-(difluoromethyl)-2,2-difluoro-1,1-dioxo-benzothiophen-3-one (40 mg, 0.097 mmol) in CD$_3$OD (1.9 mL) at 0° C. was treated with sodium borodeuteride (4 mg, 0.097 mmol) and stirred at 0° C. for 1 hour. The reaction mixture was quenched by the addition of 0.5 mL of water and 0.25 mL of saturated NH$_4$Cl. Volatiles were removed by concentration under reduced pressure. The reaction mixture was poured into 10 mL of water and extracted with 3×15 mL EtOAc. The combined organics were rinsed with 10 mL of brine, dried with MgSO$_4$, filtered, and concentrated to dryness. Purification was achieved by chromatography on silica using 10-30% EtOAc/hexane to give Compound 135

(7.0 mg, 17%). LCMS ESI (−) (M−H) m/z 414, 416; $^1$H NMR (400 MHz, CDCl$_3$): δ 7.95-7.92 (m, 1H), 7.25 (t, 1H), 7.21-7.17 (m, 1H), 7.06 (ddd, 1H), 6.92-6.89 (m, 1H), 6.75 (dt, 1H), 3.07 (d, 1H).

Examples 136 and 137

Compound 136

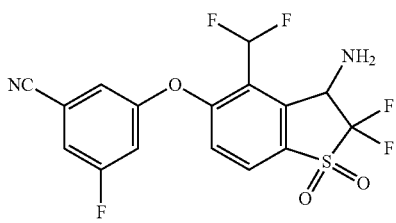

Compound 137

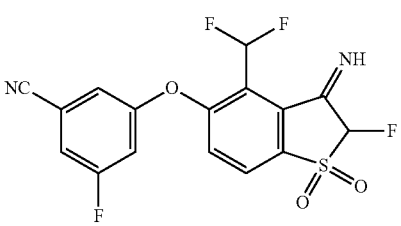

3-((3-Amino-4-(difluoromethyl)-2,2-difluoro-1,1-di-oxido-2,3-dihydrobenzo[b]thiophen-5-yl)oxy)-5-fluorobenzonitrile (Compound 136) and 3-((4-(difluoromethyl)-2-fluoro-3-imino-1,1-dioxido-2,3-dihydrobenzo[b]thiophen-5-yl)oxy)-5-fluorobenzonitrile (Compound 137)

Step A: Preparation of 3-[4-(difluoromethyl)-2,2-difluoro-3-imino-1,1-dioxo-benzothiophen-5-yl]oxy-5-fluoro-benzonitrile: 3-[3-Amino-4-(difluoromethyl)-1,1-dioxo-benzothiophen-5-yl]oxy-5-fluoro-benzonitrile was prepared similarly according to Example 17, Step A, substituting 3-fluoro-5-hydroxy-benzonitrile for 3-chloro-5-fluorophenol. A solution of 3-[3-amino-4-(difluoromethyl)-1,1-dioxo-benzothiophen-5-yl]oxy-5-fluoro-benzonitrile (25.4 mg, 0.07 mmol) in acetonitrile (2.8 mL) at 25° C. was treated with sodium carbonate (14.7 mg, 0.14 mmol). The resulting suspension was stirred for 5 minutes. Selectfluor® (49 mg, 0.14 mmol) was added and the reaction mixture left to stir at 25° C. for 1.5 hours. Solution quickly turns from orange to yellow upon Selectfluor® addition. Volatiles were removed by concentration under reduced pressure and the residue was poured into 20 mL of water and extracted with 3×15 mL 30% isopropyl alcohol/CHCl$_3$. The combined organics were rinsed with 10 mL of brine, dried with MgSO$_4$, filtered, and concentrated to dryness. The product was used without further purification. LCMS ESI (+) (M+H) m/z 403.

Step B: Preparation of 3-((3-amino-4-(difluoromethyl)-2,2-difluoro-1,1-dioxido-2,3-dihydrobenzo[b]thiophen-5-yl)oxy)-5-fluorobenzonitrile (Compound 136) and 3-((4-(difluoromethyl)-2-fluoro-3-imino-1,1-dioxido-2,3-dihydrobenzo[b]thiophen-5-yl)oxy)-5-fluorobenzonitrile (Compound 137): A solution of 3-[4-(difluoromethyl)-2,2-difluoro-3-imino-1,1-dioxo-benzothiophen-5-yl]oxy-5-fluoro-benzonitrile and 3-((4-(difluoromethyl)-2-fluoro-3-imino-1,1-dioxido-2,3-dihydrobenzo[b]thiophen-5-yl)oxy)-5-fluorobenzonitrile (17.7 mg) in methanol (2.0 mL) at 0° C. was treated with sodium borohydride (1.7 mg, 0.044 mmol) and stirred for 1 hour. The reaction mixture was quenched by the addition of 0.5 mL of water. Volatiles were removed by concentration under reduced pressure. The reaction mixture was poured into 10 mL of water and extracted with 3×15 mL EtOAc. The combined organics were rinsed with 10 mL of brine, dried with MgSO$_4$, filtered, and concentrated to dryness. Purification was achieved by chromatography on silica using 0-15% EtOAc/CHCl$_3$ to afford 3-amino-5-(3-chloro-5-fluorophenoxy)-4-(difluoromethyl)-2,2-difluoro-2,3-dihydrobenzo[b]thiophene 1,1-dioxide (Compound 136) as a thin film (5.4 mg, 30%) and 3-((4-(difluoromethyl)-2-fluoro-3-imino-1,1-dioxido-2,3-dihydrobenzo[b]thiophen-5-yl)oxy)-5-fluorobenzonitrile (Compound 137) as a thin film (1.8 mg, 11%).

Data for 3-((3-amino-4-(difluoromethyl)-2,2-difluoro-1,1-dioxido-2,3-dihydrobenzo[b]thiophen-5-yl)oxy)-5-fluorobenzonitrile (Compound 136): HPLC retention time=2.92 minutes; LCMS ESI (+) (M+H) m/z 405; $^1$H NMR (400 MHz, CDCl$_3$): δ 7.95 (d, 1H), 7.31-7.27 (m, 1H), 7.30 (dd, 1H), 7.19-7.14 (m, 2H), 7.07 (dt, 1H), 5.00-4.92 (m, 1H), 2.03 (d, 2H).

Data for 3-((4-(difluoromethyl)-2-fluoro-3-imino-1,1-dioxido-2,3-dihydrobenzo[b]thiophen-5-yl)oxy)-5-fluorobenzonitrile (Compound 137): HPLC retention time=2.68 minutes; LCMS ESI (+) (M+H) m/z 385; $^1$H NMR (400 MHz, CDCl$_3$): δ 11.26-11.22 (m, 1H), 8.09 (dd, 1H), 8.06 (d, 1H), 7.04 (d, 1H), 7.27-7.23 (m, 1H), 7.15-7.13 (m, 1H), 7.06 (dt, 1H), 5.87 (dd, 1H).

Example 138

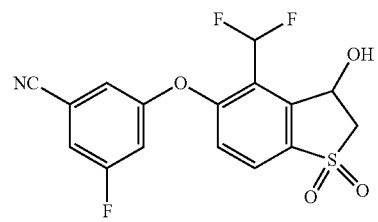 [SMILES: N#Cc1cc(F)cc(Oc2ccc3c(c2C(F)F)C(O)CS3(=O)=O)c1]

3-((4-(Difluoromethyl)-3-hydroxy-1,1-dioxido-2,3-dihydrobenzo[b]thiophen-5-yl)oxy)-5-fluorobenzonitrile (Compound 138): Reduction proceeded similarly as described in Example 115. Purification was achieved by chromatography on silica using 20-70% EtOAc/hexane to afford Compound 138 as a white solid (8.3 mg, 68%). LCMS ESI (+) (M−H) m/z 370; $^1$H NMR (400 MHz, CDCl$_3$): δ 7.89 (d, 1H), 7.28-7.25 (m, 1H), 7.20 (t, 1H), 7.17-7.13 (m, 2H), 7.04 (dt, 1H), 5.90-5.85 (m, 1H), 3.79 (dd, 1H), 3.69 (dd, 1H), 2.93 (t, 1H).

Example 139

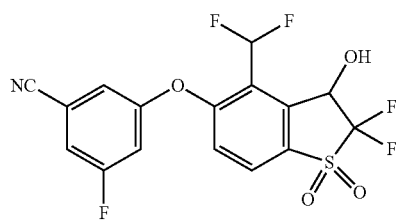

3-((4-(Difluoromethyl)-2,2-difluoro-3-hydroxy-1,1-dioxido-2,3-dihydrobenzo[b]thiophen-5-yl)oxy)-5-fluorobenzonitrile (Compound 139): Reduction proceeded similarly as described in Example 119. Purification was achieved by chromatography on silica using 10-40% EtOAc/hexane to afford Compound 139 as a white solid (8 mg, 73%). LCMS ESI (−) (M−H) m/z 404; $^1$H NMR (400 MHz, CDCl$_3$): δ 7.98 (d, 1H), 7.31 (ddd, 1H), 7.23 (t, 1H), 7.22-7.18 (m, 2H), 7.08 (dt, 1H), 5.66 (dd, 1H), 3.23 (d, 1H).

Example 140

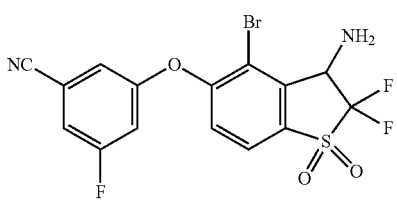 [SMILES: N#Cc1cc(F)cc(Oc2ccc3c(c2Br)C(N)C(F)(F)S3(=O)=O)c1]

3-Amino-4-bromo-5-(3,5-difluorophenoxy)-2,2-difluoro-2,3-dihydrobenzo[b]thiophene 1,1-dioxide (Compound 140)

Step A: Preparation of 2-bromo-3-fluoro-6-iodobenzamide: 2-Bromo-3-fluoro-6-iodobenzoic acid (2.33 g, 6.76 mmol) was dissolved in tetrahydrofuran (20 mL) and cooled to 0° C. The solution was treated with N,N-dimethylformamide (10 drops) followed by dropwise addition of thionyl chloride (1.0 mL, 10 mmol) then stirred for 10 minutes. The reaction was warmed to ambient temperature and stirred for 2 hours. The mixture was recooled to 0° C. and treated with concentrated ammonium hydroxide (5 mL) and the mixture was allowed to warm to ambient temperature with the bath and stirred overnight. The reaction mixture was concentrated in vacuo, then redissolved in saturated NaHCO$_3$ and ethyl acetate. The layers were separated and the organic phase was washed with saturated NaHCO$_3$, saturated NaCl, dried over Na$_2$SO$_4$ and concentrated in vacuo to give a white solid (2.2 g, 94%).

Step B: Preparation of 2-bromo-3-fluoro-6-iodobenzonitrile: 2-Bromo-3-fluoro-6-iodobenzamide (10 g, 29 mmol) was suspended in phosphorus oxychloride (41 mL), treated with triethylamine (12.2 mL, 87.2 mmol), then the mixture was heated to 75° C. for 3 hours. The reaction mixture was cooled to ambient temperature with the bath and stirred overnight. The reaction mixture was concentrated in vacuo to remove excess POCl$_3$, then the semi-dry residue was treated with ice and some water. The resulting mixture was stirred until the ice melted and a beige solid was collected by filtration, washed with water and air-dried (8.04 g, quant.).

Step C: Preparation of S-(3-bromo-2-cyano-4-fluorophenyl) ethanethioate: 2-Bromo-3-fluoro-6-iodobenzonitrile (6.5 g, 20 mmol) and 4,5-bis(diphenylphosphino)-9,9-dimethylxanthene (1.38 g, 2.4 mmol) were suspended in 2:1 toluene/acetone (80 mL). The mixture was sparged with argon, then treated with tris(dibenzylideneacetone)dipalladium (1.0 g, 1.1 mmol) and potassium ethanethioate (2.84 g, 24.9 mmol). The mixture was sealed under argon and heated to 70° C. for 3 hours, then stirred at ambient temperature overnight. The reaction was filtered through celite. The retained solids were washed with methylene chloride and the filtrate was concentrated in vacuo. The crude product was chromatographed on SiO$_2$ eluting with a gradient of ethyl acetate and hexane to give S-(3-bromo-2-cyano-4-fluorophenyl) ethanethioate as a dark brown solid (4.0 g, 73%). This material was used without further purification.

Step D: Preparation of 2-bromo-3-fluoro-6-(methylthio)benzonitrile: A solution of S-(3-bromo-2-cyano-4-fluorophenyl) ethanethioate (500 mg, 1.8 mmol) in methanol (9.1 mL) at 25° C. was sparged with nitrogen for 3 minutes and then treated with cesium carbonate (594 mg, 1.82 mmol) and stirred at 25° C. until completely dissolved. The reaction mixture was treated with iodomethane (0.15 mL, 2.4 mmol) and stirred for 1 hour. Volatiles were removed by concentration under reduced pressure. The reaction mixture was poured into 20 mL of water and extracted with 3×20 mL EtOAc. The combined organics were rinsed with 10 mL of brine, dried with MgSO$_4$, filtered, and concentrated to dryness. Purification was achieved by chromatography on silica using 5-25% EtOAc/hexane to afford 2-bromo-3-fluoro-6-(methylthio)benzonitrile as a yellow solid (388 mg, 86%).

Step E: Preparation of 2-bromo-3-fluoro-6-(methylsulfonyl)benzonitrile: A solution of 2-bromo-3-fluoro-6-methylsulfanyl-benzonitrile (286 mg, 1.16 mmol) in dichloromethane (11.6 mL) at 25° C. was treated with 3-chloroperbenzoic acid (~70% by wt, 716 mg, 2.9 mmol) and stirred at 25° C. for 6 hours. An additional equivalent of 3-chloroperbenzoic acid (286 mg, 1.16 mmol) was added to drive the reaction to completion.

The reaction mixture was poured into 10 mL of 1 N NaOH and extracted with 3×20 mL CH$_2$Cl$_2$. The combined organics were rinsed with 20 mL of brine, dried with MgSO$_4$, filtered, and concentrated to dryness to obtain a yellow solid. The yellow solid was used without further purification. LCMS ESI (+) (M+NH$_4$) m/z 295, 297.

Step F: Preparation of 3-((4-bromo-2,2-difluoro-3-imino-1,1-dioxido-2,3-dihydrobenzo[b]thiophen-5-yl)oxy)-5-fluorobenzonitrile: 2-Bromo-3-fluoro-6-(methylsulfonyl)benzonitrile was advanced sequentially through a series of steps described previously.

Step G: Preparation of 3-amino-4-bromo-5-(3,5-difluorophenoxy)-2,2-difluoro-2,3-dihydrobenzo[b]thiophene 1,1-dioxide: Reduction proceeded similarly as described in Example 136, Step B. Purification was achieved by chromatography on silica using 5-30% EtOAc/hexane to afford Compound 140 as a white solid (7.0 mg, 39%). LCMS ESI (+) (M+H) m/z 426, 428; $^1$H NMR (400 MHz, CDCl$_3$): δ 7.78 (d, 1H), 7.18 (d, 1H), 6.72 (tt, 1H), 6.63-6.54 (m, 2H), 4.70 (dt, 1H), 1.92 (d, 2H).

Examples 141 and 142

Compound 141

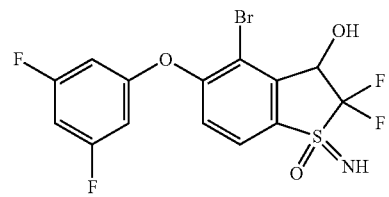

-continued

Compound 142

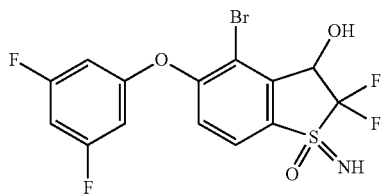

4-Bromo-5-(3,5-difluorophenoxy)-2,2-difluoro-3-hydroxy-1-imino-2,3-dihydro-1H-1λ⁴-benzo[b]thiophene 1-oxide (Compound 141) and 4-bromo-5-(3,5-difluorophenoxy)-2,2-difluoro-3-hydroxy-1-imino-2,3-dihydro-1H-1λ⁴-benzo[b]thiophene 1-oxide (Compound 142)

Step A: Preparation of 2-bromo-3-fluoro-6-(methylsulfinyl)benzonitrile: A solution of 2-bromo-3-fluoro-6-methylsulfanyl-benzonitrile (102 mg, 0.4 mmol) in methanol (10 mL) and water (5 mL) at 25° C. was treated with Oxone® (127.6 mg, 0.21 mmol) and stirred overnight at 25° C. The reaction mixture was concentrated to a thick slurry and poured into 20 mL of water and extracted with 3×20 mL EtOAc. The combined organics were rinsed with 10 mL of brine, dried with MgSO₄, filtered, and concentrated to dryness to obtain an off-white solid. The off-white solid was used without further purification. LCMS ESI (+) (M+H) m/z 262, 264.

Step B: Preparation of 2-bromo-3-(3,5-difluorophenoxy)-6-(methylsulfinyl)benzonitrile: A solution of 2-bromo-3-fluoro-6-methylsulfinyl-benzonitrile (335 mg, 1.3 mmol), 3,5-difluorophenol (141 mg, 1.1 mmol), and cesium bicarbonate (211 mg, 1.1 mmol) in N,N-dimethylformamide (6.4 mL) was stirred at 80° C. for 4 hours. The reaction mixture was poured into 60 mL of water and extracted with 3×20 mL Et₂O. The combined organics were rinsed with 20 mL of brine, dried with MgSO₄, filtered, and concentrated to dryness. Purification was achieved by chromatography on silica using 20-70% EtOAc/hexane to afford a whites solid (259 mg, 54%). LCMS ESI (+) (M+H) m/z 372, 374.

Step C: Preparation of N-((3-bromo-2-cyano-4-(3,5-difluorophenoxy)phenyl)(methyl)(oxo)-λ⁶-sulfanylidene)-2,2,2-trifluoroacetamide: A suspension of 2-bromo-3-(3,5-difluorophenoxy)-6-methylsulfinyl-benzonitrile (259 mg, 0.70 mmol), trifluoroacetamide (157 mg, 1.4 mmol), magnesium oxide (112 mg, 2.8 mmol), and bis(rhodium(α,α,α',α'-tetramethyl-1,3-benezenedipropionic acid)) (21 mg, 0.028 mmol) in dichloromethane (4.6 mL) at 25° C. was treated with (diacetoxyiodo)benzene (336 mg, 1.0 mmol) and stirred at 25° C. Over the course of the reaction, additional portions of all reactants except the sulfoxide were added to help drive the reaction to completion (judged by LCMS). When complete, the reaction mixture was filtered through a pad of celite to remove insolubles (CH₂Cl₂ was used to rinse the filtered insolubles). The filtrate was concentrated and purification achieved by chromatography on silica using 10-50% EtOAc/hexane to afford a tan solid (265 mg, 79%). LCMS ESI (+) (M+H) m/z 483, 485.

Step D: Preparation of 4-bromo-5-(3,5-difluorophenoxy)-1-imino-1,2-dihydro-3H-1λ⁴-benzo[b]thiophen-3-one 1-oxide: A solution of N-((3-bromo-2-cyano-4-(3,5-difluorophenoxy)phenyl)(methyl)(oxo)-λ⁶-sulfanylidene)-2,2,2-trifluoroacetamide (265 mg, 0.55 mmol) in tetrahydrofuran (11 mL) at 25° C. was treated with sodium hydride (33 mg, 0.82 mmol). The resulting suspension was stirred for 1 hour. Initially, the reaction was quenched by the addition of 0.5 mL of water followed by 0.2 mL of saturated aqueous NH₄Cl. Then volatiles were removed and the resulting residue dissolved in 10 mL of MeOH and 4 mL of 10% aqueous HCl. The resulting mixture was stirred for 3 hours at room temperature. The reaction mixture was concentrated and the residue poured into 20 mL of water and extracted with 3×15 mL 30% isopropyl alcohol/CHCl₃. The combined organics were rinsed with 10 mL of brine, dried with MgSO₄, filtered, and concentrated to dryness. Purification was achieved by chromatography on silica using 20-85% EtOAc/hexane to afford a beige solid (55 mg, 26%). LCMS ESI (+) (M+H) m/z 388, 390.

Step E: Preparation of 4-bromo-5-(3,5-difluorophenoxy)-2,2-difluoro-1-imino-1,2-dihydro-3H-1λ⁴-benzo[b]thiophen-3-one 1-oxide: A solution of 4-bromo-5-(3,5-difluorophenoxy)-1-imino-1,2-dihydro-3H-1λ⁴-benzo[b]thiophen-3-one 1-oxide (21.6 mg, 0.056 mmol) in acetonitrile (1.1 mL) at 25° C. was treated with sodium carbonate (13 mg, 0.12 mmol) and stirred 5 minutes. Selectfluor® (43 mg, 0.12 mmol) was then added and the reaction mixture left to stir at 25° C. for 4 hours. Volatiles were removed by concentration under reduced pressure and the residue was poured into 20 mL of water and extracted with 3×15 mL 30% isopropyl alcohol/CHCl₃. The combined organics were rinsed with 10 mL of brine, dried with MgSO₄, filtered, and concentrated to dryness. The product residue was used without further purification. LCMS ESI (+) (M+H) m/z 424, 426.

Step F: Preparation of 4-bromo-5-(3,5-difluorophenoxy)-2,2-difluoro-3-hydroxy-1-imino-2,3-dihydro-1H-1λ⁴-benzo[b]thiophene 1-oxide (Compound 141) and 4-bromo-5-(3,5-difluorophenoxy)-2,2-difluoro-3-hydroxy-1-imino-2,3-dihydro-1H-1λ⁴-benzo[b]thiophene 1-oxide (Compound 142): A solution of 4-bromo-5-(3,5-difluorophenoxy)-2,2-difluoro-1-imino-1,2-dihydro-3H-1λ⁴-benzo[b]thiophen-3-one 1-oxide (23 mg, 0.055 mmol) in methanol (1 mL) at 0° C. was treated with sodium borohydride (2.3 mg, 0.06 mmol) and stirred at 0° C. for 1 hour. The reaction mixture was quenched by the addition of 0.5 mL of water and 0.25 mL of saturated aqueous NH₄Cl. Volatiles were removed by concentration under reduced pressure. The reaction mixture was poured into 10 mL water and extracted with 3×15 mL 30% isopropyl alcohol/CHCl₃. The combined organics were rinsed with 10 mL of brine, dried with MgSO₄, filtered, and concentrated to dryness. Purification was achieved by chromatography on silica using 15-45% EtOAc/hexanes to afford 4-bromo-5-(3,5-difluorophenoxy)-2,2-difluoro-3-hydroxy-1-imino-2,3-dihydro-1H-1λ⁴-benzo[b]thiophene 1-oxide (Compound 141) as a white solid (4.5 mg, 19%) and 4-bromo-5-(3,5-difluorophenoxy)-2,2-difluoro-3-hydroxy-1-imino-2,3-dihydro-1H-1λ⁴-benzo[b]thiophene 1-oxide (Compound 142) as a white solid (4.6 mg, 20%).

Data for 4-bromo-5-(3,5-difluorophenoxy)-2,2-difluoro-3-hydroxy-1-imino-2,3-dihydro-1H-1λ⁴-benzo[b]thiophene 1-oxide (Compound 141): Retention time=2.59 minutes; LCMS ESI (+) (M+H) m/z 426, 428; ¹H NMR (400 MHz, CDCl₃): δ 7.88 (d, 1H), 7.22 (d, 1H), 6.71 (tt, 1H), 6.62-6.55 (m, 2H), 5.31 (dd, 1H), 3.43 (br s, 1H), 3.03 (d, 1H).

Data for 4-bromo-5-(3,5-difluorophenoxy)-2,2-difluoro-3-hydroxy-1-imino-2,3-dihydro-1H-1λ⁴-benzo[b]thiophene 1-oxide (Compound 142): Retention time=2.69 minutes; LCMS ESI (+) (M+H) m/z 426, 428; ¹H NMR (400 MHz, CDCl₃): δ 7.81 (d, 1H), 7.22 (d, 1H), 6.70 (tt, 1H), 6.61-6.54 (m, 2H), 5.35 (t, 1H), 3.75 (br s, 1H), 3.27 (d, 1H).

Example 143

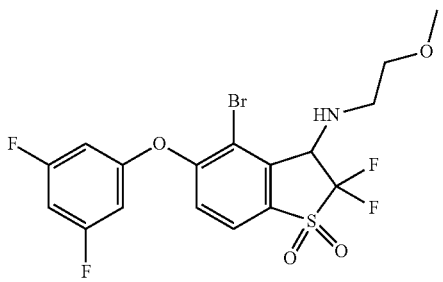 [SMILES: COCCNC1c2c(ccc(Oc3cc(F)cc(F)c3)c2Br)S(=O)(=O)C1(F)F]

4-Bromo-5-(3,5-difluorophenoxy)-2,2-difluoro-3-((2-methoxyethyl)amino)-2,3-dihydrobenzo[b]thiophene 1,1-dioxide (Compound 143)

Step A: Preparation of 4-bromo-5-(3,5-difluorophenoxy)-3-((2-methoxyethyl)amino)benzo[b]thiophene 1,1-dioxide: 4-Bromo-5-(3,5-difluorophenoxy)-1,1-dioxo-benzothiophen-3-amine was prepared similarly according to Example 140. A solution of 4-bromo-5-(3,5-difluorophenoxy)-1,1-dioxo-benzothiophen-3-amine (16.8 mg, 0.043 mmol) in benzene (1.0 mL) was treated with 2-methoxyethylamine (3.3 mg, 0.043 mmol) and stirred at 95° C. under reflux using Dean-Stark trap for 3 hours. Volatiles were removed by concentration under reduced pressure. The resulting residue was purified by chromatography on silica using 20-50% EtOAc/hexanes to afford a tan solid (11 mg, 58%). LCMS ESI (+) (M+H) m/z 446, 448.

Step B: Preparation of 4-bromo-5-(3,5-difluorophenoxy)-2,2-difluoro-3-((2-methoxyethyl)amino)-2,3-dihydrobenzo[b]thiophene 1,1-dioxide: Fluorination proceeded similarly as described in Example 136, Step A. The isolated solid was used without further purification. LCMS ESI (+) (M+H) m/z 482, 484.

Step C: Preparation of 4-bromo-5-(3,5-difluorophenoxy)-2,2-difluoro-3-((2-methoxyethyl)amino)-2,3-dihydrobenzo[b]thiophene 1,1-dioxide: A solution of 4-bromo-5-(3,5-difluorophenoxy)-2,2-difluoro-3-((2-methoxyethyl)amino)-2,3-dihydrobenzo[b]thiophene 1,1-dioxide (12 mg, 0.02 mmol) in methanol (1 mL) at 0° C. was treated with sodium borohydride (0.9 mg, 0.02 mmol) and stirred at 25° C. for 30 minutes. Additional equivalents of sodium borohydride (8 equivalents) were added to drive the reaction to completion. The reaction mixture was quenched by the addition of 0.5 mL of water and 0.25 mL of saturated NH$_4$Cl. Volatiles were removed by concentration under reduced pressure. The resulting mixture was poured into 10 mL water and extracted with 3×15 mL EtOAc. The combined organics were rinsed with 10 mL of brine, dried with MgSO$_4$, filtered, and concentrated to dryness. Purification was achieved by chromatography on silica using 20-35% EtOAc/hexane to afford Compound 143 as a white solid (2.6 mg, 22%). LCMS ESI (+) (M+H) m/z 484, 486; $^1$H NMR (400 MHz, CDCl$_3$): δ 7.75 (d, 1H), 7.16 (d, 1H), 6.71 (tt, 1H), 6.62-6.55 (m, 2H), 4.60 (dd, 1H), 3.55 (t, 2H), 3.35 (s, 3H), 3.21-3.06 (m, 2H), 2.10-2.03 (m, 1H).

Example 144

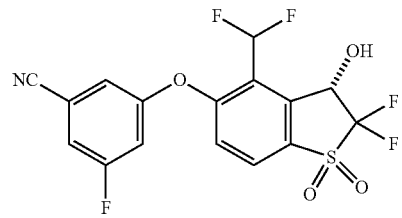

(S)-3-((4-(Difluoromethyl)-2,2-difluoro-3-hydroxy-1,1-dioxido-2,3-dihydrobenzo[b]thiophen-5-yl)oxy)-5-fluorobenzonitrile (Compound 144)

Preparation of (S)-3-((4-(difluoromethyl)-2,2-difluoro-3-hydroxy-1,1-dioxido-2,3-dihydrobenzo[b]thiophen-5-yl)oxy)-5-fluorobenzonitrile: Reduction proceeded similarly as described in Example 119. Purification of the racemic mixture was achieved by chromatography on silica using 10-40% EtOAc/hexane to afford racemic 3-((4-(Difluoromethyl)-2,2-difluoro-3-hydroxy-1,1-dioxido-2,3-dihydrobenzo[b]thiophen-5-yl)oxy)-5-fluorobenzonitrile as a white solid (8 mg, 73%). Resolution of the enantiomers was achieved using preparative SFC chromatography under the following conditions: ChiralPak AS(-H) (2×15 cm) column, 20% ethanol with carbon dioxide at 100 bar, 60 mL/min flow rate, injection volume was 0.5 mL of a 20 mg/mL solution in ethanol, peak detection at 220 nm. Compound 144 was recovered as the second peak (retention time: 1.84 minutes) eluting from the column. LCMS ESI (−) (M−H) m/z 404; $^1$H NMR (400 MHz, CDCl$_3$): δ 7.98 (d, 1H), 7.31 (ddd, 1H), 7.23 (t, 1H), 7.22-7.18 (m, 2H), 7.08 (dt, 1H), 5.66 (dd, 1H), 3.23 (d, 1H).

Example 145

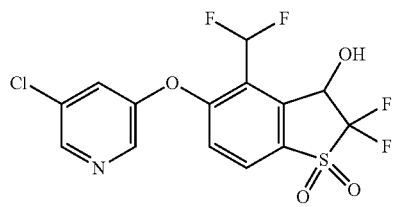 [SMILES: O=S1(=O)c2ccc(Oc3cncc(Cl)c3)c(C(F)F)c2C(O)C1(F)F]

5-((5-Chloropyridin-3-yl)oxy)-4-(difluoromethyl)-2,2-difluoro-3-hydroxy-2,3-dihydrobenzo[b]thiophene 1,1-dioxide (Compound 145): 5-((5-Chloropyridin-3-yl)oxy)-4-(difluoromethyl)-2,2-difluorobenzo[b]thiophen-3 (2H)-one 1,1-dioxide was prepared similarly according to Example 113, Steps E-G, substituting 5-chloropyridin-3-ol for 3-fluoro-5-hydroxy-benzonitrile. Reduction proceeded similarly as described in Example 119. Purification was achieved by chromatography on silica using 0-50% EtOAc/dichloromethane to afford Compound 145 as a white solid (11 mg, 30%). LCMS ESI (+) (M+H) m/z 398, 400; $^1$H NMR (400 MHz, CDCl$_3$): δ 8.55 (d, 1H), 8.38 (d, 1H), 7.96 (d, 1H), 7.46 (t, 1H), 7.29 (t, 1H), 7.16-7.13 (m, 1H), 5.67 (dd, 1H), 3.24 (dd, 1H).

Example 146

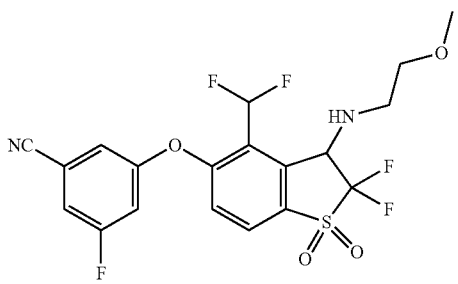 [SMILES: COCCNC1c2c(ccc(Oc3cc(F)cc(C#N)c3)c2C(F)F)S(=O)(=O)C1(F)F]

3-((4-(Difluoromethyl)-2,2-difluoro-3-((2-methoxyethyl) amino)-1,1-dioxido-2,3-dihydrobenzo[b]thiophen-5-yl) oxy)-5-fluorobenzonitrile (Compound 146): 3-((4-(Difluoromethyl)-2,2-difluoro-3-((2-methoxyethyl)imino)-1,1-dioxido-2,3-dihydrobenzo[b]thiophen-5-yl)oxy)-5-fluorobenzonitrile was prepared similarly according to Example 143, Steps A-B. Reduction proceeded similarly as described in Example 143, Step C. Purification was achieved by chromatography on silica using 5-25% EtOAc/hexane to afford Compound 146 as a thin film (5.1 mg, 51%). LCMS ESI (+) (M+H) m/z 463; $^1$H NMR (400 MHz, CDCl$_3$): δ 7.91 (d, 1H), 7.39 (t, 1H), 7.29-7.24 (m, 1H), 7.19-7.14 (m, 2H), 7.05 (dt, 1H), 4.94-4.87 (m, 1H), 3.53 (t, 2H), 3.37 (s, 3H), 3.17-3.07 (m, 2H), 2.28-2.20 (m, 1H).

Example 147

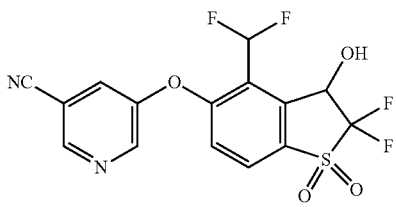 [SMILES: N#Cc1cncc(Oc2ccc3c(c2C(F)F)C(O)C(F)(F)S3(=O)=O)c1]

5-((4-(Difluoromethyl)-2,2-difluoro-3-hydroxy-1,1-dioxido-2,3-dihydrobenzo[b]thiophen-5-yl)oxy)nicotinonitrile (Compound 147): 5-((4-(Difluoromethyl)-2,2-difluoro-1,1-dioxido-3-oxo-2,3-dihydrobenzo[b]thiophen-5-yl)oxy) nicotinonitrile was prepared similarly according to Example 113, Steps E-G, substituting 5-hydroxynicotinonitrile for 3-fluoro-5-hydroxy-benzonitrile. Reduction proceeded similarly as described in Example 119. Purification was achieved by chromatography on silica using 10-50% EtOAc/CHCl$_3$ to afford Compound 147 as a white solid (12 mg, 29%). LCMS ESI (+) (M+H) m/z 389; $^1$H NMR (400 MHz, CD$_3$OD): δ 8.81 (d, 1H), 8.71 (d, 1H), 8.08 (d, 1H), 8.04 (dd, 1H), 7.42 (d, 1H), 7.38 (t, 1H), 5.69 (d, 1H).

Example 148

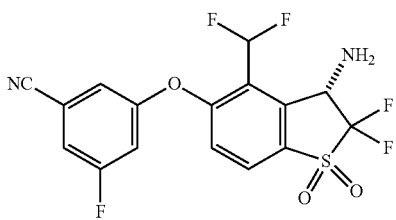 [SMILES: N#Cc1cc(F)cc(Oc2ccc3c(c2C(F)F)[C@H](N)C(F)(F)S3(=O)=O)c1]

(S)-3-((3-Amino-4-(difluoromethyl)-2,2-difluoro-1,1-dioxido-2,3-dihydrobenzo[b]thiophen-5-yl)oxy)-5-fluorobenzonitrile (Compound 148)

Step A: Preparation of (R)—N—((S)-5-(3-cyano-5-fluorophenoxy)-4-(difluoromethyl)-2,2-difluoro-1,1-dioxido-2,3-dihydrobenzo[b]thiophen-3-yl)-2-methylpropane-2-sulfinamide: 3-[4-(Difluoromethyl)-2,2-difluoro-1,1,3-trioxo-benzothiophen-5-yl]oxy-5-fluoro-benzonitrile was prepared previously according to Example 113, Steps A-G. A solution of 3-[4-(difluoromethyl)-2,2-difluoro-1,1,3-trioxo-benzothiophen-5-yl]oxy-5-fluoro-benzonitrile (100 mg, 0.25 mmol) and (R)-2-methylpropane-2-sulfinamide (36 mg, 0.30 mmol) in tetrahydrofuran (2.5 mL) was treated with titanium (IV) ethoxide (105 μL, 0.50 mmol) and heated to 50° C. for 3 hours. The reaction mixture was cooled to 0° C. and treated with sodium triacetoxyborohydride (52.6 mg, 0.25 mmol). After 1 hour an additional portion of sodium triacetoxyborohydride (52.6 mg, 0.25 mmol) was added to drive the reaction to completion. Following an additional 2 hours of reaction, the ice bath was removed and the vigorously stirred reaction mixture was quenched by the addition of 2.5 mL of brine. After 20 minutes, the resulting suspension was filtered through celite and the filter cake washed extensively with EtOAc. The filtrate was poured into 20 mL of water and extracted with 3×20 mL EtOAc. The combined organics were rinsed with 10 mL of brine, dried with MgSO$_4$, filtered, and concentrated to dryness. Purification was achieved by chromatography on silica using 10-40% EtOAc/CHCl$_3$ to afford a white solid (62 mg, 49%). LCMS ESI (+) (M+H) m/z 507.

Step B: Preparation of (S)-3-((3-amino-4-(difluoromethyl)-2,2-difluoro-1,1-dioxido-2,3-dihydrobenzo[b]thiophen-5-yl)oxy)-5-fluorobenzonitrile: A solution of (R)—N—((S)-5-(3-cyano-5-fluorophenoxy)-4-(difluoromethyl)-2,2-difluoro-1,1-dioxido-2,3-dihydrobenzo[b]thiophen-3-yl)-2-methylpropane-2-sulfinamide (62 mg, 0.12 mmol) in methanol (1.2 mL) at 25° C. was treated with a solution of 4 M HCl in dioxane (230 μL, 1.22 mmol) and stirred at 25° C. After 2 hours, volatiles were removed by concentration under reduced pressure. The reaction mixture was poured into 10 mL of saturated aqueous NaHCO$_3$ and extracted with 3×10 mL EtOAc. The combined organics were rinsed with 10 mL of brine, dried with MgSO$_4$, filtered, and concentrated to dryness. Purification was achieved by chromatography on silica using 10-35% EtOAc/hexane to afford Compound 148 as a white foam (37 mg, 76%). LCMS ESI (+) (M+H) m/z 405; $^1$H NMR (400 MHz, CDCl$_3$): δ 7.95 (d, 1H), 7.31-7.27 (m, 1H), 7.30 (dd, 1H), 7.19-7.14 (m, 2H), 7.07 (dt, 1H), 5.01-4.91 (dd, 1H), 2.06-1.99 (m, 2H).

Example 149

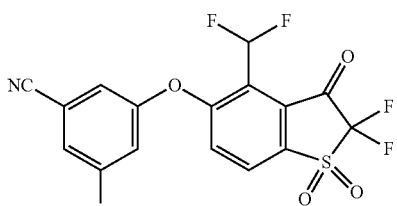

3-((4-(Difluoromethyl)-2,2-difluoro-1,1-dioxido-3-oxo-2,3-dihydrobenzo[b]thiophen-5-yl)oxy)-5-fluorobenzonitrile (Compound 149): Prepared similarly according to Example 113. Compound 149 exists as a hydrate in (CD$_3$)$_2$SO. $^1$H NMR (400 MHz, (CD$_3$)$_2$SO): δ 8.79 (s, 2H), 8.27 (d, 1H), 7.78-7.73 (m, 1H), 7.72 (t, 1H), 7.55-7.47 (m, 3H).

Example 150

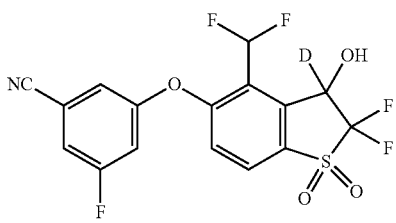 [SMILES: [2H]C1(O)c2c(ccc(Oc3cc(F)cc(C#N)c3)c2C(F)F)S(=O)(=O)C1(F)F]

3-((4-(Difluoromethyl)-2,2-difluoro-3-hydroxy-1,1-dioxido-2,3-dihydrobenzo[b]thiophen-5-yl-3-d)oxy)-5-fluorobenzonitrile (Compound 150): Prepared similarly as described in Example 135. Purification was achieved by chromatography on silica using 10-40% EtOAc/hexane to afford Compound 150 as a thin film (32 mg, 90%). LCMS ESI (−) (M−H) m/z 405; $^1$H NMR (400 MHz, CDCl$_3$): δ 7.98 (d, 1H), 7.33-7.30 (m, 1H), 7.23 (t, 1H), 7.22-7.18 (m, 2H), 7.08 (dt, 1H), 3.12 (s, 1H).

Example 151

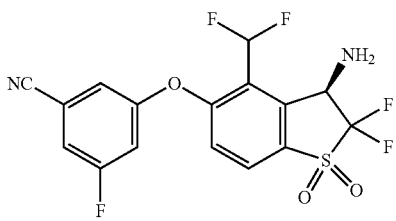

(R)-3-((3-Amino-4-(difluoromethyl)-2,2-difluoro-1,1-dioxido-2,3-dihydrobenzo[b]thiophen-5-yl)oxy)-5-fluorobenzonitrile (Compound 151): Prepared similarly according to Example 148, substituting (S)-2-methylpropane-2-sulfinamide for (R)-2-methylpropane-2-sulfinamide. Purification was achieved by chromatography on silica using 10-35% EtOAc/hexanes to afford Compound 151 as a white foam (31 mg, 68%). LCMS ESI (+) (M+H) m/z 405; $^1$H NMR (400 MHz, CDCl$_3$): δ 7.94 (d, 1H), 7.30 (d, 1H), 7.31-7.27 (m, 1H), 7.19-7.14 (m, 2H), 7.08 (dt, 1H), 5.02-4.89 (m, 1H), 2.12-1.92 (m, 2H).

Example 152

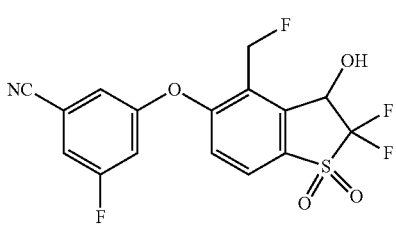 [SMILES: N#Cc1cc(F)cc(Oc2ccc3c(c2CF)C(O)C(F)(F)S3(=O)=O)c1]

3-((2,2-Difluoro-4-(fluoromethyl)-3-hydroxy-1,1-dioxido-2,3-dihydrobenzo[b]thiophen-5-yl)oxy)-5-fluorobenzonitrile (Compound 152)

Step A: Preparation of (2-bromo-3,6-difluorophenyl)methanol: A solution of 2-bromo-3,6-difluoro-benzaldehyde (1 g, 4.5 mmol) in methanol (9.0 mL) at 0° C. was treated with sodium borohydride (205 mg, 5.4 mmol) and stirred at 0° C. for 1 hour. The reaction mixture was quenched by the addition of 2 mL of water and 1 mL of saturated aqueous NH$_4$Cl. Volatiles were removed by concentration under reduced pressure. The residue was poured into 20 mL of water and extracted with 3×20 mL EtOAc. The combined organics were rinsed with 10 mL of brine, dried with MgSO$_4$, filtered, and concentrated to dryness. The product was used without further purification. LCMS ESI (+) (M−OH) m/z 205/207.

Step B: Preparation of 3-((2,2-difluoro-4-(fluoromethyl)-3-hydroxy-1,1-dioxido-2,3-dihydrobenzo[b]thiophen-5-yl)oxy)-5-fluorobenzonitrile: Prepared similarly according to Example 113, Steps A-H, substituting (2-bromo-3,6-difluorophenyl)methanol for 3,6-difluoro-benzaldehyde. Purification was achieved by chromatography on silica using 10-45% EtOAc/hexane to afford Compound 152 as a white solid (7.7 mg, 69%). LCMS ESI (+) (M+NH$_4$) m/z 405; $^1$H NMR (400 MHz, CDCl$_3$): δ 7.90 (d, 1H), 7.29-7.25 (m, 1H), 7.19 (d, 1H), 7.16-7.14 (m, 1H), 7.06-7.01 (m, 1H), 5.75 (d, 2H), 5.58 (br d, 1H), 3.30-3.22 (m, 1H).

Example 153

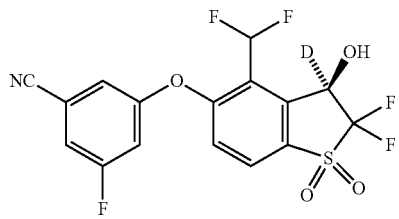 [SMILES: [2H][C@@]1(O)c2c(ccc(Oc3cc(F)cc(C#N)c3)c2C(F)F)S(=O)(=O)C1(F)F]

(R)-3-((4-(Difluoromethyl)-2,2-difluoro-3-hydroxy-1,1-dioxido-2,3-dihydrobenzo[b]thiophen-5-yl-3-d)oxy)-5-fluorobenzonitrile (Compound 153): A solution of 3-[4-(difluoromethyl)-2,2-difluoro-1,1,3-trioxo-benzothiophen-5-yl]oxy-5-fluoro-benzonitrile (1 g, 2.48 mmol) in dicholoromethane (40 mL) cooled to 0° C. was treated with d-2 formic acid (95% wt in deuterium oxide, 280 µL, 7.44 mmol) and triethylamine (690 µL, 4.96 mmol). The resulting mixture was sparged with nitrogen for 5 minutes. Then, under continuous stream of nitrogen, [N-[(1S,2S)-2-(amino-κN)-1,2-diphenylethyl]-4-methylbenzenesulfonamidato-κN]chloro [(1,2,3,4,5,6-η)-1,3,5-trimethylbenzene]-ruthenium (15.4 mg, 0.025 mmol, also known as RuCl[(S,S)-Tsdpen](mesitylene)) was added. The reaction vessel was sealed and transferred to a 4° C. refrigerator where the vessel remained for 24 hours. The reaction mixture was poured into 50 mL of water and extracted with 3×20 mL CH$_2$Cl$_2$. The combined organics were rinsed with 10 mL of saturated aqueous NaHCO$_3$, dried with MgSO$_4$, filtered, and concentrated to dryness. Purification was achieved by chromatography on silica using 10-40% EtOAc/hexane to give Compound 153. Enrichment of the desired enantiomer was achieved by crystallization using the following procedure. The sample was heated in a minimum amount of chloroform until chomogeneous. Upon cooling, solid precipitated. The solid was filtered and the filtrate was concentrated. The process was repeated 2 more times with a realization of about 2 fold improvement in % ee. A starting enantiomeric excess of about 65% was improved to about 94% over 3 crystallizations. Enantiomeric excess was evaluated using $^{19}$F NMR analysis of the corresponding Mosher ester. Compound 153 was isolated as a white solid (300 mg, 30% yield, >95% deuterium incorporation, 94% ee). LCMS ESI (−) (M−H) m/z 405; $^1$H NMR (400 MHz, CDCl$_3$): δ 7.98 (d, 1H), 7.33-7.30 (m, 1H), 7.23 (t, 1H), 7.22-7.18 (m, 2H), 7.08 (dt, 1H), 3.12 (s, 1H).

Example 154

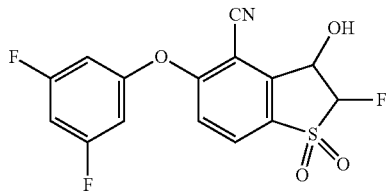 [SMILES: N#Cc1c(Oc2cc(F)cc(F)c2)ccc2c1C(O)C(F)S2(=O)=O]

5-(3,5-Difluorophenoxy)-2-fluoro-3-hydroxy-2,3-dihydrobenzo[b]thiophene-4-carbonitrile 1,1-dioxide (Compound 154)

Step A: Preparation of 4-bromo-5-(3,5-difluorophenoxy)-2-fluorobenzo[b]thiophen-3(2H)-one 1,1-dioxide: 4-Bromo-5-(3,5-difluorophenoxy)-2-fluorobenzo[b]thiophen-3(2H)-one 1,1-dioxide was prepared similarly according to Example 111, Steps A-C, substituting 3,5-difluorophenol for 3-fluoro-5-hydroxy-benzonitrile. A solution of 4-bromo-5-(3,5-difluorophenoxy)-1,1-dioxo-benzothiophen-3-one (200 mg, 0.51 mmol) in acetonitrile (12.5 mL) was treated with Selectfluor® (1.14 g, 3.1 mmol) and heated at 120° C. by microwave irradiation for 2.5 hours. The resulting residue was purified by chromatography on silica using 5-20% EtOAc/hexane to afford the title compound as an off-white solid (25 mg, 12%).

Step B: Preparation of 4-bromo-5-(3,5-difluorophenoxy)-2-fluoro-3-hydroxy-2,3-dihydrobenzo[b]thiophene 1,1-dioxide: A solution of 4-bromo-5-(3,5-difluorophenoxy)-2-fluorobenzo[b]thiophen-3(2H)-one 1,1-dioxide (25 mg, 0.06 mmol) in dicholoromethane (6 mL) cooled to 0° C. was treated with formic acid (6.9 µL, 0.18 mmol) and triethylamine (17 µL, 0.12 mmol). The resulting mixture was sparged with nitrogen for 5 minutes. Then, under continuous stream of nitrogen, N-[(1R,2R)-1,2-diphenyl-2-(2-(4-methylbenzyloxy)ethylamino)-ethyl]-4-methylbenzene sulfonamide(chloro)ruthenium(II) (1.0 mg, 0.0015 mmol, also known as RuCl[(R,R)-Ts-DENEB]) was added. The reaction vessel was sealed and transferred to a 4° C. refrigerator where the vessel remained for 24 hours. The reaction mixture was poured into 30 mL of water and extracted with 3×10 mL CH$_2$Cl$_2$. The combined organics were rinsed with 10 mL of saturated aqueous NaHCO$_3$, dried with MgSO$_4$, filtered, and concentrated to dryness. Purification was achieved by chromatography on silica using 10-50% EtOAc/hexane to afford a white solid (18 mg, 72%). LCMS ESI (+) (M+NH$_4$) m/z 426, 428; $^1$H NMR (400 MHz, CD$_3$CN): δ 7.85 (d, 1H), 7.37 (d, 1H), 6.89-6.82 (m, 1H), 6.78-6.70 (m, 2H), 5.79 (dd, 1H), 5.57 (t, 1H), 4.45 (d, 1H).

Step C: Preparation of 5-(3,5-difluorophenoxy)-2-fluoro-3-hydroxy-2,3-dihydrobenzo[b]thiophene-4-carbonitrile 1,1-dioxide (Compound 154): A solution of copper(I) cyanide (2.9 mg, 0.03 mmol) in 1-methyl-2-pyrrolidone (0.5 mL) was treated with 4-bromo-5-(3,5-difluorophenoxy)-2-fluoro-3-hydroxy-2,3-dihydrobenzo[b]thiophene 1,1-dioxide (10 mg, 0.025 mmol) and heated at 160° C. by microwave irradiation for 1 hour and 30 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 10-40% EtOAc/hexane to afford Compound 154 as a white solid (5.4 mg, 60%). LCMS ESI (+) (M+NH$_4$) m/z 373; $^1$H NMR (400 MHz, CD$_3$CN): δ 8.02 (d, 1H), 7.27 (d, 1H), 7.01-6.87 (m, 3H), 5.88-5.73 (m, 2H), 4.91 (d, 1H).

Example 155

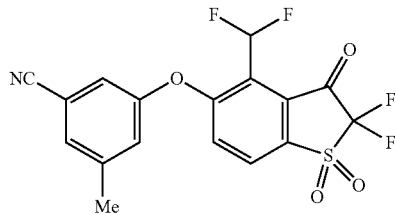 [SMILES: Cc1cc(C#N)cc(Oc2ccc3c(c2C(F)F)C(=O)C(F)(F)S3(=O)=O)c1]

3-((4-(Difluoromethyl)-2,2-difluoro-1,1-dioxido-3-oxo-2,3-dihydrobenzo[b]thiophen-5-yl)oxy)-5-methylbenzonitrile (Compound 155): Prepared similarly according to Example 113, Steps A-F, substituting 3-hydroxy-5-methylbenzonitrile for 3-fluoro-5-hydroxy-benzonitrile. Purification was achieved by chromatography on silica using 0-15% EtOAc/CH$_2$Cl$_2$ to afford to give Compound 155 as an off-white solid (292 mg, 94%). $^1$H NMR (400 MHz, CDCl$_3$): δ 8.13 (d, 1H), 7.67 (t, 1H), 7.53 (d, 1H), 7.43 (s, 1H), 7.21 (s, 1H), 7.15 (s, 1H), 2.45 (s, 3H).

Example 156

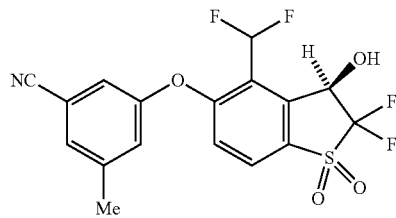 [SMILES: Cc1cc(C#N)cc(Oc2ccc3c(c2C(F)F)[C@@H](O)C(F)(F)S3(=O)=O)c1]

(R)-3-((4-(Difluoromethyl)-2,2-difluoro-3-hydroxy-1,1-dioxido-2,3-dihydrobenzo[b]thiophen-5-yl)oxy)-5-methylbenzonitrile (Compound 156): A solution of 3-((4-(difluoromethyl)-2,2-difluoro-1,1-dioxido-3-oxo-2,3-dihydrobenzo[b]thiophen-5-yl)oxy)-5-methylbenzonitrile (287 mg, 0.72 mmol) in dicholoromethane (11.4 mL) cooled to 0° C. was treated with formic acid (81 µL, 2.2 mmol) and triethylamine (200 µL, 1.4 mmol). The resulting mixture was sparged with nitrogen for 5 minutes. Then, under continuous stream of nitrogen, [N-[(1S,2S)-2-(amino-κN)-1,2-diphenylethyl]-4-methylbenzenesulfonamidato-κN]chloro[(1,2,3,4,5,6-η)-1,3,5-trimethylbenzene]-ruthenium (9 mg, 0.014 mmol, also known as RuCl[(S,S)-Tsdpen](mesitylene)) was added. The reaction vessel was sealed and transferred to a 4° C. refrigerator where the vessel remained for 24 hours. The reaction mixture was poured into 50 mL of water and extracted with 3×20 mL CH$_2$Cl$_2$. The combined organics were rinsed with 10 mL of saturated aqueous NaHCO$_3$, dried with MgSO$_4$, filtered, and concentrated to dryness. Purification was achieved by chromatography on silica using 10-40% EtOAc/hexane. Enrichment of the desired enantiomer was achieved under crystallization by the following procedure. The sample was heated in a minimum amount of 1:1 hexanes/CH$_2$Cl$_2$ solution until homogeneous. Upon cooling, solid precipitated. The solid was filtered and the filtrate concentrated. The process was repeated 2 more times. A starting enantiomeric excess of about 60% was improved to about 90% over 3 crystallizations. Enantiomeric excess was evaluated using $^{19}$F NMR analysis of the corresponding Mosher ester. Compound 156 was isolated as a white solid was isolated (58 mg, 20% yield, 90% ee). LCMS ESI (+) (M+NH$_4$) m/z 419; $^1$H NMR (400 MHz, CDCl$_3$): δ 7.91 (d, 1H), 7.41 (s, 1H), 7.27 (t, 1H), 7.21 (s, 1H), 7.13 (s, 1H), 7.10 (d, 1H), 5.71-5.64 (m, 1H), 3.04 (br d, 1H), 2.44 (s, 3H).

Example 157

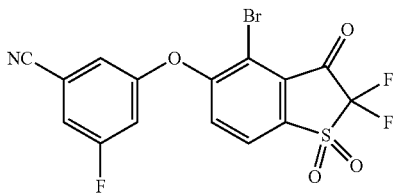 [SMILES: N#Cc1cc(F)cc(Oc2ccc3c(c2Br)C(=O)C(F)(F)S3(=O)=O)c1]

3-((4-Bromo-2,2-difluoro-1,1-dioxido-3-oxo-2,3-dihydrobenzo[b]thiophen-5-yl)oxy)-5-fluorobenzonitrile (Compound 157): Prepared similarly according to Example 111, Steps A-H, substituting 3-hydroxy-5-methylbenzonitrile for 3-fluoro-5-hydroxy-benzonitrile. Purification was achieved by chromatography on silica using 0-10% EtOAc/CH$_2$Cl$_2$ to afford Compound 157 as an off-white solid (292 mg, 94%). LCMS ESI (+) (M+H2O+NH4) m/z 467, 469; $^1$H NMR (400 MHz, CDCl$_3$): δ 8.05 (d, 1H), 7.55 (d, 1H), 7.30 (d, 1H), 7.13 (s, 1H), 7.07-7.02 (m, 1H).

Examples 158 and 159

Compound 158

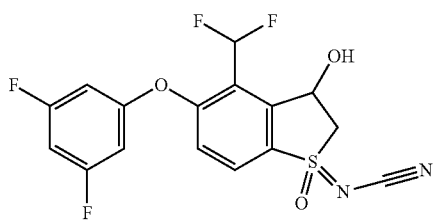

Compound 159

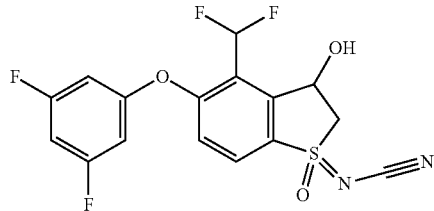

N-(4-(Difluoromethyl)-5-(3,5-difluorophenoxy)-3-hydroxy-1-oxido-2,3-dihydro-1λ$^4$-benzo[b]thiophen-1-ylidene)cyanamide (Compound 158) and N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 159)

Step A: Preparation of N-((2-cyano-3-(difluoromethyl)-4-fluorophenyl)(methyl)-λ$^4$-sulfanylidene)cyanamide: 2-(Difluoromethyl)-3-fluoro-6-(methylthio)benzonitrile was prepared similarly according to Example 113, Step A-C. (Diacetoxyiodo)benzene (890 mg, 2.76 mmol) was added to an ice-cold suspension of 2-(difluoromethyl)-3-fluoro-6-methylsulfanyl-benzonitrile (500 mg, 2.3 mmol) and cyanamide (126 mg, 3 mmol) in acetonitrile (23 mL). The ice bath was removed and the suspension slowly became a yellow solution. After 3 hours, the reaction mixture was poured into 100 mL of water containing and extracted with 3×30 mL EtOAc. The EtOAc was washed with brine, dried over MgSO$_4$, filtered, and evaporated. Purification was achieved by chromatography on silica using 60-100% EtOAc/hexane to afford a beige solid (360 mg, 61%). LCMS ESI (+) (M+H) m/z 258.

Step B: Preparation of N-((2-cyano-3-(difluoromethyl)-4-fluorophenyl)(methyl)(oxo)-λ$^6$-sulfanylidene)cyanamide: A solution of N-((2-cyano-3-(difluoromethyl)-4-fluorophenyl)(methyl)-λ$^4$-sulfanylidene)cyanamide (360 mg, 1.40 mmol) and ruthenium(III) trichloride (5.8 mg, 0.028 mmol) in a 1:1:2 mixture of CH$_3$CN/CCl$_4$/H$_2$O (26 mL) was treated with sodium periodate (449 mg, 2.1 mmol) and stirred at 25° C. for 30 minutes. The reaction mixture was poured into 100 mL of water and extracted with 3×20 mL EtOAc. The EtOAc was washed with brine, dried over MgSO$_4$, filtered, and evaporated. The product residue was used without further purification. LCMS ESI (+) (M+H) m/z 274.

Step C: Preparation of N-(3-amino-4-(difluoromethyl)-5-(3,5-difluorophenoxy)-1-oxido-1λ4-benzo[b]thiophen-1-ylidene)cyanamide: A solution of N-((2-cyano-3-(difluoromethyl)-4-fluorophenyl)(methyl)(oxo)-λ$^6$-sulfanylidene)cyanamide (390 mg, 1.40 mmol), 3,5-difluorophenol (186 mg, 1.43 mmol), and cesium bicarbonate (830 mg, 4.28 mmol) in N,N-dimethylformamide (3.6 mL) was stirred at 50° C. overnight. The reaction mixture was quenched by diluting with 40 mL of water and extracting with 6×15 mL Et$_2$O. The combined organics were rinsed with 10 mL of brine, dried with MgSO$_4$, filtered, and concentrated to dryness. The crude product was used without further purification. LCMS ESI (+) (M+H) m/z 384.

Step D: Preparation of N-(4-(difluoromethyl)-5-(3,5-difluorophenoxy)-1-oxido-3-oxo-2,3-dihydro-1λ$^4$-benzo[b]thiophen-1-ylidene)cyanamide: A solution of N-(3-amino-4-(difluoromethyl)-5-(3,5-difluorophenoxy)-1-oxido-1λ$^4$-benzo[b]thiophen-1-ylidene)cyanamide (347 mg, 0.91 mmol) in methanol (7 mL) at 25° C. was treated with 1 M aqueous HCl (2.72 mL, 2.72 mmol). The resulting mixture was stirred at 40° C. for 1 hour. Volatiles were removed by concentration under reduced pressure and the residue poured into 30 mL of water and extracted with 3×15 mL 30% isopropyl alcohol/CHCl$_3$. The combined organics were rinsed with 10 mL of brine, dried with MgSO$_4$, filtered, and concentrated to dryness. The product residue was used without further purification. LCMS ESI (+) (M+H) m/z 385.

Step E: Preparation of N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 158) and N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 159): A solution of N-(4-(difluoromethyl)-5-(3,5-difluorophenoxy)-1-oxido-3-oxo-2,3-dihydro-1λ$^4$-benzo[b]thiophen-1-ylidene)cyanamide (60 mg, 0.16 mmol) in methanol (1.6 mL) at 0° C. was treated with sodium borohydride (5.9 mg, 0.16 mmol) and stirred at 0° C. for 30 minutes. The reaction mixture was quenched by the addition of 0.5 mL of water and 0.25 mL of saturated aqueous NH$_4$Cl. Volatiles were removed by concentration under reduced pressure. The reaction mixture was poured into 10 mL water and extracted with 3×10 mL 30% isopropyl alcohol/CHCl$_3$. The combined organics were rinsed with 10 mL of brine, dried with MgSO$_4$, filtered, and concentrated to dryness. Purification was achieved by chromatography on silica using 10-40% EtOAc/CHCl$_3$ to afford N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 158) as a thin film (1.1 mg, 1.8%) and N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 159) as a thin film (0.9 mg, 1.5%).

Data for N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 158): HPLC retention time=2.62 minutes; LCMS ESI (+) (M+H) m/z 387; $^1$H NMR (400 MHz, CDCl$_3$): δ 8.01 (d, 1H), 7.28 (t, 1H), 7.21 (d, 1H), 6.83-6.76 (m, 1H), 6.69-6.63 (m, 2H), 6.03-5.97 (m, 1H), 4.20 (dd, 1H), 3.88 (dd, 1H), 3.15-3.11 (m, 1H).

Data for N-(4-(difluoromethyl)-5-(3,5-difluorophenoxy)-3-hydroxy-1-oxido-2,3-dihydro-1λ$^4$-benzo[b]thiophen-1-ylidene)cyanamide (Compound 159): HPLC retention time=2.56 minutes; LCMS ESI (+) (M+H) m/z 387; $^1$H NMR (400 MHz, CDCl$_3$): δ 7.97 (d, 1H), 7.26 (t, 1H), 7.21 (d, 1H), 6.83-6.76 (m, 1H), 6.70-6.63 (m, 2H), 5.99 (t, 1H), 4.08-4.02 (m, 1H), 3.98 (dd, 1H), 3.20-3.15 (m, 1H).

Example 160

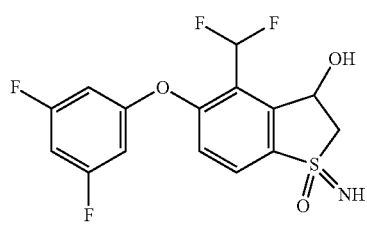 [SMILES: N=S1(=O)CC(O)c2c1ccc(Oc1cc(F)cc(F)c1)c2C(F)F]

4-(Difluoromethyl)-5-(3,5-difluorophenoxy)-3-hydroxy-1-imino-2,3-dihydro-1H-1λ$^4$-benzo[b]thiophene 1-oxide (Compound 160)

Step A: Preparation of 4-(difluoromethyl)-5-(3,5-difluorophenoxy)-1-imino-1,2-dihydro-3H-1λ$^4$-benzo[b]thiophen-3-one 1-oxide: A solution of N-(4-(difluoromethyl)-5-(3,5-difluorophenoxy)-1-oxido-3-oxo-2,3-dihydro-1λ$^4$-benzo[b]thiophen-1-ylidene)cyanamide (80 mg, 0.21 mmol) in 1,4-dioxane (1.3 mL) was treated with aqueous concentrated HCl (0.6 mL, 7.2 mmol) and heated to 120° C. by microwave irradiation for 30 minutes. Volatiles were removed by concentration under reduced pressure. The reaction mixture was poured into 10 mL of water and extracted with 3×20 mL EtOAc. The combined organics were rinsed with 10 mL of brine, dried with MgSO$_4$, filtered, and concentrated to dryness. Purification was achieved by chromatography on silica using 20-60% EtOAc/hexane to afford an off-white solid (35.4 mg, 48%).

Step B: Preparation of 4-(difluoromethyl)-5-(3,5-difluorophenoxy)-3-hydroxy-1-imino-2,3-dihydro-1H-1λ$^4$-benzo[b]thiophene 1-oxide: A solution of 4-(difluoromethyl)-5-(3,5-difluorophenoxy)-1-imino-1-oxo-benzothiophen-3-one (35 mg, 0.1 mmol) in methanol (2 mL) at 0° C. was treated with sodium borohydride (3.7 mg, 0.1 mmol) and stirred at 0° C. for 30 minutes. The reaction was quenched by the addition of 0.5 mL of water and 0.25 mL saturated aqueous NH$_4$Cl. Volatiles were removed by concentration under reduced pressure. The reaction mixture was poured into 10 mL of water and extracted with 3×10 mL 30% isopropyl alcohol/CHCl$_3$. The combined organics were rinsed with 10 mL of brine, dried with MgSO$_4$, filtered, and concentrated to dryness. Purification was achieved by chromatography on silica using 0-4% MeOH/CHCl$_3$ (6.8 mg, 19%). HPLC retention time=2.27 minutes; LCMS ESI (+) (M+H) m/z 362; $^1$H NMR (400 MHz, CDCl$^3$): δ 7.80 (d, 1H), 7.17 (t, 1H), 7.12 (d, 1H), 6.74-6.67 (m, 1H), 6.62-6.55 (m, 2H), 5.80-5.74 (m, 1H), 3.80 (dd, 1H), 3.75-3.69 (m, 2H), 3.41-3.34 (m, 1H).

Example 161

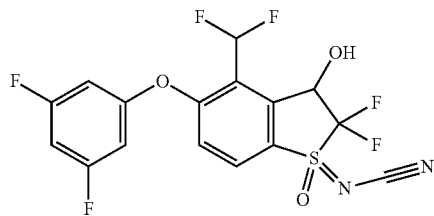

Compound 51

N-(4-(Difluoromethyl)-5-(3,5-difluorophenoxy)-2,2-difluoro-3-hydroxy-1-oxido-2,3-dihydro-1λ$^4$-benzo[b]thiophen-1-ylidene)cyanamide (Compound 161)

Step A: Preparation of 4-(difluoromethyl)-5-(3,5-difluorophenoxy)-2,2-difluoro-1-imino-1,2-dihydro-3H-1λ$^4$-benzo[b]thiophen-3-one 1-oxide: A solution of N-(4-(difluoromethyl)-5-(3,5-difluorophenoxy)-1-oxido-3-oxo-2,3-dihydro-1λ$^4$-benzo[b]thiophen-1-ylidene)cyanamide (54 mg, 0.14 mmol) in acetonitrile (1.4 mL) at 25° C. was treated with sodium carbonate (32.7 mg, 0.31 mmol). Selectfluor® (109 mg, 0.31 mmol) was added and the reaction mixture left to stir at 25° C. for 1.5 hours. Volatiles were removed by concentration under reduced pressure and the residue was poured into 30 mL of water and extracted with 3×20 mL EtOAc. The combined organics were rinsed with 10 mL of brine, dried with MgSO$_4$, filtered, and concentrated to dryness. Purification was achieved by chromatography on silica using 0%-4% MeOH/CHCl₃ to afford an off-white solid (16 mg, 27%). LCMS ESI (+) (M+H) m/z 421.

Step B: Preparation of N-(4-(difluoromethyl)-5-(3,5-difluorophenoxy)-2,2-difluoro-3-hydroxy-1-oxido-2,3-dihydro-1λ⁴-benzo[b]thiophen-1-ylidene)cyanamide: A solution of [4-(difluoromethyl)-5-(3,5-difluorophenoxy)-2,2-difluoro-1,3-dioxo-benzothiophen-1-ylidene]cyanamide (16.1 mg, 0.038 mmol) in tetrahydrofuran (1.5 mL) at 25° C. was treated with sodium triacetoxyborohydride (12.2 mg, 0.058 mmol) and stirred at 25° C. for 1 hour. Volatiles were removed by concentration under reduced pressure. The reaction mixture was poured into 10 mL of water and extracted with 3×10 mL EtOAc. The combined organics were rinsed with 10 mL of brine, dried with MgSO₄, filtered, and concentrated to dryness. Purification was achieved by chromatography on silica using 0-20% EtOAc/CHCl₃ to afford Compound 161 as a white solid (6.9 mg, 43%). HPLC retention time=2.90 minutes; LCMS ESI (+) (M+H) m/z 423; ¹H NMR (400 MHz, CDCl₃): δ 8.07-8.00 (m, 1H), 7.42-7.13 (m, 2H), 6.87-6.80 (m, 1H), 6.73-6.66 (m, 2H), 5.83-5.76 (m, 1H), 3.78-3.66 (m, 1H).

Examples 162 and 163

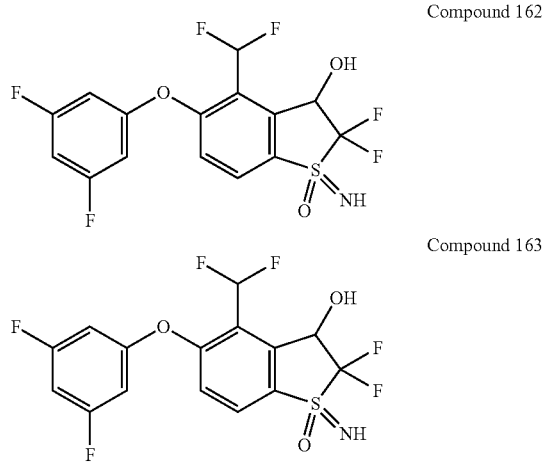

Compound 162

Compound 163

4-(Difluoromethyl)-5-(3,5-difluorophenoxy)-2,2-difluoro-3-hydroxy-1-imino-2,3-dihydro-1H-1λ⁴-benzo[b]thiophene 1-oxide (Compound 162) and 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 163)

Step A: Preparation of 4-(difluoromethyl)-5-(3,5-difluorophenoxy)-2,2-difluoro-1-imino-1,2-dihydro-3H-1λ⁴-benzo[b]thiophen-3-one 1-oxide: A solution of 4-(difluoromethyl)-5-(3,5-difluorophenoxy)-1-imino-1-oxo-benzothiophen-3-one (22.7 mg, 0.063 mmol) in acetonitrile (1.3 mL) at 25° C. was treated with sodium carbonate (14.7 mg, 0.14 mmol). Selectfluor® (49 mg, 0.14 mmol) was added and the reaction mixture left to stir at 25° C. for 1.5 hour. Volatiles were removed by concentration under reduced pressure and the residue was poured into 30 mL of water and extracted with 3×20 mL EtOAc. The combined organics were rinsed with 10 mL of brine, dried with MgSO₄, filtered, and concentrated to dryness. The product was used without further purification. LCMS ESI (−) (M−H) m/z 394.

Step B: Preparation of 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 162) and 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 163): A solution of 4-(difluoromethyl)-5-(3,5-difluorophenoxy)-2,2-difluoro-1-imino-1,2-dihydro-3H-1λ⁴-benzo[b]thiophen-3-one 1-oxide (27.3 mg, 0.069 mmol) in methanol (1.4 mL) at 0° C. was treated with sodium borohydride (2.9 mg, 0.076 mmol) and stirred at 0° C. for 30 minutes. The reaction mixture was quenched by the addition of 0.25 mL of saturated aqueous NH₄Cl and 0.5 mL of water. Volatiles were removed by concentration under reduced pressure. The reaction mixture was poured into 20 mL of water and extracted with 3×15 mL EtOAc. The combined organics were rinsed with 10 mL of brine, dried with MgSO₄, filtered, and concentrated to dryness. Purification was achieved by chromatography on silica using 15-20% EtOAc/CHCl₃ to afford 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 162) as a white solid (2.7 mg, 10%) and 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 163) as a white solid (1.7 mg, 6.2%).

Data for 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 162): Retention time=2.54 minutes; LCMS ESI (+) (M+H) m/z 398; ¹H NMR (400 MHz, CDCl₃): δ 8.02 (d, 1H), 7.22 (t, 1H), 7.19 (d, 1H), 6.79-6.72 (m, 1H), 6.66-6.59 (m, 2H), 5.60 (t, 1H), 3.39 (br s, 1H), 3.12 (d, 1H).

Data for 4-(difluoromethyl)-5-(3,5-difluorophenoxy)-2,2-difluoro-3-hydroxy-1-imino-2,3-dihydro-1H-1λ⁴-benzo[b]thiophene 1-oxide (Compound 163): Retention time=2.65 minutes; LCMS ESI (+) (M+H) m/z 398; ¹H NMR (400 MHz, CDCl₃): δ 7.95 (d, 1H), 7.23 (t, 1H), 7.19 (d, 1H), 6.79-6.72 (m, 1H), 6.66-6.59 (m, 2H), 5.64 (t, 1H), 3.68 (br s, 1H), 3.33 (d, 1H).

Example 164

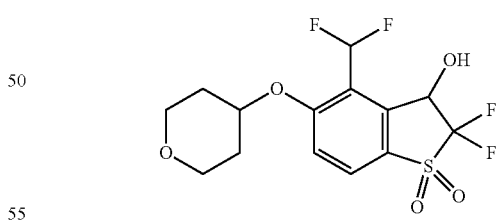

4-(Difluoromethyl)-2,2-difluoro-3-hydroxy-5-((tetrahydro-2H-pyran-4-yl)oxy)-2,3-dihydrobenzo[b]thiophene 1,1-dioxide (Compound 164)

Step A: Preparation of 2-(difluoromethyl)-6-(methylthio)-3-((tetrahydro-2H-pyran-4-yl)oxy)benzonitrile: A solution of tetrahydro-4-pyranol (160 μL, 1.66 mmol) in dimethyl sulfoxide (3.7 mL) at 25° C. was treated with sodium hydride, 60% dispersion in mineral oil (60.8 mg, 1.52 mmol) and stirred at 25° C. for 2 hours. 2-(Difluoromethyl)-3- fluoro-6-methylsulfanyl-benzonitrile (300 mg, 1.38 mmol) was added directly to the opaque solution of the alkoxide. After 2.5 hours, the reaction mixture was poured into 30 mL of water and extracted with 3×15 mL EtOAc. The combined organics were rinsed with 10 mL of brine, dried with MgSO$_4$, filtered, and concentrated to dryness. Purification was achieved by chromatography on silica using 30-80% EtOAc/hexanes to afford a white solid (253 mg, 61%). LCMS ESI (+) (M+H) m/z 300.

Step B: Preparation of 2-(difluoromethyl)-6-(methylsulfonyl)-3-((tetrahydro-2H-pyran-4-yl)oxy)benzonitrile: A solution of 2-(difluoromethyl)-6-(methylthio)-3-((tetrahydro-2H-pyran-4-yl)oxy)benzonitrile (175 mg, 0.58 mmol) in dichloromethane (5.8 mL) at 25° C. was treated with 3-chloroperbenzoic acid (~70% by wt, 346 mg, 1.4 mmol) and stirred at 25° C. for 2 hours. The reaction mixture was poured into 20 mL of 1 M NaOH and extracted with 3×20 mL CH$_2$Cl$_2$. The combined organics were rinsed with 20 mL of brine, dried with MgSO$_4$, filtered, and concentrated to dryness. The resulting white solid was used without further purification. LCMS ESI (+) (M+NH$_4$) m/z 349.

Step C: Preparation of 4-(difluoromethyl)-5-((tetrahydro-2H-pyran-4-yl)oxy)benzo[b]thiophen-3(2H)-one 1,1-dioxide: A solution of 2-(difluoromethyl)-6-(methylsulfonyl)-3-((tetrahydro-2H-pyran-4-yl)oxy)benzonitrile (193 mg, 0.58 mmol) in tetrahydrofuran (12 mL) at 25° C. was treated with sodium hydride (35 mg, 0.87 mmol) and stirred at 25° C. for 2 hours. The reaction mixture was treated with 12 mL of a 3:1 mixture of MeOH/10% aqueous HCl. The resulting mixture was stirred for 1 hour and then the volatile portion was removed by concentration under reduced pressure. The reaction mixture was extracted with 3×20 mL EtOAc. The combined organics were rinsed with 10 mL of brine, dried with MgSO$_4$, filtered, and concentrated to dryness. Purification was achieved by chromatography on silica using 30-70% EtOAc/hexanes to afford a white solid (48 mg, 25%). LCMS ESI (+) (M+H) m/z 333.

Step D: Preparation of 4-(difluoromethyl)-2,2-difluoro-5-((tetrahydro-2H-pyran-4-yl)oxy)benzo[b]thiophen-3(2H)-one 1,1-dioxide: A solution of 4-(difluoromethyl)-5-((tetrahydro-2H-pyran-4-yl)oxy)benzo[b]thiophen-3(2H)-one 1,1-dioxide (48 mg, 0.14 mmol) in acetonitrile (2.9 mL) at 25° C. was treated with sodium carbonate (33.7 mg, 0.32 mmol). Selectfluor® (113 mg, 0.32 mmol) was added and the reaction mixture left to stir at 25° C. for 1.5 hours. Volatiles were removed by concentration under reduced pressure and the residue was poured into 30 mL of water and extracted with 3×20 mL EtOAc. The combined organics were rinsed with 10 mL of brine, dried with MgSO$_4$, filtered, and concentrated to dryness. The product was used without further purification. LCMS ESI (+) (M+H) m/z 369.

Step E: Preparation of 4-(difluoromethyl)-2,2-difluoro-3-hydroxy-5-((tetrahydro-2H-pyran-4-yl)oxy)-2,3-dihydrobenzo[b]thiophene 1,1-dioxide: A solution of 4-(difluoromethyl)-2,2-difluoro-5-((tetrahydro-2H-pyran-4-yl)oxy)benzo[b]thiophen-3(2H)-one 1,1-dioxide (50 mg, 0.14 mmol) in methanol (2.8 mL) at 0° C. was treated with sodium borohydride (5.1 mg, 0.14 mmol) and stirred at 0° C. for 30 minutes. The reaction mixture was quenched by the addition of 0.5 mL of saturated aqueous NH$_4$Cl and 1.0 mL of water. Volatiles were removed by concentration under reduced pressure. The reaction mixture was poured into 20 mL of water and extracted with 3×15 mL EtOAc. The combined organics were rinsed with 10 mL of brine, dried with MgSO$_4$, filtered, and concentrated to dryness. Purification was achieved by chromatography on silica using 30-80% EtOAc/hexanes to afford Compound 164 as a white solid (12 mg, 23%). LCMS ESI (+) (M+H) m/z 387; $^1$H NMR (400 MHz, CD$_3$OD): δ 7.99 (d, 1H), 7.57 (d, 1H), 7.26 (t, 1H), 5.57-5.52 (m, 1H), 4.95-4.88 (m, 1H), 3.98-3.91 (m, 2H), 3.67-3.60 (m, 2H), 2.32-2.03 (m, 2H), 1.86-1.76 (m, 2H).

Example 165

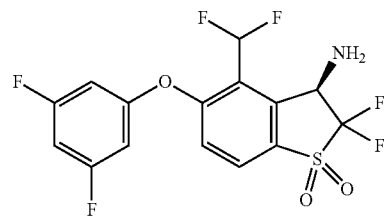 [SMILES: N[C@@H]1c2c(ccc(Oc3cc(F)cc(F)c3)c2C(F)F)S(=O)(=O)C1(F)F]

(R)-3-Amino-4-(difluoromethyl)-5-(3,5-difluorophenoxy)-2,2-difluoro-2,3-dihydrobenzo[b]thiophene 1,1-dioxide (Compound 165): Prepared similarly according to Example 151. Purification was achieved by chromatography on silica using 5-25% EtOAc/hexane to afford Compound 165 as a white solid (44.1 mg, 86%). LCMS ESI (+) (M+H) m/z 398; $^1$H NMR (400 MHz, CDCl$_3$): δ 7.90 (d, 1H), 7.29 (t, 1H), 7.16 (d, 1H), 6.76 (tt, 1H), 6.67-6.60 (m, 2H), 5.02-4.93 (m, 1H), 2.01 (br d, 2H).

Example 166

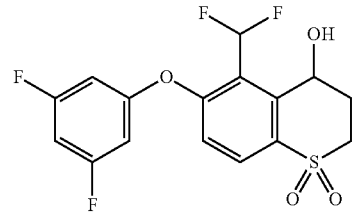 [SMILES: O=S1(=O)CCC(O)c2c1ccc(Oc1cc(F)cc(F)c1)c2C(F)F]

5-(Difluoromethyl)-6-(3,5-difluorophenoxy)-4-hydroxythiochromane 1,1-dioxide (Compound 166)

Step A: Preparation of 6-(benzylthio)-2-(difluoromethyl)-3-fluorobenzonitrile: A solution of 2-(difluoromethyl)-3,6-difluoro-benzonitrile (1.5 g, 7.93 mmol) in acetonitrile (40 mL, previously sparged with nitrogen for 5 minutes) at -40° C. was treated with sodium phenylmethanethiolate (1.16 g, 7.9 mmol) in 2 portions over 10 minutes. The resulting suspension was stirred initially at -40° C. and then allowed to slowly warm towards room temperature (the reaction remained immersed in the acetone bath during this time). The reaction was quenched when the temperature reached 10° C. The reaction mixture was poured into 300 mL of water and extracted with 3×100 mL Et$_2$O. The combined organics were rinsed with 20 mL of brine, dried with MgSO$_4$, filtered, and concentrated to dryness. Purification was achieved using reverse phase chromatography (Biotage Isolera One unit, C18 Flash 40+M column, 40-95% CH$_3$CN/water) to afford an off-white solid (650 mg, 28%). LCMS ESI (-) (M-H) m/z 293.

Step B: Preparation of 6-(benzylthio)-2-(difluoromethyl)-3-(3,5-difluorophenoxy)benzonitrile: A solution of 6-(benzylthio)-2-(difluoromethyl)-3-fluorobenzonitrile (800 mg, 2.73 mmol) and cesium hydrogen carbonate (582 mg, 3.0 mmol) in N,N-dimethylformamide (6.8 mL) was treated with 3,5-difluorophenol (355 mg, 2.73 mmol) and stirred at 100° C. for 2 hours. The reaction mixture was poured into 70 mL of water and extracted with 3×30 mL Et$_2$O. The combined organics were rinsed with 10 mL of brine, dried with MgSO$_4$, filtered, and concentrated to dryness. The product residue was used without further purification. LCMS ESI (+) (M+NH$_4$) m/z 421.

Step C: Preparation of 6-(benzylthio)-2-(difluoromethyl)-3-(3,5-difluorophenoxy)benzaldehyde: A solution of 6-(benzylthio)-2-(difluoromethyl)-3-(3,5-difluorophenoxy)benzonitrile (550 mg, 1.36 mmol) in dichloromethane (9 mL) at 0° C. was treated with diisobutylalumane (~1.0 M in heptane, 2.05 mL, 2.05 mmol) and stirred at 0° C. for 1 hour. Additional diisobutylalumane (600 μL, ~1.0 M in heptane) was added. After stirring for an additional 30 minutes, the reaction mixture was quenched by the addition of 8.5 mL of 10% aqueous HCl. The resulting mixture was stirred vigorously for 1 hour. Then the sample was treated with 8.5 mL of 20% aqueous potassium sodium tartrate and stirred vigorously an additional hour. The reaction mixture was basified with 10% aqueous NaOH. The reaction mixture was extracted with 3×20 mL CH$_2$Cl$_2$. The combined organics were rinsed with 20 mL of brine, dried with MgSO$_4$, filtered, and concentrated to dryness. The product residue was used without further purification. LCMS ESI (−) (M−H) m/z 405.

Step D: Preparation of 1-(6-(benzylthio)-2-(difluoromethyl)-3-(3,5-difluorophenoxy)phenyl)prop-2-en-1-ol: A solution of 6-(benzylthio)-2-(difluoromethyl)-3-(3,5-difluorophenoxy)benzaldehyde (91 mg, 0.22 mmol) in tetrahydrofuran (2.2 mL) at 0° C. was treated with vinylmagnesium bromide (~1.0 M in tetrahydrofuran, 220 μL, 0.22 mmol) and stirred at 0° C. for 30 minutes. The reaction was quenched by the addition of 10 mL of saturated aqueous NH$_4$Cl. The reaction mixture warmed to room temperature and was then poured into 10 mL of water and extracted with 3×15 mL EtOAc. The combined organics were rinsed with 10 mL of brine, dried with MgSO$_4$, filtered, and concentrated to dryness. Purification was achieved by chromatography on silica using 30-70% CH$_2$Cl$_2$/hexanes to afford a yellow solid (83 mg, 85%). LCMS ESI (−) (M−H) m/z 433.

Step E: Preparation of 1-(6-(benzylthio)-2-(difluoromethyl)-3-(3,5-difluorophenoxy)phenyl)prop-2-en-1-one: A solution of 1-(6-(benzylthio)-2-(difluoromethyl)-3-(3,5-difluorophenoxy)phenyl)prop-2-en-1-ol (83 mg, 0.19 mmol) in dichloromethane (1.9 mL) at 25° C. was treated with Dess-Martin periodinane (101 mg, 0.24 mmol) and stirred at 25° C. for 3 hours. The reaction mixture was diluted with water (2 mL) and treated with sodium thiosulfate pentahydrate (130 mg, 0.53 mmol). The resulting mixture was stirred for 30 minutes and was then poured into 20 mL of water and extracted with 3×10 mL CH$_2$Cl$_2$. The combined organics were rinsed with 10 mL of brine, dried with MgSO$_4$, filtered, and concentrated to dryness. The product residue was used without further purification. LCMS ESI (+) (M+H) m/z 433.

Step F: Preparation of 5-(difluoromethyl)-6-(3,5-difluorophenoxy)thiochroman-4-one: A vigorously stirred solution of 1-(6-(benzylthio)-2-(difluoromethyl)-3-(3,5-difluorophenoxy)phenyl)prop-2-en-1-one (21 mg, 0.05 mmol) in benzene (0.5 mL) at 25° C. was treated with aluminum chloride (10.8 mg, 0.08 mmol). After 1 hour, the reaction was quenched by the addition of ice chips. The reaction mixture was then diluted with 10 mL of CH$_2$Cl$_2$, poured into 10 mL of 1 M HCl and extracted with 3×10 mL CH$_2$Cl$_2$. The combined organics were rinsed with 10 mL of brine, dried with MgSO$_4$, filtered, and concentrated to dryness. Purification was achieved by chromatography on silica using 5-25% EtOAc/hexanes to afford a thin film (3.3 mg, 20%). LCMS ESI (−) (M−H) m/z 341.

Step G: Preparation of 5-(difluoromethyl)-6-(3,5-difluorophenoxy)thiochroman-4-ol: A solution of 5-(difluoromethyl)-6-(3,5-difluorophenoxy)thiochroman-4-one (3.3 mg, 0.01 mmol) in methanol (1 mL) at 25° C. was treated with sodium borohydride (0.36 mg, 0.01 mmol) and stirred at 25° C. for 1 hour. The reaction mixture was quenched by the addition of 0.25 mL of saturated NH$_4$Cl. Volatiles were removed by concentration under reduced pressure. The reaction mixture was poured into 10 mL of water and extracted with 3×10 mL EtOAc. The combined organics were rinsed with 10 mL of brine, dried with MgSO$_4$, filtered, and concentrated to dryness. The intermediate product residue was dissolved in dichloromethane (1 mL) and treated with 3-chloroperbenzoic acid (~70% by wt, 5.9 mg, 0.024 mmol). The reaction mixture stirred at 25° C. for 1.5 hours and was then poured into 10 mL of 1:1 mixture of 1 M NaOH and 20% Na$_2$S$_2$O$_3$ and extracted with 3×10 mL CH$_2$Cl$_2$. The combined organics were rinsed with 10 mL of brine, dried with MgSO4, filtered, and concentrated to dryness. Purification was achieved by chromatography on silica using 25-75% EtOAc/hexane to afford Compound 166 as a white solid (2.2 mg, 60%). LCMS ESI (+) (M+NH$_4$) m/z 394; $^1$H NMR (400 MHz, CDCl$_3$): δ 8.08 (d, 1H), 7.31 (t, 1H), 7.10 (d, 1H), 6.71 (tt, 1H), 6.61-6.54 (m, 2H), 5.52-5.48 (m, 1H), 4.05 (td, 1H), 3.32 (ddd, 1H), 2.84-2.74 (m, 1H), 2.73-2.64 (m, 2H).

Example 167

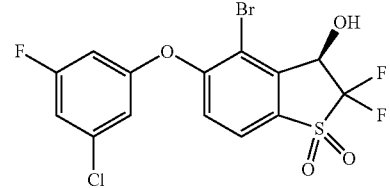 [SMILES: O=S1(=O)c2ccc(Oc3cc(F)cc(Cl)c3)c(Br)c2[C@@H](O)C1(F)F]

(3R)-4-Bromo-5-(3-chloro-5-fluoro-phenoxy)-2,2-difluoro-1,1-dioxo-3H-benzothiophen-3-ol (Compound 167)

Step A: Preparation of 4-bromo-5-(3-chloro-5-fluoro-phenoxy)-2,2-difluoro-1,1-dioxo-benzothiophen-3-one: Sodium carbonate (130 mg, 1.23 mmol) added all at once to 4-bromo-5-(3-chloro-5-fluoro-phenoxy)-1,1-dioxo-benzothiophen-3-one (226 mg, 0.56 mmol) in acetonitrile (6 mL) at room temperature under nitrogen and stirred for 45 minutes. Selectfluor® (434 mg, 1.23 mmol) was then added all at once and stirred for an additional 1 hour. The reaction mixture was concentrated to dryness in vacuo, diluted with water (20 mL), extracted with ethyl acetate (3×25 mL), washed with brine (20 mL), dried over MgSO$_4$, filtered and concentrated in vacuo. The crude product was purified on silica gel (10 g SNAP, 14 CV, 10-60% ethyl acetate/hexanes) affording 4-bromo-5-(3-chloro-5-fluoro-phenoxy)-2,2-difluoro-1,1-dioxo-benzothiophen-3-one (196 mg, 0.44 mmol, 80% yield) as a white solid.

Step B: Preparation of (3R)-4-bromo-5-(3-chloro-5-fluoro-phenoxy)-2,2-difluoro-1,1-dioxo-3H-benzothiophen- 3-ol (Compound 167): Chloro{[(1S,2S)-(+)-2-amino-1,2-diphenylethyl](4-toluenesulfonyl)amido}(p-cymene)ruthenium(II) (RuCl(p-cymene)[(S,S)-Ts-DPEN], 0.5 mg, 0.0008 mmol) was added all at once to a degassed mixture of 4-bromo-5-(3-chloro-5-fluoro-phenoxy)-2,2-difluoro-1,1-dioxo-benzothiophen-3-one (16 mg, 0.04 mmol), triethylamine (6 µL, 0.04 mmol) and formic acid (2 µL, 0.05 mmol) in dichloromethane (350 µL) at room temperature in a reaction vial equipped with a stir bar under a stream of nitrogen. The reaction vial was then tightly sealed with a teflon lined cap and stirred for 2 hours. The reaction mixture was purified directly on silica gel (10 g SNAP, 14 CV, 5-60% EtOAc/hexane) affording Compound 167 (12 mg, 0.03 mmol, 77% yield) as a clear oil. LCMS ESI (−) m/z 441, 443, 445 (M−H); $^1$H NMR (CDCl$_3$, 400 MHz) δ: 7.80 (d, 1H), 7.22 (d, 1H), 7.02-7.00 (m, 1H), 6.87-6.86 (m, 1H), 6.72 (dt, 1H), 5.38 (d, 1H).

Example 168

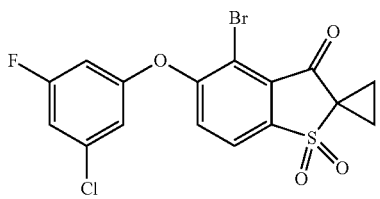 [SMILES: O=C1c2c(ccc(Oc3cc(F)cc(Cl)c3)c2Br)S(=O)(=O)C12CC2]

4-Bromo-5-(3-chloro-5-fluoro-phenoxy)-1,1-dioxo-spiro[benzothiophene-2,1'-cyclopropane]-3-one (Compound 168): 1,2-Dibromoethane (13 µL, 0.15 mmol) was added to 4-bromo-5-(3-chloro-5-fluoro-phenoxy)-1,1-dioxo-benzothiophen-3-one (40 mg, 0.10 mmol) and potassium carbonate (41 mg, 0.30 mmol) in N,N-dimethylformamide (1.0 mL) at room temperature. The reaction mixture was stirred overnight in a sealed reaction vial and then warmed to 50° C. for additional 24 hours. After cooling to room temperature, the reaction mixture was diluted with water (5 mL), extracted with diethyl ether (4×5 mL), washed with water (3×5 mL), brine (10 mL), dried over MgSO$_4$, filtered and concentrated in vacuo. The residue was purified on silica gel (10 g SNAP, 14 CV, 10-100% ethyl acetate/hexanes) affording Compound 168 (6 mg, 0.015 mmol, 15% yield). LCMS ESI (−) m/z 475, 477, 479 (M+HCO2-); $^1$H NMR (CDCl$_3$, 400 MHz) δ: 8.00 (d, 1H), 7.46 (d, 1H), 6.99-6.96 (m, 1H), 6.81-6.80 (m, 1H), 6.67 (dt, 1H), 2.08-2.04 (m, 2H), 1.96-1.93 (m, 2H).

Example 169

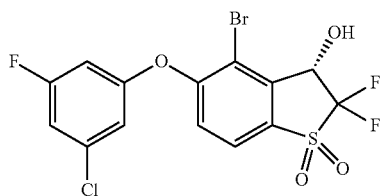 [SMILES: O=S1(=O)c2ccc(Oc3cc(F)cc(Cl)c3)c(Br)c2[C@H](O)C1(F)F]

(3S)-4-Bromo-5-(3-chloro-5-fluoro-phenoxy)-2,2-difluoro-1,1-dioxo-3H-benzothiophen-3-ol (Compound 169): An ice cold solution of N-[(1S,2S)-1,2-diphenyl-2-(2-(4-methylbenzyloxy)ethylamino)-ethyl]-4-methylbenzene sulfonamide(chloro)ruthenium(II) ((S,S)-Ts-DENEB™, 0.8 mg, 0.001 mmol) in dichloromethane (0.3 mL) was added dropwise to an ice cold solution of 4-bromo-5-(3-chloro-5-fluoro-phenoxy)-2,2-difluoro-1,1-dioxo-benzothiophen-3-one (26 mg, 0.06 mmol), triethylamine (16 µL, 0.12 mmol) and formic acid (7 µL, 0.18 mmol) under nitrogen. The reaction vial was then placed in a 4° C. fridge for 18 hours. The reaction mixture was purified directly on silica gel (10 g SNAP, 14 CV, 5-60% ethyl acetate/hexanes) affording Compound 169 (21 mg, 0.047 mmol, 80% yield). The ee was determined to be 83% by $^{19}$F NMR analysis of the corresponding Mosher ester. LCMS ESI (−) m/z 441, 443, 445 (M−H); $^1$H NMR (CDCl$_3$, 400 MHz): δ 7.80 (d, 1H), 7.22 (d, 1H), 7.02-7.00 (m, 1H), 6.87-6.86 (m, 1H), 6.72 (dt, 1H), 5.38 (d, 1H).

Example 170

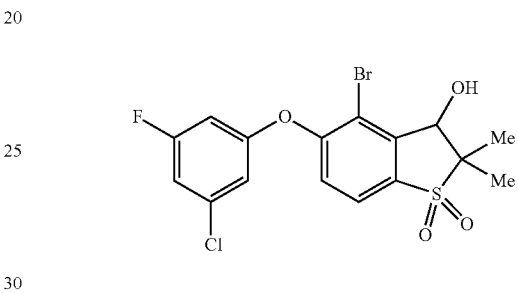

4-Bromo-5-(3-chloro-5-fluoro-phenoxy)-2,2-dimethyl-1,1-dioxo-3H-benzothiophen-3-ol (Compound 170)

Step A: Preparation of 4-bromo-5-(3-chloro-5-fluoro-phenoxy)-2,2-dimethyl-1,1-dioxo-benzothiophen-3-one: Iodomethane (31 µL, 0.49 mmol) was added all at once to 4-bromo-5-(3-chloro-5-fluoro-phenoxy)-1,1-dioxo-benzothiophen-3-one (40 mg, 0.10 mmol) and potassium carbonate (41 mg, 0.30 mmol) in N,N-dimethylformamide (1.0 mL) at room temperature and then stirred for 2 hours. The reaction mixture was diluted with water (5 mL), extracted with ethyl acetate (3×10 mL), washed with brine (10 mL), dried over MgSO$_4$, filtered and concentrated in vacuo. The crude product was used directly in the next reaction without purification. LCMS ESI (+) m/z 433, 435, 437 (M+H).

Step B: Preparation of 4-bromo-5-(3-chloro-5-fluoro-phenoxy)-2,2-dimethyl-1,1-dioxo-3H-benzothiophen-3-ol (Compound 170): Sodium borohydride (4 mg, 0.10 mmol) was added all at once to 4-bromo-5-(3-chloro-5-fluoro-phenoxy)-2,2-dimethyl-1,1-dioxo-benzothiophen-3-one (43 mg, 0.10 mmol) in methanol (2.0 mL) at room temperature and stirred for 10 minutes. The reaction was quenched with saturated ammonium chloride (2 mL), extracted with ethyl acetate (3×5 mL), washed with brine (5 mL), dried over MgSO$_4$, filtered and concentrated in vacuo. The residue was purified on silica gel (10 g SNAP, 14 CV, 5-45% ethyl acetate/hexanes) affording Compound 170 (20 mg, 0.046 mmol, 47% yield over 2 steps). LCMS ESI (−) m/z 479, 481, 483 (M+HCO$_2^-$); $^1$H NMR (CDCl$_3$, 400 MHz): δ 7.73 (dd, 1H), 7.16 (d, 1H), 6.98-6.95 (m, 1H), 6.83-6.82 (m, 1H), 6.66 (dt, 1H), 1.65 (s, 3H), 1.40 (s, 3H).

Example 171

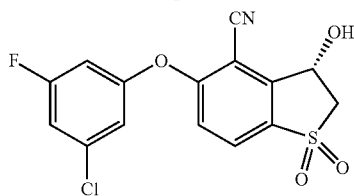 [SMILES: N#Cc1c(Oc2cc(F)cc(Cl)c2)ccc2c1[C@H](O)CS2(=O)=O]

(3S)-5-(3-Chloro-5-fluoro-phenoxy)-3-hydroxy-1,1-dioxo-2,3-dihydrobenzothiophene-4-carbonitrile (Compound 171): Copper(I) cyanide (11 mg, 0.12 mmol) was added all at once to a solution of (3S)-4-bromo-5-(3-chloro-5-fluoro-phenoxy)-1,1-dioxo-2,3-dihydrobenzothiophen-3-ol (32 mg, 0.08 mmol) in 1-methyl-2-pyrrolidone (0.4 mL). The reaction mixture was heated at 160° C. in a sealed microwave vial by microwave irradiation. The reaction mixture was purified directly on reverse phase silica gel (12+M, 14 CV, 20-100% acetonitrile/water) affording Compound 171 (23 mg, 0.064 mmol, 81% yield). The ee was determined to be 83% by $^{19}$F NMR analysis of the corresponding Mosher ester. LCMS ESI (−) m/z 352, 354 (M−H); $^1$H NMR (CDCl$_3$, 400 MHz): δ 7.89 (d, 1H), 7.13 (d, 1H), 7.09-7.06 (m, 1H), 6.96-6.94 (m, 1H), 6.80 (dt, 1H), 5.78-5.74 (m, 1H), 3.91 (dd, 1H), 3.65 (dd, 1H), 3.41 (d, 1H).

Example 172

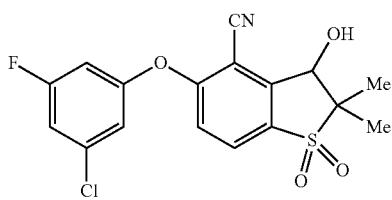 [SMILES: CC1(C)C(O)c2c(ccc(Oc3cc(F)cc(Cl)c3)c2C#N)S1(=O)=O]

5-(3-Chloro-5-fluoro-phenoxy)-3-hydroxy-2,2-dimethyl-1,1-dioxo-3H-benzothiophene-4-carbonitrile (Compound 172): To copper (I) cyanide (5 mg, 0.05 mmol) in a microwave reaction vial equipped with a stir bar was added a solution of 4-bromo-5-(3-chloro-5-fluoro-phenoxy)-2,2-dimethyl-1,1-dioxo-3H-benzothiophen-3-ol (17 mg, 0.04 mmol) in 1-methyl-2-pyrrolidone (0.25 mL). The reaction vial was sealed with a crimp cap and warmed to 160° C. under microwave irradiation for 75 minutes. The reaction mixture was purified directly on reverse phase silica gel (12+M, 14 CV, 20-100% acetonitrile/water) affording Compound 172 (10 mg, 0.026 mmol, 67% yield). LCMS ESI (−) m/z 380, 382 (M−H); $^1$H NMR (CDCl$_3$, 400 MHz): δ 7.91 (d, 1H), 7.10-7.06 (m, 2H), 6.97-6.96 (m, 1H), 6.81 (dt, 1H), 1.55 (s, 3H), 1.49 (s, 3H).

Example 173

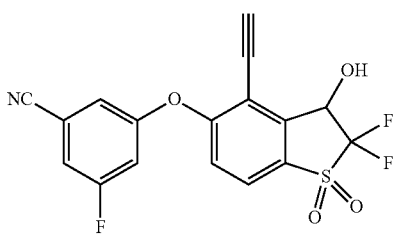 [SMILES: C#Cc1c(Oc2cc(F)cc(C#N)c2)ccc2c1C(O)C(F)(F)S2(=O)=O]

3-((4-Ethynyl-2,2-difluoro-3-hydroxy-1,1-dioxido-2,3-dihydrobenzo[b]thiophen-5-yl)oxy)-5-fluorobenzonitrile (Compound 173)

Step A: Preparation of methyl 3-(3-cyano-5-fluoro-phenoxy)-6-methylsulfonyl-2-(2-trimethylsilylethynyl)benzoate: A mixture of methyl 2-bromo-3-(3-cyano-5-fluoro-phenoxy)-6-methylsulfonyl-benzoate (500 mg, 1.2 mmol), trimethylsilyl acetylene (1.7 mL, 11.7 mmol), bis(triphenylphosphine)palladium(II) dichloride (164 mg, 0.23 mmol), N,N-diisopropylethylamine (0.6 mL, 3.5 mmol) and CuI (89 mg, 0.47 mmol) in a sealed tube under argon was heated at 95° C. overnight. After cooling to room temperature, the reaction mixture was concentrated under reduced pressure. The residue was purified by flash column chromatography with EtOAc/hexane (0% to 50%) to give methyl 3-(3-cyano-5-fluoro-phenoxy)-6-methylsulfonyl-2-(2-trimethylsilylethynyl)benzoate (186 mg, 0.42 mmol, 36% yield). LCMS ESI (+) m/z 446 (M+H), 463 (M+NH$_4$).

Step B: Preparation of 3-(4-ethynyl-1,1,3-trioxo-benzothiophen-5-yl)oxy-5-fluoro-benzonitrile: To a solution of methyl 3-(3-cyano-5-fluoro-phenoxy)-6-methylsulfonyl-2-(2-trimethylsilylethynyl)benzoate (176 mg, 0.4 mmol) in tetrahydrofuran (10 mL) at room temperature was added tetrabutylammonium fluoride (1 M in tetrahydrofuran, 0.5 mL). The reaction was stirred at room temperature for 10 minutes. Additional tetrabutylammonium fluoride (1 M in tetrahydrofuran, 0.3 mL) was added. The reaction mixture was stirred at room temperature for 40 minutes, then diluted with EtOAc, washed with saturated NaHCO$_3$ and brine, dried over MgSO$_4$, filtered, and concentrated. The residue was purified by flash column chromatography with EtOAc/hexane (0% to 60%) to give 3-(4-ethynyl-1,1,3-trioxo-benzothiophen-5-yl)oxy-5-fluoro-benzonitrile (46 mg, 0.13 mmol, 34% yield). LCMS ESI (+) m/z 391 (M+NH$_4$).

Step C: Preparation of 3-(4-ethynyl-2,2-difluoro-1,1,3-trioxo-benzothiophen-5-yl)oxy-5-fluoro-benzonitrile: To a solution of 3-(4-ethynyl-1,1,3-trioxo-benzothiophen-5-yl)oxy-5-fluoro-benzonitrile (12 mg, 0.04 mmol) in acetonitrile (4 mL) at room temperature was added sodium carbonate (12 mg, 0.11 mmol) and Selectfluor® (38 mg, 0.11 mmol). The reaction mixture was stirred at room temperature for 40 minutes. Additional Selectfluor® (38 mg, 0.11 mmol) was added and stirring was continued at room temperature for additional 40 minutes. The reaction mixture was concentrated under reduced pressure, diluted with EtOAc, washed with saturated NaHCO$_3$ and brine, dried over MgSO$_4$, filtered, and concentrated. The crude product was used in the next step without further purification. LCMS ESI (+) m/z 395 (M+NH$_4$).

Step D: Preparation of 3-((4-ethynyl-2,2-difluoro-3-hydroxy-1,1-dioxido-2,3-dihydrobenzo[b]thiophen-5-yl)oxy)-5-fluorobenzonitrile (Compound 173): To a solution of 3-(4-ethynyl-2,2-difluoro-1,1,3-trioxo-benzothiophen-5-yl)oxy-5-fluoro-benzonitrile (7 mg, 0.02 mmol) in tetrahydrofuran (2.5 mL) at room temperature was added sodium triacetoxyborohydride (12 mg, 0.06 mmol). The reaction was stirred at room temperature for 1 hour. Additional sodium triacetoxyborohydride (12 mg, 0.06 mmol) was added. The reaction mixture was stirred for additional 1 hour and directly purified by preparative TLC with EtOAc/hexane (35%) to give Compound 173 (6 mg, 0.02 mmol, 85% yield). LCMS ESI (+) m/z 397 (M+NH$_4$); $^1$H NMR (400 MHz, CDCl$_3$): δ 7.85 (d, 1H), 7.27-7.23 (m, 2H), 7.15 (s, 1H), 7.04 (d, 1H), 5.46 (dd, 1H), 3.69 (s, 1H), 3.13 (d, 1H).

Example 174

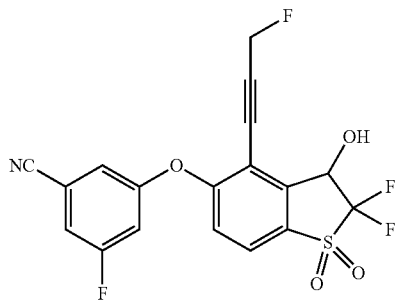 [SMILES: N#Cc1cc(F)cc(Oc2ccc3c(c2C#CCF)C(O)C(F)(F)S3(=O)=O)c1]

3-[[2,2-Difluoro-4-(3-fluoroprop-1-ynyl)-3-hydroxy-1,1-dioxo-3H-benzothiophen-5-yl]oxy]-5-fluoro-benzonitrile (Compound 174)

Step A: Preparation of 3-(3-cyano-5-fluoro-phenoxy)-2-(3-hydroxyprop-1-ynyl)-6-methylsulfonyl-benzoate: A mixture of methyl 2-bromo-3-(3-cyano-5-fluoro-phenoxy)-6-methylsulfonyl-benzoate (650 mg, 1.52 mmol), propargyl alcohol (0.18 mL, 3.0 mmol), bis(triphenylphosphine)palladium(II) dichloride (53 mg, 0.08 mmol), N,N-diisopropylethylamine (0.8 mL, 4.6 mmol) and CuI (29 mg, 0.15 mmol) in a sealed tube under argon was heated at 90° C. overnight. After cooling to room temperature, the mixture was concentrated under reduced pressure. Dichloromethane was added and the resulting suspension was filtered. The filtrate was concentrated and the residue was purified by flash column chromatography with EtOAc/hexane (0% to 80%) to give methyl 3-(3-cyano-5-fluoro-phenoxy)-2-(3-hydroxyprop-1-ynyl)-6-methylsulfonyl-benzoate (130 mg, 0.32 mmol, 21% yield). LCMS ESI (+) m/z 421 (M+NH$_4$).

Step B: Preparation of methyl 3-(3-cyano-5-fluoro-phenoxy)-2-(3-fluoroprop-1-ynyl)-6-methylsulfonyl-benzoate: To a solution of methyl 3-(3-cyano-5-fluoro-phenoxy)-2-(3-hydroxyprop-1-ynyl)-6-methylsulfonyl-benzoate (18 mg, 0.04 mmol) in dichloromethane (1 mL) at room temperature was added diethylaminosulfur trifluoride (0.01 mL, 0.09 mmol). The reaction mixture was stirred at room temperature for 1.5 hours and directly purified by preparative TLC to give methyl 3-(3-cyano-5-fluoro-phenoxy)-2-(3-fluoroprop-1-ynyl)-6-methylsulfonyl-benzoate (14 mg, 0.03 mmol, 77% yield). LCMS ESI (+) m/z 423 (M+NH$_4$).

Step C: Preparation of 3-fluoro-5-[4-(3-fluoroprop-1-ynyl)-1,1,3-trioxo-benzothiophen-5-yl]oxy-benzonitrile: To a solution of methyl 3-(3-cyano-5-fluoro-phenoxy)-2-(3-fluoroprop-1-ynyl)-6-methylsulfonyl-benzoate (14 mg, 0.03 mmol) in THF (3 mL) was added sodium hydride (10 mg, 0.25 mmol). The reaction was stirred at room temperature for 2 hours and 15 minutes. The reaction mixture was poured into ice cold 1:1 brine and 10% citric acid, and extracted with EtOAc. The organic layer was dried over MgSO$_4$, filtered, and concentrated. The residue was purified by preparative TLC (50% EtOAc/hexane) to give 3-fluoro-5-[4-(3-fluoroprop-1-ynyl)-1,1,3-trioxo-benzothiophen-5-yl]oxy-benzonitrile (11 mg, 0.03 mmol, 85% yield). LCMS ESI (−) m/z 372 (M−H).

Step D: Preparation of 3-[2,2-difluoro-4-(3-fluoroprop-1-ynyl)-1,1,3-trioxo-benzothiophen-5-yl]oxy-5-fluoro-benzonitrile: To a mixture of 3-fluoro-5-[4-(3-fluoroprop-1-ynyl)-1,1,3-trioxo-benzothiophen-5-yl]oxy-benzonitrile (11 mg, 0.03 mmol), sodium carbonate (12 mg, 0.12 mmol), and Selectfluor® (63 mg, 0.18 mmol) was added acetonitrile (2 mL). The reaction was stirred at room temperature for 1.5 hours and directly purified by preparative TLC with EtOAc/hexane (50%) to give 3-[2,2-difluoro-4-(3-fluoroprop-1-ynyl)-1,1,3-trioxo-benzothiophen-5-yl]oxy-5-fluoro-benzonitrile (6 mg, 0.015 mmol, 50% yield).

Step E: Preparation of 3-[[2,2-difluoro-4-(3-fluoroprop-1-ynyl)-3-hydroxy-1,1-dioxo-3H-benzothiophen-5-yl]oxy]-5-fluoro-benzonitrile (Compound 174): To a solution of 3-[2,2-difluoro-4-(3-fluoroprop-1-ynyl)-1,1,3-trioxo-benzothiophen-5-yl]oxy-5-fluoro-benzonitrile (6 mg, 0.01 mmol) in THF (1 mL) was added sodium triacetoxyborohydride (10 mg, 0.05 mmol). The reaction mixture was stirred at room temperature for 2 hours and then directly purified by preparative TLC with 60% EtOAc/hexane to give Compound 174 (4.4 mg, 0.01 mmol, 73% yield). LCMS ESI (−) m/z 410 (M−H); $^1$H NMR (400 MHz, CDCl$_3$): δ 7.85 (d, 1H), 7.28-7.25 (m, 1H), 7.23 (d, 1H), 7.16-7.14 (m, 1H), 7.05 (dt, 1H), 5.43 (d, 1H), 5.19 (d, 2H), 3.27 (s, 1H).

Example 175

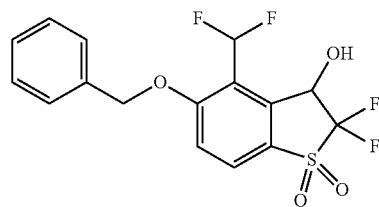 [SMILES: O=S1(=O)c2ccc(OCc3ccccc3)c(C(F)F)c2C(O)C1(F)F]

5-Benzyloxy-4-(difluoromethyl)-2,2-difluoro-1,1-dioxo-3H-benzothiophen-3-ol (Compound 175)

Step A: Preparation of 3-benzyloxy-2-(difluoromethyl)-6-methylsulfonyl-benzonitrile: To a solution of phenylmethanol (0.04 mL, 0.4 mmol) in tetrahydrofuran (4 mL) at room temperature was added sodium hydride (8 mg, 60%, 0.2 mmol). After stirring at room temperature for 15 minutes, (difluoromethyl)-3-fluoro-6-methylsulfonyl-benzonitrile (50 mg, 0.2 mmol) was added. The reaction mixture was stirred at room temperature overnight and purified directly by preparative TLC with EtOAc/hexane (40%) followed by flash column chromatography with EtOAc/hexane (20% to 80%) to give 3-benzyloxy-2-(difluoromethyl)-6-methylsulfonyl-benzonitrile (28 mg, 0.083 mmol, 41% yield). LCMS ESI (+) m/z 355 (M+NH$_4$).

Step B: Preparation of 5-benzyloxy-4-(difluoromethyl)-1,1-dioxo-benzothiophen-3-one: To a solution of 3-benzyloxy-2-(difluoromethyl)-6-methylsulfonyl-benzonitrile (27 mg, 0.08 mmol) in tetrahydrofuran (3 mL) at room temperature was added sodium hydride (25 mg, 60%, 0.6 mmol). The reaction was stirred at room temperature overnight. Aqueous KHSO$_4$ (10%, 10 mL) was added. The reaction mixture was stirred at room temperature for 30 minutes and extracted with EtOAc. The organic layer was dried over MgSO$_4$, filtered, and concentrated. The residue was purified by flash column chromatography with EtOAc/hexane (40%) to give 5-benzyloxy-4-(difluoromethyl)-1,1-dioxo-benzothiophen-3-one (6 mg, 0.018 mmol, 22% yield). LCMS ESI (+) m/z 356 (M+NH$_4$).

Step C: Preparation of 5-benzyloxy-4-(difluoromethyl)-2,2-difluoro-1,1-dioxo-benzothiophen-3-one: A mixture of 5-benzyloxy-4-(difluoromethyl)-1,1-dioxo-benzothiophen-3-one (6 mg, 0.02 mmol), Selectfluor® (38 mg, 0.11 mmol) and sodium carbonate (8 mg, 0.08 mmol) in acetonitrile (3 mL) was stirred at room temperature for 4 hours. The reaction mixture was purified directly by preparative TLC to give 5-benzyloxy-4-(difluoromethyl)-2,2-difluoro-1,1-dioxo-benzothiophen-3-one (4 mg, 0.01 mmol, 60% yield). LCMS ESI (+) m/z 410 (M+H$_2$O+NH$_4$).

Step D: Preparation of 5-benzyloxy-4-(difluoromethyl)-2,2-difluoro-1,1-dioxo-3H-benzothiophen-3-ol: To a solution of 5-benzyloxy-4-(difluoromethyl)-2,2-difluoro-1,1-dioxo-benzothiophen-3-one (4 mg, 0.011 mmol) in tetrahydrofuran (1.5 mL) at room temperature was added sodium triacetoxyborohydride (5 mg, 0.02 mmol). The reaction mixture was stirred at room temperature for 30 minutes and purified directly by preparative TLC to give Compound 175 (3 mg, 0.008 mmol, 75% yield). LCMS ESI (+) m/z 394 (M+NH$_4$). $^1$H NMR (400 MHz, CDCl$_3$): δ 7.92 (d, 1H), 7.46-7.10 (m, 7H), 5.61 (d, 1H), 5.26 (s, 2H), 3.00 (s, 1H).

Example 176

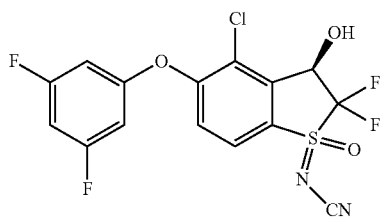 [SMILES: N#CN=S1(=O)c2ccc(Oc3cc(F)cc(F)c3)c(Cl)c2[C@@H](O)C1(F)F]

N-((3R)-4-Chloro-5-(3,5-difluorophenoxy)-2,2-difluoro-3-hydroxy-1-oxido-2,3-dihydro-1λ$^4$-benzo[b]thiophen-1-ylidene)cyanamide (Compound 176)

Step A: Preparation of 2-chloro-3-fluoro-6-(methylthio)benzonitrile: A vial containing a clear solution of 2-chloro-3,6-difluoro-benzonitrile (1.00 g, 5.8 mmol) in N,N-dimethylformamide (DMF, 5 mL) was flushed with nitrogen, cooled in ice, and treated with sodium sulfide (472 mg, 6.1 mmol). The stirred yellow suspension was allowed to slowly warm to ambient temperature. After 3 hours, the reaction mixture was treated with dimethyl sulfate (0.60 mL, 6.3 mmol). The yellow suspension turned milky white. The reaction mixture was partitioned between EtOAc and water. The EtOAc was washed with brine, dried over MgSO$_4$, filtered, and evaporated. The residue was chromatographed on a Biotage 50 g SNAP column with a 10% to 40% EtOAc/hexane gradient to afford 2-chloro-3-fluoro-6-(methylthio)benzonitrile (430 mg, 2.13 mmol, 37% yield) as a fluffy white solid.

Step B: Preparation of N-((3-chloro-2-cyano-4-fluorophenyl)(methyl)-λ$^4$-sulfanylidene)cyanamide: (Diacetoxyiodo)benzene (755 mg, 2.4 mmol) was added to an ice-cold suspension of 2-chloro-3-fluoro-6-(methylthio)benzonitrile (430 mg, 2.1 mmol) and cyanamide (107 mg, 2.6 mmol) in acetonitrile (20 mL). The suspension slowly became a yellow solution. The mixture was allowed to warm to ambient temperature. After 1.25 hours, the reaction mixture was partitioned between EtOAc and dilute aqueous NaCl. The EtOAc layer was washed with brine, dried over MgSO$_4$, filtered, and evaporated. The residue was chromatographed on a Biotage 25 g SNAP column with a 40% to 100% EtOAc/hexane gradient to afford N-((3-chloro-2-cyano-4-fluorophenyl)(methyl)-λ$^4$-sulfanylidene)cyanamide (390 mg, 1.6 mmol, 76% yield) as a white solid.

Step C: Preparation of N-((3-chloro-2-cyano-4-fluorophenyl)(methyl)(oxo)-λ$^6$-sulfanylidene)cyanamide: Sodium periodate (398 mg, 1.9 mmol) was added to N-((3-chloro-2-cyano-4-fluorophenyl)(methyl)-λ$^4$-sulfanylidene)cyanamide (150 mg, 0.6 mmol) and ruthenium (III) chloride (3.9 mg, 0.02 mmol) in a mixture of carbon tetrachloride (3 mL), acetonitrile (3 mL), and water (6 mL). This was stirred at ambient temperature. After 15 minutes, the reaction mixture was partitioned between dichloromethane and water. The dichloromethane was washed with brine, dried over MgSO$_4$, filtered, and evaporated to afford N-((3-chloro-2-cyano-4-fluorophenyl)(methyl)(oxo)-λ$^6$-sulfanylidene)cyanamide (170 mg, 0.66 mmol, quantitative yield) as a grey solid.

Step D: Preparation of N-(3-amino-4-chloro-5-(3,5-difluorophenoxy)-1-oxido-1λ$^4$-benzo[b]thiophen-1-ylidene)cyanamide: Sodium hydrogen carbonate (166 mg, 2 mmol) was added to a vial containing a solution of N-((3-chloro-2-cyano-4-fluorophenyl)(methyl)(oxo)-λ$^6$-sulfanylidene)cyanamide (170 mg, 0.66 mmol) and 3,5-difluorophenol (172 mg, 1.3 mmol) in DMF (2 mL). The sealed vial was heated at 70° C. After 3.5 hours, the reaction mixture was partitioned between EtOAc and water. The EtOAc was washed with 2 portions of brine, dried over MgSO$_4$, filtered, and evaporated. The residue was chromatographed on a Biotage 25 g SNAP column with a 40% to 100% EtOAc/hexanes gradient to afford N-(3-amino-4-chloro-5-(3,5-difluorophenoxy)-1-oxido-1λ$^4$-benzo[b]thiophen-1-ylidene)cyanamide (100 mg, 0.27 mmol, 41% yield) as a pale yellow solid. LCMS ESI-API (+) m/z 368 (M+H).

Step E: Preparation of N-(4-chloro-5-(3,5-difluorophenoxy)-1-oxido-3-oxo-2,3-dihydro-1λ$^4$-benzo[b]thiophen-1-ylidene)cyanamide: Hydrochloric acid (1.0 M, 0.65 mL, 0.65 mmol) was added to a solution of N-(3-amino-4-chloro-5-(3,5-difluorophenoxy)-1-oxido-1λ$^4$-benzo[b]thiophen-1-ylidene)cyanamide (80 mg, 0.22 mmol) in methanol (7 mL). The mixture was stirred at 40° C. After 30 minutes, the cooled reaction mixture was treated with water and the resulting solid was collected by vacuum filtration to afford N-(4-chloro-5-(3,5-difluorophenoxy)-1-oxido-3-oxo-2,3-dihydro-1λ$^4$-benzo[b]thiophen-1-ylidene)cyanamide (80 mg, 0.22 mmol, 100% yield) as a tan solid. LCMS ESI-API (+) m/z 369 (M+H).

Step F: Preparation of N-(4-chloro-5-(3,5-difluorophenoxy)-2,2-difluoro-1-oxido-3-oxo-2,3-dihydro-1λ$^4$-benzo[b]thiophen-1-ylidene)cyanamide: 1-(Chloromethyl)-4-fluoro-1,4-diazoniabicyclo[2.2.2]octane ditetrafluoroborate (190 mg, 0.54 mmol) was added to a mixture of N-(4-chloro-5-(3,5-difluorophenoxy)-1-oxido-3-oxo-2,3-dihydro-1λ$^4$-benzo[b]thiophen-1-ylidene)cyanamide (90 mg, 0.24 mmol) and sodium carbonate (57 mg, 0.54 mmol) in acetonitrile (5 mL). This was stirred at ambient temperature. After 30 minutes, the reaction mixture was partitioned between EtOAc and water. The EtOAc was washed with brine, dried over MgSO$_4$, filtered, and evaporated. The residue was chromatographed on a Biotage 10 g SNAP column with a 20% to 80% EtOAc/hexanes gradient to afford N-(4-chloro-5-(3,5-difluorophenoxy)-2,2-difluoro-1-oxido-3-oxo-2,3-dihydro-1λ$^4$-benzo[b]thiophen-1-ylidene)cyanamide (401 mg, 0.1 mmol, 41% yield). LCMS ESI-API (+) m/z 423 (M+H+H$_2$O).

Step G: Preparation of N-((3R)-4-chloro-5-(3,5-difluorophenoxy)-2,2-difluoro-3-hydroxy-1-oxido-2,3-dihydro-1λ$^4$-benzo[b]thiophen-1-ylidene)cyanamide: N-[(1R,2R)-1,2-Diphenyl-2-(2-(4-methylbenzyloxy)ethylamino)-ethyl]-4- methylbenzene sulfonamide(chloro)ruthenium(II) ((R,R)-Ts-DENEB™, 1.3 mg, 0.002 mmol) was added to a flask containing an ice-cold, nitrogen-sparged solution of N-(4-chloro-5-(3,5-difluorophenoxy)-2,2-difluoro-1-oxido-3-oxo-2,3-dihydro-1λ⁴-benzo[b]thiophen-1-ylidene)cyanamide (41 mg, 0.1 mmol), triethylamine (0.03 mL, 0.2 mmol), and formic acid (0.009 mL, 0.25 mmol) in dichloromethane (5 mL). The flask was sealed and kept in a 4° C. refrigerator over a weekend. The reaction mixture was evaporated and the residue was chromatographed on a Biotage 10 g SNAP column with a 20% to 80% EtOAc/hexane gradient to afford Compound 176 (12.5 mg, 0.03 mmol, 31% yield) as a colorless film. LCMS ESI (+) m/z 407, 409 (M+H); $^1$H NMR (400 MHz, CDCl$_3$): δ 7.89-7.81 (m, 1H), 7.31-7.26 (m, 1H), 6.78 (t, 1H), 6.65 (d, 2H), 5.59-5.51 (m, 1H), 4.60-4.38 (br s, 1H).

Example 177

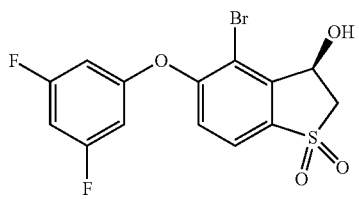 [SMILES: O=S1(=O)C[C@H](O)c2c1ccc(Oc1cc(F)cc(F)c1)c2Br]

(R)-4-bromo-5-(3,5-difluorophenoxy)-3-hydroxy-2,3-dihydrobenzo[b]thiophene 1,1-dioxide (Compound 177)

Step A: Preparation of 4-bromo-5-(3,5-difluorophenoxy)benzo[b]thiophen-3(2H)-one 1,1-dioxide: Prepared analogously to Example 111, Steps A-G utilizing 3,5-difluorophenol in Step F. $^1$H NMR (400 MHz, CDCl$_3$): δ 7.95-7.92 (m, 1H), 7.48-7.45 (m, 1H), 6.73-6.67 (m, 1H), 6.58-6.53 (m, 2H), 4.20 (s, 2H).

Step B: Preparation of (R)-4-bromo-5-(3,5-difluorophenoxy)-3-hydroxy-2,3-dihydrobenzo[b]thiophene 1,1-dioxide: 4-Bromo-5-(3,5-difluorophenoxy)benzo[b]thiophen-3(2H)-one 1,1-dioxide (267 mg, 0.69 mmol) was dissolved in dichloromethane (freshly degassed by sparging with nitrogen, 3.4 mL) and the solution was treated with triethylamine (0.19 mL, 1.37 mmol) and formic acid (0.08 mL, 2.1 mmol). This solution was cooled to 0° C. and treated with a pre-cooled (0° C.) solution of RuCl(p-cymene)(S,S)-Ts-DPEN (4.4 mg, 0.01 mmol) dissolved in dichloromethane (3.4 mL). The resultant solution was placed in the refrigerator and allowed to stand at 4° C. for 15 hours. The reaction mixture was concentrated to a small volume and chromatographed on SiO$_2$ eluting with a gradient of ethyl acetate/hexanes. The product was collected and concentrated to a colorless oil. Diethyl ether and hexane were added and the mixture was reconcentrated to give Compound 177 as a white solid (248 mg, 92%, >95% ee by Mosher ester analysis). $^1$H NMR (400 MHz, CDCl$_3$): δ 7.72 (d, 1H), 7.21 (d, 1H), 6.71-6.64 (m, 1H), 6.57-6.52 (m, 2H), 5.60 (t, 1H), 3.83-3.78 (m, 1H), 3.71-3.67 (m, 1H), 2.88 (d, 1H).

Example 178

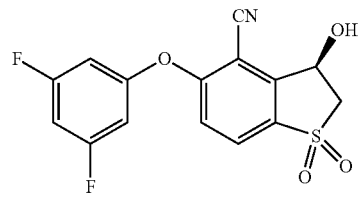

(R)-5-(3,5-difluorophenoxy)-3-hydroxy-2,3-dihydrobenzo[b]thiophene-4-carbonitrile 1,1-dioxide (Compound 178): A solution of (R)-4-bromo-5-(3,5-difluorophenoxy)-3-hydroxy-2,3-dihydrobenzo[b]thiophene 1,1-dioxide (51.7 mg, 0.13 mmol) dissolved in 1-methyl-2-pyrrolidinone (0.52 mL) was treated with copper (I) cyanide (16.6 mg, 0.19 mmol). Argon was bubbled through the solution for several minutes, then the mixture was heated to 160° C. for 60 minutes in the microwave reactor. After cooling, the mixture was diluted with Et$_2$O and water. After separation, the aqueous was washed with Et$_2$O, then the combined organics were washed five times with water, saturated NaHCO$_3$, saturated NaCl, dried over Na$_2$SO$_4$ and concentrated in vacuo. The crude material was redissolved in a small amount of methylene chloride and after a few minutes a precipitate began to form. The supernant was removed and the remaining solids were washed several times with cold 1:1 methylene chloride/hexanes. The solids were suspended in hexanes, filtered and air-dried. Compound 178 was obtained as a white solid (22.5 mg, 51%, >86% ee by Mosher ester analysis). $^1$H NMR (400 MHz, CDCl$_3$): δ 7.89 (d, 1H), 7.15 (d, 1H), 6.83-6.76 (m, 1H), 6.71-6.67 (m, 2H), 5.78-5.74 (m, 1H), 3.94-3.89 (m, 1H), 3.67-3.63 (m, 1H), 3.27-3.24 (m, 1H).

Example 179

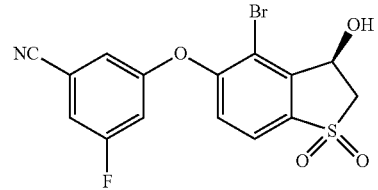 [SMILES: N#Cc1cc(F)cc(Oc2ccc3c(c2Br)[C@@H](O)CS3(=O)=O)c1]

(R)-3-((4-Bromo-3-hydroxy-1,1-dioxido-2,3-dihydrobenzo[b]thiophen-5-yl)oxy)-5-fluorobenzonitrile (Compound 179): Prepared analogously as described in Example 177, Step B using 3-((4-bromo-1,1-dioxido-3-oxo-2,3-dihydrobenzo[b]thiophen-5-yl)oxy)-5-fluorobenzonitrile (66%, >98% ee by Mosher ester analysis). $^1$H NMR (400 MHz, CDCl$_3$): δ 7.77 (d, 1H), 7.25 (d, 1H), 7.22-7.19 (m, 1H), 7.06-7.05 (m, 1H), 6.99-6.96 (m, 1H), 5.62-5.59 (m, 1H), 3.85-3.80 (m, 1H), 3.71-3.69 (m, 1H), 2.90 (d, 1H).

Example 180

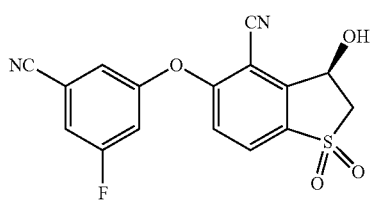 [SMILES: N#Cc1cc(F)cc(Oc2ccc3c(c2C#N)[C@@H](O)CS3(=O)=O)c1]

(R)-5-(3-Cyano-5-fluorophenoxy)-3-hydroxy-2,3-dihydrobenzo[b]thiophene-4-carbonitrile 1,1-dioxide (Compound 70): Prepared analogously as described in Example 178 using (R)-3-((4-bromo-3-hydroxy-1,1-dioxido-2,3-dihydrobenzo[b]thiophen-5-yl)oxy)-5-fluorobenzonitrile (57%, >88% ee by Mosher ester analysis). $^1$H NMR (400 MHz, CDCl$_3$): δ 7.94 (d, 1H), 7.35-7.31 (m, 1H), 7.24-7.22 (m, 1H), 7.16 (d, 1H), 7.16-7.12 (m, 1H), 5.80-5.73 (m, 1H), 3.96-3.90 (m, 1H), 3.68-3.63 (m, 1H), 3.48-3.46 (m, 1H).

Example 181

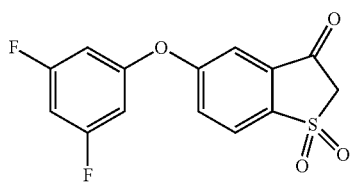 [SMILES: O=C1CS(=O)(=O)c2ccc(Oc3cc(F)cc(F)c3)cc21]

5-(3,5-Difluorophenoxy)benzo[b]thiophen-3(2H)-one 1,1-dioxide (Compound 181): A solution of 4-bromo-5-(3,5-difluorophenoxy)-1,1-dioxo-benzothiophen-3-one (60 mg, 0.15 mmol) was dissolved in MeOH (0.45 mL) and cooled to 0° C. The solution was treated with sodium borohydride (5.8 mg, 0.15 mmol) and the mixture was stirred at 0° C. for 1 hour. The mixture was treated with additional sodium borohydride (1 mg, 0.03 mmol) and stirred for an additional 30 minutes. The reaction was quenched by careful addition of 10% KHSO$_4$ and the mixture was stirred at 0° C. for 1 hour. The pH was adjusted to 7-8 with saturated NaHCO$_3$ and the aqueous was extracted three times with ethyl acetate. The combined organic layers were washed with saturated NaHCO$_3$, saturated NaCl, dried over Na$_2$SO$_4$ and concentrated in vacuo. The crude material was chromatographed on SiO$_2$ eluting with a gradient of ethyl acetate/hexane to give Compound 181 (11.9 mg, 25%). $^1$H NMR (400 MHz, CDCl$_3$): δ 8.24 (d, 1H), 7.89-7.86 (dd, 1H), 7.11 (d, 1H), 6.70-6.65 (m, 1H), 6.59-6.51 (m, 2H), 3.10 (s, 2H).

Example 182

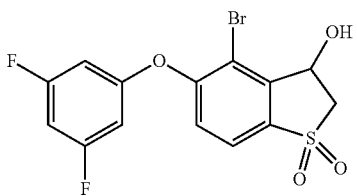 [SMILES: O=S1(=O)CC(O)c2c1ccc(Oc1cc(F)cc(F)c1)c2Br]

4-Bromo-5-(3,5-difluorophenoxy)-3-hydroxy-2,3-dihydrobenzo[b]thiophene 1,1-dioxide (Compound 182): Prepared analogously as described in Example 181 to give Compound 182 (40 mg, 66%). $^1$H NMR (400 MHz, CDCl$_3$): δ 7.72 (d, 1H), 7.20 (d, 1H), 6.70-6.65 (m, 1H), 6.58-6.52 (m, 2H), 5.62-5.58 (m, 1H), 3.83-3.78 (m, 1H), 3.71-3.67 (m, 1H), 2.93 (d, 1H).

Example 183

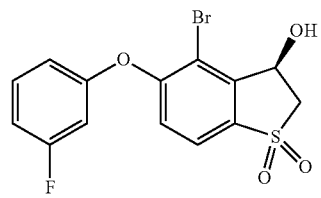 [SMILES: O=S1(=O)C[C@H](O)c2c1ccc(Oc1cccc(F)c1)c2Br]

(R)-4-bromo-5-(3-fluorophenoxy)-3-hydroxy-2,3-dihydrobenzo[b]thiophene 1,1-dioxide (Compound 183): Prepared analogously as described in Example 111, Step A-G utilizing 3-fluorophenol in Step F, followed by Example 177, Step B (92%, >96% ee by Mosher ester analysis). $^1$H NMR (400 MHz, CDCl$_3$): δ 7.66 (d, 1H), 7.40-7.35 (m, 1H), 7.10 (d, 1H), 6.97-6.93 (m, 1H), 6.83-6.76 (m, 2H), 5.62-5.59 (m, 1H), 3.82-3.77 (m, 1H), 3.70-3.66 (m, 1H), 2.96 (d, 1H).

Example 184

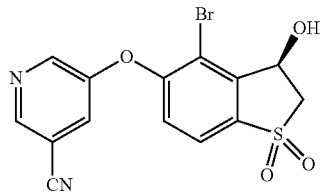 [SMILES: N#Cc1cncc(Oc2ccc3c(c2Br)[C@@H](O)CS3(=O)=O)c1]

(R)-5-((4-bromo-3-hydroxy-1,1-dioxido-2,3-dihydrobenzo[b]thiophen-5-yl)oxy)nicotinonitrile (Compound 184): Prepared analogously as described in Example 111, Step A-G utilizing 5-hydroxynicotinonitrile in Step F, followed by Example 177, Step B (70%, >96% ee by Mosher ester analysis). $^1$H NMR (400 MHz, CDCl$_3$+CD$_3$OD): δ 8.69 (d, 1H), 8.61-8.60 (d, 1H), 7.79 (d, 1H), 7.55-7.54 (m, 1H), 7.29 (d, 1H), 5.57 (d, 1H), 3.84-3.79 (m, 1H), 3.70-3.66 (m, 1H).

Example 185

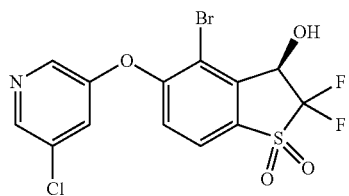 [SMILES: O=S1(=O)c2ccc(Oc3cncc(Cl)c3)c(Br)c2[C@@H](O)C1(F)F]

(R)-4-bromo-5-((5-chloropyridin-3-yl)oxy)-2,2-difluoro-3-hydroxy-2,3-dihydrobenzo[b]thiophene 1,1-dioxide (Compound 185): Prepared analogously as described in Example 111 using 5-chloropyridin-3-ol in Step F (42% ee by Mosher ester analysis). $^1$H NMR (400 MHz, CDCl$_3$): δ 8.50 (s, 1H), 8.33 (s, 1H), 7.81 (d, 1H), 7.41-7.40 (m, 1H), 7.19 (d, 1H), 5.41-5.37 (m, 1H), 3.45-3.40 (m, 1H).

Example 186

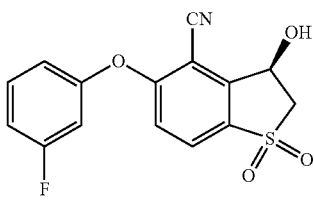 [SMILES: N#Cc1c(Oc2cccc(F)c2)ccc2c1[C@@H](O)CS2(=O)=O]

(R)-5-(3-fluorophenoxy)-3-hydroxy-2,3-dihydrobenzo[b]thiophene-4-carbonitrile 1,1-dioxide (Compound 186): Prepared analogously as described in Example 178 utilizing (R)-4-bromo-5-(3-fluorophenoxy)-3-hydroxy-2,3-dihydrobenzo[b]thiophene 1,1-dioxide (>94% ee by Mosher ester analysis). $^1$H NMR (400 MHz, CDCl$_3$): δ 7.83 (d, 1H), 7.48-7.42 (m, 1H), 7.08-7.03 (m, 1H), 7.06 (d, 1H), 6.94-6.87 (m, 2H), 5.78-5.73 (m, 1H), 3.93-3.88 (m, 1H), 3.66-3.62 (m, 1H), 3.56 (d, 1H).

Example 187

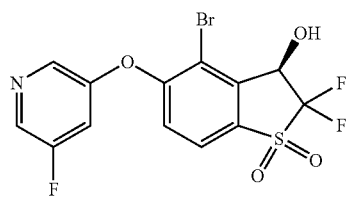 [SMILES: O=S1(=O)c2ccc(Oc3cncc(F)c3)c(Br)c2[C@@H](O)C1(F)F]

(R)-4-bromo-2,2-difluoro-5-((5-fluoropyridin-3-yl)oxy)-3-hydroxy-2,3-dihydrobenzo[b]thiophene 1,1-dioxide (Compound 187): Prepared analogously as described in Example 111 utilizing 5-fluoropyridin-3-ol in Step F. $^1$H NMR (400 MHz, CDCl$_3$): δ 8.43 (d, 1H), 8.29 (d, 1H), 7.82 (d, 1H), 7.21 (d, 1H), 7.18-7.14 (dt, 1H), 5.41-5.37 (m, 1H), 3.29-3.28 (m, 1H).

Example 188

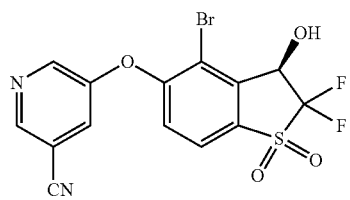 [SMILES: N#Cc1cncc(Oc2ccc3c(c2Br)[C@@H](O)C(F)(F)S3(=O)=O)c1]

(R)-5-((4-Bromo-2,2-difluoro-3-hydroxy-1,1-dioxido-2,3-dihydrobenzo[b]thiophen-5-yl)oxy)nicotinonitrile (Compound 188): Prepared analogously as described in Example 111 utilizing 5-hydroxynicotinonitrile in Step F. $^1$H NMR (400 MHz, CDCl$_3$): δ 8.76 (s, 1H), 8.64 (d, 1H), 7.87 (d, 1H), 7.59-7.58 (m, 1H), 7.27 (d, 1H), 5.42-5.36 (m, 1H), 3.36-3.32 (m, 1H).

Example 189

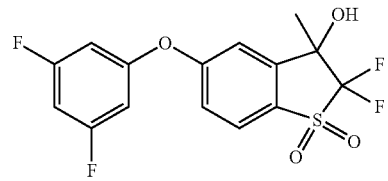 [SMILES: CC1(O)c2cc(Oc3cc(F)cc(F)c3)ccc2S(=O)(=O)C1(F)F]

5-(3,5-Difluorophenoxy)-2,2-difluoro-3-hydroxy-3-methyl-2,3-dihydrobenzo[b]thiophene 1,1-dioxide (Compound 189): 5-(3,5-Difluorophenoxy)-2,2-difluoro-3-hydroxy-3-methyl-2,3-dihydrobenzo[b]thiophene 1,1-dioxide: 3-((4-Bromo-2,2-difluoro-1,1-dioxido-3-oxo-2,3-dihydrobenzo[b]thiophen-5-yl)oxy)-5-fluorobenzonitrile (25 mg, 0.06 mmol) was dissolved in tetrahydrofuran (THF, 0.21 mL), cooled to 0° C., and treated with methylmagnesium chloride (3M in THF, 0.039 mL, 0.12 mmol). The solution was stirred at 0° C. for 2 hours, then quenched with 10% KHSO$_4$. The volatile solvents were removed with a stream of nitrogen gas, and the aqueous was treated with ethyl acetate. After separation, the aqueous was washed with ethyl acetate and the combined organics were washed with water, saturated aqueous NaHCO$_3$, saturated aqueous NaCl, dried over Na$_2$SO$_4$ and concentrated in vacuo. The crude material was chromatographed on SiO$_2$ eluting with a gradient of ethyl acetate/hexane to give Compound 189 as a colorless film (22.5 mg, 87%). LCMS ESI (−) m/z 407 (M+HCOOH—H); $^1$H NMR (400 MHz, CDCl$_3$): δ 7.81 (d, 1H), 7.28 (d, 1H), 7.24-7.21 (m, 1H), 6.76-6.70 (1H), 6.65-6.95 (m, 2H), 2.80 (m, 1H), 1.75 (m, 3H).

Example 190

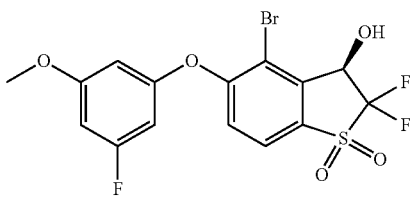 [SMILES: COc1cc(F)cc(Oc2ccc3c(c2Br)[C@@H](O)C(F)(F)S3(=O)=O)c1]

(R)-4-Bromo-2,2-difluoro-5-(3-fluoro-5-methoxyphenoxy)-3-hydroxy-2,3-dihydrobenzo[b]thiophene 1,1-dioxide (Compound 190)

Step A: Preparation of 2-bromo-3-fluoro-6-iodobenzoic acid: A stirred mixture of 2-bromo-3-fluorobenzoic acid (25 g, 114 mmol), palladium (II) acetate (1.28 g, 5.71 mmol), iodine (29 g, 114 mmol), diacetoxy iodobenzene (36.8 g, 114 mmol) and dimethylformamide (560 mL) was sparged with nitrogen for 5 minutes. The mixture was then heated at 120° C. under nitrogen for 16 hours. After cooling, the reaction mixture was poured into ice water. The solution was treated with aqueous 10% Na$_2$S$_2$O$_3$ to remove residual iodine color.

The mixture was extracted with methyl t-butyl ether. The combined organic layers were washed with water and saturated NaCl, dried over Na$_2$SO$_4$ and concentrated in vacuo. The yellow oil was triturated 10% ethyl acetate/hexanes to give a solid, which was collected by filtration. The filtrate was concentrated and triturated again with 10% ethyl acetate/hexanes. The combined solids of 2-bromo-3-fluoro-6-iodobenzoic acid (30.7 g) were used in the next step without further purification.

Step B: Preparation of methyl 2-bromo-3-fluoro-6-iodobenzoate: To a stirred solution of 2-bromo-3-fluoro-6-iodobenzoic acid (30.7 g, 89 mmol) in dimethylformamide (220 mL), fine mesh potassium carbonate (36.9 g, 267 mmol) and iodomethane (16.6 mL, 267 mmol) were added. The reaction mixture was stirred at ambient temperature for 2 hours. The reaction mixture was poured into cold water and extracted with methyl t-butyl ether. The combined organic layers were washed with water and brine, dried over sodium sulfate and concentrated in vacuo. The residue was treated with 15% ethyl acetate/hexane and stirred. The precipitated solid (18.5 g) was collected by filtration. The filtrate was concentrated in vacuo. The residue was purified by chromatography on silica gel eluting with a gradient of ethyl acetate/hexanes to give additional desired product (5.3 g). The two isolated fractions of methyl 2-bromo-3-fluoro-6-iodobenzoate were combined (23.8 g) and carried forward. LCMS ESI (+) m/z 359 (M+H). $^1$H NMR (400 MHz, CDCl$_3$): δ 7.74-7.70 (m, 1H), 6.93-6.89 (m, 1H), 4.00 (s, 3H).

Step C: Preparation of methyl 6-(acetylthio)-2-bromo-3-fluorobenzoate: A mixture of methyl 2-bromo-3-fluoro-6-iodobenzoate (17.5 g, 48.6 mmol and 4,5-bis(diphenylphosphino)-9,9-dimethylxanthene (Xantphos) (3.38 g, 5.84 mmol were suspended in 2:1 toluene/acetone (195 mL). The mixture was sparged with nitrogen for five minutes followed by addition of tris(dibenzylideneacetone)dipalladium(0) (2.67 g, 2.92 mmol) and potassium ethanethioate (6.93 g, 60.8 mmol). The mixture was heated at 70° C. for 3 hours. After cooling, the reaction mixture was filtered through a pad of celite. The filtrate was concentrated in vacuo to orange oil, which was purified by column chromatography on silica gel eluting with a gradient ethyl acetate/hexane) to give methyl 6-(acetylthio)-2-bromo-3-fluorobenzoate (14.6 g, 98%). $^1$H NMR (400 MHz, CDCl$_3$): δ 7.44-7.41 (m, 1H), 7.25-7.21 (m, 1H), 3.95 (s, 3H), 2.41 (s, 3H).

Step D: Preparation of methyl 2-bromo-3-fluoro-6-(methylthio)benzoate: A stirred solution of methyl 6-(acetylthio)-2-bromo-3-fluorobenzoate (22.2 g, 72.3 mmol) in MeOH (360 mL) was degassed by sparging with nitrogen. Solid cesium carbonate (30.6 g, 94 mmol) was added. The solution was stirred at ambient temperature for 1 hour. Iodomethane (22.5 mL, 361 mmol) was added and the reaction mixture was stirred at ambient temperature overnight under nitrogen, and then filtered through a pad of celite. The filtrate was concentrated in vacuo and redissolved in methyl t-butyl ether and water. The layers were separated. The organic layer was washed with brine and dried over Na$_2$SO$_4$. Crude methyl 2-bromo-3-fluoro-6-(methylthio)benzoate (20.7 g, quant.) was used in the next step without further purification. $^1$H NMR (400 MHz, CDCl$_3$): δ 7.38-7.35 (m, 1H), 7.16-7.11 (m, 1H), 3.98 (s, 3H), 2.45 (s, 3H).

Step E: Preparation of methyl 2-bromo-3-fluoro-6-(methylsulfonyl)benzoate: A solution of methyl 2-bromo-3-fluoro-6-(methylthio)-benzoate (20.7 g, 74 mmol) dissolved in MeOH (370 mL) was added dropwise to a solution of Oxone® (137 g, 222 mmol) in water (370 mL). The mixture was stirred at ambient temperature for 14 hours. The reaction mixture was filtered and the solids were washed with methanol. The filtrate was concentrated under reduced pressure to remove the volatile solvents. The residual aqueous mixture was extracted three times with ethyl acetate. The combined organic layers were washed with water and brine, dried over Na$_2$SO$_4$ and concentrated in vacuo. The crude product was purified by column chromatography on silica gel eluting with a gradient of ethyl acetate/hexane. After concentration in vacuo, methyl 2-bromo-3-fluoro-6-(methylsulfonyl)benzoate was obtained as a pale yellow solid (15.5 g). $^1$H NMR (400 MHz, CDCl$_3$): δ 8.04-8.01 (m, 1H), 7.37-7.33 (m, 1H), 4.02 (s, 3H), 3.17 (s, 3H).

Step F: Preparation of methyl 2-bromo-3-(3-fluoro-5-methoxyphenoxy)-6-(methylsulfonyl)benzoate: Methyl 2-bromo-3-fluoro-6-(methylsulfonyl)benzoate (200 mg, 0.64 mmol) was treated with 3-fluoro-5-methoxy-phenol (137 mg, 0.96 mmol) and dimethylformamide (2.5 mL). The solution was treated with in a single portion with sodium bicarbonate (108 mg, 1.29 mmol) and the mixture was heated to 90° C. for 18 hours. The reaction was cooled, diluted with Et$_2$O and water and then separated. The aqueous was washed with Et$_2$O and the combined organics were washed five times with 10% K$_2$CO$_3$, saturated NaHCO$_3$, saturated NaCl, dried over Na$_2$SO$_4$. After concentration in vacuo, methyl 2-bromo-3-(3-fluoro-5-methoxyphenoxy)-6-(methylsulfonyl)benzoate was recovered as an orange film (quant.). $^1$H NMR (400 MHz, CDCl$_3$): δ 7.92 (d, 1H), 7.02 (d, 1H), 6.54-6.51 (dt, 1H), 6.41-6.37 (m, 2H), 4.04 (s, 3H), 3.80 (s, 3H), 3.17 (s, 3H).

Step G: Preparation of 4-bromo-5-(3-fluoro-5-methoxyphenoxy)benzo[b]thiophen-3(2H)-one 1,1-dioxide: Sodium hydride (60% in mineral oil, 92 mg, 2.3 mmol) was washed with three portions of hexanes, then suspended in tetrahydrofuran (11 mL) and cooled to 0° C. The suspension was treated dropwise with a solution of methyl 2-bromo-3-(3-fluoro-5-methoxy-phenoxy)-6-methylsulfonyl-benzoate (331 mg, 0.76 mmol) dissolved in tetrahydrofuran (12 mL). The suspension was stirred at 0° C. for 5 minutes, then warmed to ambient temperature and stirred for 2 hours. The reaction mixture was poured slowly into cold 10% KHSO4 and swirled vigorously. The pH of the resultant aqueous phase was ~2. The suspension was concentrated in vacuo to remove tetrahydrofuran, then the mixture was diluted with ethyl acetate. The layers were separated and the aqueous was washed with ethyl acetate. The combined organic layer was washed with water, saturated NaHCO$_3$, saturated NaCl, dried over Na$_2$SO$_4$. After concentration in vacuo, 4-bromo-5-(3-fluoro-5-methoxyphenoxy)benzo[b]thiophen-3(2H)-one 1,1-dioxide was isolated as a yellow solid (199 mg, 65%). $^1$H NMR (400 MHz, CDCl$_3$): δ 7.84 (d, 1H), 7.36 (d, 1H), 6.49-6.45 (dt, 1H), 6.33-6.28 (m, 2H), 3.75 (s, 3H), 2.89 (s, 2H).

Step H: Preparation of 4-bromo-2,2-difluoro-5-(3-fluoro-5-methoxyphenoxy)benzo[b]thiophen-3(2H)-one 1,1-dioxide: A suspension of 4-bromo-5-(3-fluoro-5-methoxy-phenoxy)-1,1-dioxo-benzothiophen-3-one (100 mg, 0.25 mmol) dissolved in acetonitrile (1.3 mL) was treated with sodium carbonate (79 mg, 0.75 mmol) and Selectfluor® (265 mg, 0.75 mmol), then the resulting suspension was stirred at ambient temperature for 2 hours, then cooled to 0° C. and stirred for 2 hours. The mixture was concentrated in vacuo at ambient temperature, then the residue was diluted with ethyl acetate and water. The layers were separated and the aqueous was washed with ethyl acetate. The combined organics were washed with saturated NaHCO$_3$, saturated NaCl, dried over Na$_2$SO$_4$ and concentrated in vacuo to a waxy, light yellow solid. This material was chromatographed on silica gel eluting with a gradient of ethyl acetate/hexane. 4-Bromo-2,2-difluoro-5-(3-fluoro-5-methoxyphenoxy)benzo[b]thiophen-3(2H)-one 1,1-dioxide was isolated as a pale yellow solid (84 mg, 77%). $^1$H NMR (400 MHz, CDCl$_3$): δ 7.93 (d, 1H), 7.46 (d, 1H), 6.60-6.55 (m, 1H), 6.48-6.43 (m, 2H), 3.81 (s, 3H).

Step I: Preparation of (R)-4-bromo-2,2-difluoro-5-(3-fluoro-5-methoxyphenoxy)-3-hydroxy-2,3-dihydrobenzo[b]thiophene 1,1-dioxide (Compound 190): 4-Bromo-2,2-difluoro-5-(3-fluoro-5-methoxyphenoxy)benzo[b]thiophen-3(2H)-one 1,1-dioxide (77 mg, 0.18 mmol) was dissolved in dichloromethane (pre-sparged with nitrogen gas, 0.8 mL), then the solution was treated with triethylamine (49 μL, 0.35 mmol) and formic acid (20 μL, 0.53 mmol). This solution was cooled to 0° C. and treated with a pre-cooled (0° C.) solution of N-[(1R,2R)-1,2-diphenyl-2-(2-(4-methylbenzyloxy)ethylamino)-ethyl]-4-methylbenzene sulfonamide (chloro)ruthenium(II) (1.15 mg, 0.002 mmol) dissolved in dichloromethane (0.8 mL). The resultant suspension was placed in the refrigerator and allowed to stand at 4° C. for 100 hours. The reaction mixture was concentrated to a small volume and chromatographed on SiO$_2$, eluting with a stepped gradient of ethyl acetate/chloroform. The desired compound was collected and concentrated in vacuo. The oil was redissolved in methylene chloride and hexane, then concentrated in vacuo to a white solid to give Compound 190 (34 mg, 43%, >79% ee by Mosher ester analysis). LCMS ESI (−) m/z 437, 439 (M−H). $^1$H NMR (400 MHz, CDCl$_3$) δ 7.75 (d, 1H), 7.17 (d, 1H), 6.56-6.51 (m, 1H), 6.42-6.37 (m, 2H), 5.42-5.35 (m, 1H), 3.80 (s, 3H), 2.99-2.95 (m, 1H).

Example 191

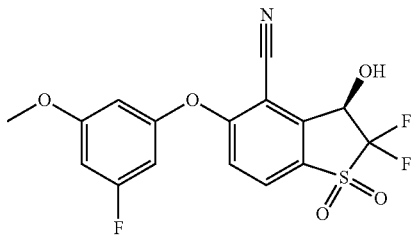 [SMILES: COc1cc(F)cc(Oc2ccc3c(c2C#N)[C@@H](O)C(F)(F)S3(=O)=O)c1]

(R)-2,2-difluoro-5-(3-fluoro-5-methoxyphenoxy)-3-hydroxy-2,3-dihydrobenzo[b]thiophene-4-carbonitrile 1,1-dioxide (Compound 191): A solution of (R)-4-bromo-2,2-difluoro-5-(3-fluoro-5-methoxyphenoxy)-3-hydroxy-2,3-dihydrobenzo[b]thiophene 1,1-dioxide (20 mg, 0.05 mmol)] dissolved in 1-methyl-2-pyrrolidinone (0.32 mL) was treated with copper (I) cyanide (5.3 mg, 0.06 mmol). Argon gas was bubbled through the solution for several minutes, then the solution was heated to 160° C. for 90 minutes in the microwave reactor. After cooling, the mixture was diluted with ethyl acetate and water. After separation, the aqueous was washed with ethyl acetate, then the combined organics were washed with water, saturated NaHCO$_3$, saturated NaCl, dried over Na$_2$SO$_4$ and concentrated in vacuo to a dark residue. The crude material was chromatographed on SiO$_2$, eluting with a stepped gradient of ethyl acetate/CHCl$_3$ to give Compound 191 as a white solid (7.2 mg, 37%, >79% ee by Mosher ester analysis). LCMS ESI (−) m/z 384 (M−H); $^1$HNMR (400 MHz, CDCl$_3$) δ 7.92 (d, 1H), 7.17 (d, 1H), 6.64-6.60 (m, 1H), 6.50-6.45 (m, 2H), 6.57-6.51 (m, 1H), 3.82 (s, 3H), 3.80-3.74 (m, 1H).

Example 192

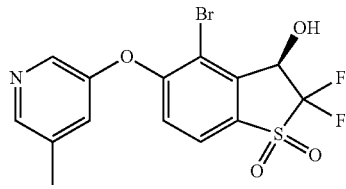 [SMILES: Cc1cncc(Oc2ccc3c(c2Br)[C@@H](O)C(F)(F)S3(=O)=O)c1]

(R)-4-bromo-2,2-difluoro-3-hydroxy-5-((5-methylpyridin-3-yl)oxy)-2,3-dihydrobenzo[b]thiophene 1,1-dioxide (Compound 82): Prepared analogously as described in Example 111 utilizing 5-methylpyridin-3-ol in Step F. $^1$H NMR (400 MHz, CDCl$_3$): δ 8.38-8.36 (m, 1H), 8.14 (d, 1H), 7.72 (d, 1H), 7.24-7.22 (m, 1H), 7.01 (d, 1H), 5.41-5.37 (m, 1H), 4.14-4.08 (m, 1H), 2.40 (s, 3H).

Example 193

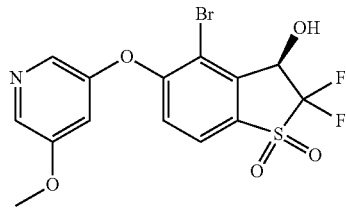 [SMILES: COc1cncc(Oc2ccc3c(c2Br)[C@@H](O)C(F)(F)S3(=O)=O)c1]

(R)-4-bromo-2,2-difluoro-3-hydroxy-5-((5-methoxypyridin-3-yl)oxy)-2,3-dihydrobenzo[b]thiophene 1,1-dioxide (Compound 193): Prepared analogously as described in Example 111 utilizing 5-methoxypyridin-3-ol in Step F. $^1$H NMR (400 MHz, CDCl$_3$): δ 8.26-8.23 (m, 1H), 7.95-7.93 (m, 1H), 7.73 (d, 1H), 7.06 (d, 1H), 6.95-6.92 (m, 1H), 5.42-5.35 (m, 1H), 4.03-3.97 (m, 1H), 3.88 (s, 3H).

Example 194

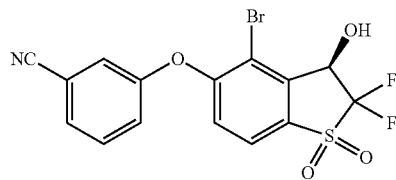 [SMILES: N#Cc1cccc(Oc2ccc3c(c2Br)[C@@H](O)C(F)(F)S3(=O)=O)c1]

(R)-3-((4-bromo-2,2-difluoro-3-hydroxy-1,1-dioxido-2,3-dihydrobenzo[b]thiophen-5-yl)oxy)benzonitrile (Compound 194): Prepared analogously as described in Example 111 utilizing 3-hydroxybenzonitrile in Step F. $^1$H NMR (400 MHz, CDCl$_3$): δ 7.80 (d, 1H), 7.59-7.54 (m, 2H), 7.37-7.35 (m, 1H), 7.32-7.27 (m, 1H), 7.15 (d, 1H), 5.42-5.37 (m, 1H), 3.11 (d, 1H).

Example 195

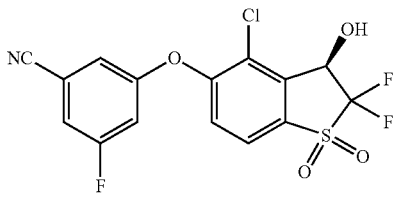 [SMILES: N#Cc1cc(F)cc(Oc2ccc3c(c2Cl)[C@@H](O)C(F)(F)S3(=O)=O)c1]

(R)-3-((4-chloro-2,2-difluoro-3-hydroxy-1,1-di-oxido-2,3-dihydrobenzo[b]thiophen-5-yl)oxy)-5-fluorobenzonitrile (Compound 195)

Step A: Preparation of 2-chloro-3-fluoro-6-iodobenzoic acid: 2-chloro-3-fluoro-benzoic acid (25.3 g, 144 mmol) was combined with palladium (II) acetate (1.62 g, 7.24 mmol), iodine (36.7 g, 144 mmol), and diacetoxy iodobenzene (46.6 g, 144 mmol) and the solids were slurried in dimethylformamide (700 mL). The resulting suspension was sparged with argon, then heated to 120° C. under nitrogen for 16 hours. The reaction was cooled and poured into water (2.5 L). Methyl t-butyl ether (800 mL) was added and the layers were separated. The aqueous was re-extracted with fresh methyl t-butyl ether (400 mL). The combined organic layers were washed with 1M $Na_2S_2O_3$, water, saturated NaCl, dried over $Na_2SO_4$ and concentrated in vacuo. The crude oil was dissolved in ethyl acetate (20 mL) and diluted with hexane (180 mL) and the solution was stirred overnight. The undesired solid was removed by filtration and washed with hexanes. Crude 2-chloro-3-fluoro-6-iodobenzoic acid was obtained, after concentration of the filtrate, as yellow oil (40 g, 94%). $^1$H NMR (400 MHz, $CDCl_3$): δ 7.74-7.70 (m, 1H), 7.01-6.96 (m, 1H).

Step B: Preparation of methyl 2-chloro-3-fluoro-6-iodobenzoate: 2-Chloro-3-fluoro-6-iodobenzoic acid (40.0 g, 133 mmol) was dissolved in dimethylformamide (300 mL), then treated with fine mesh potassium carbonate (55 g, 400 mmol) and iodomethane (24.9 mL, 400 mmol). The suspension was stirred at ambient temperature for 3.5 hours, then concentrated in vacuo to remove iodomethane. The mixture was poured into cold water (600 mL) and extracted twice with methyl t-butyl ether (200 mL). The combined organics were washed with water, saturated NaCl, dried over $Na_2SO_4$ and concentrated in vacuo. The resulting oil was dissolved in hexanes, then concentrated onto $SiO_2$ (100 g). Separately, a pad of silica gel was pre-equilibrated with hexanes, then the crude solid was placed on the top of this filter column. The column was eluted with a stepped gradient of hexanes/$Et_2O$. Fractions containing the desired product and were concentrated in vacuo. The resultant oil was treated with hexanes and concentrated to produce methyl 2-chloro-3-fluoro-6-iodobenzoate as a white solid (31 g, 74%). $^1$H NMR (400 MHz, $CDCl_3$): δ 7.70-7.67 (m, 1H), 6.97-6.93 (m, 1H), 4.00 (s, 3H).

Step C: Preparation of methyl 6-(acetylthio)-2-chloro-3-fluorobenzoate: Methyl 2-chloro-3-fluoro-6-iodobenzoate (15.3 g, 48.7 mmol) and 4,5-bis(diphenylphosphino)-9,9-dimethylxanthene (Xantphos, 3.38 g, 5.84 mmol) were suspended in 2:1 toluene/acetone (170 mL). The mixture was sparged with argon, then treated with tris(dibenzylideneacetone)dipalladium ($Pd_2dba_3$, 2.67 g, 2.9 mmol) and potassium ethanethiolate (6.93 g, 60.8 mmol). The mixture was sealed in a tube, stirred vigorously, and heated to 70° C. for 3 hours. After cooling, the mixture was filtered through a pad of celite on cellulose, then concentrated in vacuo to dark orange oil. This oil was redissolved in methylene chloride and concentrated onto $Na_2SO_4$ (200 g). The sodium sulfate powder with adhered crude product was dry-loaded onto a large column of $SiO_2$ pre-equilibrated with hexanes. The column was eluted under slight vacuum with a stepwise gradient of ethyl acetate/hexane. Methyl 6-(acetylthio)-2-chloro-3-fluorobenzoate was obtained as orange oil after concentration in vacuo (11.9 g, 93%).

Step D: Preparation of methyl 2-chloro-3-fluoro-6-(methylthio)benzoate: A solution of methyl 6-(acetylthio)-2-chloro-3-fluorobenzoate (11.9 g, 45.5 mmol) was dissolved in MeOH (225 mL), degassed with bubbling argon for 5 minutes, then the solution was treated with cesium carbonate (19.3 g, 59.1 mmol). The suspension was stirred at ambient temperature for 4 hours. The reaction mixture was treated with iodomethane (14.2 mL, 227 mmol) and stirred under argon for 60 hours. The mixture was concentrated in vacuo and redissolved in a mixture of $Et_2O$ and water. The layers were separated and the aqueous was washed with $Et_2O$. The combined organic layers were washed with saturated $NaHCO_3$, saturated NaCl, dried over $Na_2SO_4$ and concentrated in vacuo to dark oil (9.08 g, 85%).

Step E: Preparation of methyl 2-chloro-3-fluoro-6-(methylsulfonyl)benzoate: A solution of methyl 2-chloro-3-fluoro-6-(methylthio)benzoate (9.08 g, 32.5 mmol) dissolved in MeOH (160 mL) was added dropwise to a slurry of Oxone® (60.1 g, 97.6 mmol) dissolved water (160 mL). The mixture was stirred at ambient temperature for 22 hours. The suspended solids were removed by filtration and washed with water. The filtered solids were resuspended in ethyl acetate, then re-filtered. The solids were suspended once again in ethyl acetate, stirred 10 minutes and then filtered. The combined filtrates were concentrated to a yellow solid. This solid was triturated with MeOH (ca. 75 mL), filtered and washed with MeOH and then air-dried. Methyl 2-chloro-3-fluoro-6-(methylsulfonyl)benzoate was recovered as a white solid (5.04 g, 49%). $^1$H NMR (400 MHz, $CDCl_3$): δ 8.00-7.97 (m, 1H), 7.41-7.37 (m, 1H), 4.03 (s, 3H), 3.18 (s, 3H).

Step F: Preparation of methyl 2-chloro-3-(3-cyano-5-fluorophenoxy)-6-(methylsulfonyl)benzoate: Methyl 2-chloro-3-fluoro-6-(methylsulfonyl)benzoate (200 mg, 0.75 mmol) was treated with 3-fluoro-5-hydroxy-benzonitrile (205 mg, 1.5 mmol) and dimethylformamide (2.5 mL). The solution was treated with in a single portion with sodium bicarbonate (126 mg, 1.5 mmol) and the mixture was heated to 90° C. for 16 hours. The reaction was cooled, diluted with $Et_2O$ and water, then separated. The aqueous was washed with $Et_2O$. The combined organics were washed with water, three times with 10% $K_2CO_3$, saturated NaCl, dried over $Na_2SO_4$ and concentrated in vacuo to an light orange solid (262 mg, 91%). $^1$H NMR (400 MHz, $CDCl_3$): δ 7.99 (d, 1H), 7.25-7.22 (m, 1H), 7.19 (d, 1H), 7.10-7.09 (m, 1H), 7.03-7.00 (dt, 1H), 4.04 (s, 3H), 3.21 (s, 3H).

Step G: Preparation of 3-((4-chloro-1,1-dioxido-3-oxo-2,3-dihydrobenzo[b]thiophen-5-yl)oxy)-5-fluorobenzonitrile: Sodium hydride (60% in mineral oil, 81 mg, 2.0 mmol) was rinsed with three times with hexane, then resuspended in tetrahydrofuran (3.5 mL). The suspension was cooled to 0° C. and treated dropwise with a solution of methyl 2-chloro-3-(3-cyano-5-fluorophenoxy)-6-(methylsulfonyl)benzoate (260 mg, 0.68 mmol) dissolved in tetrahydrofuran (3.7 mL). After the addition, the mixture was removed from the ice bath and stirred at ambient temperature for 2 hours. The reaction was quenched with 10% $KHSO_4$ to about pH 2, and concentrated in vacuo to remove volatile solvents. Ethyl acetate was added, the solids were redissolved and the pH of the aqueous was adjusted to about 3-4 with 10% KHSO₄. After separation, the aqueous was washed twice with ethyl acetate, then the combined organics were washed twice with water, saturated NaCl, dried over Na₂SO₄ and concentrated in vacuo to a pale yellow solid (183 mg, 77%). ¹H NMR (400 MHz, CDCl₃): δ 7.95 (d, 1H), 7.56 (d, 1H), 7.24-7.21 (m, 1H), 7.05-7.04 (m, 1H), 6.99-6.96 (dt, 1H), 4.21 (s, 2H).

Step H: Preparation of 3-((4-chloro-2,2-difluoro-1,1-dioxido-3-oxo-2,3-dihydrobenzo[b]thiophen-5-yl)oxy)-5-fluorobenzonitrile: A solution of 3-((4-chloro-1,1-dioxido-3-oxo-2,3-dihydrobenzo[b]thiophen-5-yl)oxy)-5-fluorobenzonitrile (70 mg, 0.20 mmol) slurried in acetonitrile (1.15 mL) was treated with Selectfluor® (211 mg, 0.60 mmol) and sodium carbonate (63.3 mg, 0.60 mmol) and the resulting suspension was stirred at ambient temperature for 2 hours. The mixture was diluted with water and ethyl acetate and then separated. The aqueous was washed with ethyl acetate. The combined organics were washed with saturated NaHCO₃, saturated NaCl, dried over Na₂SO₄ and concentrated in vacuo to a light yellow film. The crude product was chromatographed on SiO₂ eluting with a gradient of ethyl acetate/hexane. 3-((4-Chloro-2,2-difluoro-1,1-dioxido-3-oxo-2,3-dihydrobenzo[b]thiophen-5-yl)oxy)-5-fluorobenzonitrile was obtained as a yellow solid (111 mg, quant). 3-((4-Chloro-2,2-difluoro-1,1-dioxido-3-oxo-2,3-dihydrobenzo[b]thiophen-5-yl)oxy)-5-fluorobenzonitrile was observed as about 4:1 mixture of ketone and hydrate in CDCl₃ and both sets of signals are described together below. ¹H NMR (400 MHz, CDCl₃): δ 8.01 (d, 1H), 7.83 (d, 0.25H), 7.62 (d, 1H), 7.32-7.28 (m, 1.2H), 7.14-7.11 (m, 1.2H), 7.07-7.00 (m, 1.3H).

Step I: Preparation of (R)-3-((4-chloro-2,2-difluoro-3-hydroxy-1,1-dioxido-2,3-dihydrobenzo[b]thiophen-5-yl)oxy)-5-fluorobenzonitrile (Compound 195): 3-((4-Chloro-2,2-difluoro-1,1-dioxido-3-oxo-2,3-dihydrobenzo[b]thiophen-5-yl)oxy)-5-fluorobenzonitrile (107 mg, 0.28 mmol) was dissolved in dichloromethane (freshly sparged with nitrogen, 1.25 mL) and the solution was treated with triethylamine (77 µL, 0.55 mmol) and formic acid (31 µL, 0.83 mmol). This solution was cooled to 0° C. and treated with a pre-cooled (0° C.) solution of (R,R)-Ts-DENEB™ (1.8 mg, 2.8 µmol) dissolved in dichloromethane (1.25 mL). The resultant suspension was placed in the refrigerator and allowed to stand at 4° C. for 30 hours. The reaction was concentrated with a stream of nitrogen gas, then chromatographed on SiO₂ eluting with a gradient of ethyl acetate/chloroform. Compound 195 was obtained as light yellow oil which slowly solidified (116 mg, quant., >88% ee by Mosher ester analysis). LCMS ESI (−) m/z 388, 390 (M−H); ¹H NMR (400 MHz, CDCl₃): δ 7.82 (d, 1H), 7.32 (d, 1H), 7.25-7.23 (m, 1H), 7.12-7.10 (m, 1H), 7.03-7.00 (dt, 1H), 5.44 (d, 1H), 3.39-3.25 (m, 1H).

Example 196

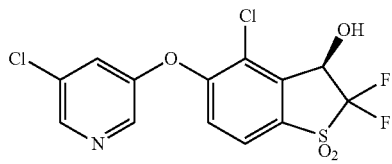 [SMILES: O=S1(=O)c2ccc(Oc3cncc(Cl)c3)c(Cl)c2[C@@H](O)C1(F)F]

(R)-4-Chloro-5-((5-chloropyridin-3-yl)oxy)-2,2-difluoro-3-hydroxy-2,3-dihydrobenzo[b]thiophene 1,1-dioxide (Compound 196): Prepared analogously as described in Example 195 utilizing 5-chloropyridin-3-ol in Step F. ¹H NMR (400 MHz, CDCl₃): δ 8.50 (d, 1H), 8.33 (d, 1H), 7.78 (d, 1H), 7.41-7.40 (m, 1H), 7.22 (d, 1H), 5.47-5.42 (m, 1H), 3.45 (d, 1H).

Example 197

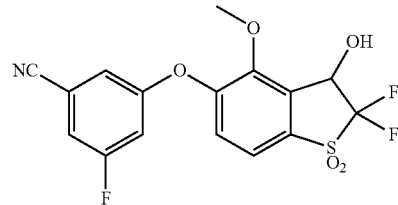 [SMILES: COc1c(Oc2cc(F)cc(C#N)c2)ccc2c1C(O)C(F)(F)S2(=O)=O]

3-((2,2-Difluoro-3-hydroxy-4-methoxy-1,1-dioxido-2,3-dihydrobenzo[b]thiophen-5-yl)oxy)-5-fluorobenzonitrile (Compound 197)

Step A: Preparation of methyl 3-(3-cyano-5-fluorophenoxy)-2-fluoro-6-(methylsulfonyl)benzoate: Prepared analogously as described in Example 111, Steps A-F utilizing 2,3-difluorobenzoic acid in Step A. ¹H NMR (400 MHz, CDCl₃): δ 7.90 (dd, 1H), 7.31-7.27 (dd, 1H), 7.24-7.21 (m, 1H), 7.12-7.11 (m, 1H), 7.04-7.01 (m, 1H), 4.02 (s, 3H), 3.27 (s, 3H).

Step B: Preparation of 3-fluoro-5-((4-methoxy-1,1-dioxido-3-oxo-2,3-dihydrobenzo[b]thiophen-5-yl)oxy)benzonitrile: Sodium hydride (60% in mineral oil, 79 mg, 2.0 mmol) was washed three times with hexanes, then resuspended in tetrahydrofuran (3.4 mL). The suspension was cooled to 0° C. and treated dropwise with a solution of methyl 3-(3-cyano-5-fluorophenoxy)-2-fluoro-6-(methylsulfonyl)benzoate (242 mg, 0.66 mmol) dissolved in tetrahydrofuran (3.4 mL). After the addition, the mixture was removed from the ice bath and stirred at ambient temperature for 60 hours. The reaction was quenched with methanol, then 10% KHSO₄ was added to adjust pH to about 2, and concentrated in vacuo. Ethyl acetate was added, then the pH of the aqueous was adjusted to about 3-4 with saturated NaHCO₃. The layers were separated and the aqueous was washed twice with ethyl acetate. The combined organics were washed twice with water, saturated NaCl, dried over Na₂SO₄ and concentrated in vacuo to yellow oil. The crude product was chromatographed on SiO₂ eluting with a gradient of ethyl acetate/hexanes. Two products were observed in the purified sample, but additional efforts at separation were unsuccessful. The crude material was carried forward as a mixture (151 mg).

Step C: Preparation of 3-((2,2-difluoro-4-methoxy-1,1-dioxido-3-oxo-2,3-dihydrobenzo[b]thiophen-5-yl)oxy)-5-fluorobenzonitrile: A solution of 3-fluoro-5-((4-methoxy-1,1-dioxido-3-oxo-2,3-dihydrobenzo[b]thiophen-5-yl)oxy)benzonitrile (151 mg, 0.45 mmol) slurried in acetonitrile (2.6 mL) was treated with Selectfluor® (479 mg, 1.35 mmol) and sodium carbonate (143 mg, 1.35 mmol) and the resulting suspension was stirred at ambient temperature for 16 hours. Additional Selectfluor® (160 mg, 0.45 mmol) was added and the mixture was stirred at ambient temperature for an additional 2 hours. The reaction mixture was diluted with water and ethyl acetate and then separated. The aqueous was washed with ethyl acetate. The combined organics were washed with saturated NaHCO$_3$, saturated NaCl, dried over Na$_2$SO$_4$ and concentrated in vacuo to yellow oil. The crude product was chromatographed on SiO$_2$ eluting with a gradient of ethyl acetate/hexane. The sample was not sufficiently purified by this method. The mixture was re-chromatographed on SiO$_2$ eluting with a gradient of methylene chloride/chloroform then with ethyl acetate/chloroform. 3-((2,2-Difluoro-4-methoxy-1,1-dioxido-3-oxo-2,3-dihydrobenzo[b]thiophen-5-yl)oxy)-5-fluorobenzonitrile eluted as the first band was concentrated in vacuo to a white solid (75 mg, 43%). $^1$H NMR (400 MHz, CDCl$_3$): δ 7.78 (d, 1H), 7.66 (d, 1H), 7.25-7.21 (m, 1H), 7.07-7.06 (m, 1H), 6.98-6.94 (m, H), 4.07 (s, 3H).

Step D: Preparation of 3-((2,2-difluoro-3-hydroxy-4-methoxy-1,1-dioxido-2,3-dihydrobenzo[b]thiophen-5-yl)oxy)-5-fluorobenzonitrile (Compound 197): 3-((2,2-Difluoro-4-methoxy-1,1-dioxido-3-oxo-2,3-dihydrobenzo[b]thiophen-5-yl)oxy)-5-fluorobenzonitrile (28.6 mg, 0.07 mmol) was dissolved in a mixture of MeOH (0.28 mL) and ethyl acetate (0.28 mL), cooled to 0° C. and treated with sodium borohydride (5.5 mg, 0.15 mmol). The mixture was stirred at 0° C. and allowed to warm to ambient temperature with the bath overnight. The reaction was cooled to 0° C. and treated with 1N KHSO$_4$ and stirred for 20 minutes. The reaction was neutralized with saturated NaHCO$_3$, diluted with ethyl acetate and separated. The aqueous was washed with ethyl acetate and the combined organics were washed with saturated NaHCO$_3$, saturated NaCl, dried over Na$_2$SO$_4$ and concentrated in vacuo. The crude product was chromatographed on silica gel eluting with a gradient of ethyl acetate/hexane. Compound 197 was obtained as a white solid (11 mg, 38%). LCMS ESI (−) m/z 430 (M+HCOOH—H); $^1$H NMR (400 MHz, CDCl$_3$): δ 7.62 (d, 1H), 7.32 (d, 1H), 7.21-7.18 (m, 1H), 7.08-7.06 (m, 1H), 6.97-6.93 (m, 1H), 5.47-5.43 (m, 1H), 4.02 (s, 3H), 3.10-3.08 (m, 1H).

Example 198

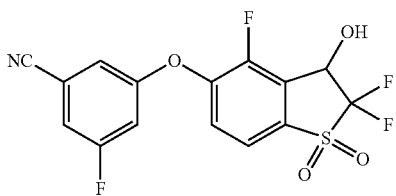 [SMILES: N#Cc1cc(F)cc(Oc2ccc3c(c2F)C(O)C(F)(F)S3(=O)=O)c1]

3-Fluoro-5-((2,2,4-trifluoro-3-hydroxy-1,1-dioxido-2,3-dihydrobenzo[b]thiophen-5-yl)oxy)benzonitrile (Compound 198)

Step A: Preparation of methyl 3-(3-cyano-5-fluorophenoxy)-2-fluoro-6-(methylsulfonyl)benzoate: Prepared analogously as described in Example 111, Steps A-F utilizing 2,3-difluorobenzoic acid in Step A. $^1$H NMR (400 MHz, CDCl$_3$): δ 7.90 (dd, 1H), 7.31-7.27 (dd, 1H), 7.24-7.21 (m, 1H), 7.12-7.11 (m, 1H), 7.04-7.01 (m, 1H), 4.02 (s, 3H), 3.27 (s, 3H).

Step B: Preparation of 3-fluoro-5-((4-fluoro-1,1-dioxido-3-oxo-2,3-dihydrobenzo[b]thiophen-5-yl)oxy)benzonitrile: Sodium hydride (60% in mineral oil, 79 mg, 2.0 mmol) was washed three times with hexanes, then resuspended in tetrahydrofuran (3.4 mL). The suspension was cooled to 0° C. and treated dropwise with a solution of methyl 3-(3-cyano-5-fluorophenoxy)-2-fluoro-6-(methylsulfonyl)benzoate (242 mg, 0.66 mmol) dissolved in tetrahydrofuran (3.4 mL). After the addition, the mixture was removed from the ice bath and stirred at ambient temperature for 60 hours. The reaction was quenched with methanol, then 10% KHSO$_4$ was added to adjust pH to about 2, and concentrated in vacuo. Ethyl acetate was added, then the pH of the aqueous was adjusted to about 3-4 with saturated NaHCO$_3$. The layers were separated and the aqueous was washed twice with ethyl acetate. The combined organics were washed twice with water, saturated NaCl, dried over Na$_2$SO$_4$ and concentrated in vacuo to a yellow oil. The crude product was chromatographed on SiO$_2$ eluting with a gradient of ethyl acetate/hexane. Two products were evident in the purified sample, but additional efforts at separation were unsuccessful. The crude material was carried forward as a mixture (151 mg).

Step C: Preparation of 3-fluoro-5-((2,2,4-trifluoro-1,1-dioxido-3-oxo-2,3-dihydrobenzo[b]thiophen-5-yl)oxy)benzonitrile: A solution of (3-fluoro-5-((4-fluoro-1,1-dioxido-3-oxo-2,3-dihydrobenzo[b]thiophen-5-yl)oxy)benzonitrile (151 mg, 0.45 mmol) slurried in acetonitrile (2.6 mL) was treated with Selectfluor® (479 mg, 1.35 mmol) and sodium carbonate (143 mg, 1.35 mmol) and the resulting suspension was stirred at ambient temperature for 16 hours. Additional Selectfluor® (160 mg, 0.45 mmol) was added and the mixture was stirred at ambient temperature for an additional 2 hours. The reaction mixture was diluted with water and ethyl acetate and then separated. The aqueous was washed with ethyl acetate. The combined organics were washed with saturated NaHCO$_3$, saturated NaCl, dried over Na$_2$SO$_4$ and concentrated in vacuo to yellow oil. The crude product was chromatographed on SiO$_2$ eluting with a gradient of ethyl acetate/hexanes. The mixture was re-chromatographed on SiO$_2$ eluting with a gradient of methylene chloride/chloroform then with ethyl acetate/chloroform. 3-Fluoro-5-((2,2,4-trifluoro-1,1-dioxido-3-oxo-2,3-dihydrobenzo[b]thiophen-5-yl)oxy)benzonitrile was isolated as a yellow film (16 mg, 10%). $^1$H NMR (400 MHz, CDCl$_3$): δ 7.92 (d, 1H), 7.78-7.74 (m, 1H), 7.29 (d, 1H), 7.16-7.14 (m, 1H), 7.09-7.05 (m, 1H).

Step D: Preparation of 3-fluoro-5-((2,2,4-trifluoro-3-hydroxy-1,1-dioxido-2,3-dihydrobenzo[b]thiophen-5-yl)oxy)benzonitrile (Compound 198): 3-Fluoro-5-((2,2,4-trifluoro-1,1-dioxido-3-oxo-2,3-dihydrobenzo[b]thiophen-5-yl)oxy)benzonitrile (16 mg, 0.04 mmol) was dissolved in dichloromethane (freshly sparged with nitrogen gas, 0.2 mL) and the solution was treated with triethylamine (12 μL, 0.09 mmol) and formic acid (4.9 μL, 0.13 mmol). This solution was cooled to 0° C. and treated with a pre-cooled (0° C.) solution of (R,R)-Ts-DENEB (0.3 mg, 0.4 μmol) dissolved in dichloromethane (0.2 mL). The resultant suspension was placed in the refrigerator and allowed to stand at 4° C. for 102 hours. The mixture was concentrated in vacuo and chromatographed on silica gel eluting with a gradient of ethyl acetate/methylene chloride. Compound 198 was obtained as a colorless film (5 mg, 31%). LCMS ESI (−) m/z 418 (M+HCOOH—H); $^1$H NMR (400 MHz, CDCl$_3$): δ 7.72 (d, 1H), 7.44-7.40 (m, 1H), 7.25-7.22 (m, 1H), 7.13-7.10 (m, 1H), 7.05-7.01 (m, 1H), 5.51 (d, 1H).

Example 199

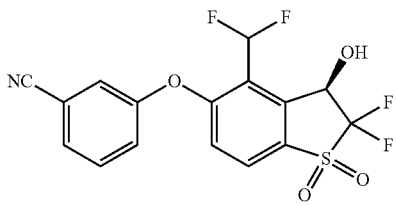 [SMILES: N#Cc1cccc(Oc2ccc3c(c2C(F)F)[C@@H](O)C(F)(F)S3(=O)=O)c1]

(R)-3-((4-(difluoromethyl)-2,2-difluoro-3-hydroxy-1,1-dioxido-2,3-dihydrobenzo[b]thiophen-5-yl)oxy)benzonitrile (Compound 199)

Step A: Preparation of 3-((4-(difluoromethyl)-2,2-difluoro-1,1-dioxido-3-oxo-2,3-dihydrobenzo[b]thiophen-5-yl)oxy)benzonitrile: Prepared analogously as described in Example 113, Steps A-G utilizing 3-hydroxybenzonitrile in Step E. $^1$H NMR (400 MHz, CDCl$_3$): δ 8.14 (d, 1H), 7.68 (t, 1H), 7.64-7.59 (m, 2H), 7.52 (d, 1H), 7.42-7.40 (m, 1H), 7.37-7.33 (m, 1H).

Step B: Preparation of (R)-3-((4-(difluoromethyl)-2,2-difluoro-3-hydroxy-1,1-dioxido-2,3-dihydrobenzo[b]thiophen-5-yl)oxy)benzonitrile (Compound 199): 3-((4-(Difluoromethyl)-2,2-difluoro-1,1-dioxido-3-oxo-2,3-dihydrobenzo[b]thiophen-5-yl)oxy)benzonitrile (11.7 mg, 0.03 mmol) was added as a solid to a pre-cooled (0° C.) solution of triethylamine (8.5 µL, 0.06 mmol), formic acid (3.4 µL, 0.09 mmol) and (R,R)-Ts-DENEB™ (0.2 mg, 0.3 µmol) dissolved in dichloromethane (freshly sparged with nitrogen gas, 0.2 mL). The resultant suspension was placed in the refrigerator and allowed to stand at 4° C. for 48 hours. The solvent was removed in a stream of nitrogen gas and the crude product was chromatographed on SiO2 eluting with a gradient of ethyl acetate/hexane. Compound 198 was isolated as a white semi-solid (7 mg, 59%). $^1$H NMR (400 MHz, CDCl$_3$): δ 7.92 (d, 1H), 7.62-7.57 (m, 2H), 7.42-7.40 (m, 1H), 7.35-7.31 (m, 1H), 7.28 (t, J=53 Hz, 1H), 7.11 (d, 1H), 5.69-5.65 (m, 1H), 3.33-3.32 (m, 1H).

Example 200

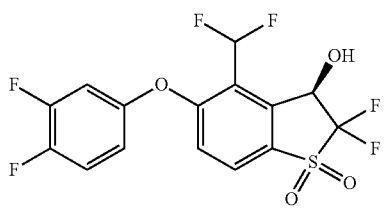 [SMILES: O=S1(=O)c2ccc(Oc3ccc(F)c(F)c3)c(C(F)F)c2[C@@H](O)C1(F)F]

(R)-4-(Difluoromethyl)-5-(3,4-difluorophenoxy)-2,2-difluoro-3-hydroxy-2,3-dihydrobenzo[b]thiophene 1,1-dioxide (Compound 200): $^1$H NMR (400 MHz, CDCl$_3$+CD$_3$OD): δ 7.80 (d, 1H), 7.23-7.15 (m, 1H), 7.20 (t, 1H), 7.02 (d, 1H), 6.94-6.88 (m, 1H), 6.80-6.75 (m, 1H), 5.50 (d, 1H).

Example 201

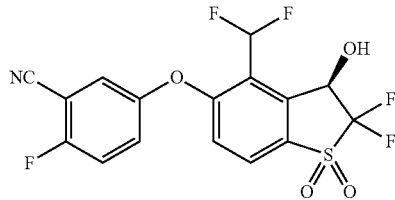 [SMILES: N#Cc1cc(Oc2ccc3c(c2C(F)F)[C@@H](O)C(F)(F)S3(=O)=O)ccc1F]

(R)-5-((4-(Difluoromethyl)-2,2-difluoro-3-hydroxy-1,1-dioxido-2,3-dihydrobenzo[b]thiophen-5-yl)oxy)-2-fluorobenzonitrile (Compound 201): $^1$H NMR (400 MHz, CDCl$_3$+CD$_3$OD): δ 7.83 (d, 1H), 7.33-7.23 (m, 3H), 7.18 (t, 1H), 7.01 (d, 1H), 5.51-5.48 (m, 1H).

Example 202

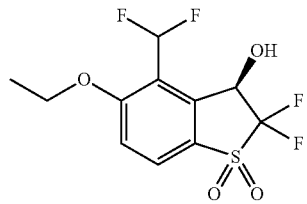 [SMILES: CCOc1ccc2c(c1C(F)F)[C@@H](O)C(F)(F)S2(=O)=O]

(R)-4-(Difluoromethyl)-5-ethoxy-2,2-difluoro-3-hydroxy-2,3-dihydrobenzo[b]thiophene 1,1-dioxide (Compound 202)

Step A: Preparation of 2-(difluoromethyl)-3-ethoxy-6-(methylsulfonyl)benzonitrile: 2-(Difluoromethyl)-3-fluoro-6-(methylsulfonyl)benzonitrile (Example 3, Step D) (200 mg, 0.80 mmol) was dissolved in tetrahydrofuran (1.6 mL) and absolute EtOH (1.6 mL), then the mixture was treated with 3N NaOH (0.27 mL, 0.80 mmol) and stirred at ambient temperature for 90 minutes. The mixture was neutralized with 10% citric acid (0.29 mL) and the volatile solvents were removed in a stream of nitrogen gas. The residue was redissolved in ethyl acetate and water and then separated. The aqueous was washed with ethyl acetate and the combined organics were washed with saturated NaHCO$_3$, saturated NaCl, dried over Na$_2$SO$_4$ and concentrated in vacuo. 2-(Difluoromethyl)-3-ethoxy-6-(methylsulfonyl)benzonitrile was isolated as an off-white solid (181 mg, 82%). $^1$H NMR (400 MHz, CDCl$_3$): δ 8.27 (d, 1H), 7.28 (d, 1H), 7.18 (t, 1H), 4.25 (q, 2H), 3.31 (s, 3H), 1.52 (t, 3H).

Step B: Preparation of 4-(difluoromethyl)-5-ethoxy-2,2-difluorobenzo[b]thiophen-3(2H)-one 1,1-dioxide: Prepared analogously as described in Example 113, Steps F and G, utilizing 2-(difluoromethyl)-3-ethoxy-6-(methylsulfonyl)benzonitrile in Step F. $^1$H NMR (400 MHz, CDCl$_3$): δ 8.15 (d, 1H), 7.61 (d, 1H), 7.52 (t, 1H), 4.30 (q, 2H), 1.55 (t, 3H).

Step C: Preparation of (R)-4-(difluoromethyl)-5-ethoxy-2,2-difluoro-3-hydroxy-2,3-dihydrobenzo[b]thiophene 1,1-dioxide: Prepared analogously as described in Example 199, Step B utilizing 4-(difluoromethyl)-5-ethoxy-2,2-difluorobenzo[b]thiophen-3(2H)-one 1,1-dioxide (96%). $^1$H NMR (400 MHz, CDCl$_3$): δ 7.93 (d, 1H), 7.24 (d, 1H), 7.21 (t, 1H), 5.63-5.58 (m, 1H), 4.23 (q, 2H), 2.94-2.89 (m, 1H), 1.51 (t, 3H).

Example 203

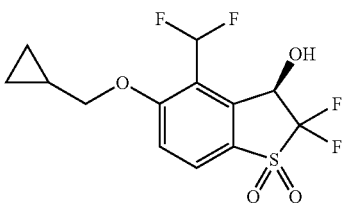 [SMILES: O=S1(=O)c2ccc(OCC3CC3)c(C(F)F)c2[C@@H](O)C1(F)F]

(R)-5-(Cyclopropylmethoxy)-4-(difluoromethyl)-2, 2-difluoro-3-hydroxy-2,3-dihydrobenzo[b]thiophene 1,1-dioxide (Compound 203)

Step A: Preparation of 3-(cyclopropylmethoxy)-2-(difluoromethyl)-6-(methylsulfonyl)benzonitrile: 2-(Difluoromethyl)-3-fluoro-6-methylsulfonyl-benzonitrile (Example 3, Step D) (200 mg, 0.80 mmol) was added to a solution of tetrahydrofuran (1.6 mL) and cyclopropanemethanol (174 mg, 2.4 mmol). The mixture was treated with 3N NaOH (0.27 mL, 0.80 mmol), then stirred at ambient temperature for 16 hours. The reaction was neutralized with 10% $KHSO_4$ (0.29 mL) and the solvent was removed in a stream of nitrogen gas. The residue was redissolved in ethyl acetate and water and then separated. The aqueous was washed with ethyl acetate and the combined organics were washed with saturated $NaHCO_3$, saturated NaCl, dried over $Na_2SO_4$ and concentrated in vacuo. 3-(Cyclopropylmethoxy)-2-(difluoromethyl)-6-(methylsulfonyl)benzonitrile was obtained as an off-white solid (187 mg, 77%). $^1H$ NMR (400 MHz, $CDCl_3$): δ 8.25 (d, 1H), 7.25 (d, 1H), 7.22 (t, 1H), 4.02 (d, 2H), 3.31 (s, 3H), 1.35-1.24 (m, 1H), 0.75-0.70 (m, 2H), 0.43-0.39 (m, 2H).

Step B: Preparation of 5-(cyclopropylmethoxy)-4-(difluoromethyl)-2,2-difluorobenzo[b]thiophen-3(2H)-one 1,1-dioxide: Prepared analogously as described in Example 113, Steps F and G, utilizing 3-(cyclopropylmethoxy)-2-(difluoromethyl)-6-(methylsulfonyl)benzonitrile in Step F. $^1H$ NMR (400 MHz, $CDCl_3$): δ 8.13 (d, 1H), 7.59 (d, 1H), 7.54 (t, 1H), 4.10 (d, 2H), 1.38-1.23 (m, 1H), 0.76-0.69 (m, 2H), 0.47-0.41 (m, 2H).

Step C: Preparation of (R)-5-(cyclopropylmethoxy)-4-(difluoromethyl)-2,2-difluoro-3-hydroxy-2,3-dihydrobenzo[b]thiophene 1,1-dioxide: Prepared analogously as described in Example 199, Step B utilizing 5-(cyclopropylmethoxy)-4-(difluoromethyl)-2,2-difluorobenzo[b]thiophen-3(2H)-one 1,1-dioxide (11%). $^1H$ NMR (400 MHz, $CDCl_3$): δ 7.92 (d, 1H), 7.26 (t, 1H), 7.21 (d, 1H), 5.63-5.59 (m, 1H), 4.01-3.98 (m, 2H), 2.95-2.92 (m, 1H), 1.37-1.27 (m, 1H), 0.74-0.70 (m, 2H), 0.42-0.38 (m, 2H).

Example 204

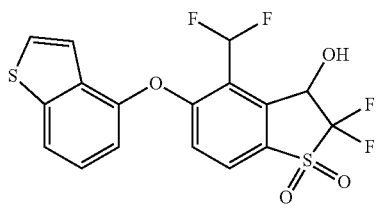 [SMILES: O=S1(=O)c2ccc(Oc3cccc4sccc34)c(C(F)F)c2C(O)C1(F)F]

5-(Benzo[b]thiophen-4-yloxy)-4-(difluoromethyl)-2, 2-difluoro-3-hydroxy-2,3-dihydrobenzo[b]thiophene 1,1-dioxide (Compound 204)

Step A: Preparation of 3-(benzo[b]thiophen-4-yloxy)-2-(difluoromethyl)-6-(methylsulfonyl)benzonitrile: Sodium hydrogen carbonate (34 mg, 0.4 mmol) was added to a vial containing 2-(difluoromethyl)-3-fluoro-6-(methylsulfonyl) benzonitrile (50 mg, 0.2 mmol) and benzothiophen-4-ol (36 mg, 0.24 mmol) in N,N-dimethylformamide (1 mL). The vial was sealed and heated at 60° C. After 3 hours, the reaction mixture was partitioned between EtOAc and water. The EtOAc was washed with brine, dried over $MgSO_4$, filtered, and evaporated. The residue was chromatographed on a Biotage 10 g SNAP column with a 10% to 80% EtOAc/hexanes to afford 3-(benzo[b]thiophen-4-yloxy)-2-(difluoromethyl)-6-(methylsulfonyl)benzonitrile (55 mg, 0.14 mmol, 72% yield).

Step B: Preparation of 5-(benzo[b]thiophen-4-yloxy)-4-(difluoromethyl)benzo[b]thiophen-3(2H)-one 1,1-dioxide: Sodium hydride (60%, 16.8 mg, 0.42 mmol) was added to a solution of 3-(benzothiophen-4-yloxy)-2-(difluoromethyl)-6-(methylsulfonyl)benzonitrile (53 mg, 0.14 mmol) in tetrahydrofuran (5 mL). Gas evolution was observed, along with a color change from colorless to orange. After 30 minutes, the reaction mixture was evaporated, the residue was taken up in methanol (5 mL), and treated with hydrochloric acid (1.0 M, 5 mL, 5 mmol). The reaction mixture was concentrated and the aqueous slurry was partitioned between EtOAc and water. The EtOAc was washed with brine, dried over $MgSO_4$, filtered, and evaporated. The residue was chromatographed on a Biotage 10 g SNAP column with a 10% to 80% EtOAc:hexane gradient to afford 5-(benzo[b]thiophen-4-yloxy)-4-(difluoromethyl)benzo[b]thiophen-3(2H)-one 1,1-dioxide (12 mg, 0.03 mmol, 23% yield).

Step C: Preparation of 5-(benzo[b]thiophen-4-yloxy)-4-(difluoromethyl)-2,2-difluorobenzo[b]thiophen-3(2H)-one 1,1-dioxide: 1-(Chloromethyl)-4-fluoro-1-propyl-piperazine-1,4-diium ditetrafluoroborate (24.5 mg, 0.07 mmol) was added to a mixture of 5-(benzo[b]thiophen-4-yloxy)-4-(difluoromethyl)benzo[b]thiophen-3(2H)-one 1,1-dioxide (12 mg, 0.03 mmol) and sodium carbonate (7 mg, 0.07 mmol) in acetonitrile (3 mL). This was stirred at ambient temperature. After 1.5 hours, the reaction mixture was evaporated and the residue was partitioned between EtOAc and water. The EtOAc was washed with brine, dried over $MgSO_4$, filtered, and evaporated. The residue was chromatographed on a Biotage 10 g SNAP column with a 10% to 80% EtOAc/hexanes to afford 5-(benzo[b]thiophen-4-yloxy)-4-(difluoromethyl)-2,2-difluorobenzo[b]thiophen-3(2H)-one 1,1-dioxide (10 mg, 0.024 mmol, 75% yield).

Step D: Preparation of 5-(benzo[b]thiophen-4-yloxy)-4-(difluoromethyl)-2,2-difluoro-3-hydroxy-2,3-dihydrobenzo[b]thiophene 1,1-dioxide: Sodium borohydride (1 mg, 0.03 mmol) was added to a solution of 5-(benzo[b]thiophen-4-yloxy)-4-(difluoromethyl)-2,2-difluorobenzo[b]thiophen-3(2H)-one 1,1-dioxide (10 mg, 0.02 mmol) in methanol (2 mL). The resulting solution was stirred at ambient temperature. After 1 hour, the reaction mixture was evaporated and the residue was partitioned between EtOAc and water. The EtOAc was washed with brine, dried over MgSO4, filtered, and evaporated to afford Compound 204 (8.4 mg, 0.02 mmol, 85% yield). $^1H$ NMR (400 MHz, $CDCl_3$): δ 7.85 (d, 1H), 7.78 (d, 1H), 7.50 (d, 1H), 7.47 (t, 1H), 7.42 (t, 1H), 7.17 (dd, 1H), 7.05 (dd, 1H), 6.96 (d, 1H), 5.73-5.67 (m, 1H), 3.20-3.13 (br s, 1H).

Example 205

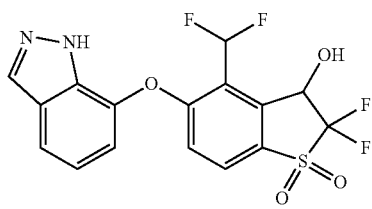 [SMILES: O=S1(=O)c2ccc(Oc3cccc4cn[nH]c34)c(C(F)F)c2C(O)C1(F)F]

5-((1H-Indazol-7-yl)oxy)-4-(difluoromethyl)-2,2-difluoro-3-hydroxy-2,3-dihydrobenzo[b]thiophene 1,1-dioxide (Compound 205): $^1$H NMR (400 MHz, CDCl$_3$): δ 8.17 (s, 1H), 7.83 (d, 1H), 7.72 (d, 1H), 7.42 (t, 1H), 7.22 (t, 1H), 7.12-7.07 (m, 2H), 5.69 (d, 1H).

Example 206

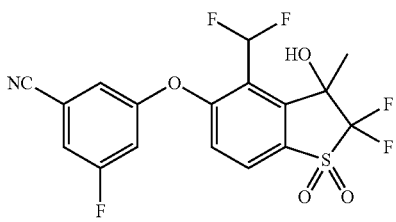 [SMILES: CC1(O)c2c(ccc(Oc3cc(F)cc(C#N)c3)c2C(F)F)S(=O)(=O)C1(F)F]

3-((4-(Difluoromethyl)-2,2-difluoro-3-hydroxy-3-methyl-1,1-dioxido-2,3-dihydrobenzo[b]thiophen-5-yl)oxy)-5-fluorobenzonitrile (Compound 206): 3-((4-(Difluoromethyl)-2,2-difluoro-1,1-dioxido-3-oxo-2,3-dihydrobenzo[b]thiophen-5-yl)oxy)-5-fluorobenzonitrile was dissolved in toluene (0.26 mL) and treated with a solution of dimethyl zinc (1M in heptane, 0.14 mL, 0.14 mmol) and the mixture was stirred at 50° C. for 60 hours. The resulting heterogeneous reaction mixture was cooled to ambient temperature, quenched with saturated NH$_4$Cl and diluted with ethyl acetate. The layers were separated and the aqueous was washed twice with ethyl acetate. The combined organic layers were washed with saturated NaHCO$_3$, saturated NaCl, dried over Na$_2$SO$_4$ and concentrated in vacuo. The crude product mixture was chromatographed on SiO$_2$ eluting with a gradient of ethyl acetate/hexane. Compound 206 was recovered as a colorless film which was redissolved in methylene chloride, treated with hexane and concentrated to form an off-white solid (19 mg, 75%). LCMS ESI (−) m/z 418 (M−H); $^1$H NMR (400 MHz, CDCl$_3$): δ 7.95-7.90 (d, 1H), 7.65 (t, 1H), 7.25-7.22 (m, 1H), 7.22-7.18 (d, 1H), 7.13-7.11 (m, 1H), 7.08-7.04 (m, 1H), 3.73 (brd s, 1H), 1.91-1.88 (m, 3H).

Example 207

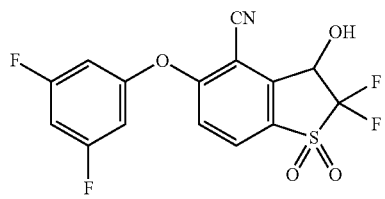 [SMILES: N#Cc1c(Oc2cc(F)cc(F)c2)ccc2c1C(O)C(F)(F)S2(=O)=O]

5-(3,5-Difluorophenoxy)-2,2-difluoro-3-hydroxy-2,3-dihydrobenzo[b]thiophene-4-carbonitrile 1,1-dioxide (Compound 207): Prepared similarly according to Example 110, Step A. 3,5-Difluorophenol was substituted for 3-chloro-5-fluorophenol earlier in the synthesis. Purification was achieved by chromatography on silica using 0-15% EtOAc/CHCl$_3$ to afford Compounds 207 as a beige solid (1.5 mg, 14%). LCMS ESI (−) (M−H) m/z 372; $^1$H NMR (400 MHz, CDCl$_3$): δ 7.97 (d, 1H), 7.20 (d, 1H), 6.87-6.81 (m, 1H), 6.76-6.69 (m, 2H), 5.55 (dd, 1H).

Example 208

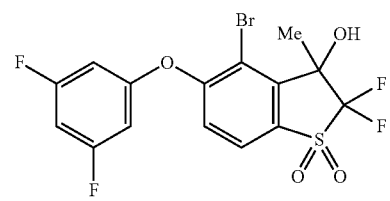 [SMILES: CC1(O)c2c(ccc(Oc3cc(F)cc(F)c3)c2Br)S(=O)(=O)C1(F)F]

4-Bromo-5-(3,5-difluorophenoxy)-2,2-difluoro-3-hydroxy-3-methyl-2,3-dihydrobenzo[b]thiophene 1,1-dioxide (Compound 208): A solution of 4-bromo-5-(3,5-difluorophenoxy)-2,2-difluorobenzo[b]thiophen-3(2H)-one 1,1-dioxide (77.0 mg, 0.18 mmol) in tetrahydrofuran (3.6 mL) at −50° C. was treated with methylmagnesium chloride (3.0 M in tetrahydrofuran, 80 μL, 0.24 mmol). After 30 minutes, additional methylmagnesium chloride (3.0 M in tetrahydrofuran, 80 μL, 0.24 mmol) was added over 5 minutes. The reaction mixture was allowed to warm to −30° C. and then quenched by the addition of 5 mL of saturated aqueous NH$_4$Cl. The reaction mixture was poured into 10 mL of water and extracted with 3×10 mL EtOAc. The combined organics were rinsed with 10 mL of brine, dried with MgSO$_4$, filtered, and concentrated to dryness. Purification was achieved by chromatography on silica using 5%->20% EtOAc/hexane to afford Compound 208 as a thin film (24.3 mg, 30%). LCMS ESI (−) (M−H) m/z 439, 441; $^1$H NMR (400 MHz, CDCl$_3$): δ 7.78 (d, 1H), 7.16 (d, 1H), 6.75-6.69 (m, 1H), 6.62-6.54 (m, 2H), 3.04-2.98 (m, 1H), 1.95 (d, 3H).

Example 209

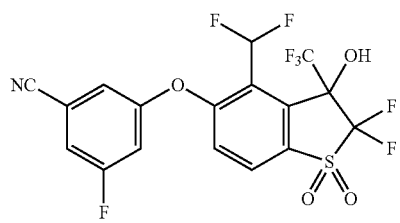 [SMILES: N#Cc1cc(F)cc(Oc2ccc3c(c2C(F)F)C(O)(C(F)(F)F)C(F)(F)S3(=O)=O)c1]

3-((4-(difluoromethyl)-2,2-difluoro-3-hydroxy-1,1-dioxido-3-(trifluoromethyl)-2,3-dihydrobenzo[b]thiophen-5-yl)oxy)-5-fluorobenzonitrile (Compound 209): A solution of trimethyl(trifluoromethyl)silane solution (2.0 M in tetrahydrofuran, 150 μL, 0.30 mmol) and 3-[4-(difluoromethyl)-2,2-difluoro-1,1,3-trioxo-benzothiophen-5-yl]oxy-5-fluoro-benzonitrile (30.0 mg, 0.074 mmol) in tetrahydrofuran (350 μL) was treated with tetrabutylammonium fluoride (1.0 M in tetrahydrofuran, 7.4 μL, 0.0074 mmol) and stirred at 120° C.

by microwave irradiation for 2 hours. The reaction mixture was poured into 10 mL of 1 M HCl and extracted with 3×15 mL EtOAc. The combined organics were rinsed with 10 mL of brine, dried with MgSO$_4$, filtered, and concentrated to dryness. Purification was achieved by chromatography on silica using 10-40% EtOAc/hexanes to afford Compound 209 as a white solid (6.8 mg, 19%). LCMS ESI (−) (M−H) m/z 472; $^1$H NMR (400 MHz, CDCl$_3$): δ 8.03 (d, 1H), 7.57 (t, 1H), 7.37 (d, 1H), 7.29-7.25 (m, 1H), 7.17-7.14 (m, 1H), 7.08 (dt, 1H), 5.40-5.10 (m, 1H).

Example 210

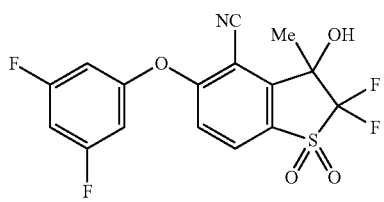 [SMILES: CC1(O)c2c(ccc(Oc3cc(F)cc(F)c3)c2C#N)S(=O)(=O)C1(F)F]

5-(3,5-Difluorophenoxy)-2,2-difluoro-3-hydroxy-3-methyl-2,3-dihydrobenzo[b]thiophene-4-carbonitrile 1,1-dioxide (Compound 210): A solution of 4-bromo-5-(3,5-difluorophenoxy)-2,2-difluoro-3-hydroxy-3-methyl-2,3-dihydrobenzo[b]thiophene 1,1-dioxide (21.7 mg, 0.049 mmol) in 1-methyl-2-pyrrolidone (0.5 mL) was treated with copper (I) cyanide (5.7 mg, 0.064 mmol) and heated at 165° C. by microwave irradiation for 45 minutes. The reaction mixture was poured into 30 mL of water and extracted with 3×10 mL Et$_2$O. The combined organics were rinsed with 10 mL of brine, dried with MgSO$_4$, filtered, and concentrated to dryness. Purification was achieved by chromatography on silica using 10-30% EtOAc/hexane to afford Compound 210 as a thin film (11.3 mg, 59%). LCMS ESI (−) (M−H) m/z 386; $^1$H NMR (400 MHz, CDCl$_3$): δ 7.93 (d, 1H), 7.13 (d, 1H), 6.83 (tt, 1H), 6.75-6.68 (m, 2H), 3.54 (s, 1H), 1.97 (d, 3H).

Example 211

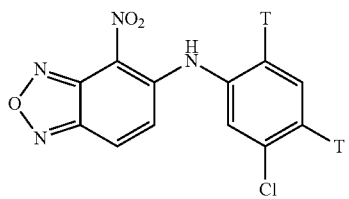

N-(3-Chlorophenyl-4,6-t2)-4-nitrobenzo[c][1,2,5]oxadiazol-5-amine (Compound 211)

Step A: Synthesis of 3-chlorobenzen-4,6-t$_2$-amine: 3-Chloro-4,6-diiodoaniline (100 mg,) was dissolved in methanol (3 mL) and added with triethylamine (0.1 mL) and submitted for overnight tritiation using 50 Ci of tritium gas, at room temperature. Labile tritium was removed by dissolving the crude reaction mixture in methanol (3 mL) and bringing to dryness under vacuum. Labile removal was done in dupicate. The crude tritiated material was purified by preparative TLC (Silica gel, 10000 using hexane:ethylacetate:AcOH (85:14:1). The product band was eluted with ethylacetate to give 3-chlorobenzen-4,6-t$_2$-amine (yield=600 mCi, radiochemical purity was >98%).

Step B: Synthesis of Compound 211: A stirred mixture of 5-chloro-4-nitro-2,1,3-benzoxadiazole (20 mg, 0.1 mmol), 3-chlorobenzen-4,6-t$_2$-amine (600 mCi) and Cs$_2$CO$_3$ (65 mg, 0.20 mmol) in DMF (1 mL) was heated at 60° C. for 1 h. After cooling, the reaction mixture was partitioned between EtOAc and water. The aqueous layer was extracted with EtOAc. The combined organic layers were washed with water and brine, dried and concentrated. The residue was purified by preparative HPLC on an ACE-5 C18 Semi-prep column, 250×10 mm, 100 Å. Elution was carried out isocratically using 0.1% TFA in water/Acetonitrile (35:65) to give Compound 211 (478 mCi, 80%).

Example 212: HIF-2α Scintillation Proximity Assay (SPA)

The total assay volume was about 100 μL in the following configuration: 2 μL compound in 100% DMSO, 88 μL buffer with protein and probe and 10 μL of SPA beads. The compound was diluted in a master plate consisting of a 10-point dose response with a 3-fold compound dilution from 100 μM to 5 nM. Assays were run on a 96-well plate in which one column, designated as the high signal control, contained DMSO with no compound and another column, designated as the low signal control, contained no protein. Prior to plating out of compound, a buffer solution, consisting of 25 mM TRIS pH 7.5 (Sigma), 150 mM NaCl (Sigma), 15% glycerol (Sigma), 0.15% BSA (Sigma), 0.001% Tween-20 (Sigma), 150 nM Compound 211 and 100 nM HIF-2α HIS TAG-PASB Domain, was made and allowed to equilibrate for 30 minutes. Compounds that were to be tested were then plated in to a 96-well white clear bottom Isoplate-96 SPA plate (Perkin Elmer). To the compounds, 88 μL of the buffer solution was then added, the plate was covered with a plastic cover and then aluminum foil, placed onto a shaker and equilibrated for 1 hour. After equilibration, 10 μL of a 2 mg/mL solution of YSi Cu His tagged SPA beads (Perkin Elmer) were then added to each well of the plate, covered and equilibrated for another 2 hours. The plates were then removed from the shaker, placed into a 1450 LSC and luminescence counter MicroBeta Trilux (Perkin Elmer) to measure the extent of probe displacement. The percent inhibition was determined and IC$_{50}$ values were calculated using the Dotmatics system based on the following equation: % inhibition=[(high control−sample)/(high control−low control)]×100.

Table 1 shows IC$_{50}$'s of Compounds in Scintillation Proximity Assay (SPA).

TABLE 1

| Compound IC$_{50}$'s in SPA | |
|---|---|
| Compound Number | SPA IC$_{50}$ (μM) |
| 1 | 0.0068 |
| 2 | 0.0054 |
| 3 | <0.005 |
| 4 | 0.035 |
| 5 | 0.0083 |
| 6 | 0.167 |
| 7 | <0.005 |
| 8 | <0.005 |
| 9 | <0.005 |
| 10 | 0.177 |
| 11 | <0.005 |

TABLE 1-continued

Compound IC$_{50}$'s in SPA

| Compound Number | SPA IC$_{50}$ (μM) |
|---|---|
| 12 | 0.8 |
| 13 | 0.083 |
| 14 | <0.005 |
| 15 | 0.013 |
| 16 | 0.017 |
| 17 | 0.045 |
| 18 | 0.038 |
| 19 | 4.9 |
| 20 | 0.027 |
| 21 | 0.068 |
| 22 | 0.23 |
| 23 | <0.005 |
| 24 | 0.076 |
| 25 | 17.6 |
| 26 | 0.10 |
| 27 | 1.44 |
| 28 | 0.066 |
| 29 | 0.09 |
| 30 | 0.019 |
| 31 | 0.11 |
| 32 | 3.51 |
| 33 | 0.31 |
| 34 | 0.097 |
| 35 | 0.34 |
| 36 | 2.0 |
| 37 | <0.005 |
| 38 | 0.094 |
| 39 | 0.076 |
| 40 | 0.058 |
| 41 | 0.13 |
| 42 | 2.2 |
| 43 | 5.1 |
| 44 | 3.39 |
| 45 | 0.73 |
| 46 | 7.2 |
| 47 | 1.4 |
| 48 | 5.6 |
| 49 | 0.071 |
| 50 | 0.024 |
| 51 | 0.55 |
| 52 | 6.5 |
| 53 | 0.01 |
| 54 | 0.018 |
| 55 | 4.9 |
| 56 | <0.005 |
| 57 | 0.72 |
| 58 | 1.1 |
| 59 | 0.23 |
| 60 | 1.34 |
| 61 | 12.4 |
| 62 | 16.1 |
| 63 | 16.1 |
| 64 | 2.03 |
| 65 | 1.85 |
| 66 | 0.063 |
| 67 | 0.037 |
| 68 | <0.005 |
| 69 | <0.005 |
| 70 | <0.005 |
| 71 | 0.37 |
| 72 | 0.068 |
| 73 | <0.005 |
| 74 | 0.016 |
| 75 | 8.7 |
| 76 | 0.15 |
| 77 | 1.8 |
| 78 | 0.025 |
| 79 | 0.023 |
| 80 | <0.005 |
| 81 | <0.005 |
| 82 | 2.4 |
| 83 | 0.014 |
| 84 | 1.57 |
| 85 | 0.032 |
| 86 | 9.9 |
| 87 | 5.3 |
| 88 | 0.054 |
| 89 | 0.18 |
| 90 | 1.28 |
| 91 | 0.028 |
| 92 | 0.032 |
| 93 | <0.005 |
| 94 | 2.1 |
| 95 | 0.0072 |
| 96 | 2.3 |
| 97 | 0.074 |
| 98 | 0.073 |
| 99 | 8.1 |
| 100 | 0.063 |
| 101 | 3.7 |
| 102 | 0.013 |
| 103 | 0.278 |
| 104 | 0.024 |
| 105 | 0.018 |
| 106 | 0.047 |
| 107 | 23.9 |
| 108 | 0.0067 |
| 109 | 2.2 |
| 110 | 0.51 |
| 111 | 0.0072 |
| 112 | 0.0465 |
| 113 | <0.005 |
| 114 | 4.4 |
| 115 | 4.9 |
| 116 | 2.43 |
| 117 | 0.061 |
| 118 | 1.4 |
| 119 | 0.0015 |
| 120 | 0.045 |
| 121 | <0.005 |
| 122 | 0.2 |
| 123 | 0.015 |
| 124 | <0.005 |
| 125 | 0.1 |
| 126 | 1.88 |
| 127 | 7.88 |
| 128 | <0.005 |
| 129 | <0.005 |
| 130 | 1.5 |
| 131 | 11.8 |
| 132 | <0.005 |
| 133 | 0.267 |
| 134 | 0.077 |
| 135 | <0.005 |
| 136 | <0.005 |
| 137 | 5.8 |
| 138 | 0.7 |
| 139 | 0.0143 |
| 140 | <0.005 |
| 141 | 4.1 |
| 142 | 0.239 |
| 143 | <0.005 |
| 144 | 4.87 |
| 145 | 0.229 |
| 146 | 2.89 |
| 147 | 0.12 |
| 148 | 13.4 |
| 149 | 2.4 |
| 150 | 0.034 |
| 151 | 0.069 |
| 152 | 0.086 |
| 153 | <0.005 |
| 154 | 1.64 |
| 155 | 18.7 |
| 156 | <0.005 |
| 157 | 9.7 |
| 158 | 1.47 |
| 159 | 17.4 |
| 160 | 14.2 |
| 161 | 0.02 |
| 162 | 0.029 |
| 163 | 0.059 |

TABLE 1-continued

Compound IC$_{50}$'s in SPA

| Compound Number | SPA IC$_{50}$ (μM) |
|---|---|
| 164 | 1.9 |
| 165 | 0.033 |
| 166 | 4.1 |
| 167 | <0.005 |
| 168 | 6.3 |
| 169 | 0.06 |
| 170 | 21.9 |
| 171 | 12.9 |
| 172 | 19.6 |
| 173 | 0.059 |
| 174 | 10.9 |
| 175 | 0.565 |
| 176 | 0.174 |
| 177 | 4.66 |
| 178 | 0.12 |
| 179 | 13.4 |
| 180 | 12.9 |
| 181 | 17.6 |
| 182 | 17.1 |
| 183 | 13.7 |
| 184 | 10.2 |
| 185 | 0.124 |
| 186 | 0.746 |
| 187 | 0.305 |
| 188 | 0.116 |
| 189 | 6.86 |
| 190 | 0.057 |
| 191 | 0.066 |
| 192 | 2.9 |
| 193 | 14.3 |
| 194 | 0.017 |
| 195 | 0.011 |
| 196 | 0.384 |
| 197 | 0.94 |
| 198 | 0.975 |
| 199 | 0.034 |
| 200 | 0.024 |
| 201 | 0.072 |
| 202 | 15.5 |
| 203 | 1.89 |
| 204 | 0.011 |
| 205 | 1.76 |
| 206 | 0.2 |
| 207 | 0.046 |
| 208 | 0.083 |
| 209 | 4.4 |
| 210 | 0.041 |

Example 213: VEGF ELISA Assay

About 7500 of 786-0 cells in 180 μL, of growth medium were seeded into each well of a 96 well plate with white clear bottom on the first day (07-200-566, Fisher scientific). Four hours later, serial dilutions of 10× compound stocks were made in growth medium from 500×DMSO stocks, and 20 μL of those 10× stocks were added to each well to make final concentrations as follows (μM): 20, 6.67, 2.22, 0.74, 0.25, 0.082, 0.027, 0.009, 0.003, 0.001, and 0. Each concentration had duplicated wells. About 20 hours later, medium was removed by suction and each well was supplied with 180 μL of growth medium. About 20 μl freshly-made 10× compound stocks were added to each well. About 24 hours later, cell culture medium was removed for the determination of VEGFA concentration using an ELISA kit purchased from R&D systems by following the manufacturer's suggested method. The EC$_{50}$ was calculated by GraphPad Prism using the dose-response-inhibition (four parameter) equation. The cell seeded plate was then subjected to CellTiter-Glo luminescence cell viability assay (Promega) by adding 50 μL of Celltiter Glo reagent into each well and shaking the plate for 8 minutes at 550 rpm (Thermomixer R, Eppendorf) then read luminescence signal in plate reader (3 second delay, 0.5 second/well integration time, Synergy 2 multi Detection Microplate reader) immediately.

Table 2 shows EC$_{50}$'s of selected compounds in VEGF ELISA Assay.

TABLE 2

EC$_{50}$'s of Selected Compounds in VEGF ELISA Assay

| Compound Number | VEGF ELISA EC$_{50}$ (μM) |
|---|---|
| 1 | 0.013 |
| 2 | 0.245 |
| 3 | 0.02 |
| 4 | 0.217 |
| 5 | 0.048 |
| 6 | 0.556 |
| 7 | 0.07 |
| 8 | 0.004 |
| 9 | 0.013 |
| 14 | 0.069 |
| 17 | 0.067 |
| 18 | 0.028 |
| 20 | 0.067 |
| 24 | 0.128 |
| 26 | 0.184 |
| 30 | 0.054 |
| 31 | 0.83 |
| 37 | 0.006 |
| 38 | 1.44 |
| 53 | 0.018 |
| 56 | 0.006 |
| 67 | 0.064 |
| 68 | 0.062 |
| 69 | 0.02 |
| 70 | 0.019 |
| 73 | 0.026 |
| 74 | 0.14 |
| 78 | 0.083 |
| 79 | 0.116 |
| 80 | 0.017 |
| 81 | 0.014 |
| 83 | 0.095 |
| 85 | 0.19 |
| 89 | 0.146 |
| 91 | 0.273 |
| 92 | 0.187 |
| 93 | 0.047 |
| 95 | 0.041 |
| 97 | 0.163 |
| 102 | 0.011 |
| 104 | 0.136 |
| 105 | 0.16 |
| 106 | 0.095 |
| 108 | 0.123 |
| 111 | 0.064 |
| 113 | 0.062 |
| 117 | 0.333 |
| 119 | 0.064 |
| 121 | 0.125 |
| 124 | 0.089 |
| 128 | 0.029 |
| 129 | 0.087 |
| 132 | 0.009 |
| 136 | 0.2 |
| 139 | 0.014 |
| 151 | 0.68 |
| 153 | 0.009 |
| 162 | 0.09 |
| 163 | 0.067 |
| 167 | 0.045 |
| 185 | 0.178 |
| 188 | 0.327 |
| 195 | 0.077 |
| 210 | 0.018 |

Example 214: Luciferase Assay

The 786-O-Hif-Luc single clone cells were obtained by infecting 786-0 cells (ATCC® CRL-1932™) with commercial lentivirus that delivers a luciferase gene driven by multiple HIF responsive elements (Cignal Lenti HIF Reporter (luc): CLS-007L, Qiagen) at Multiplicity of Infection (MOI) of 25 for 24 hours and then the cells were replenished with fresh medium (Dulbecco's Modified Eagle's Medium (DMEM, D5796, Sigma) and supplemented with 10% FBS (F6178, Sigma), 100 units penicillin and 100 µg streptomycin/mL (P4333, Sigma)) for another 24 hours. A pool of infected cells were then selected against 2 µg/mL of puromycin (P8833, Sigma) for 10 days followed by limited dilution to select single clones. The clones were tested for their response to HIF2 inhibitors and the ones that showed the biggest dynamic range (786-O-Hif-Luc) were expanded and used for the luciferase assay. For luciferase assay, about 7500 of 786-O-Hif-Luc cells in 90 µL growth medium were seeded into each well of a 96 well white opaque plate (08-771-26, Fisher scientific) a day before treatment.

On treatment day, serial dilutions of 10× compound stocks were made in growth medium from 500×DMSO stocks, and 10 µL of the 10× stocks were added to each well to make final concentrations as follows (µM): 20, 6.67, 2.22, 0.74, 0.25, 0.08, 0.027, 0.009, 0.003, 0.001, and 0. Each concentration was tested in triplicate. After about 24 hours, luciferase activity was determined using ONE-Glo Luciferase Assay Reagent (E6110, Promega) following the manufacturer's recommended procedure. $EC_{50}$ were calculated by using Dotmatics software.

Table 3 shows $EC_{50}$s of selected compounds in Luciferase Assay.

TABLE 3

$EC_{50}$s of Selected Compounds in Luciferase Assay

| Compound Number | Luciferase $EC_{50}$ (µM) |
|---|---|
| 1 | 0.007 |
| 2 | 0.106 |
| 3 | 0.007 |
| 4 | 0.074 |
| 5 | 0.024 |
| 6 | 0.244 |
| 7 | 0.034 |
| 8 | 0.003 |
| 9 | 0.011 |
| 10 | 0.277 |
| 11 | 13.5 |
| 12 | 0.775 |
| 13 | 0.177 |
| 14 | 0.025 |
| 15 | 0.003 |
| 16 | 0.024 |
| 17 | 0.036 |
| 18 | 0.015 |
| 20 | 0.028 |
| 21 | 0.137 |
| 22 | 0.512 |
| 23 | 0.024 |
| 24 | 0.097 |
| 25 | 1.1 |
| 26 | 0.119 |
| 27 | 1.39 |
| 28 | 0.173 |
| 29 | 0.897 |
| 30 | 0.03 |
| 31 | 0.16 |
| 32 | 2.45 |
| 33 | 19.4 |
| 34 | 0.1 |
| 35 | 0.473 |
| 36 | 2.28 |
| 37 | 0.005 |
| 38 | 0.195 |
| 39 | 0.255 |
| 40 | 0.153 |
| 41 | 0.074 |
| 43 | 5.9 |
| 49 | 0.1 |
| 50 | 0.14 |
| 51 | 0.65 |
| 53 | 0.004 |
| 54 | 0.17 |
| 55 | 3.1 |
| 56 | 0.003 |
| 57 | 0.779 |
| 58 | 1.02 |
| 59 | 0.39 |
| 60 | 1.32 |
| 64 | 2.83 |
| 65 | 2.1 |
| 66 | 0.115 |
| 67 | 0.035 |
| 68 | 0.022 |
| 69 | 0.013 |
| 70 | 0.03 |
| 71 | 1.67 |
| 72 | 0.69 |
| 73 | 0.009 |
| 74 | 0.113 |
| 76 | 0.631 |
| 77 | 1.07 |
| 78 | 0.148 |
| 79 | 0.106 |
| 80 | 0.012 |
| 81 | 0.012 |
| 83 | 0.083 |
| 85 | 0.114 |
| 88 | 0.475 |
| 89 | 0.488 |
| 91 | 0.129 |
| 92 | 0.162 |
| 93 | 0.034 |
| 95 | 0.041 |
| 97 | 0.174 |
| 98 | 0.224 |
| 100 | 0.067 |
| 102 | 0.006 |
| 103 | 0.253 |
| 104 | 0.125 |
| 105 | 0.114 |
| 106 | 0.088 |
| 108 | 0.042 |
| 110 | 1.65 |
| 111 | 0.023 |
| 112 | 0.226 |
| 113 | 0.007 |
| 116 | 4.8 |
| 117 | 0.451 |
| 119 | 0.046 |
| 120 | 4.17 |
| 121 | 0.134 |
| 122 | 3.72 |
| 123 | 0.449 |
| 124 | 0.075 |
| 125 | 0.725 |
| 127 | 6.89 |
| 128 | 0.017 |
| 129 | 0.068 |
| 132 | 0.013 |
| 133 | 0.124 |
| 134 | 0.7185 |
| 135 | 0.01 |
| 136 | 0.11 |
| 138 | 1.43 |

TABLE 3-continued

EC$_{50}$s of Selected Compounds in Luciferase Assay

| Compound Number | Luciferase EC$_{50}$ (μM) |
|---|---|
| 139 | 0.004 |
| 140 | 1.7 |
| 141 | 0.544 |
| 142 | 0.286 |
| 143 | 1.78 |
| 144 | 0.019 |
| 145 | 0.149 |
| 147 | 0.17 |
| 149 | 2.79 |
| 150 | 0.012 |
| 151 | 0.139 |
| 152 | 0.126 |
| 153 | 0.006 |
| 154 | 0.793 |
| 156 | 0.1 |
| 158 | 1.88 |
| 161 | 1.5 |
| 162 | 0.069 |
| 163 | 0.039 |
| 164 | 1.54 |
| 165 | 0.057 |
| 167 | 0.037 |
| 169 | 0.172 |
| 173 | 0.19 |
| 175 | 0.51 |
| 176 | 2.16 |
| 178 | 0.366 |
| 180 | 0.4 |
| 185 | 0.098 |
| 186 | 0.492 |
| 187 | 0.126 |
| 188 | 0.096 |
| 190 | 0.413 |
| 191 | 15.0 |
| 192 | 1.42 |
| 194 | 0.032 |
| 195 | 0.047 |
| 196 | 0.425 |
| 197 | 1.1 |
| 198 | 0.882 |
| 199 | 0.033 |
| 200 | 0.079 |
| 201 | 0.308 |
| 203 | 1.16 |
| 204 | 0.455 |
| 205 | 6.9 |
| 206 | 0.771 |
| 207 | 0.427 |
| 208 | 0.296 |
| 210 | 0.022 |

Wild type (WT) C57BL/6 (Jackson Laboratory Stock 000664) and HFE$^{-/-}$ (Jackson Laboratory Stock 017784) mice were maintained at the UT Southwestern Medical Center.

Example 215

To investigate whether Compound 1 (Cmpd 1) can attenuate iron absorption, animals at 13 weeks of age were pretreated with either vehicle or 100 mg/kg Compound 1 by oral gavage twice a day (b.i.d.) for 3 days. Following an overnight fast, radiolabeled 59FeCl$_3$ was directly administered via gastric gavage and the subsequent distribution of $^{59}$Fe was measured 3 and 24 h later. As shown in FIG. 1, HFE$^{-/-}$ mice absorb greater amounts of iron as compared to wild-type (WT) mice, as indicated by increased levels of $^{59}$Fe in the duodenum (iron absorption), serum (iron transport), liver (iron storage) and spleen (iron utilization) where iron is incorporated into red blood cells (RBC). Compound 1 treatment reduced $^{59}$Fe iron incorporation in each of the compartments.

Example 216

Figure 2:
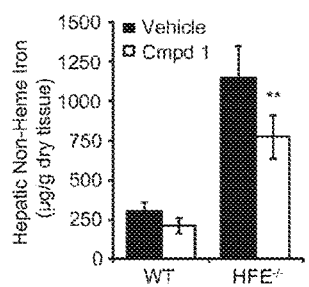
FIG. 2 shows that Compound 1 treatment in mice reduced liver iron accumulation and serum iron parameters. Male $HFE^{-/-}$ mice at 3 weeks of age were treated with either vehicle or Compound 1 at 100 mg/kg by oral gavage daily (q.d.) for 6 weeks (Prophylactic Model). Iron overloaded hemochromatotic mice at 12 weeks of age were treated with either vehicle or Compound 1 at 100 mg/kg by oral gavage twice a day (b.i.d.) for 3 weeks (Treatment Model). In both the Prophylactic (A, B, and C) and Treatment (D, E, and F) models, a significant reduction of non-heme iron was observed in the livers of $HFE^{-/-}$ mice. Serum iron and transferrin saturation were also reduced significantly in Compound 1 treated wild-type mice. $*p<0.05$, $**p<0.01$; n=5-7/group.
Figure 2:
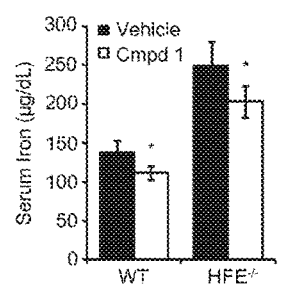
Figure 2:
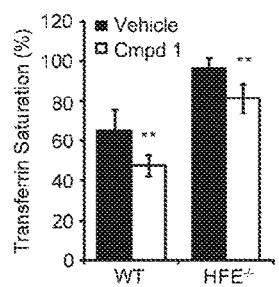
Figure 2:
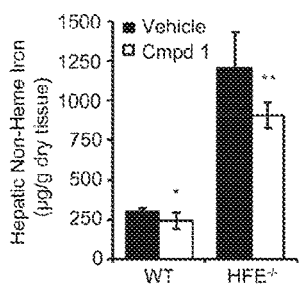
Figure 2:
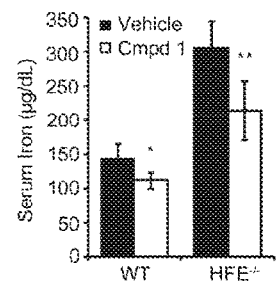
Figure 2:
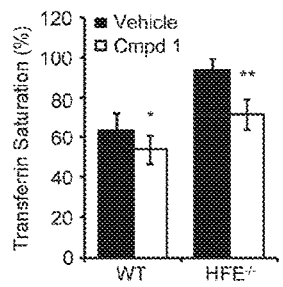

To investigate whether Compound 1 can delay onset of hemochromatosis in male HFE$^{-/-}$ mice (Prophylactic Model), animals (wild-type and HFE$^{-/-}$ mice) at 3 weeks of age were treated with either vehicle or Compound 1 at 100 mg/kg by oral gavage daily (q.d.) for 6 weeks. To investigate whether Compound 1 can ameliorate symptoms in hemochromatotic mice (Treatment Model), iron overloaded HFE$^{-/-}$ and wild-type animals at 12 weeks of age were treated with either vehicle or Compound 1 at 100 mg/kg by oral gavage twice a day (b.i.d.) for 3 weeks. Animals were sacrificed after the final dose for analyses. In both models, Compound 1 treatment resulted in reduced serum iron levels and % transferrin saturation in WT and HFE$^{-/-}$ mice. In addition, the accumulation of non-heme iron in the liver was significantly reduced in the HFE$^{-/-}$ mice (FIG. 2). The effects on other hematological parameters were relatively mild as Compound 1 treatment was accompanied by modest reductions in hemoglobin (Hb) and hematocrit levels (HCT) in the HFE$^{-/-}$ mice (Table 4). No statistically significant changes were observed in RBC numbers or mean corpuscular volumes (MCV).

TABLE 4

Effect of Compound 1 treatment in HFE$^{-/-}$ and wild-type mice on erythroid parameters as measured by complete blood count (CBC) analysis.

| Mice | n | RBC (M/μL) | Hb (g/dL) | HCT (%) | MCV (fL) |
|---|---|---|---|---|---|
| A Prophylactic Model: Erythroid Parameters | | | | | |
| WT + V | 6 | 9.8 ± 0.7 | 13.5 ± 0.8 | 47.4 ± 3.4 | 49.9 ± 2.9 |
| WT + C | 5 | 9.3 ± 1.1 | 12.0 ± 0.7* | 44.5 ± 3.8 | 48.7 ± 2.5 |
| HFE$^{-/-}$ + V | 6 | 10.3 ± 0.9 | 14.5 ± 0.6 | 48.7 ± 2.3 | 51.9 ± 2.8 |
| HFE$^{-/-}$ + C | 6 | 9.2 ± 0.8 | 12.9 ± 0.9** | 44.8 ± 3.5* | 50.1 ± 1.8 |
| B Treatment Model: Erythroid Parameters | | | | | |
| WT + V | 6 | 9.9 ± 0.7 | 13.6 ± 1.2 | 45.8 ± 2.8 | 49.4 ± 2.1 |
| WT + C | 6 | 9.1 ± 0.5 | 12.7 ± 0.6 | 43.5 ± 2.5 | 46.6 ± 3.3 |

TABLE 4-continued

Effect of Compound 1 treatment in HFE$^{-/-}$ and wild-type mice on erythroid parameters as measured by complete blood count (CBC) analysis.

| Mice | n | RBC (M/μL) | Hb (g/dL) | HCT (%) | MCV (fL) |
|---|---|---|---|---|---|
| HFE$^{-/-}$ + V | 7 | 10.1 ± 0.9 | 14.1 ± 0.7 | 46.6 ± 2.8 | 49.7 ± 3.5 |
| HFE$^{-/-}$ + C | 7 | 9.5 ± 0.5 | 13.1 ± 0.8* | 43.5 ± 2.4* | 48.0 ± 2.5 |

V: vehicle,
C: Cmpd 1;
*p < 0.05,
**p < 0.01.

Figure 3:
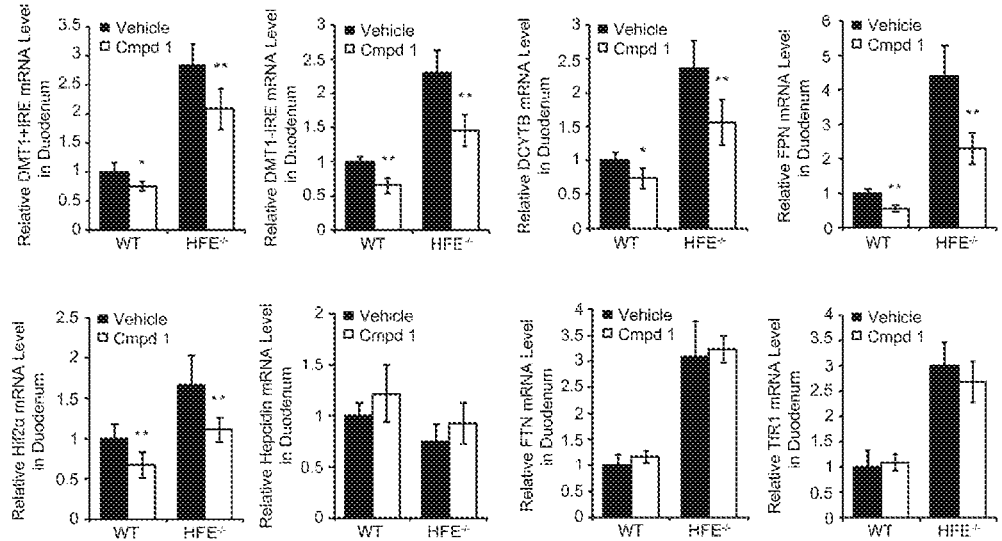
FIG. 3 shows that Compound 1 treatment in mice reduced the mRNA levels of HIF-2α and its target genes. Male $HFE^{-/-}$ and wild-type mice at 3 weeks of age were treated with either vehicle or Compound 1 at 100 mg/kg by oral gavage daily (q.d.) for 6 weeks (Prophylactic Model). Iron overloaded hemochromatotic and wild-type mice at 12 weeks of age were treated with either vehicle or Compound 1 at 100 mg/kg by oral gavage twice a day (b.i.d.) for 3 weeks (Treatment Model). The mRNA levels of HIF-2α and iron metabolism-related genes from both the Prophylactic (A-C) and Treatment (D-F) models were determined by qRT-PCR. $*p<0.05$, $**p<0.01$; n=5-7/group.
Figure 3:
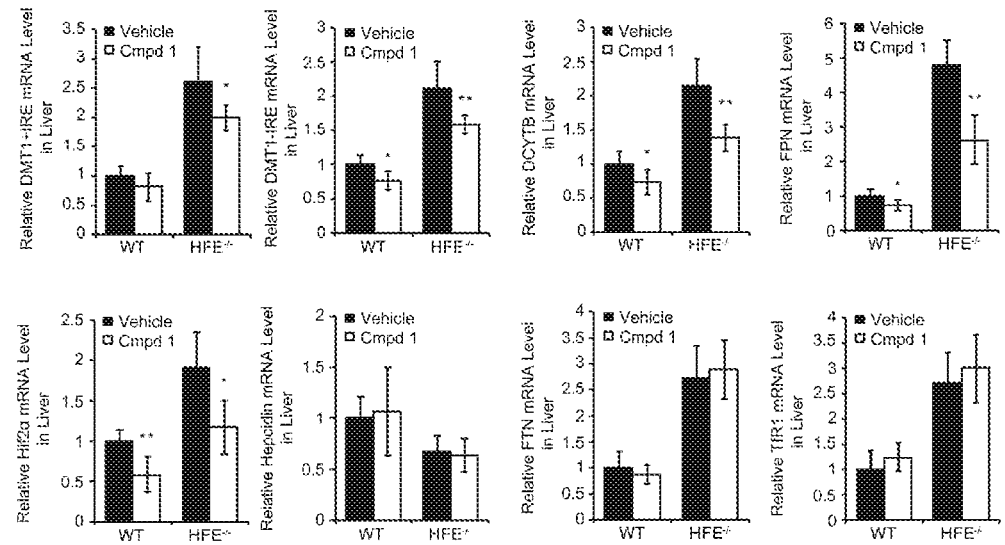
Figure 3:
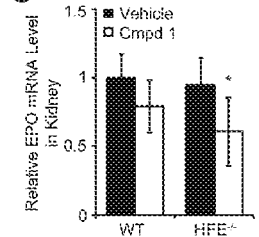
Figure 3:
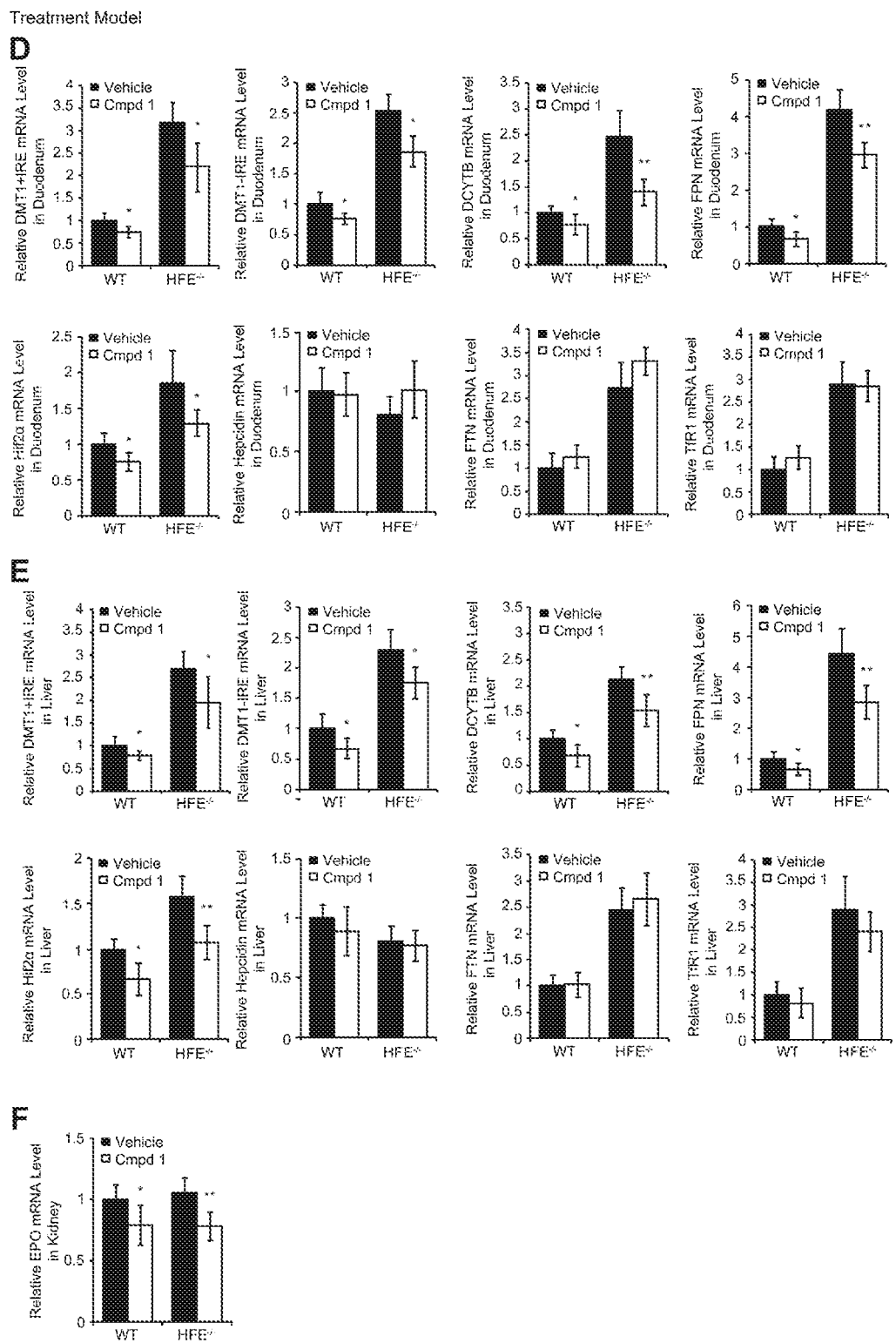
Figure 4A:
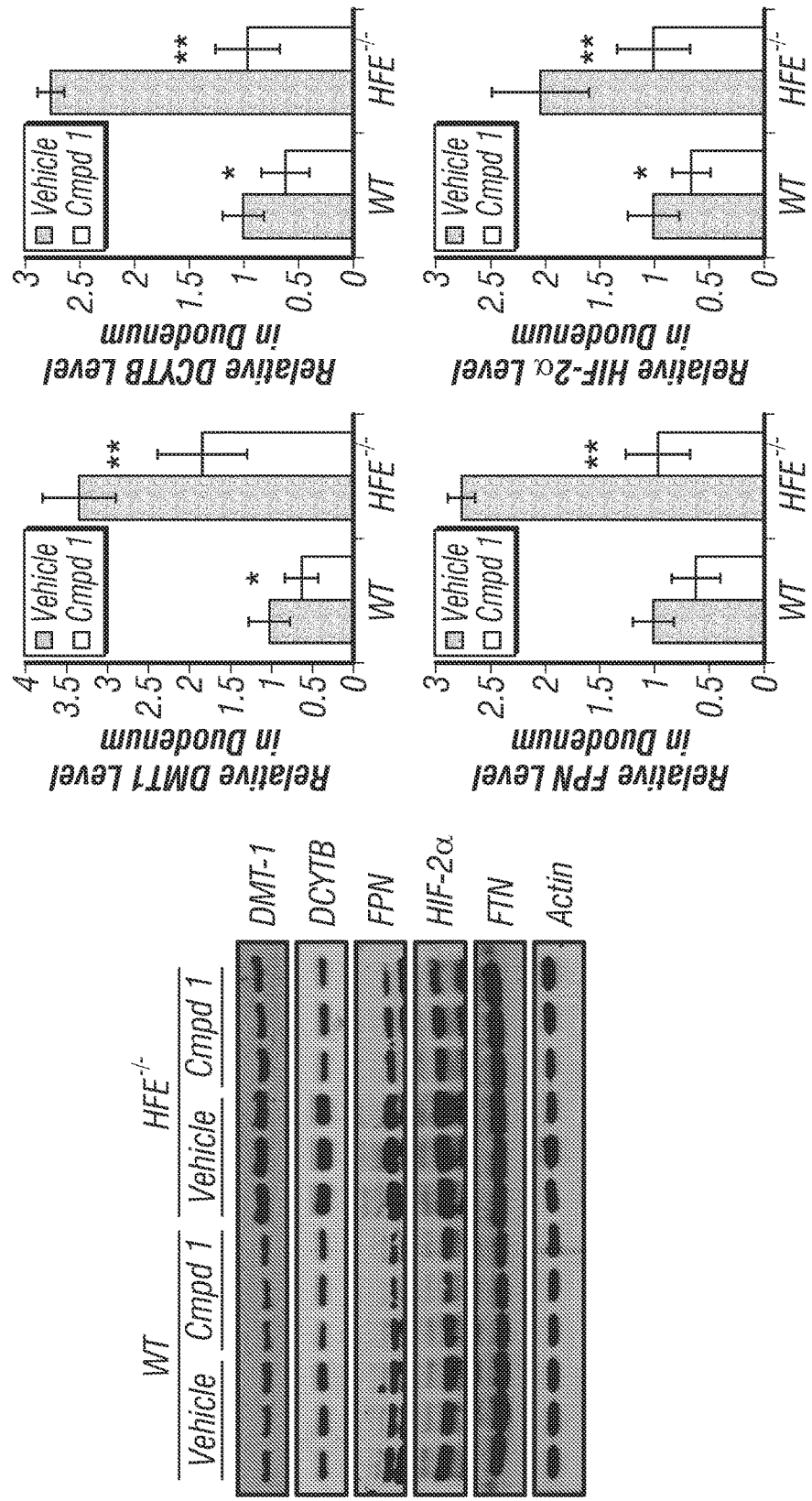
FIG. 4 shows that Compound 1 treatment in mice reduced the protein levels of HIF-2α and its target genes. Male $HFE^{-/-}$ and wild-type mice at 3 weeks of age were treated with either vehicle or Compound 1 at 100 mg/kg by oral gavage daily (q.d.) for 6 weeks (Prophylactic Model). Iron overloaded hemochromatotic and wild-type mice at 12 weeks of age were treated with either vehicle or Compound 1 at 100 mg/kg by oral gavage twice a day (b.i.d.) for 3 weeks (Treatment Model). The protein levels of HIF-2α and iron metabolism-related proteins from both the Prophylactic (A-C) and Treatment (D-F) models were determined by western blot analysis or ELISA. $*p<0.05$, $**p<0.01$; n=5-7/group. Representative Western blots are shown for 3 mice from each group.
Figure 4B:
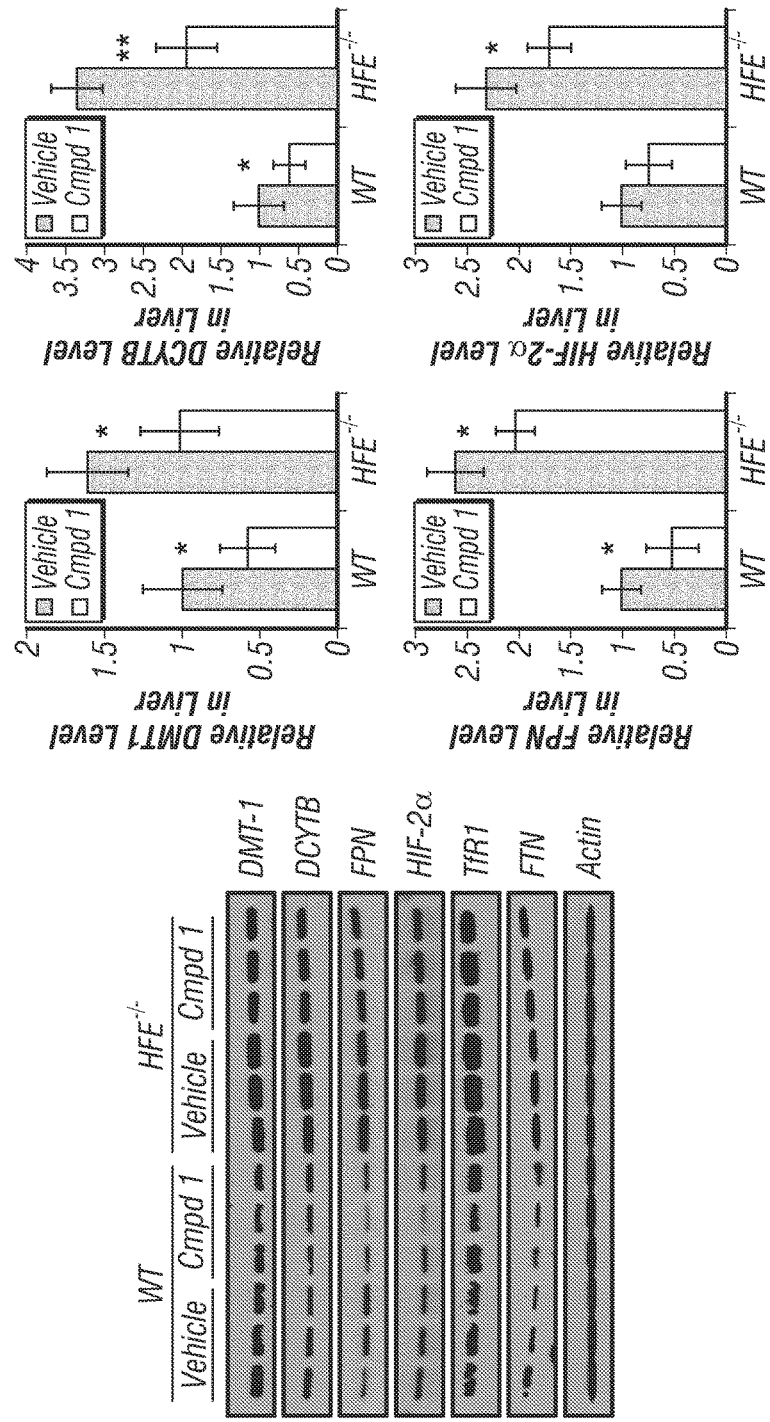
Figure 4C:
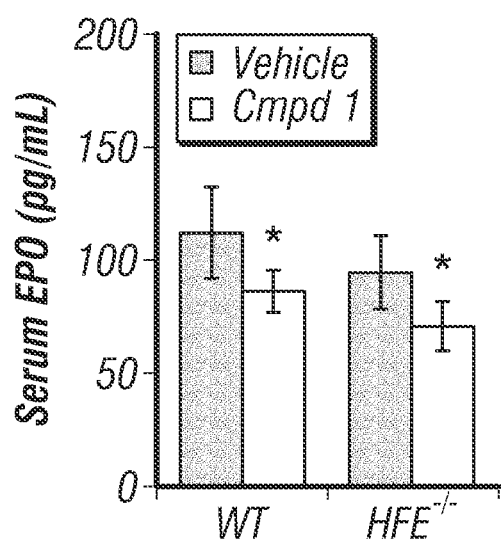
Figure 4D:
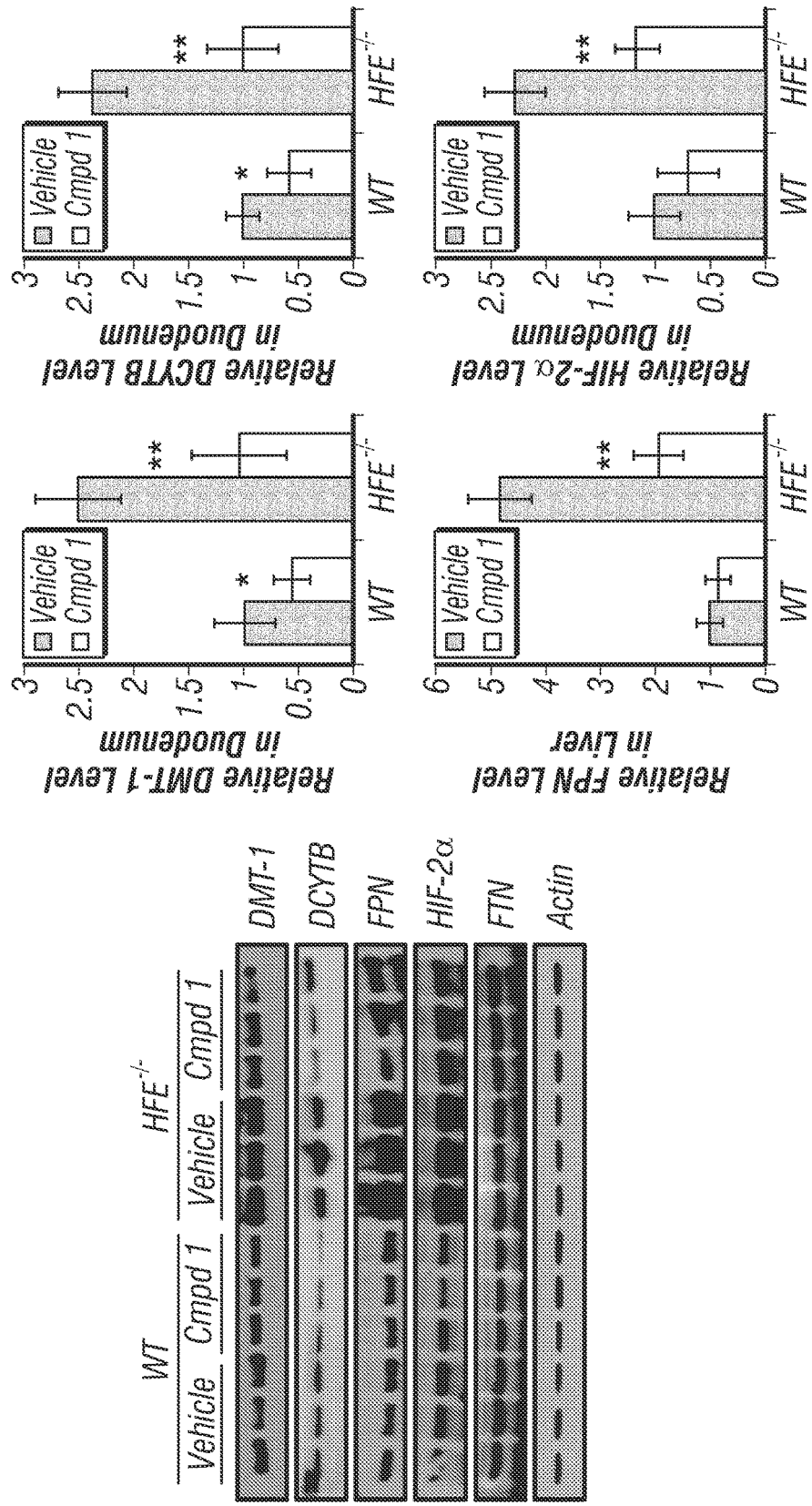
Figure 4E:
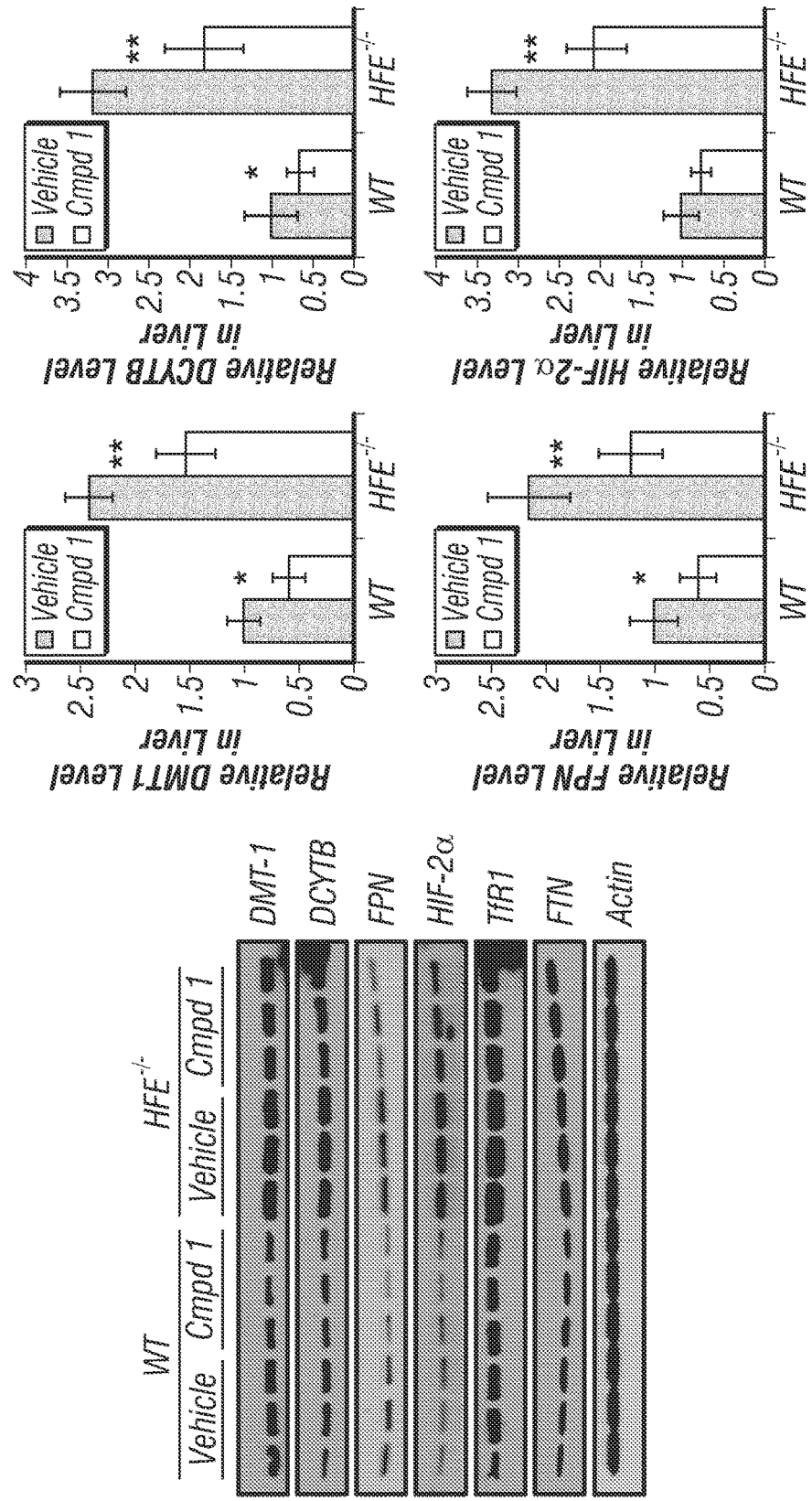
Figure 4F:
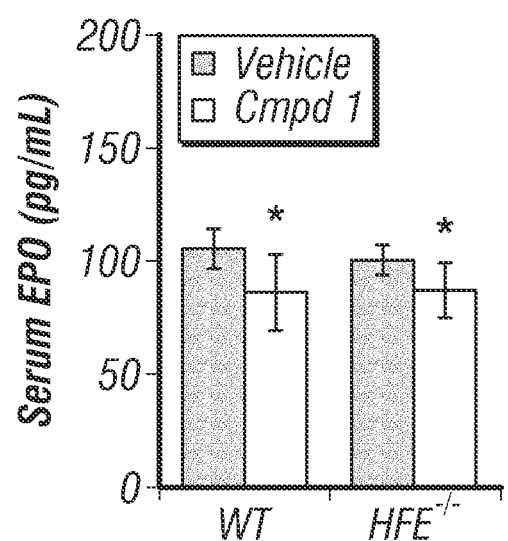

Compound 1 treatment attenuates iron uptake resulting in a corresponding reduction of iron accumulation in HFE$^{-/-}$ mice, a model for hemochromatosis. Genetic approaches with mice lacking HIF-2α expression in the duodenum have indicated that HIF-2α regulates several genes critical for intestinal iron absorption. These targets include the duodenal cytochrome B (DcytB) that reduces iron in the lumen so that it may be transported into enterocytes through the divalent metal transport protein 1 (DMT-1), which is also a HIF-2α regulated gene. A third HIF-2 target gene, ferroportin (FPN) exports iron across the basolateral membrane. Compound 1 treatment reduces expression of each of these factors at both the level of mRNA accumulation (FIG. 3) and protein accumulation (FIG. 4). The expression of iron-regulated factors not known to be HIF-2 target genes, such as the iron storage protein ferritin (FTN), transferrin receptor 1 (TfR1), and hepcidin, were not affected by Compound 1. Similar trends were also observed for the expression of these genes in the liver. Compound 1 treatments only had modest effects on the expression of erythropoietin (EPO), a well-characterized HIF-2α target gene primarily expressed in the kidney. Interestingly, expression of the EPAS1 gene encoding HIF-2α was also reduced by Compound 1 at the mRNA and protein levels.

REFERENCES

The following references, to the extent that they provide exemplary procedural or other details supplementary to those set forth herein, are specifically incorporated herein by reference Andrews, et al., *Annu. Rev. Physiol.* 69 (2007), 69-85.
Andrews, et al., *Blood* 112 (2008), 219-230.
Nicolas, et al., *J. Clin. Invest.* 110 (2002),1037-1044.
Nemeth, et al., *Science* 306 (2004), 2090-2093.
Drakesmith, et al., *Blood* 106 (2005), 1092-1097.
Pietrangelo, *Blood Cells Mol. Dis.* 32 (2004), 131-138.
Barton, *Am. J. Med. Sci.* 346 (2013), 403-412.
Crownover, et al., *Am. Family Physician* 87 (2013), 183-190.
Wu, et al., *Blood* 124 (2014), 1335-1343.
Fleming, et al., *Annu. Rev. Nutr.* 31 (2011),117-137.
Maggio, *Br. J. Haematol.* 138 (2007), 407-421.
Keith, et al., *Nature Rev. Cancer* 12 (2012), 9-22.
Mastrogiannaki, et al., *J. Clin. Invest.* 119 (2009), 1159-1166.
Mastrogiannaki, et al., *Blood* 119 (2012), 587-590.
Anderson, et al., *Proc. Natl. Acad. Sci. U.S.A.* 26 (2013), 4922-4930.
Hoye, et al., *Natural Protocol.* 2 (2007), 2451.
Moore, et al., *Acc. Chem. Res.* 40 (2007), 1412-1419.

What is claimed is:

1. A method of treating hemochromatosis comprising administering to a subject in need thereof an effective amount of a small molecule HIF-2α inhibitor, wherein said small molecule HIF-2α inhibitor is of Formula I:

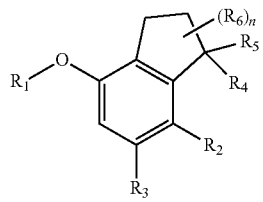

wherein:

n is 1, 2, 3 or 4;

$R_1$ is aryl or heteroaryl, optionally substituted;

$R_2$ is nitro, halo, cyano, alkyl, fluoroalkyl, sulfinyl, sulfonamide, sulfonyl, or sulfoximinyl;

$R_3$ is hydrogen, halo, or alkyl;

$R_4$ is hydrogen, deuterium ($^2$H), hydroxy, alkylamino, alkoxy, or amino;

$R_5$ is hydrogen, alkyl, alkenyl, or alkynyl; or $R_4$ and $R_5$ in combination form oxo or oxime;

each of $R_6$ is independently selected from the group consisting of hydrogen, fluoro, chloro, hydroxy, —NHBoc, alkenyl, and alkyl; or two $R_6$ and the carbon atom(s) they are attached to form a 3- to 8-membered cycloalkyl or heterocycloalkyl, or a pharmaceutically acceptable salt or enantiomer thereof.

2. The method of claim 1, wherein the small molecule HIF-2α inhibitor has an IC$_{50}$ of less than 500 nM in HIF-2α scintillation proximity assay.

3. The method of claim 1, wherein the subject is a human.

4. The method of claim 3, wherein the human has HFE gene mutation.

5. The method of claim 4, wherein the human has HFE protein with C282Y/C282Y homozygous mutation, with C282Y/H63D heterozygous mutation or with C282Y/S65C heterozygous mutation.

6. The method of claim 1, wherein the hemochromatosis is primary hemochromatosis.

7. The method of claim 1, wherein the hemochromatosis is secondary hemochromatosis.

8. The method of claim 7, wherein the secondary hemochromatosis results from β-thalassemia.

9. The method of claim 1, wherein the small molecule HIF-2α inhibitor is of one of the formulae:

IIIa

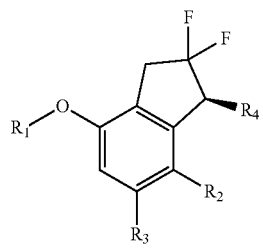

IIIb

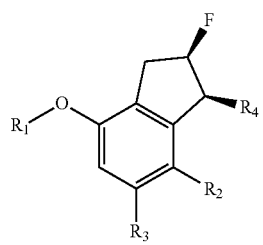

IIIc

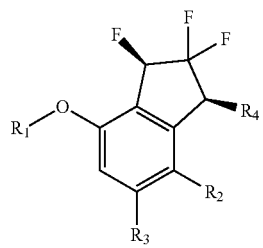

IIId

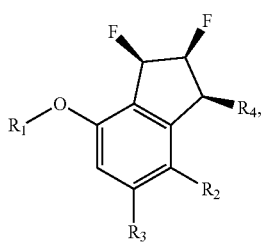

wherein:
R₁ is aryl or heteroaryl, optionally substituted;
R₂ is halo, cyano, alkyl, fluoroalkyl, sulfonamide, sulfinyl, sulfonyl, or sulfoximinyl;
R₃ is hydrogen, halo, or alkyl; and
R₄ is hydroxy, alkylamino, alkoxy, or amino.

10. The method of claim 9, wherein R₁ is phenyl or pyridyl, optionally substituted.

11. The method of claim 9, wherein R₂ is cyano, fluoroalkyl, sulfonamide, sulfinyl, sulfonyl or sulfoximinyl.

12. The method of claim 9, wherein R₂ is selected from the group consisting of —CN, —CF₃, —(=O)CH₃, —S(=O)₂CH₃, —S(=O)₂CH₂F, —S(=O)₂CHF₂, —S(=O)₂CF₃, —S(=O)₂NH₂, —S(=O)₂NHCH₃, —S(=O)(=NH)CH₃, —S(=O)(=NH)CH₂F, —S(=O)(=NH)CHF₂, —S(=O)(=NH)CF₃, —S(=O)(=N—CN)CH₃, —S(=O)(=N—CN)CH₂F, —S(=O)(=N—CN)CHF₂, and —S(=O)(=N—CN)CF₃.

13. The method of claim 9, wherein R₃ is hydrogen.

14. The method of claim 9, wherein R₄ is hydroxy or amino.

15. The method of claim 9, wherein R₁ is phenyl, monocyclic heteroaryl, or bicyclic heteroaryl, optionally substituted; R₂ is cyano, fluoroalkyl, sulfonamide, sulfinyl, sulfonyl or sulfoximinyl; R₃ is hydrogen; and R₄ is hydroxy or amino.

16. The method of claim 1, wherein the small molecule HIF-2α is of a formula selected from:

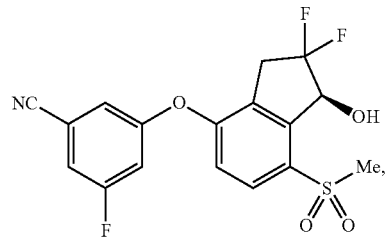

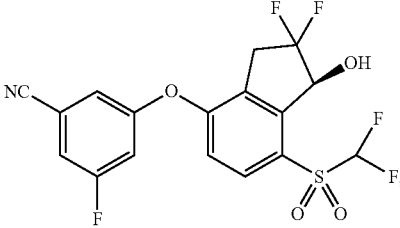

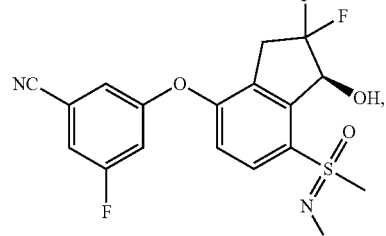

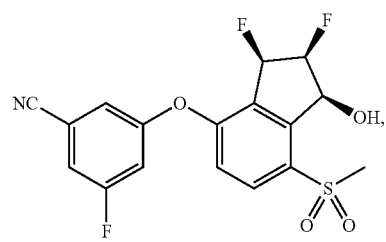

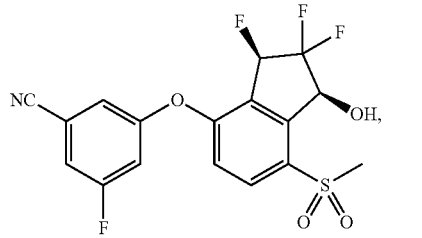

and

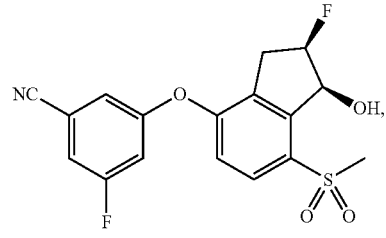

or a pharmaceutically acceptable salt thereof.

17. The method of claim 1, wherein R₁ is aryl or heteroaryl substituted with halo, C₁-C₄ alkyl, C₁-C₄ alkoxy, or cyano.

18. The method of claim 9, wherein $R_1$ is aryl or heteroaryl substituted with halo, $C_1$-$C_4$ alkyl, $C_1$-$C_4$ alkoxy, or cyano.

* * * * *

UNITED STATES PATENT AND TRADEMARK OFFICE
CERTIFICATE OF CORRECTION

PATENT NO. : 10,098,878 B2
APPLICATION NO. : 15/517528
DATED : October 16, 2018
INVENTOR(S) : Richard Keith Bruick et al.

Page 1 of 1

It is certified that error appears in the above-identified patent and that said Letters Patent is hereby corrected as shown below:

In the Claims

In Claim 12, Column 229, Line 53, delete "—(=O)CH₃" and insert -- —S(=O)CH₃ -- therefor.

In Claim 16, Column 230, Lines 51-60, delete the chemical structure and insert the following:

-- 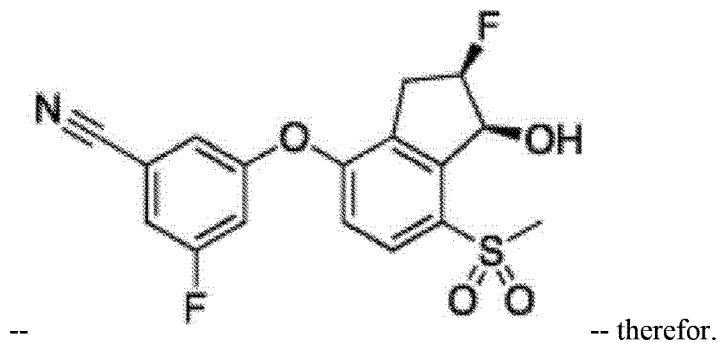 -- therefor.

Signed and Sealed this
Twenty-ninth Day of January, 2019

Andrei Iancu
*Director of the United States Patent and Trademark Office*